US012612380B2

(12) United States Patent
Kaul et al.

(10) Patent No.: US 12,612,380 B2
(45) Date of Patent: Apr. 28, 2026

(54) NON-LYSOSOMAL GLUCOSYLCERAMIDASE INHIBITORS AND USES THEREOF

(71) Applicant: ALECTOS THERAPEUTICS INC., Burnaby (CA)

(72) Inventors: Ramesh Kaul, Burnaby (CA); Ernest J. Mceachern, Burnaby (CA); Jianyu Sun, Burnaby (CA); David J. Vocadlo, Burnaby (CA); Yuanxi Zhou, Burnaby (CA); Yongbao Zhu, Burnaby (CA)

(73) Assignee: ALECTOS THERAPEUTICS 1NC (CA)

( * ) Notice: Subject to any disclaimer, the term of this patent is extended or adjusted under 35 U.S.C. 154(b) by 924 days.

(21) Appl. No.: 17/594,834

(22) PCT Filed: May 7, 2020

(86) PCT No.: PCT/IB2020/054355
§ 371 (c)(1),
(2) Date: Oct. 29, 2021

(87) PCT Pub. No.: WO2020/229968
PCT Pub. Date: Nov. 19, 2020

(65) Prior Publication Data

US 2022/0213058 A1 Jul. 7, 2022

Related U.S. Application Data

(60) Provisional application No. 62/846,011, filed on May 10, 2019.

(51) Int. Cl.

| | |
|---|---|
| *C07D 401/06* | (2006.01) |
| *C07D 211/32* | (2006.01) |
| *C07D 211/46* | (2006.01) |
| *C07D 401/14* | (2006.01) |
| *C07D 405/06* | (2006.01) |
| *C07D 405/10* | (2006.01) |
| *C07D 409/06* | (2006.01) |
| *C07D 409/14* | (2006.01) |
| *C07D 413/14* | (2006.01) |
| *C07D 417/14* | (2006.01) |

(52) U.S. Cl.
CPC .......... *C07D 401/06* (2013.01); *C07D 211/32* (2013.01); *C07D 211/46* (2013.01); *C07D 401/14* (2013.01); *C07D 405/06* (2013.01); *C07D 405/10* (2013.01); *C07D 409/06* (2013.01); *C07D 409/14* (2013.01); *C07D 413/14* (2013.01); *C07D 417/14* (2013.01)

(58) Field of Classification Search
CPC .. C07D 401/06; C07D 211/32; C07D 211/46; C07D 401/14; C07D 405/06; C07D 405/10; C07D 409/06; C07D 409/14; C07D 413/14; C07D 417/14
See application file for complete search history.

(56) References Cited

U.S. PATENT DOCUMENTS

| | | | |
|---|---|---|---|
| 4,533,668 | A | 8/1985 | Matsumura et al. |
| 8,729,099 | B2 | 5/2014 | Butters et al. |
| 2008/0269285 | A1 | 10/2008 | Martin et al. |

FOREIGN PATENT DOCUMENTS

| | | | | |
|---|---|---|---|---|
| CA | 2065446 A1 | 3/1991 | |
| EP | 0 350 012 | 1/1990 | |
| JP | S 55-47655 A | 4/1980 | |
| JP | H 2-306962 A | 5/1989 | |
| JP | H 2-131425 A | 5/1990 | |
| JP | 02-306962 A | 12/1990 | |
| JP | 6128229 A * | 5/1994 | ........... C07D 211/46 |
| JP | 2001-522833 A | 11/2001 | |
| WO | 1991/003242 | 3/1991 | |
| WO | 99/24401 A1 | 5/1999 | |
| WO | WO-2002055498 A1 * | 7/2002 | ........... A61K 31/445 |
| WO | 2004/007453 A1 | 1/2004 | |
| WO | 2004/007454 | 1/2004 | |
| WO | 2004/111001 | 12/2004 | |
| WO | 2004/111002 | 12/2004 | |
| WO | 2005/068426 | 7/2005 | |
| WO | 2006/125141 A2 | 11/2006 | |
| WO | 2006/136714 A1 | 12/2006 | |
| WO | 2014/032184 A1 | 3/2014 | |
| WO | 2015/147639 A1 | 10/2015 | |
| WO | 2017/185010 | 10/2017 | |
| WO | 2020/229968 A1 | 11/2020 | |

OTHER PUBLICATIONS

English Machine Translation of Kitatsume et al. Japanese Patent JP 6128229 A. Obtained from Google Patents. (Year: 1994).*
Volpe in The AAPS Journal, 2010, 12(4), 670-678.
International Preliminary Report on Patentability issued in corresponding International Application No. PCT/IB2020/054355 dated Nov. 25, 2021.
Extended European Search Report issued in corresponding European Patent Application No. P20805984 dated Jan. 1, 2023.

(Continued)

*Primary Examiner* — Joseph K McKane
*Assistant Examiner* — Jalisa Holmes Ferguson
(74) *Attorney, Agent, or Firm* — FROST BROWN TODD LLP

(57) ABSTRACT

The invention provides compounds for inhibiting glucosylceramidases, prodrugs of the compounds, and pharmaceutical compositions including the compounds or prodrugs of the compounds.

27 Claims, No Drawings

Specification includes a Sequence Listing.

(56) References Cited

OTHER PUBLICATIONS

International Preliminary Report on Patentability issued in related International Application No. PCT/IB2021/053863 dated Nov. 17, 2022.
International Preliminary Report on Patentability issued in related International Application No. PCT/IB2021/053864 dated Nov. 17, 2022.
Somogyi, A. et al. Int J Mol Sci 2018, 19, 625.
Goodman & Gilman's The Pharmacological Basis of Therapeutics, 9th Ed., 1996, pp. 11 to 13, (5 pages).
Ashe et al., "Iminosugar-Based Inhibitors of Glucosylceramide Synthase Increase Brain Glycosphingolipids and Survival in a Mouse Model of Sandhoff Disease" PLoS One 2011, 6, e21758.
Boudewyn et al., "N-butyldeoxynojirimycin delays motor deficits, cerebellar microgliosis, and Purkinje cell loss in a mouse model of mucolipidosis type IV" Neurobiol Dis 2017, 105, 257-270.
Di Pardo et al., "De novo Synthesis of Sphingolipids Is Defective in Experimental Models of Huntington's Disease" Front Neurosci 2017, 11, 698.
Dodge et al., "Glycosphingolipids are modulators of disease pathogenesis in amyotrophic lateral sclerosis" Proc Natl Acad Sci U S A 2015, 112, 8100-5.
Farfel-Becker et al., "Animal models for Gaucher disease research" Dis Model Mech 2011, 4, 746-752.
Ghisaidoobe et al., "Identification and Development of Biphenyl Substituted Iminosugarsas Improved Dual Glucosylceramide Synthase/Neutral Glucosylceramidase Inhibitors" J Med Chem 2014, 57, 9096-104.
Grabowski, "Phenotype, diagnosis, and treatment of Gaucher's disease" Lancet 2008, 372, 1263-1271.
Gu et al, "Structure-Activity Studies of N-Butyl-1-deoxynojirimycin (NB-DNJ) Analogues: Discovery of Potent and Selective Aminocyclopentitol Inhibitors of GBA 1 and GBA2" Structure, ChemMedChem 2017, 12, 1977-1984.
Halmer et al., "Sphingolipids: Important Players in Multiple Sclerosis" Cell Physiol Biochem 2014, 34, 111-118.
Hayashi et al., "Klotho-related Protein Is a Novel Cytosolic Neutral-Glycosylceramidase" J Biol Chem 2007, 282, 30889-30900.
Ilan, "Compounds of the sphingomyelin-ceramide-glycosphingolipid pathways as secondary messenger molecules: new targets for novel therapies for fatty liver disease and insulin resistance" Am J Physiol-Gast Liver Physiol 2016, 310, G1102-G1117.
Kawasaki et al., "The effect of vinyl esters on the enantioselectivity of the lipase-catalysed transesterification of alcohols" Tetrahedron Asymmetry, 2001, 12, 4, 585-596.
Kim et al., "GBA1 deficiency negatively affects physiological α-synuclein tetramers and related multimers" Proc Natl Acad Sci U S A 2018, 115, 798-803.
Lahav et al., "A Fluorescence Polarization Activity-Based Protein Profiling Assay in the Discovery of Potent, Selective Inhibitors for Human Nonlysosomal Glucosylceramidase" J. Am. Chem. Soc. 2017, 139, 14192-14197.
Lahiri et al., "The metabolism and function of sphingolipids and glycosphingolipids" Cell Mol Life Sci 2007, 64, 2270-2284.
Loberto et al., "GBA2-Encoded b-Glucosidase Activity Is Involved in the Inflammatory Response to Pseudomonas aeruginosa" PLoS One 2014, 9, e104763.
Margalit et al., "Glucocerebroside Ameliorates the Metabolic Syndrome in OB/OB Mice" J Pharm Exp Ther 2006, 319, 105-110.
Margalit et al., "Glucocerebroside treatment ameliorates ConA hepatitis by inhibition of NKT lymphocytes" Am J Physiol-Gast Liver Physiol 2005, 289, G917-G925.
Marques et al., "Reducing GBA2 Activity Ameliorates Neuropathology in Niemann-Pick Type C Mice" PLoS One 2015, 10, e0135889.
Massimo et al., "Current and Novel Aspects on the Non-lysosomal b-Glucosylceramidase GBA2" Neurochem Res 2016, 41, 210-20.
Mistry et al., "Glucocerebrosidase 2 gene deletion rescues type 1 Gaucher disease" Proc Natl Acad Sci U S A 2014, 111, 4934-9.
Mizrahi et al., "Glycosphingolipids Prevent APAP and HMG-CoA Reductase Inhibitors-mediated Liver Damage: A Novel Method for "Safer Drug" Formulation that Prevents Drug-induced Liver Injury" J Clin Trans Hepatol 2018, 6, 127-134.
Mutoh et al., "Role of Glycosphingolipids and Therapeutic Perspectives on Alzheimer's Disease" CNS Neurol Disord Drug Targets 2006, 5, 375-380.
Nietupski et al., "Iminosugar-based inhibitors of glucosylceramide synthase prolong survival but paradoxically increase brain glucosylceramide levels in Niemann-Pick C mice" Mol Genet Metab 2012, 105, 621-8.
Van Den Berg et al., "Assessment of Partially Deoxygenated Deoxynojirimycin Derivatives as Glucosylceramide Synthase Inhibitors", ACS Med. Chem. Lett 2011, 2, 519-522.
Woeste et al., "The Enigmatic Role of GBA2 in Controlling Locomotor Function" Front Mol Neurosci 2017, 10, 386.
Zervas et al., "Critical role for glycosphingolipids in Niemann-Pick disease type C" Curr Biol 2001, 11, 1283-7.
Zhang et al., "β-Glucosylceramide ameliorates liver inflammation in murine autoimmune cholangitis" Clin & Exp Immunol 2009, 157, 359-364.
Zigmond et al., "β-Glucosylceramide: a novel method for enhancement of natural killer T lymphoycte plasticity in murine models of immune-mediated disorders" Gut 2007, 56, 82-89.
International Search Report and Written Opinion issued Aug. 18, 2020, in respect of corresponding International Patent Application No. PCT/IB2020/054355.
International Search Report and Written Opinion issued Jul. 22, 2021, in respect of related International Patent Application No. PCT/IB2021/053863.
International Search Report and Written Opinion issued Aug. 9, 2021, in respect of related International Patent Application No. PCT/IB2021/053864.
Office Action issued in China dated May 23, 2025, issued in related Chinese Patent Application No. 202180046369.4.
Office Action dated Jun. 2, 2025 , issued in related Japanese Patent Application No. JP2022-567143.
Non-Final Office Action dated Jun. 2, 2025, issued in related U.S. Appl. No. 17/923,878.
Examination Report No. 1 dated Nov. 13, 2024, issued in corresponding Australian Patent Application No. 2020274430.
Examination Report No. 1 dated Nov. 13, 2024, issued in related Australian Patent Application No. 2021269231.
Examiner's Report dated Dec. 10, 2024, issued in related Canadian Patent Application No. 3,182,334.
Office Action dated Jan. 11, 2025 ssued in related Chinese Patent Application No. 202180046373.0.
Office Action issued in Australia dated Nov. 12, 2024, issued in related Australian Patent Application No. 2021269232.
Office Action issued in China dated Nov. 30, 2024, issued in related Chinese Patent Application No. 202180046369.4.
Examiner's Report dated Jan. 9, 2025, issued in related Canadian Patent Application No. 3,182,338.
Office Action dated Apr. 16, 2025, issued in related European Patent Application No. 21799911.9.
Examination Report dated Jan. 11, 2024, issued in related Indian Patent Application No. 202117055118.
First Office Action dated Jan. 13, 2024, issued in related Chinese Patent Application No. 202080048768.X.
Office Action dated Mar. 26, 2024, issued in related European Patent Application No. 20805984.0.
Second Office Action dated May 12, 2024, issued in related Chinese Patent Application No. 202080048768.X.
Extended European Search Report dated Feb. 4, 2024, issued in related European Patent Application No. 21799911.9.
Extended European Search Report dated May 23, 2024, issued in corresponding European Patent Application No. 21800654.2.
Yu et al., "Design, Synthesis, and Biological Evaluation of N-Alkylated Deoxynojirimycin (DNJ) Derivatives for the Treatment of Dengue Virus Infection", Journal of Medicinal Chemistry, vol. 55, No. 13, Jul. 12, 2012 (Jul. 12, 2012), pp. 6061-6075, XP055116892, ISSN: 0022-2623, DOI: 10.1021/jm30017lv.
Van Den Berg et al., "Synthesis and Evaluation of Hybrid Structures Composed of Two Glucosylceramide Synthase Inhibitors",

(56) References Cited

OTHER PUBLICATIONS

Chemmedchem Communications, Wiley-VCH, DE, vol. 10, No. 12, Oct. 23, 2015 (Oct. 23, 2015), pp. 2042-2062.
Patani et al. Chem Rev 1996, 96, 3147-3716.
Office Action dated Oct. 2, 2024, issued in related Japanese Patent Application No. JP2022-567142.
Bernotas et al. Tetrahedron Letters, 1990, 31, 3393.
Hausler et al. Monatschefte fur Chemie 133, 555-560 (2002).
Shankar et al . Tetrahedron Letters, 1993, 34, 7171.
Restriction Requirement for Election dated Aug. 13, 2025, issued in related U.S. Appl. No. 17/923,875.
Notice of Reasons for Refusal (English) dated May 30, 2024 issued in related Japanese Patent Application No. 2021-566468.
Non-Final Office Action dated Dec. 11, 2025, issued in respect of related U.S. Appl. No. 17/923,875.
Zeng, F.; Yin, Z.; Chen, J.; Nie, X.; Lin, P.; Lu, T.; Wang, M.; Peng, D. Design, Synthesis, and Activity Evaluation of Novel N-benzyl Deoxynojirimycin Derivatives for Use as a-Glucosidase Inhibitors. Molecules 2019, 24, 3309. (Year: 2019).

* cited by examiner

NON-LYSOSOMAL GLUCOSYLCERAMIDASE INHIBITORS AND USES THEREOF

CROSS-REFERENCE TO RELATED APPLICATIONS

This application is a U.S. National Phase Patent Application of International Application Number PCT/IB2020/054355, filed on May 7, 2020, which claims priority to and the benefit of U.S. Provisional Patent Application No. 62/846,011, filed on May 10, 2019, the entire contents of all of which are incorporated herein by reference.

SEQUENCE LISTING

The instant application contains a Sequence Listing in ASCII format and the entire content of the electronic submission of the sequence listing is incorporated by reference in its entirety for all purposes. The ASCII file is named "214015 Updated_Sequence_Listing.txt," was last modified on Nov. 14, 2023, and is 8,612 bytes in size.

FIELD OF THE INVENTION

This application relates in part to compounds that inhibit glucosylceramidases and uses thereof.

BACKGROUND OF THE INVENTION

The glucosylceramidases are a group of enzymes that catalyze the hydrolytic cleavage of the beta-glucosidic linkage of the glycosphingolipid glucosylceramide (GlcCer, also known as glucocerebroside) to produce D-glucose and ceramide. In humans, there are three distinct enzymes that possess glucosylceramidase activity: the lysosomal beta-glucocerebrosidase (GCase or GBA1, EC 3.2.1.45), the non-lysosomal glucosylceramidase (GBA2, EC 3.2.1.45), and the cytosolic beta-glucosidase (GBA3, EC 3.2.1.21). GCase is a lysosomal enzyme encoded by the gene GBA; homozygous loss of function mutations in GBA cause the lysosomal storage disorder Gaucher disease, which is characterized by the pathological accumulation of glucosylceramide within lysosomes.[1] GBA2 is a membrane-associated protein located at the cytoplasmic side of the endoplasmic reticulum (ER) and Golgi membrane, and is expressed at high levels in the central nervous system (CNS).[2,3]_ENREF_2 GBA3 is cytosolic enzyme predominantly expressed in the liver.[3,4]_ENREF_3

The glucosylceramidases play an important role in regulating cellular levels of their substrate molecule, glucosylceramide, which is the simplest member and biosynthetic precursor of an extensive class of cellular membrane lipids, the glycosphingolipids (GSLs).[3,5]_ENREF_2 Dysregulation of GSL metabolism and homeostasis is implicated in a broad range of diseases, including: the neurological disorders Alzheimer's disease (AD),[6] Parkinson's disease (PD),[7] multiple sclerosis (MS),[8] Huntington's disease (HD),[9] and amyotrophic lateral sclerosis (ALS);[10] the lysosomal storage diseases Niemann-Pick type C disease (NPC),[11] mucolipidosis type IV (MLIV),[12] and Sandhoff disease;[13] and the liver diseases non-alcoholic fatty liver disease (NAFLD)[14] and non-alcoholic steatohepatitis (NASH).[14] Small-molecule GBA2 inhibitors have been shown to extend lifespan and improve motor coordination in a rodent model of NPC.[15,16] Similarly, evidence indicates that GBA2 inhibition improves lifespan and delays motor deficits in rodent models of MLIV[12] and Sandhoff disease.[13] In a murine model with synucleinopathy, small-molecule GBA2 inhibitors have been shown to reduce the accumulation of alpha-synuclein aggregates in the brain.[13] Reduction of GBA2 activity has also been demonstrated to rescue the clinical phenotype in a rodent model of Gaucher disease.[17] In addition, studies have shown that GBA2 is involved in regulating the inflammatory response,[2] and that reduction of GBA2 activity reduces inflammation in a cell model of cystic fibrosis (CF).[18] Increased levels of glucosylceramide have also demonstrated beneficial effects in rodent models of liver disease, including non-alcoholic steatohepatitis (NASH),[19] hepatitis,[20] hepatocellular carcinoma (HCC),[21] autoimmune cholangitis,[22] and drug-induced liver injury (DILI).[23]

The enzymatic activity of GBA2 can be pharmacologically blocked by the iminosugars N-butyldeoxynojirimycin (NB-DNJ, miglustat) and N-(5-adamantane-1-yl-methoxy)pentyl)-deoxynojirimycin (AMP-DNM, Genz-529648); however, these compounds are not selective for GBA2 as they also exhibit inhibitory activity toward other enzymes, including GCase, glucosylceramide synthase (GCS, EC 2.4.1.80), and intestinal alpha-glucosidases.[24]

International patent applications PCT/GB2003/003099, filed 17 Jul. 2003, published under No. WO 2004/007453 on 22 Jan. 2004; PCT/GB2004/002450, filed 9 Jun. 2004, published under No. WO 2004/111001 on 23 Dec. 2004; PCT/GB2004/002451, filed 9 Jun. 2004, published under No. WO 2004/111002 on 23 Dec. 2004; PCT/GB2005/000071, filed 11 Jan. 2005, published under No. WO 2005/068426 on 28 Jul. 2005; and PCT/NL2015/050188, filed 23 Mar. 2015, published under No. WO 2015/147639 on 1 Oct. 2015, are directed to small-molecule inhibitors of GBA2.

SUMMARY OF THE INVENTION

The invention provides, in part, compounds for inhibiting a non-lysosomal glucosylceramidase (GBA2), prodrugs of the compounds, uses of the compounds and the prodrugs, pharmaceutical compositions including the compounds or prodrugs of the compounds, and methods of treating diseases and disorders modulated by levels of GBA2 activity, and/or levels of glucosylceramide, and/or dysregulation of glycosphingolipid metabolism or homeostasis. In some embodiments, the invention provides compositions and methods to prevent and/or treat a neurological disease, including Alzheimer's disease, Parkinson's disease, multiple sclerosis, Huntington's disease, and amyotrophic lateral sclerosis (ALS), or a lysosomal storage disease, including Gaucher disease, Niemann-Pick type C disease, mucolipidosis type IV, and Sandhoff disease, or a liver disease, including non-alcoholic steatohepatitis (NASH), by administering to a patient in need thereof an effective amount of one or more of the compounds or prodrugs of the compounds described herein.

In one aspect, the invention provides a compound of Formula (I) or a pharmaceutically acceptable salt thereof:

(I)

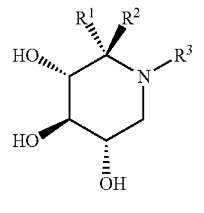

where $R^1$ may be H and $R^2$ may be $CH_3$, $CH_2F$, or $CHF_2$; or $R^1$ may be $CH_3$ or $CH_2F$ and $R^2$ may be H; and $R^3$ may be $(CH_2)_nR^4$, wherein n may be 1 or 2, and $R^4$ may be cyclohexyl, cyclohexylmethyl, phenylethyl, 4-phenylcyclohexyl, spiro[2.5]octan-6-yl, spiro[3.5]nonan-7-yl, spiro[4.5]decan-8-yl, (5S,8s)-3,3-dimethyl-2-oxaspiro[4.5]decan-8-yl, 1,2,3,4-tetrahydronaphthalen-2-yl, 2,3-dihydro-1H-inden-2-yl, (adamantyl)methyl, (pyridine-2-yl)methyl, (benzo[d][1,3]dioxol-5-yl)methyl, (2,3-dihydrobenzo[b][1,4]dioxin-6-yl)methyl, ([1,1'-biphenyl]-4-yl)methyl, 1-(2,2,2-trifluoroethyl)piperidin-4-yl, 1-(pyridin-3-yl)piperidin-4-yl, 1-(cyclohexylcarbamoyl)piperidin-4-yl, 1-(cyclohexylcarbamothioyl)piperidin-4-yl, 1-phenylpiperidin-4-yl, 1-cyclohexylazetidin-3-yl, 2-(thiophen-2-yl)methyl, or 2-(thiophen-3-yl)methyl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$; or $R^3$ may be phenylethyl, optionally substituted from one up to the maximum number of substituents with one or more of pyrrolidin-1-yl, piperidin-1-yl, 4-morpholino, cyclopropylmethoxy, (tetrahydrofuran-3-yl)oxy, (tetrahydro-2H-pyran-3-yl)oxy, (tetrahydro-2H-pyran-4-yl)oxy, phenoxy, (tetrahydrofuran-3-yl)methoxy, tetrahydro-2H-pyran-4-yl, 3,5-dimethylisoxazol-4-yl, 3,5-dimethyl-1H-pyrazol-4-yl, F, Cl, $C_{1-6}$ alkyl, cyclopropyl, propen-2-yl, $OCH_3$, and/or $CF_3$; or $R^3$ may be (1-formylpiperidin-4-yl)methyl, substituted on the formyl group with one of: $C_{1-6}$ alkyl, $C_{3-7}$ cycloalkyl, phenyl, thiophen-3-yl, phenylmethyl, or cyclopentylmethyl, each optionally substituted from one up to the maximum number of substituents with one or more of F, $C_{1-6}$ alkyl, $OCH_3$, and/or $CF_3$; or $R^3$ may be

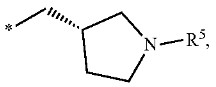 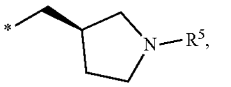

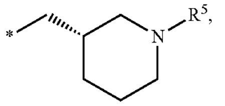 or 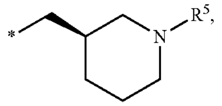

where $R^5$ may be selected from the group consisting of: phenyl, pyridin-2-yl, pyridin-3-yl, pyrimidin-5-yl, thiophen-3-yl, benzo[d]thiazol-4-yl, benzo[d]thiazol-2-yl, phenylcarbonyl, thiazol-2-yl, benzo[d]oxazol-2-yl, and benzo[d]thiazol-2-yl, each optionally substituted from one up to the maximum number of substituents with one or more of F, Cl, $C_{1-6}$ alkyl, $C_{1-6}$ alkoxyl, $OCF_3$, and/or $CF_3$.

In alternative embodiments, the invention provides a compound of Formula (Ia) or a pharmaceutically acceptable salt thereof:

(Ia)

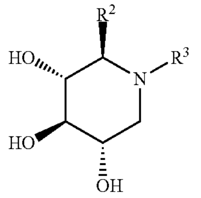

where $R^2$ may be $CH_3$, $CH_2F$, or $CHF_2$; and $R^3$ may be $(CH_2)_nR^4$, wherein n may be 1 or 2, and $R^4$ may be cyclohexyl, cyclohexylmethyl, phenylethyl, 4-phenylcyclohexyl, spiro[2.5]octan-6-yl, spiro[3.5]nonan-7-yl, spiro[4.5]decan-8-yl, (5S,8s)-3,3-dimethyl-2-oxaspiro[4.5]decan-8-yl, 1,2,3,4-tetrahydronaphthalen-2-yl, 2,3-dihydro-1H-inden-2-yl, (adamantyl)methyl, (pyridine-2-yl)methyl, (benzo[d][1,3]dioxol-5-yl)methyl, (2,3-dihydrobenzo[b][1,4]dioxin-6-yl)methyl, ([1,1'-biphenyl]-4-yl)methyl, 1-(2,2,2-trifluoroethyl)piperidin-4-yl, 1-(pyridin-3-yl)piperidin-4-yl, 1-(cyclohexylcarbamoyl)piperidin-4-yl, 1-(cyclohexylcarbamothioyl)piperidin-4-yl, 1-phenylpiperidin-4-yl, 1-cyclohexylazetidin-3-yl, 2-(thiophen-2-yl)methyl, or 2-(thiophen-3-yl)methyl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$; or $R^3$ may be phenylethyl, optionally substituted from one up to the maximum number of substituents with one or more of pyrrolidin-1-yl, piperidin-1-yl, 4-morpholino, cyclopropylmethoxy, (tetrahydrofuran-3-yl)oxy, (tetrahydro-2H-pyran-3-yl)oxy, (tetrahydro-2H-pyran-4-yl)oxy, phenoxy, (tetrahydrofuran-3-yl)methoxy, tetrahydro-2H-pyran-4-yl, 3,5-dimethylisoxazol-4-yl, 3,5-dimethyl-1H-pyrazol-4-yl, F, Cl, $C_{1-6}$ alkyl, cyclopropyl, propen-2-yl, $OCH_3$, and/or $CF_3$; or $R^3$ may be (1-formylpiperidin-4-yl)methyl, substituted on the formyl group with one of: $C_{1-6}$ alkyl, $C_{3-7}$ cycloalkyl, phenyl, thiophen-3-yl, phenylmethyl, or cyclopentylmethyl, each optionally substituted from one up to the maximum number of substituents with one or more of F, $C_{1-6}$ alkyl, $OCH_3$, and/or $CF_3$; or $R^3$ may be

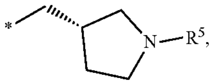 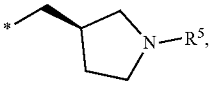

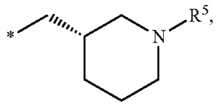 or 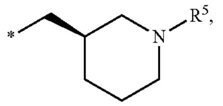

where $R^5$ may be selected from the group consisting of: phenyl, pyridin-2-yl, pyridin-3-yl, pyrimidin-5-yl, thiophen-3-yl, benzo[d]thiazol-4-yl, benzo[d]thiazol-2-yl, phenylcarbonyl, thiazol-2-yl, benzo[d]oxazol-2-yl, and benzo[d]thiazol-2-yl, each optionally substituted from one up to the maximum number of substituents with one or more of F, Cl, $C_{1-6}$ alkyl, $C_{1-6}$ alkoxyl, $OCF_3$, and/or $CF_3$.

In alternative embodiments, the invention provides a compound of Formula (Ib) or a pharmaceutically acceptable salt thereof:

(Ib)

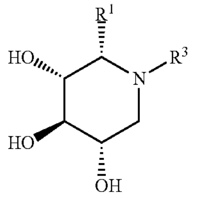

where $R^1$ may be $CH_3$ or $CH_2F$; and $R^3$ may be $(CH_2)_nR^4$, wherein n may be 1 or 2, and $R^4$ may be cyclohexyl, cyclohexylmethyl, phenylethyl, 4-phenylcyclohexyl, spiro[2.5]octan-6-yl, spiro[3.5]nonan-7-yl, spiro[4.5]decan-8-yl, (5S,8s)-3,3-dimethyl-2-oxaspiro[4.5]decan-8-yl, 1,2,3,4-tetrahydronaphthalen-2-yl, 2,3-dihydro-1H-inden-2-yl, (adamantyl)methyl, (pyridine-2-yl)methyl, (benzo[d][1,3]dioxol-5-yl)methyl, (2,3-dihydrobenzo[b][1,4]dioxin-6-yl)methyl, ([1,1'-biphenyl]-4-yl)methyl, 1-(2,2,2-trifluoroethyl)piperidin-4-yl, 1-(pyridin-3-yl)piperidin-4-yl, 1-(cyclohexylcarbamoyl)piperidin-4-yl, 1-(cyclohexylcarbamothioyl)piperidin-4-yl, 1-phenylpiperidin-4-yl, 1-cyclohexylazetidin-3-yl, 2-(thiophen-2-yl)methyl, or 2-(thiophen-3-yl)methyl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$; or $R^3$ may be phenylethyl, optionally substituted from one up to the maximum number of substituents with one or more of pyrrolidin-1-yl, piperidin-1-yl, 4-morpholino, cyclopropylmethoxy, (tetrahydrofuran-3-yl)oxy, (tetrahydro-2H-pyran-3-yl)oxy, (tetrahydro-2H-pyran-4-yl)oxy, phenoxy, (tetrahydrofuran-3-yl)methoxy, tetrahydro-2H-pyran-4-yl, 3,5-dimethylisoxazol-4-yl, 3,5-dimethyl-1H-pyrazol-4-yl, F, Cl, $C_{1-6}$ alkyl, cyclopropyl, propen-2-yl, $OCH_3$, and/or $CF_3$; or $R^3$ may be (1-formylpiperidin-4-yl)methyl, substituted on the formyl group with one of: $C_{1-6}$ alkyl, $C_{3-7}$ cycloalkyl, phenyl, thiophen-3-yl, phenylmethyl, or cyclopentylmethyl, each optionally substituted from one up to the maximum number of substituents with one or more of F, $C_{1-6}$ alkyl, $OCH_3$, and/or $CF_3$; or $R^3$ may be

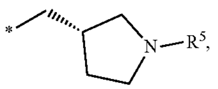
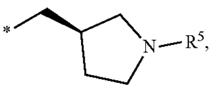
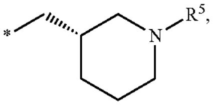
or
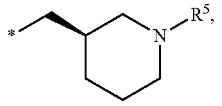

where $R^5$ may be selected from the group consisting of: phenyl, pyridin-2-yl, pyridin-3-yl, pyrimidin-5-yl, thiophen-3-yl, benzo[d]thiazol-4-yl, benzo[d]thiazol-2-yl, phenylcarbonyl, thiazol-2-yl, benzo[d]oxazol-2-yl, and benzo[d]thiazol-2-yl, each optionally substituted from one up to the maximum number of substituents with one or more of F, Cl, $C_{1-6}$ alkyl, $C_{1-6}$ alkoxyl, $OCF_3$, and/or $CF_3$.

In alternative embodiments, the invention provides a compound of Formula (Ic) or a pharmaceutically acceptable salt thereof:

(Ic)

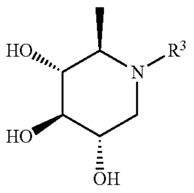

where $R^3$ may be $(CH_2)_nR^4$, wherein n may be 1 or 2, and $R^4$ may be cyclohexyl, cyclohexylmethyl, phenylethyl, 4-phenylcyclohexyl, spiro[2.5]octan-6-yl, spiro[3.5]nonan-7-yl, spiro[4.5]decan-8-yl, (5S,8s)-3,3-dimethyl-2-oxaspiro[4.5]decan-8-yl, 1,2,3,4-tetrahydronaphthalen-2-yl, 2,3-dihydro-1H-inden-2-yl, (adamantyl)methyl, (pyridine-2-yl)methyl, (benzo[d][1,3]dioxol-5-yl)methyl, (2,3-dihydrobenzo[b][1,4]dioxin-6-yl)methyl, ([1,1'-biphenyl]-4-yl)methyl, 1-(2,2,2-trifluoroethyl)piperidin-4-yl, 1-(pyridin-3-yl)piperidin-4-yl, 1-(cyclohexylcarbamoyl)piperidin-4-yl, 1-(cyclohexylcarbamothioyl)piperidin-4-yl, 1-phenylpiperidin-4-yl, 1-cyclohexylazetidin-3-yl, 2-(thiophen-2-yl)methyl, or 2-(thiophen-3-yl)methyl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$; or $R^3$ may be phenylethyl, optionally substituted from one up to the maximum number of substituents with one or more of pyrrolidin-1-yl, piperidin-1-yl, 4-morpholino, cyclopropylmethoxy, (tetrahydrofuran-3-yl)oxy, (tetrahydro-2H-pyran-3-yl)oxy, (tetrahydro-2H-pyran-4-yl)oxy, phenoxy, (tetrahydrofuran-3-yl)methoxy, tetrahydro-2H-pyran-4-yl, 3,5-dimethylisoxazol-4-yl, 3,5-dimethyl-1H-pyrazol-4-yl, F, Cl, $C_{1-6}$ alkyl, cyclopropyl, propen-2-yl, $OCH_3$, and/or $CF_3$; or $R^3$ may be (1-formylpiperidin-4-yl)methyl, substituted on the formyl group with one of: $C_{1-6}$ alkyl, $C_{3-7}$ cycloalkyl, phenyl, thiophen-3-yl, phenylmethyl, or cyclopentylmethyl, each optionally substituted from one up to the maximum number of substituents with one or more of F, $C_{1-6}$ alkyl, $OCH_3$, and/or $CF_3$; or $R^3$ may be

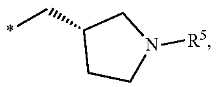
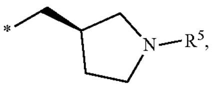
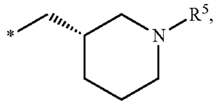
or
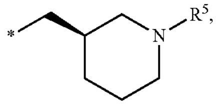

where $R^5$ may be selected from the group consisting of: phenyl, pyridin-2-yl, pyridin-3-yl, pyrimidin-5-yl, thiophen-3-yl, benzo[d]thiazol-4-yl, benzo[d]thiazol-2-yl, phenylcarbonyl, thiazol-2-yl, benzo[d]oxazol-2-yl, and benzo[d]thiazol-2-yl, each optionally substituted from one up to the maximum number of substituents with one or more of F, Cl, $C_{1-6}$ alkyl, $C_{1-6}$ alkoxyl, $OCF_3$, and/or $CF_3$.

In alternative embodiments, the invention provides a compound of Formula (Id) or a pharmaceutically acceptable salt thereof:

(Id)

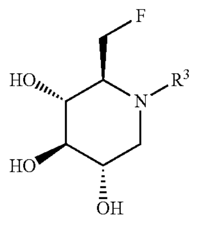

where $R^3$ may be $(CH_2)_nR^4$, wherein n may be 1 or 2, and $R^4$ may be cyclohexyl, cyclohexylmethyl, phenylethyl, 4-phenylcyclohexyl, spiro[2.5]octan-6-yl, spiro[3.5]nonan-7-yl, spiro[4.5]decan-8-yl, (5S,8s)-3,3-dimethyl-2-oxaspiro[4.5]decan-8-yl, 1,2,3,4-tetrahydronaphthalen-2-yl, 2,3-dihydro-1H-inden-2-yl, (adamantyl)methyl, (pyridine-2-yl)methyl, (benzo[d][1,3]dioxol-5-yl)methyl, (2,3-dihydrobenzo[b][1,4]dioxin-6-yl)methyl, ([1,1'-biphenyl]-4-yl)methyl, 1-(2,2,2-trifluoroethyl)piperidin-4-yl, 1-(pyridin-3-yl)piperidin-4-yl, 1-(cyclohexylcarbamoyl)piperidin-4-yl, 1-(cyclohexylcarbamothioyl)piperidin-4-yl, 1-phenylpiperidin-4-yl, 1-cyclohexylazetidin-3-yl, 2-(thiophen-2-yl)methyl, or 2-(thiophen-3-yl)methyl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$; or $R^3$ may be phenylethyl, optionally substituted from one up to the maximum number of substituents with one or more of pyrrolidin-1-yl, piperidin-1-yl, 4-morpholino, cyclopropylmethoxy, (tetrahydrofuran-3-yl)oxy, (tetrahydro-2H-pyran-3-yl)oxy, (tetrahydro-2H-pyran-4-yl)oxy, phenoxy, (tetrahydrofuran-3-yl)methoxy, tetrahydro-2H-pyran-4-yl, 3,5-dimethylisoxazol-4-yl, 3,5-dimethyl-1H-pyrazol-4-yl, F, Cl, $C_{1-6}$ alkyl, cyclopropyl, propen-2-yl, $OCH_3$, and/or $CF_3$; or $R^3$ may be (1-formylpiperidin-4-yl)methyl, substituted on the formyl group with one of: $C_{1-6}$ alkyl, $C_{3-7}$ cycloalkyl, phenyl, thiophen-3-yl, phenylmethyl, or cyclopentylmethyl, each optionally substituted from one up to the maximum number of substituents with one or more of F, $C_{1-6}$ alkyl, $OCH_3$, and/or $CF_3$; or $R^3$ may be

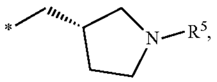
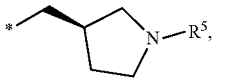
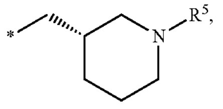
or
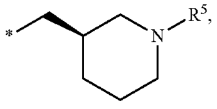

where $R^5$ may be selected from the group consisting of: phenyl, pyridin-2-yl, pyridin-3-yl, pyrimidin-5-yl, thiophen-3-yl, benzo[d]thiazol-4-yl, benzo[d]thiazol-2-yl, phenylcarbonyl, thiazol-2-yl, benzo[d]oxazol-2-yl, and benzo[d]thiazol-2-yl, each optionally substituted from one up to the maximum number of substituents with one or more of F, Cl, $C_{1-6}$ alkyl, $C_{1-6}$ alkoxyl, $OCF_3$, and/or $CF_3$.

In alternative embodiments, the invention provides a compound of Formula (Ie) or a pharmaceutically acceptable salt thereof:

(Ie)

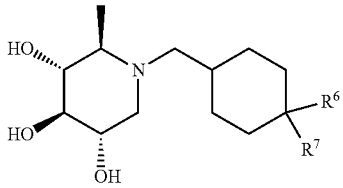

where $R^6$ and $R^7$ may be independently selected from the group consisting of: H, F, Cl, $C_{1-6}$ alkyl, $OCH_3$, phenyl, cyclopropyl, vinyl, methoxymethyl, 2-fluoropropan-2-yl, and/or $CF_3$. In some embodiments, $R^6$ may be H, and $R^7$ may be $CF_3$, 2-fluoropropan-2-yl, isopropyl, or tert-butyl. In some embodiments, $R^6$ may be $CF_3$, 2-fluoropropan-2-yl, isopropyl, or tert-butyl, and $R^7$ may be H.

In alternative embodiments, the invention provides a compound of Formula (If) or a pharmaceutically acceptable salt thereof:

(If)

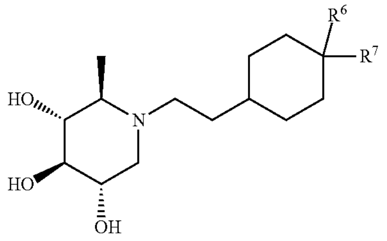

where $R^6$ and $R^7$ may be independently selected from the group consisting of: H, F, Cl, $C_{1-6}$ alkyl, $OCH_3$, phenyl, cyclopropyl, vinyl, methoxymethyl, 2-fluoropropan-2-yl, and/or $CF_3$.

In alternative embodiments, the invention provides a compound of Formula (Ig) or a pharmaceutically acceptable salt thereof:

(Ig)

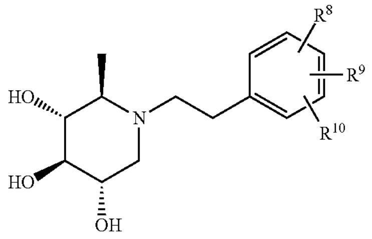

where $R^8$, $R^9$ and $R^{10}$ may be independently selected from the group consisting of: pyrrolidin-1-yl, piperidin-1-yl, 4-morpholino, cyclopropylmethoxy, (tetrahydrofuran-3-yl)oxy, (tetrahydro-2H-pyran-3-yl)oxy, (tetrahydro-2H-pyran-4-yl)oxy, phenoxy, (tetrahydrofuran-3-yl)methoxy, tetrahydro-2H-pyran-4-yl, 3,5-dimethylisoxazol-4-yl, 3,5-dimethyl-1H-pyrazol-4-yl, H, F, Cl, $C_{1-6}$ alkyl, cyclopropyl, propen-2-yl, $OCH_3$, and/or $CF_3$.

In some embodiments, $R^8$, $R^9$ and $R^{10}$ may be independently selected from the group consisting of: H, F, Cl, tetrahydro-2H-pyran-4-yl, 4-morpholino, pyrrolidin-1-yl, and piperidin-1-yl.

In alternative embodiments, the invention provides a compound of Formula (Ih) or a pharmaceutically acceptable salt thereof:

(Ih)

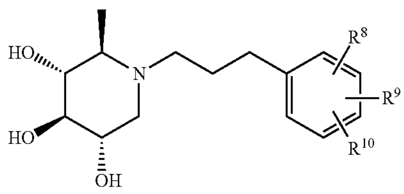

where $R^8$, $R^9$ and $R^{10}$ may be independently selected from the group consisting of: H, F, Cl, $C_{1-6}$ alkyl, cyclopropyl, vinyl, 2-fluoropropan-2-yl, methoxymethyl, $C_{1-6}$ alkoxy, and/or $CF_3$.

In alternative embodiments, the invention provides a compound of Formula (Ii) or a pharmaceutically acceptable salt thereof:

(Ii)

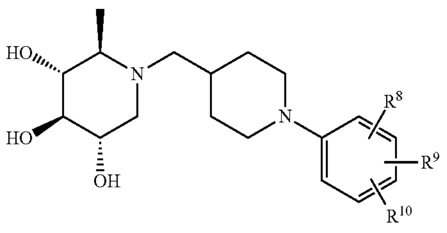

where $R^8$, $R^9$ and $R^{10}$ may be independently selected from the group consisting of: H, F, Cl, $C_{1-6}$ alkyl, cyclopropyl, vinyl, 2-fluoropropan-2-yl, methoxymethyl, $C_{1-6}$ alkoxy, and/or $CF_3$. In some embodiments, $R^8$, $R^9$ and $R^{10}$ may be independently selected from the group consisting of: H, F, and $CF_3$.

In alternative embodiments, the invention provides a compound of Formula (Ij) or a pharmaceutically acceptable salt thereof:

(Ij)

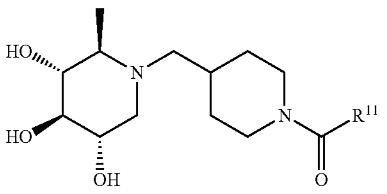

where $R^{11}$ may be selected from the group consisting of: $C_{1-6}$ alkyl, $C_{3-7}$ cycloalkyl, phenyl, thiophen-3-yl, phenylmethyl, or cyclopentylmethyl, each optionally substituted from one up to the maximum number of substituents with one or more of F, $C_{1-6}$ alkyl, $OCH_3$, and/or $CF_3$.

In alternative embodiments, the invention provides a compound of Formula (Ik) or a pharmaceutically acceptable salt thereof:

(Ik)

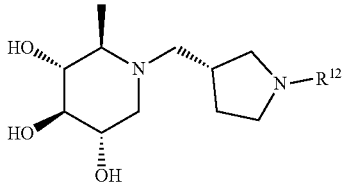

where $R^{12}$ may be selected from the group consisting of: phenyl, pyridin-2-yl, pyridin-3-yl, pyrimidin-5-yl, thiophen-3-yl, benzo[d]thiazol-4-yl, benzo[d]thiazol-2-yl, or phenylcarbonyl, each optionally substituted from one up to the maximum number of substituents with one or more of F, Cl, $C_{1-6}$ alkyl, $C_{1-6}$ alkoxyl, $OCF_3$, and/or $CF_3$. In some embodiments, $R^{12}$ may be selected from the group consisting of: 2-(trifluoromethyl)phenyl, 2-(trifluoromethyl)pyridin-3-yl, 3-(trifluoromethyl)pyridin-2-yl, 4-(trifluoromethyl)pyridin-2-yl, 5-(trifluoromethyl)pyridin-3-yl, 6-(trifluoromethyl)pyridin-2-yl, 4-(trifluoromethyl)pyrimidin-5-yl, and 4-(trifluoromethyl)thiazol-2-yl.

In alternative embodiments, the invention provides a compound of Formula (Il) or a pharmaceutically acceptable salt thereof:

(Il)

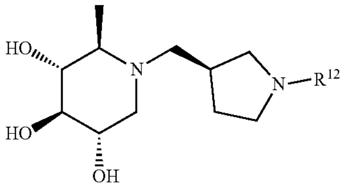

where $R^{12}$ may be selected from the group consisting of: phenyl, pyridin-2-yl, pyridin-3-yl, pyrimidin-5-yl, thiophen-3-yl, benzo[d]thiazol-4-yl, benzo[d]thiazol-2-yl, or phenylcarbonyl, each optionally substituted from one up to the maximum number of substituents with one or more of F, Cl, $C_{1-6}$ alkyl, $C_{1-6}$ alkoxyl, $OCF_3$, and/or $CF_3$. In some embodiments, $R^{12}$ may be selected from the group consisting of: 2-(trifluoromethyl)phenyl, 2-(trifluoromethyl)pyridin-3-yl, 3-(trifluoromethyl)pyridin-2-yl, 4-(trifluoromethyl)pyridin-2-yl, 5-(trifluoromethyl)pyridin-3-yl, 6-(trifluoromethyl)pyridin-2-yl, 4-(trifluoromethyl)pyrimidin-5-yl, and 4-(trifluoromethyl)thiazol-2-yl.

In alternative embodiments, the invention provides a compound of Formula (Im) or a pharmaceutically acceptable salt thereof:

(Im)

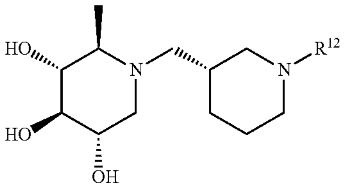

where $R^{12}$ may be selected from the group consisting of: phenyl, pyridin-2-yl, pyridin-3-yl, pyrimidin-5-yl, thiophen-3-yl, benzo[d]thiazol-4-yl, benzo[d]thiazol-2-yl, or phenylcarbonyl, each optionally substituted from one up to the maximum number of substituents with one or more of F, Cl, $C_{1-6}$ alkyl, $C_{1-6}$ alkoxyl, $OCF_3$, and/or $CF_3$. In some embodiments, $R^{12}$ may be selected from the group consisting of: 2-(trifluoromethyl)phenyl, 2-(trifluoromethyl)pyridin-3-yl, 3-(trifluoromethyl)pyridin-2-yl, 4-(trifluoromethyl)pyridin-2-yl, 5-(trifluoromethyl)pyridin-3-yl, 6-(trifluoromethyl) pyridin-2-yl, 4-(trifluoromethyl)pyrimidin-5-yl, and 4-(trifluoromethyl)thiazol-2-yl.

In alternative embodiments, the invention provides a compound of Formula (In) or a pharmaceutically acceptable salt thereof:

(In)

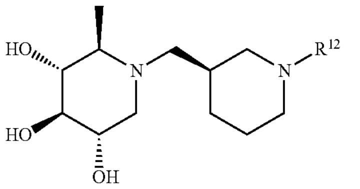

where $R^{12}$ may be selected from the group consisting of: phenyl, pyridin-2-yl, pyridin-3-yl, pyrimidin-5-yl, thiophen-3-yl, benzo[d]thiazol-4-yl, benzo[d]thiazol-2-yl, or phenylcarbonyl, each optionally substituted from one up to the maximum number of substituents with one or more of F, Cl, $C_{1-6}$ alkyl, $C_{1-6}$ alkoxyl, $OCF_3$, and/or $CF_3$. In some embodiments, $R^{12}$ may be selected from the group consisting of: 2-(trifluoromethyl)phenyl, 2-(trifluoromethyl)pyridin-3-yl, 3-(trifluoromethyl)pyridin-2-yl, 4-(trifluoromethyl)pyridin-2-yl, 5-(trifluoromethyl)pyridin-3-yl, 6-(trifluoromethyl) pyridin-2-yl, 4-(trifluoromethyl)pyrimidin-5-yl, and 4-(trifluoromethyl)thiazol-2-yl.

In alternative embodiments, the compound may be a prodrug; the compound may inhibit a non-lysosomal glucosylceramidase (GBA2); the compound may inhibit a GBA2 (e.g., a mammalian GBA2); the compound may inhibit a wild-type GBA2; or the compound may inhibit a mutant GBA2.

In alternative embodiments, a compound according to Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im), or Formula (In) may exhibit enhanced selectivity and/or permeability.

In alternative embodiments, a compound according to Formula (Ic), Formula (Id), Formula (Ie), Formula (If), Formula (Ig), Formula (Ih), Formula (Ii), Formula (Ij), Formula (Ik), Formula (Il), Formula (Im), or Formula (In) may exhibit enhanced selectivity and/or permeability.

In alternative embodiments, a compound according to Formula (Ie), Formula (Ig), Formula (Ik), Formula (Il), Formula (Im), or Formula (In) may exhibit enhanced selectivity and/or permeability.

In alternative embodiments, a compound according to Formula (Ic), Formula (Ie), or Formula (Ig), Formula (Ik), Formula (Il), Formula (Im), or Formula (In) may exhibit enhanced selectivity. In alternative embodiments, a compound according to Formula (Ie) may exhibit enhanced selectivity. In alternative embodiments, a compound according to Formula (Ig) may exhibit enhanced selectivity. In alternative embodiments, a compound according to Formula (Ik) or Formula (Il) may exhibit enhanced selectivity. In alternative embodiments, a compound according to Formula (Im) or Formula (In) may exhibit enhanced selectivity.

In alternative embodiments, a compound according to Formula (Ic), Formula (Ie), Formula (Ig), Formula (Ii), Formula (Ik), Formula (Il), Formula (Im), or Formula (In) may achieve higher brain concentrations when administered in vivo. In alternative embodiments, a compound according to Formula (Ie) may achieve higher brain concentrations when administered in vivo. In alternative embodiments, a compound according to Formula (Ig) may achieve higher brain concentrations when administered in vivo. In alternative embodiments, a compound according to Formula (Ii) may achieve higher brain concentrations when administered in vivo. In alternative embodiments, a compound according to Formula (Ik) or Formula (Il) may achieve higher brain concentrations when administered in vivo. In alternative embodiments, a compound according to Formula (Im) or Formula (In) may achieve higher brain concentrations when administered in vivo.

In alternative aspects, the invention provides a pharmaceutical composition including a compound according to the invention, or a pharmaceutically acceptable salt thereof, in combination with a pharmaceutically acceptable carrier.

In alternative aspects, the invention provides methods of inhibiting a GBA2 in a subject in need thereof, or of treating a neurological disease, or a lysosomal storage disease, or a liver disease, in a subject in need thereof, by administering to the subject an effective amount of a compound of Formula (I), including any one or more of Formula (Ia)-(In), or a pharmaceutically acceptable salt thereof, as described herein. The neurological disease may be, without limitation, Alzheimer's disease, Parkinson's disease, multiple sclerosis, Huntington's disease, amyotrophic lateral sclerosis (ALS), amyotrophic lateral sclerosis with cognitive impairment (ALSci), addiction, anxiety, argyrophilic grain dementia, ataxia-telangiectasia (A-T), attention deficit/hyperactivity disorder (ADHD), autism spectrum disorder (ASD), Becker muscular dystrophy (BMD), bipolar disorder (BD), Bluit disease, cerebellar ataxia, Charcot-Marie-Tooth disease (CMT), chronic fatigue syndrome, corticobasal degeneration (CBD), dementia pugilistica, dementia with Lewy bodies (DLB), Dejerine-Sottas disease, diffuse neurofibrillary tangles with calcification, Down's syndrome, Duchenne muscular dystrophy (DMD), epilepsy, essential tremor (ET), familial British dementia, familial Danish dementia, fibromyalgia, frontotemporal dementia with parkinsonism linked to chromosome 17 (FTDP-17), Friedreich's ataxia, Gerstmann-Straussler-Scheinker disease, glaucoma, Guadeloupean parkinsonism, Guillain-Barré syndrome, Hallevorden-Spatz disease (neurodegeneration with brain iron accumulation type 1), insomnia, Lambert-Eaton myasthenic syndrome (LEMS), major depressive disorder (MDD), migraine, mild cognitive impairment (MCI), multi-infarct dementia, multiple system atrophy (MSA), myasthenia gravis, myotonic dystrophy (including types DM1 and DM2), neuronal ceroid lipofuscinosis (including types 1, 2, 3, 4, 5, 6, 7, 8, 9, and 10), neuropathy (including peripheral neuropathy, autonomic neuropathy, neuritis, and diabetic neuropathy), oculopharyngeal muscular dystrophy, pain, pallido-ponto-nigral degeneration, parkinsonism-dementia complex of Guam, Pick's disease (PiD), post-encephalitic parkinsonism (PEP), primary lateral sclerosis (PLS), prion diseases (including Creutzfeldt-Jakob Disease (CJD), variant Creutzfeldt-Jakob Disease (vCJD), fatal familial insomnia, and kuru), progressive supercortical gliosis, progressive supranuclear palsy (PSP), Richardson's syndrome, schizophrenia, seizures, spinal cord injury, spinal muscular atrophy (SMA), spinocerebellar ataxia (including types 1, 2, 3, 4, 5, 6, 7, 8, 10, 11, 12, 13, 14, 16, 17, 18, 19, 20, 21, 22, 23, 25, 26, 27, 28, and 29), stroke, subacute sclerosing panencephalitis, tangle-only dementia, tardive dyskinesia, Tourette syndrome (TS), vascular dementia, or Wilson's disease.

The lysosomal storage disease may be, without limitation, Gaucher disease (including types I, II, and III), Niemann-Pick disease (including types A, B, and C), mucolipidosis (including types I, II, III, IV, VI, and VII), cerebrotendineous xanthomatosis, Fabry disease, Farber disease, GM1 gangliosidosis, Krabbe disease, metachromatic leukodystrophy (MLD), multiple sulfatase deficiency, Pompe disease, Sandhoff disease, or Tay-Sach's disease.

The liver disease may be, without limitation, non-alcoholic fatty liver disease (NAFLD), non-alcoholic steatohepatitis (NASH), Alagille syndrome, alcohol-related liver disease, alpha-1 antitrypsin deficiency, autoimmune hepatitis, autoimmune cholangitis, benign liver tumors, biliary atresia, cirrhosis, Crigler-Najjar syndrome, drug-induced liver injury (DILI), galactosemia, Gilbert syndrome, hemochromatosis, hepatic encephalopathy, hepatocellular carcinoma (HCC), intrahepatic cholestasis of pregnancy (ICP), lysosomal acid lipase deficiency (LAL-D), liver cysts, liver cancer, newborn jaundice, primary biliary cholangitis (PBC), primary sclerosing cholangitis (PSC), Reye syndrome, type I glycogen storage disease, or viral hepatitis (including types A, B, C, D, and E).

In alternative embodiments, the invention provides methods of treating a neurological disease in a subject in need thereof by administering to the subject an effective amount of a compound of any one or more of Formula (Ic), Formula (Ie), Formula (Ig), Formula (Ii), Formula (Ik), Formula (Il), Formula (Im), or Formula (In), or a pharmaceutically acceptable salt thereof, as described herein. In alternative embodiments, the invention provides methods of treating a neurological disease in a subject in need thereof by administering to the subject an effective amount of a compound of Formula (Ie), or a pharmaceutically acceptable salt thereof, as described herein. In alternative embodiments, the invention provides methods of treating a neurological disease in a subject in need thereof by administering to the subject an effective amount of a compound of Formula (Ig), or a pharmaceutically acceptable salt thereof, as described herein. In alternative embodiments, the invention provides methods of treating a neurological disease in a subject in need thereof by administering to the subject an effective amount of a compound of Formula (Ik), or a pharmaceutically acceptable salt thereof, as described herein. In alternative embodiments, the invention provides methods of treating a neurological disease in a subject in need thereof by administering to the subject an effective amount of a compound of Formula (Il), or a pharmaceutically acceptable salt thereof, as described herein. In alternative embodiments, the invention provides methods of treating a neurological disease in a subject in need thereof by administering to the subject an effective amount of a compound of Formula (Im), or a pharmaceutically acceptable salt thereof, as described herein. In alternative embodiments, the invention provides methods of treating a neurological disease in a subject in need thereof by administering to the subject an effective amount of a compound of Formula (In), or a pharmaceutically acceptable salt thereof, as described herein.

In alternative embodiments, the administering may reduce the enzymatic activity level of GBA2 in a subject. In alternative embodiments, the administering may modulate the levels of glucosylceramide and/or glycosphingolipids in a subject. In alternative embodiments, the administering may elevate the levels of glucosylceramide in a subject. In alternative embodiments, the administering may elevate the levels of the ganglioside GM1 in a subject. In alternative embodiments, the administering may modulate the levels of ceramide and/or glucosylsphingosine and/or sphingosine and/or sphingosine-1-phosphate (SiP) in a subject. The subject may be a human.

In alternative aspects, the invention provides use of a compound of an effective amount of a compound of Formula (I), including any one or more of Formula (Ia)-(In), or a pharmaceutically acceptable salt thereof, as described herein, in the preparation of a medicament. The medicament may be for inhibiting a GBA2, for treating a condition modulated by a GBA2, or for treating a neurological disease or a lysosomal storage disease or a liver disease.

This summary of the invention does not necessarily describe all features of the invention.

DETAILED DESCRIPTION

The invention provides, in part, compounds for inhibiting a non-lysosomal glucosylceramidase (GBA2) and uses thereof.

By a "non-lysosomal glucosylceramidase" or "GBA2" is meant a non-lysosomal membrane-associated enzyme located at the cytoplasmic side of the ER and Golgi membrane with glucosylceramidase activity (EC 3.2.1.45) that catalyzes the hydrolytic cleavage of the beta-glucosidic linkage of the glycolipid glucosylceramide. Alternative names for a GBA2 include: NLGase, glucosylceramidase beta 2, beta-glucocerebrosidase 2, beta-glucosidase 2, glucosylceramidase 2, bile acid beta-glucosidase, "glucosidase, beta (bile acid) 2", KIAA1605, DKFZp762K054, SPG46, and AD035. In some embodiments, the GBA2 may be a mammalian GBA2, such as a rat, mouse, or human GBA2. The GBA2 may be a wild-type GBA2 or a mutant GBA2. In some embodiments, the GBA2 may be a wild-type mammalian GBA2, such as a rat, mouse, or human wild-type GBA2. In some embodiments, the GBA2 may be a mutant mammalian GBA2, such as a rat, mouse, or human mutant GBA2. In some embodiments, the GBA2 may have a sequence as set forth in any one of the following Accession numbers: Q9HCG7, Q69ZF3, D3DRP2, Q5TCV6, Q96A51, Q96LY1, Q96SJ2, Q9H2L8, Q5M868, or 016581. In alternative embodiments, the GBA2 may have an alternative splice isoform sequence as set forth in any one of the following Accession numbers: Q9HCG7-1, Q9HCG7-2, Q9HCG7-3. In alternative embodiments, the GBA2 may be encoded by a sequence as set forth in any one of the following Accession numbers: NP_065995.1, NP_001317589.1, NP_766280.2, NP_001013109.2, NM_020944, NM_172692, NM_001330660, XM_011517973, XP_005251583.1, XP_006716872.1, XP_011516275.1, XP_016870426.1, XP_016870427.1, XP_016870428.1, XP_016870429.1, XP_016870430.1, XP_016870431.1, XP_016870432.1, XP_016870433.1, XP_016870434.1, or XP_016870435.1. In alternative embodiments, the human GBA2 may have the sequence set forth below:

(SEQ ID NO: 1)

```
        10         20         30         40
MGTQDPGNMG TGVPASEQIS CAKEDPQVYC PEETGGTKDV
```

-continued

```
        50         60         70         80
QVTDCKSPED SRPPKETDCC NPEDSGQLMV SYEGKAMGYQ

        90        100        110        120
VPPFGWRICL AHEFTEKRKP FQANNVSLSN MIKHIGMGLR

       130        140        150        160
YLQWWYRKTH VEKKTPFIDM INSVPLRQIY GCPLGGIGGG

       170        180        190        200
TITRGWRGQF CRWQLNPGMY QHRTVIADQF TVCLRREGQT

       210        220        230        240
VYQQVLSLER PSVLRSWNWG LCGYFAFYHA LYPRAWTVYQ

       250        260        270        280
LPGQNVTLTC RQITPILPHD YQDSSLPVGV FVWDVENEGD

       290        300        310        320
EALDVSIMFS MRNGLGGGDD APGGLWNEPF CLERSGETVR

       330        340        350        360
GLLLHHPTLP NPYTMAVAAR VTAATTVTHI TAFDPDSTGQ

       370        380        390        400
QVWQDLLQDG QLDSPTGQST PTQKGVGIAG AVCVSSKLRP

       410        420        430        440
RGQCRLEFSL AWDMPRIMFG AKGQVHYRRY TRFFGQDGDA

       450        460        470        480
APALSHYALC RYAEWEERIS AWQSPVLDDR SLPAWYKSAL

       490        500        510        520
FNELYFLADG GTVWLEVLED SLPEELGRNM CHLRPTLRDY

       530        540        550        560
GRFGYLEGQE YRMYNTYDVH FYASFALIML WPKLELSLQY

       570        580        590        600
DMALATLRED LTRRRYLMSG VMAPVKRRNV IPHDIGDPDD

       610        620        630        640
EPWLRVNAYL IHDTADWKDL NLKFVLQVYR DYYLTGDQNF

       650        660        670        680
LKDMWPVCLA VMESEMKFDK DHDGLIENGG YADQTYDGWV

       690        700        710        720
TTGPSAYCGG LWLAAVAVMV QMAALCGAQD IQDKFSSILS

       730        740        750        760
RGQEAYERLL WNGRYYNYDS SSRPQSRSVM SDQCAGQWFL

       770        780        790        800
KACGLGEGDT EVFPTQHVVR ALQTIFELNV QAFAGGAMGA

       810        820        830        840
VNGMQPHGVP DKSSVQSDEV WVGVVYGLAA TMIQEGLTWE

       850        860        870        880
GFQTAEGCYR TVWERLGLAF QTPEAYCQQR VFRSLAYMRP

       890        900        910        920
LSIWAMQLAL QQQQHKKASW PKVKQGTGLR TGPMFGPKEA MANLSPE
```

In alternative embodiments, the human GBA2 may have the nucleic acid sequence of a nucleic acid molecule encoding the sequence set forth in SEQ ID NO: 1.

In some embodiments, one or more of the compounds according to the invention may inhibit the activity of a GBA2, for example, the ability to inhibit the cleavage of glucose from glucosylceramide or the ability to inhibit the cleavage of glucose from a suitable substrate molecule such as, for example, 4-methylumbelliferone-β-D glucopyranoside. By "inhibit," "inhibition" or "inhibiting" means a decrease in the activity of a GBA2 by any value between about 10% and about 90%, or of any value between about 30% and about 60%, or over about 100%, or a decrease by about 1-fold, 2-fold, 5-fold, 10-fold or more, in comparison to a reference sample or compound, or in comparison to a wild-type GBA2. It is to be understood that the inhibiting does not require full inhibition. In some embodiments, the inhibition may be transient, for example, for a period of 5 min-60 min, 1 h-5 h, 1 h-12 h, 1 h-24 h, 24 h-48 h, 1 day-2 days, 1 day-5 days, 1 day-7 days, 1 day-14 days, 1 day-28 days, or any specific time within any of these ranges, such as 5 min, 10 min, 15 min, 20 min, 25 min, 30 min, 60 min, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 1.5 days, 2 days, 2.5 days, 3 days, 3.5 days, 4 days, 4.5 days, 5 days, 6 days, 7 days, 8 days, 9 days, 10 days, 11 days, 12 days, 13 days, or 14 days. In some embodiments, the inhibition may be localized. For example, one or more of the compounds according to the invention may inhibit a GBA2 within a specific cellular compartment, such as the endoplasmic reticulum (ER) or Golgi apparatus (Golgi); or one or more of the compounds according to the invention may inhibit a GBA2 within a specific tissue type, such as brain or liver.

In some embodiments, one or more of the compounds according to the invention may specifically bind a GBA2. In alternative embodiments, one or more of the compounds according to the invention may specifically bind the active site of a GBA2. In some embodiments, one or more of the compounds according to the invention that specifically bind the active site of a GBA2 may also inhibit the activity of a GBA2. In alternative embodiments, one or more of the compounds according to the invention may specifically bind the human non-lysosomal glucosylceramidase (GBA2) over the human lysosomal glucosylceramidase (GCase) and/or the human cytosolic glucosylceramidase (GBA3). In alternative embodiments, one or more of the compounds according to the invention may specifically bind the human non-lysosomal glucosylceramidase (GBA2) over the human glucosylceramide synthase (GCS). In alternative embodiments, one or more of the compounds according to the invention may specifically bind the human non-lysosomal glucosylceramidase (GBA2) over an intestinal alpha-glucosidase, where the intestinal alpha-glucosidase may be a sucrase-isomaltase or a maltase-glucoamylase. By "specifically binds" is meant a compound that binds a GBA2 but does not substantially bind other molecules in a sample, such as a lactase, a sucrase, a maltase, an isomaltase, a sucrase-isomaltase, a glucoamylase, a maltase-glucoamylase, a glucosylceramide synthase, an alpha-glucosidase II, an ER alpha-glucosidase, an intestinal alpha-glucosidase, a glycogen phosphorylase, an acid alpha-glucosidase, a beta-hexosaminidase, an O-GlcNAcase, a GCase, or a GBA3. By "not substantially bind" is meant a binding specificity in the range of about 5-fold to about 100,000-fold, or about 10-fold to about 100,000-fold, or in the range of about 100-fold to about 100,000-fold, or in the range of about 1000-fold to about 100,000-fold, or at least about 5-fold, 10-fold, 20-fold, 50-fold, 100-fold, 200-fold, 500-fold, 1000-fold, 1500-fold, 2000-fold, 2500-fold, 3000-fold, 3500-fold, 4000-fold, 4500-fold, 5000-fold, 6000-fold, 7000-fold, 10,000-fold, 25,000-fold, 50,000-fold, 75,000-fold, or any value within or about the described range, where "binding specificity" means the ratio of the respective binding constants, that is, $Ki_{(other\ molecule)}/K_{(GBA2)}$, or the ratio of the respective $IC_{50}$ values, that is $IC_{50(other\ molecule)}/IC_{50(GBA2)}$. Examples of compounds that exhibit enhanced binding specificity include, without limitation, the compounds of Examples 7, 9, 11, 12, 13, 20, 24, 45, 49, 51, 52, 53, 54, 55, 56, 57, 58, 59, 60, 70, 71, 73, 114, 115, 116, 117, 118, 119, 120, 129, 131, 136, 137, 138, 139, 140, 141, 142, 147, 151, or 152. In some embodiments, one or more compounds according to the invention may exhibit enhanced binding specificity or enhanced selectivity compared to a suitable reference compound such as, for example, N-butyldeoxynojirimycin (NB-DNJ, miglustat) or N-(5-adamantane-1-yl-methoxy)pentyl)-deoxynojirimycin (AMP-DNM, Genz-529648). In some embodiments, "enhanced binding specificity" or "enhanced selectivity" means an increase in measured binding specificity (as defined above) by any value between about 10% and about 100%, or of any integer value between about 10% and about 100%, for example, about 10%, 20%, 30%, 40%, 50%, 60%, 70%, 80%, 90%, 100%, or over 100%, or an increase by about 1-fold to about 100,000-fold, or about 5-fold to about 100,000-fold, or about 10-fold to about 100,000-fold, or in the range of about 100-fold to about 100,000-fold, or in the range of about 1000-fold to about 100,000-fold, or at least about 1-fold, 2-fold, 3-fold, 4-fold, 5-fold, 10-fold, 20-fold, 30-fold, 40-fold, 50-fold, 100-fold, 150-fold, 200-fold, 250-fold, 300-fold, 350-fold, 400-fold, 450-fold, 500-fold, 1000-fold, 1500-fold, 2000-fold, 2500-fold, 3000-fold, 3500-fold, 4000-fold, 4500-fold, 5000-fold, 6000-fold, 7000-fold, 10,000-fold, 25,000-fold, 50,000-fold, 75,000-fold, 100,000-fold, or any value within or about the described range, or more, as compared to a suitable reference compound.

In some embodiments, one or more of the compounds of the present invention may inhibit the cleavage of glucose from glucosylceramide by a GBA2. In some embodiments, one or more of the compounds of the present invention may inhibit aggregation of an alpha-synuclein protein and/or inhibit formation of Lewy bodies. By "inhibit," "inhibition" or "inhibiting" means a decrease by any value between about 10% and about 90%, or of any value between about 30% and about 60%, or over about 100%, or a decrease by about 1-fold, 2-fold, 5-fold, 10-fold or more, in comparison to a reference sample or compound, or in comparison to a wild-type GBA2. It is to be understood that the inhibiting does not require full inhibition. In some embodiments, the inhibition may be transient.

In some embodiments, one or more of the compounds of the present invention may decrease inflammation in the CNS. In some embodiments, one or more of the compounds of the present invention may decrease alpha-synuclein aggregation and/or Lewy body formation. By "decreasing" or "decrease" is meant a decrease by any value between about 5% and about 90%, or of any value between about 30% and about 60%, or over about 100%, or a decrease by about 1-fold, 2-fold, 5-fold, 10-fold, 15-fold, 25-fold, 50-fold, 100-fold or more, in comparison to a reference sample or compound.

In some embodiments, one or more of the compounds of the present invention may elevate glucosylceramide levels. In some embodiments, one or more of the compounds of the present invention may elevate glycosphingolipid levels. In some embodiments, one or more of the compounds of the present invention may elevate GM1 ganglioside levels. By "elevating" or "enhancing" or "increasing" is meant an increase by any value between about 5% and about 90%, or of any value between about 30% and about 60%, or over about 100%, or an increase by about 1-fold, 2-fold, 5-fold, 10-fold, 15-fold, 25-fold, 50-fold, 100-fold, or more, in comparison to a reference sample. In some embodiments, one or more of the compounds according to the invention may elevate glucosylceramide levels and/or glycosphingolipid levels and/or GM1 ganglioside levels, in brain.

In some embodiments, one or more of the compounds of the present invention may elevate GCase activity levels, and/or GCase protein levels, in vivo and may be effective in treating conditions which require or respond to enhancement of GCase activity. In some embodiments, one or more of the compounds of the present invention may elevate GCase activity levels, and/or GCase protein levels, in vivo specifically via interaction with a GBA2, and may be effective in treating conditions which require or respond to enhancement of GCase activity. By "elevating" or "enhancing" or "increasing" is meant an increase by any value between about 5% and about 100%, for example, about 5%, 10%, 20%, 30%, 40%, 50%, 60%, 70%, 80%, 90%, 100%, or over 100%, or an increase by about 1-fold, 2-fold, 5-fold, 10-fold, 15-fold, 25-fold, 50-fold, 100-fold or more, in comparison to a reference sample or compound, or in comparison to a wild type or mutant GCase.

In some embodiments, one or more of the compounds according to the invention may exhibit enhanced permeability. Permeability can be assessed using a variety of standard experimental techniques, including without limitation in situ perfusion, ex vivo tissue diffusion, in vitro cell monolayers (e.g. Caco-2 cells, MDCK cells, LLC-PK1 cells), and artificial cell membranes (e.g. PAMPA assay); suitable techniques for measuring effective permeability ($P_{eff}$) or apparent permeability ($P_{app}$) are reviewed for example by Volpe in *The AAPS Journal,* 2010, 12(4), 670-678. In some embodiments, one or more of the compounds according to the invention may show enhanced permeability when tested in one or more of these assays for determining $P_{eff}$ or $P_{app}$. In some embodiments, a compound that exhibits enhanced permeability may exhibit greater oral absorption. In some embodiments, a compound that exhibits enhanced permeability may exhibit greater brain penetrance when administered in vivo. In some embodiments, a compound that exhibits enhanced permeability may achieve higher brain concentrations when administered in vivo. Examples of compounds that exhibit higher brain concentrations when administered in vivo include, without limitation, the compounds of Examples 7, 12, 45, 49, 70, and 85. In some embodiments, a compound that exhibits enhanced permeability may exhibit a higher brain/plasma concentration ratio when administered in vivo. In some embodiments, "enhanced permeability" means an increase in measured $P_{eff}$ or $P_{app}$ by any value between about 10% and about 100%, or of any integer value between about 10% and about 100%, for example, about 10%, 20%, 30%, 40%, 50%, 60%, 70%, 80%, 90%, 100%, or over 100%, or an increase by about 1-fold, 2-fold, or 3-fold, or more, as compared to a suitable reference compound such as, for example, N-butyldeoxynojirimycin (NB-DNJ, miglustat) or N-(5-adamantane-1-yl-methoxy)pentyl)-deoxynojirimycin (AMP-DNM, Genz-529648). In some embodiments, "enhanced permeability" means a measurable $P_{app}$ value (i.e. a value greater than zero) in a suitable assay to measure $P_{app}$ using in vitro cell monolayers. In some embodiments, "enhanced permeability" means a $P_{app}$ value greater than $2\times10^{-6}$ cm/s in a suitable assay to measure $P_{app}$ using in vitro cell monolayers. In alternative embodiments, "enhanced permeability" means a $P_{app}$ value in the range $2\times10^{-6}$ cm/s to $40\times10^{-6}$ cm/s in a suitable assay to measure $P_{app}$ using in vitro cell monolayers. In some embodiments, "higher brain concentration" means an increase in measured brain concentration when the compound is administered in vivo by any value between about 10% and about 100%, or of any integer value between about 10% and about 100%, for example, about 10%, 20%, 30%, 40%, 50%, 60%, 70%, 80%, 90%, 100%, or over 100%, or an increase by about 1-fold, 2-fold, 3-fold, 4-fold, 5-fold, 10-fold, 20-fold, 30-fold, 40-fold, or 50-fold, or more, as compared to a suitable reference compound such as, for example, N-butyldeoxynojirimycin (NB-DNJ, miglustat) or N-(5-adamantane-1-yl-methoxy)pentyl)-deoxynojirimycin (AMP-DNM, Genz-529648).

A "reference compound" or "control" may be a carbohydrate mimetic iminosugar described in the literature that is a GBA2 inhibitor. Examples of reference compounds or controls that are GBA2 inhibitors include, without limitation, N-butyldeoxynojirimycin (NB-DNJ, miglustat) and N-(5-adamantane-1-yl-methoxy)pentyl)-deoxynojirimycin (AMP-DNM, Genz-529648).[24]

In some embodiments, the invention provides compounds described generally by Formula (I), including any one or more of Formula (Ia)-(In), and the salts, prodrugs, and enantiomeric forms thereof:

(I)

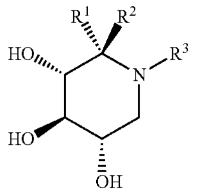

as set forth in Formula (I): $R^1$ may be H and $R^2$ may be $CH_3$, $CH_2F$, or $CHF_2$; or $R^1$ may be $CH_3$ or $CH_2F$ and $R^2$ may be H; and $R^3$ may be $(CH_2)_nR^4$, wherein n may be 1 or 2, and $R^4$ may be cyclohexyl, cyclohexylmethyl, phenylethyl, 4-phenylcyclohexyl, spiro[2.5]octan-6-yl, spiro[3.5]nonan-7-yl, spiro[4.5]decan-8-yl, (5S,8s)-3,3-dimethyl-2-oxaspiro[4.5]decan-8-yl, 1,2,3,4-tetrahydronaphthalen-2-yl, 2,3-dihydro-1H-inden-2-yl, (adamantyl)methyl, (pyridine-2-yl)methyl, (benzo[d][1,3]dioxol-5-yl)methyl, (2,3-dihydrobenzo[b][1,4]dioxin-6-yl)methyl, ([1,1'-biphenyl]-4-yl)methyl, 1-(2,2,2-trifluoroethyl)piperidin-4-yl, 1-(pyridin-3-yl)piperidin-4-yl, 1-(cyclohexylcarbamoyl)piperidin-4-yl, 1-(cyclohexylcarbamothioyl)piperidin-4-yl, 1-phenylpiperidin-4-yl, 1-cyclohexylazetidin-3-yl, 2-(thiophen-2-yl)methyl, or 2-(thiophen-3-yl)methyl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$; or $R^3$ may be phenylethyl, optionally substituted from one up to the maximum number of substituents with one or more of pyrrolidin-1-yl, piperidin-1-yl, 4-morpholino, cyclopropylmethoxy, (tetrahydrofuran-3-yl)oxy, (tetrahydro-2H-pyran-3-yl)oxy, (tetrahydro-2H-pyran-4-yl)oxy, phenoxy, (tetrahydrofuran-3-yl)methoxy, tetrahydro-2H-pyran-4-yl, 3,5-dimethylisoxazol-4-yl, 3,5-dimethyl-1H-pyrazol-4-yl, F, Cl, $C_{1-6}$ alkyl, cyclopropyl, propen-2-yl, $OCH_3$, and/or $CF_3$; or $R^3$ may be (1-formylpiperidin-4-yl)methyl, substituted on the formyl group with one of: $C_{1-6}$ alkyl, $C_{3-7}$ cycloalkyl, phenyl, thiophen-3-yl, phenylmethyl, or cyclopentylmethyl, each optionally substituted from one up to the maximum number of substituents with one or more of F, $C_{1-6}$ alkyl, $OCH_3$, and/or $CF_3$; or $R^3$ may be

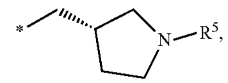 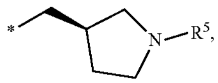

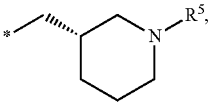 or 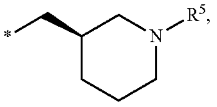

where $R^5$ may be selected from the group consisting of: phenyl, pyridin-2-yl, pyridin-3-yl, pyrimidin-5-yl, thiophen-3-yl, benzo[d]thiazol-4-yl, benzo[d]thiazol-2-yl, phenylcarbonyl, thiazol-2-yl, benzo[d]oxazol-2-yl, and benzo[d]thiazol-2-yl, each optionally substituted from one up to the maximum number of substituents with one or more of F, Cl, $C_{1-6}$ alkyl, $C_{1-6}$ alkoxyl, $OCF_3$, and/or $CF_3$.

In some embodiments, $R^1$ as set forth in Formula (I) may be H, $CH_3$, or $CH_2F$. In some embodiments, $R^1$ may be $CH_3$. In some embodiments, $R^1$ may be $CH_2F$. In some embodiments, $R^1$ may be H, provided that $R^2$ is other than H.

In some embodiments, $R^2$ as set forth in Formula (I) may be H, $CH_3$, $CH_2F$, or $CHF_2$. In some embodiments, $R^2$ may be $CH_2F$. In some embodiments, $R^2$ may be $CHF_2$. In some embodiments, $R^2$ may be $CH_3$. In some embodiments, $R^2$ may be H, provided that $R^1$ is other than H.

In some embodiments, $R^3$ as set forth in Formula (I) may be $(CH_2)_nR^4$, wherein n may be 1 or 2, and $R^4$ may be cyclohexyl, cyclohexylmethyl, phenylethyl, 4-phenylcyclohexyl, spiro[2.5]octan-6-yl, spiro[3.5]nonan-7-yl, spiro[4.5]decan-8-yl, (5S,8s)-3,3-dimethyl-2-oxaspiro[4.5]decan-8-yl, 1,2,3,4-tetrahydronaphthalen-2-yl, 2,3-dihydro-1H-inden-2-yl, (adamantyl)methyl, (pyridine-2-yl)methyl, (benzo[d][1,3]dioxol-5-yl)methyl, (2,3-dihydrobenzo[b][1,4]dioxin-6-yl)methyl, ([1,1'-biphenyl]-4-yl)methyl, 1-(2,2,2-trifluoroethyl)piperidin-4-yl, 1-(pyridin-3-yl)piperidin-4-yl, 1-(cyclohexylcarbamoyl)piperidin-4-yl, 1-(cyclohexylcarbamothioyl)piperidin-4-yl, 1-phenylpiperidin-4-yl, 1-cyclohexylazetidin-3-yl, 2-(thiophen-2-yl)methyl, or 2-(thiophen-3-yl)methyl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$; or $R^3$ may be phenylethyl, optionally substituted from one up to the maximum number of substituents with one or more of pyrrolidin-1-yl, piperidin-1-yl, 4-morpholino, cyclopropylmethoxy, (tetrahydrofuran-3-yl)oxy, (tetrahydro-2H-pyran-3-yl)oxy, (tetrahydro-2H-pyran-4-yl)oxy, phenoxy, (tetrahydrofuran-3-yl)methoxy, tetrahydro-2H-pyran-4-yl, 3,5-dimethylisoxazol-4-yl, 3,5-dimethyl-1H-pyrazol-4-yl, F, Cl, $C_{1-6}$ alkyl, cyclopropyl, propen-2-yl, $OCH_3$, and/or $CF_3$; or $R^3$ may be (1-formylpiperidin-4-yl)methyl, substituted on the formyl group with one of: $C_{1-6}$ alkyl, $C_{3-7}$ cycloalkyl, phenyl, thiophen-3-yl, phenylmethyl, or cyclopentylmethyl, each optionally substituted from one up to the maximum number of substituents with one or more of F, $C_{1-6}$ alkyl, $OCH_3$, and/or $CF_3$;

or $R^3$ may be

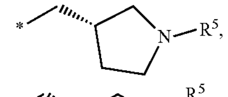 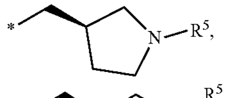

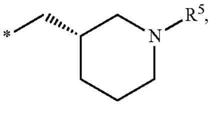 or 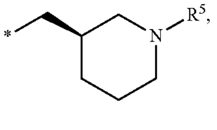

where $R^5$ may be selected from the group consisting of: phenyl, pyridin-2-yl, pyridin-3-yl, pyrimidin-5-yl, thiophen-3-yl, benzo[d]thiazol-4-yl, benzo[d]thiazol-2-yl, phenylcarbonyl, thiazol-2-yl, benzo[d]oxazol-2-yl, and benzo[d]thiazol-2-yl, each optionally substituted from one up to the maximum number of substituents with one or more of F, Cl, $C_{1-6}$ alkyl, $C_{1-6}$ alkoxyl, $OCF_3$, and/or $CF_3$.

In some embodiments, $R^3$ may be $(CH_2)_nR^4$, wherein n may be 1 or 2, and $R^4$ may be cyclohexyl, cyclohexylmethyl, phenylethyl, 4-phenylcyclohexyl, spiro[2.5]octan-6-yl, spiro[3.5]nonan-7-yl, spiro[4.5]decan-8-yl, (5S,8s)-3,3-dimethyl-2-oxaspiro[4.5]decan-8-yl, 1,2,3,4-tetrahydronaphthalen-2-yl, 2,3-dihydro-1H-inden-2-yl, (adamantyl)methyl, (pyridine-2-yl)methyl, (benzo[d][1,3]dioxol-5-yl)methyl, (2,3-dihydrobenzo[b][1,4]dioxin-6-yl)methyl, ([1,1'-biphenyl]-4-yl)methyl, 1-(2,2,2-trifluoroethyl)piperidin-4-yl, 1-(pyridin-3-yl)piperidin-4-yl, 1-(cyclohexylcarbamoyl)piperidin-4-yl, 1-(cyclohexylcarbamothioyl)piperidin-4-yl, 1-phenylpiperidin-4-yl, 1-cyclohexylazetidin-3-yl, 2-(thiophen-2-yl)methyl, or 2-(thiophen-3-yl)methyl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$.

In some embodiments, $R^3$ may be phenylethyl, optionally substituted from one up to the maximum number of substituents with one or more of pyrrolidin-1-yl, piperidin-1-yl, 4-morpholino, cyclopropylmethoxy, (tetrahydrofuran-3-yl)oxy, (tetrahydro-2H-pyran-3-yl)oxy, (tetrahydro-2H-pyran-4-yl)oxy, phenoxy, (tetrahydrofuran-3-yl)methoxy, tetrahydro-2H-pyran-4-yl, 3,5-dimethylisoxazol-4-yl, 3,5-dimethyl-1H-pyrazol-4-yl, F, Cl, $C_{1-6}$ alkyl, cyclopropyl, propen-2-yl, $OCH_3$, and/or $CF_3$.

In some embodiments, $R^3$ may be (1-formylpiperidin-4-yl)methyl, substituted on the formyl group with one of: $C_{1-6}$ alkyl, $C_{3-7}$ cycloalkyl, phenyl, thiophen-3-yl, phenylmethyl, or cyclopentylmethyl, each optionally substituted from one up to the maximum number of substituents with one or more of F, $C_{1-6}$ alkyl, $OCH_3$, and/or $CF_3$.

In some embodiments, $R^3$ may be may be

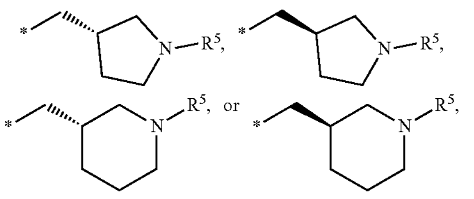

where $R^5$ may be selected from the group consisting of: phenyl, pyridin-2-yl, pyridin-3-yl, pyrimidin-5-yl, thiophen-3-yl, benzo[d]thiazol-4-yl, benzo[d]thiazol-2-yl, phenylcarbonyl, thiazol-2-yl, benzo[d]oxazol-2-yl, and benzo[d]thiazol-2-yl, each optionally substituted from one up to the maximum number of substituents with one or more of F, Cl, $C_{1-6}$ alkyl, $C_{1-6}$ alkoxyl, $OCF_3$, and/or $CF_3$. In some embodiments, $R^3$ may be $(CH_2)_nR^4$, where n may be 1, and $R^4$ may be cyclohexyl or 1-phenylpiperidin-4-yl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$.

In some embodiments, $R^3$ may be cyclohexylmethyl, (4,4-dimethylcyclohexyl)methyl, (4,4-difluorocyclohexyl)methyl, (4,4-dichlorocyclohexyl)methyl, (4-ethylcyclohexyl)methyl, ((1s,4S)-4-vinylcyclohexyl)methyl, ((1s,4S)-4-isopropylcyclohexyl)methyl, ((1r,4R)-4-isopropylcyclohexyl)methyl, 4-(tert-butyl)cyclohexyl)methyl, ((1s,4S)-4-(tert-butyl)cyclohexyl)methyl, ((1r,4R)-4-(tert-butyl)cyclohexyl)methyl, ((1s,4S)-4-(trifluoromethyl)cyclohexyl)methyl, ((1r,4R)-4-(trifluoromethyl)cyclohexyl)methyl, ((1s,4S)-4-(2-fluoropropan-2-yl)cyclohexyl)methyl, ((1r,4R)-4-(2-fluoropropan-2-yl)cyclohexyl)methyl, ((trans)-3-(trifluoromethyl)cyclohexyl)methyl, ((cis)-3-(trifluoromethyl)cyclohexyl)methyl, ((1s,4S)-4-methoxycyclohexyl)methyl, ((1r,4R)-4-methoxycyclohexyl)methyl, (4-(methoxymethyl)cyclohexyl)methyl, ((1s,4S)-4-cyclopropylcyclohexyl)methyl, ((1r,4R)-4-cyclopropylcyclohexyl)methyl, (4-phenylcyclohexyl)methyl, (spiro[2.5]octan-6-yl)methyl, (spiro[3.5]nonan-7-yl)methyl, (spiro[4.5]decan-8-yl)methyl, 2-cyclohexylethyl, 2-(4,4-difluorocyclohexyl)ethyl, 2-((1s,4S)-4-(trifluoromethyl)cyclohexyl)ethyl, 2-((1r,4R)-4-(trifluoromethyl)cyclohexyl)ethyl, 2-(adamantan-1-yl)ethyl, 3-cyclohexylpropyl, phenethyl, 2-methylphenethyl, 2-methoxyphenethyl, 2-fluorophenethyl, 2-chlorophenethyl, 2,3-difluorophenethyl, 2,4-difluorophenethyl, 2,5-difluorophenethyl, 3,4-difluorophenethyl, 2-fluoro-4-methoxyphenethyl, 3-chloro-2-fluorophenethyl, 4-chloro-2-fluorophenethyl, 5-chloro-2-fluorophenethyl, 2,6-difluorophenethyl, 3-chloro-2,6-difluorophenethyl, 2,6-difluoro-4-(prop-1-en-2-yl)phenethyl, 2,6-difluoro-4-isopropylphenethyl, 2,6-difluoro-3-isopropylphenethyl, 4-cyclopropyl-2,6-difluorophenethyl, 2,6-difluoro-4-(trifluoromethyl)phenethyl, 2,6-difluoro-4-(pyrrolidin-1-yl)phenethyl, 2,6-difluoro-4-(piperidin-1-yl)phenethyl, 2,6-difluoro-4-morpholinophenethyl, 4-butoxy-2,6-difluorophenethyl, 4-(cyclopropylmethoxy)-2,6-difluorophenethyl, 4-((tetrahydrofuran-3-yl)oxy)phenethyl, 4-((tetrahydro-2H-pyran-3-yl)oxy)phenethyl, 4-((tetrahydro-2H-pyran-4-yl)oxy)phenethyl, 4-phenoxyphenethyl, 4-((tetrahydrofuran-3-yl)methoxy)phenethyl, (R)-2-phenylpropyl, (S)-2-phenylpropyl, 2-([1,1'-biphenyl]-4-yl)ethyl, 2-(3,5-difluoro-[1,1'-biphenyl]-4-yl)ethyl, 2-(benzo[d][1,3]dioxol-5-yl)ethyl, 2-(6-fluorobenzo[d][1,3]dioxol-5-yl)ethyl, 2-(2,2-difluorobenzo[d][1,3]dioxol-5-yl)ethyl, 2-(2,3-dihydrobenzo[b][1,4]dioxin-6-yl)ethyl, 2-(thiophen-2-yl)ethyl, 2-(thiophen-3-yl)ethyl, 2-(pyridine-2-yl)ethyl, 3-phenylpropyl, 3-(2-fluorophenyl)propyl, 3-(4-fluorophenyl)propyl, 3-(thiophen-2-yl)propyl, 3-(thiophen-3-yl)propyl, (1-phenylpiperidin-4-yl)methyl, (1-(2-fluorophenyl)piperidin-4-yl)methyl, (1-(3-fluorophenyl)piperidin-4-yl)methyl, (1-(4-fluorophenyl)piperidin-4-yl)methyl, (1-(4-(trifluoromethyl)phenyl)piperidin-4-yl)methyl, (4-methyl-1-phenylpiperidin-4-yl)methyl, (4-fluoro-1-phenylpiperidin-4-yl)methyl, 2-(1-phenylpiperidin-4-yl)ethyl, (1-(2,2,2-trifluoroethyl)piperidin-4-yl)methyl, (1-isobutyrylpiperidin-4-yl)methyl, (1-pivaloylpiperidin-4-yl)methyl, (1-butyrylpiperidin-4-yl)methyl, (1-(3-methylbutanoyl)piperidin-4-yl)methyl, (1-(3,3-dimethylbutanoyl)piperidin-4-yl)methyl, (1-(2-cyclopentylacetyl)piperidin-4-yl)methyl, (1-(cyclopropanecarbonyl)piperidin-4-yl)methyl, (1-(cyclobutanecarbonyl)piperidin-4-yl)methyl, (1-(cyclopentanecarbonyl)piperidin-4-yl)methyl, (1-(cyclohexanecarbonyl)piperidin-4-yl)methyl, (1-((1s,4s)-4-(tert-butyl)cyclohexanecarbonyl)piperidin-4-yl)methyl, (1-((1r,4r)-4-(tert-butyl)cyclohexanecarbonyl)piperidin-4-yl)methyl, (1-(4-methoxycyclohexanecarbonyl)piperidin-4-yl)methyl, (1-(4-(trifluoromethyl)cyclohexanecarbonyl)piperidin-4-yl)methyl, (1-benzoylpiperidin-4-yl)methyl, (1-(3-(trifluoromethyl)benzoyl)piperidin-4-yl)methyl, (1-(2- phenylacetyl)piperidin-4-yl)methyl, (1-(thiophene-3-carbonyl)piperidin-4-yl)methyl, ((5S,8s)-3,3-dimethyl-2-oxaspiro[4.5]decan-8-yl)methyl, (1,2,3,4-tetrahydronaphthalen-2-yl)methyl, (2,3-dihydro-1H-inden-2-yl)methyl, 2,6-difluoro-4-(tetrahydro-2H-pyran-4-yl)phenethyl, (1-(pyridin-3-yl)piperidin-4-yl)methyl, (1-(cyclohexylcarbamoyl)piperidin-4-yl)methyl, (1-(cyclohexylcarbamothioyl)piperidin-4-yl)methyl, (1-((1S,2R)-2-(trifluoromethyl)cyclohexyl)azetidin-3-yl)methyl, ((R)-1-phenylpyrrolidin-3-yl)methyl, ((R)-1-(o-tolyl)pyrrolidin-3-yl)methyl, ((R)-1-(2-(trifluoromethyl)phenyl)pyrrolidin-3-yl)methyl, ((S)-1-(2-(trifluoromethyl)phenyl)pyrrolidin-3-yl)methyl, (R)-1-(2-fluorophenyl)pyrrolidin-3-yl)methyl, (R)-1-(3-fluorophenyl)pyrrolidin-3-yl)methyl, ((R)-1-(2-(trifluoromethoxy)phenyl)pyrrolidin-3-yl)methyl, ((R)-1-(6-(trifluoromethyl)pyridin-2-yl)pyrrolidin-3-yl)methyl, ((R)-1-(3-(trifluoromethyl)pyridin-2-yl)pyrrolidin-3-yl)methyl, ((R)-1-(4-(trifluoromethyl)pyridin-2-yl)pyrrolidin-3-yl)methyl, ((R)-1-(pyridin-3-yl)pyrrolidin-3-yl)methyl, ((R)-1-(4-methylpyridin-3-yl)pyrrolidin-3-yl)methyl, ((R)-1-(4-(trifluoromethyl)pyridin-3-yl)pyrrolidin-3-yl)methyl, ((R)-1-(5-(trifluoromethyl)pyridin-3-yl)pyrrolidin-3-yl)methyl, ((R)-1-(2-(trifluoromethyl)pyridin-3-yl)pyrrolidin-3-yl)methyl, ((R)-1-(4-(trifluoromethyl)pyrimidin-5-yl)pyrrolidin-3-yl)methyl, ((R)-1-(thiophen-3-yl)pyrrolidin-3-yl)methyl, ((R)-1-(benzo[d]thiazol-4-yl)pyrrolidin-3-yl)methyl, (S)-(1-(4-(trifluoromethyl)benzoyl)pyrrolidin-3-yl)methyl, ((R)-1-(o-tolyl)piperidin-3-yl)methyl, ((R)-1-(2-fluorophenyl)piperidin-3-yl)methyl, ((R)-1-(3-(trifluoromethyl)pyridin-2-yl)piperidin-3-yl)methyl, ((R)-1-(6-(trifluoromethyl)pyridin-2-yl)piperidin-3-yl)methyl, ((R)-1-(4-(trifluoromethyl)pyridin-3-yl)piperidin-3-yl)methyl, 3-fluorophenethyl, 4-fluorophenethyl, 3,4-dichlorophenethyl, 3-(trifluoromethyl)phenethyl, 4-(trifluoromethyl)phenethyl, ((R)-1-(benzo[d]thiazol-2-yl)pyrrolidin-3-yl)methyl, ((R)-1-(2-(trifluoromethyl)pyridin-3-yl)piperidin-3-yl)methyl, 4-(3,5-dimethylisoxazol-4-yl)-2,6-difluorophenethyl, 4-(3,5-dimethyl-1H-pyrazol-4-yl)-2,6-difluorophenethyl, ((R)-1-(4-(trifluoromethyl)thiazol-2-yl)pyrrolidin-3-yl)methyl, ((R)-1-(benzo[d]oxazol-2-yl)pyrrolidin-3-yl)methyl, ((R)-1-(5-isopropylthiazol-2-yl)piperidin-3-yl)methyl, ((R)-1-(4-(trifluoromethyl)thiazol-2-yl)piperidin-3-yl)methyl, ((R)-1-(benzo[d]thiazol-2-yl)piperidin-3-yl)methyl, ((R)-1-(benzo[d]thiazol-4-yl)piperidin-3-yl)methyl, ((S)-1-(3-(trifluoromethyl)pyridin-2-yl)pyrrolidin-3-yl)methyl, ((S)-1-(4-(trifluoromethyl)pyridin-3-yl)pyrrolidin-3-yl)methyl, ((S)-1-(4-(trifluoromethyl)pyrimidin-5-yl)pyrrolidin-3-yl)methyl, ((S)-1-(4-(trifluoromethyl)thiazol-2-yl)pyrrolidin-3-yl)methyl, ((S)-1-(3-(trifluoromethyl)pyridin-2-yl)piperidin-3-yl)methyl, ((S)-1-(4-(trifluoromethyl)pyridin-3-yl)piperidin-3-yl)methyl, ((S)-1-(6-(trifluoromethyl)pyridin-2-yl)piperidin-3-yl)methyl, or ((S)-1-(4-(trifluoromethyl)thiazol-2-yl)piperidin-3-yl)methyl.

In some embodiments, $R^1$ may be H and $R^2$ may be $CH_3$. In some embodiments, $R^1$ may be H and $R^2$ may be $CH_2F$. In some embodiments, $R^1$ may be H and $R^2$ may be $CHF_2$. In some embodiments, $R^1$ may be $CH_3$ and $R^2$ may be H. In some embodiments, $R^1$ may be $CH_2F$ and $R^2$ may be H.

In some embodiments, $R^1$ may be H; $R^2$ may be $CH_3$; and $R^3$ may be $(CH_2)_nR^4$, where n may be 1, and $R^4$ may be cyclohexyl or 1-phenylpiperidin-4-yl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$.

In some embodiments, $R^1$ may be H; $R^2$ may be $CH_3$; and $R^3$ may be (4-phenylcyclohexyl)methyl, (4-(2-fluoropropan-2-yl)cyclohexyl)methyl, (4-(methoxymethyl)cyclohexyl)methyl, (spiro[2.5]octan-6-yl)methyl, (spiro[3.5]nonan-7-yl)methyl, (spiro[4.5]decan-8-yl)methyl, (2-adamantyl)ethyl, 2-(benzo[d][1,3]dioxol-5-yl)ethyl, 2-(2,3-dihydrobenzo[b][1,4]dioxin-6-yl)ethyl, 2-([1,1'-biphenyl]-4-yl)ethyl, 2-(pyridine-2-yl)ethyl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$.

In some embodiments, $R^1$ may be H; $R^2$ may be $CH_3$; and $R^3$ may be phenylethyl, optionally substituted from one up to the maximum number of substituents with one or more of pyrrolidin-1-yl, piperidin-1-yl, 4-morpholino, cyclopropylmethoxy, (tetrahydrofuran-3-yl)oxy, (tetrahydro-2H-pyran-3-yl)oxy, (tetrahydro-2H-pyran-4-yl)oxy, phenoxy, (tetrahydrofuran-3-yl)methoxy, tetrahydro-2H-pyran-4-yl, 3,5-dimethylisoxazol-4-yl, 3,5-dimethyl-1H-pyrazol-4-yl, F, Cl, $C_{1-6}$ alkyl, cyclopropyl, propen-2-yl, $OCH_3$, and/or $CF_3$;

In some embodiments, $R^1$ may be H; $R^2$ may be $CH_3$; and $R^3$ may be (1-formylpiperidin-4-yl)methyl, substituted on the formyl group with one of: $C_{1-6}$ alkyl, $C_{3-7}$ cycloalkyl, phenyl, thiophen-3-yl, phenylmethyl, or cyclopentylmethyl, each optionally substituted from one up to the maximum number of substituents with one or more of F, $C_{1-6}$ alkyl, $OCH_3$, and/or $CF_3$.

In some embodiments, $R^1$ may be H; $R^2$ may be $CH_3$; and $R^3$ may be

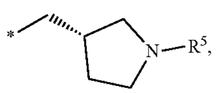 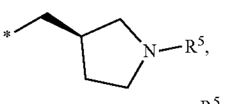

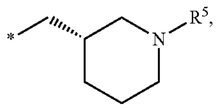 or 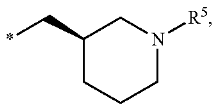

where $R^5$ may be selected from the group consisting of: phenyl, pyridin-2-yl, pyridin-3-yl, pyrimidin-5-yl, thiophen-3-yl, benzo[d]thiazol-4-yl, benzo[d]thiazol-2-yl, phenylcarbonyl, thiazol-2-yl, benzo[d]oxazol-2-yl, and benzo[d]thiazol-2-yl, each optionally substituted from one up to the maximum number of substituents with one or more of F, Cl, $C_{1-6}$ alkyl, $C_{1-6}$ alkoxyl, $OCF_3$, and/or $CF_3$.

In some embodiments, $R^1$ may be H; $R^2$ may be $CH_3$; and $R^3$ may be (4-ethylcyclohexyl)methyl, ((1s,4S)-4-isopropylcyclohexyl)methyl, ((1r,4R)-4-isopropylcyclohexyl)methyl, ((1s,4S)-4-(tert-butyl)cyclohexyl)methyl, ((1r,4R)-4-(tert-butyl)cyclohexyl)methyl, ((1s,4S)-4-(trifluoromethyl)cyclohexyl)methyl, ((1r,4R)-4-(trifluoromethyl)cyclohexyl)methyl, ((1s,4S)-4-(2-fluoropropan-2-yl)cyclohexyl)methyl, ((1r,4R)-4-(2-fluoropropan-2-yl)cyclohexyl)methyl, ((1s,4S)-4-cyclopropylcyclohexyl)methyl, ((1r,4R)-4-cyclopropylcyclohexyl)methyl, 2-((1s,4S)-4-(trifluoromethyl)cyclohexyl)ethyl, 2-((1r,4R)-4-(trifluoromethyl)cyclohexyl)ethyl, 2,5-difluorophenethyl, 3-chloro-2-fluorophenethyl, 5-chloro-2-fluorophenethyl, 2,6-difluorophenethyl, 3-chloro-2,6-difluorophenethyl, 2,6-difluoro-4-(prop-1-en-2-yl)phenethyl, 2,6-difluoro-4-isopropylphenethyl, 2,6-difluoro-3-isopropylphenethyl, 4-cyclopropyl-2,6-difluorophenethyl, 2,6-difluoro-4-(pyrrolidin-1-yl)phenethyl, 2,6-difluoro-4-(piperidin-1-yl)phenethyl, 2,6-difluoro-4-morpholinophenethyl, 4-butoxy-2,6-difluorophenethyl, 4-(cyclopropylmethoxy)-2,6-difluorophenethyl, 2-([1,1'-biphenyl]-4-yl)ethyl, 2-(3,5-difluoro-[1,1'-biphenyl]-4-yl)ethyl, 2-(benzo[d][1,3]dioxol-5-yl)ethyl, 2-(6-fluorobenzo[d][1,3]dioxol-5-yl)ethyl, 2-(2,2-difluorobenzo[d][1,3]dioxol-5-yl)ethyl, 2-(2,3-dihydrobenzo[b][1,4]dioxin-6-yl)ethyl, (1-(2-fluorophenyl)piperidin-4-yl)methyl, (1-(3-fluorophenyl)piperidin-4-yl)methyl, (1-(4-fluorophenyl)piperidin-4-yl)methyl, (1-(4-(trifluoromethyl)phenyl)piperidin-4-yl)methyl, (2,3-dihydro-1H-inden-2-yl)methyl, (1,2,3,4-tetrahydronaphthalen-2-yl)methyl, ((R)-1-(2-(trifluoromethyl)phenyl)pyrrolidin-3-yl)methyl, ((S)-1-(2-(trifluoromethyl)phenyl)pyrrolidin-3-yl)methyl, ((R)-1-phenylpyrrolidin-3-yl)methyl, ((R)-1-(thiophen-3-yl)pyrrolidin-3-yl)methyl, ((R)-1-(2-(trifluoromethyl)pyridin-3-yl)pyrrolidin-3-yl)methyl, ((R)-1-(4-(trifluoromethyl)pyridin-3-yl)pyrrolidin-3-yl)methyl, ((R)-1-(2-fluorophenyl)piperidin-3-yl)methyl, ((R)-1-(2-fluorophenyl)pyrrolidin-3-yl)methyl, ((R)-1-(3-fluorophenyl)pyrrolidin-3-yl)methyl, ((R)-1-(o-tolyl)pyrrolidin-3-yl)methyl, ((R)-1-(2-(trifluoromethoxy)phenyl)pyrrolidin-3-yl)methyl, ((R)-1-(5-(trifluoromethyl)pyridin-3-yl)pyrrolidin-3-yl)methyl, ((R)-1-(4-(trifluoromethyl)pyridin-2-yl)pyrrolidin-3-yl)methyl, ((R)-1-(4-(trifluoromethyl)pyrimidin-5-yl)pyrrolidin-3-yl)methyl, ((R)-1-(3-(trifluoromethyl)pyridin-2-yl)pyrrolidin-3-yl)methyl, ((R)-1-(6-(trifluoromethyl)pyridin-2-yl)pyrrolidin-3-yl)methyl, ((R)-1-(o-tolyl)piperidin-3-yl)methyl, ((R)-1-(benzo[d]thiazol-4-yl)pyrrolidin-3-yl)methyl, ((R)-1-(4-(trifluoromethyl)pyridin-3-yl)piperidin-3-yl)methyl, ((R)-1-(6-(trifluoromethyl)pyridin-2-yl)piperidin-3-yl)methyl, ((R)-1-(3-(trifluoromethyl)pyridin-2-yl)piperidin-3-yl)methyl, 2,6-difluoro-4-(tetrahydro-2H-pyran-4-yl)phenethyl, ((S)-1-(3-(trifluoromethyl)pyridin-2-yl)pyrrolidin-3-yl)methyl, ((S)-1-(4-(trifluoromethyl)pyridin-3-yl)pyrrolidin-3-yl)methyl, ((S)-1-(4-(trifluoromethyl)pyrimidin-5-yl)pyrrolidin-3-yl)methyl, ((S)-1-(4-(trifluoromethyl)thiazol-2-yl)pyrrolidin-3-yl)methyl, ((S)-1-(3-(trifluoromethyl)pyridin-2-yl)piperidin-3-yl)methyl, ((S)-1-(4-(trifluoromethyl)pyridin-3-yl)piperidin-3-yl)methyl, ((S)-1-(6-(trifluoromethyl)pyridin-2-yl)piperidin-3-yl)methyl, or ((S)-1-(4-(trifluoromethyl)thiazol-2-yl)piperidin-3-yl)methyl.

In specific embodiments of the invention, compounds according to Formula (I) include the compounds described in Table 1.

TABLE 1

| Example | Name | Structure |
|---|---|---|
| 1 | (2R,3R,4R,5S)-1-(cyclohexylmethyl)-2-methylpiperidine-3,4,5-triol | 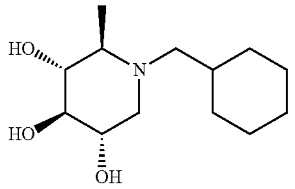 [SMILES: C[C@@H]1[C@@H](O)[C@H](O)[C@@H](O)CN1CC1CCCCC1] |
| 2 | (2R,3R,4R,5S)-1-((4,4-dimethylcyclohexyl)methyl)-2-methylpiperidine-3,4,5-triol | 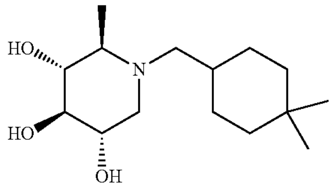 [SMILES: C[C@@H]1[C@@H](O)[C@H](O)[C@@H](O)CN1CC1CCC(C)(C)CC1] |
| 3 | (2R,3R,4R,5S)-1-((4,4-difluorocyclohexyl)methyl)-2-methylpiperidine-3,4,5-triol | 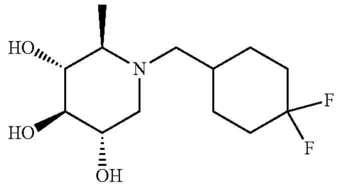 [SMILES: C[C@@H]1[C@@H](O)[C@H](O)[C@@H](O)CN1CC1CCC(F)(F)CC1] |
| 4 | (2R,3R,4R,5S)-1-((4,4-dichlorocyclohexyl)methyl)-2-methylpiperidine-3,4,5-triol | 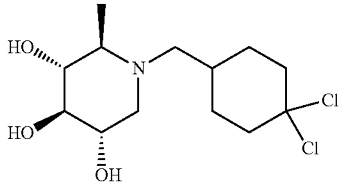 [SMILES: C[C@@H]1[C@@H](O)[C@H](O)[C@@H](O)CN1CC1CCC(Cl)(Cl)CC1] |
| 5 | (2R,3R,4R,5S)-1-((4-ethylcyclohexyl)methyl)-2-methylpiperidine-3,4,5-triol | 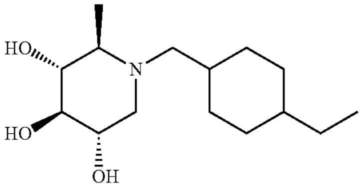 [SMILES: CCC1CCC(CN2C[C@H](O)[C@@H](O)[C@H](O)[C@H]2C)CC1] |

TABLE 1-continued

| Example | Name | Structure |
|---|---|---|
| 6 | (2R,3R,4R,5S)-2-methyl-1-(((1s,4S)-4-vinylcyclohexyl)methyl)piperidine-3,4,5-triol | 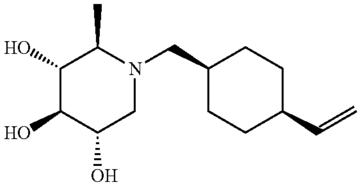 [SMILES: C=C[C@H]1CC[C@@H](CN2C[C@H](O)[C@@H](O)[C@H](O)[C@H]2C)CC1] |
| 7 | (2R,3R,4R,5S)-1-(((1s,4S)-4-isopropylcyclohexyl)methyl)-2-methylpiperidine-3,4,5-triol | 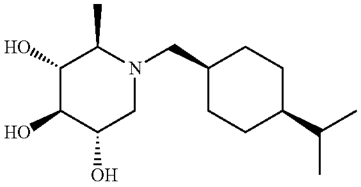 [SMILES: CC(C)[C@H]1CC[C@@H](CN2C[C@H](O)[C@@H](O)[C@H](O)[C@H]2C)CC1] |
| 8 | (2R,3R,4R,5S)-1-(((1r,4R)-4-isopropylcyclohexyl)methyl)-2-methylpiperidine-3,4,5-triol | 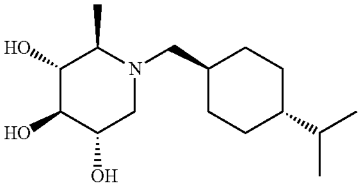 [SMILES: CC(C)[C@H]1CC[C@H](CN2C[C@H](O)[C@@H](O)[C@H](O)[C@H]2C)CC1] |
| 9 | (2R,3R,4R,5S)-1-(((1s,4S)-4-(tert-butyl)cyclohexyl)methyl)-2-methylpiperidine-3,4,5-triol | 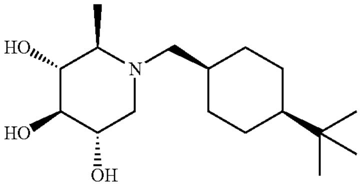 [SMILES: C[C@@H]1[C@@H](O)[C@H](O)[C@@H](O)CN1C[C@H]1CC[C@@H](C(C)(C)C)CC1] |
| 10 | (2R,3R,4R,5S)-1-(((1r,4R)-4-(tert-butyl)cyclohexyl)methyl)-2-methylpiperidine-3,4,5-triol | 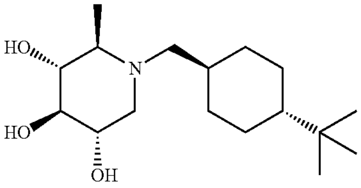 [SMILES: C[C@@H]1[C@@H](O)[C@H](O)[C@@H](O)CN1C[C@H]1CC[C@H](C(C)(C)C)CC1] |
| 11 | (2R,3R,4R,5S)-2-methyl-1-(((1s,4S)-4-(trifluoromethyl)cyclohexyl)methyl) piperidine-3,4,5-triol | 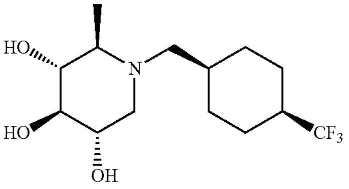 [SMILES: C[C@@H]1[C@@H](O)[C@H](O)[C@@H](O)CN1C[C@H]1CC[C@@H](C(F)(F)F)CC1] |
| 12 | (2R,3R,4R,5S)-2-methyl-1-(((1r,4R)-4-(trifluoromethyl)cyclohexyl)methyl) piperidine-3,4,5-triol | 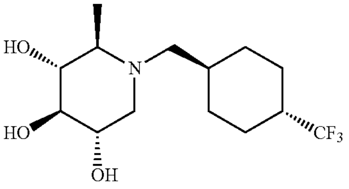 [SMILES: C[C@@H]1[C@@H](O)[C@H](O)[C@@H](O)CN1C[C@H]1CC[C@H](C(F)(F)F)CC1] |
| 13 | (2R,3R,4R,5S)-1-(((1s,4S)-4-(2-fluoropropan-2-yl)cyclohexyl)methyl)-2-methylpiperidine-3,4,5-triol | 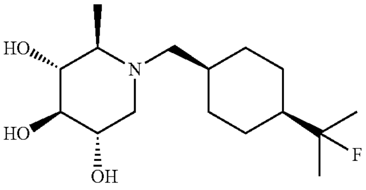 [SMILES: C[C@@H]1[C@@H](O)[C@H](O)[C@@H](O)CN1C[C@H]1CC[C@@H](C(C)(C)F)CC1] |

TABLE 1-continued

| Example | Name | Structure |
|---|---|---|
| 14 | (2R,3R,4R,5S)-1-(((1r,4R)-4-(2-fluoropropan-2-yl)cyclohexyl)methyl)-2-methylpiperidine-3,4,5-triol | 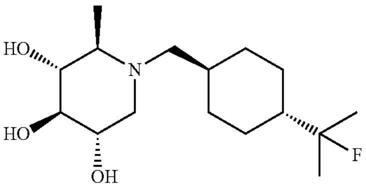 [SMILES: C[C@@H]1[C@@H](O)[C@H](O)[C@@H](O)CN1C[C@H]1CC[C@H](C(C)(C)F)CC1] |
| 15 | (2R,3R,4R,5S)-2-methyl-1-(((trans)-3-(trifluoromethyl)cyclohexyl)methyl) piperidine-3,4,5-triol | 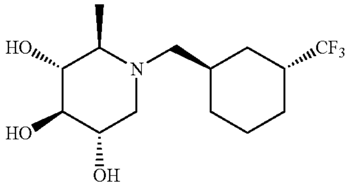 + 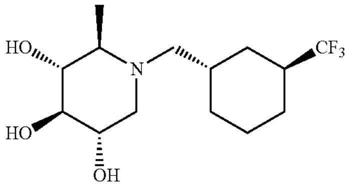 |
| 16 | (2R,3R,4R,5S)-2-methyl-1-(((cis)-3-(trifluoromethyl)cyclohexyl)methyl) piperidine-3,4,5-triol | 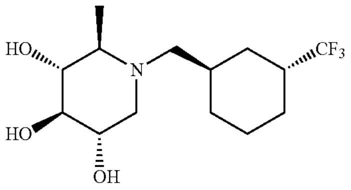 + 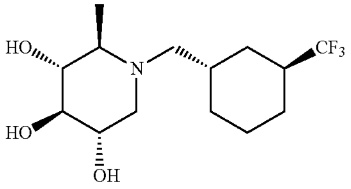 |
| 17 | (2R,3R,4R,5S)-1-(((1s,4S)-4-methoxycyclohexyl)methyl)-2-methylpiperidine-3,4,5-triol | 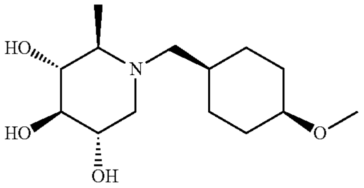 [SMILES: CO[C@H]1CC[C@@H](CN2C[C@H](O)[C@@H](O)[C@H](O)[C@H]2C)CC1] |
| 18 | (2R,3R,4R,5S)-1-(((1r,4R)-4-methoxycyclohexyl)methyl)-2-methylpiperidine-3,4,5-triol | 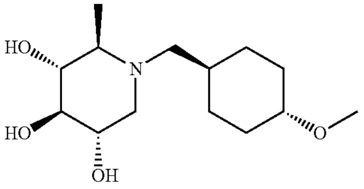 [SMILES: CO[C@H]1CC[C@H](CN2C[C@H](O)[C@@H](O)[C@H](O)[C@H]2C)CC1] |

TABLE 1-continued

| Example | Name | Structure |
|---|---|---|
| 19 | (2R,3R,4R,5S)-1-((4-(methoxymethyl)cyclohexyl)methyl)-2-methylpiperidine-3,4,5-triol | 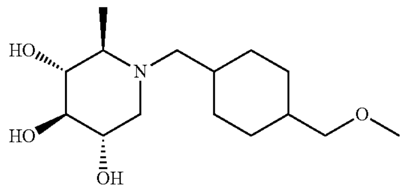 [SMILES: COCC1CCC(CN2C[C@H](O)[C@@H](O)[C@H](O)[C@H]2C)CC1] |
| 20 | (2R,3R,4R,5S)-1-(((1s,4S)-4-cyclopropylcyclohexyl)methyl)-2-methylpiperidine-3,4,5-triol | 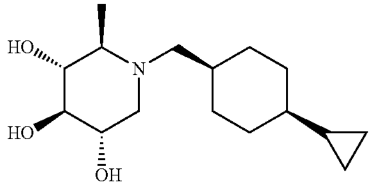 [SMILES: C[C@@H]1[C@@H](O)[C@H](O)[C@@H](O)CN1C[C@H]1CC[C@@H](C2CC2)CC1] |
| 21 | (2R,3R,4R,5S)-1-(((1r,4R)-4-cyclopropylcyclohexyl)methyl)-2-methylpiperidine-3,4,5-triol | 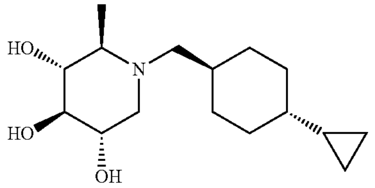 [SMILES: C[C@@H]1[C@@H](O)[C@H](O)[C@@H](O)CN1C[C@H]1CC[C@H](C2CC2)CC1] |
| 22 | (2R,3R,4R,5S)-2-methyl-1-((4-phenylcyclohexyl)methyl)piperidine-3,4,5-triol | 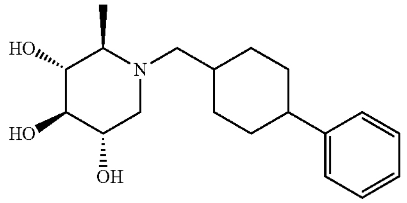 [SMILES: C[C@@H]1[C@@H](O)[C@H](O)[C@@H](O)CN1CC1CCC(c2ccccc2)CC1] |
| 23 | (2R,3R,4R,5S)-2-methyl-1-(spiro[2.5]octan-6-ylmethyl)piperidine-3,4,5-triol | 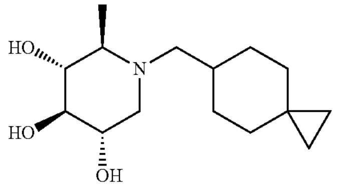 [SMILES: C[C@@H]1[C@@H](O)[C@H](O)[C@@H](O)CN1CC1CCC2(CC1)CC2] |
| 24 | (2R,3R,4R,5S)-2-methyl-1-(spiro[3.5]nonan-7-ylmethyl)piperidine-3,4,5-triol | 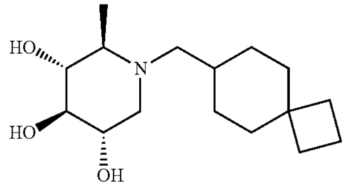 [SMILES: C[C@@H]1[C@@H](O)[C@H](O)[C@@H](O)CN1CC1CCC2(CCC2)CC1] |
| 25 | (2R,3R,4R,5S)-2-methyl-1-(spiro[4.5]decan-8-ylmethyl)piperidine-3,4,5-triol | 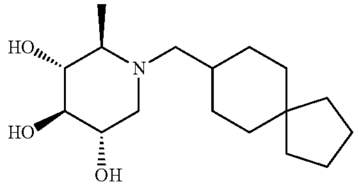 [SMILES: C[C@@H]1[C@@H](O)[C@H](O)[C@@H](O)CN1CC1CCC2(CCCC2)CC1] |
| 26 | (2R,3R,4R,5S)-1-(((5S,8s)-3,3-dimethyl-2-oxaspiro[4.5]decan-8-yl)methyl)-2-methylpiperidine-3,4,5-triol | 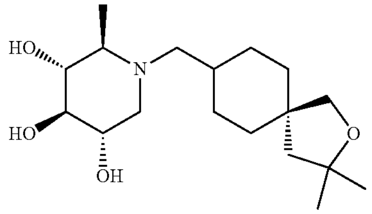 |

TABLE 1-continued

| Example | Name | Structure |
|---|---|---|
| 27 | (2R,3R,4R,5S)-2-methyl-1-((1,2,3,4-tetrahydronaphthalen-2-yl)methyl)piperidine-3,4,5-triol | 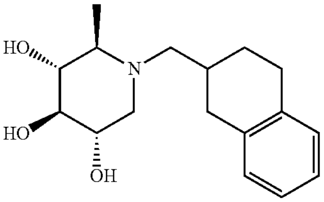 [SMILES: C[C@@H]1[C@@H](O)[C@H](O)[C@@H](O)CN1CC1CCc2ccccc2C1] |
| 28 | (2R,3R,4R,5S)-1-((2,3-dihydro-1H-inden-2-yl)methyl)-2-methylpiperidine-3,4,5-triol | 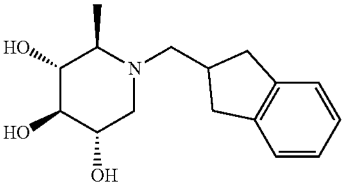 [SMILES: C[C@@H]1[C@@H](O)[C@H](O)[C@@H](O)CN1CC1Cc2ccccc2C1] |
| 29 | (2R,3R,4R,5S)-1-(2-cyclohexylethyl)-2-methylpiperidine-3,4,5-triol | 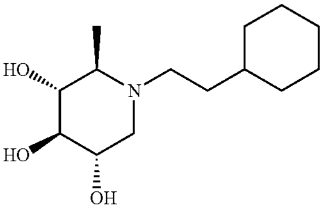 [SMILES: C[C@@H]1[C@@H](O)[C@H](O)[C@@H](O)CN1CCC1CCCCC1] |
| 30 | (2R,3R,4R,5S)-1-(2-(4,4-difluorocyclohexyl)ethyl)-2-methylpiperidine-3,4,5-triol | 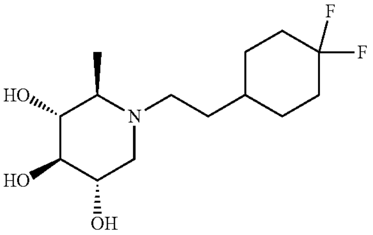 [SMILES: C[C@@H]1[C@@H](O)[C@H](O)[C@@H](O)CN1CCC1CCC(F)(F)CC1] |
| 31 | (2R,3R,4R,5S)-2-methyl-1-(2-((1s,4S)-4-(trifluoromethyl)cyclohexyl)ethyl)piperidine-3,4,5-triol | 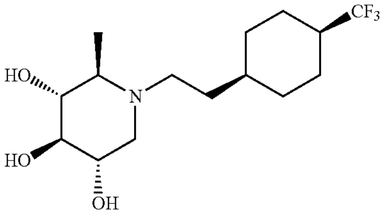 [SMILES: C[C@@H]1[C@@H](O)[C@H](O)[C@@H](O)CN1CC[C@H]1CC[C@@H](C(F)(F)F)CC1] |
| 32 | (2R,3R,4R,5S)-2-methyl-1-(2-((1r,4R)-4-(trifluoromethyl)cyclohexyl)ethyl)piperidine-3,4,5-triol | 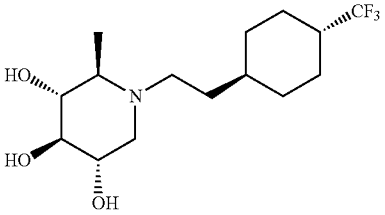 [SMILES: C[C@@H]1[C@@H](O)[C@H](O)[C@@H](O)CN1CC[C@H]1CC[C@H](C(F)(F)F)CC1] |
| 33 | (2R,3R,4R,5S)-1-((2-adamantan-1-yl)ethyl)-2-methylpiperidine-3,4,5-triol | 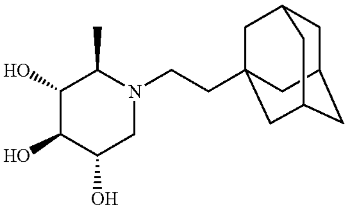 [SMILES: C[C@@H]1[C@@H](O)[C@H](O)[C@@H](O)CN1CCC12CC3CC(CC(C3)C1)C2] |

TABLE 1-continued

| Example | Name | Structure |
|---|---|---|
| 34 | (2R,3R,4R,5S)-1-(3-cyclohexylpropyl)-2-methylpiperidine-3,4,5-triol | 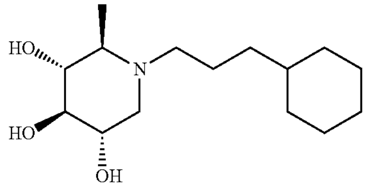 [SMILES: C[C@@H]1[C@@H](O)[C@H](O)[C@@H](O)CN1CCCC1CCCCC1] |
| 35 | (2R,3R,4R,5S)-2-methyl-1-phenethylpiperidine-3,4,5-triol | 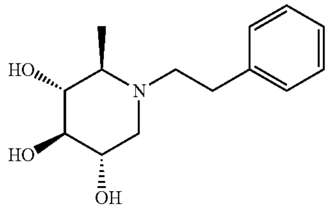 [SMILES: C[C@@H]1[C@@H](O)[C@H](O)[C@@H](O)CN1CCc1ccccc1] |
| 36 | (2R,3R,4R,5S)-2-methyl-1-(2-methylphenethyl)piperidine-3,4,5-triol | 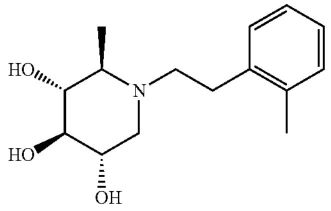 [SMILES: Cc1ccccc1CCN1C[C@H](O)[C@@H](O)[C@H](O)[C@H]1C] |
| 37 | (2R,3R,4R,5S)-1-(2-methoxyphenethyl)-2-methylpiperidine-3,4,5-triol | 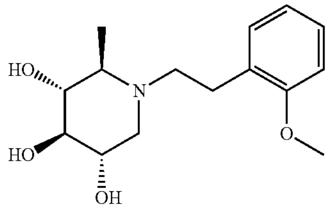 [SMILES: COc1ccccc1CCN1C[C@H](O)[C@@H](O)[C@H](O)[C@H]1C] |
| 38 | (2R,3R,4R,5S)-1-(2-fluorophenethyl)-2-methylpiperidine-3,4,5-triol | 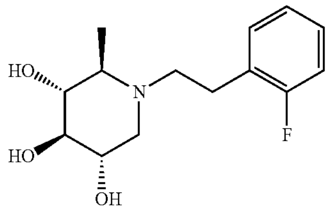 [SMILES: C[C@@H]1[C@@H](O)[C@H](O)[C@@H](O)CN1CCc1ccccc1F] |
| 39 | (2R,3R,4R,5S)-1-(2-chlorophenethyl)-2-methylpiperidine-3,4,5-triol | 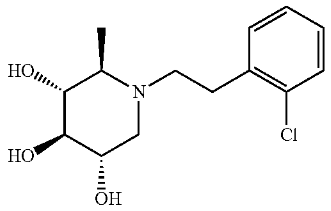 [SMILES: C[C@@H]1[C@@H](O)[C@H](O)[C@@H](O)CN1CCc1ccccc1Cl] |
| 40 | (2R,3R,4R,5S)-1-(2,3-difluorophenethyl)-2-methylpiperidine-3,4,5-triol | 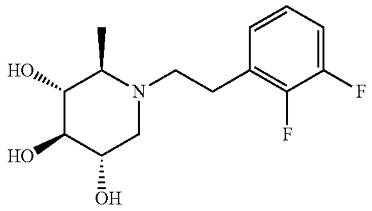 [SMILES: C[C@@H]1[C@@H](O)[C@H](O)[C@@H](O)CN1CCc1cccc(F)c1F] |

TABLE 1-continued

| Example | Name | Structure |
| --- | --- | --- |
| 41 | (2R,3R,4R,5S)-1-(2,4-difluorophenethyl)-2-methylpiperidine-3,4,5-triol | 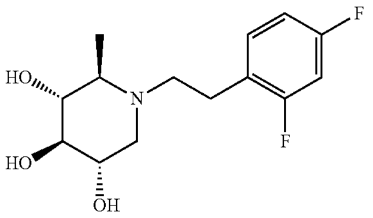 [SMILES: C[C@@H]1[C@@H](O)[C@H](O)[C@@H](O)CN1CCc1ccc(F)cc1F] |
| 42 | (2R,3R,4R,5S)-1-(2,5-difluorophenethyl)-2-methylpiperidine-3,4,5-triol | 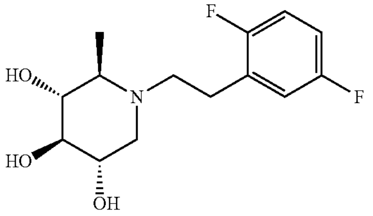 [SMILES: C[C@@H]1[C@@H](O)[C@H](O)[C@@H](O)CN1CCc1cc(F)ccc1F] |
| 43 | (2R,3R,4R,5S)-1-(3,4-difluorophenethyl)-2-methylpiperidine-3,4,5-triol | 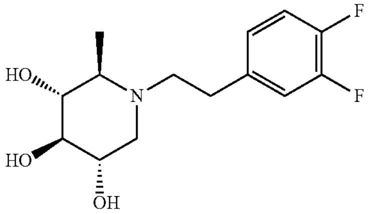 [SMILES: C[C@@H]1[C@@H](O)[C@H](O)[C@@H](O)CN1CCc1ccc(F)c(F)c1] |
| 44 | (2R,3R,4R,5S)-1-(2-fluoro-4-methoxyphenethyl)-2-methylpiperidine-3,4,5-triol | 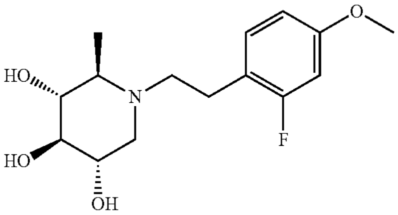 [SMILES: COc1ccc(CCN2C[C@H](O)[C@@H](O)[C@H](O)[C@H]2C)c(F)c1] |
| 45 | (2R,3R,4R,5S)-1-(3-chloro-2-fluorophenethyl)-2-methylpiperidine-3,4,5-triol | 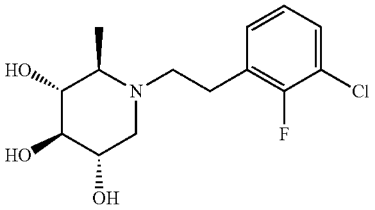 [SMILES: C[C@@H]1[C@@H](O)[C@H](O)[C@@H](O)CN1CCc1cccc(Cl)c1F] |
| 46 | (2R,3R,4R,5S)-1-(4-chloro-2-fluorophenethyl)-2-methylpiperidine-3,4,5-triol | 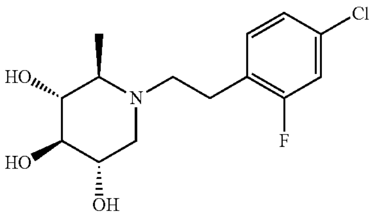 [SMILES: C[C@@H]1[C@@H](O)[C@H](O)[C@@H](O)CN1CCc1ccc(Cl)cc1F] |
| 47 | (2R,3R,4R,5S)-1-(5-chloro-2-fluorophenethyl)-2-methylpiperidine-3,4,5-triol | 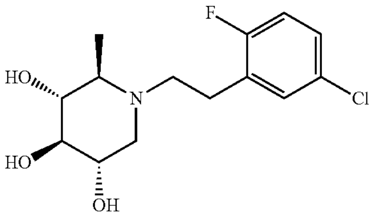 [SMILES: C[C@@H]1[C@@H](O)[C@H](O)[C@@H](O)CN1CCc1cc(Cl)ccc1F] |

TABLE 1-continued

| Example | Name | Structure |
| --- | --- | --- |
| 48 | (2R,3R,4R,5S)-1-(2,6-difluorophenethyl)-2-methylpiperidine-3,4,5-triol | 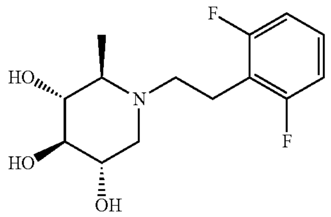 [SMILES: C[C@@H]1[C@@H](O)[C@H](O)[C@@H](O)CN1CCc1c(F)cccc1F] |
| 49 | (2R,3R,4R,5S)-1-(3-chloro-2,6-difluorophenethyl)-2-methylpiperidine-3,4,5-triol | 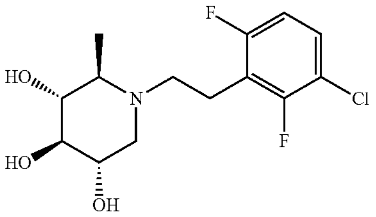 [SMILES: C[C@@H]1[C@@H](O)[C@H](O)[C@@H](O)CN1CCc1c(F)ccc(Cl)c1F] |
| 50 | (2R,3R,4R,5S)-1-(2,6-difluoro-4-(prop-1-en-2-yl)phenethyl)-2-methylpiperidine-3,4,5-triol | 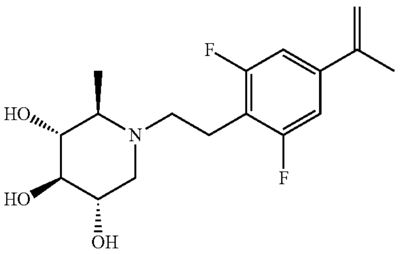 [SMILES: C=C(C)c1cc(F)c(CCN2C[C@H](O)[C@@H](O)[C@H](O)[C@H]2C)c(F)c1] |
| 51 | (2R,3R,4R,5S)-1-(2,6-difluoro-4-isopropylphenethyl)-2-methylpiperidine-3,4,5-triol | 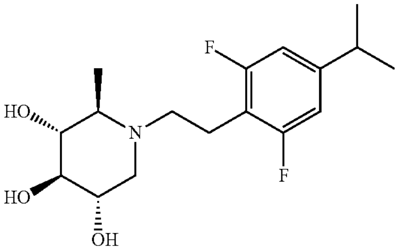 [SMILES: CC(C)c1cc(F)c(CCN2C[C@H](O)[C@@H](O)[C@H](O)[C@H]2C)c(F)c1] |
| 52 | (2R,3R,4R,5S)-1-(2,6-difluoro-3-isopropylphenethyl)-2-methylpiperidine-3,4,5-triol | 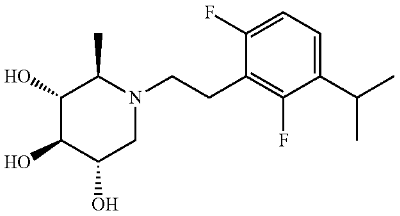 [SMILES: CC(C)c1ccc(F)c(CCN2C[C@H](O)[C@@H](O)[C@H](O)[C@H]2C)c1F] |
| 53 | (2R,3R,4R,5S)-1-(4-cyclopropyl-2,6-difluorophenethyl)-2-methylpiperidine-3,4,5-triol | 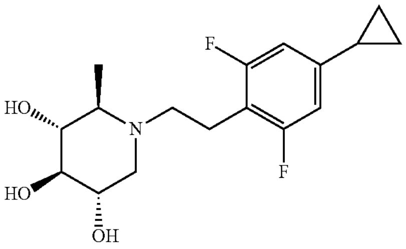 [SMILES: C[C@@H]1[C@@H](O)[C@H](O)[C@@H](O)CN1CCc1c(F)cc(C2CC2)cc1F] |

TABLE 1-continued

| Example | Name | Structure |
|---|---|---|
| 54 | (2R,3R,4R,5S)-1-(2,6-difluoro-4-(tetrahydro-2H-pyran-4-yl)phenethyl)-2-methylpiperidine-3,4,5-triol | 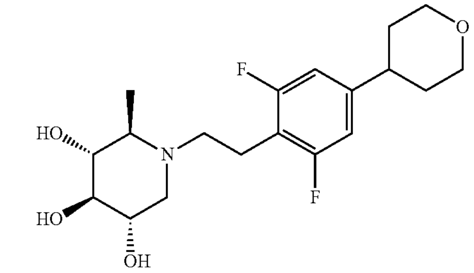 |
| 55 | (2R,3R,4R,5S)-1-(2,6-difluoro-4-(trifluoromethyl)phenethyl)-2-methylpiperidine-3,4,5-triol | 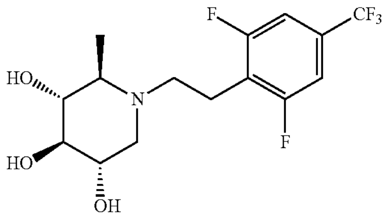 [SMILES: C[C@@H]1[C@@H](O)[C@H](O)[C@@H](O)CN1CCc1c(F)cc(C(F)(F)F)cc1F] |
| 56 | (2R,3R,4R,5S)-1-(2,6-difluoro-4-(pyrrolidin-1-yl)phenethyl)-2-methylpiperidine-3,4,5-triol | 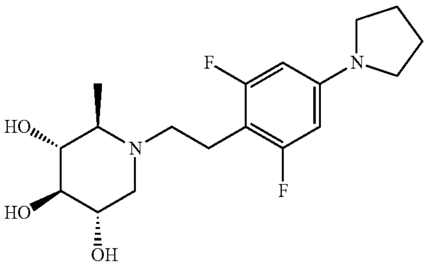 [SMILES: C[C@@H]1[C@@H](O)[C@H](O)[C@@H](O)CN1CCc1c(F)cc(N2CCCC2)cc1F] |
| 57 | (2R,3R,4R,5S)-1-(2,6-difluoro-4-(piperidin-1-yl)phenethyl)-2-methylpiperidine-3,4,5-triol | 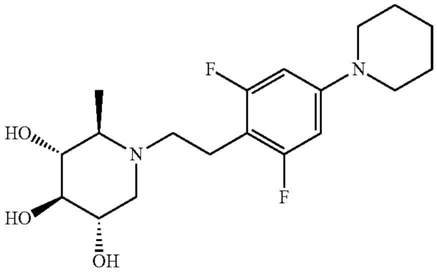 [SMILES: C[C@@H]1[C@@H](O)[C@H](O)[C@@H](O)CN1CCc1c(F)cc(N2CCCCC2)cc1F] |
| 58 | (2R,3R,4R,5S)-1-(2,6-difluoro-4-morpholinophenethyl)-2-methylpiperidine-3,4,5-triol | 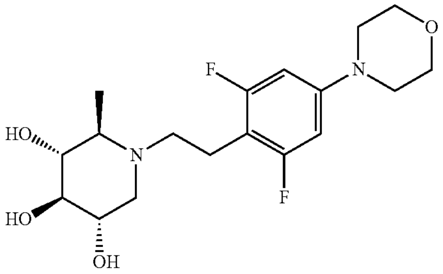 |
| 59 | (2R,3R,4R,5S)-1-(4-butoxy-2,6-difluorophenethyl)-2-methylpiperidine-3,4,5-triol | 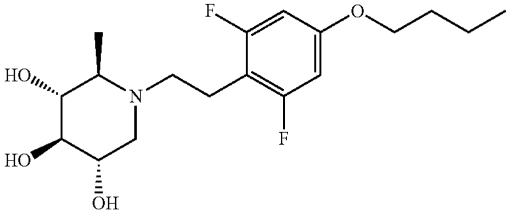 [SMILES: CCCCOc1cc(F)c(CCN2C[C@H](O)[C@@H](O)[C@H](O)[C@H]2C)c(F)c1] |

TABLE 1-continued

| Example | Name | Structure |
| --- | --- | --- |
| 60 | (2R,3R,4R,5S)-1-(4-(cyclopropylmethoxy)-2,6-difluorophenethyl)-2-methylpiperidine-3,4,5-triol | 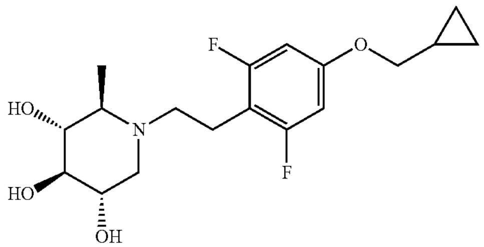 [SMILES: C[C@@H]1[C@@H](O)[C@H](O)[C@@H](O)CN1CCc1c(F)cc(OCC2CC2)cc1F] |
| 61 | (2R,3R,4R,5S)-2-methyl-1-(4-((tetrahydrofuran-3-yl)oxy)phenethyl)piperidine-3,4,5-triol | 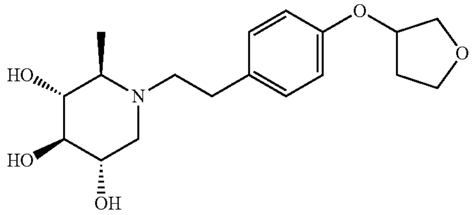 [SMILES: C[C@@H]1[C@@H](O)[C@H](O)[C@@H](O)CN1CCc1ccc(OC2CCOC2)cc1] |
| 62 | (2R,3R,4R,5S)-2-methyl-1-(4-((tetrahydro-2H-pyran-3-yl)oxy)phenethyl)piperidine-3,4,5-triol | 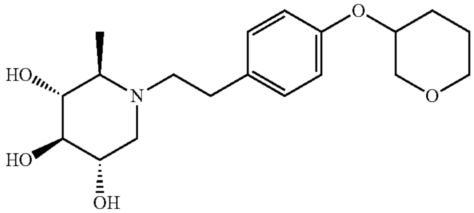 [SMILES: C[C@@H]1[C@@H](O)[C@H](O)[C@@H](O)CN1CCc1ccc(OC2CCCOC2)cc1] |
| 63 | (2R,3R,4R,5S)-2-methyl-1-(4-((tetrahydro-2H-pyran-4-yl)oxy)phenethyl)piperidine-3,4,5-triol | 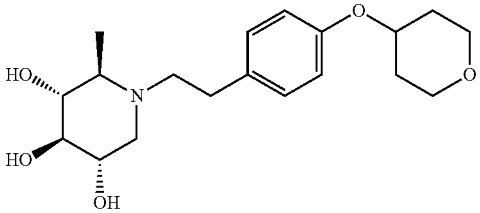 [SMILES: C[C@@H]1[C@@H](O)[C@H](O)[C@@H](O)CN1CCc1ccc(OC2CCOCC2)cc1] |
| 64 | (2R,3R,4R,5S)-2-methyl-1-(4-phenoxyphenethyl)piperidine-3,4,5-triol | 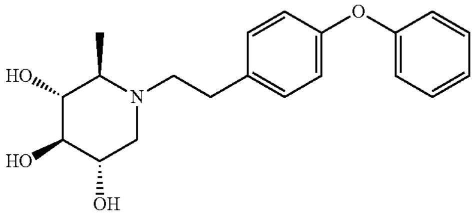 [SMILES: C[C@@H]1[C@@H](O)[C@H](O)[C@@H](O)CN1CCc1ccc(Oc2ccccc2)cc1] |
| 65 | (2R,3R,4R,5S)-2-methyl-1-(4-((tetrahydrofuran-3-yl)methoxy)phenethyl)piperidine-3,4,5-triol | 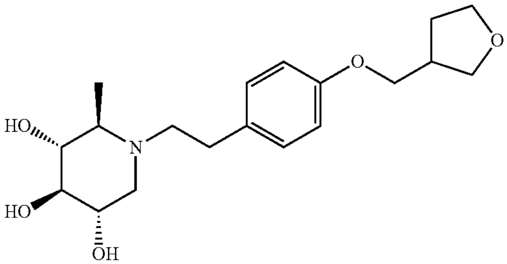 [SMILES: C[C@@H]1[C@@H](O)[C@H](O)[C@@H](O)CN1CCc1ccc(OCC2CCOC2)cc1] |

TABLE 1-continued
| Example | Name | Structure |
|---|---|---|
| 66 | (2R,3R,4R,5S)-2-methyl-1-((R)-2-phenylpropyl)piperidine-3,4,5-triol | 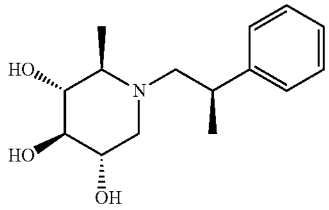 [SMILES: C[C@@H]1[C@@H](O)[C@H](O)[C@@H](O)CN1C[C@H](C)c1ccccc1] |
| 67 | (2R,3R,4R,5S)-2-methyl-1-((S)-2-phenylpropyl)piperidine-3,4,5-triol | 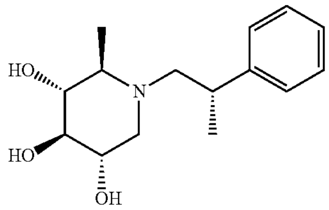 [SMILES: C[C@H](CN1C[C@H](O)[C@@H](O)[C@H](O)[C@H]1C)c1ccccc1] |
| 68 | (2R,3R,4R,5S)-1-(2-([1,1'-biphenyl]-4-yl)ethyl)-2-methylpiperidine-3,4,5-triol | 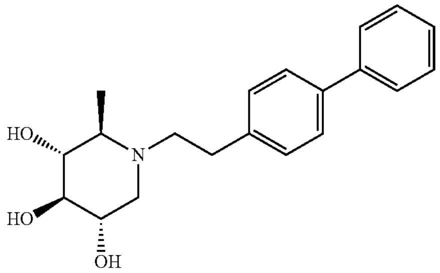 [SMILES: C[C@@H]1[C@@H](O)[C@H](O)[C@@H](O)CN1CCc1ccc(-c2ccccc2)cc1] |
| 69 | (2R,3R,4R,5S)-1-(2-(3,5-difluoro-[1,1'-biphenyl]-4-yl)ethyl)-2-methylpiperidine-3,4,5-triol | 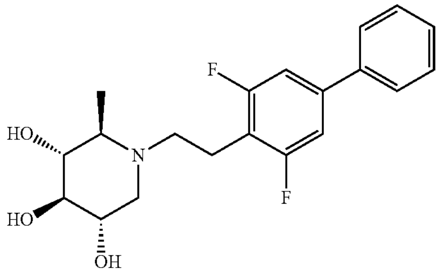 [SMILES: C[C@@H]1[C@@H](O)[C@H](O)[C@@H](O)CN1CCc1c(F)cc(-c2ccccc2)cc1F] |
| 70 | (2R,3R,4R,5S)-1-(2-(benzo[d][1,3]dioxol-5-yl)ethyl)-2-methylpiperidine-3,4,5-triol | 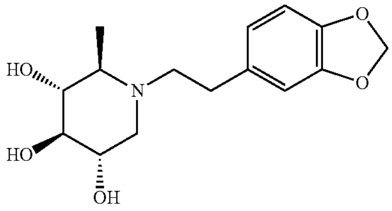 [SMILES: C[C@@H]1[C@@H](O)[C@H](O)[C@@H](O)CN1CCc1ccc2c(c1)OCO2] |
| 71 | (2R,3R,4R,5S)-1-(2-(6-fluorobenzo[d][1,3]dioxol-5-yl)ethyl)-2-methylpiperidine-3,4,5-triol | 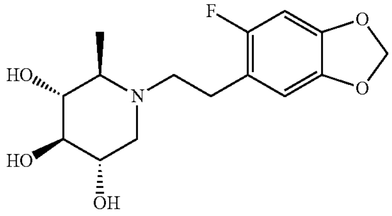 [SMILES: C[C@@H]1[C@@H](O)[C@H](O)[C@@H](O)CN1CCc1cc2c(cc1F)OCO2] |

TABLE 1-continued

| Example | Name | Structure |
| --- | --- | --- |
| 72 | (2R,3R,4R,5S)-1-(2-(2,2-difluorobenzo[d][1,3]dioxol-5-yl)ethyl)-2-methylpiperidine-3,4,5-triol | 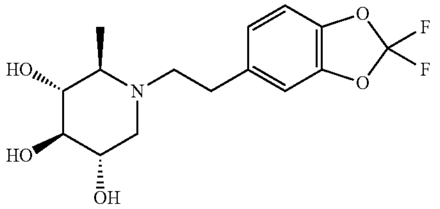 [SMILES: C[C@@H]1[C@@H](O)[C@H](O)[C@@H](O)CN1CCc1ccc2c(c1)OC(F)(F)O2] |
| 73 | (2R,3R,4R,5S)-1-(2-(2,3-dihydrobenzo[b][1,4]dioxin-6-yl)ethyl)-2-methylpiperidine-3,4,5-triol | 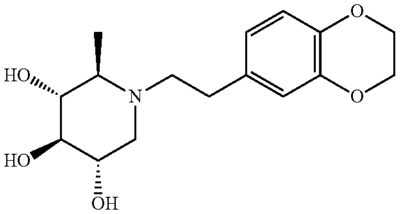 [SMILES: C[C@@H]1[C@@H](O)[C@H](O)[C@@H](O)CN1CCc1ccc2c(c1)OCCO2] |
| 74 | (2R,3R,4R,5S)-2-methyl-1-(2-(thiophen-2-yl)ethyl)piperidine-3,4,5-triol | 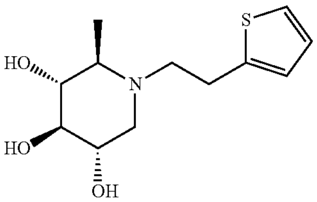 [SMILES: C[C@@H]1[C@@H](O)[C@H](O)[C@@H](O)CN1CCc1cccs1] |
| 75 | (2R,3R,4R,5S)-2-methyl-1-(2-(thiophen-3-yl)ethyl)piperidine-3,4,5-triol | 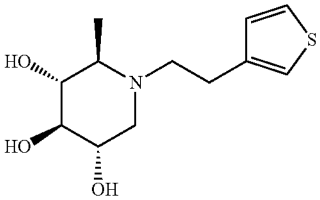 [SMILES: C[C@@H]1[C@@H](O)[C@H](O)[C@@H](O)CN1CCc1ccsc1] |
| 76 | (2R,3R,4R,5S)-2-methyl-1-(2-(pyridin-2-yl)ethyl)piperidine-3,4,5-triol | 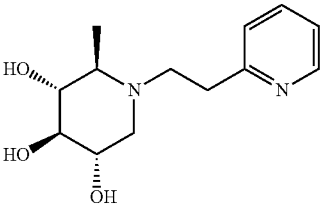 [SMILES: C[C@@H]1[C@@H](O)[C@H](O)[C@@H](O)CN1CCc1ccccn1] |
| 77 | (2R,3R,4R,5S)-2-methyl-1-(3-phenylpropyl)piperidine-3,4,5-triol | 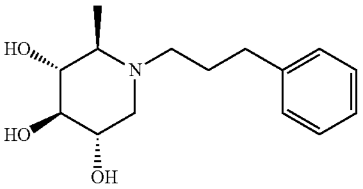 [SMILES: C[C@@H]1[C@@H](O)[C@H](O)[C@@H](O)CN1CCCc1ccccc1] |
| 78 | (2R,3R,4R,5S)-1-(3-(2-fluorophenyl)propyl)-2-methylpiperidine-3,4,5-triol | 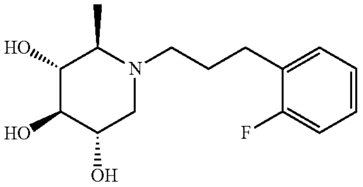 [SMILES: C[C@@H]1[C@@H](O)[C@H](O)[C@@H](O)CN1CCCc1ccccc1F] |

TABLE 1-continued

| Example | Name | Structure |
|---|---|---|
| 79 | (2R,3R,4R,5S)-1-(3-(4-fluorophenyl)propyl)-2-methylpiperidine-3,4,5-triol | 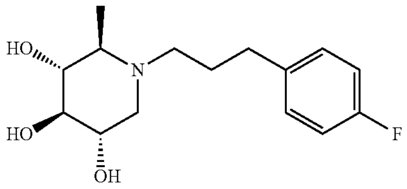 [SMILES: C[C@@H]1[C@@H](O)[C@H](O)[C@@H](O)CN1CCCc1ccc(F)cc1] |
| 80 | (2R,3R,4R,5S)-2-methyl-1-(3-(thiophen-2-yl)propyl)piperidine-3,4,5-triol | 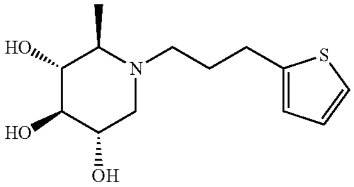 [SMILES: C[C@@H]1[C@@H](O)[C@H](O)[C@@H](O)CN1CCCc1cccs1] |
| 81 | (2R,3R,4R,5S)-2-methyl-1-(3-(thiophen-3-yl)propyl)piperidine-3,4,5-triol | 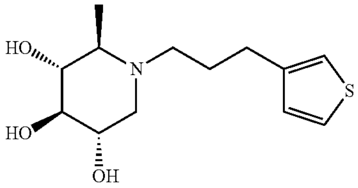 [SMILES: C[C@@H]1[C@@H](O)[C@H](O)[C@@H](O)CN1CCCc1ccsc1] |
| 82 | (2R,3R,4R,5S)-2-methyl-1-((1-phenylpiperidin-4-yl)methyl)piperidine-3,4,5-triol | 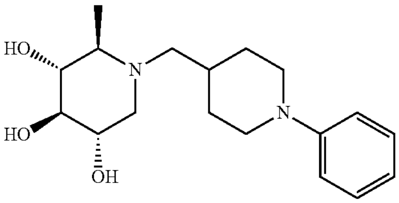 [SMILES: C[C@@H]1[C@@H](O)[C@H](O)[C@@H](O)CN1CC1CCN(c2ccccc2)CC1] |
| 83 | (2R,3R,4R,5S)-1-((1-(2-fluorophenyl)piperidin-4-yl)methyl)-2-methylpiperidine-3,4,5-triol | 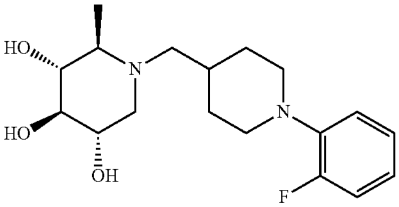 [SMILES: C[C@@H]1[C@@H](O)[C@H](O)[C@@H](O)CN1CC1CCN(c2ccccc2F)CC1] |
| 84 | (2R,3R,4R,5S)-1-((1-(3-fluorophenyl)piperidin-4-yl)methyl)-2-methylpiperidine-3,4,5-triol | 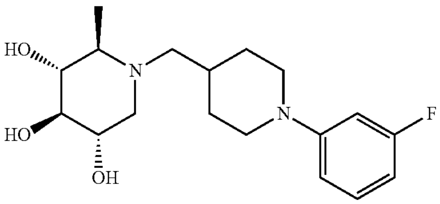 [SMILES: C[C@@H]1[C@@H](O)[C@H](O)[C@@H](O)CN1CC1CCN(c2cccc(F)c2)CC1] |
| 85 | (2R,3R,4R,5S)-1-((1-(4-fluorophenyl)piperidin-4-yl)methyl)-2-methylpiperidine-3,4,5-triol | 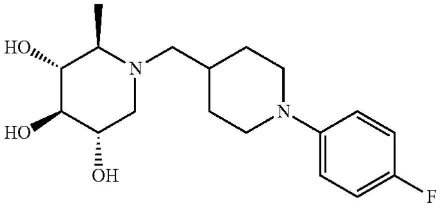 [SMILES: C[C@@H]1[C@@H](O)[C@H](O)[C@@H](O)CN1CC1CCN(c2ccc(F)cc2)CC1] |

TABLE 1-continued

| Example | Name | Structure |
|---|---|---|
| 86 | (2R,3R,4R,5S)-2-methyl-1-((1-(4-(trifluoromethyl)phenyl)piperidin-4-yl)methyl)piperidine-3,4,5-triol | 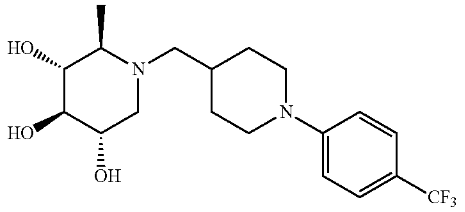 [SMILES: C[C@@H]1[C@@H](O)[C@H](O)[C@@H](O)CN1CC1CCN(c2ccc(C(F)(F)F)cc2)CC1] |
| 87 | (2R,3R,4R,5S)-2-methyl-1-((4-methyl-1-phenylpiperidin-4-yl)methyl)piperidine-3,4,5-triol | 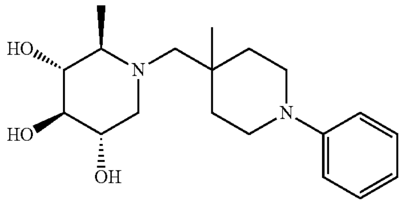 [SMILES: C[C@@H]1[C@@H](O)[C@H](O)[C@@H](O)CN1CC1(C)CCN(c2ccccc2)CC1] |
| 88 | (2R,3R,4R,5S)-1-((4-fluoro-1-phenylpiperidin-4-yl)methyl)-2-methylpiperidine-3,4,5-triol | 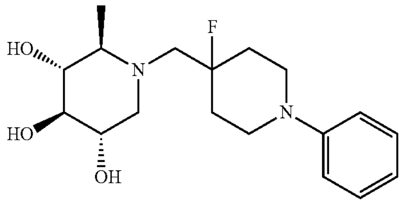 |
| 89 | (2R,3R,4R,5S)-2-methyl-1-(2-(1-phenylpiperidin-4-yl)ethyl)piperidine-3,4,5-triol | 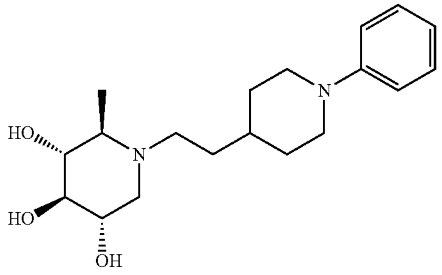 [SMILES: C[C@@H]1[C@@H](O)[C@H](O)[C@@H](O)CN1CCC1CCN(c2ccccc2)CC1] |
| 90 | (2R,3R,4R,5S)-2-methyl-1-((1-(pyridin-3-yl)piperidin-4-yl)methyl)piperidine-3,4,5-triol | 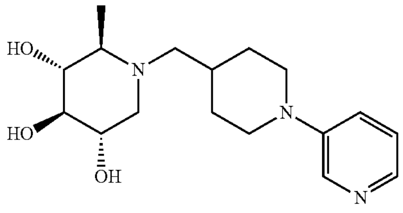 [SMILES: C[C@@H]1[C@@H](O)[C@H](O)[C@@H](O)CN1CC1CCN(c2cccnc2)CC1] |
| 91 | (2R,3R,4R,5S)-2-methyl-1-((1-(2,2,2-trifluoroethyl)piperidin-4-yl)methyl)piperidine-3,4,5-triol | 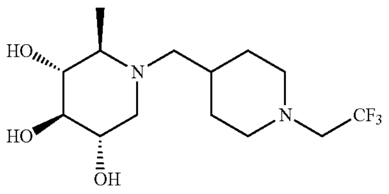 [SMILES: C[C@@H]1[C@@H](O)[C@H](O)[C@@H](O)CN1CC1CCN(CC(F)(F)F)CC1] |
| 92 | 2-methyl-1-(4-(((2R,3R,4R,5S)-3,4,5-trihydroxy-2-methylpiperidin-1-yl)methyl)piperidin-1-yl)propan-1-one | 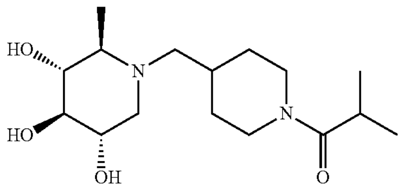 [SMILES: CC(C)C(=O)N1CCC(CN2C[C@H](O)[C@@H](O)[C@H](O)[C@H]2C)CC1] |

TABLE 1-continued

| Example | Name | Structure |
| --- | --- | --- |
| 93 | 2,2-dimethyl-1-(4-(((2R,3R,4R,5S)-3,4,5-trihydroxy-2-methylpiperidin-1-yl)methyl)piperidin-1-yl)propan-1-one | 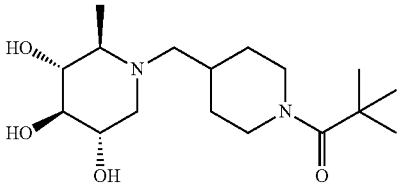 [SMILES: C[C@@H]1[C@@H](O)[C@H](O)[C@@H](O)CN1CC1CCN(C(=O)C(C)(C)C)CC1] |
| 94 | 1-(4-(((2R,3R,4R,5S)-3,4,5-trihydroxy-2-methylpiperidin-1-yl)methyl)piperidin-1-yl)butan-1-one | 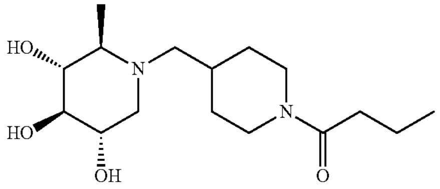 [SMILES: CCCC(=O)N1CCC(CN2C[C@H](O)[C@@H](O)[C@H](O)[C@H]2C)CC1] |
| 95 | 3-methyl-1-(4-(((2R,3R,4R,5S)-3,4,5-trihydroxy-2-methylpiperidin-1-yl)methyl)piperidin-1-yl)butan-1-one | 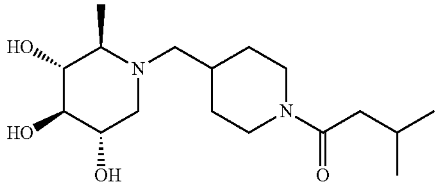 [SMILES: CC(C)CC(=O)N1CCC(CN2C[C@H](O)[C@@H](O)[C@H](O)[C@H]2C)CC1] |
| 96 | 3,3-dimethyl-1-(4-(((2R,3R,4R,5S)-3,4,5-trihydroxy-2-methylpiperidin-1-yl)methyl)piperidin-1-yl)butan-1-one | 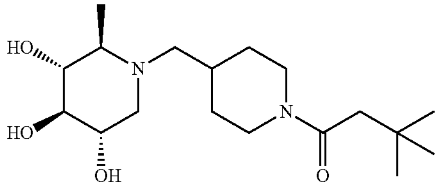 [SMILES: C[C@@H]1[C@@H](O)[C@H](O)[C@@H](O)CN1CC1CCN(C(=O)CC(C)(C)C)CC1] |
| 97 | 2-cyclopentyl-1-(4-(((2R,3R,4R,5S)-3,4,5-trihydroxy-2-methylpiperidin-1-yl)methyl)piperidin-1-yl)ethanone | 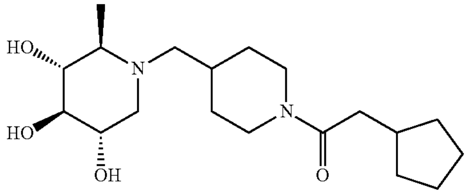 [SMILES: C[C@@H]1[C@@H](O)[C@H](O)[C@@H](O)CN1CC1CCN(C(=O)CC2CCCC2)CC1] |
| 98 | cyclopropyl(4-(((2R,3R,4R,5S)-3,4,5-trihydroxy-2-methylpiperidin-1-yl)methyl)piperidin-1-yl)methanone | 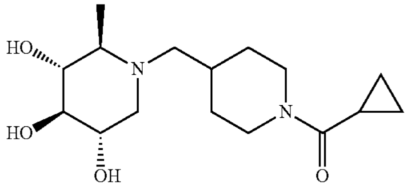 [SMILES: C[C@@H]1[C@@H](O)[C@H](O)[C@@H](O)CN1CC1CCN(C(=O)C2CC2)CC1] |
| 99 | cyclobutyl(4-(((2R,3R,4R,5S)-3,4,5-trihydroxy-2-methylpiperidin-1-yl)methyl)piperidin-1-yl)methanone | 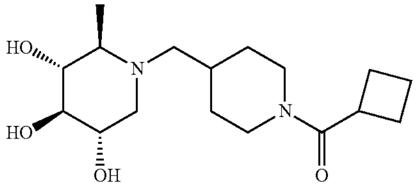 [SMILES: C[C@@H]1[C@@H](O)[C@H](O)[C@@H](O)CN1CC1CCN(C(=O)C2CCC2)CC1] |
| 100 | cyclopentyl(4-(((2R,3R,4R,5S)-3,4,5-trihydroxy-2-methylpiperidin-1-yl)methyl)piperidin-1-yl)methanone | 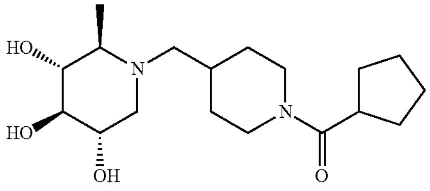 [SMILES: C[C@@H]1[C@@H](O)[C@H](O)[C@@H](O)CN1CC1CCN(C(=O)C2CCCC2)CC1] |

TABLE 1-continued

| Example | Name | Structure |
|---|---|---|
| 101 | cyclohexyl(4-(((2R,3R,4R,5S)-3,4,5-trihydroxy-2-methylpiperidin-1-yl)methyl)piperidin-1-yl)methanone | 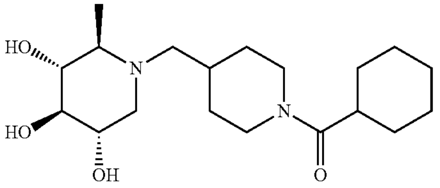 [SMILES: C[C@@H]1[C@@H](O)[C@H](O)[C@@H](O)CN1CC1CCN(C(=O)C2CCCCC2)CC1] |
| 102 | ((1s,4S)-4-(tert-butyl)cyclohexyl)(4-(((2R,3R,4R,5S)-3,4,5-trihydroxy-2-methylpiperidin-1-yl)methyl)piperidin-1-yl)methanone | 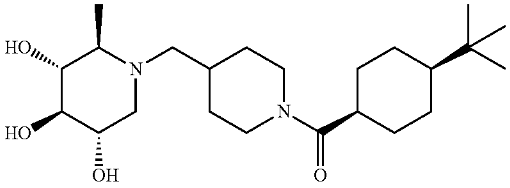 [SMILES: C[C@@H]1[C@@H](O)[C@H](O)[C@@H](O)CN1CC1CCN(C(=O)[C@H]2CC[C@@H](C(C)(C)C)CC2)CC1] |
| 103 | ((1r,4R)-4-(tert-butyl)cyclohexyl)(4-(((2R,3R,4R,5S)-3,4,5-trihydroxy-2-methylpiperidin-1-yl)methyl)piperidin-1-yl)methanone | 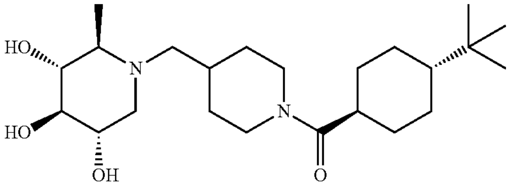 [SMILES: C[C@@H]1[C@@H](O)[C@H](O)[C@@H](O)CN1CC1CCN(C(=O)[C@H]2CC[C@H](C(C)(C)C)CC2)CC1] |
| 104 | (4-methoxycyclohexyl)(4-(((2R,3R,4R,5S)-3,4,5-trihydroxy-2-methylpiperidin-1-yl)methyl)piperidin-1-yl)methanone | 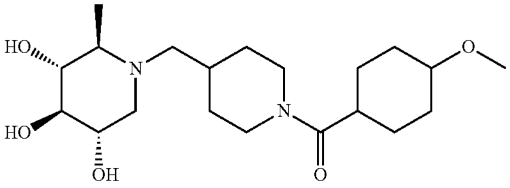 [SMILES: COC1CCC(C(=O)N2CCC(CN3C[C@H](O)[C@@H](O)[C@H](O)[C@H]3C)CC2)CC1] |
| 105 | (4-(trifluoromethyl)cyclohexyl)(4-(((2R,3R,4R,5S)-3,4,5-trihydroxy-2-methylpiperidin-1-yl)methyl)piperidin-1-yl)methanone | 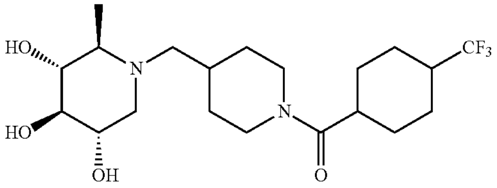 [SMILES: C[C@@H]1[C@@H](O)[C@H](O)[C@@H](O)CN1CC1CCN(C(=O)C2CCC(C(F)(F)F)CC2)CC1] |
| 106 | phenyl(4-(((2R,3R,4R,5S)-3,4,5-trihydroxy-2-methylpiperidin-1-yl)methyl)piperidin-1-yl)methanone | 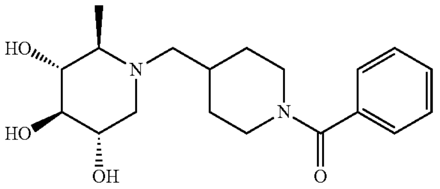 [SMILES: C[C@@H]1[C@@H](O)[C@H](O)[C@@H](O)CN1CC1CCN(C(=O)c2ccccc2)CC1] |
| 107 | (3-(trifluoromethyl)phenyl)(4-(((2R,3R,4R,5S)-3,4,5-trihydroxy-2-methylpiperidin-1-yl)methyl)piperidin-1-yl)methanone | 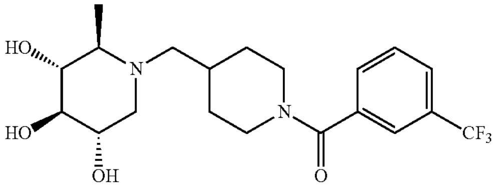 [SMILES: C[C@@H]1[C@@H](O)[C@H](O)[C@@H](O)CN1CC1CCN(C(=O)c2cccc(C(F)(F)F)c2)CC1] |

TABLE 1-continued

| Example | Name | Structure |
| --- | --- | --- |
| 108 | 2-phenyl-1-(4-(((2R,3R,4R,5S)-3,4,5-trihydroxy-2-methylpiperidin-1-yl)methyl)piperidin-1-yl)ethanone | 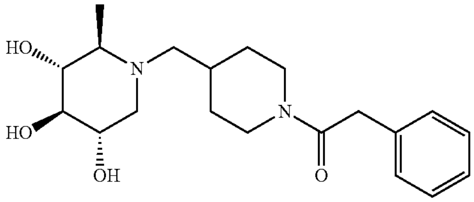 [SMILES: C[C@@H]1[C@@H](O)[C@H](O)[C@@H](O)CN1CC1CCN(C(=O)Cc2ccccc2)CC1] |
| 109 | thiophen-3-yl(4-(((2R,3R,4R,5S)-3,4,5-trihydroxy-2-methylpiperidin-1-yl)methyl)piperidin-1-yl)methanone | 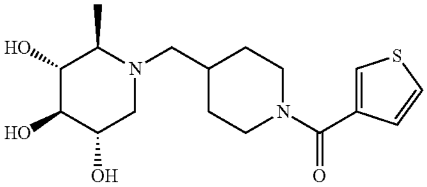 [SMILES: C[C@@H]1[C@@H](O)[C@H](O)[C@@H](O)CN1CC1CCN(C(=O)c2ccsc2)CC1] |
| 110 | N-cyclohexyl-4-(((2R,3R,4R,5S)-3,4,5-trihydroxy-2-methylpiperidin-1-yl)methyl)piperidine-1-carboxamide | 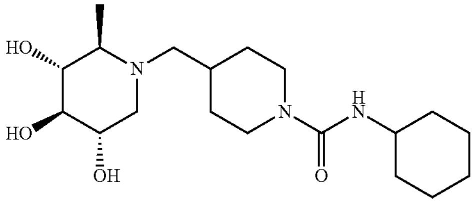 |
| 111 | N-cyclohexyl-4-(((2R,3R,4R,5S)-3,4,5-trihydroxy-2-methylpiperidin-1-yl)methyl)piperidine-1-carbothioamide | 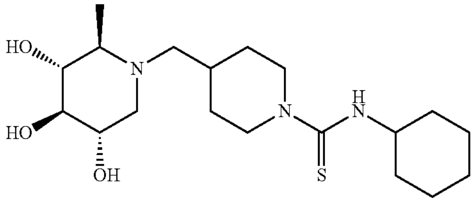 |
| 112 | (2R,3R,4R,5S)-2-methyl-1-((1-((1S,2R)-2-(trifluoromethyl)cyclohexyl)azetidin-3-yl)methyl)piperidine-3,4,5-triol | 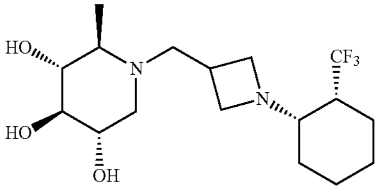 [SMILES: C[C@@H]1[C@@H](O)[C@H](O)[C@@H](O)CN1CC1CN([C@H]2CCCC[C@H]2C(F)(F)F)C1] |
| 113 | (2R,3R,4R,5S)-2-methyl-1-(((R)-1-phenylpyrrolidin-3-yl)methyl)piperidine-3,4,5-triol | 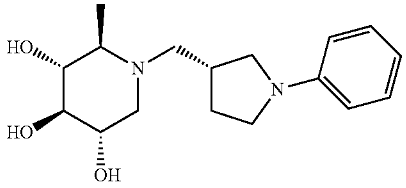 [SMILES: C[C@@H]1[C@@H](O)[C@H](O)[C@@H](O)CN1C[C@H]1CCN(c2ccccc2)C1] |
| 114 | (2R,3R,4R,5S)-2-methyl-1-(((R)-1-(o-tolyl)pyrrolidin-3-yl)methyl)piperidine-3,4,5-triol | 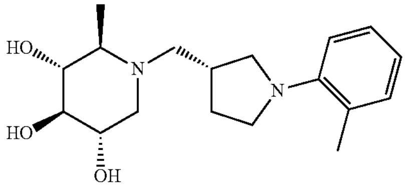 [SMILES: Cc1ccccc1N1CC[C@H](CN2C[C@H](O)[C@@H](O)[C@H](O)[C@H]2C)C1] |

TABLE 1-continued

| Example | Name | Structure |
|---|---|---|
| 115 | (2R,3R,4R,5S)-2-methyl-1-(((R)-1-(2-(trifluoromethyl)phenyl)pyrrolidin-3-yl)methyl)piperidine-3,4,5-triol | 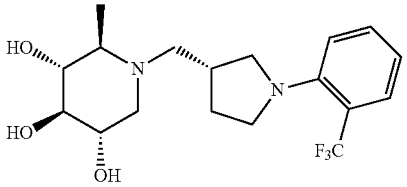 |
| 116 | (2R,3R,4R,5S)-1-(((R)-1-(2-fluorophenyl)pyrrolidin-3-yl)methyl)-2-methylpiperidine-3,4,5-triol | 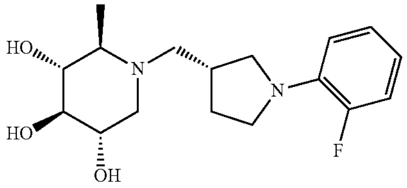 [SMILES: C[C@@H]1[C@@H](O)[C@H](O)[C@@H](O)CN1C[C@H]1CCN(c2ccccc2F)C1] |
| 117 | (2R,3R,4R,5S)-1-(((R)-1-(3-fluorophenyl)pyrrolidin-3-yl)methyl)-2-methylpiperidine-3,4,5-triol | 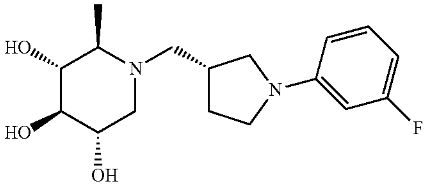 [SMILES: C[C@@H]1[C@@H](O)[C@H](O)[C@@H](O)CN1C[C@H]1CCN(c2cccc(F)c2)C1] |
| 118 | (2R,3R,4R,5S)-2-methyl-1-(((R)-1-(2-(trifluoromethoxy)phenyl)pyrrolidin-3-yl)methyl)piperidine-3,4,5-triol | 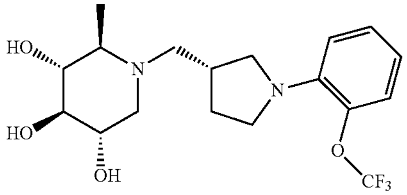 [SMILES: C[C@@H]1[C@@H](O)[C@H](O)[C@@H](O)CN1C[C@H]1CCN(c2ccccc2OC(F)(F)F)C1] |
| 119 | (2R,3R,4R,5S)-2-methyl-1-(((R)-1-(6-(trifluoromethyl)pyridin-2-yl)pyrrolidin-3-yl)methyl)piperidine-3,4,5-triol | 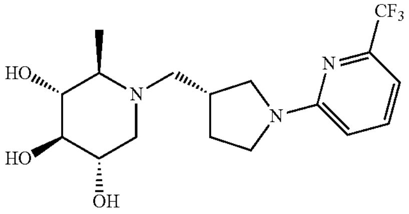 [SMILES: C[C@@H]1[C@@H](O)[C@H](O)[C@@H](O)CN1C[C@H]1CCN(c2cccc(C(F)(F)F)n2)C1] |
| 120 | (2R,3R,4R,5S)-2-methyl-1-(((R)-1-(3-(trifluoromethyl)pyridin-2-yl)pyrrolidin-3-yl)methyl)piperidine-3,4,5-triol | 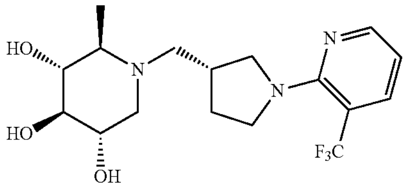 [SMILES: C[C@@H]1[C@@H](O)[C@H](O)[C@@H](O)CN1C[C@H]1CCN(c2ncccc2C(F)(F)F)C1] |
| 121 | (2R,3R,4R,5S)-2-methyl-1-(((R)-1-(4-(trifluoromethyl)pyridin-2-yl)pyrrolidin-3-yl)methyl)piperidine-3,4,5-triol | 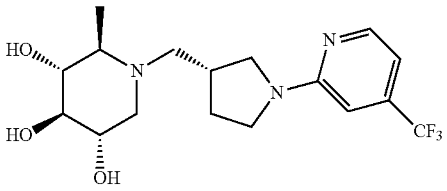 [SMILES: C[C@@H]1[C@@H](O)[C@H](O)[C@@H](O)CN1C[C@H]1CCN(c2cc(C(F)(F)F)ccn2)C1] |

TABLE 1-continued

| Example | Name | Structure |
| --- | --- | --- |
| 122 | (2R,3R,4R,5S)-2-methyl-1-(((R)-1-(pyridin-3-yl)pyrrolidin-3-yl)methyl)piperidine-3,4,5-triol | 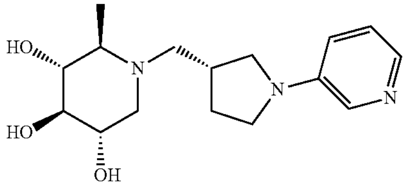 [SMILES: C[C@@H]1[C@@H](O)[C@H](O)[C@@H](O)CN1C[C@H]1CCN(c2cccnc2)C1] |
| 123 | (2R,3R,4R,5S)-2-methyl-1-(((R)-1-(4-methylpyridin-3-yl)pyrrolidin-3-yl)methyl)piperidine-3,4,5-triol | 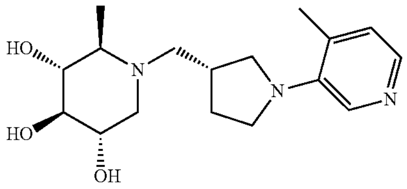 [SMILES: Cc1ccncc1N1CC[C@H](CN2C[C@H](O)[C@@H](O)[C@H](O)[C@H]2C)C1] |
| 124 | (2R,3R,4R,5S)-2-methyl-1-(((R)-1-(4-(trifluoromethyl)pyridin-3-yl)pyrrolidin-3-yl)methyl)piperidine-3,4,5-triol | 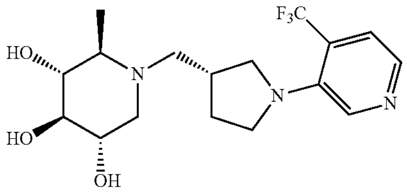 [SMILES: C[C@@H]1[C@@H](O)[C@H](O)[C@@H](O)CN1C[C@H]1CCN(c2cnccc2C(F)(F)F)C1] |
| 125 | (2R,3R,4R,5S)-2-methyl-1-(((R)-1-(5-(trifluoromethyl)pyridin-3-yl)pyrrolidin-3-yl)methyl)piperidine-3,4,5-triol | 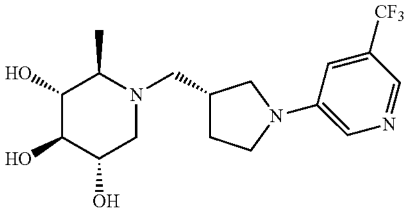 [SMILES: C[C@@H]1[C@@H](O)[C@H](O)[C@@H](O)CN1C[C@H]1CCN(c2cncc(C(F)(F)F)c2)C1] |
| 126 | (2R,3R,4R,5S)-2-methyl-1-(((R)-1-(2-(trifluoromethyl)pyridin-3-yl)pyrrolidin-3-yl)methyl)piperidine-3,4,5-triol | 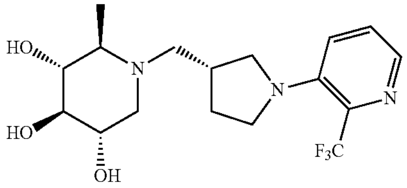 [SMILES: C[C@@H]1[C@@H](O)[C@H](O)[C@@H](O)CN1C[C@H]1CCN(c2cccnc2C(F)(F)F)C1] |
| 127 | (2R,3R,4R,5S)-2-methyl-1-(((R)-1-(4-(trifluoromethyl)pyrimidin-5-yl)pyrrolidin-3-yl)methyl)piperidine-3,4,5-triol | 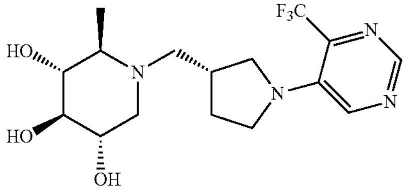 [SMILES: C[C@@H]1[C@@H](O)[C@H](O)[C@@H](O)CN1C[C@H]1CCN(c2cncnc2C(F)(F)F)C1] |
| 128 | (2R,3R,4R,5S)-2-methyl-1-(((R)-1-(thiophen-3-yl)pyrrolidin-3-yl)methyl)piperidine-3,4,5-triol | 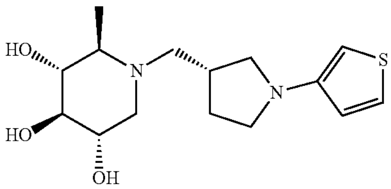 [SMILES: C[C@@H]1[C@@H](O)[C@H](O)[C@@H](O)CN1C[C@H]1CCN(c2ccsc2)C1] |

TABLE 1-continued

| Example | Name | Structure |
| --- | --- | --- |
| 129 | (2R,3R,4R,5S)-1-(((R)-1-(benzo[d]thiazol-4-yl)pyrrolidin-3-yl)methyl)-2-methylpiperidine-3,4,5-triol | 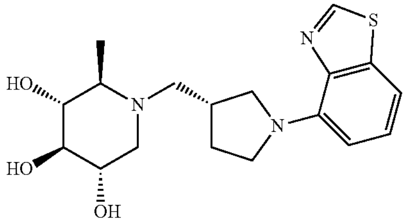 [SMILES: C[C@@H]1[C@@H](O)[C@H](O)[C@@H](O)CN1C[C@H]1CCN(c2cccc3scnc23)C1] |
| 130 | (4-(trifluoromethyl)phenyl)((R)-3-(((2R,3R,4R,5S)-3,4,5-trihydroxy-2-methylpiperidin-1-yl)methyl)pyrrolidin-1-yl)methanone | 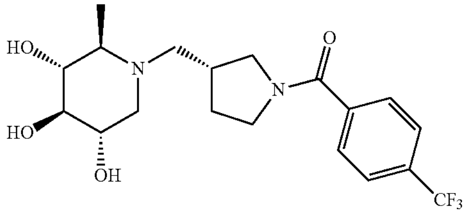 [SMILES: C[C@@H]1[C@@H](O)[C@H](O)[C@@H](O)CN1C[C@H]1CCN(C(=O)c2ccc(C(F)(F)F)cc2)C1] |
| 131 | (2R,3R,4R,5S)-2-methyl-1-(((S)-1-(2-(trifluoromethyl)phenyl)pyrrolidin-3-yl)methyl)piperidine-3,4,5-triol | 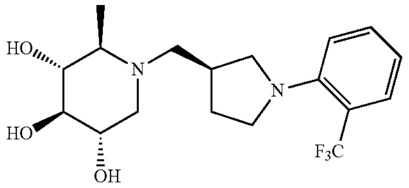 |
| 132 | (2R,3R,4R,5S)-2-methyl-1-(((S)-1-(3-(trifluoromethyl)pyridin-2-yl)pyrrolidin-3-yl)methyl)piperidine-3,4,5-triol | 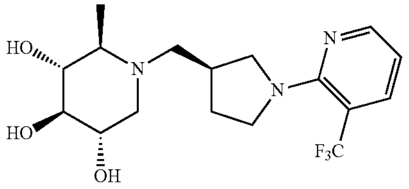 |
| 133 | (2R,3R,4R,5S)-2-methyl-1-(((S)-1-(4-(trifluoromethyl)pyridin-3-yl)pyrrolidin-3-yl)methyl)piperidine-3,4,5-triol | 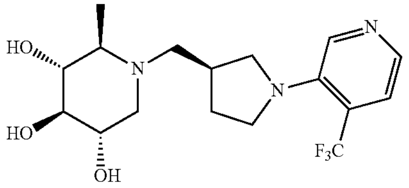 [SMILES: C[C@@H]1[C@@H](O)[C@H](O)[C@@H](O)CN1C[C@@H]1CCN(c2cnccc2C(F)(F)F)C1] |
| 134 | (2R,3R,4R,5S)-2-methyl-1-(((S)-1-(4-(trifluoromethyl)pyrimidin-5-yl)pyrrolidin-3-yl)methyl)piperidine-3,4,5-triol | 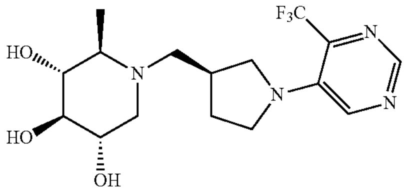 [SMILES: C[C@@H]1[C@@H](O)[C@H](O)[C@@H](O)CN1C[C@@H]1CCN(c2cncnc2C(F)(F)F)C1] |
| 135 | (2R,3R,4R,5S)-2-methyl-1-(((S)-1-(4-(trifluoromethyl)thiazol-2-yl)pyrrolidin-3-yl)methyl)piperidine-3,4,5-triol | 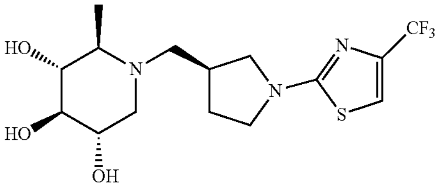 [SMILES: C[C@@H]1[C@@H](O)[C@H](O)[C@@H](O)CN1C[C@@H]1CCN(c2nc(C(F)(F)F)cs2)C1] |

TABLE 1-continued

| Example | Name | Structure |
| --- | --- | --- |
| 136 | (2R,3R,4R,5S )-2-methyl-1-(((R)-1-(o-tolyl)piperidin-3-yl)methyl)piperidine-3,4,5-triol | 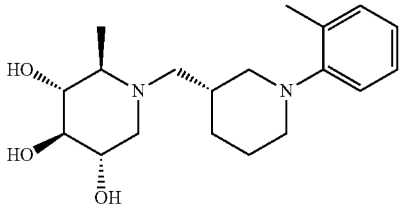 [SMILES: Cc1ccccc1N1CCC[C@H](CN2C[C@H](O)[C@@H](O)[C@H](O)[C@H]2C)C1] |
| 137 | (2R,3R,4R,5S)-1-(((R)-1-(2-fluorophenyl)piperidin-3-yl)methyl)-2-methylpiperidine-3,4,5-triol | 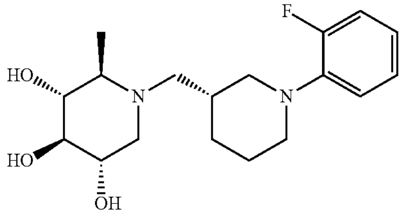 [SMILES: C[C@@H]1[C@@H](O)[C@H](O)[C@@H](O)CN1C[C@H]1CCCN(c2ccccc2F)C1] |
| 138 | (2R,3R,4R,5S)-2-methyl-1-(((R)-1-(3-(trifluoromethyl)pyridin-2-yl)piperidin-3-yl)methyl)piperidine-3,4,5-triol | 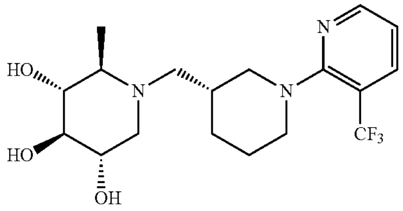 [SMILES: C[C@@H]1[C@@H](O)[C@H](O)[C@@H](O)CN1C[C@H]1CCCN(c2ncccc2C(F)(F)F)C1] |
| 139 | (2R,3R,4R,5S)-2-methyl-1-(((R)-1-(6-(trifluoromethyl)pyridin-2-yl)piperidin-3-yl)methyl)piperidine-3,4,5-triol | 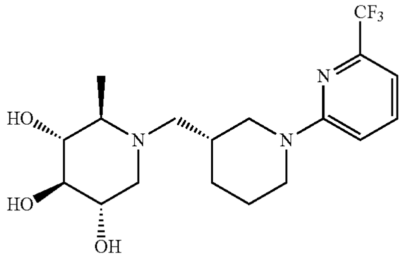 [SMILES: C[C@@H]1[C@@H](O)[C@H](O)[C@@H](O)CN1C[C@H]1CCCN(c2cccc(C(F)(F)F)n2)C1] |
| 140 | (2R,3R,4R,5S)-2-methyl-1-(((R)-1-(4-(trifluoromethyl)pyridin-3-yl)piperidin-3-yl)methyl)piperidine-3,4,5-triol | 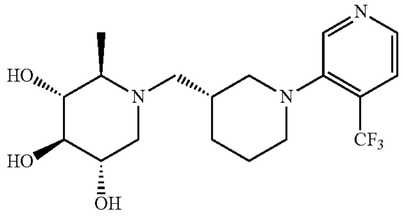 [SMILES: C[C@@H]1[C@@H](O)[C@H](O)[C@@H](O)CN1C[C@H]1CCCN(c2cnccc2C(F)(F)F)C1] |
| 141 | (2R,3R,4R,5S)-2-methyl-1-(((S)-1-(3-(trifluoromethyl)pyridin-2-yl)piperidin-3-yl)methyl)piperidine-3,4,5-triol | 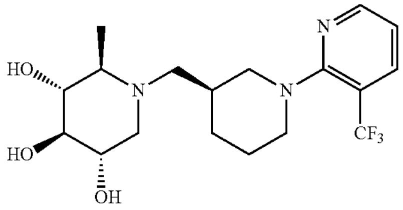 [SMILES: C[C@@H]1[C@@H](O)[C@H](O)[C@@H](O)CN1C[C@@H]1CCCN(c2ncccc2C(F)(F)F)C1] |
| 142 | (2R,3R,4R,5S)-2-methyl-1-(((S)-1-(4-(trifluoromethyl)pyridin-3-yl)piperidin-3-yl)methyl)piperidine-3,4,5-triol | 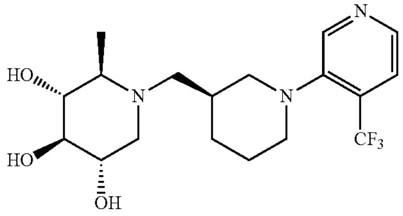 [SMILES: C[C@@H]1[C@@H](O)[C@H](O)[C@@H](O)CN1C[C@@H]1CCCN(c2cnccc2C(F)(F)F)C1] |

TABLE 1-continued

| Example | Name | Structure |
| --- | --- | --- |
| 143 | (2R,3R,4R,5S)-2-methyl-1-(((S)-1-(6-(trifluoromethyl)pyridin-2-yl)piperidin-3-yl)methyl)piperidine-3,4,5-triol | 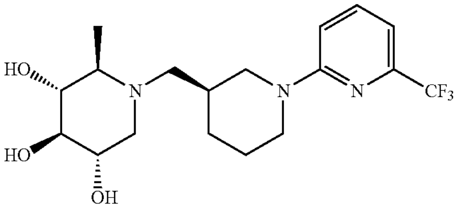 [SMILES: C[C@@H]1[C@@H](O)[C@H](O)[C@@H](O)CN1C[C@@H]1CCCN(c2cccc(C(F)(F)F)n2)C1] |
| 144 | (2R,3R,4R,5S)-2-methyl-1-(((S)-1-(4-(trifluoromethyl)thiazol-2-yl)piperidin-3-yl)methyl)piperidine-3,4,5-triol | 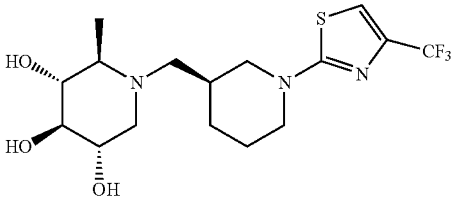 [SMILES: C[C@@H]1[C@@H](O)[C@H](O)[C@@H](O)CN1C[C@@H]1CCCN(c2nc(C(F)(F)F)cs2)C1] |
| 145 | (2S,3R,4R,5S)-2-(fluoromethyl)-1-((4-isopropylcyclohexyl)methyl)piperidine-3,4,5-triol | 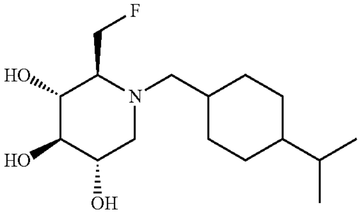 [SMILES: CC(C)C1CCC(CN2C[C@H](O)[C@@H](O)[C@H](O)[C@H]2CF)CC1] |
| 146 | (2S,3R,4R,5S)-1-((4-(tert-butyl)cyclohexyl)methyl)-2-(fluoromethyl)piperidine-3,4,5-triol | 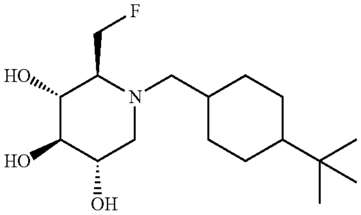 [SMILES: CC(C)(C)C1CCC(CN2C[C@H](O)[C@@H](O)[C@H](O)[C@H]2CF)CC1] |
| 147 | (2S,3R,4R,5S)-2-(fluoromethyl)-1-(((1r,4S)-4-(trifluoromethyl)cyclohexyl)methyl) piperidine-3,4,5-triol | 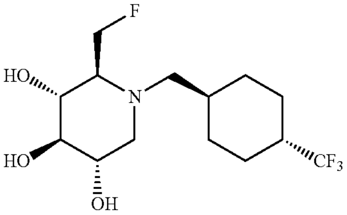 [SMILES: O[C@H]1[C@H](O)[C@@H](O)CN(C[C@H]2CC[C@H](C(F)(F)F)CC2)[C@@H]1CF] |
| 148 | (2S,3R,4R,5S)-2-(fluoromethyl)-1-phenethylpiperidine-3,4,5-triol | 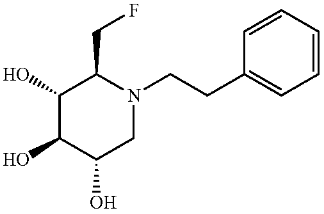 [SMILES: O[C@H]1[C@H](O)[C@@H](O)CN(CCc2ccccc2)[C@@H]1CF] |
| 149 | (2S,3R,4R,5S)-2-(fluoromethyl)-1-(2-fluorophenethyl)piperidine-3,4,5-triol | 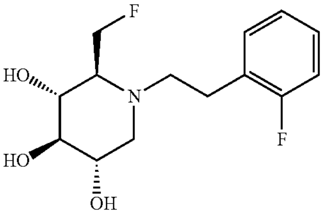 [SMILES: O[C@H]1[C@H](O)[C@@H](O)CN(CCc2ccccc2F)[C@@H]1CF] |

TABLE 1-continued

| Example | Name | Structure |
|---|---|---|
| 150 | (2S,3R,4R,5S)-1-(2,6-difluoro-4-isopropylphenethyl)-2-(fluoromethyl)piperidine-3,4,5-triol | 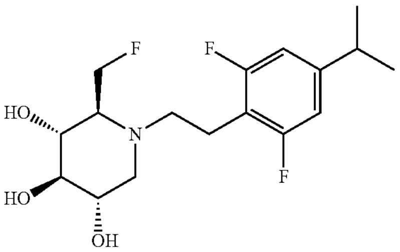 [SMILES: CC(C)c1cc(F)c(CCN2C[C@H](O)[C@@H](O)[C@H](O)[C@H]2CF)c(F)c1] |
| 151 | (2S,3R,4R,5S)-1-(2-(3,5-difluoro-[1,1'-biphenyl]-4-yl)ethyl)-2-(fluoromethyl)piperidine-3,4,5-triol | 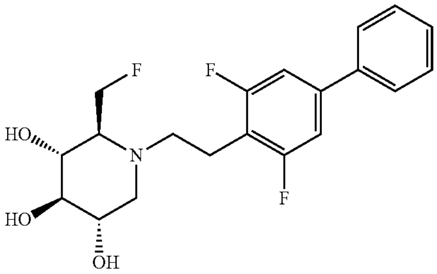 [SMILES: O[C@H]1[C@H](O)[C@@H](O)CN(CCc2c(F)cc(-c3ccccc3)cc2F)[C@@H]1CF] |
| 152 | (2S,3R,4R,5S)-1-(2-(6-fluorobenzo[d][1,3]dioxol-5-yl)ethyl)-2-(fluoromethyl)piperidine-3,4,5-triol | 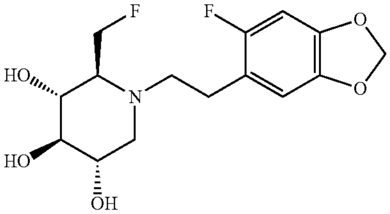 [SMILES: O[C@H]1[C@H](O)[C@@H](O)CN(CCc2cc3c(cc2F)OCO3)[C@@H]1CF] |
| 153 | (2S,3R,4R,5S)-1-(2-(2,3-dihydrobenzo[b][1,4]dioxin-6-yl)ethyl)-2-(fluoromethyl)piperidine-3,4,5-triol | 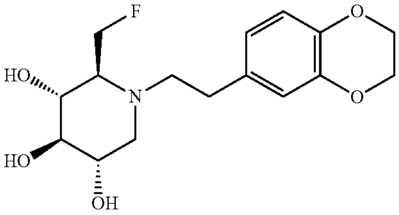 [SMILES: O[C@H]1[C@H](O)[C@@H](O)CN(CCc2ccc3c(c2)OCCO3)[C@@H]1CF] |
| 154 | (2S,3R,4R,5S)-2-(fluoromethyl)-1-((1-phenylpiperidin-4-yl)methyl)piperidine-3,4,5-triol | 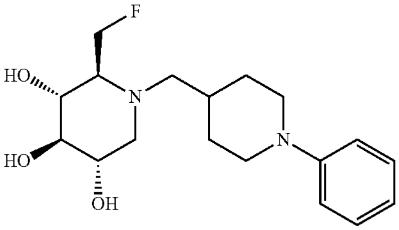 [SMILES: O[C@H]1[C@H](O)[C@@H](O)CN(CC2CCN(c3ccccc3)CC2)[C@@H]1CF] |
| 155 | (2S,3R,4R,5S)-2-(fluoromethyl)-1-((1-(4-(trifluoromethyl)phenyl)piperidin-4-yl)methyl)piperidine-3,4,5-triol | 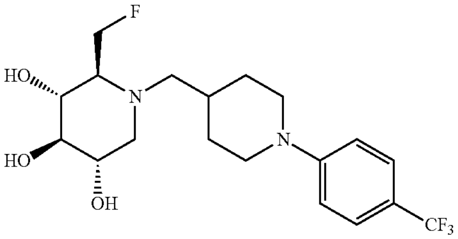 [SMILES: O[C@H]1[C@H](O)[C@@H](O)CN(CC2CCN(c3ccc(C(F)(F)F)cc3)CC2)[C@@H]1CF] |

TABLE 1-continued

| Example | Name | Structure |
| --- | --- | --- |
| 156 | (2S,3R,4R,5S)-2-(difluoromethyl)-1-phenethylpiperidine-3,4,5-triol | 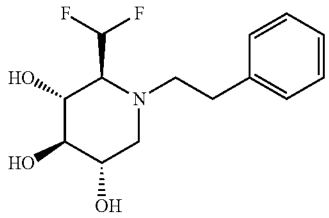 [SMILES: O[C@H]1[C@H](O)[C@@H](O)CN(CCc2ccccc2)[C@@H]1C(F)F] |
| 157 | (2S,3R,4R,5S)-1-(2-fluorophenethyl)-2-methylpiperidine-3,4,5-triol | 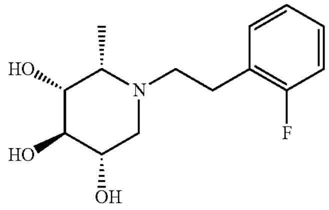 [SMILES: C[C@H]1[C@@H](O)[C@H](O)[C@@H](O)CN1CCc1ccccc1F] |
| 158 | (2S,3R,4R,5S)-1-(4-butoxy-2,6-difluorophenethyl)-2-methylpiperidine-3,4,5-triol | 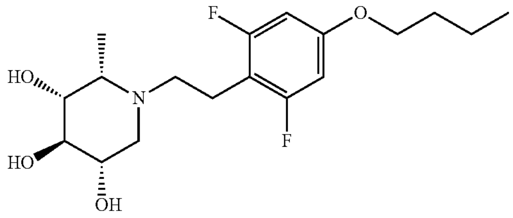 [SMILES: CCCCOc1cc(F)c(CCN2C[C@H](O)[C@@H](O)[C@H](O)[C@@H]2C)c(F)c1] |
| 159 | (2R,3R,4R,5S)-2-(fluoromethyl)-1-(2-fluorophenethyl)piperidine-3,4,5-triol | 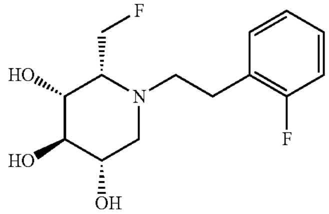 [SMILES: O[C@H]1[C@H](O)[C@H](CF)N(CCc2ccccc2F)C[C@@H]1O] |
| 160 | (2R,3R,4R,5S)-1-(4-butoxy-2,6-difluorophenethyl)-2-(fluoromethyl)piperidine-3,4,5-triol | 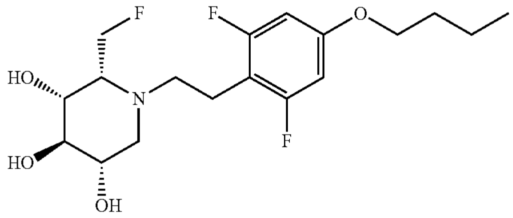 [SMILES: CCCCOc1cc(F)c(CCN2C[C@H](O)[C@@H](O)[C@H](O)[C@@H]2CF)c(F)c1] |
| 161 | (2R,3R,4R,5S)-1-(3-fluorophenethyl)-2-methylpiperidine-3,4,5-triol | 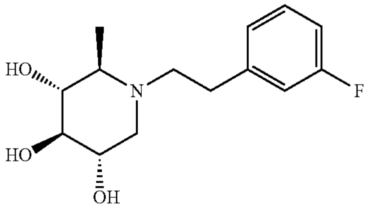 [SMILES: C[C@@H]1[C@@H](O)[C@H](O)[C@@H](O)CN1CCc1cccc(F)c1] |
| 162 | (2R,3R,4R,5S)-1-(4-fluorophenethyl)-2-methylpiperidine-3,4,5-triol | 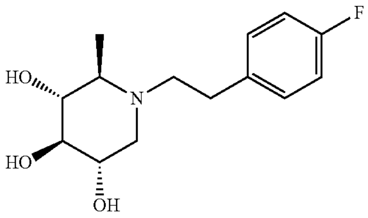 [SMILES: C[C@@H]1[C@@H](O)[C@H](O)[C@@H](O)CN1CCc1ccc(F)cc1] |

TABLE 1-continued

| Example | Name | Structure |
| --- | --- | --- |
| 163 | (2R,3R,4R,5S)-1-(3,4-dichlorophenethyl)-2-methylpiperidine-3,4,5-triol | 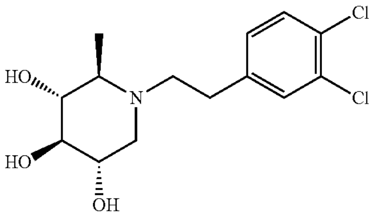 [SMILES: C[C@@H]1[C@@H](O)[C@H](O)[C@@H](O)CN1CCc1ccc(Cl)c(Cl)c1] |
| 164 | (2R,3R,4R,5S)-2-methyl-1-(3-(trifluoromethyl)phenethyl)piperidine-3,4,5-triol | 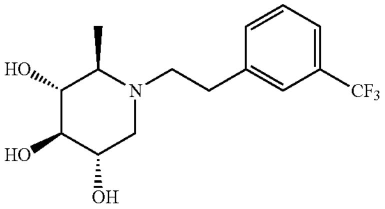 [SMILES: C[C@@H]1[C@@H](O)[C@H](O)[C@@H](O)CN1CCc1cccc(C(F)(F)F)c1] |
| 165 | (2R,3R,4R,5S)-2-methyl-1-(4-(trifluoromethyl)phenethyl)piperidine-3,4,5-triol | 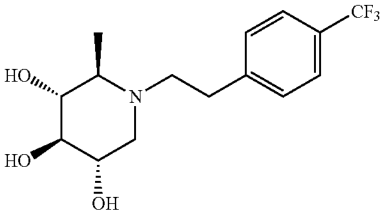 [SMILES: C[C@@H]1[C@@H](O)[C@H](O)[C@@H](O)CN1CCc1ccc(C(F)(F)F)cc1] |
| 166 | (2R,3R,4R,5S)-1-(4-(3,5-dimethylisoxazol-4-yl)-2,6-difluorophenethyl)-2-methylpiperidine-3,4,5-triol | 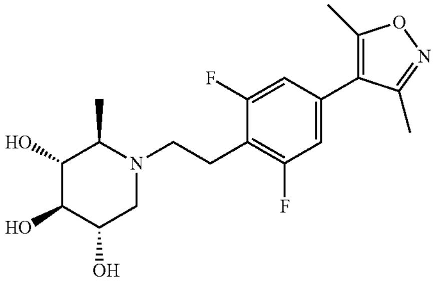 [SMILES: Cc1noc(C)c1-c1cc(F)c(CCN2C[C@H](O)[C@@H](O)[C@H](O)[C@H]2C)c(F)c1] |
| 167 | (2R,3R,4R,5S)-1-(4-(3,5-dimethyl-1H-pyrazol-4-yl)-2,6-difluorophenethyl)-2-methylpiperidine-3,4,5-triol | 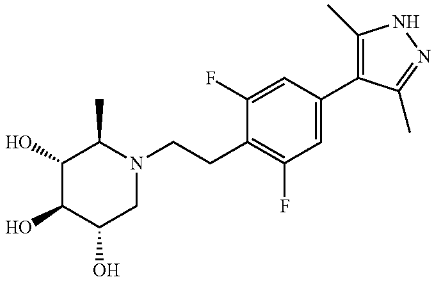 [SMILES: Cc1n[nH]c(C)c1-c1cc(F)c(CCN2C[C@H](O)[C@@H](O)[C@H](O)[C@H]2C)c(F)c1] |
| 168 | (2R,3R,4R,5S)-2-methyl-1-(((R)-1-(4-(trifluoromethyl)thiazol-2-yl)pyrrolidin-3-yl)methyl)piperidine-3,4,5-triol | 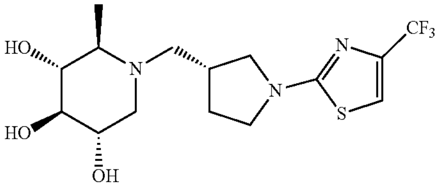 [SMILES: C[C@@H]1[C@@H](O)[C@H](O)[C@@H](O)CN1C[C@H]1CCN(c2nc(C(F)(F)F)cs2)C1] |

TABLE 1-continued

| Example | Name | Structure |
|---|---|---|
| 169 | (2R,3R,4R,5S)-1-(((R)-1-(benzo[d]oxazol-2-yl)pyrrolidin-3-yl)methyl)-2-methylpiperidine-3,4,5-triol | 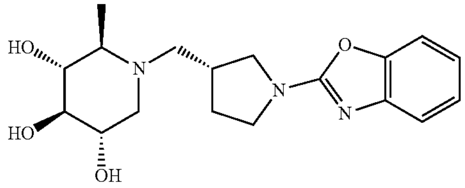 [SMILES: C[C@@H]1[C@@H](O)[C@H](O)[C@@H](O)CN1C[C@H]1CCN(c2nc3ccccc3o2)C1] |
| 170 | (2R,3R,4R,5S)-1-(((R)-1-(benzo[d]thiazol-2-yl)pyrrolidin-3-yl)methyl)-2-methylpiperidine-3,4,5-triol | 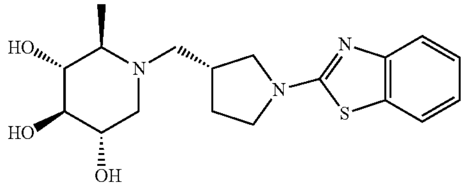 [SMILES: C[C@@H]1[C@@H](O)[C@H](O)[C@@H](O)CN1C[C@H]1CCN(c2nc3ccccc3s2)C1] |
| 171 | (2R,3R,4R,5S)-1-(((R)-1-(5-isopropylthiazol-2-yl)piperidin-3-yl)methyl)-2-methylpiperidine-3,4,5-triol | 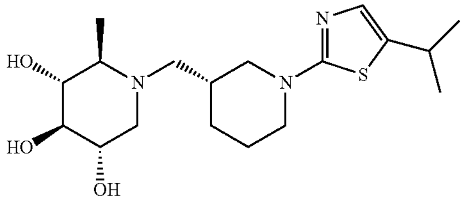 [SMILES: CC(C)c1cnc(N2CCC[C@H](CN3C[C@H](O)[C@@H](O)[C@H](O)[C@H]3C)C2)s1] |
| 172 | (2R,3R,4R,5S)-2-methyl-1-(((R)-1-(4-(trifluoromethyl)thiazol-2-yl)piperidin-3-yl)methyl)piperidine-3,4,5-triol | 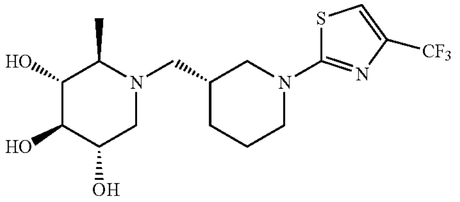 [SMILES: C[C@@H]1[C@@H](O)[C@H](O)[C@@H](O)CN1C[C@H]1CCCN(c2nc(C(F)(F)F)cs2)C1] |
| 173 | (2R,3R,4R,5S)-2-methyl-1-(((R)-1-(2-(trifluoromethyl)pyridin-3-yl)piperidin-3-yl)methyl)piperidine-3,4,5-triol | 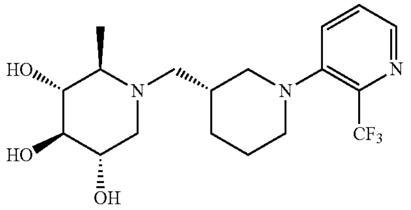 [SMILES: C[C@@H]1[C@@H](O)[C@H](O)[C@@H](O)CN1C[C@H]1CCCN(c2cccnc2C(F)(F)F)C1] |
| 174 | (2R,3R,4R,5S)-1-(((R)-1-(benzo[d]thiazol-2-yl)piperidin-3-yl)methyl)-2-methylpiperidine-3,4,5-triol | 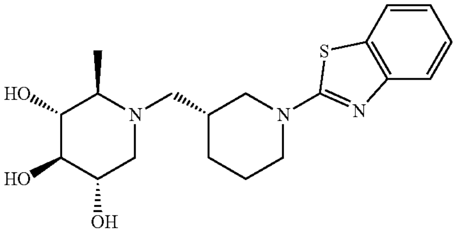 [SMILES: C[C@@H]1[C@@H](O)[C@H](O)[C@@H](O)CN1C[C@H]1CCCN(c2nc3ccccc3s2)C1] |
| 175 | (2R,3R,4R,5S)-1-(((R)-1-(benzo[d]thiazol-4-yl)piperidin-3-yl)methyl)-2-methylpiperidine-3,4,5-triol | 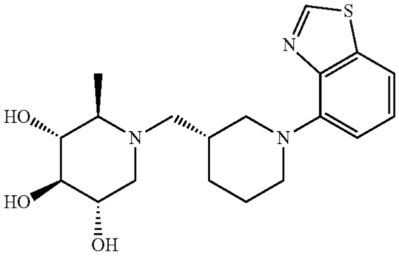 [SMILES: C[C@@H]1[C@@H](O)[C@H](O)[C@@H](O)CN1C[C@H]1CCCN(c2cccc3scnc23)C1] |

As will be appreciated by a person skilled in the art, Formula (I) above may also be represented alternatively as follows:

(I)

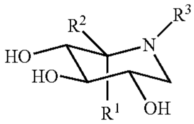

As used herein the singular forms "a", "and", and "the" include plural referents unless the context clearly dictates otherwise. For example, "a compound" refers to one or more of such compounds, while "the enzyme" includes a particular enzyme as well as other family member equivalents thereof as known to those skilled in the art.

Throughout this application, it is contemplated that the term "compound" or "compounds" refers to the compounds discussed herein and includes precursors and derivatives of the compounds, including acyl-protected derivatives, and pharmaceutically acceptable salts of the compounds, precursors, and derivatives. The invention also includes prodrugs of the compounds, pharmaceutical compositions including the compounds and a pharmaceutically acceptable carrier, and pharmaceutical compositions including prodrugs of the compounds and a pharmaceutically acceptable carrier.

The compounds of the present invention may contain one or more additional asymmetric centers beyond those specified in Formula (I), including any one or more of Formula (Ia)-(In), and can thus occur as single enantiomers, diastereomeric mixtures and individual diastereomers. Such additional asymmetric centers may be present depending upon the nature of the various substituents on the molecule. Each such additional asymmetric center will independently produce two optical isomers and it is intended that all such possible optical isomers and diastereomers in mixtures and as pure or partially purified compounds are included within the ambit of this invention. Any formulas, structures or names of compounds described in this specification that do not specify a particular stereochemistry of an additional asymmetric center are meant to encompass any and all existing isomers as described above and mixtures thereof in any proportion. When stereochemistry of an additional asymmetric center is specified, the invention is meant to encompass that particular isomer in pure form or as part of a mixture with other isomers in any proportion.

"Alkyl" refers to a straight or branched hydrocarbon chain group consisting solely of carbon and hydrogen atoms, containing no unsaturation and including, for example, from one to ten carbon atoms, such as 1, 2, 3, 4, 5, 6, 7, 8, 9, or 10 carbon atoms, and which is attached to the rest of the molecule by a single bond. In alternative embodiments, the alkyl group may contain from one to eight carbon atoms, such as 1, 2, 3, 4, 5, 6, 7, or 8 carbon atoms. In alternative embodiments, the alkyl group may contain from one to six carbon atoms, such as 1, 2, 3, 4, 5, or 6 carbon atoms. Unless stated otherwise specifically in the specification, the alkyl group may be optionally substituted by one or more substituents as described herein. Unless stated otherwise specifically herein, it is understood that the substitution can occur on any carbon of the alkyl group.

"Cycloalkyl" refers to a stable monovalent monocyclic, bicyclic or tricyclic hydrocarbon group consisting solely of carbon and hydrogen atoms, having for example from 3 to 15 carbon atoms, and which is saturated and attached to the rest of the molecule by a single bond. In alternative embodiments, the cycloalkyl group may contain from three to six carbon atoms, such as 3, 4, 5, or 6 carbon atoms. Unless otherwise stated specifically herein, the term "cycloalkyl" is meant to include cycloalkyl groups which are optionally substituted as described herein.

"Alkoxy" refers to a group of the formula $—OR_a$, where each $R_a$ is independently a $C_{1-10}$ alkyl or a $C_{1-6}$ alkyl or a $C_{1-5}$ alkyl group as described herein. The alkoxy group(s) may be optionally substituted as described herein.

"Optional" or "optionally" means that the subsequently described event of circumstances may or may not occur, and that the description includes instances where the event or circumstance occurs one or more times and instances in which it does not. For example, "optionally substituted alkyl" means that the alkyl group may or may not be substituted and that the description includes both substituted alkyl groups and alkyl groups having no substitution, and that the alkyl groups may be substituted one or more times. Examples of optionally substituted alkyl groups include, without limitation, methyl, ethyl, propyl, butyl, pentyl, hexyl, isopropyl, isobutyl, sec-butyl, tert-butyl, etc. Examples of suitable optional substituents include, without limitation, H, F, Cl, $CH_3$, OH, $OCH_3$, $CF_3$, $CHF_2$, $CH_2F$, and CN.

Therapeutic Indications

The invention provides, in part, methods of treating conditions that are modulated, directly or indirectly, by a GBA2 enzyme or GBA2 activity levels, for example, a condition that is benefited by inhibiting a GBA2 enzyme or by a reduction of GBA2 enzyme activity levels. Such conditions may include, without limitation, neurological diseases, such as Alzheimer's disease, Parkinson's disease, multiple sclerosis, Huntington's disease, and amyotrophic lateral sclerosis (ALS), and lysosomal storage diseases, such as Gaucher disease, Niemann-Pick type C disease, mucolipidosis type IV, and Sandhoff disease, and liver diseases, such as non-alcoholic steatohepatitis (NASH). Thus, one or more of the compounds of the invention may be used to treat a subject at risk for developing, or already diagnosed with, various neurological or other diseases. The term "treating" as used herein may include treatment, prevention, and/or amelioration.

In alternative embodiments, one or more of the compounds of the invention may also be useful in the treatment of diseases or disorders related to deficiency or over-expression of GBA2 or accumulation or depletion of glucosylceramide, or any disease or disorder responsive to glycosidase inhibitor therapy, or glycosidase inhibition therapy. Such diseases and disorders may include, but are not limited to, neurological diseases, such as Alzheimer's disease, Parkinson's disease, multiple sclerosis, Huntington's disease, and amyotrophic lateral sclerosis (ALS), and lysosomal storage diseases, such as Gaucher disease, Niemann-Pick type C disease, mucolipidosis type IV, and Sandhoff disease, and liver diseases, such as non-alcoholic steatohepatitis (NASH). Such diseases and disorders may also include diseases or disorders related to accumulation or deficiency in the enzyme glucosylceramide synthase, or dysregulation of glycosphingolipid metabolism and/or homeostasis. Also included is a method of protecting or treating target cells expressing GBA2, the dysregulation of which may result in disease or pathology.

In alternative embodiments, the invention provides methods of reducing levels of GBA2 enzyme activity in animal subjects, such as veterinary and human subjects. This reduction of GBA2 activity levels may be useful for the prevention or treatment of neurological or neurodegenerative diseases (e.g. Alzheimer's disease, Parkinson's disease, multiple sclerosis, Huntington's disease, and amyotrophic lateral sclerosis (ALS)); providing neuroprotective effects; preventing damage to dopaminergic neurons; and the prevention or treatment of lysosomal storage diseases (e.g. Gaucher disease, Niemann-Pick type C disease, mucolipidosis type IV, and Sandhoff disease); and the prevention or treatment of liver diseases (e.g. non-alcoholic steatohepatitis (NASH)).

In alternative embodiments, the invention provides methods of inhibiting a GBA2 enzyme in animal subjects, such as veterinary and human subjects.

In alternative embodiments, the invention provides methods of reducing CNS inflammation in animal subjects, such as veterinary and human subjects. Disease states of interest may include neurodegenerative diseases such as Alzheimer's disease, Parkinson's disease, multiple sclerosis, Huntington's disease, and amyotrophic lateral sclerosis (ALS), in which neuroinflammation is implicated in disease pathogenesis. In some embodiments, a compound according to the invention may be used to prevent, treat, or ameliorate neuroinflammation by reducing GBA2 enzyme activity levels, thereby providing therapeutic benefit.

In alternative embodiments, the invention provides methods of inhibiting aggregation of alpha-synuclein protein, or inhibiting formation of Lewy bodies, in animal subjects, such as veterinary and human subjects. Disease states of interest may include Parkinson's disease (PD) and related neurodegenerative synucleinopathies, in which abnormal aggregation of the alpha-synuclein protein is implicated in disease pathogenesis. In some embodiments, a compound according to the invention may be used to block aggregation of alpha-synuclein protein by reducing GBA2 enzyme activity levels, thereby providing therapeutic benefit.

Neurological diseases that may be treated with a compound of the invention include, without limitation: Alzheimer's disease, Parkinson's disease, multiple sclerosis, Huntington's disease, amyotrophic lateral sclerosis (ALS), amyotrophic lateral sclerosis with cognitive impairment (ALSci), addiction, anxiety, argyrophilic grain dementia, ataxia-telangiectasia (A-T), attention deficit/hyperactivity disorder (ADHD), autism spectrum disorder (ASD), Becker muscular dystrophy (BMD), bipolar disorder (BD), Bluit disease, cerebellar ataxia, Charcot-Marie-Tooth disease (CMT), chronic fatigue syndrome, corticobasal degeneration (CBD), dementia pugilistica, dementia with Lewy bodies (DLB), Dejerine-Sottas disease, diffuse neurofibrillary tangles with calcification, Down's syndrome, Duchenne muscular dystrophy (DMD), epilepsy, essential tremor (ET), familial British dementia, familial Danish dementia, fibromyalgia, frontotemporal dementia with parkinsonism linked to chromosome 17 (FTDP-17), Friedreich's ataxia, Gerstmann-Straussler-Scheinker disease, glaucoma, Guadeloupean parkinsonism, Guillain-Barré syndrome, Hallevorden-Spatz disease (neurodegeneration with brain iron accumulation type 1), insomnia, Lambert-Eaton myasthenic syndrome (LEMS), major depressive disorder (MDD), migraine, mild cognitive impairment (MCI), multi-infarct dementia, multiple system atrophy (MSA), myasthenia gravis, myotonic dystrophy (including types DM1 and DM2), neuronal ceroid lipofuscinosis (including types 1, 2, 3, 4, 5, 6, 7, 8, 9, and 10), neuropathy (including peripheral neuropathy, autonomic neuropathy, neuritis, and diabetic neuropathy), oculopharyngeal muscular dystrophy, pain, pallido-ponto-nigral degeneration, parkinsonism-dementia complex of Guam, Pick's disease (PiD), post-encephalitic parkinsonism (PEP), primary lateral sclerosis (PLS), prion diseases (including Creutzfeldt-Jakob Disease (CJD), variant Creutzfeldt-Jakob Disease (vCJD), fatal familial insomnia, and kuru), progressive supercortical gliosis, progressive supranuclear palsy (PSP), Richardson's syndrome, schizophrenia, seizures, spinal cord injury, spinal muscular atrophy (SMA), spinocerebellar ataxia (including types 1, 2, 3, 4, 5, 6, 7, 8, 10, 11, 12, 13, 14, 16, 17, 18, 19, 20, 21, 22, 23, 25, 26, 27, 28, and 29), stroke, subacute sclerosing panencephalitis, tangle-only dementia, tardive dyskinesia, Tourette syndrome (TS), vascular dementia, and Wilson's disease.

Lysosomal storage diseases that may be treated with a compound of the invention may include, without limitation: Gaucher disease (including types I, II, and III), Niemann-Pick disease (including types A, B, and C), mucolipidosis (including types I, II, III, IV, VI, and VII), cerebrotendineous xanthomatosis, Fabry disease, Farber disease, GM1 gangliosidosis, Krabbe disease, metachromatic leukodystrophy (MLD), multiple sulfatase deficiency, Pompe disease, Sandhoff disease, and Tay-Sach's disease.

Liver diseases that may be treated with a compound of the invention may include, without limitation: non-alcoholic fatty liver disease (NAFLD), non-alcoholic steatohepatitis (NASH), Alagille syndrome, alcohol-related liver disease, alpha-1 antitrypsin deficiency, autoimmune hepatitis, autoimmune cholangitis, benign liver tumors, biliary atresia, cirrhosis, Crigler-Najjar syndrome, drug-induced liver injury (DILI), galactosemia, Gilbert syndrome, hemochromatosis, hepatic encephalopathy, hepatocellular carcinoma (HCC), intrahepatic cholestasis of pregnancy (ICP), lysosomal acid lipase deficiency (LAL-D), liver cysts, liver cancer, newborn jaundice, primary biliary cholangitis (PBC), primary sclerosing cholangitis (PSC), Reye syndrome, type I glycogen storage disease, or viral hepatitis (including types A, B, C, D, and E).

In some embodiments, a compound according to the invention may be useful in the treatment of a disorder in which the regulation of GBA2 enzyme activity levels are implicated, or any condition as described herein.

Other conditions that may be treated using one or more of the compounds according the invention are those triggered, affected, or in any other way correlated with levels of GBA2 enzyme activity. It is expected that one or more of the compounds of this invention may be useful for the treatment of such conditions and in particular, but not limited to, Parkinson's disease, Gaucher disease, Niemann-Pick type C disease, mucolipidosis type IV, and Sandhoff disease.

Pharmaceutical & Veterinary Compositions, Dosages, and Administration

Pharmaceutical compositions including compounds according to the invention, or for use according to the invention, are contemplated as being within the scope of the invention.

In some embodiments, pharmaceutical compositions including an effective amount of a compound of Formula (I), including any one or more of Formula (Ia)-(In), are provided.

The compounds of Formula (I), including any one or more of Formula (Ia)-(In), and their pharmaceutically acceptable salts, enantiomers, solvates, or derivatives may be useful because they may have pharmacological activity in animals, including humans. In some embodiments, one or more of the compounds according to the invention may be stable in plasma, when administered to a subject, such as a human.

In general, a compound according to the invention may be administered to a subject in need thereof, or by contacting a cell or a sample, for example, with a pharmaceutical composition comprising a therapeutically effective amount of the compound according to Formula (I), including any one or more of Formula (Ia)-(In).

In some embodiments, a compound according to the invention, or for use according to the invention, may be provided in combination with any other active agents or pharmaceutical compositions where such combined therapy may be useful to inhibit GBA2 activity levels, for example, to treat neurological diseases, or lysosomal storage diseases, or liver diseases, or any condition described herein. In some embodiments, a compound according to the invention, or for use according to the invention, may be provided in combination with one or more agents useful in the prevention or treatment of Parkinson's disease. Examples of such agents may include, without limitation:

- Levodopa (L-DOPA);
- A peripheral DOPA decarboxylase inhibitor (DDCI), such as Carbidopa (Lodosyn®);
- Combined carbidopa/levodopa (Kinson®, Sinemet®, Parcopa®, Atamet®);
- Combined carbidopa/levodopa/entacapone (Stalevo®);
- Amantadine (Symmetrel®);
- Dopamine antagonists, such as bromocriptine (Cycloset®, Parlodel®), pergolide (Permax®), pramipexole (Mirapexin®, Sifrol®, Mirapex®), ropinirole (Ronirol®, Adartrel®, Requip®), piribedil (Trivastal Retard®, Trastal®, Trivastan®, Clarium®, Pronoran®), cabergoline (Cabaser®, Dostinex®), apomorphine (Ixense®, Spontane®, Uprima®, Apokyn®), Lisuride® (Dopergin®, Proclacam®, Revanil®), rotigotine (Neupro®), Ciladopa® (AY-27,110), Dihydrexidine® (DAR-0100), Dinapsoline®, Doxanthrine®, epicriptine (beta-dihydroergocryptine), N-n-propylnorapomorphine (NPA), quinagolide (Norprolac®), Roxindole® (EMD-49,980), Sumanirole® (PNU-95,666), pardoprunox, aplindore, etc.;
- Monoamine oxidase-B (MAO-B) inhibitors, such as selegiline (Anipryl®, L-deprenyl®, Eldepryl®, Emsam®, Zelapar®) rasagiline (Azilect®, AGN 1135), safinamide, etc.;
- Anticholinergics, such as benzatropine (benztropine, Cogentin®), diphenhydramine (Benadryl®, Dimedrol®, Daedalon®, Nytol®), orphenadrine (Norflex®, Mephenamin®, Disipal®, Banflex®, Flexon®, Biorphen®, Brocasipal®, Dolan®, Norgesic®, Orfen-Ace®), trihexyphenidyl (Artane®, Apo-Trihex®, Parkin®, Pacitane®, benzhexol, trihex), etc.;
- Catechol-O-methyl transferase (COMT) inhibitors, such as entacapone (COMTan®), tolcapone (Tasmar®), nitecapone, nebicapone, etc.;
- Adenosine $A_{2A}$ receptor antagonists, such as istradefylline (KW-6002), preladenant, fipamezole (JP-1730), SCH-420814, BIIA-014, Lu AA4707, etc.;
- Metabotropic glutamate receptor 5 (mgluR5) modulators, such as dipraglurant, etc.;
- AMPA receptor antagonists, such as perampanel (Fycompa®), etc.;
- Anticonvulsants, such as zonisamide (Tremode®), etc.;
- Nicotinic acetylcholine receptor (nAChR) agonists, such as nicotine, ABT-418, WAY-317,538 (SEN-12333), EVP-6124, MEM 3454, Nefiracetam, etc.
- Acetylcholine esterase inhibitors (AChEIs) such as Aricept® (Donepezil), Exelon® (Rivastigmine), Razadyne® (Razadyne ER®, Reminyl®, Nivalin®, galantamine), Cognex® (Tacrine), Huperzine A, Phenserine, Debio-9902 SR (ZT-1 SR), Zanapezil (TAK0147), ganstigmine, NP7557, etc.;
- Atypical antipsychotics, such as clozapine, etc.; or
- Modafinil (Alertec®, Modavigil®, Provigil®).

It is to be understood that combination of compounds according to the invention, or for use according to the invention, with agents useful for the treatment of Parkinson's disease is not limited to the examples described herein, but may include combination with any agent useful for the treatment of Parkinson's disease. Combination of compounds according to the invention, or for use according to the invention, and other agents useful for the treatment of Parkinson's disease may be administered separately or in conjunction. The administration of one agent may be prior to, concurrent to, or subsequent to the administration of other agent(s).

In some embodiments, a compound according to the invention, or for use according to the invention, may be provided in combination with one or more agents useful in the prevention or treatment of Gaucher disease. Examples of such agents may include, without limitation:

- Recombinant human GCase enzyme replacement therapy, such as imiglucerase (Cerezyme®), velaglucerase alfa (VPRIV®), taliglucerase alfa (Elelyso®), etc.;
- Glucosylceramide synthase inhibitors, such as EXEL-0346, Genz-123346, Eliglustat® (Genz-112638), etc.;
- Bisphosphonates, such as zoledronate (Zometa®, Zomera®, Aclasta®, Reclast®), alendronate sodium (Fosamax®), etidronate (Didronel®), clodronate (Bonefos®, Loron®), tiludronate (Skelid®), pamidronate (APD®, Aredia®), neridronate (Nerixia®), olpadronate, ibandronate (Boniva®), risedronate (Actonel®), etc.;
- Antiepileptics, such as Tegretol® (Carbatrol®, carbamazepine), Zarontin® (ethosuximide), Felbatol® (felbamate), Gabitril® (tiagabine), Keppra® (levetiracetam), Lamictal® (lamotrigine), Lyrica® (pregabalin), Neurontin® (gabapentin), Dilantin® (phenytoin), Topamax® (topiramate), Trileptal® (oxcarbazepine), Depakene® (Depakote®, valproate, valproic acid), Zonegran® (zonisamide), Valium® (diazepam), Ativan® (lorazepam) Klonopin® (clonazepam), Fycompa® (perampanel), Oxtellar XR® (oxcarbazepine), etc.; or
- Gene therapy.

It is to be understood that combination of compounds according to the invention, or for use according to the invention, with agents useful for the treatment of Gaucher disease is not limited to the examples described herein, but may include combination with any agent useful for the treatment of Gaucher disease. Combination of compounds according to the invention, or for use according to the invention, and other agents useful for the treatment of Gaucher disease may be administered separately or in conjunction. The administration of one agent may be prior to, concurrent to, or subsequent to the administration of other agent(s).

In alternative embodiments, a compound according to the invention may be supplied as a "prodrug" or as protected forms, which release the compound after administration to a subject. For example, a compound may carry a protective group which is split off by hydrolysis in body fluids, e.g., in the bloodstream, thus releasing the active compound or is oxidized or reduced in body fluids to release the compound. Accordingly, a "prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but may be converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a subject.

The term "prodrug" is also meant to include any covalently bonded carriers which release the active compound of the invention in vivo when such prodrug is administered to a subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention where a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and acetamide, formamide, and benzamide derivatives of amine functional groups in one or more of the compounds of the invention and the like.

A discussion of prodrugs may be found in "Smith and Williams' Introduction to the Principles of Drug Design," H. J. Smith, Wright, Second Edition, London (1988); Bundgard, H., *Design of Prodrugs* (1985), pp. 7-9, 21-24 (Elsevier, Amsterdam); The Practice of Medicinal Chemistry, Camille G. Wermuth et al., Ch 31, (Academic Press, 1996); A Textbook of Drug Design and Development, P. Krogsgaard-Larson and H. Bundgaard, eds. Ch 5, pgs 113 191 (Harwood Academic Publishers, 1991); Higuchi, T., et al., "Pro-drugs as Novel Delivery Systems," A.C.S. Symposium Series, Vol. 14; or in Bioreversible Carriers in Drug Design, ed. Edward B. Roche, American Pharmaceutical Association and Pergamon Press, 1987.

Suitable prodrug forms of one or more of the compounds of the invention may include embodiments in which one or more OH groups as set forth in Formula (I), including any one or more of Formula (Ia)-(In), may be protected as OC(O)R, where R may be optionally substituted $C_{1-6}$ alkyl. In these cases, the ester groups may be hydrolyzed in vivo (e.g. in bodily fluids), liberating the OH groups and releasing the active compounds. Preferred prodrug embodiments of the invention may include compounds of Formula (I), including any one or more of Formula (Ia)-(In), where one or more OH groups may be protected with acetate, for example as $OC(O)CH_3$.

Compounds according to the invention, or for use according to the invention, may be provided alone or in combination with other compounds in the presence of a liposome, a nanoparticle, an adjuvant, or any pharmaceutically acceptable carrier, diluent or excipient, in a form suitable for administration to a subject such as a mammal, for example, humans, cattle, sheep, etc. If desired, treatment with a compound according to the invention may be combined with more traditional and existing therapies for the therapeutic indications described herein. Compounds according to the invention may be provided chronically or intermittently. "Chronic" administration refers to administration of the compound(s) in a continuous mode as opposed to an acute mode, so as to maintain the initial therapeutic effect (activity) for an extended period of time. "Intermittent" administration is treatment that is not consecutively done without interruption, but rather is cyclic in nature. The terms "administration," "administrable," or "administering" as used herein should be understood to mean providing a compound of the invention to the subject in need of treatment.

"Pharmaceutically acceptable carrier, diluent or excipient" may include, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that has been approved, for example, by the United States Food and Drug Administration or other governmental agency as being acceptable for use in humans or domestic animals.

A compound of the present invention may be administered in the form of a pharmaceutically acceptable salt. In such cases, pharmaceutical compositions in accordance with this invention may comprise a salt of such a compound, preferably a physiologically acceptable salt, which are known in the art. In some embodiments, the term "pharmaceutically acceptable salt" as used herein means an active ingredient comprising compounds of Formula I, including any one or more of Formula (Ia)-(In), used in the form of a salt thereof, particularly where the salt form confers on the active ingredient improved pharmacokinetic properties as compared to the free form of the active ingredient or other previously disclosed salt form.

A "pharmaceutically acceptable salt" may include both acid and base addition salts. A "pharmaceutically acceptable acid addition salt" refers to those salts which retain the biological effectiveness and properties of the free bases, which are not biologically or otherwise undesirable, and which may be formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

A "pharmaceutically acceptable base addition salt" refers to those salts which may retain the biological effectiveness and properties of the free acids, which may not be biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. Preferred inorganic salts may be the ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases may be isopropylamine, diethylamine, ethanolamine, trimethylamine, dicyclohexylamine, choline and caffeine.

Thus, the term "pharmaceutically acceptable salt" encompasses all acceptable salts including but not limited to acetate, lactobionate, benzenesulfonate, laurate, benzoate, malate, bicarbonate, maleate, bisulfate, mandelate, bitartrate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of a compound of the present invention may be used as a dosage for modifying solubility or hydrolysis characteristics, or may be used in sustained release or prodrug formulations. Also, pharmaceutically acceptable salts of a compound of this invention may include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

Pharmaceutical formulations may typically include one or more carriers acceptable for the mode of administration of the preparation, be it by injection, inhalation, topical administration, lavage, or other modes suitable for the selected treatment. Suitable carriers may be those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water-soluble compounds such as those used for vitamin K. For enteral administration, the compound may be administered in a tablet, capsule or dissolved in liquid form. The table or capsule may be enteric coated, or in a formulation for sustained release. Many suitable formulations are known, including, polymeric or protein microparticles encapsulating a compound to be released, ointments, gels, hydrogels, or solutions which can be used topically or locally to administer a compound. A sustained release patch or implant may be employed to provide release over a prolonged period of time. Many techniques known to skilled practitioners are described in *Remington: The Science & Practice of Pharmacy* by Alfonso Gennaro, $20^{th}$ ed., Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of a compound. Other potentially useful parenteral delivery systems for modulatory compounds may include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

A compound or a pharmaceutical composition according to the present invention may be administered by oral or non-oral, e.g., intramuscular, intraperitoneal, intravenous, intracisternal injection or infusion, subcutaneous injection, transdermal or transmucosal routes. In some embodiments, a compound or pharmaceutical composition in accordance with this invention or for use in this invention may be administered by means of a medical device or appliance such as an implant, graft, prosthesis, stent, etc. Implants may be devised which are intended to contain and release such compounds or compositions. An example would be an implant made of a polymeric material adapted to release the compound over a period of time. A compound may be administered alone or as a mixture with a pharmaceutically acceptable carrier e.g., as solid formulations such as tablets, capsules, granules, powders, etc.; liquid formulations such as syrups, injections, etc.; injections, drops, suppositories, pessaryies. In some embodiments, compounds or pharmaceutical compositions in accordance with this invention or for use in this invention may be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

A compound of the invention may be used to treat animals, including mice, rats, horses, cattle, sheep, dogs, cats, and monkeys. However, a compound of the invention may also be used in other organisms, such as avian species (e.g., chickens). One or more of the compounds of the invention may also be effective for use in humans. The term "subject" or alternatively referred to herein as "patient" is intended to be referred to an animal, preferably a mammal, most preferably a human, who has been the object of treatment, observation or experiment. However, one or more of the compounds, methods and pharmaceutical compositions of the present invention may be used in the treatment of animals. Accordingly, as used herein, a "subject" may be a human, non-human primate, rat, mouse, cow, horse, pig, sheep, goat, dog, cat, etc. The subject may be suspected of having or at risk for having a condition that may require inhibition of GBA2 activity.

An "effective amount" of a compound according to the invention may include a therapeutically effective amount or a prophylactically effective amount. A "therapeutically effective amount" refers to an amount effective, at dosages and for periods of time necessary, to achieve the desired therapeutic result, such as inhibition of a GBA2, reducing GBA2 enzyme activity levels, inhibition of alpha-synuclein aggregation, or any condition described herein. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount may also be one in which any toxic or detrimental effects of the compound are outweighed by the therapeutically beneficial effects. A "prophylactically effective amount" may refer to an amount effective, at dosages and for periods of time necessary, to achieve the desired prophylactic result, such as inhibition of a GBA2, reduction of GBA2 enzyme activity levels, inhibition of alpha-synuclein aggregation, or any condition described herein. Typically, a prophylactic dose may be used in subjects prior to or at an earlier stage of disease, so that a prophylactically effective amount may be less than a therapeutically effective amount. A suitable range for therapeutically or prophylactically effective amounts of a compound may be any integer from 0.1 nM-0.1 M, 0.1 nM-0.05 M, 0.05 nM-15 M or 0.01 nM-10 μM.

In alternative embodiments, in the treatment or prevention of conditions which may require inhibition of GBA2 activity, an appropriate dosage level may generally be about 0.01 to 500 mg per kg subject body weight per day and may be administered in single or multiple doses. In some embodiments, the dosage level may be about 0.1 to about 250 mg/kg per day. It will be understood that the specific dose level and frequency of dosage for any particular patient may be varied and may depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. In general, compounds of the invention should be used without causing substantial toxicity, and as described herein, one or more of the compounds may exhibit a suitable safety profile for therapeutic use. Toxicity of a compound of the invention may be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

In the compounds of generic Formula (I), including any one or more of Formula (Ia)-(In), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I), including any one or more of Formula (Ia)-(In). For example, different isotopic forms of hydrogen (H) include protium ($^1H$), deuterium ($^2H$) and tritium (H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I), including any one or more of Formula (Ia)-(In), may be prepared by conventional techniques well known to those skilled in the art or by processes analogous to those described in the schemes and examples herein using appropriate isotopically-enriched reagents and/or intermediates.

Other Uses

In alternative embodiments, one or more of the compounds of the invention may be used in studying the physiological role of GBA2 at the cellular and organismal level. In some embodiments, one or more of the compounds may be useful in the development of animal models for studying diseases or disorders that may be related to deficiencies in GBA2, over-expression of GBA2, accumulation of glucosylceramide, depletion of glucosylceramide, accumulation of glycosphingolipids, depletion of glycosphingolipids, and for studying treatment of diseases and disorders that may be related to deficiency or over-expression of GBA2, or accumulation or depletion of glucosylceramide, or accumulation or depletion of glycosphingolipids. Such diseases and disorders may include, without limitation, neurological diseases, including Alzheimer's disease, Parkinson's disease, multiple sclerosis, Huntington's disease, and amyotrophic lateral sclerosis (ALS); lysosomal storage diseases, including Gaucher disease, Niemann-Pick type C disease, mucolipidosis type IV and Sandhoff disease; or liver diseases, including non-alcoholic steatohepatitis (NASH).

The effectiveness of a compound in treating pathology associated with a lysosomal storage disease (for example, Gaucher disease, Niemann-Pick type C disease, mucolipidosis type IV, or Sandhoff disease) may be confirmed using standard techniques, for example, by testing the ability of a compound to prevent, treat, or ameliorate disease symptoms in established cellular and/or transgenic animal models of disease.[12,13,15,16,25]_ENREF_18

Various alternative embodiments and examples of the invention are described herein. These embodiments and examples are illustrative and should not be construed as limiting the scope of the invention.

EXAMPLES

The following examples are intended to illustrate embodiments of the invention and are not intended to be construed in a limiting manner.

Abbreviations

ABCN=1,1'-azobis(cyclohexanecarbonitrile)
BzCl=benzoyl chloride
DAST=diethylaminosulfur trifluoride
DCM=dichloromethane
DIAD=diisopropyl azodicarboxylate
DIPEA=diisopropylethylamine
DMA=dimethylacetamide
DMAP=4-dimethylaminopyridine
DMF=N,N-dimethylformamide
DMP=Dess-Martin periodinane
$Et_2O$=diethyl ether
HOAc=acetic acid
LAH=lithium aluminum hydride
MeOH=methanol
MsCl=methanesulfonyl chloride
RT=room temperature
TBDMSCl=tert-butyldimethylsilyl chloride
TFA=2,2,2-trifluoroacetic acid
THE=tetrahydrofuran Example 1

(2R,3R,4R,5S)-1-(cyclohexylmethyl)-2-methylpiperidine-3,4,5-triol

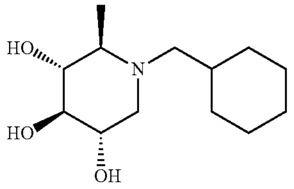 [SMILES: C[C@@H]1[C@@H](O)[C@H](O)[C@@H](O)CN1CC1CCCCC1]

To a stirred solution of (2R,3R,4R,5S)-3,4,5-tris(benzyloxy)-2-methylpiperidine (43 mg, 0.10 mmol) and cyclohexanecarboxaldehyde (23 mg, 0.20 mmol) in anhydrous MeOH (5 mL) was added HOAc (0.10 mL, 1.75 mmol) and the mixture was stirred for 30 min. $NaBH_3CN$ (13 mg, 0.20 mmol) was added and the resulting mixture was stirred at RT for 18 h. The reaction was quenched with satd. aqueous $NaHCO_3$ at 0° C. The mixture was extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-1-(cyclohexylmethyl)-2-methylpiperidine as an oil (49 mg, 95%). ESI MS m/z 514.32 $[M+H]^+$.

To a stirred solution of the above material (49 mg, 0.096 mmol) in anhydrous DCM (3 mL) was added $BCl_3$ solution (1M in DCM, 0.70 mL, 0.70 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-1-(cyclohexylmethyl)-2-methylpiperidine-3,4,5-triol as a white solid (15 mg, 64%). $^1H$ NMR (400 MHz, $CD_3OD$) δ 3.52-3.42 (m, 1H), 3.12 (t, J=9.0 Hz, 1H), 3.03 (dd, J=11.4, 4.8 Hz, 1H), 2.96 (t, J=9.1 Hz, 1H), 2.57 (dd, J=12.8, 8.9 Hz, 1H), 2.11-1.85 (m, 4H), 1.79-1.63 (m, 4H), 1.58-1.43 (m, 1H), 1.39-1.20 (m, 3H), 1.19 (d, J=6.1 Hz, 3H), 1.01-0.79 (m, 2H); ESI MS m/z 244.18 $[M+H]^+$.

Example 2

(2R,3R,4R,5S)-1-((4,4-dimethylcyclohexyl)methyl)-2-methylpiperidine-3,4,5-triol

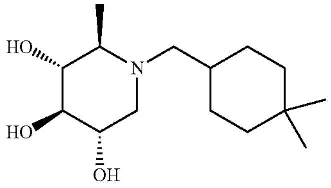 [SMILES: C[C@@H]1[C@@H](O)[C@H](O)[C@@H](O)CN1CC1CCC(C)(C)CC1]

To a solution of spiro[2.5]octan-6-ylmethanol (100 mg, 0.71 mmol) in HOAc (5 mL) was added $PtO_2$ (48 mg, 0.21 mmol). The mixture was treated with hydrogen (40 psi) for 18 h. Catalyst was filtered off through celite and the solvent was evaporated under reduced pressure. The residue was purified by silica gel chromatography to give (4,4-dimethylcyclohexyl)methanol as an oil (51 mg, 51%). $^1H$ NMR (400 MHz, $CDCl_3$) δ 3.50 (d, J=6.4 Hz, 2H), 1.70-1.55 (m, 3H), 1.49-1.37 (m, 3H), 1.29-1.08 (m, 4H), 0.93 (s, 3H), 0.90 (s, 3H).

To a solution of the above material (50 mg, 0.35 mmol) in anhydrous DCM (10 mL) at 0° C., was added DMP (194 mg, 0.46 mmol), and the mixture was stirred at 0° C. for 2 h. The mixture was quenched slowly with $Na_2S_3O_5$ solution. The mixture was extracted with DCM (3×10 mL). The combined organic layer was washed with water (2×10 mL), separated, dried over $Na_2SO_4$. After filtration, the solvent was evaporated under reduced pressure, and the residue was purified on silica gel by flash chromatography affording 4,4-dimethylcyclohexanecarbaldehyde as an oil (30 mg, not pure).

To a stirred solution of (2R,3R,4R,5S)-3,4,5-tris(benzyloxy)-2-methylpiperidine (30 mg, 0.072 mmol) and 4,4-dimethylcyclohexanecarbaldehyde (30 mg, 0.21 mmol) in anhydrous DCM (5 mL) was added HOAc (0.10 mL, 1.75 mmol) and the mixture was stirred for 30 min. $NaBH_3CN$ (13 mg, 0.20 mmol) was added and the resulting mixture was stirred at RT for 18 h. The reaction was quenched with satd. aqueous $NaHCO_3$ at 0° C. The mixture was extracted with EtOAc (3×20 mL). The combined organic layer was washed with water (2×10 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-1-((4,4-dimethylcyclohexyl)methyl)-2-methylpiperidine as an oil (10 mg, 26%). ESI MS m/z 542.34 $[M+H]^+$.

To a stirred solution of the above material (10 mg, 0.018 mmol) in anhydrous DCM (3 mL) was added $BCl_3$ solution (1M in DCM, 0.50 mL, 0.50 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-1-((4,4-dimethylcyclohexyl)methyl)-2-methylpiperidine-3,4,5-triol as a white solid (4 mg, 82%). $^1H$ NMR (400 MHz, $CD_3OD$) δ 3.52-3.43 (m, 1H), 3.12 (t, J=9.0 Hz, 1H), 3.03 (dd, J=11.4, 4.8 Hz, 1H), 2.96 (t, J=9.1 Hz, 1H), 2.62 (dd, J=12.8, 8.9 Hz, 1H), 2.11-1.93 (m, 3H), 1.77-1.67 (m, 1H), 1.57-1.48 (m, 1H), 1.47-1.37 (m, 3H), 1.33-1.01 (m, 7H), 0.92 (d, J=5.4 Hz, 6H); ESI MS m/z 272.20 $[M+H]^+$.

Example 3

(2R,3R,4R,5S)-1-((4,4-difluorocyclohexyl)methyl)-2-methylpiperidine-3,4,5-triol

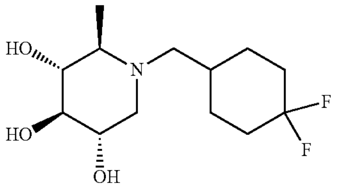 [SMILES: C[C@@H]1[C@@H](O)[C@H](O)[C@@H](O)CN1CC1CCC(F)(F)CC1]

Under $N_2$, a mixture of (2R,3R,4R,5S)-3,4,5-tris(benzyloxy)-2-methylpiperidine (0.090 g, 0.22 mmol), 4,4-difluorocyclohexanecarbaldehyde (0.080 g, 0.54 mmol) and $NaBH(OAc)_3$ (0.13 g, 0.60 mmol) in DCM (8 mL) was stirred at RT for 16 h. The reaction mixture was diluted with satd. aqueous $NaHCO_3$ (10 mL), and extracted with DCM (3×15 mL). The combined extract was dried over anhydrous $Na_2SO_4$. After filtration the solvent was evaporated under reduced pressure, and the residue was purified on silica gel by flash chromatography (EtOAc/hexanes, 1:9 to 1:6), affording (2R,3R,4R,5S)-3,4,5-tris(benzyloxy)-1-((4,4-difluorocyclohexyl)methyl)-2-methylpiperidine as a clear oil (0.10 g, 84%); ESI MS m/z 550.309 $[M+H]^+$.

A mixture of the above material (0.015 g, 0.027 mmol) and $Pd(OH)_2/C$ (20% Pd in weight, 0.015 g, 0.028 mmol) and aqueous HCl (5 N, one drop) in MeOH (3 mL) was stirred under hydrogen at one atmosphere of pressure overnight. The mixture was filtered through a celite cake, and the filtrate was collected and concentrated to dryness. The residue was neutralized with 1 M $NH_3$ in MeOH and purified on silica gel by flash chromatography (1 M $NH_3$ MeOH/DCM, 1:7), affording (2R,3R,4R,5S)-1-((4,4-difluorocyclohexyl)methyl)-2-methylpiperidine-3,4,5-triol (0.0067 g, 89%) as a white solid. $^1H$ NMR (400 MHz, $CD_3OD$) δ 3.44 (ddd, J=10.5, 9.0, 4.8 Hz, 1H), 3.10 (t, J=9.0 Hz, 1H), 3.01 (dd, J=11.3, 4.8 Hz, 1H), 2.92 (t, J=9.0 Hz, 1H), 2.59 (dd, J=12.9, 9.2 Hz, 1H), 2.05-1.93 (m, 6H), 1.77-1.66 (m, 3H), 1.63-1.58 (m, 1H), 1.30-1.10 (m, 5H, including 1.17 (d, J=6.1 Hz, 3H)); ESI MS m/z 280.162 $[M+H]^+$.

Example 4

(2R,3R,4R,5S)-1-((4,4-dichlorocyclohexyl)methyl)-2-methylpiperidine-3,4,5-triol

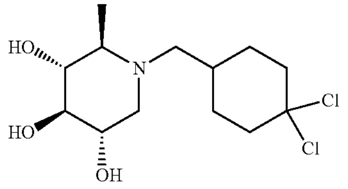 [SMILES: C[C@@H]1[C@@H](O)[C@H](O)[C@@H](O)CN1CC1CCC(Cl)(Cl)CC1]

At −78° C. and under $N_2$, to a solution of (2R,3R,4R,5S)-3,4,5-tris(benzyloxy)-1-((4,4-difluorocyclohexyl)methyl)-2-methylpiperidine (0.10 g, 0.18 mmol) in anhydrous DCM (8 mL) was added $BCl_3$ (1.0 M in DCM, 1.5 mL, 1.5 mmol), and the mixture was stirred at 0° C. for 3 h. The reaction mixture was cooled at −78° C., quenched with MeOH, and then concentrated to dryness. The residue was neutralized with a few drops of satd. aqueous $NaHCO_3$ and purified on silica gel by flash chromatography (1 M $NH_3$ in MeOH/DCM, 1:7), affording (2R,3R,4R,5S)-1-((4,4-dichlorocyclohexyl)methyl)-2-methylpiperidine-3,4,5-triol as a white solid (0.046 g, 80%). $^1H$ NMR (500 MHz, DMSO-$d_6$) δ 4.69-4.65 (m, 3H), 3.25-3.18 (m, 1H), 2.89 (td, J=8.8, 4.3 Hz, 1H), 2.83 (dd, J=11.2, 4.7 Hz, 1H), 2.69 (td, J=8.8, 5.4 Hz, 1H), 2.48-2.41 (m, 3H), 2.30-2.17 (m, 2H), 1.91-1.75 (m, 4H), 1.68-1.57 (m, 2H), 1.32-1.16 (m, 2H), 1.05 (d, J=6.0 Hz, 3H); ESI MS m/z 312.105 $[M+H]^+$.

Example 5

(2R,3R,4R,5S)-1-((4-ethylcyclohexyl)methyl)-2-methylpiperidine-3,4,5-triol

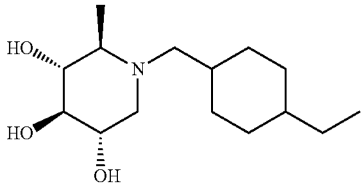 [SMILES: CCC1CCC(CN2C[C@H](O)[C@@H](O)[C@H](O)[C@H]2C)CC1]

A mixture of (2R,3R,4R,5S)-3,4,5-tris(benzyloxy)-2-methyl-1-(((1s,4S)-4-vinylcyclohexyl)methyl)piperidine (0.180 g, 0.333 mmol) and $Pd(OH)_2/C$ (20% Pd in weight, 0.20 g, 0.38 mmol) and 5 drops of concentrated HCl in MeOH (25 mL) was stirred under hydrogen at one atmosphere of pressure overnight. The mixture was filtered through a celite cake, and the filtrate was collected and concentrated under reduced pressure to dryness. The residue was neutralized with 1 M $NH_3$ in MeOH and purified on silica gel by flash chromatography (1 M $NH_3$ MeOH/DCM, 1:6), affording (2R,3R,4R,5S)-1-((4-ethylcyclohexyl)methyl)-2-methylpiperidine-3,4,5-triol as a white solid (0.083 g, 92%). $^1H$ NMR indicated the solid contains a mixture of cis and trans isomers in a ratio of cis:trans=0.65:0.35). $^1H$ NMR (400 MHz, DMSO-$d_6$) δ 4.74-4.59 (m, 3H), 3.26-3.14 (m, 1H), 2.94-2.78 (m, 2H), 2.76-2.57 (m, 1.65H), 2.40 (dd, J=12.6, 9.2 Hz, 0.35H), 1.90-1.80 (m, 1.65H), 1.79-1.69 (m, 2H), 1.64-1.56 (m, 1H), 1.51-1.11 (m, 9H), 1.06 (d, J=6.0 Hz, 1.65H), 1.03 (d, J=6.0 Hz, 1.35H), 0.90-0.69 (m, 4.35H); ESI MS m/z 272.228 $[M+H]^+$.

Example 6

(2R,3R,4R,5S)-2-methyl-1-(((1s,4S)-4-vinylcyclohexyl)methyl)piperidine-3,4,5-triol

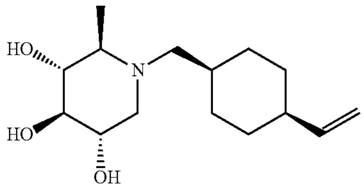 [SMILES: C=C[C@H]1CC[C@@H](CN2C[C@H](O)[C@@H](O)[C@H](O)[C@H]2C)CC1]

To a solution of cis-4-(hydroxymethyl)cyclohexanecarboxylic acid (1.00 g, 6.32 mmol) in anhydrous MeOH (25 mL) was added $SOCl_2$ (1.55 g, 13.0 mmol) dropwise, and the mixture was stirred at RT for 4 h. The solvent was then removed under reduced pressure, and the residue was diluted with satd. aqueous $NaHCO_3$ (30 mL). After extraction with DCM (3×30 mL) the combined extract was dried over anhydrous $Na_2SO_4$. After filtration the solvent was evaporated under reduced pressure to give clear liquid. The liquid was dissolved in anhydrous DMF (20 mL), and to which, at 0° C., was added imidazole (1.36 g, 20.0 mmol) and TBDMSCl (1.51 g, 10.0 mmol). After stirring at RT for 16 h the reaction mixture was diluted with brine (60 mL) and extracted with EtOAc (3×30 mL). The combined extract was washed with brine (2×50 mL) and dried over anhydrous $Na_2SO_4$. After filtration the solvent was evaporated under reduced pressure, and the residue was purified on silica gel by flash chromatography (EtOAc/hexanes, 1:9), affording (1s,4s)-methyl 4-(((tert-butyldimethylsilyl)oxy)methyl)cyclohexanecarboxylate as a clear liquid (1.60 g, 88%, two steps).

At 0° C. and under $N_2$, to a solution of the above material (1.60 g, 5.58 mmol) in anhydrous THE (25 mL) was added LAH (0.380 g, 10.0 mmol), and the mixture was stirred at 0° C. for 2 h. Wet sodium sulfate heptahydrate (50 g) was added to quench the reaction, and the suspension was stirred for 30 min. After filtration the solvent was evaporated under reduced pressure, and the residue was purified on silica gel by flash chromatography (EtOAc/hexanes, 1:4 to 1:2) to give a clear liquid. The liquid was dissolved in DCM (40 mL), and to which was added DMP (4.50 g, 10.6 mmol). The reaction mixture was stirred at RT for 1.5 h, forming a white suspension. Hexanes (50 mL) was added, and the suspension was filtered through a celite cake. The filtrate was collected and concentrated under reduced pressure, and the residue was purified on silica gel by flash chromatography (EtOAc/hexanes, 1:20 to 1:9), affording (1s,4s)-4-(((tert-butyldimethylsilyl)oxy)methyl)cyclohexanecarbaldehyde as a clear liquid (0.98 g, 68%, two steps). $^1H$ NMR (400 MHz, $CDCl_3$) δ 9.70 (s, 1H), 3.37 (d, J=6.6 Hz, 2H), 2.44-2.39 (m, 1H), 2.16-2.06 (m, 2H), 1.70-1.45 (m, 5H), 1.11-0.96 (m, 2H), 0.87 (s, 9H), 0.02 (s, 6H).

At 0° C., to a solution of methyltriphenylphosphonium bromide (1.30 g, 3.61 mmol) in anhydrous THE (40 mL) was added $KO^tBu$ (0.390 g, 3.50 mmol), and the mixture was stirred at 0° C. for 20 min. A solution of (1s,4s)-4-(((tert-butyldimethylsilyl)oxy)methyl)cyclohexanecarbaldehyde (0.620 g, 2.41 mmol) in anhydrous THE (10 mL) was added, and the mixture was stirred at RT for 2 h. The reaction mixture was diluted with satd. aqueous $NH_4Cl$ (30 mL), and then extracted with EtOAc (2×30 mL). The combined extract was dried over anhydrous $Na_2SO_4$. After filtration the solvent was evaporated under reduced pressure, and the residue was dissolved in anhydrous THE (20 mL) and cooled at 0° C. TBAF (1.0 M in THF, 5.0 mL, 5.0 mmol) was added, and the mixture was stirred at RT for 1 h. After diluted with brine (30 mL) the mixture was extracted with EtOAc (3×20 mL), and the combined extract was dried over anhydrous $Na_2SO_4$. After filtration the solvent was evaporated under reduced pressure, and the residue was purified on silica gel by flash chromatography (EtOAc/hexanes, 1:4 to 1:2), affording ((1s,4s)-4-vinylcyclohexyl)methanol as a clear oil (0.26 g, 77%, two steps)

A mixture of the above material (0.260 g, 1.85 mmol) and DMP (1.10 g, 2.59 mmol) in DCM (40 mL) was stirred at RT for 1 h, forming a white suspension. Hexanes (20 mL) was added, and the suspension was filtered through a celite cake. The filtrate was collected and concentrated under reduced pressure, and the residue was purified on silica gel by flash chromatography (EtOAc/hexanes, 1:5), affording (1s,4s)-4-vinylcyclohexanecarbaldehyde as a clear liquid (0.190 g, 74%). $^1H$ NMR (400 MHz, $CDCl_3$) δ 9.69 (s, 1H), 5.75 (ddd, J=17.1, 10.4, 6.3 Hz, 1H), 5.00-4.89 (m, 2H), 2.42-2.37 (m, 1H), 2.17-2.00 (m, 3H), 1.73-1.55 (m, 4H), 1.33-1.21 (m, 2H).

Under $N_2$, a mixture of (2R,3R,4R,5S)-3,4,5-tris(benzyloxy)-2-methylpiperidine (0.417 g, 1.00 mmol), (1s,4s)-4-vinylcyclohexanecarbaldehyde (0.19 g, 1.4 mmol) and $NaBH(OAc)_3$ (0.45 g, 2.1 mmol) in DCM (40 mL) was stirred at RT for 16 h. The reaction mixture was diluted with satd. aqueous $NaHCO_3$ (30 mL), and extracted with DCM (3×20 mL). The combined extract was dried over anhydrous $Na_2SO_4$. After filtration the solvent was evaporated under reduced pressure, and the residue was purified on silica gel by flash chromatography (EtOAc/hexanes, 1:13 to 1:9), affording (2R,3R,4R,5S)-3,4,5-tris(benzyloxy)-2-methyl-1-(((1s,4S)-4-vinylcyclohexyl)methyl)piperidine as a clear oil (0.39 g, 72%).

At −78° C. and under $N_2$, to a solution of the above material (0.180 g, 0.333 mmol) in anhydrous DCM (6 mL) was added $BCl_3$ (1.0 M in DCM, 3.0 mL, 3.0 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:6), affording (2R,3R,4R,5S)-2-methyl-1-(((1s,4S)-4-vinylcyclohexyl)methyl)piperidine-3,4,5-triol as a white solid (0.078 g, 87%). $^1H$ NMR (400 MHz, $CD_3OD$) δ 5.88 (ddd, J=17.4, 10.5, 6.3 Hz, 1H), 5.02-4.93 (m, 2H), 3.45 (ddd, J=10.5, 9.0, 4.8 Hz, 1H), 3.10 (t, J=9.0 Hz, 1H), 3.02 (dd, J=11.3, 4.8 Hz, 1H), 2.94 (t, J=9.1 Hz, 1H), 2.75 (dd, J=12.9, 9.2 Hz, 1H), 2.21-2.18 (m, 1H), 2.06-2.00 (m, 1H), 1.96-1.91 (m, 2H), 1.71-1.67 (m, 1H), 1.62-1.35 (m, 8H), 1.18 (d, J=6.1 Hz, 3H); ESI MS m/z 270.213 $[M+H]^+$.

Examples 7 and 8

(2R,3R,4R,5S)-1-(((1s,4S)-4-isopropylcyclohexyl)methyl)-2-methylpiperidine-3,4,5-triol and (2R,3R,4R,5S)-1-(((1r,4R)-4-isopropylcyclohexyl)methyl)-2-methylpiperidine-3,4,5-triol

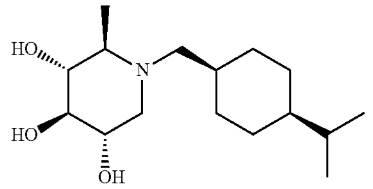

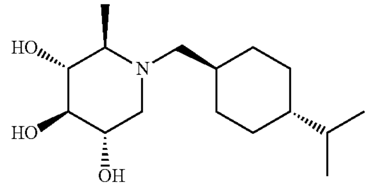

Under $N_2$, a mixture of (2R,3R,4R,5S)-3,4,5-tris(benzyloxy)-2-methylpiperidine (0.18 g, 0.43 mmol), 4-isopropylcyclohexanecarbaldehyde (0.10 g, 0.65 mmol) and $NaBH(OAc)_3$ (0.16 g, 0.75 mmol) in DCM (10 mL) was stirred at RT for 16 h. The reaction mixture was diluted with satd. aqueous $NaHCO_3$ (15 mL) and extracted with DCM (3×15 mL). The combined extract was dried over anhydrous $Na_2SO_4$. After filtration the solvent was evaporated under reduced pressure, and the residue was purified on silica gel by flash chromatography (EtOAc/hexanes, 1:16 to 1:10), affording (2R,3R,4R,5S)-3,4,5-tris(benzyloxy)-1-(((1S,4s)-4-isopropylcyclohexyl)methyl)-2-methylpiperidine as a clear oil (0.099 g, 41%) and (2R,3R,4R,5S)-3,4,5-tris(benzyloxy)-1-(((1r,4R)-4-isopropylcyclohexyl)methyl)-2-methylpiperidine as a clear oil (0.027 g, 11%).

At −78° C. and under $N_2$, to a solution of (2R,3R,4R,5S)-3,4,5-tris(benzyloxy)-1-(((1S,4s)-4-isopropylcyclohexyl)methyl)-2-methylpiperidine (0.098 g, 0.18 mmol) in anhydrous DCM (6 mL) was added $BCl_3$ (1.0 M in DCM, 1.5 mL, 1.5 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:6), affording (2R,3R,4R,5S)-1-(((1s,4S)-4-isopropylcyclohexyl)methyl)-2-methylpiperidine-3,4,5-triol as a white solid (0.045 g, 88%). $^1H$ NMR (400 MHz, DMSO-$d_6$) δ 4.67-4.64 (m, 3H), 3.24-3.16 (m, 1H), 2.89 (td, J=8.8, 4.3 Hz, 1H), 2.83 (dd, J=11.2, 4.8 Hz, 1H), 2.75-2.67 (m, 2H), 1.92-1.84 (m, 1H), 1.76-1.67 (m, 3H), 1.51-1.33 (m, 7H), 1.30-1.21 (m, 2H), 1.07 (d, J=6.0 Hz, 3H), 1.04-1.01 (m, 1H), 0.83 (d, J=6.7 Hz, 6H); ESI MS m/z 286.225 $[M+H]^+$.

At −78° C. and under $N_2$, to a solution of (2R,3R,4R,5S)-3,4,5-tris(benzyloxy)-1-(((1r,4R)-4-isopropylcyclohexyl)methyl)-2-methylpiperidine (0.027 g, 0.049 mmol) in anhydrous DCM (5 mL) was added $BCl_3$ (1.0 M in DCM, 1.0 mL, 1.0 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:6), affording (2R,3R,4R,5S)-1-(((1r,4R)-4-isopropylcyclohexyl)methyl)-2-methylpiperidine-3,4,5-triol as a white solid (0.013 g, 92%). $^1H$ NMR (400 MHz, $CD_3OD$) δ 3.49-3.42 (m, 1H), 3.10 (t, J=9.1 Hz, 1H), 3.02 (dd, J=11.3, 4.8 Hz, 1H), 2.95 (t, J=9.1 Hz, 1H), 2.53 (dd, J=12.8, 8.8 Hz, 1H), 2.07-1.91 (m, 4H), 1.77-1.71 (m, 3H), 1.50-1.35 (m, 3H), 1.17 (d, J=6.1 Hz, 3H), 1.02-0.80 (m, 10H, including 0.88 (d, J=6.8 Hz, 6H)); ESI MS m/z 286.226 $[M+H]^+$.

Examples 9 and 10

(2R,3R,4R,5S)-1-(((1s,4S)-4-(tert-butyl)cyclohexyl)methyl)-2-methylpiperidine-3,4,5-triol and (2R,3R,4R,5S)-1-(((1r,4R)-4-(tert-butyl)cyclohexyl)methyl)-2-methylpiperidine-3,4,5-triol

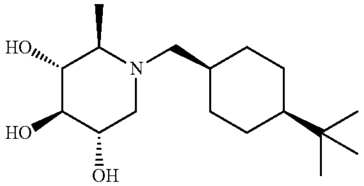

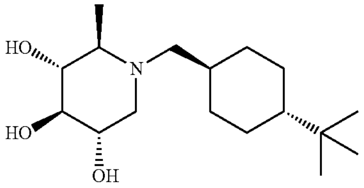

Under $N_2$, a mixture of (2R,3R,4R,5S)-3,4,5-tris(benzyloxy)-2-methylpiperidine (0.18 g, 0.43 mmol), 4-(tert-butyl)cyclohexanecarbaldehyde (0.15 g, 0.89 mmol) and NaBH$(OAc)_3$ (0.16 g, 0.75 mmol) in DCM (10 mL) was stirred at RT for 16 h. The reaction mixture was diluted with satd. aqueous $NaHCO_3$ (15 mL) and extracted with DCM (3×15 mL). The combined extract was dried over anhydrous $Na_2SO_4$. After filtration the solvent was evaporated under reduced pressure, and the residue was purified on silica gel by flash chromatography (EtOAc/hexanes, 1:16 to 1:10), affording (2R,3R,4R,5S)-3,4,5-tris(benzyloxy)-1-(((1S,4s)-4-(tert-butyl)cyclohexyl)methyl)-2-methylpiperidine as a clear oil (0.080 g, 33%) and (2R,3R,4R,5S)-3,4,5-tris(benzyloxy)-1-(((1r,4R)-4-(tert-butyl)cyclohexyl)methyl)-2-methylpiperidine as a clear oil (0.088 g, 36%).

At −78° C. and under $N_2$, to a solution of (2R,3R,4R,5S)-3,4,5-tris(benzyloxy)-1-(((1S,4s)-4-(tert-butyl)cyclohexyl)methyl)-2-methylpiperidine (0.080 g, 0.14 mmol) in anhydrous DCM (8 mL) was added $BCl_3$ (1.0 M in DCM, 1.5 mL, 1.5 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:6), affording (2R,3R,4R,5S)-1-(((1s,4S)-4-(tert-butyl)cyclohexyl)methyl)-2-methylpiperidine-3,4,5-triol as a white solid (0.038 g, 91%). $^1H$ NMR (400 MHz, DMSO-$d_6$) δ 4.67-4.64 (m, 3H), 3.24-3.16 (m, 1H), 2.92-2.81 (m, 3H), 2.74-2.68 (m, 1H), 1.92-1.85 (m, 1H), 1.79-1.68 (m, 4H), 1.55-1.42 (m, 4H), 1.28-1.18 (m, 1H), 1.07 (d, J=6.0 Hz, 3H), 1.05-0.91 (m, 3H), 0.81 (s, 9H); ESI MS m/z 300.244 $[M+H]^+$.

At −78° C. and under $N_2$, to a solution of (2R,3R,4R,5S)-3,4,5-tris(benzyloxy)-1-(((1r,4R)-4-(tert-butyl)cyclohexyl)methyl)-2-methylpiperidine (0.088 g, 0.15 mmol) in anhydrous DCM (8 mL) was added $BCl_3$ (1.0 M in DCM, 1.5 mL, 1.5 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:6), affording (2R,3R,4R,5S)-1-(((1r,4R)-4-(tert-butyl)cyclohexyl)methyl)-2-methylpiperidine-3,4,5-triol as a white solid (0.043 g, 93%). $^1H$ NMR (400 MHz, DMSO-$d_6$) δ 4.66-4.63 (m, 3H), 3.24-3.16 (m, 1H), 2.88 (td, J=8.8, 4.3 Hz, 1H), 2.82 (dd, J=11.2, 4.7 Hz, 1H), 2.73-2.67 (m, 1H), 2.39 (dd, J=12.5, 9.1 Hz, 1H), 1.90-1.65 (m, 7H), 1.35-1.24 (m, 1H), 1.03 (d, J=6.0 Hz, 3H), 0.95-0.82 (m, 4H), 0.82 (s, 9H), 0.77-0.68 (m, 1H),); ESI MS m/z 300.245 $[M+H]^+$.

Examples 11 and 12

(2R,3R,4R,5S)-2-methyl-1-(((1s,4S)-4-(trifluoromethyl)cyclohexyl)methyl)piperidine-3,4,5-triol and (2R,3R,4R,5S)-2-methyl-1-(((1r,4R)-4-(trifluoromethyl)cyclohexyl)methyl)piperidine-3,4,5-triol

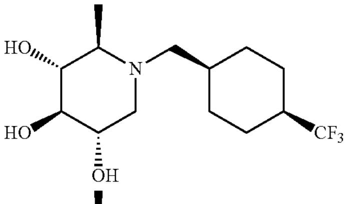

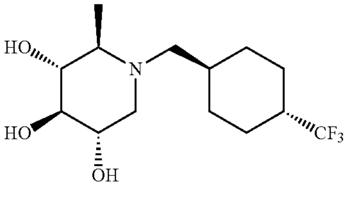

Under $N_2$, a mixture of (2R,3R,4R,5S)-3,4,5-tris(benzyloxy)-2-methylpiperidine (0.195 g, 0.467 mmol), 4-(trifluoromethyl)cyclohexanecarbaldehyde (0.150 g, 0.842 mmol) and $NaBH(OAc)_3$ (0.212 g, 1.00 mmol) in DCM (10 mL) was stirred at RT for 16 h. The reaction mixture was diluted with satd. aqueous $NaHCO_3$ (15 mL) and extracted with DCM (3×15 mL). The combined extract was dried over anhydrous $Na_2SO_4$. After filtration the solvent was evaporated under reduced pressure, and the residue was purified on silica gel by flash chromatography (EtOAc/hexanes, 1:12 to 1:7), affording (2R,3R,4R,5S)-3,4,5-tris(benzyloxy)-2-methyl-1-(((1s,4S)-4-(trifluoromethyl)cyclohexyl)methyl) piperidine as a clear oil (0.101 g, 37%) and (2R,3R,4R,5S)-3,4,5-tris(benzyloxy)-2-methyl-1-(((1r,4R)-4-(trifluoromethyl)cyclohexyl)methyl)piperidine as a clear oil (0.047 g, 17%); ESI MS m/z 582.303 $[M+H]^+$.

At −78° C. and under $N_2$, to a solution of (2R,3R,4R,5S)-3,4,5-tris(benzyloxy)-2-methyl-1-(((1s,4S)-4-(trifluoromethyl)cyclohexyl)methyl)piperidine (0.10 g, 0.17 mmol) in anhydrous DCM (5 mL) was added $BCl_3$ (1.0 M in DCM, 1.5 mL, 1.5 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:6), affording (2R,3R,4R,5S)-2-methyl-1-(((1s,4S)-4-(trifluoromethyl)cyclohexyl)methyl)piperidine-3,4,5-triol as a white solid (0.047 g, 89%). $^1H$ NMR (400 MHz, DMSO-$d_6$) δ 4.67-4.65 (m, 3H), 3.25-3.18 (m, 1H), 2.90 (td, J=8.8, 4.3 Hz, 1H), 2.83 (dd, J=11.2, 4.8 Hz, 1H), 2.78-2.68 (m, 2H), 2.30-2.22 (m, 1H), 1.93-1.86 (m, 1H), 1.79-1.72 (m, 3H), 1.65-1.50 (m, 4H), 1.46-1.34 (m, 4H), 1.07 (d, J=6.0 Hz, 3H); ESI MS m/z 312.170 $[M+H]^+$.

At −78° C. and under $N_2$, to a solution of (2R,3R,4R,5S)-3,4,5-tris(benzyloxy)-2-methyl-1-(((1r,4R)-4-(trifluoromethyl)cyclohexyl)methyl)piperidine (0.047 g, 0.081 mmol) in anhydrous DCM (3 mL) was added $BCl_3$ (1.0 M in DCM, 1.5 mL, 1.5 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:6), affording (2R,3R,4R,5S)-2-methyl-1-(((1r,4R)-4-(trifluoromethyl)cyclohexyl)methyl)piperidine-3,4,5-triol as a white solid (0.021 g, 84%). $^1H$ NMR (400 MHz, DMSO-$d_6$) δ 4.67-4.64 (m, 3H), 3.25-3.18 (m, 1H), 2.90 (td, J=8.8, 4.3 Hz, 1H), 2.83 (dd, J=11.2, 4.7 Hz, 1H), 2.70 (td, J=8.8, 5.4 Hz, 1H), 2.42 (dd, J=11.7, 9.3 Hz, 1H), 2.22-2.10 (m, 1H), 1.93-1.67 (m, 7H), 1.45-1.35 (m, 1H), 1.30-1.14 (m, 2H), 1.04 (d, J=6.0 Hz, 3H), 0.97-0.87 (m, 1H), 0.85-0.75 (m, 1H); ESI MS m/z 312.164 $[M+H]^+$.

Examples 13 and 14

(2R,3R,4R,5S)-1-(((1s,4S)-4-(2-fluoropropan-2-yl)cyclohexyl)methyl)-2-methylpiperidine-3,4,5-triol and (2R,3R,4R,5S)-1-(((1r,4R)-4-(2-fluoropropan-2-yl)cyclohexyl)methyl)-2-methylpiperidine-3,4,5-triol

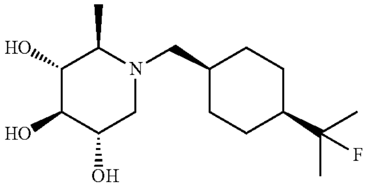

-continued

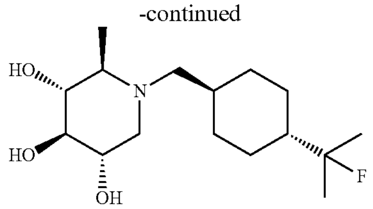

To a solution of 4-(hydroxymethyl)cyclohexanecarboxylic acid (1.00 g, 6.32 mmol) in anhydrous MeOH (25 mL) was added $SOCl_2$ (1.55 g, 13.0 mmol) dropwise, and the mixture was stirred at RT for 4 h. The solvent was then removed under reduced pressure, and the residue was diluted with satd. aqueous $NaHCO_3$ (30 mL). After extraction with DCM (3×30 mL) the combined extract was dried over anhydrous $Na_2SO_4$. After filtration the solvent was evaporated under reduced pressure to give clear liquid. The liquid was dissolved in anhydrous THE (40 mL), and to which, at 0° C., was added MeMgBr (3.0 M in $Et_2O$, 10 mL, 30 mmol). After stirring at RT for 16 h the reaction mixture was diluted with satd. aqueous $NH_4Cl$ (50 mL) and extracted with EtOAc (5×50 mL). The combined extract was dried over anhydrous $Na_2SO_4$. After filtration the solvent was evaporated under reduced pressure, and the residue was purified on silica gel by flash chromatography (EtOAc), affording 2-(4-(hydroxymethyl)cyclohexyl)propan-2-ol as a white solid (1.05 g, 96%, two steps). $^1H$ NMR indicated the solid contains a mixture of cis and trans isomers in a ratio of cis:trans=0.82:0.18).

At 0° C. and under $N_2$, to a solution of the above material (1.05 g, 6.09 mmol) in anhydrous DCM (30 mL) added DIPEA (1.41 g 10.9 mol), DMAP (0.24 g, 2.0 mmol) and BzCl (1.29 g, 9.18 mmol). The mixture was stirred at RT for 16 h, and then diluted with satd. aqueous $NaHCO_3$ (50 mL). After extraction with DCM (3×50 mL) the combined extract was dried over anhydrous $Na_2SO_4$. After filtration the solvent was evaporated under reduced pressure, and the residue was purified on silica gel by flash chromatography (EtOAc/hexanes, 1:4 to 1:1), affording (4-(2-hydroxypropan-2-yl)cyclohexyl)methyl benzoate as a clear oil (1.68 g, 100%). $^1H$ NMR indicated the oil contains a mixture of cis and trans isomers in a ratio of cis:trans=0.82:0.18).

To a solution of the above material (1.65 g, 5.97 mmol) in anhydrous DCM (30 mL), at −78° C. and under $N_2$, was added DAST (1.45 g, 9.06 mmol), and the mixture was stirred at RT for 2 h. The reaction mixture was cooled at −78° C., and quenched with satd. aqueous $NaHCO_3$ (50 mL). The organic layer was collected, and the aqueous was extracted with DCM (3×40 mL). The combined extract was dried over anhydrous $Na_2SO_4$. After filtration the solvent was evaporated under reduced pressure, and the residue was purified on silica gel by flash chromatography (EtOAc/hexanes, 1:19), affording (4-(2-fluoropropan-2-yl)cyclohexyl)methyl benzoate as a clear oil (1.07 g, 66%). $^1H$ NMR indicated the oil contains a mixture of cis and trans isomers in a ratio of cis:trans=0.82:0.18).

A mixture of the above material (0.850 g, 3.05 mmol) and $K_2CO_3$ (0.80 g, 0.58 mmol) in MeOH (60 mL) was stirred at RT for 4 h. The solvent was removed under reduced pressure, and the residue was diluted with satd. aqueous $NaHCO_3$ (40 mL). After extraction with DCM (3×40 mL) and the combined extract was dried over anhydrous $Na_2SO_4$. After filtration the solvent was evaporated under reduced pressure, and the residue was purified on silica gel by flash chromatography (EtOAc/hexanes, 1:1 to 3:2), affording (4-

(2-fluoropropan-2-yl)cyclohexyl)methanol as a clear oil (0.49 g, 92%). $^1H$ NMR indicated the oil contains a mixture of cis and trans isomers in a ratio of cis:trans=0.82:0.18).

A mixture of the above material (0.47 g, 2.7 mmol) and DMP (1.7 g, 4.0 mmol) in DCM (30 mL) was stirred at RT for 1.5 h, forming a white suspension. Hexanes (20 mL) was added, and the suspension was filtered through a celite cake. The filtrate was collected and concentrated under reduced pressure, and the residue was purified on silica gel by flash chromatography (EtOAc/hexanes, 1:13 to 1:9), affording cis-4-(2-fluoropropan-2-yl)cyclohexanecarbaldehyde as a clear liquid (0.21 g, 44%); $^1H$ NMR (400 MHz, $CDCl_3$) δ 9.72 (s, 1H), 2.50-2.43 (m, 1H), 2.37-2.27 (m, 2H), 1.78-1.67 (m, 2H), 1.62-1.45 (m, 3H), 1.27 (s, 3H), 1.21 (s, 3H), 1.07-0.96 (m, 2H). Also isolated was trans-4-(2-fluoropropan-2-yl)cyclohexanecarbaldehyde as a white solid (impure, est. 0.045 g, est. 10%).

Under $N_2$, a mixture of cis-4-(2-fluoropropan-2-yl)cyclohexanecarbaldehyde (0.10 g, 0.58 mmol), (2R,3R,4R,5S)-3,4,5-tris(benzyloxy)-2-methylpiperidine (0.20 g, 0.48 mmol), and $NaBH(OAc)_3$ (0.17 g, 0.80 mmol) in DCM (6 mL) was stirred at RT for 16 h. The reaction mixture was diluted with satd. aqueous $NaHCO_3$ (20 mL), and extracted with DCM (3×20 mL). The combined extract was dried over anhydrous $Na_2SO_4$. After filtration the solvent was evaporated under reduced pressure, and the residue was purified on silica gel by flash chromatography (EtOAc/hexanes, 1:12 to 1:8), affording (2R,3R,4R,5S)-3,4,5-tris(benzyloxy)-1-(((1s,4S)-4-(2-fluoropropan-2-yl)cyclohexyl)methyl)-2-methylpiperidine as a clear oil (0.24 g, 87%).

A mixture of the above material (0.24 g, 0.42 mmol) and $Pd(OH)_2/C$ (20% Pd in weight, 0.080 g, 0.15 mmol) and four drops of concentrated HCl in MeOH (20 mL) was stirred under hydrogen at one atmosphere of pressure overnight. The mixture was filtered through a celite cake, and the filtrate was collected and concentrated to dryness. The residue was dissolved in anhydrous pyridine (3 mL), and at 0° C., to which was added $Ac_2O$ (0.5 mL). The mixture was stirred at RT for 16 h, and diluted with satd. aqueous $NaHCO_3$ (20 mL). After extraction with EtOAc (2×20 mL) the combined extract was dried over anhydrous $Na_2SO_4$. After filtration the solvent was evaporated under reduced pressure, and the residue was treated with 1 M $NH_3$ in MeOH (5 mL) at RT for 16 h. After concentrated under reduced pressure the residue was purified on silica gel by flash chromatography (1 M $NH_3$ MeOH/DCM, 1:6), affording (2R,3R,4R,5S)-1-(((1s,4S)-4-(2-fluoropropan-2-yl)cyclohexyl)methyl)-2-methylpiperidine-3,4,5-triol (0.098 g, 77%, three steps) as a white solid. $^1H$ NMR (400 MHz, $CD_3OD$) δ 3.45 (ddd, J=10.6, 9.1, 4.8 Hz, 1H), 3.11 (t, J=9.0 Hz, 1H), 3.04-2.92 (m, 3H), 2.10-2.03 (m, 1H), 1.95-1.86 (m, 4H), 1.66-1.37 (m, 6H), 1.29 (s, 3H), 1.24 (s, 3H), 1.24-1.15 (m, 5H, including 1.20 (d, J=6.1 Hz, 3H)); ESI MS m/z 304.226 $[M+H]^+$.

Under $N_2$, a mixture of (2R,3R,4R,5S)-3,4,5-tris(benzyloxy)-2-methylpiperidine (0.16 g, 0.38 mmol), trans-4-(2-fluoropropan-2-yl)cyclohexanecarbaldehyde (0.040 g, ~90% pure, 0.20 mmol) and $NaBH(OAc)_3$ (0.17 g, 0.80 mmol) in DCM (6 mL) was stirred at RT for 16 h. The reaction mixture was diluted with satd. aqueous $NaHCO_3$ (20 mL), and extracted with DCM (3×20 mL). The combined extract was dried over anhydrous $Na_2SO_4$. After filtration the solvent was evaporated under reduced pressure, and the residue was purified on silica gel by flash chromatography (EtOAc/hexanes, 1:12 to 1:8), affording (2R,3R,4R,5S)-3,4,5-tris(benzyloxy)-1-(((1r,4R)-4-(2-fluoropropan-2-yl)cyclohexyl)methyl)-2-methylpiperidine as a clear oil (0.061 g, 51%).

A mixture of the above material (0.0600 g, 0.105 mmol), $Pd(OH)_2/C$ (20% Pd in weight, 0.050 g, 0.094 mmol) and two drops of concentrated HCl in MeOH (15 mL) was stirred under hydrogen at one atmosphere of pressure overnight. The mixture was filtered through a celite cake, and the filtrate was collected and concentrated to dryness. The residue was dissolved in anhydrous pyridine (3 mL), and at 0° C., to which was added $Ac_2O$ (0.5 mL). The mixture was stirred at RT for 16 h, and diluted with satd. aqueous $NaHCO_3$ (20 mL). After extraction with EtOAc (2×20 mL) the combined extract was dried over anhydrous $Na_2SO_4$. After filtration the solvent was evaporated under reduced pressure, and the residue was purified on silica gel by flash chromatography (EtOAc/hexanes, 1:6 to 1:4), affording a white foam. The white foam was treated with 1 M $NH_3$ in MeOH (5 mL) at RT for 16 h. After concentrating under reduced pressure, the residue was purified on silica gel by flash chromatography (1 M $NH_3$ MeOH/DCM, 1:6), affording (2R,3R,4R,5S)-1-(((1r,4R)-4-(2-fluoropropan-2-yl)cyclohexyl)methyl)-2-methylpiperidine-3,4,5-triol (0.0037 g, 12%, three steps) as a white solid. $^1H$ NMR (400 MHz, $CD_3OD$) δ 3.46 (ddd, J=10.6, 9.1, 4.8 Hz, 1H), 3.10 (t, J=9.0 Hz, 1H), 3.02 (dd, J=11.4, 4.8 Hz, 1H), 2.94 (t, J=9.1 Hz, 1H), 2.55 (dd, J=12.9, 9.0 Hz, 1H), 2.10-1.95 (m, 4H), 1.87-1.75 (m, 3H), 1.52-1.42 (m, 2H), 1.29 (s, 3H), 1.24 (s, 3H), 1.17 (d, J=6.1 Hz, 3H), 1.17-1.02 (m, 2H), 0.99-0.80 (m, 2H); ESI MS m/z 304.230 $[M+H]^+$.

Example 15

(2R,3R,4R,5S)-2-methyl-1-(((trans)-3-(trifluoromethyl)cyclohexyl)methyl)piperidine-3,4,5-triol

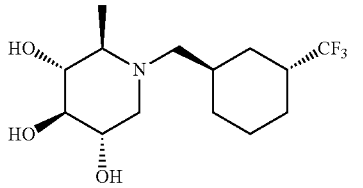

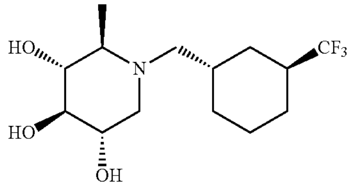

Under Ar, to a solution of (2R,3R,4R,5S)-3,4,5-tris(benzyloxy)-2-methyl-1-(piperidin-4-ylmethyl)piperidine (186 mg, 0.36 mmol), trans-3-(trifluoromethyl) cyclohexanecarbaldehyde (100 mg, 0.55 mmol) and HOAc (three drops) in anhydrous MeOH (5 mL) was added $NaBH_3CN$ (40 mg, 95%, 0.60 mmol). The mixture was stirred at RT for 18 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 20% EtOAc in hexanes, affording (2R,3R,4R,5S)-3,4,5-tris(benzyloxy)-2-methyl-1-((3-(trifluoromethyl) cyclohexyl) methyl) piperidine as a white foam (140 mg, 67%). $^1$H NMR indicated this material is a mixture of two stereoisomers.

At −78° C. under Ar, to a solution of the above material (140 mg, 0.24 mmol) in anhydrous DCM (2 mL) was added $BCl_3$ solution (2.4 mL, 1 M in DCM, 2.40 mmol). The mixture was stirred at −78 for 1 h and 0° C. for 4 h; MeOH (20 mL) was added. The mixture was stirred for an additional 2 h at 0° C., and evaporated to dryness under reduced pressure. The residue was purified on silica gel by flash chromatography (dry load) using 10% MeOH and 2% $NH_3$ solution in DCM, affording mixture of (2R,3R,4R,5S)-2-methyl-1-(((1S,3S)-3-(trifluoromethyl)cyclohexyl)methyl) piperidine-3,4,5-triol and (2R,3R,4R,5S)-2-methyl-1-(((1R,3R)-3-(trifluoromethyl)cyclohexyl)methyl)piperidine-3,4,5-triol (16) as a white foam (46 mg, 61%). $^1$H NMR (400 MHz, DMSO) δ 4.70-4.66 (m, 3H), 3.24-3.18 (m, 1H), 3.04-2.59 (m, 4H), 2.30-2.78 (m, 1H), 2.12-1.66 (m, 5H), 1.65-1.17 (m, 7H), 1.16-0.90 (m, 3H); ESI MS m/z 312.16 $[M+H]^+$.

Example 16

(2R,3R,4R,5S)-2-methyl-1-(((cis)-3-(trifluoromethyl)cyclohexyl)methyl)piperidine-3,4,5-triol

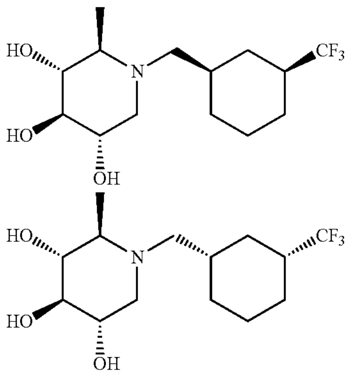

Under Ar, to a solution of (2R,3R,4R,5S)-3,4,5-tris(benzyloxy)-2-methyl-1-(piperidin-4-ylmethyl)piperidine (186 mg, 0.36 mmol), cis-3-(trifluoromethyl)cyclohexanecarbaldehyde (98 mg, 0.54 mmol) and HOAc (three drops) in anhydrous MeOH (5 mL) was added $NaBH_3CN$ (36 mg, 95%, 0.54 mmol). The mixture was stirred at RT for 18 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 20% EtOAc in hexanes, affording (2R,3R,4R,5S)-3,4,5-tris(benzyloxy)-2-methyl-1-((3-(trifluoromethyl) cyclohexyl) methyl) piperidine as a white foam (100 mg, 48%). $^1$H NMR indicated this material is a mixture of two stereoisomers.

At −78° C. under Ar, to a solution of the above material (100 mg, 0.17 mmol) in anhydrous DCM (2 mL) was added $BCl_3$ solution (1.7 mL, 1 M in DCM, 1.70 mmol). The mixture was stirred at −78 for 1 h and 0° C. for 4 h; MeOH (20 mL) was added. The mixture was stirred for an additional 2 h at 0° C., and evaporated to dryness under reduced pressure. The residue was purified on silica gel by flash chromatography (dry load) using 10% MeOH and 2% $NH_3$ solution in DCM, affording a mixture of (2R,3R,4R,5S)-2-methyl-1-(((1R,3S)-3-(trifluoromethyl)cyclohexyl)methyl) piperidine-3,4,5-triol and (2R,3R,4R,5S)-2-methyl-1-(((1S,3R)-3-(trifluoromethyl)cyclohexyl)methyl)piperidine-3,4,5-triol as a white foam (38 mg, 67%). $^1$H NMR (400 MHz, DMSO) δ 4.68-4.57 (m, 3H), 3.23-3.19 (m, 1H), 2.96-2.78 (m, 2H), 2.77-2.65 (m, 1H), 2.48-2.44 (m, 1H), 2.27-2.21 (m, 1H), 2.15-1.44 (m, 8H), 1.42-1.10 (m, 2H), 1.05 (d, J=6.0 Hz, 3H), 0.85-0.50 (m, 2H); ESI MS m/z 312.16 $[M+H]^+$.

Examples 17 and 18

(2R,3R,4R,5S)-1-(((1s,4S)-4-methoxycyclohexyl) methyl)-2-methylpiperidine-3,4,5-triol and (2R,3R,4R,5S)-1-(((1r,4R)-4-methoxycyclohexyl)methyl)-2-methylpiperidine-3,4,5-triol

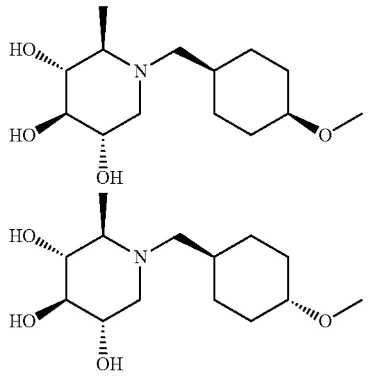

To a solution of 4-methoxycyclohexanecarboxylic acid (340 mg, 2.15 mmol) in anhydrous THE (10 mL) at 0° C., was added LAH (245 mg, 6.45 mmol), and the mixture was stirred at 0° C. for 1 h. The mixture was quenched slowly with satd. aqueous $Na_2SO_4$ and filtered. The solid was washed with EtOAc. The combined organic layer was washed with water (2×20 mL), separated, dried over $Na_2SO_4$. After filtration, the solvent was evaporated under reduced pressure, to obtain crude (4-methoxycyclohexyl) methanol as an oil (320 mg).

To a solution of the above material (180 mg, 1.25 mmol) in anhydrous DCM (10 mL) at 0° C., was added DMP (689 mg, 1.63 mmol), and the mixture was stirred at 0° C. for 2 h. The mixture was quenched slowly with $Na_2S_3O_5$ solution. The mixture was extracted with DCM (3×20 mL). The combined organic layer was washed with water (2×10 mL), separated, dried over $Na_2SO_4$. After filtration, the solvent was evaporated under reduced pressure, and the residue was purified on silica gel by flash chromatography affording (1s,4s)-4-methoxycyclohexanecarbaldehyde as an oil (67 mg, 38%); $^1$H NMR (400 MHz, $CDCl_3$) δ 9.64 (d, J=1.3 Hz, 1H), 3.39 (dq, J=5.7, 2.9 Hz, 1H), 3.33 (s, 3H), 2.28 (ttd, J=8.9, 4.2, 1.2 Hz, 1H), 1.93-1.74 (m, 4H), 1.73-1.55 (m, 4H). Also isolated was (1r,4r)-4-methoxycyclohexanecarbaldehyde as an oil (20 mg, 11%); $^1$H NMR (400 MHz, $CDCl_3$) δ 9.67 (d, J=1.3 Hz, 1H), 3.38 (s, 3H), 3.20-3.08 (m, 1H), 2.31-2.20 (m, 1H), 2.16-2.00 (m, 4H), 1.45-1.25 (m, 4H).

To a stirred solution of (2R,3R,4R,5S)-3,4,5-tris(benzyloxy)-2-methylpiperidine (80 mg, 0.19 mmol) and (1s,4s)-

4-methoxycyclohexanecarbaldehyde (55 mg, 0.39 mmol) in anhydrous MeOH (5 mL) was added HOAc (0.10 mL, 1.75 mmol) and stirred for 30 min. $NaBH_3CN$ (24 mg, 0.39 mmol) was added, and the resulting mixture was stirred at RT for 18 h. The reaction was quenched with satd. aqueous $NaHCO_3$ at 0° C. The mixture was extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-1-(((1s,4S)-4-methoxycyclohexyl)methyl)-2-methylpiperidine as an oil (92 mg, 95%). $^1H$ NMR (400 MHz, $CDCl_3$) δ 7.40-7.26 (m, 15H), 4.97 (dd, J=13.3, 10.9 Hz, 2H), 4.85 (d, J=11.0 Hz, 1H), 4.78-4.57 (m, 3H), 3.59 (td, J=9.8, 4.5 Hz, 1H), 3.51 (t, J=9.0 Hz, 1H), 3.43 (s, 1H), 3.33 (s, 3H), 3.16-2.98 (m, 2H), 2.57 (dd, J=12.8, 8.6 Hz, 1H), 2.26 (dd, J=9.3, 6.0 Hz, 1H), 2.10-1.93 (m, 2H), 1.90-1.80 (m, 2H), 1.62-1.22 (m, 7H), 1.19 (d, J=6.1 Hz, 3H).

To a solution of the above material (90 mg, 0.16 mmol) in EtOH (10 mL) was added $Pd(OH)_2/C$ (20 wt. %, 8.6 mg, 0.012 mmol) and 6N HCl (0.1 mL). The mixture was treated with hydrogen (1 atm) for 18 h. Catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2R,3R,4R,5S)-1-(((1s,4S)-4-methoxycyclohexyl)methyl)-2-methylpiperidine-3,4,5-triol as a white solid (30 mg, 67%). $^1H$ NMR (400 MHz, $CD_3OD$) δ 3.51-3.43 (m, 2H), 3.32 (s, 3H), 3.12 (t, J=9.0 Hz, 1H), 3.03 (dd, J=11.4, 4.8 Hz, 1H), 2.95 (t, J=9.1 Hz, 1H), 2.63 (dd, J=12.8, 8.9 Hz, 1H), 2.09-2.01 (m, 1H), 2.00-1.92 (m, 2H), 1.91-1.82 (m, 2H), 1.67-1.41 (m, 5H), 1.36-1.23 (m, 2H), 1.19 (d, J=6.1 Hz, 3H); ESI MS m/z 274.20 $[M+H]^+$.

To a stirred solution of (2R,3R,4R,5S)-3,4,5-tris(benzyloxy)-2-methylpiperidine (40 mg, 0.096 mmol) and (1r,4r)-4-methoxycyclohexanecarbaldehyde (20 mg, 0.14 mmol) in anhydrous MeOH (5 mL) was added HOAc (0.10 mL, 1.75 mmol) and stirred for 30 min. $NaBH_3CN$ (12 mg, 0.19 mmol) was added, and the resulting mixture was stirred at RT for 18 h. The reaction was quenched with satd. aqueous $NaHCO_3$ at 0° C. The mixture was extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-1-(((1r,4R)-4-methoxycyclohexyl)methyl)-2-methylpiperidine as an oil (34 mg, 65%).

To a solution of the above material (30 mg, 0.055 mmol) in EtOH (10 mL) was added $Pd(OH)_2/C$ (20 wt. %, 8.6 mg, 0.012 mmol) and 6N HCl (0.1 mL). The mixture was treated with hydrogen (1 atm) for 18 h. Catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2R,3R,4R,5S)-1-(((1r,4R)-4-methoxycyclohexyl)methyl)-2-methylpiperidine-3,4,5-triol as a white solid (12 mg, 80%). $^1H$ NMR (400 MHz, $CD_3OD$) δ 3.51-3.43 (m, 1H), 3.36 (s, 3H), 3.21-3.08 (m, 2H), 3.03 (dd, J=11.4, 4.8 Hz, 1H), 2.95 (t, J=9.1 Hz, 1H), 2.55 (dd, J=12.8, 8.9 Hz, 1H), 2.15-1.92 (m, 6H), 1.81-1.72 (m, 1H), 1.54-1.40 (m, 1H), 1.27-1.08 (m, 5H), 1.05-0.83 (m, 2H); ESI MS m/z 274.20 $[M+H]^+$.

Example 19

(2R,3R,4R,5S)-1-((4-(methoxymethyl)cyclohexyl)methyl)-2-methylpiperidine-3,4,5-triol

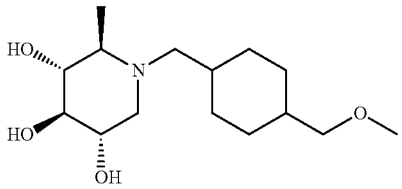 [SMILES: COCC1CCC(CN2C[C@H](O)[C@@H](O)[C@H](O)[C@H]2C)CC1]

Under Ar, to a solution of (2R,3R,4R,5S)-3,4,5-tris(benzyloxy)-2-methyl-1-(piperidin-4-ylmethyl)piperidine (82 mg, 0.19 mmol) and 4-(methoxymethyl)cyclohexanecarbaldehyde (33 mg, 0.21 mmol) in anhydrous DCM (5 mL) was added $NaBH(OAc)_3$ (84 mg, 0.39 mmol). The mixture was stirred at RT for 18 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 20% EtOAc in hexanes, affording (2R,3R,4R,5S)-3,4,5-tris(benzyloxy)-1-((4-(methoxymethyl)cyclohexyl)methyl)-2-methylpiperidine as a mixture of cis and trans isomers (92 mg, 85%).

At −78° C. under Ar, to a solution of the above material (92 mg, 0.17 mmol) in anhydrous DCM (5 mL) was added $BCl_3$ solution (1.3 mL, 1 M in DCM, 1.3 mmol). The mixture was stirred at −78 for 1 h and 0° C. for 4 h; MeOH (20 mL) was added. The mixture was stirred for additional 2 h at 0° C., and evaporated to dryness. The residue was purified on silica gel by flash chromatography using 10% MeOH and 2% $NH_3$ solution in DCM, affording mixture of (2R,3R,4R,5S)-1-((4-(methoxymethyl)cyclohexyl)methyl)-2-methylpiperidine-3,4,5-triol as a white foam (35 mg, 74%); this material was isolated as a mixture of cis and trans isomers. $^1H$ NMR (400 MHz, $CD_3OD$) δ 3.57-3.40 (m, 1H), 3.35-3.31 (m, 3.5H), 3.22 (d, J=6.4 Hz, 1.5H), 3.18-3.09 (m, 1H), 3.04 (dd, J=11.3, 4.8 Hz, 1H), 2.97 (t, J=9.1 Hz, 1H), 2.81 (dd, J=12.9, 9.3 Hz, 0.25H), 2.81 (dd, J=12.9, 9.3 Hz, 0.75H), 2.17-1.90 (m, 4H), 1.87-1.69 (m, 2H), 1.56-1.33 (m, 4H), 1.57-1.54 (m, 3H), 1.11-0.75 (m, 3H); ESI MS m/z 288.2 $[M+H]^+$.

Example 20

(2R,3R,4R,5S)-1-(((1s,4S)-4-cyclopropylcyclohexyl)methyl)-2-methylpiperidine-3,4,5-triol

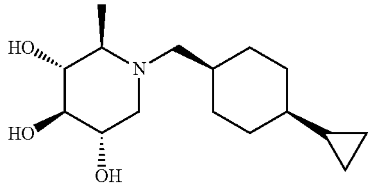 [SMILES: C[C@@H]1[C@@H](O)[C@H](O)[C@@H](O)CN1C[C@H]1CC[C@@H](C2CC2)CC1]

To a solution of cis-cyclohexane-1,4-dicarboxylic acid monomethyl ester (3.7 g, 19.8 mmol) in THE (100 mL) was added borane-dimethyl sulfide complex (2.25 g, 29.7 mmol), under ice-cooling, and the mixture was stirred for 15 min and at RT for 4 h. MeOH (5 mL) was added and the contents were evaporated under reduced pressure. To the residue was added 1M NaOH (20 mL) and the mixture was extracted with EtOAc and organics were washed with brine, dried over anhydrous $Na_2SO_4$ and concentrated. The residue was purified on silica gel by flash chromatography (EtOAc/hexanes, 1:4), affording (Is, 4s)-methyl 4-(hydroxymethyl) cyclohexanecarboxylate (2.35 g, 69%) as an oil. $^1$H NMR (500 MHz, $CDCl_3$) δ 3.65 (s, 3H), 3.45 (dd, J=6.3, 0.9 Hz, 2H), 2.56-2.53 (m, 1H), 2.01-1.94 (m, 2H), 1.89-1.85 (m, 1H), 1.63-1.49 (m, 5H), 1.31-1.21 (m, 2H).

To a stirred solution of the above material (0.78 g, 4.52 mmol) at 0° C. in dry DCM (35 mL) was added DMP (2.8 g, 6.7 mmol). After stirring at RT for 2 h, the reaction mixture was quenched with a 1:1 mixture of 1M $Na_2S_2O_3$: satd. $NaHCO_3$ solution (20 mL) and further stirred for 30 min before being diluted with DCM (40 mL). Organics were separated, dried over anhydrous $Na_2SO_4$ and concentrated. The crude residue was purified on silica gel by flash chromatography (EtOAc/hexanes, 1:4), affording (1s,4s)-methyl 4-formylcyclohexanecarboxylate (0.57 g, 74%) as an oil. $^1$H NMR (400 MHz, $CDCl_3$) δ 9.61 (s, 1H), 3.61 (s, 3H), 2.45-2.37 (m, 1H), 2.35-2.29 (m, 1H), 1.94-1.85 (m, 2H), 1.75-1.59 (m, 6H).

To a mixture of methyl triphenylphosphonium bromide (1.5 g, 4.4 mmol) in anhydrous THE (15 mL) at 0° C. was added KOtBu (0.5 g, 4.4 mmol). The mixture was stirred for 30 min before (1s,4s)-methyl 4-formylcyclohexanecarboxylate (0.5 g, 2.9 mmol) pre-dissolved in anhydrous THE (10 mL) was added slowly. The mixture was warmed to RT and stirred for 2 h before being concentrated under reduced pressure. The resulting crude residue was purified on silica gel by flash chromatography (EtOAc/hexanes, 1:4), affording (1s,4s)-methyl 4-vinylcyclohexanecarboxylate (0.5 g, 68%) as an oil. $^1$H NMR (400 MHz, $CDCl_3$) δ 5.78 (ddd, J=17.1, 10.5, 6.3 Hz, 1H), 4.98-4.89 (m, 2H), 3.65 (s, 3H), 2.50 (ddd, J=10.4, 5.9, 4.4 Hz, 1H), 2.16-2.05 (m, 1H), 2.03-1.92 (m, 2H), 1.63-1.51 (m, 4H), 1.46-1.36 (m, 2H).

To a mixture of the above material (0.20 g, 1.18 mmol) in DCE (8 mL) at 0° C. was added diethylzinc (1.0 M hexanes, 3.5 mL, 3.5 mmol) followed by chloroiodomethane (0.51 mL, 7.08 mmol). The mixture was stirred at 0° C. for 2 h and then at RT for 2 h before being quenched with satd. aqueous $NH_4Cl$. The reaction mixture was partitioned between DCM and water, organics were separated and dried over anhydrous $Na_2SO_4$ and concentrated. The crude residue was purified on silica gel by flash chromatography (EtOAc/hexanes, 1:4), affording (1s,4s)-methyl 4-cyclopropylcyclohexanecarboxylate (0.18 g, 83.6%) as an oil. $^1$H NMR (400 MHz, $CDCl_3$) δ 3.67 (s, 3H), 2.48 (tt, J=6.3, 4.3 Hz, 1H), 2.02-1.92 (m, 2H), 1.64-1.49 (m, 4H), 1.48-1.38 (m, 2H), 0.71-0.62 (m, 1H), 0.61-0.51 (m, 1H), 0.41-0.32 (m, 2H), 0.04-0.03 (m, 2H).

To a cooled (0° C.) solution of the above material (0.19 g, 1.04 mmol) in 5 mL of anhydrous THF, 0.11 g (3.12 mmol) of LAH was added portion wise while stirring, under Ar. The mixture was stirred at 0° C. for 2.5 h then at reflux for 5 h until disappearance of starting material. The mixture was diluted with EtOAc, washed with 1.0 M HCl, water and brine. The organics were dried over anhydrous $Na_2SO_4$ and concentrated to yield ((1s,4s)-4-cyclopropylcyclohexyl) methanol (0.13 g, 84%) as an oil. $^1$H NMR (400 MHz, $CDCl_3$) δ 3.54 (d, J=6.8 Hz, 2H), 1.62 (ttd, J=10.2, 6.8, 3.0 Hz, 1H), 1.57-1.48 (m, 7H), 1.48-1.39 (m, 2H), 0.80-0.71 (m, 1H), 0.68-0.60 (m, 1H), 0.42-0.35 (m, 2H), 0.04-0.01 (m, 2H).

To a stirred solution of the above material (0.135 g, 0.87 mmol) at 0° C. in dry DCM (6 mL) was added DMP (0.55 g, 1.3 mmol). After stirring at RT for 2 h, the reaction mixture was quenched with a 1:1 mixture of 1M $Na_2S_2O_3$: satd. $NaHCO_3$ solution (20 mL) and further stirred for 30 min before being diluted with DCM (40 mL). Organics were separated, dried over anhydrous $Na_2SO_4$ and concentrated. The crude residue was purified on silica gel by flash chromatography (EtOAc/hexanes, 1:9), affording (1s,4s)-4-cyclopropylcyclohexanecarbaldehyde (0.06 g, 45%) as an oil. $^1$H NMR (500 MHz, $CDCl_3$) δ 9.70 (s, 1H), 2.37-2.33 (m, 1H), 2.09-2.01 (m, 2H), 1.69-1.60 (m, 2H), 1.59-1.51 (m, 2H), 1.29-1.20 (m, 2H), 0.57-0.50 (m, 2H), 0.40-0.33 (m, 2H), 0.04-0.02 (m, 2H).

To a solution of (2R,3R,4R,5S)-3,4,5-tris(benzyloxy)-2-methylpiperidine (0.2 g, 0.5 mmol) and (1s,4s)-4-cyclopropylcyclohexanecarbaldehyde (0.06 g, 0.40 mmol) in anhydrous MeOH (5 mL) was added AcOH (few drops) and the mixture was stirred at RT for 10 min. Sodium cyanoborohydride (0.032 g, 0.50 mmol) was added and the reaction was stirred at RT overnight. The mixture was concentrated and diluted with EtOAc (30 mL) and washed organics with satd. $NaHCO_3$ solution. The organics were dried over anhydrous $Na_2SO_4$ and concentrated, and the crude residue was purified on silica gel by flash chromatography (EtOAc/hexanes, 1:9), affording (2R,3R,4R,5S)-3,4,5-tris(benzyloxy)-1-(((1s,4S)-4-cyclopropylcyclohexyl)methyl)-2-methyl piperidine (0.11 g, 50.9%) as a yellow solid. $^1$H NMR (500 MHz, $CDCl_3$) δ 7.39-7.27 (m, 15H), 4.98 (dd, J=16.1, 10.9 Hz, 2H), 4.85 (d, J=11.0 Hz, 1H), 4.77-4.65 (m, 2H), 4.63 (d, J=10.8 Hz, 1H), 3.64-3.58 (m, 1H), 3.57-3.49 (m, 1H), 3.16-3.04 (m, 2H), 2.69 (dd, J=12.8, 9.0 Hz, 1H), 2.29 (dq, J=12.4, 6.2 Hz, 1H), 2.08-1.97 (m, 2H), 1.60-1.45 (m, 8H), 1.41-1.29 (m, 2H), 1.24-1.19 (m, 2H), 0.81-0.72 (m, 1H), 0.68-0.61 (m, 1H), 0.45-0.38 (m, 2H), 0.09-0.03 (m, 2H); ESI MS m/z 554.349 $[M+H]^+$.

At −78° C., under Ar, to a solution of the above material (0.1 g, 0.18 mmol) in DCM (5 mL) was added $BCl_3$ (1.0 M in DCM, 0.95 mL, 0.95 mmol), and the mixture was stirred for 2 h while the bath temperature reached 0° C. The mixture was further stirred at 0° C. for 2 h and then quenched by adding MeOH (2 mL) slowly. After stirring at RT for 30 min the mixture was concentrated under reduced pressure. The resulting residue was taken in a mixture of AcO/pyridine (4.5 mL, 1:9) and stirred overnight before evaporating under reduced pressure. A 2M $NH_3$/MeOH solution (8 mL) was then added to the crude and the mixture was stirred overnight and concentrated to dryness. The residue was purified and separated on silica gel by flash chromatography (MeOH/DCM, 1:9), affording (2R,3R,4R,5S)-1-(((1s,4S)-4-cyclopropylcyclohexyl)methyl)-2-methylpiperidine-3,4,5-triol (0.02 g, 39.2%) as a white solid. $^1$H NMR (400 MHz, $CD_3OD$) δ 3.51-3.43 (m, 1H), 3.15-3.09 (m, 1H), 3.05 (dd, J=11.3, 4.8 Hz, 1H), 3.00-2.94 (m, 1H), 2.80 (dd, J=12.9, 9.2 Hz, 1H), 2.10-2.04 (m, 1H), 2.02-1.94 (m, 2H), 1.75-1.63 (m, 1H), 1.63-1.48 (m, 6H), 1.47-1.38 (m, 2H), 1.22 (d, J=6.1 Hz, 3H), 0.83-0.74 (m, 1H), 0.67-0.59 (m, 1H), 0.46-0.39 (m, 2H), 0.07-0.02 (m, 2H); ESI MS m/z 284.218 $[M+H]^+$.

Example 21

(2R,3R,4R,5S)-1-(((1r,4R)-4-cyclopropylcyclohexyl)methyl)-2-methylpiperidine-3,4,5-triol

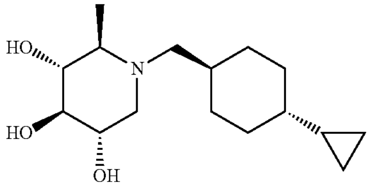 [SMILES: C[C@@H]1[C@@H](O)[C@H](O)[C@@H](O)CN1C[C@H]1CC[C@H](C2CC2)CC1]

To a solution of trans-1,4-cyclohexane dicarboxylic acid monomethyl ester (1.86 g, 10 mmol) in THE (60 mL) and $Et_3N$ (1.5 mL, 10.8 mmol) at −5° C. was added methyl chloroformate (1.0 mL, 10.8 mmol) while maintaining the temperature between −5° C. and 0° C. After 1 h, the mixture was added via a cannula into a solution of $NaBH_4$ (0.8 g, 21.6 mmol) in water (30 mL) at 10° C. The reaction mixture was further stirred at 10° C. for 30 min before quenching with 1N HCl to pH=1. The mixture was partitioned with EtOAc and organics were washed with brine, dried over anhydrous $Na_2SO_4$ and concentrated. The residue was purified on silica gel by flash chromatography (EtOAc/hexanes, 1:9), affording (1r,4r)-methyl 4-(hydroxymethyl) cyclohexanecarboxylate (1.34 g, 77.8%) as an oil. $^1H$ NMR (400 MHz, $CDCl_3$) 3.66 (s, 3H), 3.64-3.46 (m, 2H), 2.35-2.20 (m, 1H), 2.13-1.97 (m, 2H), 1.93-1.79 (m, 1H), 1.60-1.33 (m, 4H), 1.05 (m, 2H).

To a stirred solution of the above material (0.6 g, 3.48 mmol) at 0° C. in dry DCM (10 mL) was added DMP (2.2 g, 5.2 mmol). After stirring at RT for 2 h, the reaction mixture was quenched with a 1:1 mixture of 1M $Na_2S_2O_3$: satd. $NaHCO_3$ solution (20 mL) and further stirred for 30 min before being diluted with DCM (40 mL). Organics were separated, dried over anhydrous $Na_2SO_4$ and concentrated. The crude residue was purified on silica gel by flash chromatography (EtOAc/hexanes, 1:4), affording (1r,4r)-methyl 4-formylcyclohexanecarboxylate (0.36 g, 60.7%) as an oil. $^1H$ NMR (500 MHz, $CDCl_3$) δ 9.50 (s, 1H), 3.54 (s, 3H), 2.24-2.08 (m, 2H), 2.0-1.9 (m, 4H), 1.37 (qt, J=13.6, 3.4 Hz, 2H), 1.18 (qt, J=12.6, 3.4 Hz, 2H).

To a mixture of methyl triphenylphosphonium bromide (1.14 g, 3.2 mmol) in anhydrous THE (8 mL) at 0° C. was added KOtBu (0.36 g, 3.2 mmol). The mixture was stirred for 30 min before (1r,4r)-methyl 4-formylcyclohexanecarboxylate (0.36 g, 2.12 mmol) pre-dissolved in anhydrous THE (8 mL) was added slowly. The mixture was warmed to RT and stirred for 2 h before being concentrated under reduced pressure. The resulting crude residue was purified on silica gel by flash chromatography (EtOAc/hexanes, 1:4), affording (1r,4r)-methyl 4-vinylcyclohexanecarboxylate (0.25 g, 70%) as an oil. $^1H$ NMR (400 MHz, $CDCl_3$) δ 5.71 (ddd, J=17.1, 10.4, 6.4 Hz, 1H), 4.99-4.81 (m, 2H), 3.62 (s, 3H), 2.20 (tt, J=12.3, 3.6 Hz, 1H), 2.02-1.85 (m, 3H), 1.85-1.73 (m, 2H), 1.48-1.37 (m, 2H), 1.13-1.02 (m, 2H).

To a mixture of the above material (0.25 g, 1.48 mmol) in DCE (8 mL) at 0° C. was added diethylzinc (1.0 M hexanes, 4.4 mL, 4.4 mmol) followed by chloroiodomethane (0.65 mL, 8.88 mmol). The mixture was stirred at 0° C. for 2 h and then at RT for 2 h before being quenched with satd. aqueous $NH_4Cl$. The reaction mixture was partitioned between DCM and water, organics were separated and dried over anhydrous $Na_2SO_4$ and concentrated. The crude residue was purified on silica gel by flash chromatography (EtOAc/hexanes, 1:4), affording (1r,4r)-methyl 4-cyclopropylcyclohexanecarboxylate (0.24 g, 88.9%) as an oil. $^1H$ NMR (400 MHz, $CDCl_3$) δ 3.63 (s, 3H), 2.21 (tt, J=12.2, 3.6 Hz, 1H), 1.99-1.90 (m, 2H), 1.89-1.81 (m, 2H), 1.33 (tdd, J=13.1, 12.0, 3.4 Hz, 2H), 1.13-1.00 (m, 2H), 0.50-0.38 (m, 2H), 0.38-0.30 (m, 2H), 0.05-0.03 (m, 2H).

To a cooled (0° C.) solution of the above material (0.24 g, 1.31 mmol) in 5 mL of anhydrous THF, 0.15 g (3.95 mmol) of LAH was added portion wise while stirring, under Ar. The mixture was stirred at 0° C. for 2.5 h then at reflux for 5 h until disappearance of starting material. The mixture was diluted with EtOAc, washed with 1.0 M HCl, water and brine. The organics were dried over anhydrous $Na_2SO_4$ and concentrated to yield ((1r,4r)-4-cyclopropylcyclohexyl) methanol (0.19 g, 94%) as an oil. $^1H$ NMR (400 MHz, $CDCl_3$) δ 3.44 (d, J=6.4 Hz, 2H), 1.91-1.70 (m, 4H), 1.45 (tdt, J=12.0, 6.4, 3.2 Hz, 1H), 1.10 (qd, J=13.1, 12.7, 3.2 Hz, 2H), 0.88 (qd, J=12.7, 3.2 Hz, 2H), 0.46 (dddd, J=13.1, 11.3, 7.6, 3.8 Hz, 2H), 0.39-0.32 (m, 2H), 0.08-0.00 (m, 2H).

To a stirred solution of the above material (0.19 g, 1.23 mmol) at 0° C. in dry DCM (5 mL) was added DMP (0.78 g, 1.84 mmol). After stirring at RT for 2 h, the reaction mixture was quenched with a 1:1 mixture of 1M $Na_2S_2O_3$: satd. $NaHCO_3$ solution (20 mL) and further stirred for 30 min before being diluted with DCM (40 mL). Organics were separated, dried over anhydrous $Na_2SO_4$ and concentrated. The crude residue was purified on silica gel by flash chromatography (EtOAc/hexanes, 1:9), affording (1r, 4r)-4-cyclopropylcyclohexanecarbaldehyde (0.14 g, 74.7%) as an oil. $^1H$ NMR (400 MHz, $CDCl_3$) δ 9.59 (s, 1H), 2.22-2.11 (m, 1H), 2.06-1.84 (m, 4H), 1.27-1.04 (m, 4H), 0.52-0.40 (m, 2H), 0.40-0.33 (m, 2H), 0.04 (m, 2H).

To a solution of (2R,3R,4R,5S)-3,4,5-tris(benzyloxy)-2-methylpiperidine (0.23 g, 0.55 mmol) and (1r,4r)-4-cyclopropylcyclohexanecarbaldehyde (0.07 g, 0.46 mmol) in anhydrous MeOH (8 mL) was added AcOH (few drops) and the mixture was stirred at RT for 10 min. Sodium cyanoborohydride (0.034 g, 0.55 mmol) was added and reaction stirred at RT overnight. The mixture was concentrated and diluted with EtOAc (30 mL) and the organics were washed with satd. aqueous $NaHCO_3$. The organics were dried over anhydrous $Na_2SO_4$ and concentrated, then the crude residue was purified on silica gel by flash chromatography (EtOAc/hexanes, 1:9), affording (2R,3R,4R,5S)-3,4,5-tris(benzyloxy)-1-(((1r,4R)-4-cyclopropylcyclohexyl)methyl)-2-methyl piperidine (0.1 g, 39.2%) as a yellow solid. $^1H$ NMR (400 MHz, $CDCl_3$) δ 7.39-7.26 (m, 15H), 4.97 (dd, J=14.9, 10.9 Hz, 2H), 4.85 (d, J=11.0 Hz, 1H), 4.78-4.58 (m, 3H), 3.59 (td, J=9.7, 4.5 Hz, 1H), 3.51 (t, J=9.0 Hz, 1H), 3.16-2.99 (m, 2H), 2.44 (dd, J=12.8, 8.7 Hz, 1H), 2.29-2.21 (m, 1H), 2.09-1.92 (m, 2H), 1.90-1.77 (m, 3H), 1.73-1.61 (m, 1H), 1.39-1.28 (m, 1H), 1.18 (d, J=6.1 Hz, 3H), 1.15-0.99 (m, 2H), 0.87-0.65 (m, 2H), 0.54-0.41 (m, 2H), 0.40-0.33 (m, 2H), 0.08-0.04 (m, 2H); ESI MS m/z 554.354 $[M+H]^+$.

At −78° C., under Ar, to a solution of the above material (0.1 g, 0.18 mmol) in DCM (5 mL) was added $BCl_3$ (1.0 M in DCM, 0.9 mL, 0.9 mmol), and the mixture was stirred for 2 h while the bath temperature reached 0° C. The mixture was further stirred at 0° C. for 2 h and then quenched by adding MeOH (2 mL) slowly. After stirring at RT for 30 min the mixture was concentrated under reduced pressure. The resulting residue was neutralized with $NH_4OH$ (0.5 mL) and concentrated again under reduced pressure. The crude residue was purified on silica gel by flash chromatography (MeOH/DCM, 1:9), affording (2R,3R,4R,5S)-1-(((1r,4R)-4-cyclopropylcyclohexyl)methyl)-2-methylpiperidine-3,4,5-triol (0.039 g, 77%) as a white solid. $^1$H NMR (400 MHz, $CD_3OD$) δ 3.55 (td, J=9.9, 4.5 Hz, 1H), 3.23-3.13 (m, 2H), 3.07 (t, J=9.0 Hz, 1H), 2.77-2.68 (m, 1H), 2.39-2.14 (m, 3H), 2.01-1.84 (m, 3H), 1.75 (dt, J=12.7, 3.1 Hz, 1H), 1.61-1.50 (m, 1H), 1.26 (d, J=6.2 Hz, 3H), 1.23-1.07 (m, 2H), 1.02-0.80 (m, 2H), 0.54-0.43 (m, 2H), 0.41-0.36 (m, 2H), 0.09-0.03 (m, 2H); ESI MS m/z 284.218 [M+H]$^+$.

Example 22

(2R,3R,4R,5S)-2-methyl-1-((4-phenylcyclohexyl) methyl)piperidine-3,4,5-triol

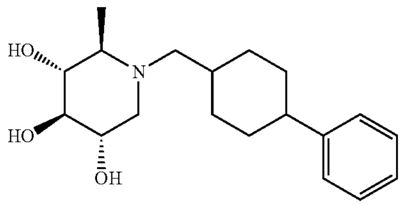

To a solution of (2R,3R,4R,5S)-3,4,5-tris(benzyloxy)-2-methylpiperidine (0.2 g, 0.5 mmol) in DCM (8 mL) was added 4-phenylcyclohexanecarbaldehyde (0.18 g, 1.0 mmol) and $Na(OAc)_3BH$ (0.2 g, 1.0 mmol) mL, 0.77 mmol). The reaction was stirred at RT overnight before diluting with DCM (25 mL). Organics were washed with satd. aqueous $NaHCO_3$, brine, dried over anhydrous $Na_2SO_4$ and concentrated. The residue was purified on silica gel by flash chromatography (EtOAc/hexanes, 1:9), affording a 1:1 cis/trans mixture of (2R,3R,4R,5S)-3,4,5-tris(benzyloxy)-2-methyl-1-((4-phenylcyclohexyl) methyl) piperidine (0.19 g, 64%) as an oil. ESI MS m/z 590.329 [M+H]$^+$.

At −78° C., under Ar, to a solution of the above material (0.1 g, 0.17 mmol) in DCM (5 mL) was added $BCl_3$ (1.0 M in DCM, 1.7 mL, 1.7 mmol), and the mixture was stirred for 2 h while the bath temperature warmed to 0° C. The mixture was stirred at 0° C. for next 2 h and then quenched by adding MeOH (2 mL) slowly. After stirring at RT for 30 min the mixture was concentrated under reduced pressure. The resulting residue was neutralized with $NH_4OH$ (0.5 mL) and concentrated again under reduced pressure. The crude residue was purified and separated on silica gel by flash chromatography (MeOH/DCM, 1:9), affording (2R,3R,4R,5S)-2-methyl-1-((4-phenylcyclohexyl) methyl) piperidine-3,4,5-triol (0.047 g, 86.5%) as a white solid. $^1$H NMR analysis indicated that this material was a ~1:1 mixture of cis/trans isomers; ESI MS m/z 320.21 [M+H]$^+$.

Example 23

(2R,3R,4R,5S)-2-methyl-1-(spiro[2.5]octan-6-ylmethyl)piperidine-3,4,5-triol

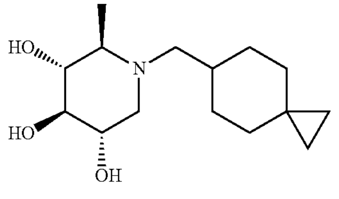 [SMILES: C[C@@H]1[C@@H](O)[C@H](O)[C@@H](O)CN1CC1CCC2(CC1)CC2]

To a stirred solution of methyltriphenylphosphonium bromide (10.7 g, 300 mmol) in anhydrous THE (100 mL) was added KO$^t$Bu (3.36 g, 300 mmol) at 0° C. under $N_2$, and stirred for 30 min. Subsequently, ethyl 4-oxocyclohexanecarboxylate (3.4 g, 200 mmol) was dissolved in 20 mL of THE and added dropwise to the mixture under $N_2$, and reacted at RT for 3 h. The reaction was quenched with satd. aqueous $NaHCO_3$ at 0° C. The mixture was extracted with EtOAc (3×40 mL). The combined organic layer was washed with water (2×20 mL), separated, dried over $Na_2SO_4$. After filtration, the solvent was evaporated under reduced pressure, and the residue was purified on silica gel by flash chromatography affording ethyl 4-methylenecyclohexanecarboxylate as an oil (2.25 g, 67%). $^1$H NMR (400 MHz, $CDCl_3$) δ 4.67 (d, J=1.5 Hz, 2H), 4.15 (q, J=7.1 Hz, 2H), 2.46 (tt, J=11.0, 3.6 Hz, 1H), 2.36 (dt, J=12.7, 3.7 Hz, 2H), 2.15-1.94 (m, 4H), 1.69-1.50 (m, 2H), 1.28 (t, J=7.1 Hz, 3H).

To a stirred solution of diethyl zinc (16.5 mL, 1M in hexane, 16.5 mmol) in anhydrous DCM (25 mL) was added TFA (1.1 mL, 16.4 mmol) at 0° C. under $N_2$, and the mixture was stirred for 60 min. Subsequently, ethyl 4-methylenecyclohexanecarboxylate (1.1 g, 6.54 mmol) was dissolved in 3 mL of DCM and added dropwise to the mixture under $N_2$, reacted at 0° C. for 2 h. The reaction was quenched with water at 0° C. The mixture was extracted with DCM (3×20 mL). The combined organic layer was washed with water (2×10 mL), separated, dried over $Na_2SO_4$. After filtration, the solvent was evaporated under reduced pressure, and the residue was purified on silica gel by flash chromatography affording ethyl spiro[2.5]octane-6-carboxylate as an oil (0.90 g, 76%). $^1$H NMR (400 MHz, $CDCl_3$) δ 4.15 (q, J=7.1 Hz, 2H), 2.33 (tt, J=10.8, 3.7 Hz, 1H), 1.91 (dt, J=11.5, 3.1 Hz, 2H), 1.77-1.52 (m, 4H), 1.28 (t, J=7.1 Hz, 3H), 1.06-0.96 (m, 2H), 0.35-0.18 (m, 4H).

To a solution of the above material (800 mg, 4.39 mmol) in anhydrous THE (10 mL) at 0° C., was added LAH (500 mg, 13.2 mmol), and the mixture was stirred at 0° C. for 1 h. The mixture was quenched slowly with satd. aqueous $Na_2SO_4$ and filtered. The solid was washed with EtOAc. The combined organic layer was washed with water (2×20 mL), separated, dried over $Na_2SO_4$. After filtration, the solvent was evaporated under reduced pressure, to obtain crude spiro[2.5]octan-6-ylmethanol as an oil (725 mg). $^1$H NMR (400 MHz, $CDCl_3$) δ 3.52 (dd, J=6.4, 1.0 Hz, 2H), 1.75 (ddd, J=13.3, 8.2, 4.2 Hz, 4H), 1.60-1.41 (m, 2H), 1.25-1.07 (m, 2H), 1.01-0.87 (m, 2H), 0.43-0.11 (m, 4H).

To a solution of the above material (190 mg, 1.36 mmol) in anhydrous DCM (20 mL) at 0° C., was added DMP (748 mg, 1.76 mmol), and the mixture was stirred at 0° C. for 2 h. The mixture was quenched slowly with $Na_2S_3O_5$ solution. The mixture was extracted with DCM (3×20 mL). The combined organic layer was washed with water (2×10 mL), separated and dried over $Na_2SO_4$. After filtration, the solvent was evaporated under reduced pressure, and the residue was purified on silica gel by flash chromatography affording spiro[2.5]octane-6-carbaldehyde as an oil (63 mg, 34%). $^1$H NMR (400 MHz, $CDCl_3$) δ 9.69 (d, J=1.4 Hz, 1H), 2.30 (ddtd, J=10.4, 7.3, 3.7, 1.3 Hz, 1H), 1.92 (ddd, J=12.3, 6.2, 2.5 Hz, 2H), 1.72-1.46 (m, 4H), 1.10 (dt, J=13.0, 3.9 Hz, 2H), 0.41-0.14 (m, 4H).

To a stirred solution of (2R,3R,4R,5S)-3,4,5-tris(benzyloxy)-2-methylpiperidine (92 mg, 0.22 mmol) and spiro[2.5] octane-6-carbaldehyde (60 g, 0.43 mmol) in anhydrous MeOH (5 mL) was added HOAc (0.10 mL, 1.75 mmol) and the mixture was stirred for 30 min. $NaBH_3CN$ (27 mg, 0.43 mmol) was added, and the resulting mixture was stirred at RT for 18 h. The reaction was quenched with satd. aqueous $NaHCO_3$ at 0° C. The mixture was extracted with EtOAc (3×20 mL). The combined organic layer was washed with water (2×10 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-2-methyl-1-(spiro[2.5]octan-6-ylmethyl)piperidine as an oil (59 mg, 50%). ESI MS m/z 540.32 $[M+H]^+$.

To a stirred solution of the above material (55 mg, 0.10 mmol) in anhydrous DCM (3 mL) was added $BCl_3$ solution (1M in DCM, 0.80 mL, 0.80 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(spiro[2.5]octan-6-ylmethyl)piperidine-3,4,5-triol as a white solid (17 mg, 63%). $^1$H NMR (400 MHz, $CD_3OD$) δ 3.52-3.43 (m, 1H), 3.12 (t, J=9.0 Hz, 1H), 3.06 (dd, J=11.4, 4.8 Hz, 1H), 2.96 (t, J=9.1 Hz, 1H), 2.63 (dd, J=12.8, 8.9 Hz, 1H), 2.11-1.93 (m, 3H), 1.92-1.83 (m, 1H), 1.82-1.61 (m, 3H), 1.61-1.47 (m, 1H), 1.19 (d, J=6.1 Hz, 3H), 1.18-0.99 (m, 2H), 0.98-0.88 (m, 2H), 0.32-0.16 (m, 4H); ESI MS m/z 270.19 $[M+H]^+$.

Example 24

(2R,3R,4R,5S)-2-methyl-1-(spiro[3.5]nonan-7-ylmethyl)piperidine-3,4,5-triol

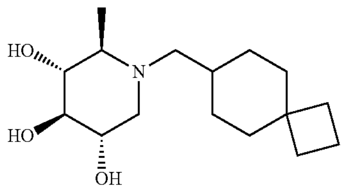 [SMILES: C[C@@H]1[C@@H](O)[C@H](O)[C@@H](O)CN1CC1CCC2(CCC2)CC1]

Under Ar, to a solution of (2R,3R,4R,5S)-3,4,5-tris(benzyloxy)-2-methyl-1-(piperidin-4-ylmethyl)piperidine (491 mg, 1.1 mmol) and spiro[3.5]nonane-7-carbaldehyde (179 mg, 1.12 mmol) in anhydrous DCM (10 mL) was added $NaBH(OAc)_3$ (499 mg, 2.3 mmol). The mixture was stirred at RT for 18 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 20% EtOAc in hexanes, affording (2R,3R,4R,5S)-3,4,5-tris(benzyloxy)-2-methyl-1-(spiro[3.5]nonan-7-ylmethyl)piperidine as a white form (203 mg, 31%).

At −78° C. under Ar, to a solution of the above material (203 mg, 0.37 mmol) in anhydrous DCM (15 mL) was added $BCl_3$ solution (10 mL, 1 M in DCM, 10 mmol). The mixture was stirred at −78 for 1 h and 0° C. for 4 h; MeOH (20 mL) was added. The mixture was stirred for additional 2 h at 0° C., and evaporated to dryness under rotavap. The residue was purified on silica gel by flash chromatography using 10% MeOH and 2% $NH_3$ solution in DCM, affording (2R,3R,4R,5S)-2-methyl-1-(spiro[3.5]nonan-7-ylmethyl)piperidine-3,4,5-triol as a white solid (88 mg, 85%). $^1$H NMR (400 MHz, $CD_3OD$) δ 3.70-3.50 (m, 1H), 3.24 (t, J=9.0 Hz, 2H), 3.16 (d, J=9.1 Hz, 1H), 2.84 (bs, 1H), 2.50-2.45 (b, 3H), 1.97-1.66 (m, 9H), 1.64-1.47 (m, 2H), 1.44-1.21 (m, 5H), 1.15-0.89 (m, 2H); ESI MS m/z 284.2 $[M+H]^+$.

Example 25

(2R,3R,4R,5S)-2-methyl-1-(spiro[4.5]decan-8-ylmethyl)piperidine-3,4,5-triol

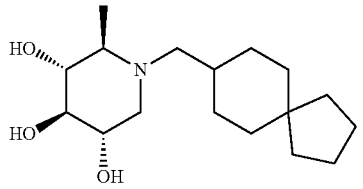 [SMILES: C[C@@H]1[C@@H](O)[C@H](O)[C@@H](O)CN1CC1CCC2(CCCC2)CC1]

To a suspension of LAH (1.80 g, 48.3 mmol) in anhydrous THE (60 mL) at 0° C. was added a solution of 2,2'-(cyclopentane-1,1-diyl)diacetic acid (1.50 g, 8.05 mmol) slowly, and the mixture was refluxed for 2 h. The mixture was quenched slowly with satd. aqueous $Na_2SO_4$ and filtered. The solid was washed with EtOAc. The combined organic layer was washed with water (2×20 mL), separated, dried over $Na_2SO_4$. After filtration, the solvent was evaporated under reduced pressure, and the residue was purified on silica gel by flash chromatography affording 2,2'-(cyclopentane-1,1-diyl)diethanol as a white solid (1.01 g, 79%). $^1$H NMR (400 MHz, $CDCl_3$) δ 3.76 (t, J=6.9 Hz, 4H), 1.89 (s, 2H), 1.74-1.62 (m, 8H), 1.51-1.38 (m, 4H).

To a solution of the above material (500 mg, 3.16 mmol) in anhydrous pyridine (8 mL) at 0° C., was added p-toluenesulfonyl chloride (1.27 g, 6.64 mmol), and the mixture was stirred at RT for 18 h. The mixture was quenched slowly with satd. aqueous $Na_2CO_3$ at 0° C. The mixture was extracted with EtOAc (3×30 mL). The combined organic layer was washed with water (2×20 mL), separated, dried over $Na_2SO_4$. After filtration, the solvent was evaporated under reduced pressure, and the residue was purified on silica gel by flash chromatography affording cyclopentane-1,1-diylbis(ethane-2,1-diyl) bis(4-methylbenzenesulfonate) as a white solid (660 mg, 45%). $^1$H NMR (400 MHz, $CDCl_3$) δ 7.81-7.72 (m, 4H), 7.44-7.33 (m, 4H), 4.03 (t, J=7.1 Hz, 4H), 2.48 (s, 6H), 1.65 (t, J=7.1 Hz, 4H), 1.59-1.54 (m, 4H), 1.42-1.32 (m, 4H).

To a suspension of NaH (227 mg, 5.68 mmol) in anhydrous THE (10 mL) at 0° C. was added a solution of dimethylmalonate (0.94 mL, 7.10 mmol) in THE (5 mL) slowly, and the mixture was stirred for 10 min at 0° C. A solution of cyclopentane-1,1-diylbis(ethane-2,1-diyl) bis(4-methylbenzenesulfonate) (660 mg, 1.42 mmol) in THE (5 mL) was added slowly and stirred for 1 h at 0° C. The mixture was refluxed for 20 h before quenched slowly with satd. aqueous $NH_4Cl$. The mixture was extracted with EtOAc (3×30 mL). The combined organic layer was washed with water (2×20 mL), separated, dried over $Na_2SO_4$. After filtration, the solvent was evaporated under reduced pressure, and the residue was purified on silica gel by flash chromatography affording dimethyl spiro[4.5]decane-8,8-dicarboxylate as a clear oil (250 mg, 69%). $^1$H NMR (400 MHz, $CDCl_3$) δ 3.74 (s, 6H), 2.04 (dd, J=7.6, 4.7 Hz, 4H), 1.68-1.54 (m, 4H), 1.47-1.35 (m, 8H).

To a solution of the above material (250 mg, 0.98 mmol) in DMSO (5 mL) at RT, was added LiCl (166 mg, 3.92 mmol) and water (0.04 mL), and the mixture was stirred at 185° C. for 5 h. The mixture was quenched slowly with satd. aqueous $Na_2CO_3$ at 0° C. The mixture was extracted with EtOAc (3×20 mL). The combined organic layer was washed with water (2×10 mL), separated, dried over $Na_2SO_4$. After filtration, the solvent was evaporated under reduced pressure, and the residue was purified on silica gel by flash chromatography affording methyl spiro[4.5]decane-8-carboxylate as a clear oil (123 mg, 64%). $^1H$ NMR (400 MHz, $CDCl_3$) δ 3.69 (s, 3H), 2.34-2.21 (m, 1H), 1.88-1.78 (m, 2H), 1.66-1.51 (m, 8H), 1.44 (t, J=6.9 Hz, 2H), 1.37 (t, J=7.1 Hz, 2H), 1.33-1.24 (m, 2H).

To a solution of the above material (120 mg, 0.61 mmol) in anhydrous THE (5 mL) at 0° C., was added LAH (93 mg, 2.45 mmol), and the mixture was stirred at 0° C. for 2 h. The mixture was quenched slowly with satd. aqueous $Na_2SO_4$ and filtered. The solid was washed with EtOAc. The combined organic layer was washed with water (2×20 mL), separated, dried over $Na_2SO_4$. After filtration, the solvent was evaporated under reduced pressure, and the residue was purified on silica gel by flash chromatography affording spiro[4.5]decan-8-ylmethanol as a clear oil (101 mg, 99%). $^1H$ NMR (400 MHz, $CDCl_3$) δ 3.48 (d, J=6.4 Hz, 2H), 1.69-1.34 (m, 14H), 1.29 (td, J=13.1, 3.6 Hz, 2H), 1.15-1.01 (m, 2H).

To a solution of the above material (110 mg, 0.65 mmol) in anhydrous DCM (10 mL) at 0° C., was added DMP (361 mg, 0.85 mmol), and the mixture was stirred at 0° C. for 2 h. The mixture was quenched slowly with $Na_2S_3O_5$ solution. The mixture was extracted with DCM (3×20 mL). The combined organic layer was washed with water (2×10 mL), separated, dried over $Na_2SO_4$. After filtration, the solvent was evaporated under reduced pressure, and the residue was purified on silica gel by flash chromatography affording spiro[4.5]decane-8-carbaldehyde as an oil (60 mg, 55%).

To a stirred solution of (2R,3R,4R,5S)-3,4,5-tris(benzyloxy)-2-methylpiperidine (97 mg, 0.23 mmol) and spiro[4.5]decane-8-carbaldehyde (58 mg, 0.35 mmol) in anhydrous DCM (5 mL) was added HOAc (0.10 mL, 1.75 mmol) and stirred for 30 min. $Na(OAc)_3BH$ (74 mg, 0.35 mmol) was added, and the resulting mixture was stirred at RT for 18 h. The reaction was quenched with satd. aqueous $NaHCO_3$ at 0° C. The mixture was extracted with EtOAc (3×20 mL). The combined organic layer was washed with water (2×10 mL), separated, dried over $Na_2SO_4$. After filtration, the solvent was evaporated under reduced pressure, and the residue was purified on silica gel by flash chromatography affording (2R (2R,3R,4R,5S)-3,4,5-tris(benzyloxy)-2-methyl-1-(spiro[4.5]decan-8-ylmethyl)piperidine as an oil (115 mg, 88%). ESI MS m/z 568.37 $[M+H]^+$.

To a stirred solution of the above material (87 mg, 0.16 mmol) in anhydrous DCM (5 mL) was added $BCl_3$ solution (1M in DCM, 1.27 mL, 1.27 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(spiro[4.5]decan-8-ylmethyl)piperidine-3,4,5-triol as a white solid (35 mg, 77%). $^1H$ NMR (400 MHz, $CD_3OD$) δ 3.51-3.43 (m, 1H), 3.12 (t, J=9.0 Hz, 1H), 3.04 (dd, J=11.3, 4.8 Hz, 1H) 2.96 (t, J=9.1 Hz, 1H), 2.58 (dd, J=12.8, 8.8 Hz, 1H), 2.09-1.92 (m, 3H), 1.82-1.74 (m, 1H), 1.68-1.41 (m, 10H), 1.41-1.22 (m, 4H), 1.19 (d, J=6.1 Hz, 3H), 1.14-0.92 (m, 2H); ESI MS m/z 298.24 $[M+H]^+$.

Example 26

(2R,3R,4R,5S)-1-(((5S,8s)-3,3-dimethyl-2-oxaspiro[4.5]decan-8-yl)methyl)-2-methylpiperidine-3,4,5-triol

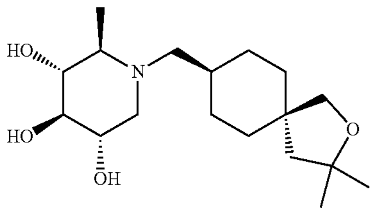 [SMILES: C[C@@H]1[C@@H](O)[C@H](O)[C@@H](O)CN1C[C@H]1CC[C@]2(CC1)COC(C)(C)C2]

To a solution of ((5s,8s)-3,3-dimethyl-2-oxaspiro[4.5]decan-8-yl)methanol (Bioorg. Med. Chem. Lett. 2019, 29, 373) (0.37 g, 1.86 mmol) at 0° C. in dry DCM (8 mL) was added DMP (1.19 g, 2.82 mmol). After stirring at 0° C. for 30 min, the reaction mixture was warmed to RT for 1.5 h. The reaction mixture was diluted with a 1:1 mixture of 1M $Na_2S_2O_3$ and satd. $NaHCO_3$ (50 mL) and stirred for 30 min. DCM (30 mL) was added and organics were separated, dried over anhydrous $Na_2SO_4$ and concentrated. The crude residue was purified on silica gel by flash chromatography (EtOAc/hexanes, 1:1), affording (5s, 8s)-3,3-dimethyl-2-oxaspiro[4.5]decane-8-carbaldehyde (0.25 g, 70.7%) as a gummy solid. $^1H$ NMR (500 MHz, $CDCl_3$) δ 9.60 (s, 1H), 3.59 (s, 2H), 2.24-2.13 (m, 1H), 1.86-1.82 (m, 2H), 1.76-1.74 (m, 2H), 1.58 (d, J=1.8 Hz, 2H), 1.48-1.32 (m, 4H), 1.23 (d, J=2.2 Hz, 6H).

To a solution of (2R,3R,4R,5S)-3,4,5-tris(benzyloxy)-2-methylpiperidine (0.18 g, 0.43 mmol) in MeOH (5 mL) was added (5s,8s)-3,3-dimethyl-2-oxaspiro[4.5]decane-8-carbaldehyde (0.08 g, 0.43 mmol) and acetic acid (0.3 mL). After stirring at RT for 10 min, $NaCNBH_3$ (0.04 g, 0.66 mmol) was added and the mixture was stirred at RT overnight. The reaction mixture was concentrated before diluting with DCM (25 mL). Organics were washed with satd. aqueous $NaHCO_3$, brine, dried over anhydrous $Na_2SO_4$ and concentrated. The residue was purified on silica gel by flash chromatography (EtOAc/hexanes, 1:9), affording (2R,3R,4R,5S)-3,4,5-tris(benzyloxy)-1-((3,3-dimethyl-2-oxaspiro[4.5]decan-8-yl)methyl)-2-methylpiperidine (0.17 g, 66%) as an oil. $^1H$ NMR (500 MHz, $CDCl_3$) δ 7.40-7.23 (m, 15H), 4.96 (dd, J=16.8, 10.9 Hz, 2H), 4.84 (d, J=11.0 Hz, 1H), 4.74 (d, J=11.6 Hz, 1H), 4.64 (dd, J=26.8, 11.2 Hz, 2H), 3.65 (d, J=1.8 Hz, 2H), 3.61-3.54 (m, 1H), 3.50 (t, J=9.0 Hz, 1H), 3.09 (t, J=9.0 Hz, 1H), 3.03 (dd, J=11.5, 4.7 Hz, 1H), 2.46 (dd, J=12.8, 8.9 Hz, 1H), 2.24 (dq, J=12.1, 6.2 Hz, 1H), 2.07-1.94 (m, 2H), 1.81-1.67 (m, 3H), 1.64-1.52 (m, 3H), 1.40-1.30 (m, 3H), 1.27 (m, 6H), 1.20-1.14 (m, 3H), 0.96-0.74 (m, 2H); ESI MS m/z 598.394 $[M+H]^+$.

A mixture of the above material (0.17 g, 0.28 mmol) and $Pd(OH)_2/C$ (20% wt, 0.02 g) in EtOH/2N HCl (25/1 mL) was stirred under 50 psi hydrogen pressure overnight. The mixture was then filtered through a celite cake, and the filtrate was collected and concentrated to dryness. To the residue was added $NH_4OH$ solution (3 mL) and the mixture was concentrated again. The crude residue was re-dissolved in pyridine (6 mL) and treated with $Ac_2O$ (0.6 mL). After stirring overnight at RT, the mixture was concentrated and purified on silica gel by flash chromatography (EtOAc/hexanes, 1:1), affording (2R,3R,4R,5S)-1-((3,3-dimethyl-2-oxaspiro[4.5]decan-8-yl)methyl)-2-methylpiperidine-3,4,5-triyl triacetate, which was hydrolyzed by stirring with 1M $NH_3$ solution in MeOH (10 mL) overnight. The crude residue was purified on silica gel by flash chromatography (MeOH/DCM, 1:9), affording (2R,3R,4R,5S)-1-((3,3-dimethyl-2-oxaspiro[4.5]decan-8-yl)methyl)-2-methylpiperidine-3,4,5-triol (0.052 g, 56%) as a white solid. $^1H$ NMR (400 MHz, $CD_3OD$) δ 3.69 (s, 2H), 3.46 (ddd, J=10.5, 9.0, 4.7 Hz, 1H), 3.11 (t, J=9.0 Hz, 1H), 3.02 (dd, J=11.3, 4.8 Hz, 1H), 2.95 (t, J=9.1 Hz, 1H), 2.58 (dd, J=12.9, 8.8 Hz, 1H), 2.09-1.92 (m, 3H), 1.88-1.72 (m, 3H), 1.67-1.59 (m, 3H), 1.53-1.31 (m, 3H), 1.26 (s, 6H), 1.19 (d, J=6.1 Hz, 3H), 1.05-0.84 (m, 2H); ESI MS m/z 328.245 $[M+H]^+$.

Example 27

(2R,3R,4R,5S)-2-methyl-1-((1,2,3,4-tetrahydronaphthalen-2-yl)methyl)piperidine-3,4,5-triol

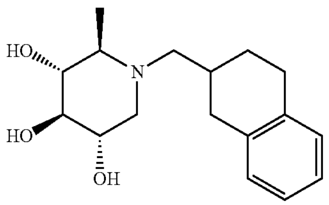 [SMILES: C[C@@H]1[C@@H](O)[C@H](O)[C@@H](O)CN1CC1CCc2ccccc2C1]

To a solution of 1,2,3,4-tetrahydro-2-naphthoic acid (120 mg, 0.68 mmol) in anhydrous THE (5 mL) at 0° C., was added LAH (78 mg, 2.04 mmol), and the mixture was stirred at 0° C. for 2 h. The mixture was quenched slowly with satd. aqueous $Na_2SO_4$ and filtered. The solid was washed with EtOAc. The combined organic layer was washed with $H_2O$ (2×20 mL), separated, and dried over $Na_2SO_4$. After filtration, the solvent was evaporated under reduced pressure affording the crude (1,2,3,4-tetrahydronaphthalen-2-yl)methanol as a clear oil. To a solution of the obtained oil in anhydrous DCM (5 mL) at 0° C., was added DMP (375 mg, 0.88 mmol), and the mixture was stirred at 0° C. for 2 h. The mixture was quenched slowly with $Na_2S_3O_5$ solution. The mixture was extracted with DCM (3×20 mL). The combined organic layer was washed with $H_2O$ (2×10 mL), separated, and dried over $Na_2SO_4$. After filtration, the solvent was evaporated under reduced pressure, and the residue was purified on silica gel by flash chromatography affording 1,2,3,4-tetrahydronaphthalene-2-carbaldehyde as an oil (44 mg, 40%).

To a solution of (2R,3R,4R,5S)-3,4,5-tris(benzyloxy)-2-methylpiperidine (80 mg, 0.19 mmol) and 1,2,3,4-tetrahydronaphthalene-2-carbaldehyde (40 mg, 0.25 mmol) in anhydrous DCM (5 mL) was added HOAc (0.10 mL, 1.75 mmol) and stirred for 30 min. $NaBH(OAc)_3$ (52 mg, 0.25 mmol) was added, and the resulting mixture was stirred at RT for 18 h. The reaction was quenched with satd. aqueous $NaHCO_3$ at 0° C. The mixture was extracted with EtOAc (3×20 mL). The combined organic layer was washed with $H_2O$ (2×10 mL), separated, and dried over $Na_2SO_4$. After filtration, the solvent was evaporated under reduced pressure, and the residue was purified on silica gel by flash chromatography affording (2R,3R,4R,5S)-3,4,5-tris(benzyloxy)-2-methyl-1-((1,2,3,4-tetrahydronaphthalen-2-yl)methyl)piperidine as an oil (90 mg, 84%). ESI MS m/z 562.71 $[M+H]^+$.

To a solution of the above material (90 mg, 0.16 mmol) in anhydrous DCM (5 mL) was added $BCl_3$ (1M in DCM, 0.97 mL, 0.97 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-((1,2,3,4-tetrahydronaphthalen-2-yl)methyl)piperidine-3,4,5-triol as a white solid (15 mg, 32%). This material was isolated as a ~1:1.2 mixture of diastereomers based on $^1H$ NMR analysis. $^1H$ NMR (400 MHz, $CD_3OD$) δ 7.06-7.03 (m, 4H), 3.60-3.47 (m, 1H), 3.23-3.07 (m, 2H), 3.04-2.69 (m, 5H), 2.49-2.34 (m, 1H), 2.21-1.83 (m, 5H), 1.46-1.29 (m, 1H), 1.24-1.16 (m, 3H); ESI MS m/z 292.19 $[M+H]^+$.

Example 28

(2R,3R,4R,5S)-1-((2,3-dihydro-1H-inden-2-yl)methyl)-2-methylpiperidine-3,4,5-triol

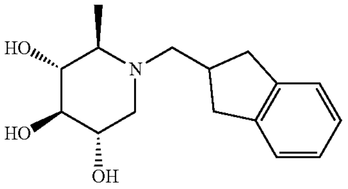 [SMILES: C[C@@H]1[C@@H](O)[C@H](O)[C@@H](O)CN1CC1Cc2ccccc2C1]

To a solution of 2-indanecarboxylic acid (200 mg, 1.23 mmol) in anhydrous THE (8 mL) at 0° C., was added LAH (141 mg, 3.70 mmol), and the mixture was stirred at 0° C. for 2 h. The mixture was quenched slowly with satd. aqueous $Na_2SO_4$ and filtered. The solid was washed with EtOAc. The combined organic layer was washed with $H_2O$ (2×20 mL), separated, and dried over $Na_2SO_4$. After filtration, the solvent was evaporated under reduced pressure, and the residue was purified on silica gel by flash chromatography affording (2,3-dihydro-1H-inden-2-yl)methanol as a clear oil (180 mg, 99%).

To a solution of the above material (180 mg, 1.22 mmol) in anhydrous DCM (10 mL) at 0° C., was added DMP (678 mg, 1.60 mmol), and the mixture was stirred at 0° C. for 2 h. The mixture was quenched slowly with $Na_2S_3O_5$ solution. The mixture was extracted with DCM (3×20 mL). The combined organic layer was washed with $H_2O$ (2×10 mL), separated, and dried over $Na_2SO_4$. After filtration, the solvent was evaporated under reduced pressure, and the residue was purified on silica gel by flash chromatography affording 2,3-dihydro-1H-indene-2-carbaldehyde as an oil (130 mg, 72%).

To a solution of (2R,3R,4R,5S)-3,4,5-tris(benzyloxy)-2-methylpiperidine (80 mg, 0.19 mmol) and 2,3-dihydro-1H-indene-2-carbaldehyde (42 mg, 0.29 mmol) in anhydrous DCM (5 mL) was added HOAc (0.10 mL, 1.75 mmol) and stirred for 30 min. $NaBH(OAc)_3$ (61 mg, 0.29 mmol) was added, and the resulting mixture was stirred at RT for 18 h. The reaction was quenched with satd. aqueous $NaHCO_3$ at 0° C. The mixture was extracted with EtOAc (3×20 mL).

The combined organic layer was washed with $H_2O$ (2×10 mL), separated, and dried over $Na_2SO_4$. After filtration, the solvent was evaporated under reduced pressure, and the residue was purified on silica gel by flash chromatography affording (2R,3R,4R,5S)-3,4,5-tris(benzyloxy)-1-((2,3-dihydro-1H-inden-2-yl)methyl)-2-methylpiperidine as an oil (89 mg, 86%). ESI MS m/z 548.69 $[M+H]^+$.

To a solution of the above material (89 mg, 0.16 mmol) in anhydrous DCM (5 mL) was added $BCl_3$ (1M in DCM, 0.97 mL, 0.97 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-1-((2,3-dihydro-1H-inden-2-yl)methyl)-2-methylpiperidine-3,4,5-triol as a white solid (21 mg, 47%). $^1H$ NMR (400 MHz, $CD_3OD$) δ 7.20-7.14 (m, 2H), 7.12-7.06 (m, 2H), 3.56-3.47 (m, 1H), 3.18-3.11 (m, 2H), 3.10-2.95 (m, 3H), 2.85-2.65 (m, 3H), 2.59 (dd, J=15.4, 6.5 Hz, 1H), 2.35 (dd, J=12.5, 4.7 Hz, 1H), 2.16-2.04 (m, 2H), 1.17 (d, J=6.1 Hz, 3H); ESI MS m/z 278.17 $[M+H]^+$.

Example 29

(2R,3R,4R,5S)-1-(2-cyclohexylethyl)-2-methylpiperidine-3,4,5-triol

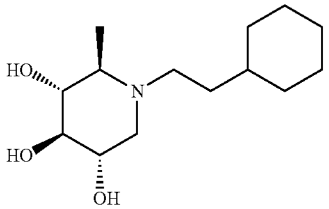 [SMILES: C[C@@H]1[C@@H](O)[C@H](O)[C@@H](O)CN1CCC1CCCCC1]

To a solution of ((2R,3R,4R,5S)-3,4,5-tris(benzyloxy)piperidin-2-yl)methanol (0.2 g, 0.46 mmol) (J. Carb. Chem. 2017, 36, 295) in DMF (4 mL) and DIPEA (0.64 mL, 3.68 mmol) was added 2-cyclohexylethyl bromide (0.36 mL, 2.3 mmol). The reaction mixture was heated at 85° C. overnight before diluting with EtOAc (30 mL). Organics were washed with brine, dried over anhydrous $Na_2SO_4$ and concentrated. The residue was purified on silica gel by flash chromatography (EtOAc/hexanes, 1:4), affording ((2R,3R,4R,5S)-3,4,5-tris(benzyloxy)-1-(2-cyclohexylethyl)piperidin-2-yl)methanol (0.156 g, 62%) as a gummy solid. $^1H$ NMR (500 MHz, $CDCl_3$) δ 7.38-7.27 (m, 15H), 4.98 (dd, J=11.0, 5.1 Hz, 2H), 4.86 (d, J=11.0 Hz, 1H), 4.76-4.65 (m, 3H), 3.79 (s, 2H), 3.63-3.49 (m, 3H), 3.10 (dd, J=11.3, 4.6 Hz, 1H), 2.76 (ddd, J=13.3, 10.5, 5.8 Hz, 1H), 2.50 (ddd, J=13.3, 10.3, 5.2 Hz, 1H), 2.32-2.22 (m, 2H), 1.73-1.61 (m, 5H), 1.38-1.25 (m, 7H), 0.97-0.83 (m, 2H); ESI MS m/z 544.34 $[M+H]^+$.

To a stirred solution of the above material (0.15 g, 0.28 mmol) at 0° C. in dry DCM (15 mL) was added $Ph_3P$ (0.15 g, 0.57 mmol) followed by $CBr_4$ (0.19 g, 0.57). After stirring at 0° C. for 2 h, the reaction mixture was diluted with DCM (30 mL) and washed with satd. aqueous $NaHCO_3$. Organics were dried over anhydrous $Na_2SO_4$ and concentrated. The crude residue was purified on silica gel by flash chromatography (EtOAc/hexanes, 1:4), affording (2S,3R,4R,5S)-3,4,5-tris(benzyloxy)-2-(bromomethyl)-1-(2-cyclohexylethyl)piperidine (0.13 g, 74.6%) as a yellow solid. $^1H$ NMR (500 MHz, $CDCl_3$) δ 7.38-7.27 (m, 15H), 5.01 (dd, J=14.3, 10.9 Hz, 2H), 4.84 (d, J=11.0 Hz, 1H), 4.75 (d, J=10.8 Hz, 1H), 4.74-4.66 (m, 2H), 3.95 (dd, J=11.5, 1.7 Hz, 1H), 3.72-3.50 (m, 4H), 3.15 (dd, J=11.2, 4.9 Hz, 1H), 2.74 (q, J=9.2, 5.1 Hz, 1H), 2.69-2.57 (m, 1H), 2.39-2.27 (m, 2H), 1.76-1.54 (m, 5H), 1.39 (dp, J=11.2, 5.5 Hz, 1H), 1.31-1.11 (m, 5H), 0.92 (m, 2H); ESI MS m/z 606.25 $[M+H]^+$.

To a stirred solution of the above material (0.13 g, 0.21 mmol) in dry toluene (7 mL) was added $Bu_3SnH$ (0.085 mL, 0.31 mmol) followed by ABCN (0.024 g, 0.1 mmol). The reaction mixture was heated at 100° C. overnight before cooling and concentrating. The resulting crude mixture was purified on silica gel by flash chromatography (EtOAc/hexanes, 1:4), affording (2R,3R,4R,5S)-3,4,5-tris(benzyloxy)-1-(2-cyclohexylethyl)-2-methylpiperidine (0.69 g, 40.6%) as a yellow solid. ESI MS m/z 528.34 $[M+H]^+$.

At −78° C., under Ar, to a solution of the above material (0.045 g, 0.085 mmol) in DCM (5 mL) was added $BCl_3$ (1.0 M in DCM, 0.85 mL, 0.85 mmol) was added, and the mixture was stirred for 4 h while the bath temperature reached RT. The mixture was then cooled at −78° C., and MeOH (2 mL) was added carefully. After stirring at RT for 30 min the mixture was concentrated under reduced pressure. The resulting residue was neutralized with $NH_4OH$ (0.5 mL) and concentrated again under reduced pressure. The crude residue was purified on silica gel by flash chromatography (MeOH/DCM, 1:9), affording (2R,3R,4R,5S)-1-(2-cyclohexylethyl)-2-methylpiperidine-3,4,5-triol (0.0053 g, 24%) as a white solid. $^1H$ NMR (400 MHz, $CD_3OD$) δ 3.52 (ddd, J=10.4, 9.1, 4.9 Hz, 1H), 3.14 (t, J=8.9 Hz, 1H), 3.06-2.98 (m, 2H), 2.90-2.80 (m, 1H), 2.65-2.61 (m, 1H), 2.31-2.18 (m, 2H), 1.80-1.64 (m, 5H), 1.43-1.37 (m, 2H), 1.34-1.27 (m, 2H), 1.26-1.18 (m, 2H), 1.25 (d, J=6.1 Hz, 3H), 1.06-0.91 (m, 2H); ESI MS m/z 258.20 $[M+H]^+$.

Example 30

(2R,3R,4R,5S)-1-(2-(4,4-difluorocyclohexyl)ethyl)-2-methylpiperidine-3,4,5-triol

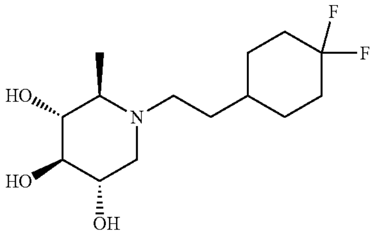 [SMILES: C[C@@H]1[C@@H](O)[C@H](O)[C@@H](O)CN1CCC1CCC(F)(F)CC1]

At 0° C., to a solution of (methoxymethyl)triphenylphosphonium chloride (1.3 g, 3.8 mmol) in anhydrous DMF (20 mL) was added KO$^t$Bu (0.43 g, 3.8 mmol) and 4,4-difluorocyclohexanecarbaldehyde (0.28 g, 1.9 mmol), and the mixture was stirred at RT for 64 h. The reaction mixture was diluted with satd. aqueous $NaHCO_3$ (20 mL) and extracted with EtOAc (3×20 mL). The combined extract was washed with brine (30 mL) and dried over anhydrous $Na_2SO_4$. After filtration the solvent was evaporated under reduced pressure, and the residue was dissolved in mixed THE (10 mL) and aqueous HCl (5 N, 10 mL). After stirring at reflux for 5 h the mixture was cooled and diluted with satd. aqueous $NaHCO_3$ (30 mL). After extraction with EtOAc (2×30 mL) the combined extract was washed with brine (50 mL) and dried over anhydrous $Na_2SO_4$. After filtration the solvent was evaporated under reduced pressure, and the residue was purified on silica gel by flash chromatography (EtOAc/hexanes, 1:13 to 1:6), affording 2-(4,4-difluorocyclohexyl)acetaldehyde as a clear oil (0.21 g, 68%). $^1H$ NMR (500 MHz, $CDCl_3$) δ 9.77 (t, J=1.7 Hz, 1H), 2.40 (dd, J=6.7, 1.7 Hz, 2H), 2.12-1.95 (m, 4H), 1.86-1.67 (m, 3H), 1.43-1.27 (m, 2H).

Under $N_2$, a mixture of (2R,3R,4R,5S)-3,4,5-tris(benzyloxy)-2-methylpiperidine (0.10 g, 0.24 mmol), 2-(4,4-difluorocyclohexyl)acetaldehyde (0.081 g, 0.50 mmol) and $NaBH(OAc)_3$ (0.15 g, 0.71 mmol) in DCM (10 mL) was stirred at RT for 16 h. The reaction mixture was diluted with satd. aqueous $NaHCO_3$ (10 mL) and extracted with DCM (3×15 mL). The combined extract was dried over anhydrous $Na_2SO_4$. After filtration the solvent was evaporated under reduced pressure, and the residue was purified on silica gel by flash chromatography (EtOAc/hexanes, 1:5 to 1:3), affording (2R,3R,4R,5S)-3,4,5-tris(benzyloxy)-1-(2-(4,4-difluorocyclohexyl)ethyl)-2-methylpiperidine as a clear oil (0.084 g, 62%); ESI MS m/z 564.316 $[M+H]^+$.

A mixture of the above material (0.080 g, 0.14 mmol) and $Pd(OH)_2/C$ (20% Pd in weight, 0.030 g, 0.056 mmol) and one drop of concentrated HCl in MeOH (15 mL) was stirred under hydrogen at one atmosphere of pressure overnight. The mixture was filtered through a celite cake, and the filtrate was collected and concentrated to dryness. The residue was neutralized with 1 M $NH_3$ in MeOH and purified on silica gel by flash chromatography (1 M $NH_3$ MeOH/DCM, 1:7), affording (2R,3R,4R,5S)-1-(2-(4,4-difluorocyclohexyl)ethyl)-2-methylpiperidine-3,4,5-triol (0.030 g, 73%) as a white solid. $^1H$ NMR (400 MHz, DMSO-$d_6$) δ 4.67-4.64 (m, 3H), 3.25-3.18 (m, 1H), 2.87 (td, J=8.8, 4.3 Hz, 1H), 2.77 (dd, J=11.1, 4.9 Hz, 1H), 2.72-2.61 (m, 2H), 2.32-2.25 (m, 1H), 2.01-1.87 (m, 4H), 1.82-1.66 (m, 4H), 1.33-1.23 (m, 3H), 1.19-1.10 (m, 2H), 1.05 (d, J=6.0 Hz, 3H); ESI MS m/z 294.177 $[M+H]^+$.

Examples 31 and 32

(2R,3R,4R,5S)-2-methyl-1-(2-((1s,4S)-4-(trifluoromethyl)cyclohexyl)ethyl)piperidine-3,4,5-triol and (2R,3R,4R,5S)-2-methyl-1-(2-((1r,4R)-4-(trifluoromethyl)cyclohexyl)ethyl)piperidine-3,4,5-triol

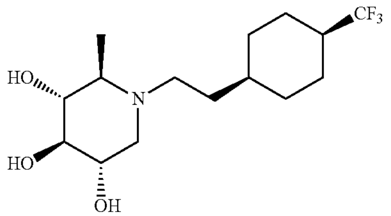

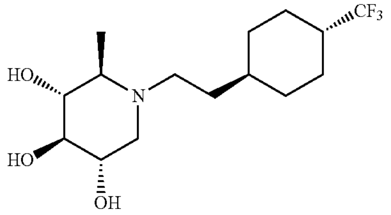

At 0° C., to a solution of (methoxymethyl)triphenylphosphonium chloride (0.77 g, 2.5 mmol) in anhydrous DMF (20 mL) was added $KO^tBu$ (0.28 g, 2.5 mmol) and 4-(trifluoromethyl)cyclohexanecarbaldehyde (0.27 g, 1.5 mmol), and the mixture was stirred at RT for 16 h. The reaction mixture was diluted with satd. aqueous $NaHCO_3$ (20 mL), and then extracted with EtOAc (3×30 mL). The combined extract was washed with brine (30 mL) and dried over anhydrous $Na_2SO_4$. After filtration the solvent was evaporated under reduced pressure, and the residue was dissolved in mixed THE (10 mL) and aqueous HCl (5 N, 10 mL). After stirring at reflux for 4 h the mixture was cooled and diluted with satd. aqueous $NaHCO_3$ (30 mL). After extraction with EtOAc (2×30 mL) the combined extract was washed with brine (50 mL) and dried over anhydrous $Na_2SO_4$. After filtration the solvent was evaporated under reduced pressure, and the residue was purified on silica gel by flash chromatography (EtOAc/hexanes, 1:13 to 1:7), affording 2-(4-(trifluoromethyl)cyclohexyl)acetaldehyde of mixed cis and trans isomers as a clear oil (0.087 g, 29%).

Under $N_2$, a mixture of (2R,3R,4R,5S)-3,4,5-tris(benzyloxy)-2-methylpiperidine (0.150 g, 0.359 mmol), the 2-(4-(trifluoromethyl)cyclohexyl)acetaldehyde from above (0.087 g, 0.45 mmol) and $NaBH(OAc)_3$ (0.15 g, 0.71 mmol) in DCM (5 mL) was stirred at RT for 16 h. The reaction mixture was diluted with satd. aqueous $NaHCO_3$ (15 mL), and extracted with DCM (3×15 mL). The combined extract was dried over anhydrous $Na_2SO_4$. After filtration the solvent was evaporated under reduced pressure, and the residue was purified on silica gel by flash chromatography (EtOAc/hexanes, 1:7 to 1:3), affording (2R,3R,4R,5S)-3,4,5-tris(benzyloxy)-2-methyl-1-(2-((1s,4S)-4-(trifluoromethyl)cyclohexyl)ethyl)piperidine as a clear oil (0.083 g, 39%) and (2R,3R,4R,5S)-3,4,5-tris(benzyloxy)-2-methyl-1-(2-((1r,4R)-4-(trifluoromethyl)cyclohexyl)ethyl)piperidine as a clear oil (0.042 g, 17%); ESI MS m/z 596.313 $[M+H]^+$.

A mixture of (2R,3R,4R,5S)-3,4,5-tris(benzyloxy)-2-methyl-1-(2-((1s,4S)-4-(trifluoromethyl)cyclohexyl)ethyl)piperidine (0.081 g, 0.14 mmol) and $Pd(OH)_2/C$ (20% Pd in weight, 0.050 g, 0.094 mmol) and one drop of concentrated HCl in MeOH (10 mL) was stirred under hydrogen at one atmosphere of pressure overnight. The mixture was filtered through a celite cake, and the filtrate was collected and concentrated to dryness. The residue was neutralized with 1 M $NH_3$ in MeOH and purified on silica gel by flash chromatography (1 M $NH_3$ MeOH/DCM, 1:6), affording (2R,3R,4R,5S)-2-methyl-1-(2-((1s,4S)-4-(trifluoromethyl)cyclohexyl)ethyl)piperidine-3,4,5-triol (0.036 g, 79%) as a white solid. $^1H$ NMR (400 MHz, $CD_3OD$) δ 3.47 (ddd, J=101.6, 9.1, 4.9 Hz, 1H), 3.09 (t, J=9.0 Hz, 1H), 2.98-2.93 (m, 2H), 2.83-2.76 (m, 1H), 2.56-2.48 (m, 1H), 2.18-2.02 (m, 3H), 2.00-1.80 (m, 5H), 1.20 (d, J=6.1 Hz, 3H), 1.09-0.96 (m, 2H),); ESI MS m/z 326.172 $[M+H]^+$.

A mixture of (2R,3R,4R,5S)-3,4,5-tris(benzyloxy)-2-methyl-1-(2-((1r,4R)-4-(trifluoromethyl)cyclohexyl)ethyl)piperidine (0.040 g, 0.067 mmol) and $Pd(OH)_2/C$ (20% Pd in weight, 0.030 g, 0.056 mmol) and one drop of concentrated HCl in MeOH (10 mL) was stirred under hydrogen at one atmosphere of pressure overnight. The mixture was filtered through a celite cake, and the filtrate was collected and concentrated to dryness. The residue was neutralized with 1 M $NH_3$ in MeOH and purified on silica gel by flash chromatography (1 M $NH_3$ MeOH/DCM, 1:6), affording (2R,3R,4R,5S)-2-methyl-1-(2-((1r,4R)-4-(trifluoromethyl)cyclohexyl)ethyl)piperidine-3,4,5-triol (0.016 g, 73%) as a white solid. $^1H$ NMR (400 MHz, $CD_3OD$) δ 3.48 (ddd, J=10.6, 9.0, 4.9 Hz, 1H), 3.10 (t, J=9.0 Hz, 1H), 3.00-2.93

(m, 2H), 2.78-2.74 (m, 1H), 2.52-2.45 (m, 1H), 2.19-2.12 (m, 3H), 1.71-1.50 (m, 11H), 1.22 (d, J=6.1 Hz, 3H); ESI MS m/z 326.171 [M+H]+.

Example 33

(2R,3R,4R,5S)-1-((2-adamantan-1-yl)ethyl)-2-methylpiperidine-3,4,5-triol

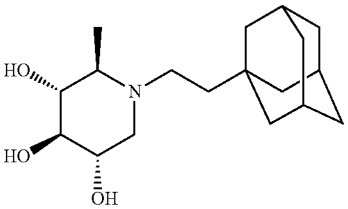 [SMILES: C[C@@H]1[C@@H](O)[C@H](O)[C@@H](O)CN1CCC12CC3CC(CC(C3)C1)C2]

To a solution of 2-((3r,5r,7r)-adamantan-1-yl)ethanol (200 mg, 1.11 mmol) in anhydrous DCM (10 mL) at 0° C., was added DMP (612 mg, 1.44 mmol), and the mixture was stirred at 0° C. for 2 h. The mixture was quenched slowly with $Na_2S_3O_5$ solution. The mixture was extracted with DCM (3×20 mL). The combined organic layer was washed with water (2×10 mL), separated, dried over $Na_2SO_4$. After filtration, the solvent was evaporated under reduced pressure, and the residue was purified on silica gel by flash chromatography affording 2-((3r,5r,7r)-adamantan-1-yl)acetaldehyde as an oil (128 mg, 64%).

To a stirred solution of (2R,3R,4R,5S)-3,4,5-tris(benzyloxy)-2-methylpiperidine (76 mg, 0.18 mmol) and 2-((3r,5r,7r)-adamantan-1-yl)acetaldehyde (65 mg, 0.37 mmol) in anhydrous MeOH (5 mL) was added HOAc (0.10 mL, 1.75 mmol) and stirred for 30 min. $NaBH_3CN$ (23 mg, 0.37 mmol) was added, and the resulting mixture was stirred at RT for 18 h. The reaction was quenched with satd. aqueous $NaHCO_3$ at 0° C. The mixture was extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-1-(2-((3R,5R,7R)-adamantan-1-yl)ethyl)-3,4,5-tris(benzyloxy)-2-methylpiperidine as an oil (88 mg, 84%). ESI MS m/z 580.36 [M+H]+.

To a stirred solution of the above material (150 mg, 0.26 mmol) in anhydrous DCM (8 mL) was added $BCl_3$ solution (1M in DCM, 2.07 mL, 2.07 mmol) at −78° C. under $N_2$. The mixture was stirred at 0° C. for 2 h before being quenched with anhydrous MeOH (1 mL). The mixture was stirred at ambient temperature for 10 min. Solid formed was collected by filtration to give (2R,3R,4R,5S)-1-((2-adamantan-1-yl)ethyl)-2-methylpiperidine-3,4,5-triol as the HCl salt (38 mg, 42%). $^1$H NMR (400 MHz, $CD_3OD$) δ 3.76-3.64 (m, 1H), 3.52-3.42 (m, 1H), 3.41-3.24 (m, 3H), 3.25-3.06 (m, 2H), 2.96 (t, J=11.8 Hz, 1H), 2.05-1.96 (m, 3H), 1.85-1.68 (m, 6H), 1.67-1.52 (m, 7H), 1.52-1.40 (m, 4H); ESI MS m/z 310.23 [M+H]+.

Example 34

(2R,3R,4R,5S)-1-(3-cyclohexylpropyl)-2-methylpiperidine-3,4,5-triol

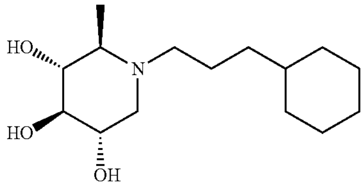 [SMILES: C[C@@H]1[C@@H](O)[C@H](O)[C@@H](O)CN1CCCC1CCCCC1]

A mixture of ((2R,3R,4R,5S)-3,4,5-tris(benzyloxy)piperidin-2-yl)methanol (0.17 g, 0.39 mmol), (3-bromopropyl)cyclohexane (0.30 g, 1.5 mmol) and DIPEA (0.22 g, 1.7 mmol) in anhydrous DMF (4 mL) in a sealed tube was stirred at 90° C. for 16 h. The reaction mixture was cooled at RT and diluted with satd. aqueous $NaHCO_3$ (20 mL). After extraction with EtOAc (3×20 mL) the combined extract was washed with brine (2×20 mL) and dried over anhydrous $Na_2SO_4$. After filtration the solvent was evaporated under reduced pressure, and the residue was purified on silica gel by flash chromatography (EtOAc/hexanes, 1:4 to 1:3), affording ((2R,3R,4R,5S)-3,4,5-tris(benzyloxy)-1-(3-cyclohexylpropyl)piperidin-2-yl)methanol as a pale-yellow oil (0.21 g, 97%); ESI MS m/z 558.386 [M+H]+.

At 0° C., to a solution of the above material (0.21 g, 0.38 mmol) in anhydrous DCM (15 mL) was added $PPh_3$ (0.20 g, 0.76 mmol), and $CBr_4$ (0.20 g, 0.60 mmol), and the mixture was stirred at RT for 16 h. The solvent was evaporated under reduced pressure, and the residue was purified on silica gel by flash chromatography (EtOAc/hexanes, 1:9 to 1:7), affording (2S,3R,4R,5S)-3,4,5-tris(benzyloxy)-2-(bromomethyl)-1-(3-cyclohexylpropyl)piperidine as a clear oil (0.17 g, 72%); ESI MS m/z 620.299 and 622.297 [M+H]+.

A mixture of the above material (0.17 g, 0.27 mmol), $Bu_3SnH$ (0.22 g, 0.75 mmol) and ABCN (0.015 g, 0.063 mmol) in anhydrous toluene (15 mL) was stirred at 95° C. for 4 h. After cooling the solvent was evaporated under reduced pressure, and the residue was purified on silica gel by flash chromatography (EtOAc/hexanes, 1:5 to 2:3), affording a mixture containing (2R,3R,4R,5S)-3,4,5-tris(benzyloxy)-1-(3-cyclohexylpropyl)-2-methylpiperidine and its partially protected analogue with two benzyl groups.

At −78° C. and under $N_2$, to a solution of the above mixture in anhydrous DCM (5 mL) was added $BCl_3$ (1.0 M in DCM, 1.0 mL, 1.0 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:6), affording (2R,3R,4R,5S)-1-(3-cyclohexylpropyl)-2-methylpiperidine-3,4,5-triol as a white solid (0.018 g, 25%, two steps). $^1$H NMR (500 MHz, $CD_3OD$) δ 3.48 (td, J=9.3, 4.4 Hz, 1H), 3.11 (t, J=9.3 Hz, 1H), 3.01-2.95 (m, 2H), 2.75-2.69 (m, 1H), 2.50-2.44 (m, 1H), 2.18 (t, J=10.7 Hz, 2H), 1.78-1.62 (m, 5H), 1.53-1.45 (m, 2H), 1.34-1.09 (m, 8H), 0.95-0.87 (m, 2H); ESI MS m/z 272.219 [M+H]+.

Example 35

(2R,3R,4R,5S)-2-methyl-1-phenethylpiperidine-3,4,5-triol

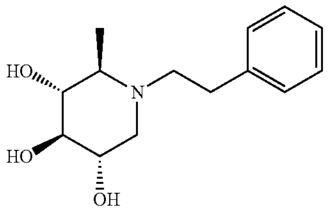 [SMILES: C[C@@H]1[C@@H](O)[C@H](O)[C@@H](O)CN1CCc1ccccc1]

$K_2CO_3$ (1.64 g, 11.8 mmol) was added to a solution of ((2R,3R,4R,5S)-3,4,5-tris(benzyloxy)piperidin-2-yl)methanol (641 mg, 1.48 mmol) and (2-bromoethyl)benzene (1.09 g, 5.92 mmol) in DMF (20 mL) in a sealed tube. The mixture was stirred at 80° C. for 18 h, and cooled to ambient temperature. The reaction mixture was poured into ice water (50 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording ((2R,3R,4R,5S)-3,4,5-tris(benzyloxy)-1-phenethylpiperidin-2-yl)methanol as a clear oil (615 mg, 77%). ESI MS m/z 538.29 $[M+H]^+$.

To a stirred solution of the above material (336 mg, 0.63 mmol) in pyridine (5 mL) was added MsCl (0.10 mL, 1.25 mmol) slowly at 0° C. The reaction mixture was stirred at 50° C. for 1 h, and quenched with satd. aqueous $NaHCO_3$ (20 mL). The mixture was extracted with EtOAc (3×20 mL). The combined organic layer was washed with water (2×20 mL), separated, dried over $Na_2SO_4$. After filtration, the solvent was evaporated under reduced pressure. The residue was purified on silica gel by flash chromatography affording (2S,3R,4R,5S)-3,4,5-tris(benzyloxy)-2-(chloromethyl)-1-phenethylpiperidine as an oil (182 mg, 52%). ESI MS m/z 556.27, 558.27 $[M+H]^+$.

A mixture of the above material (90 mg, 0.24 mmol), $Bu_3SnH$ (0.065 mL, 0.24 mmol) and ABCN (20 mg, 0.08 mmol) in anhydrous toluene (10 mL) was stirred at 100° C. for 16 h. After cooling the solvent was evaporated under reduced pressure, and the residue was purified on silica gel flash chromatography affording (2R,3R,4R,5S)-3,4,5-tris(benzyloxy)-2-methyl-1-phenethylpiperidine as an oil (18 mg, 20%). ESI MS m/z 522.30 $[M+H]^+$.

To a solution of the above material (18 mg, 0.035 mmol) in EtOH (10 mL) was added $Pd(OH)_2/C$ (20 wt. %, 8.6 mg, 0.012 mmol) and 6N HCl (0.05 mL). The mixture was treated with hydrogen (1 atm) for 18 h. Catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-phenethylpiperidine-3,4,5-triol as a white solid (3 mg, 35%). $^1H$ NMR (400 MHz, $CD_3OD$) δ 7.33-7.25 (m, 2H), 7.23-7.16 (m, 3H), 3.57-3.48 (m, 1H), 3.15 (t, J=8.8 Hz, 1H), 3.09 (dd, J=11.2, 4.9 Hz, 1H), 2.98 (t, J=9.1 Hz, 1H), 2.95-2.88 (m, 1H), 2.87-2.70 (m, 3H), 2.40-2.25 (m, 2H), 1.27 (d, J=5.6 Hz, 3H); ESI MS m/z 252.16 $[M+H]^+$.

Example 36

(2R,3R,4R,5S)-2-methyl-1-(2-methylphenethyl)piperidine-3,4,5-triol

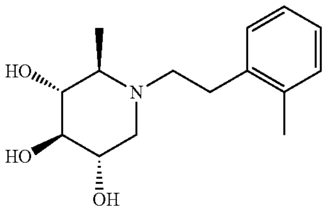

DIPEA (0.17 mL, 0.96 mmol) was added to a solution of (2R,3R,4R,5S)-3,4,5-tris(benzyloxy)-2-methylpiperidine (52 mg, 0.12 mmol) and 1-(2-bromoethyl)-2-methylbenzene (124 mg, 0.62 mmol) in DMF (5 mL) in a sealed tube. The mixture was stirred at 80° C. for 18 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified by silica gel flash chromatography affording (2R,3R,4R,5S)-3,4,5-tris(benzyloxy)-2-methyl-1-(2-methylphenethyl)piperidine as a white solid (38 mg, 59%). ESI MS m/z 536.31 $[M+H]^+$.

To a stirred solution of the above material (39 mg, 0.070 mmol) in anhydrous DCM (3 mL) was added $BCl_3$ solution (1M in DCM, 0.50 mL, 0.50 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(2-methylphenethyl)piperidine-3,4,5-triol as a white solid (8.0 mg, 43%). $^1H$ NMR (400 MHz, DMSO-$d_6$) δ 7.15-7.05 (m, 4H), 4.73-4.68 (m, 3H), 3.31-3.23 (m, 1H), 2.96-2.88 (m, 2H), 2.77-2.56 (m, 5H), 2.28 (s, 3H), 2.20 (t, J=10.6 Hz, 1H), 2.16-2.07 (m, 1H), 1.12 (d, J=6.0 Hz, 3H); ESI MS m/z 266.17 $[M+H]^+$.

Example 37

(2R,3R,4R,5S)-1-(2-methoxyphenethyl)-2-methylpiperidine-3,4,5-triol

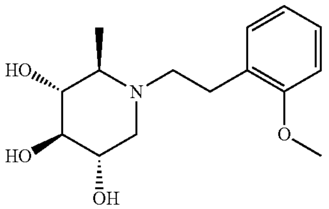 [SMILES: COc1ccccc1CCN1C[C@H](O)[C@@H](O)[C@H](O)[C@H]1C]

DIPEA (0.18 mL, 1.04 mmol) was added to a solution of (2R,3R,4R,5S)-3,4,5-tris(benzyloxy)-2-methylpiperidine (55 mg, 0.13 mmol) and 1-(2-bromoethyl)-2-methoxybenzene (141 mg, 0.66 mmol) in DMF (5 mL) in a sealed tube. The mixture was stirred at 80° C. for 18 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-1-(2-methoxyphenethyl)-2-methylpiperidine as a white solid (40 mg, 56%). ESI MS m/z 552.30 $[M+H]^+$.

To a solution of the above material (40 mg, 0.072 mmol) in EtOH (10 mL) was added $Pd(OH)_2/C$ (20 wt. %, 8.6 mg, 0.012 mmol) and 6N HCl (0.1 mL). The mixture was treated with hydrogen (1 atm) for 18 h. Catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2R,3R,4R,5S)-1-(2-methoxyphenethyl)-2-methylpiperidine-3,4,5-triol as a white solid (20 mg, 98%). $^1H$ NMR (400 MHz, $CD_3OD$) δ 7.29-7.23 (m, 1H), 7.21 (dd, J=7.4, 1.7 Hz, 1H), 6.99 (d, J=8.2 Hz, 1H), 6.92 (td, J=7.4, 1.0 Hz, 1H), 3.88 (s, 3H), 3.72-3.61 (m, 1H), 3.47-3.27 (m, 2H), 3.28-3.10 (m, 3H), 3.06-2.76 (m, 4H), 1.45 (d, J=6.3 Hz, 3H); ESI MS m/z 282.16 $[M+H]^+$.

Example 38

(2R,3R,4R,5S)-1-(2-fluorophenethyl)-2-methylpiperidine-3,4,5-triol

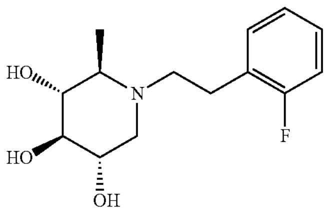

$K_2CO_3$ (630 g, 5.52 mmol) was added to a solution of ((2R,3R,4R,5S)-3,4,5-tris(benzyloxy)piperidin-2-yl)methanol (300 mg, 0.69 mmol) and 1-(2-bromoethyl)-2-fluorobenzene (582 mg, 3.45 mmol) in DMF (5 mL) in a sealed tube. The mixture was stirred at 80° C. for 18 h, and cooled to ambient temperature. The reaction mixture was poured into ice water (50 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording ethyl ((2R,3R,4R,5S)-3,4,5-tris(benzyloxy)-1-(2-fluorophenethyl)piperidin-2-yl)methanol as a clear oil (225 mg, 59%). ESI MS m/z 556.30 $[M+H]^+$.

To a stirred solution of the above material (68 mg, 0.12 mmol) in anhydrous DCM (5 mL) was added $PPh_3$ (81 mg, 0.31 mmol), imidazole (21 mg, 0.31 mmol) and iodine (30 mg, 0.24 mmol) at 0° C. The resulting mixture was stirred at RT for 2 h, before being quenched with satd. aqueous $Na_2S_2O_5$ at 0° C. The mixture was diluted with DCM and washed with satd. aqueous $NaHCO_3$ and the organic phase was separated, dried over $Na_2SO_4$. After filtration, the solvent was evaporated under reduced pressure, and the residue was purified on silica gel by flash chromatography affording (2S,3R,4R,5S)-3,4,5-tris(benzyloxy)-1-(2-fluorophenethyl)-2-(iodomethyl)piperidine as an oil (crude). ESI MS m/z 666.18 $[M+H]^+$.

A mixture of the above material (0.12 mmol), $Bu_3SnH$ (0.048 mL, 0.18 mmol) and ABCN (15 mg, 0.06 mmol) in anhydrous toluene (10 mL) was stirred at 100° C. for 16 h. After cooling the solvent was evaporated under reduced pressure, and the residue was purified on silica gel flash chromatography affording (2R,3R,4R,5S)-3,4,5-tris(benzyloxy)-1-(2-fluorophenethyl)-2-methylpiperidine as an oil (25 mg, 38% over two steps). ESI MS m/z 540.28 $[M+H]^+$.

To a stirred solution of the above material (22 mg, 0.040 mmol) in anhydrous DCM (3 mL) was added $BCl_3$ solution (1M in DCM, 0.50 mL, 0.50 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-1-(2-fluorophenethyl)-2-methylpiperidine-3,4,5-triol as a white solid (9 mg, 83%). $^1H$ NMR (400 MHz, $CD_3OD$) δ 7.29-7.19 (m, 2H), 7.11 (td, J=7.5, 1.3 Hz, 1H), 7.05 (ddd, J=10.5, 8.1, 1.2 Hz, 1H), 3.56-3.47 (m, 1H), 3.14 (t, J=9.0 Hz, 1H), 3.07 (dd, J=11.2, 4.9 Hz, 1H), 2.96 (t, J=9.0 Hz, 1H), 2.93-2.77 (m, 4H), 2.39 (t, J=10.9 Hz, 1H), 2.35-2.26 (m, 1H), 1.26 (d, J=6.2 Hz, 3H); ESI MS m/z 270.15 $[M+H]^+$.

Example 39

(2R,3R,4R,5S)-1-(2-chlorophenethyl)-2-methylpiperidine-3,4,5-triol

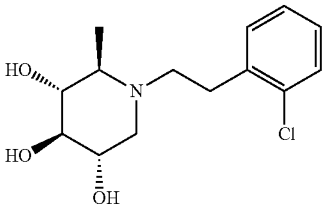

DIPEA (0.15 mL, 0.88 mmol) was added to a solution of (2R,3R,4R,5S)-3,4,5-tris(benzyloxy)-2-methylpiperidine (45 mg, 0.11 mmol) and 1-(2-bromoethyl)-2-chlorobenzene (118 mg, 0.55 mmol) in DMF (5 mL) in a sealed tube. The mixture was stirred at 80° C. for 18 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified by silica gel flash chromatography affording (2R,3R,4R,5S)-3,4,5-tris(benzyloxy)-1-(2-chlorophenethyl)-2-methylpiperidine as a white solid (29 mg, 48%). ESI MS m/z 556.26 $[M+H]^+$.

To a stirred solution of the above material (28 mg, 0.050 mmol) in anhydrous DCM (3 mL) was added $BCl_3$ solution (1M in DCM, 0.50 mL, 0.50 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-1-(2-chlorophenethyl)-2-methylpiperidine-3,4,5-triol as a white solid (10 mg, 70%). $^1$H NMR (400 MHz, $CD_3OD$) δ 7.37 (dd, J=7.7, 1.6 Hz, 1H), 7.31 (dd, J=7.5, 2.0 Hz, 1H), 7.28-7.18 (m, 2H), 3.58-3.49 (m, 1H), 3.15 (t, J=9.0 Hz, 1H), 3.10 (dd, J=11.2, 4.9 Hz, 1H), 3.00-2.79 (m, 5H), 2.42 (t, J=10.9 Hz, 1H), 2.37-2.28 (m, 1H), 1.28 (d, J=6.2 Hz, 3H); ESI MS m/z 286.12 $[M+H]^+$.

Example 40

(2R,3R,4R,5S)-1-(2,3-difluorophenethyl)-2-methylpiperidine-3,4,5-triol

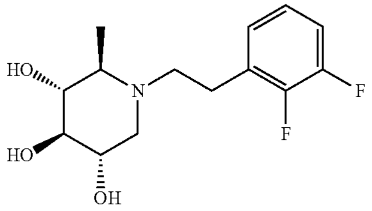 [SMILES: C[C@@H]1[C@@H](O)[C@H](O)[C@@H](O)CN1CCc1cccc(F)c1F]

To a cooled (0° C.) solution of 2-(2,3-difluorophenyl) acetic acid (1.0 g, 5.8 mmol) in 15 mL of anhydrous THF, LAH (0.6 g, 17.4 mmol) was added portionwise while stirring, under Ar. When effervescence ceased, the mixture was heated at reflux for 5 h until disappearance of starting material. The mixture was diluted with EtOAc, washed with 1.0 M HCl, water and brine. The organics were dried over anhydrous $Na_2SO_4$ and concentrated to yield 2-(2,3-difluorophenyl)ethanol (0.98 g, 98%) as an oil. $^1$H NMR (400 MHz, $CDCl_3$) δ 7.09-6.94 (m, 3H), 3.83 (m, 2H), 2.92 (m, 2H), 2.28-2.05 (m, 1H).

The above material (0.4 g, 2.5 mmol) and $CBr_4$ (1.0 g, 3.0 mmol) were dissolved in DCM (15 mL), the mixture was cooled to 0° C. and $Ph_3P$ (0.8 g, 3.0 mmol)) was added in small portions. The reaction mixture was warmed to RT and stirred for 2 h before the solvent was removed in vacuo. Flash chromatography (EtOAc/hexanes, 1:4) yielded 1-(2-bromoethyl)-2,3-difluorobenzene (0.5 g, 89%). $^1$H NMR (400 MHz, $CDCl_3$) δ 7.12-6.95 (m, 3H), 3.58 (t, J=7.3 Hz, 2H), 3.24 (td, J=7.3, 1.3 Hz, 2H).

To a solution of (2R,3R,4R,5S)-3,4,5-tris(benzyloxy)-2-methylpiperidine (0.1 g, 0.24 mmol) in DMF (4 mL) and DIPEA (0.32 mL, 1.84 mmol) was added 1-(2-bromoethyl)-2,3-difluorobenzene (0.2 g, 1.0 mmol). The reaction mixture was heated at 85° C. overnight before diluting with EtOAc (30 mL). Organics were washed with brine, dried over anhydrous $Na_2SO_4$ and concentrated. The residue was purified on silica gel by flash chromatography (EtOAc/hexanes, 1:4), affording (2R,3R,4R,5S)-3,4,5-tris(benzyloxy)-1-(2,3-difluorophenethyl)-2-methylpiperidine (0.049 g, 36.7%) as a gummy solid. $^1$H NMR (400 MHz, $CDCl_3$) δ 7.40-7.24 (m, 15H), 7.06-6.94 (m, 2H), 6.89 (dt, J=8.8, 3.4 Hz, 1H), 4.97 (t, J=10.7 Hz, 2H), 4.84 (d, J=11.0 Hz, 1H), 4.77-4.65 (m, 2H), 4.61 (d, J=10.8 Hz, 1H), 3.67-3.57 (m, 1H), 3.51 (t, J=9.0 Hz, 1H), 3.17-3.03 (m, 2H), 2.94-2.71 (m, 4H), 2.49-2.32 (m, 2H), 1.22 (d, J=6.1 Hz, 3H); ESI MS m/z 558.267 $[M+H]^+$.

At −78° C., under Ar, to a solution of the above material (0.049 g, 0.087 mmol) in DCM (5 mL) was added $BCl_3$ (1.0 M in DCM, 0.87 mL, 0.87 mmol), and the mixture was stirred for 2 h while the bath temperature warmed to 0° C. The mixture was stirred at 0° C. for next 2 h and then quenched by adding MeOH (2 mL) slowly. After stirring at RT for 30 min the mixture was concentrated under reduced pressure. The resulting residue was neutralized with $NH_4OH$ (0.5 mL) and concentrated again under reduced pressure. The crude residue was purified on silica gel by flash chromatography (MeOH/DCM, 1:9), affording (2R,3R,4R,5S)-1-(2,3-difluorophenethyl)-2-methylpiperidine-3,4,5-triol (0.021 g, 87%) as a white solid. $^1$H NMR (400 MHz, $CD_3OD$) δ 7.15-7.04 (m, 3H), 3.51 (ddd, J=10.5, 9.0, 4.9 Hz, 1H), 3.14 (t, J=9.0 Hz, 1H), 3.07 (dd, J=11.2, 4.9 Hz, 1H), 2.97-2.90 (m, 2H), 2.89-2.78 (m, 3H), 2.36 (t, J=10.9 Hz, 1H), 2.29 (dt, J=9.1, 6.1 Hz, 1H), 1.24 (d, J=6.1 Hz, 3H); ESI MS m/z 288.137 $[M+H]^+$.

Example 41

(2R,3R,4R,5S)-1-(2,4-difluorophenethyl)-2-methylpiperidine-3,4,5-triol

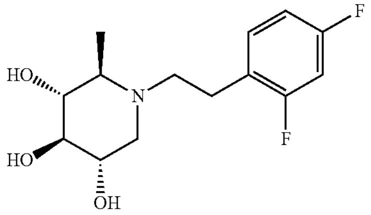 [SMILES: C[C@@H]1[C@@H](O)[C@H](O)[C@@H](O)CN1CCc1ccc(F)cc1F]

DIPEA (0.50 mL, 2.87 mmol) was added to a solution of (2R,3R,4R,5S)-3,4,5-tris(benzyloxy)-2-methylpiperidine (18 mg, 0.043 mmol) and 1-(2-bromoethyl)-2,4-difluorobenzene (200 mg, 0.91 mmol) in DMF (5 mL) in a sealed tube. The mixture was stirred at 80° C. for 18 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-1-(2,4-difluorophenethyl)-2-methylpiperidine as an oil (13 mg, 54%).

To a stirred solution of the above material (13 mg, 0.023 mmol) in anhydrous DCM (3 mL) was added $BCl_3$ solution (1M in DCM, 0.50 mL, 0.50 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-1-(2,4-difluorophenethyl)-2-methylpiperidine-3,4,5-triol as a white solid (5 mg, 75%). $^1$H NMR (400 MHz, $CD_3OD$) δ 7.33-7.25 (m, 1H), 6.95-6.86 (m, 2H), 3.55-3.47 (m, 1H), 3.13 (t, J=9.0 Hz, 1H), 3.06 (dd, J=11.2, 4.9 Hz, 1H), 2.94 (t, J=9.1 Hz, 1H), 2.91-2.74 (m, 4H), 2.35 (t, J=10.9 Hz, 1H), 2.32-2.24 (m, 1H), 1.24 (d, J=6.2 Hz, 3H); ESI MS m/z 288.14 $[M+H]^+$.

Example 42

(2R,3R,4R,5S)-1-(2,5-difluorophenethyl)-2-methylpiperidine-3,4,5-triol

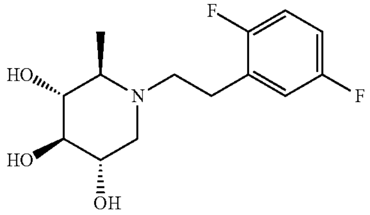 [SMILES: C[C@@H]1[C@@H](O)[C@H](O)[C@@H](O)CN1CCc1cc(F)ccc1F]

To a cooled (0° C.) solution of 2-(2,5-difluorophenyl) acetic acid (1.0 g, 5.8 mmol) in 15 mL of anhydrous THF, LAH (0.6 g, 17.4 mmol) was added portionwise while stirring, under Ar. When effervescence ceased, the mixture was heated at reflux for 5 h until disappearance of starting material. The mixture was diluted with EtOAc, washed with 1.0 M HCl, water and brine. The organics were dried over anhydrous $Na_2SO_4$ and concentrated to yield 2-(2,5-difluorophenyl)ethanol (0.9 g, 98%) as an oil. $^1$H NMR (500 MHz, $CDCl_3$) δ 7.00-6.91 (m, 2H), 6.87 (ddd, J=8.9, 7.5, 3.5 Hz, 1H), 3.83 m, 2H), 2.86 (m, 2H), 2.28-2.10 (bs, 1H).

The above material (0.4 g, 2.5 mmol) and $CBr_4$ (1.0 g, 3.0 mmol) were dissolved in DCM (15 mL), the mixture was cooled to 0° C. and $Ph_3P$ (0.8 g, 3.0 mmol)) was added in small portions. The reaction mixture was warmed to RT and stirred for 2 h before the solvent was removed in vacuo. Flash chromatography (EtOAc/hexanes, 1:4) yielded 2-(2-bromoethyl)-1,4-difluorobenzene (0.45 g, 81%). $^1$H NMR (400 MHz, $CDCl_3$) δ 7.04-6.87 (m, 3H), 3.57 (t, J=7.3 Hz, 2H), 3.18 (td, J=7.3, 1.2 Hz, 2H).

To a solution of (2R,3R,4R,5S)-3,4,5-tris(benzyloxy)-2-methylpiperidine (0.06 g, 0.14 mmol) in DMF (5 mL) and DIPEA (0.32 mL, 1.84 mmol) was added 2-(2-bromoethyl)-1,4-difluorobenzene (0.15 g, 0.71 mmol). The reaction mixture was heated at 85° C. overnight before diluting it with EtOAc (30 mL). Organics were washed with brine, dried over anhydrous $Na_2SO_4$ and concentrated. The residue was purified on silica gel by flash chromatography (EtOAc/hexanes, 1:4), affording (2R,3R,4R,5S)-3,4,5-tris(benzyloxy)-1-(2,5-difluorophenethyl)-2-methylpiperidine (0.044 g, 55%) as a gummy solid. $^1$H NMR (400 MHz, $CDCl_3$) δ 7.39-7.27 (m, 15H), 7.00-6.92 (m, 1H), 6.86 (td, J=8.1, 7.6, 4.3 Hz, 2H), 4.97 (t, J=10.6 Hz, 2H), 4.84 (d, J=11.0 Hz, 1H), 4.76-4.66 (m, 2H), 4.61 (d, J=10.9 Hz, 1H), 3.62 (bs, 1H), 3.50 (t, J=9.0 Hz, 1H), 3.17-3.03 (m, 2H), 2.92-2.78 (m, 2H), 2.70 (t, J=7.8 Hz, 2H), 2.43 (s, 1H), 2.37 (t, J=10.8 Hz, 1H), 1.22 (d, J=6.1 Hz, 3H); ESI MS m/z 558.27 $[M+H]^+$.

At −78° C., under Ar, to a solution of the above material (0.044 g, 0.078 mmol) in DCM (5 mL) was added $BCl_3$ (1.0 M in DCM, 0.78 mL, 0.78 mmol), and the mixture was stirred for 2 h while the bath temperature warmed to 0° C. The mixture was stirred at 0° C. for next 2 h and then quenched by adding MeOH (2 mL) slowly. After stirring at RT for 30 min the mixture was concentrated under reduced pressure. The resulting residue was neutralized with $NH_4OH$ (0.5 mL) and concentrated again under reduced pressure. The crude residue was purified on silica gel by flash chromatography (MeOH/DCM, 1:9), affording (2R,3R,4R,5S)-1-(2,5-difluorophenethyl)-2-methylpiperidine-3,4,5-triol (0.018 g, 81.6%) as a white solid. $^1$H NMR (400 MHz, $CD_3OD$) δ 7.11-7.01 (m, 2H), 6.96 (ddd, J=8.6, 6.4, 3.7 Hz, 1H), 3.51 (ddd, J=10.5, 9.0, 4.9 Hz, 1H), 3.14 (t, J=9.0 Hz, 1H), 3.06 (dd, J=11.2, 4.9 Hz, 1H), 2.98-2.86 (m, 2H), 2.87-2.77 (m, 3H), 2.36 (t, J=10.9 Hz, 1H), 2.28 (dt, J=9.1, 6.1 Hz, 1H), 1.24 (d, J=6.1 Hz, 3H); ESI MS m/z 288.13 $[M+H]^+$.

Example 43

(2R,3R,4R,5S)-1-(3,4-difluorophenethyl)-2-methylpiperidine-3,4,5-triol

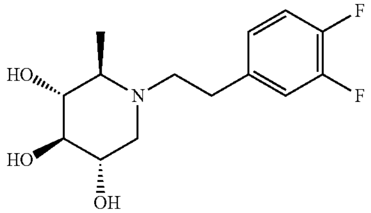 [SMILES: C[C@@H]1[C@@H](O)[C@H](O)[C@@H](O)CN1CCc1ccc(F)c(F)c1]

To a solution of ((2R,3R,4R,5S)-3,4,5-tris(benzyloxy)piperidin-2-yl)methanol (0.2 g, 0.46 mmol) in DMF (4 mL) and DIPEA (0.64 mL, 3.68 mmol) was added 4-(2-bromoethyl)-1,2-difluorobenzene (0.5 g, 2.4 mmol). The reaction mixture was heated at 85° C. overnight before diluting it with EtOAc (30 mL). Organics were washed with brine, dried over anhydrous $Na_2SO_4$ and concentrated. The residue was purified on silica gel by flash chromatography (EtOAc/hexanes, 1:4), affording ((2R,3R,4R,5S)-3,4,5-tris(benzyloxy)-1-(3,4-difluorophenethyl)piperidin-2-yl)methanol (0.2 g, 68%) as a gummy solid. ESI MS m/z 574.272 $[M+H]^+$.

To a stirred solution of the above material (0.2 g, 0.39 mmol) at 0° C. in dry DCM (15 mL) was added $Ph_3P$ (0.20 g, 0.78 mmol) followed by $CBr_4$ (0.26 g, 0.78 mmol). After stirring at 0° C. for 2 h, reaction mixture was diluted with DCM (30 mL) and washed with satd. aqueous $NaHCO_3$. Organics were dried over anhydrous $Na_2SO_4$ and concentrated. The crude residue was purified on silica gel by flash chromatography (EtOAc/hexanes, 1:4), affording (2S,3R,4R,5S)-3,4,5-tris(benzyloxy)-2-(bromomethyl)-1-(3,4-difluorophenethyl)piperidine (0.05 g, 21%) as a yellow solid. ESI MS m/z 638.179 $[M+H]^+$.

A mixture of the above material (0.087 g, 0.13 mmol) and Raney Ni (0.050 g) in EtOH was stirred under 50 psi hydrogen pressure overnight. The mixture was then filtered through a celite cake, and the filtrate was collected and concentrated to dryness. The crude was dissolved in DCM (5 mL) and at −78° C., under Ar, was added $BCl_3$ (1.0 M in DCM, 0.8 mL, 0.8 mmol) dropwise, and the mixture was stirred for 2 h while the bath temperature warmed to 0° C. The mixture was stirred at 0° C. for next 2 h and then quenched by adding MeOH (2 mL) slowly. After stirring at RT for 30 min the mixture was concentrated under reduced pressure. The resulting residue was neutralized with $NH_4OH$ (0.5 mL) and concentrated again under reduced pressure. The crude residue was purified on silica gel by flash chromatography (MeOH/DCM, 1:9), affording (2R,3R,4R,5S)-1-(3,4-difluorophenethyl)-2-methylpiperidine-3,4,5-triol (0.017 g, 74%) as a white solid. $^1$H NMR (400 MHz, $CD_3OD$) δ 7.25-7.16 (m, 2H), 7.08 (ddd, J=8.9, 4.4, 2.2 Hz, 1H), 3.60 (td, J=9.6, 4.5 Hz, 1H), 3.30-3.21 (m, 2H), 3.21-3.07 (m, 2H), 3.06-2.96 (m, 1H), 2.96-2.85 (m, 2H), 2.66-2.56 (m, 2H), 1.35 (d, J=6.2 Hz, 3H); ESI MS m/z 288.13 s $[M+H]^+$.

Example 44

(2R,3R,4R,5S)-1-(2-fluoro-4-methoxyphenethyl)-2-methylpiperidine-3,4,5-triol

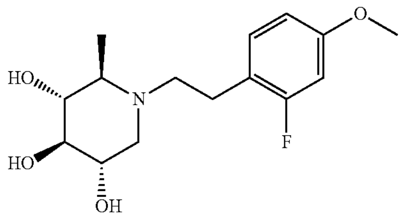 [SMILES: COc1ccc(CCN2C[C@H](O)[C@@H](O)[C@H](O)[C@H]2C)c(F)c1]

DIPEA (0.12 mL, 0.7 mmol) was added to a solution of (2R,3R,4R,5S)-3,4,5-tris(benzyloxy)-2-methylpiperidine (43 mg, 0.10 mmol) and 1-(2-bromoethyl)-2-fluoro-4-methoxybenzene (121 mg, 0.52 mmol) in DMF (5 mL) in a sealed tube. The mixture was stirred at 80° C. for 18 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified by silica gel flash chromatography affording (2R,3R,4R,5S)-3,4,5-tris(benzyloxy)-1-(2-fluoro-4-methoxyphenethyl)-2-methylpiperidine as a white solid (35 mg, 61%). ESI MS m/z 570.30 $[M+H]^+$.

To a solution of the above material (23 mg, 0.04 mmol) in EtOH (10 mL) was added $Pd(OH)_2/C$ (20 wt. %, 8.6 mg, 0.012 mmol) and 6N HCl (0.1 mL). The mixture was treated with hydrogen (1 atm) for 18 h. The catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2R,3R,4R,5S)-1-(2-fluoro-4-methoxyphenethyl)-2-methylpiperidine-3,4,5-triol as a white solid (9 mg, 75%). $^1H$ NMR (400 MHz, $CD_3OD$) δ 7.15 (t, J=8.6 Hz, 1H), 6.74-6.61 (m, 2H), 3.78 (s, 3H), 3.56-3.47 (m, 1H), 3.14 (t, J=9.0 Hz, 1H), 3.06 (dd, J=11.2, 4.9 Hz, 1H), 2.96 (t, J=9.1 Hz, 1H), 2.92-2.67 (m, 4H), 2.37 (t, J=10.9 Hz, 1H), 2.33-2.26 (m, 1H), 1.25 (d, J=6.2 Hz, 3H); ESI MS m/z 300.16 $[M+H]^+$.

Example 45

(2R,3R,4R,5S)-1-(3-chloro-2-fluorophenethyl)-2-methylpiperidine-3,4,5-triol

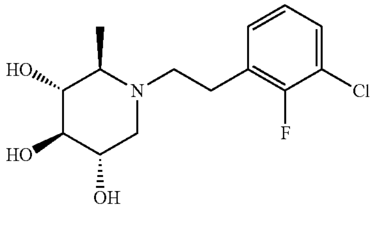 [SMILES: C[C@@H]1[C@@H](O)[C@H](O)[C@@H](O)CN1CCc1cccc(Cl)c1F]

To a cooled (0° C.) solution of 2-(3-chloro-2-fluorophenyl)acetic acid (0.5 g, 2.6 mmol) in 15 mL of anhydrous THF, LAH (0.3 g, 8.7 mmol) was added portionwise while stirring, under Ar. When effervescence ceased, the mixture was heated at reflux for 5 h until disappearance of starting material. The mixture was diluted with EtOAc, washed with 1.0 M HCl, water and brine. The organics were dried over anhydrous $Na_2SO_4$ and concentrated to yield 2-(3-chloro-2-fluorophenyl) ethanol (0.4 g, 90%) as an oil. $^1H$ NMR (400 MHz, $CDCl_3$) δ 7.29-6.98 (m, 3H), 3.87-3.79 (m, 2H), 2.91 (td, J=6.4, 4.1 Hz, 2H), 1.99-1.88 (m, 1H).

The above material (0.20 g, 1.16 mmol) and $CBr_4$ (0.5 g, 1.5 mmol) were dissolved in DCM (15 mL), the mixture was cooled to 0° C. and $Ph_3P$ (0.4 g, 1.5 mmol)) was added in small portions. The reaction mixture was warmed to RT and stirred for 2 h before the solvent was removed in vacuo. Flash chromatography (EtOAc/hexanes, 1:4) yielded 1-(2-bromoethyl)-3-chloro-2-fluorobenzene (0.23 g, 82.7%). $^1H$ NMR (400 MHz, $CDCl_3$) δ 7.79-7.62 (m, 1H), 7.60-7.44 (m, 2H), 4.02 (td, J=7.4, 1.2 Hz, 2H), 3.70-3.62 (m, 2H).

To a solution of (2R,3R,4R,5S)-3,4,5-tris(benzyloxy)-2-methylpiperidine (0.06 g, 0.14 mmol) in DMF (5 mL) and DIPEA (0.32 mL, 1.84 mmol) was added 2-(2-bromoethyl)-1,4-difluorobenzene (0.16 g, 0.70 mmol). The reaction mixture was heated at 85° C. overnight before diluting with EtOAc (30 mL). Organics were washed with brine, dried over anhydrous $Na_2SO_4$ and concentrated. The residue was purified on silica gel by flash chromatography (EtOAc/hexanes, 1:4), affording (2R,3R,4R,5S)-3,4,5-tris(benzyloxy)-1-(3-chloro-2-fluorophenethyl)-2-methylpiperidine (0.032 g, 55%) as a gummy solid. ESI MS m/z 574.23 $[M+H]^+$.

At −78° C., under Ar, to a solution of the above material (0.032 g, 0.055 mmol) in DCM (5 mL) was added $BCl_3$ (1.0 M in DCM, 0.55 mL, 0.55 mmol), and the mixture was stirred for 2 h while the bath temperature warmed to 0° C. The mixture was stirred at 0° C. for next 2 h and then quenched by adding MeOH (2 mL) slowly. After stirring at RT for 30 min the mixture was concentrated under reduced pressure. The resulting residue was neutralized with $NH_4OH$ (0.5 mL) and concentrated again under reduced pressure. The crude residue was purified on silica gel by flash chromatography (MeOH/DCM, 1:9), affording (2R,3R,4R,5S)-1-(3-chloro-2-fluorophenethyl)-2-methylpiperidine-3,4,5-triol (0.014 g, 83.7%) as a white solid. $^1H$ NMR (400 MHz, $CD_3OD$) δ 7.33 (m, 1H), 7.23 (m, 1H), 7.10 (m, 1H), 3.51 (td, J=9.8, 4.9 Hz, 1H), 3.14 (t, J=9.0 Hz, 1H), 3.07 (dd, J=11.2, 4.9 Hz, 1H), 2.98-2.89 (m, 2H), 2.88-2.79 (m, 3H), 2.36 (t, J=10.8 Hz, 1H), 2.32-2.25 (m, 1H), 1.24 (d, J=6.2 Hz, 3H); ESI MS m/z 304.11 $[M+H]^+$.

Example 46

(2R,3R,4R,5S)-1-(4-chloro-2-fluorophenethyl)-2-methylpiperidine-3,4,5-triol

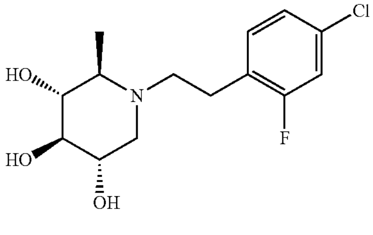 [SMILES: C[C@@H]1[C@@H](O)[C@H](O)[C@@H](O)CN1CCc1ccc(Cl)cc1F]

$K_2CO_3$ (121 mg, 0.88 mmol) was added to a solution of (2R,3R,4R,5S)-3,4,5-tris(benzyloxy)-2-methylpiperidine (45 mg, 0.11 mmol) and 1-(2-bromoethyl)-4-chloro-2-fluorobenzene (130 mg, 0.55 mmol) in DMF (5 mL) in a sealed tube. The mixture was stirred at 80° C. for 18 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified by silica gel flash chromatography affording (2R,3R,4R,5S)-3,4,5-tris(benzyloxy)-1-(4-chloro-2-fluorophenethyl)-2-methylpiperidine as a white solid (15 mg, 24%). ESI MS m/z 574.25 $[M+H]^+$.

To a stirred solution of the above material (15 mg, 0.026 mmol) in anhydrous DCM (3 mL) was added $BCl_3$ solution (1M in DCM, 0.50 mL, 0.50 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-1-(4-chloro-2-fluorophenethyl)-2-methylpiperidine-3,4,5-triol as a white solid (6 mg, 76%). $^1H$ NMR (400 MHz, $CD_3OD$) δ 7.28 (t, J=8.3 Hz, 1H), 7.19-7.12 (m, 2H), 3.55-3.45 (m, 1H), 3.13 (t, J=9.0 Hz, 1H), 3.06 (dd, J=11.2, 4.9 Hz, 1H), 2.98-2.75 (m, 5H), 2.35 (t, J=10.9 Hz, 1H), 2.33-2.26 (m, 1H), 1.23 (d, J=6.2 Hz, 3H); ESI MS m/z 304.11 $[M+H]^+$.

Example 47

(2R,3R,4R,5S)-1-(5-chloro-2-fluorophenethyl)-2-methylpiperidine-3,4,5-triol

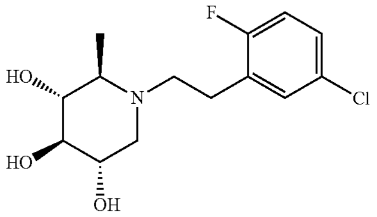 [SMILES: C[C@@H]1[C@@H](O)[C@H](O)[C@@H](O)CN1CCc1cc(Cl)ccc1F]

To a cooled (0° C.) solution of 2-(5-chloro-2-fluorophenyl)acetic acid (0.5 g, 2.6 mmol) in 15 mL of anhydrous THF, LAH (0.3 g, 8.7 mmol) was added portionwise while stirring, under Ar. When effervescence ceased, the mixture was heated at reflux for 5 h until disappearance of starting material. The mixture was diluted with EtOAc, washed with 1.0 M HCl, water and brine. The organics were dried over anhydrous $Na_2SO_4$ and concentrated to 2-(5-chloro-2-fluorophenyl) ethanol (0.46 g, 99%) as an oil. $^1H$ NMR (400 MHz, $CDCl_3$) δ 7.22 (dd, J=6.5, 2.7 Hz, 1H), 7.15 (dddd, J=8.4, 4.2, 2.7, 0.9 Hz, 1H), 6.99-6.92 (m, 1H), 3.81 (td, J=6.6, 2.4 Hz, 2H), 2.84 (td, J=6.6, 3.2 Hz, 2H), 2.26 (bs, 1H).

The above material (0.46 g, 2.6 mmol) and $CBr_4$ (1.1 g, 3.4 mmol) were dissolved in DCM (15 mL), the mixture was cooled to 0° C. and $Ph_3P$ (0.9 g, 3.4 mmol)) was added in small portions. The reaction mixture was warmed at RT and stirred for 2 h before the solvent was removed in vacuo. Flash chromatography (EtOAc/hexanes, 1:4) yielded 2-(2-bromoethyl)-4-chloro-1-fluorobenzene (0.99 g, 97%). $^1H$ NMR (400 MHz, $CDCl_3$) δ 7.69-7.60 (m, 2H), 7.45-7.39 (m, 1H), 4.00 (t, J=7.4 Hz, 2H), 3.64-3.58 (m, 2H).

To a solution of (2R,3R,4R,5S)-3,4,5-tris(benzyloxy)-2-methylpiperidine (0.06 g, 0.14 mmol) in DMF (5 mL) and DIPEA (0.32 mL, 1.84 mmol) was added 2-(2-bromoethyl)-1,4-difluorobenzene (0.16 g, 0.70 mmol). The reaction mixture was heated at 85° C. overnight before diluting with EtOAc (30 mL). Organics were washed with brine, dried over anhydrous $Na_2SO_4$ and concentrated. The residue was purified on silica gel by flash chromatography (EtOAc/hexanes, 1:4), affording (2R,3R,4R,5S)-3,4,5-tris(benzyloxy)-1-(5-chloro-2-fluorophenethyl)-2-methylpiperidine (0.044 g, 54%) as a gummy solid. $^1H$ NMR (400 MHz, $CDCl_3$) δ 7.39-7.27 (m, 15H), 7.14 (dd, J=7.8, 5.0 Hz, 2H), 6.95 (dd, J=10.2, 7.9 Hz, 1H), 4.97 (t, J=10.5 Hz, 2H), 4.84 (d, J=10.9 Hz, 1H), 4.76-4.66 (m, 2H), 4.61 (d, J=10.8 Hz, 1H), 3.62 (td, J=9.6, 4.6 Hz, 1H), 3.50 (t, J=9.0 Hz, 1H), 3.14-3.04 (m, 2H), 2.84 (m, 2H), 2.69 (m, 2H), 2.43 (dd, J=9.2, 6.0 Hz, 1H), 2.37 (t, J=10.8 Hz, 1H), 1.22 (d, J=6.1 Hz, 3H); ESI MS m/z 574.25 $[M+H]^+$.

At −78° C., under Ar, to a solution of the above material (0.044 g, 0.076 mmol) in DCM (5 mL) was added $BCl_3$ (1.0 M in DCM, 0.76 mL, 0.76 mmol), and the mixture was stirred for 2 h while the bath temperature reached to 0° C. The mixture was stirred at 0° C. for next 2 h and then quenched by adding MeOH (2 mL) slowly. After stirring at RT for 30 min the mixture was concentrated under reduced pressure. The resulting residue was neutralized with $NH_4OH$ (0.5 mL) and concentrated again under reduced pressure. The crude residue was purified on silica gel by flash chromatography (MeOH/DCM, 1:9), affording (2R,3R,4R,5S)-1-(5-chloro-2-fluorophenethyl)-2-methylpiperidine-3,4,5-triol (0.021 g, 93.5%) as a white solid. $^1H$ NMR (400 MHz, $CD_3OD$) δ 7.31 (dd, J=6.5, 2.7 Hz, 1H), 7.23 (ddd, J=8.8, 4.4, 2.7 Hz, 1H), 7.07 (t, J=9.2 Hz, 1H), 3.50 (ddd, J=10.5, 9.0, 4.9 Hz, 1H), 3.13 (t, J=9.0 Hz, 1H), 3.06 (dd, J=11.2, 4.9 Hz, 1H), 2.97-2.87 (m, 2H), 2.86-2.77 (m, 3H), 2.35 (t, J=10.9 Hz, 1H), 2.28 (dt, J=9.2, 6.2 Hz, 1H), 1.23 (d, J=6.1 Hz, 3H); ESI MS m/z 304.11 $[M+H]^+$.

Example 48

(2R,3R,4R,5S)-1-(2,6-difluorophenethyl)-2-methylpiperidine-3,4,5-triol

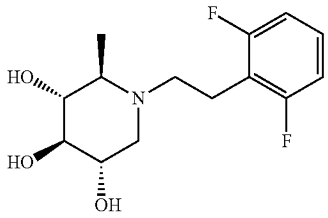 [SMILES: C[C@@H]1[C@@H](O)[C@H](O)[C@@H](O)CN1CCc1c(F)cccc1F]

DIPEA (0.16 mL, 0.96 mmol) was added to a solution of (2R,3R,4R,5S)-3,4,5-tris(benzyloxy)-2-methylpiperidine (50 mg, 0.12 mmol) and 2-(2-bromoethyl)-1,3-difluorobenzene (132 mg, 0.60 mmol) in DMF (5 mL) in a sealed tube. The mixture was stirred at 80° C. for 18 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-1-(2,6-difluorophenethyl)-2-methylpiperidine as a white solid (28 mg, 42%). ESI MS m/z 558.27 $[M+H]^+$.

To a stirred solution of the above material (28 mg, 0.050 mmol) in anhydrous DCM (3 mL) was added $BCl_3$ solution (1M in DCM, 0.50 mL, 0.50 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-1-(2,6-difluorophenethyl)-2-methylpiperidine-3,4,5-triol as a white solid (12 mg, 83%). $^1H$ NMR (400 MHz, $CD_3OD$) δ 7.31-7.20 (m, 1H), 6.99-6.89 (m, 2H), 3.55-3.45 (m, 1H), 3.14 (t, J=9.0 Hz, 1H), 3.07 (dd, J=11.2, 4.9 Hz, 1H), 2.98-2.77 (m, 5H), 2.40 (t, J=10.9 Hz, 1H), 2.36-2.27 (m, 1H), 1.23 (d, J=6.2 Hz, 3H); ESI MS m/z 288.13 $[M+H]^+$.

Example 49

(2R,3R,4R,5S)-1-(3-chloro-2,6-difluorophenethyl)-2-methylpiperidine-3,4,5-triol

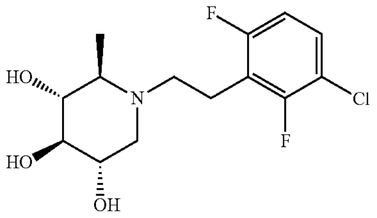 [SMILES: C[C@@H]1[C@@H](O)[C@H](O)[C@@H](O)CN1CCc1c(F)ccc(Cl)c1F]

At 0° C., to a solution of (methoxymethyl)triphenylphosphonium chloride (4.30 g, 12.5 mmol) in anhydrous DMF (30 mL) was added $KO^tBu$ (1.40 g, 12.5 mmol) and 3-chloro-2,6-difluorobenzaldehyde (1.77 g, 10.0 mmol), and the mixture was stirred at RT for 16 h. The reaction was quenched with aqueous HCl (2 N, 20 mL), and the mixture was extracted with EtOAc (3×30 mL). The combined extract was washed with satd. aqueous $NaHCO_3$ (50 mL), brine (50 mL) and water (50 mL), and then dried over anhydrous $Na_2SO_4$. After filtration the solvent was evaporated under reduced pressure, and the residue was dissolved in mixed THF (40 mL) and aqueous HCl (3 N, 40 mL). After stirring at reflux for 5 h the mixture was cooled and extracted with EtOAc (2×50 mL). The combined extract was washed with satd. aqueous $NaHCO_3$ (50 mL) and dried over anhydrous $Na_2SO_4$. After filtration the solvent was evaporated under reduced pressure, and the residue was purified on silica gel by flash chromatography (EtOAc/hexanes, 1:20 to 1:9), affording 2-(3-chloro-2,6-difluorophenyl)acetaldehyde as a pale-yellow liquid (0.55 g, 28%). $^1H$ NMR (500 MHz, $CDCl_3$) δ 9.76 (p, J=1.3 Hz, 1H), 7.34 (ddd, J=8.8, 8.3, 5.7 Hz, 1H), 6.91 (td, J=8.8, 1.8 Hz, 1H), 3.84 (q, J=1.3 Hz, 2H).

Under $N_2$, a mixture of (2R,3R,4R,5S)-3,4,5-tris(benzyloxy)-2-methylpiperidine (0.10 g, 0.24 mmol), 2-(3-chloro-2,6-difluorophenyl)acetaldehyde (0.10 g, 0.52 mmol) and $NaBH(OAc)_3$ (0.17 g, 0.80 mmol) in DCM (10 mL) was stirred at RT for 16 h. The reaction mixture was diluted with satd. aqueous $NaHCO_3$ (10 mL), and extracted with DCM (3×15 mL). The combined extract was dried over anhydrous $Na_2SO_4$. After filtration the solvent was evaporated under reduced pressure, and the residue was purified on silica gel by flash chromatography (EtOAc/hexanes, 1:12 to 1:6), affording (2R,3R,4R,5S)-3,4,5-tris(benzyloxy)-1-(3-chloro-2,6-difluorophenethyl)-2-methylpiperidine as a white solid (0.13 g, 92%); ESI MS m/z 592.236 $[M+H]^+$.

At −78° C. and under $N_2$, to a solution of the above material (0.13 g, 0.22 mmol) in anhydrous DCM (5 mL) was added $BCl_3$ (1.0 M in DCM, 2.0 mL, 2.0 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:6), affording (2R,3R,4R,5S)-1-(3-chloro-2,6-difluorophenethyl)-2-methylpiperidine-3,4,5-triol as a white solid (0.058 g, 83%). $^1H$ NMR (500 MHz, DMSO-$d_6$) δ 7.49 (td, J=8.8, 5.7 Hz, 1H), 7.14 (td, J=9.0, 1.7 Hz, 1H), 4.74-4.67 (m, 3H), 3.27-3.18 (m, 1H), 2.93-2.81 (m, 2H), 2.82-2.68 (m, 3H), 2.70-2.60 (m, 2H), 2.17 (t, J=10.6 Hz, 1H), 2.10 (dq, J=8.9, 6.1 Hz, 1H), 1.02 (d, J=6.1 Hz, 3H); ESI MS m/z 322.095 $[M+H]^+$.

Example 50

(2R,3R,4R,5S)-1-(2,6-difluoro-4-(prop-1-en-2-yl)phenethyl)-2-methylpiperidine-3,4,5-triol

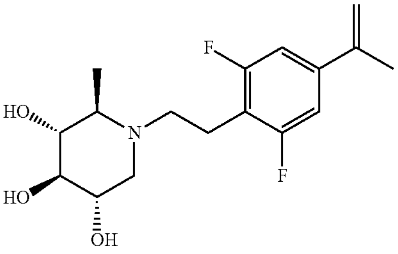

To a stirred solution of (methoxymethyl)triphenylphosphonium chloride (8.57 g, 25 mmol) in anhydrous THF (60 mL) was added $KO^tBu$ (2.81 g, 25 mmol) at 0° C. under $N_2$, and stirred for 30 min. Subsequently, 4-bromo-2,6-difluorobenzaldehyde (2.21 g, 10 mmol) was dissolved in 20 mL of THF and added dropwise to the mixture under $N_2$, reacted at RT for 18 h. The reaction was quenched with satd. aqueous $NaHCO_3$ at 0° C. The mixture was extracted with EtOAc (3×40 mL). The combined organic layer was washed with water (2×20 mL), separated, dried over $Na_2SO_4$. After filtration, the solvent was evaporated under reduced pressure, and the residue was purified on silica gel by flash chromatography affording the product as an oil with two isomers. The oil was dissolved in THF (30 mL), 2N HCl aqueous solution (30 mL) was added, and the mixture was stirred at 80° C. for 8 h. The reaction mixture was cooled to RT and extracted with EtOAc (3×30 mL). The combined organic layer was washed with water (2×20 mL), separated, dried over $Na_2SO_4$. After filtration, the solvent was evaporated under reduced pressure, and the residue was purified on silica gel by flash chromatography affording 2-(4-bromo-2,6-difluorophenyl)acetaldehyde as an oil (1.27 g, 54%). $^1H$ NMR (400 MHz, $CDCl_3$) δ 9.76 (p, J=1.2 Hz, 1H), 7.25-7.00 (m, 2H), 3.79 (q, J=1.3 Hz, 2H).

To a stirred solution of (2R,3R,4R,5S)-3,4,5-tris(benzyloxy)-2-methylpiperidine (600 mg, 1.44 mmol) and 2-(4- bromo-2,6-difluorophenyl)acetaldehyde (673 g, 2.88 mmol) in anhydrous MeOH (45 mL) was added HOAc (0.20 mL, 3.5 mmol) and stirred for 30 min. $NaBH_3CN$ (181 mg, 2.88 mmol) was added, and the resulting mixture was stirred at RT for 18 h. The reaction was quenched with satd. aqueous $NaHCO_3$ at 0° C. The mixture was extracted with EtOAc (3×30 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-1-(4-bromo-2,6-difluorophenethyl)-2-methylpiperidine as a white solid (904 mg, 99%). ESI MS m/z 636.15, 638.15 $[M+H]^+$.

To a stirred solution of the above material (88 mg, 0.14 mmol) and 2-isopropenylboronic acid pinacol ester (47 mg, 0.28 mmol) in toluene (5 mL) was added $Pd(PPh_3)_4$ (32 mg, 0.028 mmol), followed with $K_2CO_3$ (97 mg, 0.70 mmol) and water (1 mL) under Ar. The mixture was stirred at 100° C. for 18 h, and then water was added. The mixture was extracted with EtOAc (2×20 mL). The combined organic layer was washed with water (2×10 mL), separated, dried over $Na_2SO_4$. After filtration the solvent was evaporated under reduced pressure, and the residue was purified on silica gel by flash chromatography affording (2R,3R,4R,5S)-3,4,5-tris(benzyloxy)-1-(2,6-difluoro-4-(prop-1-en-2-yl)phenethyl)-2-methylpiperidine as a white solid (60 mg, 72%). ESI MS m/z 598.27 $[M+H]^+$.

To a stirred solution of the above material (26 mg, 0.043 mmol) in anhydrous DCM (3 mL) was added $BCl_3$ solution (1M in DCM, 0.50 mL, 0.50 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-1-(2,6-difluoro-4-(prop-1-en-2-yl)phenethyl)-2-methylpiperidine-3,4,5-triol as a white solid (11 mg, 78%). $^1H$ NMR (400 MHz, $CD_3OD$) δ 7.13-7.04 (m, 2H), 5.46 (t, J=1.0 Hz, 1H), 5.18 (t, J=1.5 Hz, 1H), 3.55-3.47 (m, 1H), 3.13 (t, J=9.0 Hz, 1H), 3.07 (dd, J=11.1, 5.0 Hz, 1H), 2.96-2.77 (m, 5H), 2.40 (t, J=10.8 Hz, 1H), 2.36-2.27 (m, 1H), 2.13 (dd, J=1.5, 0.8 Hz, 3H), 1.23 (d, J=6.2 Hz, 3H); ESI MS m/z 328.15 $[M+H]^+$.

Example 51

(2R,3R,4R,5S)-1-(2,6-difluoro-4-isopropylphenethyl)-2-methylpiperidine-3,4,5-triol

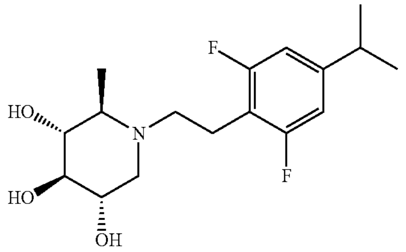

To a solution of (2R,3R,4R,5S)-3,4,5-tris(benzyloxy)-1-(2,6-difluoro-4-(prop-1-en-2-yl)phenethyl)-2-methylpiperidine (32 mg, 0.054 mmol) in EtOH (10 mL) was added $Pd(OH)_2/C$ (20 wt. %, 8.6 mg, 0.012 mmol) and 6N HCl (0.1 mL). The mixture was treated with hydrogen (1 atm) for 18 h. Catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2R,3R,4R,5S)-1-(2,6-difluoro-4-isopropylphenethyl)-2-methylpiperidine-3,4,5-triol as a white solid (13 mg, 73%). $^1H$ NMR (400 MHz, $CD_3OD$) δ 6.87-6.80 (m, 2H), 3.55-3.47 (m, 1H), 3.13 (t, J=9.0 Hz, 1H), 3.07 (dd, J=11.1, 5.0 Hz, 1H), 2.97-2.74 (m, 6H), 2.40 (t, J=10.8 Hz, 1H), 2.35-2.27 (m, 1H), 1.25 (d, J=6.9 Hz, 6H), 1.23 (d, J=6.2 Hz, 3H); ESI MS m/z 330.16 $[M+H]^+$.

Example 52

(2R,3R,4R,5S)-1-(2,6-difluoro-3-isopropylphenethyl)-2-methylpiperidine-3,4,5-triol

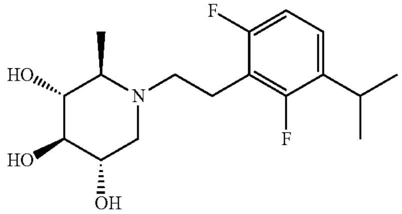 [SMILES: CC(C)c1ccc(F)c(CCN2C[C@H](O)[C@@H](O)[C@H](O)[C@H]2C)c1F]

At 0° C., under Ar, to a solution of (methoxymethyl)triphenylphosphonium chloride (8.57 g, 25.0 mmol) in anhydrous dioxane (20 mL) was added $KO^tBu$ (2.81 g, 25.0 mmol). After the mixture was stirred at 0° C. for 0.5 h, 3-bromo-2,6-difluorobenzaldehyde (2.21 g, 10.0 mmoL) was added. The reaction mixture was brought to 60° C. and stirred overnight, and satd. aqueous $NH_4Cl$ (30 mL) was added, and the mixture was extracted with EtOAc (3×10 mL). The combined organic extract was dried over anhydrous $Na_2SO_4$. After filtration the solvent was evaporated under reduced pressure, and the residue was dissolved in HCl solution (30 mL, 6 N), the resulted mixture was stirred for an additional 2 h at 60° C., and cooled to RT. Extracting aqueous with EtOAc (3×50 mL), combined organic solution was washed with satd. aqueous $NaHCO_3$, brine, dried over $Na_2SO_4$. Evaporation of solvent followed by silica gel flash chromatography using 30% EtOAc in hexanes afforded 2-(3-bromo-2,6-difluorophenyl)acetaldehyde as a white foam (1.66 g, 67%). $^1H$ NMR (400 MHz, $CDCl_3$) δ 9.78 (t, J=1.2 Hz, 1H), 7.52 (ddd, J=9.1, 7.8, 5.9 Hz, 1H), 6.90 (ddd, J=8.7, 8.7, 1.7 Hz, 1H), 3.87 (s, 2H).

Under Ar, to a mixture of 2-(3-bromo-2,6-difluorophenyl)acetaldehyde (368 mg, 1.48 mmol), 2-isopropenylboronic acid pinacol ester (0.55 mL, 2.90 mmol), $K_2CO_3$ (612 mg, 4.40 mmol) in anhydrous and degassed toluene (5 mL) and water (1 mL) was added $Pd(PPh_3)_4$ (34 mg, 0.03 mmol). The mixture was stirred at 115° C. in a sealed tube for 19 h, then cooled down to RT. $Et_2O$ (50 mL) was added, and the resulted precipitate was filtered off. The filtrate was concentrated under reduced pressure, and the residue was purified on silica gel by flash chromatography using 5% EtOAc in hexanes, affording ethyl 2-(2,6-difluoro-3-(prop-1-en-2-yl)phenyl)acetaldehyde as a white solid (238 mg, 82%).

Under Ar, to a solution of (2R,3R,4R,5S)-3,4,5-tris(benzyloxy)-2-methyl-1-(piperidin-4-ylmethyl)piperidine (239 mg, 0.57 mmol), and 2-(2,6-difluoro-3-(prop-1-en-2-yl)phenyl)acetaldehyde (210 mg, 0.86 mmol) in anhydrous DCM (8 mL) was added $NaBH(OAC)_3$ (241 mg, 1.13 mmol). The mixture was stirred at RT for 18 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 20% EtOAc in hexanes, affording (2R,3R,4R,5S)-3,4,5-tris(benzyloxy)-1-(2,6-difluoro-3-(prop-1-en-2-yl)phenethyl)-2-methylpiperidine as a white foam (320 mg, 94%). $^1$H NMR (400 MHz, $CDCl_3$) δ 7.46-7.20 (m, 15H), 7.13 (td, J=8.5, 6.4 Hz, 1H), 6.83 (t, J=8.6 Hz, 1H), 5.28-5.13 (m, 2H), 4.98 (dd, J=15.3, 10.9 Hz, 2H), 4.86 (d, J=11.0 Hz, 1H), 4.73 (s, 2H), 4.63 (d, J=10.8 Hz, 1H), 3.66-3.62 (m, 1H), 3.53 (t, J=9.0 Hz, 1H), 3.20 (dd, J=11.2, 4.8 Hz, 1H), 3.08 (t, J=9.0 Hz, 1H), 2.96-2.62 (m, 4H), 2.54-2.37 (m, 2H), 2.21-2.05 (m, 3H), 1.27 (dd, J=24.1, 6.6 Hz, 3H).

The above material (300 mg, 0.50 mmol), 6N HCl (0.7 mL) in EtOH (30 mL) was treated with hydrogen in balloon overnight in presence of $Pd(OH)_2$ (cat.). Removal of $Pd(OH)_2$ by filtration and evaporation of solvent followed by purification on silica gel chromatography using 10% MeOH and 2% $NH_3$ solution in DCM and dry load, afforded 2 (2R,3R,4R,5S)-1-(2,6-difluoro-3-isopropylphenethyl)-2-methylpiperidine-3,4,5-triol (113 mg, 70%). $^1$H NMR (400 MHz, $CD_3OD$) δ 7.28-7.09 (m, 1H), 7.01-6.68 (m, 1H), 3.56-3.50 (m, 1H), 3.24-3.16 (m, 3H), 3.02-2.94 (m, 6H), 2.57 (bs, 1H), 1.30 (d, J=6.1 Hz, 3H), 1.26 (d, J=6.9 Hz, 6H); ESI MS m/z 330.19 $[M+H]^+$.

Example 53

(2R,3R,4R,5S)-1-(4-cyclopropyl-2,6-difluorophenethyl)-2-methylpiperidine-3,4,5-triol

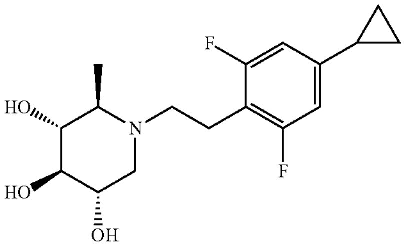 [SMILES: C[C@@H]1[C@@H](O)[C@H](O)[C@@H](O)CN1CCc1c(F)cc(C2CC2)cc1F]

To a stirred solution of (2R,3R,4R,5S)-3,4,5-tris(benzyloxy)-1-(4-bromo-2,6-difluorophenethyl)-2-methylpiperidine (100 mg, 0.16 mmol) and cyclopropylboronic acid (27 mg, 0.32 mmol) in toluene (5 mL) was added $Pd(OAc)_2$ (7 mg, 0.032 mmol), followed with tricyclohexylphosphine (0.1 mL, 0.064 mmol) and $K_3PO_4$ (133 mg, 0.64 mmol) and water (0.3 mL) under Ar. The mixture was stirred at 100° C. for 18 h, and then water was added. The mixture was extracted with EtOAc (2×20 mL). The combined organic layer was washed with water (2×10 mL), separated, dried over $Na_2SO_4$. After filtration the solvent was evaporated under reduced pressure, and the residue was purified on silica gel by flash chromatography affording (2R,3R,4R,5S)-3,4,5-tris(benzyloxy)-1-(4-cyclopropyl-2,6-difluorophenethyl)-2-methylpiperidine as a white solid (82 mg, 86%). ESI MS m/z 598.29 $[M+H]^+$.

To a stirred solution of the above material (80 mg, 0.13 mmol) in anhydrous DCM (5 mL) was added $BCl_3$ solution (1M in DCM, 1.0 mL, 1.0 mmol) at −78° C. under $N_2$. The mixture was stirred at 0° C. for 2 h before being quenched with anhydrous MeOH (1 mL).

The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-1-(4-cyclopropyl-2,6-difluorophenethyl)-2-methylpiperidine-3,4,5-triol as a white solid (30 mg, 71%). $^1$H NMR (400 MHz, $CD_3OD$) δ 6.71-6.63 (m, 2H), 3.55-3.46 (m, 1H), 3.13 (t, J=9.0 Hz, 1H), 3.05 (dd, J=11.1, 5.0 Hz, 1H), 2.93 (t, J=9.1 Hz, 1H), 2.89-2.73 (m, 4H), 2.39 (t, J=10.8 Hz, 1H), 2.35-2.27 (m, 1H), 1.96-1.87 (m, 1H), 1.22 (d, J=6.2 Hz, 3H), 1.05-0.97 (m, 2H), 0.73-0.66 (m, 2H); ESI MS m/z 328.17 $[M+H]^+$.

Example 54

(2R,3R,4R,5S)-1-(2,6-difluoro-4-(tetrahydro-2H-pyran-4-yl)phenethyl)-2-methylpiperidine-3,4,5-triol

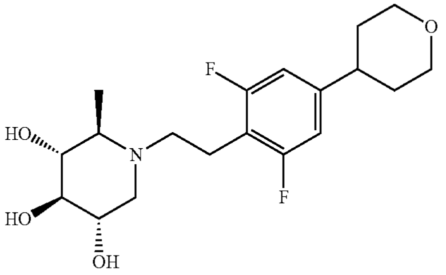 [SMILES: C[C@@H]1[C@@H](O)[C@H](O)[C@@H](O)CN1CCc1c(F)cc(C2CCOCC2)cc1F]

Under Ar, a mixture of 4-bromo-2,6-difluorobenzaldehyde (4.42 g, 20.0 mmol), 3,6-dihydro-2H-pyran-4-boronic acid pinacol ester (38A) (4.20 g, 20.0 mmol), $Pd(PPh_3)_4$ (1.15 g, 1.00 mmol) and aqueous $K_2CO_3$ solution (4.0 M, 10.0 mL, 40 mmol) in 1,4-dioxane (60 mL) was stirred at 85° C. for 16 h, and then cooled at RT. Brine (50 mL) was added, and the mixture was extracted with EtOAc (3×30 mL). The combined extract was washed with brine (50 mL) and dried over anhydrous $Na_2SO_4$. After filtration the solvent was evaporated under reduced pressure, and the residue was purified on silica gel by flash chromatography (EtOAc/hexanes, 1:5 to 1:4), affording 4-(3,6-dihydro-2H-pyran-4-yl)-2,6-difluorobenzaldehyde as a white solid (1.75 g, 39%). $^1$H NMR (400 MHz, $CDCl_3$) δ 10.31 (s, 1H), 7.04-6.97 (m, 2H), 6.38-6.36 (m, 1H), 4.35 (q, J=2.9 Hz, 2H), 3.93 (t, J=5.4 Hz, 2H), 2.50-2.45 (m, 2H), At −10° C., to a solution of (methoxymethyl)triphenylphosphonium chloride (3.42 g, 10.0 mmol) in anhydrous THE (40 ml) was added KO$^t$Bu (1.12 g, 10.0 mmol), and the mixture was stirred at −10° C. for 1 h. 4-(3,6-Dihydro-2H-pyran-4-yl)-2,6-difluorobenzaldehyde (1.00 g, 4.46 mmol) was added, and the mixture was stirred at RT for 24 h. The mixture was diluted with satd. aqueous $NaHCO_3$ (50 mL) and extracted with EtOAc (3×30 mL). The combined extract was dried over anhydrous $Na_2SO_4$. After filtration the solvent was evaporated under reduced pressure, and the residue was purified on silica gel by flash chromatography (EtOAc/hexanes, 1:6), affording the desired product. The product was dissolved in mixed THE (40 mL) and aqueous HCl (2.5 N, 40 mL). After stirring at reflux for 5 h the mixture was cooled and diluted with icy water (50 mL). After extraction with EtOAc (3×30 mL) the combined extract was washed with satd. aqueous $NaHCO_3$ (30 mL) and dried over anhydrous $Na_2SO_4$. After filtration the solvent was evaporated under reduced pressure, and the residue was purified on silica gel by flash chromatography (EtOAc/hexanes, 1:6 to 1:4), affording 2-(4-(3,6-dihydro-2H-pyran-4-yl)-2,6-difluorophenyl)acetaldehyde as a pale yellow solid (0.65 g, 61%, 2 steps). $^1$H NMR (500 MHz, $CDCl_3$) δ 9.75 (p, J=1.3 Hz, 1H), 7.03-6.75 (m, 2H), 6.19 (tt, J=3.1, 1.6 Hz, 1H), 4.32 (q, J=2.8 Hz, 2H), 3.92 (t, J=5.4 Hz, 2H), 3.86-3.68 (m, 2H), 2.46 (ttd, J=5.5, 2.8, 1.6 Hz, 2H).

Under $N_2$, a mixture of (2R,3R,4R,5S)-3,4,5-tris(benzyloxy)-2-methylpiperidine (0.208 g, 0.500 mmol), 2-(4-(3,6-dihydro-2H-pyran-4-yl)-2,6-difluorophenyl)acetaldehyde (0.16 g, 0.67 mmol) and $NaBH(OAc)_3$ (0.21 g, 1.0 mmol) in DCM (15 mL) was stirred at RT for 16 h. The reaction mixture was diluted with satd. aqueous $NaHCO_3$ (15 mL), and extracted with DCM (2×20 mL). The combined extract was dried over anhydrous $Na_2SO_4$. After filtration the solvent was evaporated under reduced pressure, and the residue was purified on silica gel by flash chromatography (EtOAc/hexanes, 1:6 to 1:4), affording (2R,3R,4R,5S)-3,4,5-tris(benzyloxy)-1-(4-(3,6-dihydro-2H-pyran-4-yl)-2,6-difluorophenethyl)-2-methylpiperidine as a pale yellow solid (0.29 g, 90%). ESI MS m/z 640.3328 $[M+H]^+$.

A mixture of the above material (0.15 g, 0.26 mmol) and $Pd(OH)_2/C$ (20% Pd in weight, 0.075 g, 0.14 mmol) and five drops of conc. HCl in MeOH/THF (15/5 mL) was stirred under hydrogen at one atmosphere of pressure overnight. The mixture was filtered through a celite cake, and the filtrate was collected and concentrated to dryness. The residue was neutralized with 1 M $NH_3$ in MeOH and subsequently purified on silica gel by flash column chromatography (0.5 M $NH_3$ MeOH/DCM, 1:6), affording (2R,3R,4R,5S)-1-(2,6-difluoro-4-(tetrahydro-2H-pyran-4-yl)phenethyl)-2-methylpiperidine-3,4,5-triol (0.060 g, 70%) as a white solid. $^1$H NMR (500 MHz, DMSO-$d_6$) δ 6.99-6.94 (m, 2H), 4.75-4.61 (m, 3H), 3.98-3.90 (m, 2H), 3.39 (td, J=11.5, 2.5 Hz, 2H) 3.29-3.21 (m, 1H), 2.90 (td, J=8.8, 4.4 Hz, 1H), 2.84 (dd, J=10.9, 4.9 Hz, 1H), 2.80-2.74 (m, 1H), 2.72-2.65 (m, 5H), 2.20 (t, J=10.6 Hz, 1H), 2.12 (dq, J=8.9, 6.1 Hz, 1H), 1.72-1.53 (m, 4H), 1.06 (d, J=6.1 Hz, 3H); ESI MS m/z 372.1970 $[M+H]^+$.

Example 55

(2R,3R,4R,5S)-1-(2,6-difluoro-4-(trifluoromethyl)phenethyl)-2-methylpiperidine-3,4,5-triol

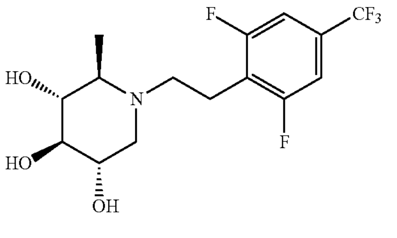 [SMILES: C[C@@H]1[C@@H](O)[C@H](O)[C@@H](O)CN1CCc1c(F)cc(C(F)(F)F)cc1F]

To a stirred solution of 3,5-difluorobenzotrifluoride (1.50 g, 8.24 mmol) in anhydrous $Et_2O$ (70 mL) was added n-BuLi solution (2.5M in hex, 5.0 mL, 12.5 mmol) at −78° C. under $N_2$. The mixture was stirred at −78° C. for 1 h. Anhydrous DMF (3.19 mL, 41.2 mmol) was added and stirred at −78° C. for another 1 h. The reaction was quenched with satd. aqueous $NH_4Cl$ at −78° C. The mixture was extracted with $Et_2O$ (3×20 mL). The combined organic layer was washed with water (2×20 mL), separated and dried over $Na_2SO_4$. After filtration, the solvent was evaporated under reduced pressure, and the residue was purified on silica gel by flash chromatography affording 2,6-difluoro-4-(trifluoromethyl)benzaldehyde as a clear liquid (1.07 g, 62%). $^1$H NMR (400 MHz, $CDCl_3$) δ 10.40 (s, 1H), 7.35-7.27 (m, 2H).

To a stirred solution of (methoxymethyl)triphenylphosphonium chloride (4.08 g, 11.9 mmol) in anhydrous THE (30 mL) was added $KO^tBu$ (1.33 g, 11.9 mmol) at 0° C. under $N_2$, and stirred for 30 min. Subsequently, 2,6-difluoro-4-(trifluoromethyl)benzaldehyde (1.0 g, 4.76 mmol) was dissolved in 5 mL of THE and added dropwise to the mixture under $N_2$, reacted at RT for 4 h. The reaction was quenched with satd. aqueous $NH_4Cl$ at 0° C. The mixture was extracted with EtOAc (3×40 mL). The combined organic layer was washed with water (2×20 mL), separated, dried over $Na_2SO_4$. After filtration, the solvent was evaporated under reduced pressure, and the residue was purified on silica gel by flash chromatography affording the product as an oil with two isomers. The oil was dissolved in THE (25 mL), 2N HCl aqueous solution (25 mL) was added, and the mixture was stirred at 80° C. for 8 h. The reaction mixture was cooled to RT and extracted with EtOAc (3×30 mL). The combined organic layer was washed with water (2×20 mL), separated, dried over $Na_2SO_4$. After filtration, the solvent was evaporated under reduced pressure, and the residue was purified on silica gel by flash chromatography affording 2-(2,6-difluoro-4-(trifluoromethyl)phenyl)acetaldehyde as a white solid (370 mg, 35%). $^1$H NMR (400 MHz, $CDCl_3$) δ 9.80 (t, J=1.2 Hz, 1H), 7.30-7.25 (m, 2H), 3.91 (s, 2H).

To a stirred solution of (2R,3R,4R,5S)-3,4,5-tris(benzyloxy)-2-methylpiperidine (260 mg, 0.62 mmol) and 2-(2,6-difluoro-4-(trifluoromethyl)phenyl)acetaldehyde (278 mg, 1.24 mmol) in anhydrous DCM (10 mL) was added HOAc (0.10 mL, 1.75 mmol) and stirred for 30 min. $NaBH_3CN$ (264 mg, 1.24 mmol) was added, and the resulting mixture was stirred at RT for 18 h. The reaction was quenched with satd. aqueous $NaHCO_3$ at 0° C. The mixture was extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-1-(2,6-difluoro-4-(trifluoromethyl)phenethyl)-2-methylpiperidine as a white solid (349 mg, 90%). $^1$H NMR (400 MHz, $CDCl_3$) δ 7.42-7.26 (m, 15H), 7.16 (d, J=6.4 Hz, 2H), 4.98 (t, J=11.5 Hz, 2H), 4.85 (d, J=11.0 Hz, 1H), 4.73 (d, J=2.5 Hz, 2H), 4.61 (d, J=10.8 Hz, 1H), 3.66-3.57 (m, 1H), 3.52 (t, J=9.0 Hz, 1H), 3.2-3.12 (m, 1H), 3.05 (t, J=8.9 Hz, 1H), 2.94-2.75 (m, 4H), 2.50-2.34 (m, 2H), 1.19 (d, J=6.1 Hz, 3H).

To a stirred solution of the above material (185 mg, 0.30 mmol) in anhydrous DCM (10 mL) was added $BCl_3$ solution (1M in DCM, 1.80 mL, 1.80 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-1-(2,6-difluoro-4-(trifluoromethyl)phenethyl)-2-methylpiperidine-3,4,5-triol as a white solid (62 mg, 58%). $^1$H NMR (400 MHz, $CD_3OD$) δ 7.39-7.30 (m, 2H), 3.53-3.44 (m, 1H), 3.13 (t, J=9.0 Hz, 1H), 3.07 (dd, J=11.1, 5.0 Hz, 1H), 3.01-2.76 (m, 5H), 2.36 (t, J=10.8 Hz, 1H), 2.33-2.24 (m, 1H), 1.19 (d, J=6.1 Hz, 3H); ESI MS m/z 356.12 $[M+H]^+$.

Example 56

(2R,3R,4R,5S)-1-(2,6-difluoro-4-(pyrrolidin-1-yl) phenethyl)-2-methylpiperidine-3,4,5-triol

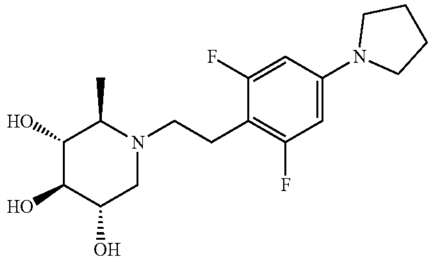 [SMILES: C[C@@H]1[C@@H](O)[C@H](O)[C@@H](O)CN1CCc1c(F)cc(N2CCCC2)cc1F]

A mixture of (E & Z)-5-bromo-1,3-difluoro-2-(2-methoxyvinyl)benzene (0.506 g, 2.00 mmol), pyrrolidine (0.32 g, 4.6 mmol), $KO^tBu$ (0.45 g, 4.0 mmol), BINAP (0.18 g, 0.30 mmol) and $Pd_2(dba)_3$ (0.092 g, 0.10 mmol) in anhydrous toluene (15 mL) was bubbled with Ar for 10 min, and then stirred at 85° C. for 16 h. The reaction mixture was cooled to RT and diluted with satd. aqueous $NaHCO_3$ (30 mL). After extraction with EtOAc (2×30 mL) the combined extract was dried over anhydrous $Na_2SO_4$. After filtration the solvent was evaporated under reduced pressure, and the residue was purified on silica gel by flash chromatography (EtOAc/hexanes, 1:12 to 1:9), affording (E & Z)-1-(3,5-difluoro-4-(2-methoxyvinyl)phenyl)piperidine as a pale-yellow oil (0.29 g, 61%, a mixture of trans & cis isomers). ESI MS m/z 240.115 $[M+H]^+$.

To a solution of the above material (0.29 g, 1.2 mmol) in THE (20 mL) was added aqueous HCl (3.5 N, 20 mL), and the mixture was stirred at reflux for 4 h. The reaction mixture was cooled to RT, and diluted with satd. aqueous $NaHCO_3$ (50 mL). After extraction with EtOAc (2×30 mL) the combined extract was dried over anhydrous $Na_2SO_4$. After filtration the solvent was evaporated under reduced pressure, and the residue was purified on silica gel by flash chromatography (EtOAc/hexanes, 1:9 to 1:6), affording 2-(2,6-difluoro-4-(pyrrolidin-1-yl)phenyl)acetaldehyde as a pale-yellow oil (0.17 g, 62%). $^1H$ NMR (400 MHz, $CDCl_3$) δ 9.68 (p, J=1.5 Hz, 1H), 6.14-6.02 (m, 2H), 3.61 (s, 2H), 3.28-3.18 (m, 4H), 2.06-1.94 (m, 4H); ESI MS m/z 226.104 $[M+H]^+$.

Under $N_2$, a mixture of (2R,3R,4R,5S)-3,4,5-tris(benzyloxy)-2-methylpiperidine (0.20 g, 0.48 mmol), 2-(2,6-difluoro-4-(pyrrolidin-1-yl)phenyl)acetaldehyde (0.15 g, 0.67 mmol) and $NaBH(OAc)_3$ (0.20 g, 0.94 mmol) in DCM (10 mL) was stirred at RT for 16 h. The reaction mixture was diluted with satd. aqueous $NaHCO_3$ (20 mL), and extracted with DCM (3×20 mL). The combined extract was dried over anhydrous $Na_2SO_4$. After filtration the solvent was evaporated under reduced pressure, and the residue was purified on silica gel by flash chromatography (EtOAc/hexanes, 1:8 to 1:5), affording (2R,3R,4R,5S)-3,4,5-tris(benzyloxy)-1-(2,6-difluoro-4-(pyrrolidin-1-yl)phenethyl)-2-methylpiperidine as a white solid (0.25 g, 83%). ESI MS m/z 627.331 $[M+H]^+$.

At −78° C. and under $N_2$, to a solution of the above material (0.25 g, 0.40 mmol) in anhydrous DCM (8 mL) was added $BCl_3$ (1.0 M in DCM, 2.0 mL, 2.0 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash column chromatography (1 M $NH_3$ in MeOH/DCM, 1:6), affording (2R,3R,4R,5S)-1-(2,6-difluoro-4-(pyrrolidin-1-yl)phenethyl)-2-methylpiperidine-3,4,5-triol as a white solid (0.121 g, 85%). $^1H$ NMR (400 MHz, DMSO-$d_6$) δ 6.37-6.03 (m, 2H), 4.93-4.59 (m, 3H), 3.30-3.11 (m, 5H), 2.90 (td, J=8.9, 4.4 Hz, 1H), 2.83 (dd, J=10.9, 4.9 Hz, 1H), 2.75-2.53 (m, 5H), 2.19 (t, J=10.6 Hz, 1H), 2.14-2.08 (m, 1H), 2.01-1.87 (m, 4H), 1.07 (d, J=6.1 Hz, 3H); ESI MS m/z 357.201 $[M+H]^+$.

Example 57

(2R,3R,4R,5S)-1-(2,6-difluoro-4-(piperidin-1-yl) phenethyl)-2-methylpiperidine-3,4,5-triol

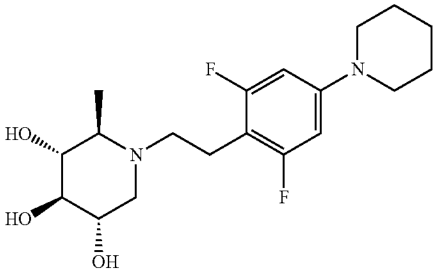 [SMILES: C[C@@H]1[C@@H](O)[C@H](O)[C@@H](O)CN1CCc1c(F)cc(N2CCCCC2)cc1F]

At 0° C., to a solution of (methoxymethyl)triphenylphosphonium chloride (5.14 g, 15.0 mmol) in anhydrous DMF (35 mL) was added $KO^tBu$ (1.70 g, 15.0 mmol) and 4-bromo-2,6-difluorobenzaldehyde (2.21 g, 10.0 mmol), and the mixture was stirred at RT for 16 h. The reaction mixture was diluted with satd. aqueous $NaHCO_3$ (200 mL), and then extracted with EtOAc (3×50 mL). The combined extract was washed with brine (2×50 mL) and dried over anhydrous $Na_2SO_4$. After filtration the solvent was evaporated under reduced pressure, and the residue was purified on silica gel by flash chromatography (EtOAc/hexanes, 1:19 to 1:9), affording (E & Z)-5-bromo-1,3-difluoro-2-(2-methoxyvinyl)benzene as a pale yellow solid (2.30 g, 92%, a mixture of trans & cis isomers).

A mixture of the above material (0.506 g, 2.00 mmol), piperidine (0.34 g, 4.0 mmol), $KO^tBu$ (0.45 g, 4.0 mmol), BINAP (0.18 g, 0.30 mmol) and $Pd_2(dba)_3$ (0.092 g, 0.10 mmol) in anhydrous toluene (15 mL) was bubbled with Ar for 10 min, and then stirred at 85° C. for 16 h. The reaction mixture was cooled to RT and diluted with satd. aqueous $NaHCO_3$ (30 mL). After extraction with EtOAc (2×30 mL) the combined extract was dried over anhydrous $Na_2SO_4$. After filtration the solvent was evaporated under reduced pressure, and the residue was purified on silica gel by flash chromatography (EtOAc/hexanes, 1:16 to 1:9), affording (E & Z)-1-(3,5-difluoro-4-(2-methoxyvinyl)phenyl)piperidine as a pale-yellow oil (0.30 g, 59%, a mixture of trans & cis isomers). ESI MS m/z 254.136 $[M+H]^+$.

To a solution of the above material (0.30 g, 1.2 mmol) in THE (20 mL) was added aqueous HCl (2.5 N, 20 mL), and the mixture was stirred at reflux for 4 h. The reaction mixture was cooled at RT, and diluted with satd. aqueous $NaHCO_3$ (50 mL). After extraction with EtOAc (2×30 mL) the combined extract was dried over anhydrous $Na_2SO_4$. After filtration the solvent was evaporated under reduced pressure, and the residue was purified on silica gel by flash chromatography (EtOAc/hexanes, 1:12 to 1:8), affording 2-(2,6-difluoro-4-(piperidin-1-yl)phenyl)acetaldehyde as a pale-yellow oil (0.21 g, 74%). $^1$H NMR (400 MHz, $CDCl_3$) δ 9.69 (p, J=1.4 Hz, 1H), 6.47-6.36 (m, 2H), 3.63 (q, J=1.4 Hz, 2H), 3.21-3.14 (m, 4H), 1.72-1.55 (m, 6H); ESI MS m/z 240.120 $[M+H]^+$.

Under $N_2$, a mixture of (2R,3R,4R,5S)-3,4,5-tris(benzyloxy)-2-methylpiperidine (0.25 g, 0.60 mmol), 2-(2,6-difluoro-4-(piperidin-1-yl)phenyl)acetaldehyde (0.12 g, 0.50 mmol) and $NaBH(OAc)_3$ (0.18 g, 0.85 mmol) in DCM (10 mL) was stirred at RT for 16 h. The reaction mixture was diluted with satd. aqueous $NaHCO_3$ (20 mL), and extracted with DCM (3×20 mL). The combined extract was dried over anhydrous $Na_2SO_4$. After filtration the solvent was evaporated under reduced pressure, and the residue was purified on silica gel by flash chromatography (EtOAc/hexanes, 1:12 to 1:8), affording (2R,3R,4R,5S)-3,4,5-tris(benzyloxy)-1-(2,6-difluoro-4-(piperidin-1-yl)phenethyl)-2-methylpiperidine as a white solid (0.179 g, 56%). ESI MS m/z 641.351 $[M+H]^+$.

At −78° C. and under $N_2$, to a solution of the above material (0.13 g, 0.20 mmol) in anhydrous DCM (8 mL) was added $BCl_3$ (1.0 M in DCM, 1.5 mL, 1.5 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:6), affording (2R,3R,4R,5S)-1-(2,6-difluoro-4-(piperidin-1-yl)phenethyl)-2-methylpiperidine-3,4,5-triol as a white solid (0.070 g, 94%). $^1$H NMR (400 MHz, DMSO-$d_6$) δ 6.60-6.51 (m, 2H), 4.71-4.65 (m, 3H), 3.24 (ddd, J=14.3, 11.2, 6.5 Hz, 1H), 3.17-3.12 (m, 4H), 2.94-2.78 (m, 2H), 2.72-2.51 (m, 5H), 2.23-2.06 (m, 2H), 1.60-1.50 (m, 6H), 1.06 (d, J=6.1 Hz, 3H); ESI MS m/z 371.215 $[M+H]^+$.

Example 58

(2R,3R,4R,5S)-1-(2,6-difluoro-4-morpholinophenethyl)-2-methylpiperidine-3,4,5-triol

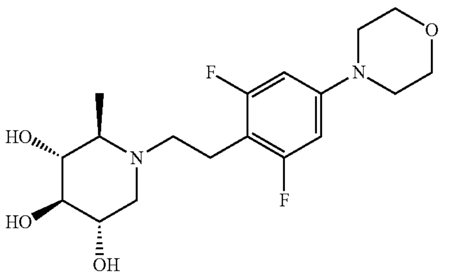 [SMILES: C[C@@H]1[C@@H](O)[C@H](O)[C@@H](O)CN1CCc1c(F)cc(N2CCOCC2)cc1F]

A mixture of (E & Z)-5-bromo-1,3-difluoro-2-(2-methoxyvinyl)benzene (0.506 g, 2.00 mmol), morpholine (0.35 g, 4.0 mmol), KO$^t$Bu (0.45 g, 4.0 mmol), BINAP (0.18 g, 0.30 mmol) and $Pd_2(dba)_3$ (0.092 g, 0.10 mmol) in anhydrous toluene (15 mL) was bubbled with Ar for 10 min, and then stirred at 85° C. for 16 h. The reaction mixture was cooled to RT and diluted with satd. aqueous $NaHCO_3$ (30 mL). After extraction with EtOAc (2×30 mL) the combined extract was dried over anhydrous $Na_2SO_4$. After filtration the solvent was evaporated under reduced pressure, and the residue was purified on silica gel by flash chromatography (EtOAc/hexanes, 1:9 to 1:6), affording (E & Z)-4-(3,5-difluoro-4-(2-methoxyvinyl)phenyl)morpholine as a pale-yellow oil (0.25 g, 49%, a mixture of trans & cis isomers). ESI MS m/z 256.110 $[M+H]^+$.

Synthesis of 2-(2,6-difluoro-4-morpholinophenyl)acetaldehyde (34B)

To a solution of the above material (0.25 g, 0.98 mmol) in mixed THE (15 mL) was added aqueous HCl (3.5 N, 15 mL) and the mixture was stirred at reflux for 4 h. The reaction mixture was cooled to RT and diluted with satd. aqueous $NaHCO_3$ (50 mL). After extraction with EtOAc (2×30 mL) the combined extract was dried over anhydrous $Na_2SO_4$. After filtration the solvent was evaporated under reduced pressure, and the residue was purified on silica gel by flash chromatography (EtOAc/hexanes, 1:6 to 1:4), affording 2-(2,6-difluoro-4-morpholinophenyl)acetaldehyde as a pale-yellow oil (0.12 g, 51%). $^1$H NMR (400 MHz, $CDCl_3$) δ 9.70 (s, 1H), 6.51-6.29 (m, 2H), 3.88-3.79 (m, 4H), 3.66 (s, 2H), 3.16-3.11 (m, 4H); ESI MS m/z 242.094 $[M+H]^+$.

Under $N_2$, a mixture of (2R,3R,4R,5S)-3,4,5-tris(benzyloxy)-2-methylpiperidine (0.19 g, 0.46 mmol), 2-(2,6-difluoro-4-morpholinophenyl)acetaldehyde (0.12 g, 0.50 mmol) and $NaBH(OAc)_3$ (0.23 g, 1.1 mmol) in DCM (10 mL) was stirred at RT for 16 h. The reaction mixture was diluted with satd. aqueous $NaHCO_3$ (20 mL) and extracted with DCM (3×20 mL). The combined extract was dried over anhydrous $Na_2SO_4$. After filtration the solvent was evaporated under reduced pressure, and the residue was purified on silica gel by flash chromatography (EtOAc/hexanes, 1:4 to 1:3), affording 4-(3,5-difluoro-4-(2-((2R,3R,4R,5S)-3,4,5-tris(benzyloxy)-2-methylpiperidin-1-yl)ethyl)phenyl)morpholine as a white solid (0.26 g, 88%). ESI MS m/z 643.329 $[M+H]^+$.

At −78° C. and under $N_2$, to a solution of the above material (0.26 g, 0.40 mmol) in anhydrous DCM (8 mL) was added $BCl_3$ (1.0 M in DCM, 2.0 mL, 2.0 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash column chromatography (1 M $NH_3$ in MeOH/DCM, 1:6), affording (2R,3R,4R,5S)-1-(2,6-difluoro-4-morpholinophenethyl)-2-methylpiperidine-3,4,5-triol as a white solid (0.124 g, 83%). $^1$H NMR (400 MHz, DMSO-$d_6$) δ 6.82-6.46 (m, 2H), 4.86-4.41 (m, 3H), 3.69 (dd, J=6.0, 3.8 Hz, 4H), 3.29-3.19 (m, 1H), 3.11 (dd, J=6.0, 3.8 Hz, 4H), 2.89 (td, J=8.8, 4.3 Hz, 1H), 2.83 (dd, J=10.9, 4.9 Hz, 1H), 2.73-2.54 (m, 5H), 2.18 (t, J=10.6 Hz, 1H), 2.14-2.07 (m, 1H), 1.06 (d, J=6.1 Hz, 3H); ESI MS m/z 373.195 $[M+H]^+$.

Example 59

(2R,3R,4R,5S)-1-(4-butoxy-2,6-difluorophenethyl)-2-methylpiperidine-3,4,5-triol

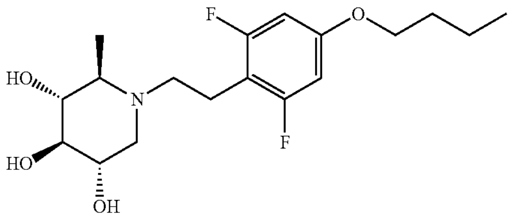 [SMILES: CCCCOc1cc(F)c(CCN2C[C@H](O)[C@@H](O)[C@H](O)[C@H]2C)c(F)c1]

A mixture of 3,5-difluorophenol (2.60 g, 20.0 mmol), 1-bromobutane (4.00 g, 29.2 mmol), $K_2CO_3$ (5.00 g, 36.3 mmol) in DMF (25 mL) was stirred at 80° C. for 2 h, and then cooled at RT. The mixture was diluted with water (50 mL) and extracted with hexanes (2×50 mL). The combined extract was washed with brine (2×50 mL) and then dried over anhydrous $Na_2SO_4$. After filtration the solvent was evaporated under reduced pressure, and the residue was purified on silica gel by flash chromatography (hexanes), affording 1-butoxy-3,5-difluorobenzene as a clear colorless liquid (3.50 g, 94%). $^1H$ NMR (400 MHz, $CDCl_3$) δ 6.45-6.34 (m, 3H), 3.92 (t, J=6.5 Hz, 2H), 1.80-1.71 (m, 2H), 1.55-1.41 (m, 2H), 0.98 (t, J=7.4 Hz, 3H).

At −78° C. and under $N_2$, to a solution of the above material (3.50 g, 18.8 mmol) in anhydrous THE (20 mL) was added fresh prepared LDA (22.0 mmol) in mixed THF/hexanes (20 mL/10 mL), and the mixture was stirred at −78° C. for 1 h. Anhydrous DMF (2.92 g, 40.0 mmol) was added, and the mixture was stirred at −78° C. for 30 min and then at 0° C. for 1 h. Diluted aqueous HCl (0.5 N, 50 mL) was added, and the mixture was extracted with EtOAc (2×50 mL). The combined extract was washed with brine (2×50 mL) and dried over anhydrous $Na_2SO_4$. After filtration the solvent was evaporated under reduced pressure, and the residue was purified on silica gel by flash chromatography (EtOAc/hexanes, 1:20), affording 4-butoxy-2,6-difluorobenzaldehyde as a white solid (3.8 g, 94%). $^1H$ NMR (500 MHz, $CDCl_3$) δ 10.18 (s, 1H), 6.52-6.42 (m, 2H), 4.00 (t, J=6.5 Hz, 2H), 1.83-1.73 (m, 2H), 1.52-1.42 (m, 2H), 0.97 (t, J=7.4 Hz, 3H).

At 0° C., to a solution of (methoxymethyl)triphenylphosphonium chloride (2.30 g, 6.50 mmol) in anhydrous DMF (30 mL) was added KO$^t$Bu (0.729 g, 6.50 mmol) and 4-butoxy-2,6-difluorobenzaldehyde (1.15 g, 5.37 mmol), and the mixture was stirred at RT for 16 h. The mixture was diluted with satd. aqueous $NaHCO_3$ (50 mL) and extracted with EtOAc (2×40 mL). The combined extract was washed with brine (2×50 mL) and dried over anhydrous $Na_2SO_4$. After filtration the solvent was evaporated under reduced pressure, and the residue was purified on silica gel by flash chromatography (EtOAc/hexanes, 1:30 to 1:9), affording a clear liquid. The clear liquid was dissolved in mixed THE (25 mL) and aqueous HCl (2.5 N, 25 mL). After stirring at reflux for 2 h the mixture was cooled and diluted with ice water (50 mL). After extraction with EtOAc (2×40 mL) the combined extract was washed with satd. aqueous $NaHCO_3$ (50 mL) and dried over anhydrous $Na_2SO_4$. After filtration the solvent was evaporated under reduced pressure, and the residue was purified on silica gel by flash chromatography (EtOAc/hexanes, 1:20 to 1:9), affording 2-(4-butoxy-2,6-difluorophenyl)acetaldehyde as a colorless oil (0.20 g, 16%, 2 steps). $^1H$ NMR (500 MHz, $CDCl_3$) δ 9.71 (p, J=1.3 Hz, 1H), 6.44-6.39 (m, 2H), 3.91 (t, J=6.5 Hz, 2H), 3.69 (s, 2H), 1.80-1.69 (m, 2H), 1.50-1.43 (m, 2H), 0.97 (t, J=7.4 Hz, 3H).

Under $N_2$, a mixture of (2R,3R,4R,5S)-3,4,5-tris(benzyloxy)-2-methylpiperidine (0.25 g, 0.60 mmol), 2-(4-butoxy-2,6-difluorophenyl)acetaldehyde (0.20 g, 0.88 mmol) and $NaBH(OAc)_3$ (0.32 g, 1.5 mmol) in DCM (15 mL) was stirred at RT for 16 h. The reaction mixture was diluted with satd. aqueous $NaHCO_3$ (20 mL), and extracted with DCM (3×15 mL). The combined extract was dried over anhydrous $Na_2SO_4$. After filtration the solvent was evaporated under reduced pressure, and the residue was purified on silica gel by flash chromatography (EtOAc/hexanes, 1:20 to 1:8), affording (2R,3R,4R,5S)-3,4,5-tris(benzyloxy)-1-(4-butoxy-2,6-difluorophenethyl)-2-methylpiperidine as a colorless oil (0.31 g, 82%). ESI MS m/z 630.335 $[M+H]^+$.

A mixture of the above material (0.230 g, 0.365 mmol) and $Pd(OH)_2/C$ (20% Pd in weight, 0.080 g, 0.15 mmol) and five drops of concentrated HCl in MeOH (20 mL) was stirred under $H_2$ at one atmosphere of pressure overnight. The mixture was filtered through a celite cake, and the filtrate was collected and concentrated to dryness. The residue was neutralized with 1 M $NH_3$ in MeOH and purified on silica gel by flash chromatography (1 M $NH_3$ MeOH/DCM, 1:6), affording (2R,3R,4R,5S)-1-(4-butoxy-2,6-difluorophenethyl)-2-methylpiperidine-3,4,5-triol (0.115 g, 88%) as a white solid. $^1H$ NMR (400 MHz, $CD_3OD$) δ 6.59-6.44 (m, 2H), 3.94 (t, J=6.4 Hz, 2H), 3.52-3.45 (m, 1H), 3.11 (t, J=9.0 Hz, 1H), 3.03 (dd, J=11.2, 4.9 Hz, 1H), 2.91 (t, J=9.1 Hz, 1H), 2.86-2.65 (m, 4H), 2.36 (t, J=10.8 Hz, 1H), 2.28 (dq, J=9.1, 6.1 Hz, 1H), 1.81-1.67 (m, 2H), 1.58-1.39 (m, 2H), 1.21 (d, J=6.1 Hz, 3H), 0.98 (t, J=7.4 Hz, 3H); ESI MS m/z 360.201 $[M+H]^+$.

Example 60

(2R,3R,4R,5S)-1-(4-(cyclopropylmethoxy)-2,6-difluorophenethyl)-2-methylpiperidine-3,4,5-triol

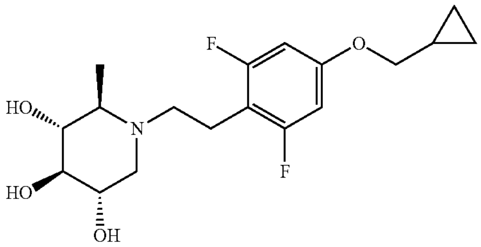 [SMILES: C[C@@H]1[C@@H](O)[C@H](O)[C@@H](O)CN1CCc1c(F)cc(OCC2CC2)cc1F]

A mixture of 3,5-difluorophenol (1.80 g, 13.8 mmol), (bromomethyl)cyclopropane (2.00 g, 14.8 mmol), $K_2CO_3$ (3.00 g, 21.7 mmol) in DMF (20 mL) was stirred at 80° C. for 16 h, and then cooled to RT. The mixture was diluted with water (50 mL) and extracted with hexanes (2×50 mL). The combined extract was washed with brine (2×50 mL) and then dried over anhydrous $Na_2SO_4$. After filtration the solvent was evaporated under reduced pressure, and the residue was purified on silica gel by flash chromatography (hexanes), affording 1-(cyclopropylmethoxy)-3,5-difluorobenzene as a clear colorless liquid (2.30 g, 90%).

At −78° C. and under $N_2$, to a solution of the above material (2.30 g, 12.5 mmol) in anhydrous THE (20 mL) was added freshly prepared LDA (14.0 mmol) in mixed THF/hexanes (20 ml/10 mL), and the mixture was stirred at −78° C. for 1 h. Anhydrous DMF (1.83 g, 25.0 mmol) was added, and the mixture was stirred at −78° C. for 30 min and then at 0° C. for 1 h. Diluted aqueous HCl (0.5 N, 50 mL) was added, and the mixture was extracted with EtOAc (2×50 mL). The combined extract was washed with brine (2×50 mL) and dried over anhydrous $Na_2SO_4$. After filtration the solvent was evaporated under reduced pressure, and the residue was purified on silica gel by flash chromatography (EtOAc/hexanes, 1:10), affording 4-(cyclopropylmethoxy)-2,6-difluorobenzaldehyde as a white solid (2.35 g, 90%). $^1$H NMR (400 MHz, $CDCl_3$) δ 10.18 (s, 1H), 6.63-6.39 (m, 2H), 3.85 (d, J=7.0 Hz, 2H), 1.37-1.08 (m, 1H), 0.73-0.59 (m, 2H), 0.39-0.35 (m, 2H).

At 0° C., to a solution of (methoxymethyl)triphenylphosphonium chloride (2.40 g, 7.00 mmol) in anhydrous DMF (20 ml) was added KO$^t$Bu (0.841 g, 7.50 mmol) and 4-(cyclopropylmethoxy)-2,6-difluorobenzaldehyde (1.00 g, 4.71 mmol), and the mixture was stirred at RT for 16 h. The mixture was diluted with satd. aqueous $NaHCO_3$ (50 mL) and extracted with EtOAc (2×40 mL). The combined extract was washed with brine (2×50 mL) and dried over anhydrous $Na_2SO_4$. After filtration the solvent was evaporated under reduced pressure, and the residue was purified on silica gel by flash chromatography (EtOAc/hexanes, 1:30 to 1:9), affording a clear liquid. The clear liquid was dissolved in mixed THE (25 mL) and aqueous HCl (3.5 N, 25 mL). After stirring at reflux for 4 h the mixture was cooled and diluted with ice water (50 mL). After extraction with EtOAc (2×40 mL) the combined extract was washed with satd. aqueous $NaHCO_3$ (50 mL) and dried over anhydrous $Na_2SO_4$. After filtration the solvent was evaporated under reduced pressure, and the residue was purified on silica gel by flash chromatography (EtOAc/hexanes, 1:12 to 1:7), affording 2-(4-(cyclopropylmethoxy)-2,6-difluorophenyl)acetaldehyde as a colorless oil (0.43 g, 40%, 2 steps). $^1$H NMR (400 MHz, $CDCl_3$) δ 9.71 (p, J=1.3 Hz, 1H), 6.62-6.36 (m, 2H), 3.77 (d, J=6.9 Hz, 2H), 3.68 (q, J=1.3 Hz, 2H), 1.32-1.18 (m, 1H), 0.71-0.58 (m, 2H), 0.40-0.28 (m, 2H).

Under $N_2$, a mixture of (2R,3R,4R,5S)-3,4,5-tris(benzyloxy)-2-methylpiperidine (0.22 g, 0.53 mmol), 2-(4-(cyclopropylmethoxy)-2,6-difluorophenyl)acetaldehyde (0.20 g, 0.88 mmol) and $NaBH(OAc)_3$ (0.30 g, 1.4 mmol) in DCM (10 mL) was stirred at RT for 16 h. The reaction mixture was diluted with satd. aqueous $NaHCO_3$ (20 mL), and extracted with DCM (3×15 mL). The combined extract was dried over anhydrous $Na_2SO_4$. After filtration the solvent was evaporated under reduced pressure, and the residue was purified on silica gel by flash chromatography (EtOAc/hexanes, 1:10 to 1:7), affording (2R,3R,4R,5S)-3,4,5-tris(benzyloxy)-1-(4-(cyclopropylmethoxy)-2,6-difluorophenethyl)-2-methylpiperidine as a colorless oil (0.315 g, 95%). ESI MS m/z 628.322 [M+H]$^+$.

A mixture of the above material (0.31 g, 0.50 mmol) and $Pd(OH)_2/C$ (20% Pd in weight, 0.080 g, 0.15 mmol) and six drops of concentrated HCl in MeOH (25 mL) was stirred under hydrogen at one atmosphere of pressure overnight. The mixture was filtered through a celite cake, and the filtrate was collected and concentrated to dryness. The residue was neutralized with 1 M $NH_3$ in MeOH and purified on silica gel by flash column chromatography (1 M $NH_3$ MeOH/DCM, 1:6), affording (2R,3R,4R,5S)-1-(4-(cyclopropylmethoxy)-2,6-difluorophenethyl)-2-methylpiperidine-3,4,5-triol (0.157 g, 88%) as a white solid. $^1$H NMR (400 MHz, $CD_3OD$) δ 6.59-6.46 (m, 2H), 3.78 (d, J=6.9 Hz, 2H), 3.49 (ddd, J=10.5, 9.0, 4.9 Hz, 1H), 3.11 (t, J=9.0 Hz, 1H), 3.03 (dd, J=11.1, 4.9 Hz, 1H), 2.91 (t, J=9.1 Hz, 1H), 2.87-2.66 (m, 4H), 2.36 (t, J=10.9 Hz, 1H), 2.27 (dt, J=9.1, 6.1 Hz, 1H), 1.27-1.12 (m, 4H), 0.67-0.55 (m, 2H), 0.40-0.28 (m, 2H); ESI MS m/z 358.183 [M+H]$^+$.

Example 61

(2R,3R,4R,5S)-2-methyl-1-(4-((tetrahydrofuran-3-yl)oxy)phenethyl)piperidine-3,4,5-triol

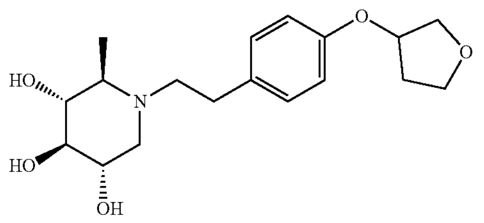 [SMILES: C[C@@H]1[C@@H](O)[C@H](O)[C@@H](O)CN1CCc1ccc(OC2CCOC2)cc1]

To a stirred solution of ethyl 2-(4-hydroxyphenyl)acetate (1.0 g, 5.5 mmol), $PPh_3$ (2.18 g, 8.32 mmol), and tetrahydrofuran-3-ol (0.73 g, 8.32 mmol) in anhydrous THE (10 mL) was added DIAD (1.68 g, 8.32 mmol) slowly. The resulting mixture was stirred at RT for 18 h. The solvent was removed under reduced pressure and the crude material was purified on a silica gel flash chromatography affording ethyl 2-(4-((tetrahydrofuran-3-yl)oxy)phenyl)acetate as an oil (0.55 g, 40%). $^1$H NMR (400 MHz, $CDCl_3$) δ 7.26-7.19 (m, 2H), 6.87-6.82 (m, 2H), 4.93 (ddt, J=6.5, 4.5, 2.2 Hz, 1H), 4.17 (q, J=7.1 Hz, 2H), 4.06-3.97 (m, 3H), 3.92 (td, J=8.2, 4.4 Hz, 1H), 3.57 (s, 2H), 2.28-2.14 (m, 2H), 1.28 (t, J=7.1 Hz, 3H).

To a solution of the above material (550 mg, 2.20 mmol) in anhydrous THE (10 mL) at 0° C., was added LAH (204 mg, 5.34 mmol), and the mixture was stirred at 0° C. for 1 h. The mixture was quenched slowly with satd. aqueous $Na_2SO_4$ and filtered. The solid was washed with EtOAc. The combined organic layer was washed with water (2×20 mL), separated, dried over $Na_2SO_4$. After filtration, the solvent was evaporated under reduced pressure, to obtain the crude 2-(4-((tetrahydrofuran-3-yl)oxy)phenyl)ethanol as an oil (490 mg).

A solution of the above material (310 mg, 1.49 mmol) and $CBr_4$ (593 mg, 1.79 mmol) in DCM (10 mL) was cooled to 0° C., and $PPh_3$ (469 mg, 1.79 mmol) was added portionwise. The reaction mixture was stirred at RT for 1 h. The mixture was diluted with DCM, and washed with satd. aqueous $NaHCO_3$ and the organic phase was separated, dried over $Na_2SO_4$. After filtration, the solvent was evaporated under reduced pressure, and the residue was purified on silica gel by flash chromatography affording 3-(4-(2-bromoethyl)phenoxy)tetrahydrofuran as an oil (311 mg, 77%). $^1$H NMR (400 MHz, $CDCl_3$) δ 7.18-7.12 (m, 2H), 6.87-6.81 (m, 2H), 4.93 (ddt, J=6.4, 4.5, 2.2 Hz, 1H), 4.05-3.97 (m, 3H), 3.92 (td, J=8.2, 4.4 Hz, 1H), 3.56 (t, J=7.6 Hz, 2H), 3.13 (t, J=7.6 Hz, 2H), 2.28-2.12 (m, 2H).

DIPEA (0.16 mL, 0.96 mmol) was added to a solution of (2R,3R,4R,5S)-3,4,5-tris(benzyloxy)-2-methylpiperidine (50 mg, 0.12 mmol) and 3-(4-(2-bromoethyl)phenoxy)tetrahydrofuran (130 mg, 0.48 mmol) in DMF (5 mL) in a sealed tube. The mixture was stirred at 80° C. for 18 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-2-methyl-1-(4-((tetrahydrofuran-3-yl)oxy)phenethyl) piperidine as a white solid (39 mg, 52%). ESI MS m/z 608.32 $[M+H]^+$.

To a solution of the above material (35 mg, 0.058 mmol) in EtOH (10 mL) was added $Pd(OH)_2/C$ (20 wt. %, 8.6 mg, 0.012 mmol) and 6N HCl (0.1 mL). The mixture was treated with hydrogen (1 atm) for 18 h. Catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(4-((tetrahydrofuran-3-yl)oxy)phenethyl)piperidine-3,4,5-triol as a white solid (14 mg, 72%). $^1H$ NMR (400 MHz, $CD_3OD$) δ 7.20-7.13 (m, 2H), 6.89-6.83 (m, 2H), 5.03-4.97 (m, 1H), 4.05-3.80 (m, 4H), 3.63-3.52 (m, 1H), 3.21 (t, J=8.7 Hz, 2H), 3.13-3.00 (m, 2H), 2.99-2.87 (m, 1H), 2.87-2.71 (m, 2H), 2.61-2.41 (br, 2H), 2.31-2.18 (m, 1H), 2.15-2.06 (m, 1H), 1.33 (d, J=6.2 Hz, 3H); ESI MS m/z 338.19 $[M+H]^+$.

Example 62

(2R,3R,4R,5S)-2-methyl-1-(4-((tetrahydro-2H-pyran-3-yl)oxy)phenethyl)piperidine-3,4,5-triol

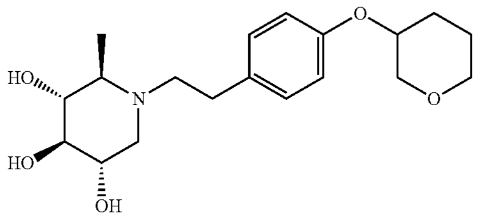 [SMILES: C[C@@H]1[C@@H](O)[C@H](O)[C@@H](O)CN1CCc1ccc(OC2CCCOC2)cc1]

A solution of (2S,3R,4S,5S)-3,4,5-tris(benzyloxy)-2-methoxy-6-methylenetetrahydro-2H-pyran (24.4 g, 54.6 mmol) (Heterocycles, 2007, 73, C, 165-168) in THE (400 mL) was added aqueous HCl (2.5 N, 200 mL), and the mixture was stirred at 50° C. for 2 h. The reaction mixture was diluted with ice water (400 mL) and extracted with EtOAc (3×300 mL). The combined extract was washed with satd. aqueous $NaHCO_3$ (500 mL) and dried over anhydrous $Na_2SO_4$. After filtration the solvent was evaporated under reduced pressure at RT to give (2R,3R,4S)-2,3,4-tris(benzyloxy)-5-oxohexanal as a white solid. This material was dissolved in mixed solvent of anhydrous DCM (50 mL) and anhydrous MeOH (450 mL), and, at 0° C. and under $N_2$, was added $NH_4OAc$ (75.0 g, 973 mmol), $Na_2SO_4$ (50.0 g, 352 mmol) and $NaBH_3CN$ (20.0 g, 318 mmol). After stirring at RT for 16 h the mixture was diluted with satd. aqueous $NaHCO_3$ (1 L) and extracted with DCM (3×500 mL). The combined extract was dried over anhydrous $Na_2SO_4$. After filtration the solvent was evaporated under reduced pressure, and the residue was purified on silica gel by flash chromatography (EtOAc/hexanes, 3:7, and then 1 M $NH_3$ in MeOH/DCM, 1:20), affording (2R,3R,4R,5S)-3,4,5-tris(benzyloxy)-2-methylpiperidine as a white solid (20.3 g, 89%, 2 steps). $^1H$ NMR (400 MHz, DMSO-$d_6$) δ 7.43-7.15 (m, 15H), 4.86 (d, J=11.2 Hz, 1H), 4.77 (d, J=11.2 Hz, 1H), 4.72 (d, J=11.2 Hz, 1H), 4.65 (d, J=12.0 Hz, 1H), 4.62-4.53 (m, 2H), 3.43-3.34 (m, 2H), 3.14 (dd, J=11.9, 4.4 Hz, 1H), 2.89 (t, J=8.8 Hz, 1H), 2.41 (dd, J=9.4, 6.3 Hz, 1H), 2.28 (dd, J=11.9, 9.4 Hz, 1H), 2.08 (s, br., 1H), 1.05 (d, J=6.2 Hz, 3H); ESI MS m/z 418.235 $[M+H]^+$.

At 0° C., to a solution of ethyl 2-(4-hydroxyphenyl) acetate (2.00 g, 11.1 mmol), $PPh_3$ (4.50 g, 17.2 mmol) and tetrahydro-2H-pyran-3-ol (1.70 g, 16.6 mmol) in anhydrous THE (30 mL) was added DIAD (3.40 g, 16.8 mmol) slowly, and the mixture was stirred at RT for 16 h. The solvent was removed under reduced pressure at RT, and the residue was purified on silica gel by flash chromatography (EtOAc/hexanes, 1:7 to 1:3), affording ethyl 2-(4-((tetrahydro-2H-pyran-3-yl)oxy)phenyl)acetate as a pale-yellow oil (1.50 g, 51%).

At 0° C. and under $N_2$, to a solution of the above material (0.650 g, 2.46 mmol) in anhydrous THE (20 mL) was added LAH (0.152 g, 4.00 mmol), and the mixture was stirred at 0° C. for 1 h. Wet sodium sulfate heptahydrate (50 g) was added to quench the reaction, and the suspension was stirred at RT for 30 min. After filtration the solvent was evaporated, affording 2-(4-((tetrahydro-2H-pyran-3-yl)oxy)phenyl)ethanol as a clear oil.

At 0° C., to a solution of the above material in anhydrous DCM (30 mL) was added $PPh_3$ (0.84 g, 3.2 mmol) and $CBr_4$ (1.0 g, 3.0 mmol), and the mixture was stirred at RT for 16 h. The solvent was evaporated under reduced pressure, and the residue was purified on silica gel by flash chromatography (EtOAc/hexanes, 1:9 to 1:7), affording 3-(4-(2-bromoethyl)phenoxy)tetrahydro-2H-pyran as a clear oil (0.61 g, 87%, two steps). $^1H$ NMR (500 MHz, $CDCl_3$) δ 7.14-7.08 (m, 2H), 6.92-6.80 (m, 2H), 4.28 (tt, J=7.6, 3.6 Hz, 1H), 3.95 (ddd, J=11.5, 3.6, 1.6 Hz, 1H), 3.80-3.72 (m, 1H), 3.60-3.53 (m, 2H), 3.52 (t, J=7.7 Hz, 2H), 3.09 (t, J=7.7 Hz, 2H), 2.14-2.03 (m, 1H), 1.94-1.83 (m, 1H), 1.81-1.74 (m, 1H), 1.68-1.59 (m, 1H).

A mixture of (2R,3R,4R,5S)-3,4,5-tris(benzyloxy)-2-methylpiperidine (0.10 g, 0.24 mmol), 3-(4-(2-bromoethyl) phenoxy)tetrahydro-2H-pyran (0.20 g, 0.70 mmol) and DIPEA (0.20 g, 2.3 mmol) in anhydrous DMF (5 mL) in a sealed tube was stirred at 85° C. for 16 h. The reaction mixture was cooled at RT and diluted with satd. aqueous $NaHCO_3$ (20 mL). After extraction with EtOAc (3×20 mL) the combined extract was washed with brine (2×20 mL) and dried over anhydrous $Na_2SO_4$. After filtration the solvent was evaporated under reduced pressure, and the residue was purified on silica gel by flash chromatography (EtOAc/hexanes, 1:7 to 1:3), affording (2R,3R,4R,5S)-3,4,5-tris(benzyloxy)-2-methyl-1-(4-((tetrahydro-2H-pyran-3-yl)oxy)phenethyl)piperidine as a pale-yellow oil (0.11 g, 74%); ESI MS m/z 622.342 $[M+H]^+$.

A mixture of the above material (0.10 g, 0.16 mmol) and $Pd(OH)_2/C$ (20% Pd in weight, 0.075 g, 0.14 mmol) and two drops of concentrated HCl in MeOH (20 mL) was stirred under hydrogen at one atmosphere of pressure overnight. The mixture was filtered through a celite cake, and the filtrate was collected and concentrated to dryness. The residue was neutralized with 1 M $NH_3$ in MeOH and purified on silica gel by flash chromatography (1 M $NH_3$ MeOH/DCM, 1:8), affording (2R,3R,4R,5S)-2-methyl-1-(4-((tetrahydro-2H-pyran-3-yl)oxy)phenethyl)piperidine-3,4,5-triol (0.042 g, 75%) as a white foam. $^1H$ NMR (400 MHz, DMSO-$d_6$) δ 7.08 (d, J=8.5 Hz, 2H), 6.85 (d, J=8.5 Hz, 2H), 4.71-4.64 (m, 3H), 4.29 (tt, J=7.0, 3.5 Hz, 1H), 3.82-3.76 (m, 1H), 3.66-3.58 (m, 1H), 3.53-3.39 (m, 2H), 3.28-3.16 (m, 1H), 2.93-3.84 (m, 2H), 2.79-2.65 (m, 2H), 2.64-2.54 (m, 3H), 2.15-1.96 (m, 3H), 1.78-1.71 (m, 1H), 1.68-1.60 (m, 1H), 1.55-1.47 (m, 1H), 1.09 (d, J=6.1 Hz, 3H); ESI MS m/z 352.207 $[M+H]^+$.

Example 63

(2R,3R,4R,5S)-2-methyl-1-(4-((tetrahydro-2H-pyran-4-yl)oxy)phenethyl)piperidine-3,4,5-triol

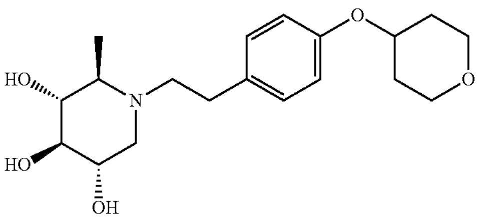 [SMILES: C[C@@H]1[C@@H](O)[C@H](O)[C@@H](O)CN1CCc1ccc(OC2CCOCC2)cc1]

To a stirred solution of ethyl 2-(4-hydroxyphenyl)acetate (2.0 g, 11.1 mmol), $PPh_3$ (4.36 g, 16.6 mmol), and tetrahydro-2H-pyran-4-ol (1.70 g, 16.6 mmol) in anhydrous THE (20 mL) was added DIAD (3.36 g, 16.6 mmol) slowly. The resulting mixture was stirred at RT for 18 h. The solvent was removed under reduced pressure and the crude material was purified on a silica gel flash chromatography affording ethyl 2-(4-((tetrahydro-2H-pyran-4-yl)oxy)phenyl)acetate as an oil (1.45 g, 54%). $^1$H NMR (400 MHz, $CDCl_3$) δ 7.25-7.17 (m, 2H), 6.97-6.85 (m, 2H), 4.48 (tt, J=7.8, 3.8 Hz, 1H), 4.17 (q, J=7.1 Hz, 2H), 4.00 (ddd, J=11.7, 6.1, 3.8 Hz, 2H), 3.64-3.55 (m, 4H), 2.08-1.96 (m, 2H), 1.81 (dtd, J=12.4, 8.1, 3.8 Hz, 2H), 1.28 (t, J=7.1 Hz, 3H).

To a solution of the above material (1.0 g, 3.79 mmol) in anhydrous THE (20 mL) at 0° C., was added LAH (431 mg, 11.4 mmol), and the mixture was stirred at 0° C. for 1 h. The mixture was quenched slowly with satd. aqueous $Na_2SO_4$ and filtered. The solid was washed with EtOAc. The combined organic layer was washed with water (2×20 mL), separated, dried over $Na_2SO_4$. After filtration, the solvent was evaporated under reduced pressure, to obtain crude 2-(4-((tetrahydro-2H-pyran-4-yl)oxy)phenyl)ethanol as an oil (890 mg, 100%).

A solution of the above material (540 mg, 2.43 mmol) and $CBr_4$ (967 mg, 2.92 mmol) in DCM (20 mL) was cooled to 0° C., and $PPh_3$ (766 mg, 2.92 mmol) was added portionwise. The reaction mixture was stirred at RT for 1 h. The mixture was diluted with DCM and washed with satd. aqueous $NaHCO_3$ and the organic phase was separated, dried over $Na_2SO_4$. After filtration, the solvent was evaporated under reduced pressure, and the residue was purified on silica gel by flash chromatography affording 4-(4-(2-bromoethyl)phenoxy)tetrahydro-2H-pyran as an oil (568 mg, 82%). $^1$H NMR (400 MHz, $CDCl_3$) δ 7.17-7.09 (m, 2H), 6.94-6.84 (m, 2H), 4.48 (tt, J=7.8, 3.9 Hz, 1H), 4.01 (ddd, J=10.7, 6.0, 3.8 Hz, 2H), 3.67-3.45 (m, 4H), 3.12 (t, J=7.6 Hz, 2H), 2.08-1.97 (m, 2H), 1.81 (dtd, J=12.4, 8.1, 3.8 Hz, 2H).

DIPEA (0.16 mL, 0.96 mmol) was added to a solution of (2R,3R,4R,5S)-3,4,5-tris(benzyloxy)-2-methylpiperidine (50 mg, 0.12 mmol) and 4-(4-(2-bromoethyl)phenoxy)tetrahydro-2H-pyran (136 mg, 0.48 mmol) in DMF (5 mL) in a sealed tube. The mixture was stirred at 80° C. for 18 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-2-methyl-1-(4-((tetrahydro-2H-pyran-4-yl)oxy)phenethyl)piperidine as a white solid (38 mg, 52%). ESI MS m/z 622.34 $[M+H]^+$.

To a solution of the above material (33 mg, 0.053 mmol) in EtOH (10 mL) was added $Pd(OH)_2/C$ (20 wt. %, 8.6 mg, 0.012 mmol) and 6N HCl (0.1 mL). The mixture was treated with hydrogen (1 atm) for 18 h. Catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(4-((tetrahydro-2H-pyran-4-yl)oxy)phenethyl)piperidine-3,4,5-triol as a white solid (14 mg, 75%). $^1$H NMR (400 MHz, $CD_3OD$) δ 7.24-7.16 (m, 2H), 6.97-6.90 (m, 2H), 4.60-4.49 (m, 1H), 4.01-3.90 (m, 2H), 3.72-3.54 (m, 3H), 3.47-3.04 (m, 5H), 3.00-2.70 (m, 4H), 2.07-1.97 (m, 2H), 1.77-1.65 (m, 2H), 1.42 (d, J=6.3 Hz, 3H); ESI MS m/z 352.20 $[M+H]^+$.

Example 64

(2R,3R,4R,5S)-2-methyl-1-(4-phenoxyphenethyl)piperidine-3,4,5-triol

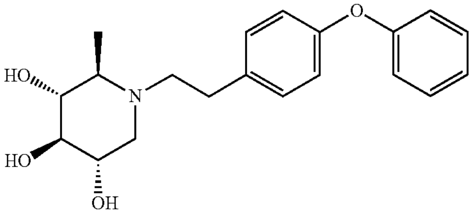 [SMILES: C[C@@H]1[C@@H](O)[C@H](O)[C@@H](O)CN1CCc1ccc(Oc2ccccc2)cc1]

To a cooled (0° C.) solution of 2-(4-phenoxyphenyl)acetic acid (3.0 g, 13.1 mmol) in 70 mL of anhydrous THF, LAH (1.4 g, 39.3 mmol) was added portionwise while stirring, under Ar. When effervescence ceased, the mixture was heated at reflux for 5 h until disappearance of starting material. The mixture was diluted with EtOAc, washed with 1.0 M HCl, water and brine. The organics were dried over anhydrous $Na_2SO_4$ and concentrated to yield 2-(4-phenoxyphenyl) ethanol (2.75 g, 98%) as an oil. $^1$H NMR (500 MHz, $CDCl_3$) δ 7.36-7.31 (m, 2H), 7.22-7.17 (m, 2H), 7.10 (tt, J=7.4, 1.1 Hz, 1H), 7.03-6.94 (m, 4H), 3.85 (t, J=6.6 Hz, 2H), 2.85 (t, J=6.6 Hz, 2H), 2.10-2.00 (m, 1H).

The above material (1.5 g, 7.2 mmol) and $CBr_4$ (2.6 g, 8.0 mmol) were dissolved in DCM (18 mL), the mixture was cooled to 0° C. and $Ph_3P$ (2.3 g, 8.7 mmol)) was added in small portions. The reaction mixture was warmed at RT and stirred for 2 h before the solvent was removed in vacuo. Flash chromatography (EtOAc/hexanes, 1:4) yielded 1-(2-bromoethyl)-4-phenoxybenzene (1.4 g, 70%). $^1$H NMR (500 MHz, $CDCl_3$) δ 7.36 (qd, J=8.3, 3.7 Hz, 2H), 7.20 (tt, J=8.3, 3.6 Hz, 2H), 7.12 (q, J=7.2, 6.4 Hz, 1H), 7.08-6.94 (m, 4H), 3.58 (m, 2H), 3.16 (m, 2H).

To a solution of ((2R,3R,4R,5S)-3,4,5-tris(benzyloxy)piperidin-2-yl)methanol (0.2 g, 0.46 mmol) in DMF (4 mL) and DIPEA (0.64 mL, 3.68 mmol) was added 4-(2-bromoethyl)-1,1'-biphenyl (0.6 g, 2.3 mmol). The reaction mixture was heated at 85° C. overnight before diluting it with EtOAc (30 mL). Organics were washed with brine, dried over anhydrous $Na_2SO_4$ and concentrated. The residue was purified on silica gel by flash chromatography (EtOAc/hexanes, 1:4), affording ((2R,3R,4R,5S)-3,4,5-tris(benzyloxy)-1-(4-phenoxyphenethyl)piperidin-2-yl)methanol (0.2 g, 68%) as a gummy solid. ESI MS m/z 630.316 $[M+H]^+$.

To a stirred solution of the above material (0.2 g, 0.34 mmol) at 0° C. in dry DCM (15 mL) was added $Ph_3P$ (0.18 g, 0.69 mmol) followed by $CBr_4$ (0.23 g, 0.69 mmol). After stirring at 0° C. for 2 h, the reaction mixture was diluted with DCM (30 mL) and washed with satd. aqueous $NaHCO_3$. Organics were dried over anhydrous $Na_2SO_4$ and concentrated. The crude residue was purified on silica gel by flash chromatography (EtOAc/hexanes, 1:4), affording (2S,3R,4R,5S)-3,4,5-tris(benzyloxy)-2-(bromomethyl)-1(4-phenoxyphenethyl) piperidine (0.13 g, 61.8%) as a yellow solid. ESI MS m/z 630.331 $[M+H]^+$.

A mixture of the above material (0.057 g, 0.082 mmol) and Raney Ni (0.050 g) in EtOH was stirred under 50 psi hydrogen pressure overnight. The mixture was then filtered through a celite cake, and the filtrate was collected and concentrated to dryness. The crude was dissolved in DCM (5 mL) and at −78° C., under Ar, was added $BCl_3$ (1.0 M in DCM, 0.65 mL, 0.65 mmol) dropwise, and the mixture was stirred for 2 h while the bath temperature warmed to 0° C. The mixture was stirred at 0° C. for next 2 h and then quenched by adding MeOH (2 mL) slowly. After stirring at RT for 30 min the mixture was concentrated under reduced pressure. The resulting residue was neutralized with $NH_4OH$ (0.5 mL) and concentrated again under reduced pressure. The crude residue was purified on silica gel by flash chromatography (MeOH/DCM, 1:9), affording (2R,3R,4R,5S)-2-methyl-1-(4-phenoxyphenethyl)piperidine-3,4,5-triol (0.0056 g, 24%) as a white solid. $^1H$ NMR (500 MHz, $CD_3OD$) δ 7.37-7.32 (m, 2H), 7.24-7.20 (m, 2H), 7.12-7.07 (m, 1H), 6.95 (ddd, J=16.5, 7.6, 1.6 Hz, 4H), 3.57-3.50 (m, 1H), 3.15 (t, J=9.0 Hz, 1H), 3.10 (dd, J=11.3, 4.9 Hz, 1H), 3.02-2.91 (m, 2H), 2.80 (ddt, J=21.7, 11.2, 5.8 Hz, 3H), 2.35 (dt, J=20.6, 9.8 Hz, 2H), 1.28 (d, J=6.2 Hz, 3H); ESI MS m/z 344.18 $[M+H]^+$.

Example 65

(2R,3R,4R,5S)-2-methyl-1-(4-((tetrahydrofuran-3-yl)methoxy)phenethyl)piperidine-3,4,5-triol

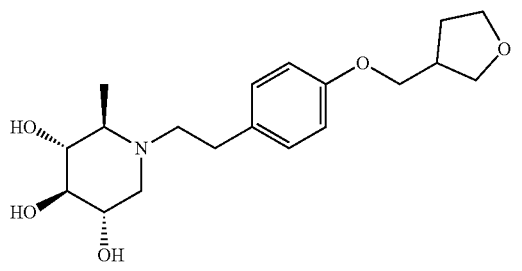 [SMILES: C[C@@H]1[C@@H](O)[C@H](O)[C@@H](O)CN1CCc1ccc(OCC2CCOC2)cc1]

To a stirred solution of ethyl 2-(4-hydroxyphenyl)acetate (1.0 g, 5.5 mmol), $PPh_3$ (2.18 g, 8.32 mmol), and (tetrahydrofuran-3-yl)methanol (0.85 g, 8.32 mmol) in anhydrous THE (10 mL) was added DIAD (1.68 g, 8.32 mmol) slowly. The resulting mixture was stirred at RT for 18 h. The solvent was removed under reduced pressure and the crude material was purified by silica gel flash chromatography affording ethyl 2-(4-((tetrahydrofuran-3-yl)methoxy)phenyl)acetate as an oil (0.67 g, 46%). ESI MS m/z 287.12 $[M+Na]^+$.

To a solution of the above material (470 mg, 1.78 mmol) in anhydrous THE (10 mL) at 0° C., was added LAH (204 mg, 5.34 mmol), and the mixture was stirred at 0° C. for 1 h. The mixture was quenched slowly with satd. aqueous $Na_2SO_4$ and filtered. The solid was washed with EtOAc. The combined organic layer was washed with water (2×20 mL), separated, dried over $Na_2SO_4$. After filtration, the solvent was evaporated under reduced pressure, to obtain the crude 2-(4-((tetrahydrofuran-3-yl)methoxy)phenyl)ethanol as an oil (390 mg, 99%).

A solution of the above material (195 mg, 0.88 mmol) and $CBr_4$ (349 mg, 1.05 mmol) in DCM (10 mL) was cooled to 0° C., and $PPh_3$ (275 mg, 1.05 mmol) was added portion-wise. The reaction mixture was stirred at RT for 1 h. The mixture was diluted with DCM and washed with satd. aqueous $NaHCO_3$. The organic phase was separated, dried over $Na_2SO_4$. After filtration, the solvent was evaporated under reduced pressure, and the residue was purified on silica gel by flash chromatography affording 3-((4-(2-bromoethyl)phenoxy)methyl)tetrahydrofuran as an oil (204 mg, 82%).

DIPEA (0.16 mL, 0.96 mmol) was added to a solution of (2R,3R,4R,5S)-3,4,5-tris(benzyloxy)-2-methylpiperidine (50 mg, 0.12 mmol) and 3-((4-(2-bromoethyl)phenoxy)methyl)tetrahydrofuran (136 mg, 0.48 mmol) in DMF (5 mL) in a sealed tube. The mixture was stirred at 80° C. for 18 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-2-methyl-1-(4-((tetrahydrofuran-3-yl)methoxy)phenethyl)piperidine as a white solid (39 mg, 52%). ESI MS m/z 622.35 $[M+H]^+$.

To a solution of the above material (39 mg, 0.063 mmol) in EtOH (10 mL) was added $Pd(OH)_2/C$ (20 wt. %, 8.6 mg, 0.012 mmol) and 6N HCl (0.1 mL). The mixture was treated with hydrogen (1 atm) for 18 h. Catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(4-((tetrahydrofuran-3-yl)methoxy)phenethyl)piperidine-3,4,5-triol as a white solid (20 mg, 90%). $^1H$ NMR (400 MHz, $CD_3OD$) δ 7.20-7.10 (m, 2H), 6.92-6.85 (m, 2H), 3.99-3.85 (m, 4H), 3.83-3.75 (m, 1H), 3.69 (dd, J=8.7, 5.5 Hz, 1H), 3.61-3.50 (m, 1H), 3.24-3.13 (m, 2H), 3.09-2.95 (m, 2H), 2.93-2.67 (m, 4H), 2.54-2.37 (m, 2H), 2.19-2.07 (m, 1H), 1.85-1.70 (m, 1H), 1.31 (d, J=6.2 Hz, 3H); ESI MS m/z 352.20 $[M+H]^+$.

Example 66

(2R,3R,4R,5S)-2-methyl-1-((R)-2-phenylpropyl)piperidine-3,4,5-triol

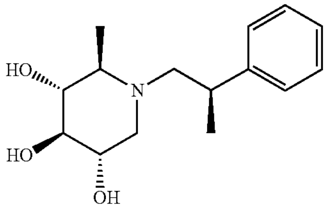 [SMILES: C[C@@H]1[C@@H](O)[C@H](O)[C@@H](O)CN1C[C@H](C)c1ccccc1]

To a stirred solution of (((2R,3R,4R,5S)-3,4,5-tris(benzyloxy)piperidin-2-yl)methanol (150 mg, 0.35 mmol) and 2-phenylpropanal (71 mg, 0.53 mmol) in anhydrous MeOH (10 mL) was added HOAc (0.10 mL, 1.75 mmol) and stirred for 30 min. $NaBH_3CN$ (33 mg, 0.53 mmol) was added, and the resulting mixture was stirred at RT for 18 h. The reaction was quenched with satd. aqueous $NaHCO_3$ solution at 0° C. The mixture was extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording ((2R,3R,4R,5S)-3,4,5-tris(benzyloxy)-1-(2-phenylpropyl)piperidin-2-yl)methanol as an oil (187 mg, 98%). ESI MS m/z 552.34 $[M+H]^+$.

A solution of the above material (185 mg, 0.34 mmol) and $CBr_4$ (189 mg, 0.57 mmol) in DCM (10 mL) was cooled to 0° C., and $PPh_3$ (150 mg, 0.57 mmol) was added portion-wise. The reaction mixture was stirred at RT for 1 h. The mixture was diluted with DCM and washed with satd. aqueous $NaHCO_3$ and the organic phase was separated, dried over $Na_2SO_4$. After filtration, the solvent was evaporated under reduced pressure, and the residue was purified on silica gel by flash chromatography affording (2S,3R,4R,5S)-3,4,5-tris(benzyloxy)-2-(bromomethyl)-1-(2-phenylpropyl) piperidine as an oil (155 mg, 74%). ESI MS m/z 614.25, 616.25 $[M+H]^+$.

A mixture of the above material (150 mg, 0.24 mmol), $Bu_3SnH$ (0.10 mL, 0.37 mmol) and ABCN (29 mg, 0.12 mmol) in anhydrous toluene (10 mL) was stirred at 100° C. for 16 h. The solvent was evaporated under reduced pressure, and the residue was purified on silica gel flash chromatography affording (2R,3R,4R,5S)-3,4,5-tris(benzyloxy)-2-methyl-1-((R)-2-phenylpropyl)piperidine as an oil (35 mg, 27%). ESI MS m/z 536.34 $[M+H]^+$.

To a stirred solution of the above material (35 mg, 0.065 mmol) in anhydrous DCM (3 mL) was added $BCl_3$ solution (1M in DCM, 0.50 mL, 0.50 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-((R)-2-phenylpropyl)piperidine-3,4,5-triol as a white solid (11 mg, 64%). This material was isolated as a single diastereomer with the stereochemistry of the phenylpropyl group assigned randomly. $^1H$ NMR (400 MHz, $CD_3OD$) δ 7.31-7.25 (m, 2H), 7.25-7.21 (m, 2H), 7.20-7.15 (m, 1H), 3.37-3.29 (m, 1H), 3.07-2.93 (m, 4H), 2.85-2.78 (m, 1H), 2.51-2.44 (m, 1H), 2.23-2.14 (m, 1H), 2.03-1.94 (m, 1H), 1.25-1.21 (m, 3H), 1.16-1.11 (m, 3H); ESI MS m/z 266.17 $[M+H]^+$.

Example 67

(2R,3R,4R,5S)-2-methyl-1-((S)-2-phenylpropyl)piperidine-3,4,5-triol

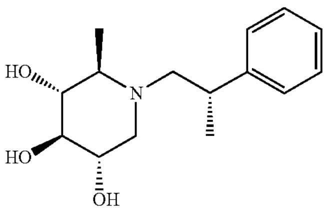 [SMILES: C[C@H](CN1C[C@H](O)[C@@H](O)[C@H](O)[C@H]1C)c1ccccc1]

A mixture of (2S,3R,4R,5S)-3,4,5-tris(benzyloxy)-2-(bromomethyl)-1-(2-phenylpropyl)piperidine (150 mg, 0.24 mmol), $Bu_3SnH$ (0.10 mL, 0.37 mmol) and ABCN (29 mg, 0.12 mmol) in anhydrous toluene (10 mL) was stirred at 100° C. for 16 h. After cooling the solvent was evaporated under reduced pressure, and the residue was purified on silica gel flash chromatography affording (2R,3R,4R,5S)-3,4,5-tris(benzyloxy)-2-methyl-1-((S)-2-phenylpropyl)piperidine as an oil (44 mg, 34%). ESI MS m/z 536.34 $[M+H]^+$.

To a stirred solution of the above material (44 mg, 0.082 mmol) in anhydrous DCM (3 mL) was added $BCl_3$ solution (1M in DCM, 0.50 mL, 0.50 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-((S)-2-phenylpropyl)piperidine-3,4,5-triol as a white solid (13 mg, 60%). This material was isolated as a single diastereomer with the stereochemistry of the phenylpropyl group assigned randomly. $^1H$ NMR (400 MHz, $CD_3OD$) δ 7.32-7.27 (m, 2H), 7.26-7.22 (m, 2H), 7.21-7.16 (m, 1H), 3.49-3.41 (m, 1H), 3.14-3.03 (m, 2H), 2.99-2.92 (m, 2H), 2.91-2.84 (m, 1H), 2.38-2.32 (m, 1H), 2.11-2.00 (m, 2H), 1.30-1.25 (m, 3H), 1.21-1.16 (m, 3H); ESI MS m/z 266.17 $[M+H]^+$.

Example 68

(2R,3R,4R,5S)-1-(2-([1,1'-biphenyl]-4-yl)ethyl)-2-methylpiperidine-3,4,5-triol

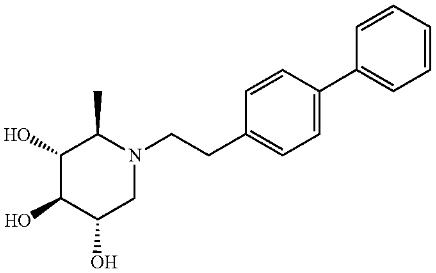 [SMILES: C[C@@H]1[C@@H](O)[C@H](O)[C@@H](O)CN1CCc1ccc(-c2ccccc2)cc1]

To a cooled (0° C.) solution of 2-([1,1'-biphenyl]-4-yl) acetic acid (3.0 g, 14.1 mmol) in 70 mL of anhydrous THF, 1.6 g (42.4 mmol) of LAH was added portion wise while stirring, under Ar. When effervescence ceased, the mixture was heated at reflux for 5 h until disappearance of starting material. The mixture was diluted with EtOAc, washed with 1.0 M HCl, water and brine. The organics were dried over anhydrous $Na_2SO_4$ and concentrated to yield 2-([1,1'-biphenyl]-4-yl)ethanol (2.76 g, 99%) as an oil. $^1$H NMR (500 MHz, $CDCl_3$) δ 7.62-7.53 (m, 4H), 7.48-7.41 (m, 2H), 7.39-7.29 (m, 3H), 3.91 (t, J=6.5 Hz, 2H), 2.92 (t, J=6.5 Hz, 2H), 1.54 (s, 1H).

The above material (2.5 g, 12.6 mmol) and $CBr_4$ (4.6 g, 13.8 mmol) were dissolved in DCM (30 mL), the mixture was cooled to 0° C. and $Ph_3P$ (4.0 g, 15.2 mmol)) was added in small portions. The reaction mixture was warmed at RT and stirred for 2 h before the solvent was removed in vacuo. Flash chromatography (EtOAc/hexanes, 1:4) yielded 4-(2-bromoethyl)-1,1'-biphenyl (3.2 g, 97.2%). $^1$H NMR (500 MHz, $CDCl_3$) δ 7.66-7.55 (m, 4H), 7.51-7.43 (m, 2H), 7.43-7.35 (m, 1H), 7.35-7.28 (m, 2H), 3.64 (m, 2H), 3.24 (t, J=7.6 Hz, 2H).

To a solution of ((2R,3R,4R,5S)-3,4,5-tris(benzyloxy) piperidin-2-yl)methanol (0.2 g, 0.46 mmol) (J. Carb. Chem. 2017, 36, 295) in DMF (4 mL) and DIPEA (0.64 mL, 3.68 mmol) was added 4-(2-bromoethyl)-1,1'-biphenyl (0.6 g, 2.3 mmol). The reaction mixture was heated at 85° C. overnight before diluting with EtOAc (30 mL). Organics were washed with brine, dried over anhydrous $Na_2SO_4$ and concentrated. The residue was purified on silica gel by flash chromatography (EtOAc/hexanes, 1:4), affording ((2R,3R,4R,5S)-1-(2-([1,1'-biphenyl]-4-yl)ethyl)-3,4,5-tris(benzyloxy)piperidin-2-yl)methanol (0.2 g, 70%) as a gummy solid. ESI MS m/z 614.324 $[M+H]^+$.

To a stirred solution of the above material (0.2 g, 0.32 mmol) at 0° C. in dry DCM (15 mL) was added $Ph_3P$ (0.17 g, 0.64 mmol) followed by $CBr_4$ (0.21 g, 0.64 mmol). After stirring at 0° C. for 2 h, the reaction mixture was diluted with DCM (30 mL) and washed with satd. aqueous $NaHCO_3$. Organics were dried over anhydrous $Na_2SO_4$ and concentrated. The crude residue was purified on silica gel by flash chromatography (EtOAc/hexanes, 1:4), affording (2S,3R,4R,5S)-1-(2-([1,1'-biphenyl]-4-yl)ethyl)-3,4,5-tris(benzyloxy)-2-(bromomethyl)piperidine (0.13 g, 61.8%) as a yellow solid. $^1$H NMR (400 MHz, $CDCl_3$) δ 7.62-7.57 (m, 2H), 7.57-7.53 (m, 2H), 7.47-7.42 (m, 2H), 7.38-7.29 (m, 15H), 7.28-7.24 (m, 2H), 5.07-5.02 (m, 2H), 4.86 (d, J=11.0 Hz, 1H), 4.80-4.69 (m, 3H), 3.98 (d, J=11.4 Hz, 1H), 3.76-3.54 (m, 4H), 3.26 (dd, J=11.3, 4.8 Hz, 1H), 3.08-2.93 (m, 1H), 2.95-2.70 (m, 2H), 2.51-2.41 (m, 2H), 1.57 (s, 1H); ESI MS m/z 678.230 $[M+H]^+$.

To a stirred solution of the above material (0.13 g, 0.19 mmol) in dry toluene (7 mL) was added $Bu_3SnH$ (0.26 mL, 0.99 mmol) followed by ABCN (0.024 g, 0.09 mmol). The reaction mixture was heated at 100° C. overnight before cooling and concentrating. The resulting crude mixture was purified on silica gel by flash chromatography (EtOAc/hexanes, 1:4), affording (2R,3R,4R,5S)-1-(2-([1,1'-biphenyl]-4-yl)ethyl)-3,4,5-tris(benzyloxy)-2-methyl piperidine (0.067 g, 56%) as a yellow solid. ESI MS m/z 598.317 $[M+H]^+$.

At −78° C., under Ar, to a solution of the above material (0.067 g, 0.112 mmol) in DCM (5 mL) was added $BCl_3$ (1.0 M in DCM, 1.1 mL, 1.1 mmol), and the mixture was stirred for 2 h while the bath temperature warmed to 0° C. The mixture was stirred at 0° C. for next 2 h and then quenched by adding MeOH (2 mL) slowly. After stirring at RT for 30 min the mixture was concentrated under reduced pressure. The resulting residue was neutralized with $NH_4OH$ (0.5 mL) and concentrated again under reduced pressure. The crude residue was purified on silica gel by flash chromatography (MeOH/DCM, 1:9), affording (2R,3R,4R,5S)-1-(2-([1,1'-biphenyl]-4-yl)ethyl)-2-methylpiperidine-3,4,5-triol (0.014 g, 39%) as a white solid. $^1$H NMR (400 MHz, $CD_3OD$) δ 7.65-7.59 (m, 4H), 7.44 (q, J=8.4, 7.9 Hz, 4H), 7.38-7.31 (m, 1H), 3.82-3.73 (m, 1H), 3.60 (dd, J=12.2, 4.5 Hz, 1H), 3.55-3.48 (m, 1H), 3.44-3.33 (m, 3H), 3.20-2.99 (m, 4H), 1.53 (d, J=6.4 Hz, 3H); ESI MS m/z 328.186 $[M+H]^+$.

Example 69

(2R,3R,4R,5S)-1-(2-(3,5-difluoro-[1,1'-biphenyl]-4-yl)ethyl)-2-methylpiperidine-3,4,5-triol

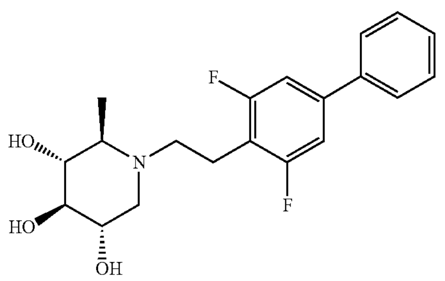 [SMILES: C[C@@H]1[C@@H](O)[C@H](O)[C@@H](O)CN1CCc1c(F)cc(-c2ccccc2)cc1F]

Under Ar, a mixture of 4-bromo-2,6-difluorobenzaldehyde (1.00 g, 4.52 mmol), $PhB(OH)_2$ (0.731 g, 6.00 mmol), $Pd(PPh_3)_4$ (0.266 g, 0.230 mmol) and aqueous $K_2CO_3$ solution (2.0 M, 3.0 mL, 6.0 mmol) in 1,4-dioxane (25 mL) was stirred at 95° C. for 4 h, and then cooled at RT. Satd. aqueous $NaHCO_3$ (50 mL) was added, and the mixture was extracted with EtOAc (2×50 mL). The combined extract was washed with brine (50 mL) and dried over anhydrous $Na_2SO_4$. After filtration the solvent was evaporated under reduced pressure, and the residue was purified on silica gel by flash chromatography (EtOAc/hexanes, 1:11 to 1:8), affording 3,5-difluoro-[1,1'-biphenyl]-4-carbaldehyde (0.99 g, 100%) as a white solid. $^1$H NMR (400 MHz, $CDCl_3$) δ 10.37 (s, 1H), 7.63-7.56 (m, 2H), 7.54-7.43 (m, 3H), 7.25-7.18 (m, 2H).

At 0° C., to a solution of (methoxymethyl)triphenylphosphonium chloride (1.54 g, 4.50 mmol) in anhydrous DMF (20 mL) was added KO$^t$Bu (0.505 g, 4.50 mmol) and 3,5-difluoro-[1,1'-biphenyl]-4-carbaldehyde (0.654 g, 3.00 mmol), and the mixture was stirred at RT for 16 h. The reaction mixture was diluted with satd. aqueous $NaHCO_3$ (50 mL), and then extracted with EtOAc (2×50 mL). The combined extract was washed with brine (2×50 mL) and dried over anhydrous $Na_2SO_4$. After filtration the solvent was evaporated under reduced pressure, and the residue was dissolved in mixed THE (30 mL) and aqueous HCl (2.5 N, 15 mL). After stirring at reflux for 4 h the mixture was cooled at RT and diluted with satd. aqueous $NaHCO_3$ (40 mL). After extraction with EtOAc (2×30 mL) the combined extract was washed with brine (50 mL) and dried over anhydrous $Na_2SO_4$. After filtration the solvent was evaporated under reduced pressure, and the residue was purified on silica gel by flash chromatography (EtOAc/hexanes, 1:13 to 1:7), affording 2-(3,5-difluoro-[1,1'-biphenyl]-4-yl)acetaldehyde as a pale-yellow oil (0.16 g, 23%). $^1$H NMR (400

MHz, $CDCl_3$) δ 9.81-9.78 (m, 1H), 7.58-7.53 (m, 2H), 7.49-7.43 (m, 2H), 7.43-7.37 (m, 1H), 7.17 (d, J=8.3 Hz, 2H), 3.83 (d, J=1.3 Hz, 2H).

Under $N_2$, a mixture of (2R,3R,4R,5S)-3,4,5-tris(benzyloxy)-2-methylpiperidine (0.15 g, 0.36 mmol), 2-(3,5-difluoro-[1,1'-biphenyl]-4-yl)acetaldehyde (0.090 g, 0.39 mmol) and $NaBH(OAc)_3$ (0.10 g, 0.47 mmol) in DCM (10 mL) was stirred at RT for 16 h. The reaction mixture was diluted with satd. aqueous $NaHCO_3$ (25 mL), and extracted with DCM (3×20 mL). The combined extract was dried over anhydrous $Na_2SO_4$. After filtration the solvent was evaporated under reduced pressure, and the residue was purified on silica gel by flash chromatography (EtOAc/hexanes, 1:12 to 1:7), affording (2R,3R,4R,5S)-3,4,5-tris(benzyloxy)-1-(2-(3,5-difluoro-[1,1'-biphenyl]-4-yl)ethyl)-2-methylpiperidine as a white solid (0.23 g, 100%).

At −78° C. and under $N_2$, to a solution of the above material (0.23 g, 0.36 mmol) in anhydrous DCM (8 mL) was added $BCl_3$ (1.0 M in DCM, 2.0 mL, 2.0 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:6), affording (2R,3R,4R,5S)-1-(2-(3,5-difluoro-[1,1'-biphenyl]-4-yl)ethyl)-2-methylpiperidine-3,4,5-triol as a white solid (0.69 g, 52%). $^1H$ NMR (400 MHz, DMSO-$d_6$) δ 7.74-7.71 (m, 2H), 7.49-7.38 (m, 5H), 4.72-4.36 (m, 3H), 3.29-3.16 (m, 1H), 2.94-2.85 (m, 2H), 2.79-2.66 (m, 5H), 2.22 (t, J=10.6 Hz, 1H), 2.19-2.11 (m, 1H), 1.08 (d, J=6.1 Hz, 3H); ESI MS m/z 364.149 $[M+H]^+$.

Example 70

(2R,3R,4R,5S)-1-(2-(benzo[d][1,3]dioxol-5-yl)ethyl)-2-methylpiperidine-3,4,5-triol

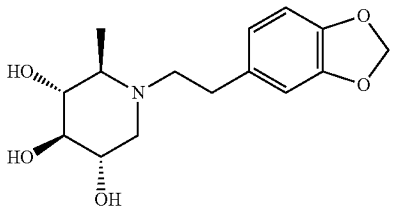 [SMILES: C[C@@H]1[C@@H](O)[C@H](O)[C@@H](O)CN1CCc1ccc2c(c1)OCO2]

DIPEA (0.38 mL, 2.2 mmol) was added to a solution of (2R,3R,4R,5S)-3,4,5-tris(benzyloxy)-2-methylpiperidine (184 mg, 0.44 mmol) and 5-(2-bromoethyl)benzo[d][1,3]dioxole (300 mg, 1.3 mmol) in DMF (5 mL) in a sealed tube. The mixture was stirred at 80° C. for 18 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-1-(2-(benzo[d][1,3]dioxol-5-yl)ethyl)-3,4,5-tris(benzyloxy)-2-methylpiperidine as a white solid (179 mg, 72%). ESI MS m/z 566.28 $[M+H]^+$.

To a solution of the above material (175 mg, 0.31 mmol) in EtOH (20 mL) was added $Pd(OH)_2/C$ (20 wt. %, 43 mg, 0.06 mmol) and 6N HCl (0.4 mL). The mixture was treated with hydrogen (1 atm) for 18 h. Catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2R,3R,4R,5S)-1-(2-(benzo[d][1,3]dioxol-5-yl)ethyl)-2-methylpiperidine-3,4,5-triol as a white solid (48 mg, 52%). $^1H$ NMR (400 MHz, $CD_3OD$) δ 6.75-6.71 (m, 2H), 6.67 (dd, J=7.8, 1.7 Hz, 1H), 5.91 (s, 2H), 3.55-3.47 (m, 1H), 3.14 (t, J=9.0 Hz, 1H), 3.06 (dd, J=11.2, 4.9 Hz, 1H), 2.97 (t, J=9.1 Hz, 1H), 2.94-2.86 (m, 1H), 2.81-2.64 (m, 3H), 2.37-2.24 (m, 2H), 1.26 (d, J=6.2 Hz, 3H); ESI MS m/z 296.14 $[M+H]^+$.

Example 71

(2R,3R,4R,5S)-1-(2-(6-fluorobenzo[d][1,3]dioxol-5-yl)ethyl)-2-methylpiperidine-3,4,5-triol

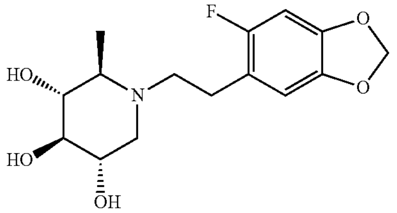 [SMILES: C[C@@H]1[C@@H](O)[C@H](O)[C@@H](O)CN1CCc1cc2c(cc1F)OCO2]

A mixture of 6-nitropiperonal (1.95 g, 10.0 mmol), KF (1.45 g, 25.0 mmol) and 1,4,7,10,13,16-hexaoxacyclooctadecane (18-crown-6) (2.64 g, 10.0 mmol) in DMSO (40 mL) was stirred at 130° C. for 1 h, and then cooled at RT. Satd. aqueous $NaHCO_3$ (200 mL) was added, and the mixture was extracted with EtOAc (2×50 mL). The combined extract was washed with brine (2×100 mL) and dried over anhydrous $Na_2SO_4$. After filtration the solvent was evaporated under reduced pressure, and the residue was purified on silica gel by flash chromatography (EtOAc/hexanes, 1:9 to 1:3), affording 6-fluorobenzo[d][1,3]dioxole-5-carbaldehyde (0.13 g, 8%) as a pale-yellow solid. $^1H$ NMR (400 MHz, $CDCl_3$) δ 10.18 (s, 1H), 7.23 (d, J=5.6 Hz, 1H), 6.63 (d, J=9.7 Hz, 1H), 6.07 (s, 2H).

At 0° C., to a solution of (methoxymethyl)triphenylphosphonium chloride (1.37 g, 4.00 mmol) in anhydrous DMF (15 mL) was added $KO^tBu$ (0.449 g, 4.00 mmol) and 6-fluorobenzo[d][1,3]dioxole-5-carbaldehyde (0.416 g, 2.47 mmol), and the mixture was stirred at RT for 16 h. The reaction mixture was diluted with satd. aqueous $NaHCO_3$ (50 mL), and then extracted with EtOAc (3×30 mL). The combined extract was washed with brine (2×50 mL) and dried over anhydrous $Na_2SO_4$. After filtration the solvent was evaporated under reduced pressure, and the residue was dissolved in mixed THE (12 mL) and aqueous HCl (2.5 N, 4 mL). After stirring at reflux for 4 h the mixture was cooled at RT and diluted with satd. aqueous $NaHCO_3$ (40 mL). After extraction with EtOAc (2×30 mL) the combined extract was washed with brine (50 mL) and dried over anhydrous $Na_2SO_4$. After filtration the solvent was evaporated under reduced pressure, and the residue was purified on silica gel by flash chromatography (EtOAc/hexanes, 1:13 to 1:8), affording 2-(6-fluorobenzo[d][1,3]dioxol-5-yl)acetaldehyde as a pale-yellow oil (0.30 g, 67%). $^1H$ NMR (400 MHz, $CDCl_3$) δ 9.71 (td, J=1.9, 1.3 Hz, 1H), 6.64 (d, J=8.9 Hz, 1H), 6.60 (d, J=6.1 Hz, 1H), 5.97 (s, 2H), 3.63-3.61 (m, 2H).

Under $N_2$, a mixture of (2R,3R,4R,5S)-3,4,5-tris(benzyloxy)-2-methylpiperidine (0.210 g, 0.503 mmol), 2-(6-fluorobenzo[d][1,3]dioxol-5-yl)acetaldehyde (0.20 g, 1.1 mmol) and $NaBH(OAc)_3$ (0.25 g, 1.2 mmol) in DCM (10 mL) was stirred at RT for 16 h. The reaction mixture was diluted with satd. aqueous $NaHCO_3$ (25 mL), and extracted with DCM (3×20 mL). The combined extract was dried over anhydrous $Na_2SO_4$. After filtration the solvent was evaporated under reduced pressure, and the residue was purified on silica gel by flash chromatography (EtOAc/hexanes, 1:7 to 1:4), affording (2R,3R,4R,5S)-3,4,5-tris(benzyloxy)-1-(2-(6-fluorobenzo[d][1,3]dioxol-5-yl)ethyl)-2-methylpiperidine as a white solid (0.28 g, 96%); ESI MS m/z 584.245 $[M+H]^+$.

A mixture of the above material (0.28 g, 0.48 mmol) and $Pd(OH)_2/C$ (20% Pd in weight, 0.050 g, 0.094 mmol) and four drops of concentrated HCl in MeOH (25 mL) was stirred under hydrogen at one atmosphere of pressure overnight. The mixture was filtered through a celite cake, and the filtrate was collected and concentrated to dryness. The residue was neutralized with 1 M $NH_3$ in MeOH and purified on silica gel by flash chromatography (1 M $NH_3$ MeOH/DCM, 1:6), affording (2R,3R,4R,5S)-1-(2-(6-fluorobenzo[d][1,3]dioxol-5-yl)ethyl)-2-methylpiperidine-3,4,5-triol (0.105 g, 83%) as a white solid. $^1H$ NMR (400 MHz, DMSO-$d_6$) δ 6.87-6.84 (m, 2H), 4.69-4.67 (m, 3H), 3.26-3.17 (m, 1H), 2.92-2.82 (m, 2H), 2.71-2.65 (m, 2H), 2.62-2.53 (m, 3H), 2.14 (t, J=10.7 Hz, 1H), 2.10-2.06 (m, 1H), 1.07 (d, J=6.1 Hz, 3H); ESI MS m/z 314.127 $[M+H]^+$.

Example 72

(2R,3R,4R,5S)-1-(2-(2,2-difluorobenzo[d][1,3]dioxol-5-yl)ethyl)-2-methylpiperidine-3,4,5-triol

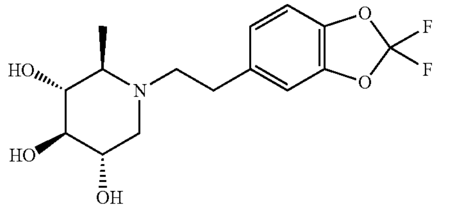 [SMILES: C[C@@H]1[C@@H](O)[C@H](O)[C@@H](O)CN1CCc1ccc2c(c1)OC(F)(F)O2]

To a stirred solution of methyltriphenylphosphonium bromide (4.29 g, 12.0 mmol) in anhydrous THE (30 mL) was added n-butyllithium (4.8 mL, 2.5M, 12.0 mmol) at 0° C. under $N_2$, and stirred for 30 min. Subsequently, 2,2-difluorobenzo[d][1,3]dioxole-5-carbaldehyde (1.88 g, 10.0 mmol) was dissolved in 5 mL of THF and added dropwise to the mixture under $N_2$, reacted at RT for 3 h. The reaction was quenched with satd. aqueous $NaHCO_3$ at 0° C. The mixture was extracted with EtOAc (3×40 mL). The combined organic layer was washed with water (2×20 mL), separated, dried over $Na_2SO_4$. After filtration, the solvent was evaporated under reduced pressure, and the residue was purified on silica gel by flash chromatography affording 2,2-difluoro-5-vinylbenzo[d][1,3]dioxole as an oil (1.4 g, 76%). $^1H$ NMR (400 MHz, $CDCl_3$) δ 7.18 (d, J=1.6 Hz, 1H), 7.09 (dd, J=8.3, 1.6 Hz, 1H), 7.02 (d, J=8.2 Hz, 1H), 6.69 (dd, J=17.5, 10.8 Hz, 1H), 5.68 (d, J=17.5 Hz, 1H), 5.28 (d, J=10.8 Hz, 1H).

A solution of 9-borabicyclo[3.3.1]nonane in tetrahydrofuran (0.5 M, 12.6 mL, 6.3 mmol) was added slowly to a solution of 2,2-difluoro-5-vinylbenzo[d][1,3]dioxole (580 mg, 3.2 mmol) in tetrahydrofuran (20 mL) at 0° C. The solution was warmed to RT, stirred for 16 h and was again cooled to 0° C. MeOH (3 mL) was added carefully, and stirring was continued for 15 min. Then, aqueous NaOH solution (2 M, 15 mL, 30 mmol) and aqueous $H_2O_2$ solution (30% w v, 6.0 mL, 50 mmol) were added, the mixture was allowed to warm to RT and stirred for 4 h. The organic layer was separated, and the aqueous layer was extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording 2-(2,2-difluorobenzo[d][1,3]dioxol-5-yl)ethanol as a white solid (410 mg, 64%). $^1H$ NMR (400 MHz, $CDCl_3$) δ 7.06-6.82 (m, 3H), 3.88 (t, J=6.4 Hz, 2H), 2.88 (t, J=6.4 Hz, 2H), 1.53 (s, 1H).

A solution of the above material (205 mg, 1.01 mmol) and $CBr_4$ (404 mg, 1.22 mmol) in DCM (10 mL) was cooled to 0° C., and $PPh_3$ (320 mg, 1.22 mmol) was added portion-wise. The reaction mixture was stirred at RT for 1 h. The mixture was diluted with DCM and washed with satd. aqueous $NaHCO_3$. The organic phase was separated, dried over $Na_2SO_4$. After filtration, the solvent was evaporated under reduced pressure, and the residue was purified on silica gel by flash chromatography affording 5-(2-bromoethyl)-2,2-difluorobenzo[d][1,3]dioxole as an oil (260 mg, 98%). $^1H$ NMR (400 MHz, $CDCl_3$) δ 7.11-6.89 (m, 3H), 3.56 (t, J=7.3 Hz, 2H), 3.17 (t, J=7.3 Hz, 2H).

DIPEA (0.20 mL, 1.15 mmol) was added to a solution of (2R,3R,4R,5S)-3,4,5-tris(benzyloxy)-2-methylpiperidine (85 mg, 0.20 mmol) and 5-(2-bromoethyl)-2,2-difluorobenzo[d][1,3]dioxole (158 mg, 0.60 mmol) in DMF (5 mL) in a sealed tube. The mixture was stirred at 80° C. for 18 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-1-(2-(2,2-difluorobenzo[d][1,3]dioxol-5-yl)ethyl)-2-methylpiperidine as a white solid (43 mg, 36%). ESI MS m/z 602.27 $[M+H]^+$.

To a solution of the above material (40 mg, 0.067 mmol) in EtOH (10 mL) was added $Pd(OH)_2/C$ (20 wt. %, 8.6 mg, 0.012 mmol) and 6N HCl (0.1 mL). The mixture was treated with hydrogen (1 atm) for 18 h. Catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2R,3R,4R,5S)-1-(2-(2,2-difluorobenzo[d][1,3]dioxol-5-yl)ethyl)-2-methylpiperidine-3,4,5-triol as a white solid (15 mg, 68%). $^1H$ NMR (400 MHz, $CD_3OD$) δ 7.16-7.10 (m, 2H), 7.06-7.01 (m, 1H), 3.60-3.48 (m, 1H), 3.22-3.10 (m, 2H), 3.08-2.96 (m, 2H), 2.91-2.78 (m, 3H), 2.50-2.33 (m, 2H), 1.28 (d, J=6.3 Hz, 3H); ESI MS m/z 332.12 $[M+H]^+$.

Example 73

(2R,3R,4R,5S)-1-(2-(2,3-dihydrobenzo[b][1,4]dioxin-6-yl)ethyl)-2-methylpiperidine-3,4,5-triol

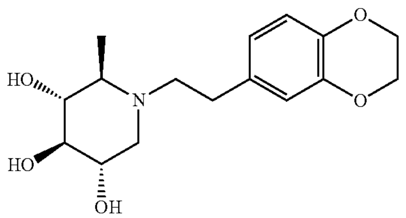 [SMILES: C[C@@H]1[C@@H](O)[C@H](O)[C@@H](O)CN1CCc1ccc2c(c1)OCCO2]

To a solution of methyl triphenylphosphonium bromide (4.2 g, 12 mmol) in anhydrous THE (35 mL) at −78° C. was added n-BuLi (2.5 M in hexanes, 4.8 mL, 12 mmol) via a syringe and stirred at this temperature for 25 min. A solution of dihydrobenzo[b][1,4]dioxine-6-carbaldehyde (1.64 g, 10 mmol) in THE (5 mL) was then added and the reaction warmed to RT and stirred for 2 h. The reaction mixture was diluted with EtOAc (40 mL) and organics were washed with brine, dried over anhydrous $Na_2SO_4$ and concentrated. The residue was purified on silica gel by flash chromatography (EtOAc/hexanes, 1:9), affording 6-vinyl-2,3-dihydrobenzo[b][1,4]dioxine (0.8 g, 49%) as an oil. $^1H$ NMR (500 MHz, $CDCl_3$) δ 6.95 (d, J=2.1 Hz, 1H), 6.91 (dd, J=8.3, 2.1 Hz, 1H), 6.82 (d, J=8.3 Hz, 1H), 6.60 (dd, J=17.5, 10.8 Hz, 1H), 5.60 (dd, J=17.5, 0.9 Hz, 1H), 5.13 (dd, J=10.9, 0.9 Hz, 1H), 4.25 (s, 4H).

To a solution of the above material (0.57 g, 3.5 mmol) in THE (15 mL), 9-BBN (0.5 M in THF, 14 mL, 7.0 mmol) was added and stirred for 18 h at RT. Thereafter, the reaction mixture was cooled to 0° C., and MeOH (3 mL), a 2 N aqueous solution of sodium hydroxide (12 mL) and hydrogen peroxide (30% solution, 6 mL) were added. The reaction mixture was stirred for 1 h at RT, and then extracted with EtOAc (100 mL). Organics were washed with brine, dried over anhydrous $Na_2SO_4$ and concentrated. The residue was purified on silica gel by flash chromatography (EtOAc/hexanes, 3:7), affording 2-(2,3-dihydrobenzo[b][1,4]dioxin-6-yl)ethanol (0.54 g, 85.4%) as an oil. $^1H$ NMR (400 MHz, $CDCl_3$) δ 6.79 (d, J=8.2 Hz, 1H), 6.72 (d, J=2.0 Hz, 1H), 6.68 (dd, J=8.2, 2.0 Hz, 1H), 4.22 (s, 4H), 3.79 (t, J=6.6 Hz, 2H), 2.74 (t, J=6.5 Hz, 2H), 1.72 (s, 1H); ESI MS m/z 203.07 $[M+Na]^+$.

The above material (0.54 g, 3.0 mmol) and $CBr_4$ (1.3 g, 3.9 mmol) were dissolved in DCM (15 mL), the mixture was cooled to 0° C. and $Ph_3P$ (1.0 g, 3.9 mmol) was added in small portions. The reaction mixture was warmed at RT and stirred for 2 h before the solvent was removed in vacuo. Flash chromatography (EtOAc/hexanes, 1:4) yielded 6-(2-bromoethyl)-2,3-dihydrobenzo[b][1,4]dioxine (0.7 g, 95.4%). $^1H$ NMR (400 MHz, $CDCl_3$) δ 6.81 (d, J=8.2 Hz, 1H), 6.72 (d, J=2.1 Hz, 1H), 6.67 (dd, J=8.2, 2.1 Hz, 1H), 4.24 (s, 4H), 3.51 (t, J=7.7 Hz, 2H), 3.05 (t, J=7.7 Hz, 2H).

To a solution of (2R,3R,4R,5S)-3,4,5-tris(benzyloxy)-2-methylpiperidine (xx) (0.1 g, 0.24 mmol) in DMF (5 mL) and DIPEA (0.32 mL, 1.84 mmol) was added 6-(2-bromoethyl)-2,3-dihydrobenzo[b][1,4]dioxine (0.29 g, 1.2 mmol). The reaction mixture was heated at 85° C. overnight before diluting with EtOAc (30 mL). Organics were washed with brine, dried over anhydrous $Na_2SO_4$ and concentrated. The residue was purified on silica gel by flash chromatography (EtOAc/hexanes, 1:4), affording (2R,3R,4R,5S)-3,4,5-tris(benzyloxy)-1-(2-(2,3-dihydrobenzo[b][1,4]dioxin-6-yl)ethyl)-2-methylpiperidine (0.11 g, 79%) as a gummy solid. $^1H$ NMR (500 MHz, $CDCl_3$) δ 7.41-7.28 (m, 15H), 6.81 (d, J=8.2 Hz, 1H), 6.70 (d, J=2.1 Hz, 1H), 6.64 (dd, J=8.2, 2.1 Hz, 1H), 4.99 (t, J=11.1 Hz, 2H), 4.87 (d, J=11.0 Hz, 1H), 4.77-4.68 (m, 2H), 4.64 (d, J=10.9 Hz, 1H), 4.27-4.22 (s, 4H), 3.69-3.62 (m, 1H), 3.53 (t, J=9.0 Hz, 1H), 3.17-3.10 (m, 2H), 2.92-2.77 (m, 2H), 2.61 (m, 2H), 2.44 (dq, J=9.2, 6.1 Hz, 1H), 2.37 (t, J=10.8 Hz, 1H), 1.26 (d, J=6.1 Hz, 3H); ESI MS m/z 580.30 $[M+H]^+$.

A mixture of the above material (0.11 g, 3.7 mmol) and $Pd(OH)_2/C$ (20% wt, 0.02 g) in EtOH/2N HCl (25/1 mL) was stirred under 50 psi hydrogen pressure overnight. The mixture was then filtered through a celite cake, and the filtrate was collected and concentrated to dryness. To the residue was added $NH_4OH$ solution (3 mL) and the mixture was concentrated again. The crude residue was purified on silica gel by flash chromatography (MeOH/DCM, 1:9), affording (2R,3R,4R,5S)-1-(2-(2,3-dihydrobenzo[b][1,4]dioxin-6-yl)ethyl)-2-methylpiperidine-3,4,5-triol (0.038 g, 65%) as a white solid. $^1H$ NMR (400 MHz, $CD_3OD$) δ 6.76 (d, J=8.2 Hz, 1H), 6.72 (d, J=2.0 Hz, 1H), 6.68 (dd, J=8.2, 2.1 Hz, 1H), 4.22 (s, 4H), 3.57 (td, J=9.9, 9.3, 4.5 Hz, 1H), 3.25-3.16 (m, 2H), 3.11-3.01 (m, 2H), 2.97-2.85 (m, 1H), 2.81-2.66 (m, 2H), 2.59-2.42 (m, 2H), 1.32 (d, J=6.3 Hz, 3H); ESI MS m/z 310.16 $[M+H]^+$.

Example 74

(2R,3R,4R,5S)-2-methyl-1-(2-(thiophen-2-yl)ethyl)piperidine-3,4,5-triol

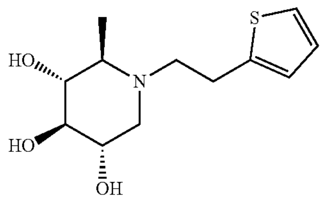 [SMILES: C[C@@H]1[C@@H](O)[C@H](O)[C@@H](O)CN1CCc1cccs1]

To a stirred solution of 2-(thiophen-2-yl)ethanol (0.64 g, 5 mmol) at 0° C. in dry DCM (8 mL) was added DMP (2.5 g, 6.0 mmol). After stirring at RT for 2 h, the reaction mixture was quenched with a 1:1 mixture of 1M $Na_2S_2O_3$: satd. $NaHCO_3$ solution (20 mL) and further stirred for 30 min before being diluted with DCM (40 mL). Organics were separated, dried over anhydrous $Na_2SO_4$ and concentrated. The crude residue was purified on silica gel by flash chromatography (EtOAc/hexanes, 1:9), affording 2-(thiophen-2-yl)acetaldehyde (0.37 g, 60%) as an oil. $^1H$ NMR (400 MHz, $CDCl_3$) δ 9.73 (s, 1H), 7.27 (d, J=5.2 Hz, 1H), 7.03 (dd, J=5.2, 4.6 Hz, 1H), 6.94 (d, J=4.6 Hz, 1H), 3.88 (d, J=2.2 Hz, 2H).

To a solution of (2R,3R,4R,5S)-3,4,5-tris(benzyloxy)-2-methylpiperidine (0.16 g, 0.4 mmol) and 2-(thiophen-2-yl)acetaldehyde (0.075 g, 0.6 mmol) in anhydrous MeOH (8 mL) was added AcOH (few drops) and the mixture was stirred at RT for 10 min. Sodium cyanoborohydride (0.04 g, 0.63 mmol) was added and the reaction was stirred at RT overnight. The mixture was concentrated and diluted with EtOAc (30 mL) and the organics were washed with satd. $NaHCO_3$ solution. Organics were dried over anhydrous $Na_2SO_4$ and concentrated, then the crude residue was purified on silica gel by flash chromatography (EtOAc/hexanes, 1:9), affording (2R,3R,4R,5S)-3,4,5-tris(benzyloxy)-2-methyl-1-(2-(thiophen-2-yl)ethyl)piperidine (0.039 g, 18.4%) as a yellow solid. $^1$H NMR (500 MHz, $CDCl_3$) δ 7.44-7.31 (m, 15H), 7.18 (dd, J=5.1, 1.2 Hz, 1H), 6.98 (dd, J=5.1, 3.4 Hz, 1H), 6.85 (dd, J=3.5, 1.1 Hz, 1H), 5.03 (t, J=11.0 Hz, 2H), 4.91 (d, J=11.0 Hz, 1H), 4.80-4.72 (m, 2H), 4.68 (d, J=10.8 Hz, 1H), 3.71 (td, J=9.8, 4.7 Hz, 1H), 3.57 (t, J=9.0 Hz, 1H), 3.22-3.14 (m, 2H), 3.08-3.01 (m, 1H), 3.00-2.95 (m, 2H), 2.94-2.86 (m, 1H), 2.48 (dq, J=9.4, 6.2 Hz, 1H), 2.38 (t, J=10.8 Hz, 1H), 1.29 (d, J=6.2 Hz, 3H); ESI MS m/z 528.257 $[M+H]^+$.

At −78° C., under Ar, to a solution of the above material (0.11 g, 0.22 mmol) in DCM (8 mL) was added $BCl_3$ (1.0 M in DCM, 1.8 mL, 1.8 mmol), and the mixture was stirred for 2 h while the bath temperature reached 0° C. The mixture was further stirred at 0° C. for 2 h and then quenched by adding MeOH (2 mL) slowly. After stirring at RT for 30 min the mixture was concentrated under reduced pressure. The resulting residue was neutralized with $NH_4OH$ (0.5 mL) and concentrated again under reduced pressure. The crude residue was purified on silica gel by flash chromatography (MeOH/DCM, 1:9), affording (2R,3R,4R,5S)-2-methyl-1-(2-(thiophen-2-yl)ethyl)piperidine-3,4,5-triol (0.026 g, 46%) as a white solid. $^1$H NMR (400 MHz, $CD_3OD$) δ 7.21 (dd, J=5.1, 1.2 Hz, 1H), 6.93 (dd, J=5.1, 3.4 Hz, 1H), 6.87 (d, J=3.4 Hz, 1H), 3.53 (ddd, J=10.5, 9.1, 4.9 Hz, 1H), 3.16 (t, J=9.0 Hz, 1H), 3.10 (dd, J=11.4, 4.9 Hz, 1H), 3.13-2.96 (m, 4H), 2.86 (t, J=8.9 Hz, 1H), 2.40-2.29 (m, 2H), 1.27 (d, J=6.2 Hz, 3H); ESI MS m/z 258.117 $[M+H]^+$.

Example 75

(2R,3R,4R,5S)-2-methyl-1-(2-(thiophen-3-yl)ethyl)piperidine-3,4,5-triol

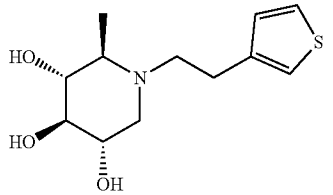 [SMILES: C[C@@H]1[C@@H](O)[C@H](O)[C@@H](O)CN1CCc1ccsc1]

2-(Thiophen-3-yl)ethanol (0.6 g, 4.6 mmol) and $CBr_4$ (1.8 g, 5.6 mmol) were dissolved in THE (18 mL), the mixture was cooled to 0° C. and $Ph_3P$ (1.4 g, 5.6 mmol)) was added in small portions. The reaction mixture was stirred at 70° C. for 3 h and then evaporated under reduced pressure. Flash chromatography (EtOAc/hexanes, 1:4) of the crude yielded 3-(2-bromoethyl)thiophene (0.63 g, 70%). $^1$H NMR (400 MHz, $CDCl_3$) δ 7.32 (dd, J=5.0, 2.9 Hz, 1H), 7.10 (m, 1H), 7.01 (dd, J=5.0, 1.3 Hz, 1H), 3.60 (m, 2H), 3.24 (m, 2H).

To a solution of (2R,3R,4R,5S)-3,4,5-tris(benzyloxy)-2-methylpiperidine (0.12 g, 0.3 mmol, in DMF (4 mL) and DIPEA (0.26 mL, 1.5 mmol) was added 3-(2-bromoethyl)thiophene (0.6 g, 2.3 mmol). The reaction mixture was heated at 85° C. overnight before diluting with EtOAc (30 mL). Organics were washed with brine, dried over anhydrous $Na_2SO_4$ and concentrated. The residue was purified on silica gel by flash chromatography (EtOAc/hexanes, 1:4), affording (2R,3R,4R,5S)-3,4,5-tris(benzyloxy)-2-methyl-1-(2-(thiophen-3-yl)ethyl)piperidine (0.15 g, 94%) as a gummy solid. $^1$H NMR (400 MHz, $CDCl_3$) δ 7.39-7.24 (m, 16H), 6.95 (dd, J=3.0, 1.3 Hz, 1H), 6.92 (dd, J=4.9, 1.3 Hz, 1H), 4.97 (dd, J=10.9, 7.9 Hz, 2H), 4.84 (d, J=11.0 Hz, 1H), 4.75-4.65 (m, 2H), 4.62 (d, J=10.8 Hz, 1H), 3.68-3.57 (m, 1H), 3.51 (t, J=9.0 Hz, 1H), 3.16-3.06 (m, 2H), 3.01-2.68 (m, 4H), 2.46-2.38 (m, 1H), 2.33 (t, J=10.8 Hz, 1H), 1.27-1.14 (m, 3H); ESI MS m/z 528.254 $[M+H]^+$.

At −78° C., under Ar, to a solution of the above material (0.15 g, 0.28 mmol) in DCM (8 mL) was added $BCl_3$ (1.0 M in DCM, 1.4 mL, 1.4 mmol), and the mixture was stirred for 2 h while the bath temperature reached 0° C. The mixture was further stirred at 0° C. for 2 h and then quenched by adding MeOH (2 mL) slowly. After stirring at RT for 30 min the mixture was concentrated under reduced pressure. The resulting residue was neutralized with $NH_4OH$ (0.5 mL) and concentrated again under reduced pressure. The crude residue was purified on silica gel by flash chromatography (MeOH/DCM, 1:9), affording (2R,3R,4R,5S)-2-methyl-1-(2-(thiophen-3-yl)ethyl)piperidine-3,4,5-triol (0.022 g, 30%) as a white solid. $^1$H NMR (400 MHz, $CD_3OD$) δ 7.37 (dd, J=5.0, 2.9 Hz, 1H), 7.18-7.13 (m, 1H), 7.02 (dd, J=5.0, 1.3 Hz, 1H), 3.58 (td, J=9.8, 4.6 Hz, 1H), 3.26-3.16 (m, 2H), 3.17-3.03 (m, 2H), 3.03-2.85 (m, 3H), 2.58-2.46 (m, 2H), 1.33 (d, J=6.2 Hz, 3H); ESI MS m/z 258.112 $[M+H]^+$.

Example 76

(2R,3R,4R,5S)-2-methyl-1-(2-(pyridin-2-yl)ethyl)piperidine-3,4,5-triol

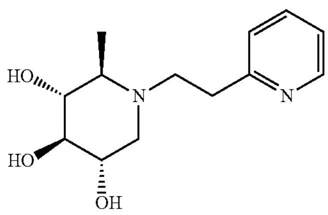

To a solution of (2R,3R,4R,5S)-3,4,5-tris(benzyloxy)-2-methylpiperidine (0.16 g, 0.38 mmol, in DMF (5 mL) and DIPEA (0.33 mL, 1.9 mmol) was added 2-(2-bromoethyl)pyridine hydrobromide (0.32 g, 1.2 mmol). The reaction mixture was heated at 85° C. overnight before diluting with EtOAc (30 mL). Organics were washed with brine, dried over anhydrous $Na_2SO_4$ and concentrated. The residue was purified on silica gel by flash chromatography (EtOAc/hexanes, 1:4), affording 2-(2-((2R,3R,4R,5S)-3,4,5-tris(benzyloxy)-2-methylpiperidin-1-yl)ethyl)pyridine (0.14 g, 72%) as a gummy solid. $^1$H NMR (400 MHz, $CDCl_3$) δ 8.56-8.52 (m, 1H), 7.58 (td, J=7.7, 1.9 Hz, 1H), 7.39-7.27 (m, 15H), 7.13 (d, J=1.4 Hz, 1H), 7.12-7.10 (m, 1H), 4.97 (m, 2H), 4.84 (d, J=11.0 Hz, 1H), 4.70 (s, 2H), 4.62 (d, J=10.8 Hz, 1H), 3.64 (td, J=9.7, 4.7 Hz, 1H), 3.51 (t, J=9.0 Hz, 1H), 3.18 (dd, J=11.2, 4.8 Hz, 1H), 3.14-2.97 (m, 3H), 2.95-2.83 (m, 2H), 2.48-2.42 (m, 1H), 2.38 (t, J=10.8 Hz, 1H), 1.26 (d, J=6.2 Hz, 3H); ESI MS m/z 523.284 $[M+H]^+$.

At −78° C., under Ar, to a solution of the above material (0.14 g, 0.26 mmol) in DCM (8 mL) was added $BCl_3$ (1.0 M in DCM, 1.3 mL, 1.3 mmol), and the mixture was stirred for 2 h while the bath temperature reached 0° C. The mixture was further stirred at 0° C. for 2 h and then quenched by adding MeOH (2 mL) slowly. After stirring at RT for 30 min the mixture was concentrated under reduced pressure. The resulting residue was further neutralized with $NH_4OH$ (0.5 mL) and concentrated again under reduced pressure. The crude residue was purified and separated on silica gel by flash chromatography (MeOH/DCM, 1:9), affording (2R,3R,4R,5S)-2-methyl-1-(2-(pyridin-2-yl)ethyl)piperidine-3,4,5-triol (0.049 g, 74.6%) as a white solid. $^{1}H$ NMR (500 MHz, $CD_3OD$) δ 8.46 (ddd, J=5.0, 1.8, 0.9 Hz, 1H), 7.77 (td, J=7.7, 1.8 Hz, 1H), 7.36 (dt, J=7.8, 1.1 Hz, 1H), 7.27 (ddd, J=7.6, 5.0, 1.2 Hz, 1H), 3.50 (ddd, J=10.5, 9.1, 4.9 Hz, 1H), 3.14 (t, J=9.0 Hz, 1H), 3.11-3.03 (m, 2H), 2.98-2.90 (m, 4H), 2.34 (t, J=10.9 Hz, 1H), 2.30-2.25 (m, 1H), 1.25 (d, J=6.1 Hz, 3H); ESI MS m/z 253.156 $[M+H]^+$.

Example 77

(2R,3R,4R,5S)-2-methyl-1-(3-phenylpropyl)piperidine-3,4,5-triol

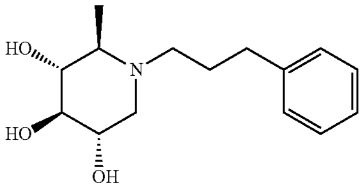 [SMILES: C[C@@H]1[C@@H](O)[C@H](O)[C@@H](O)CN1CCCc1ccccc1]

A mixture of ((2R,3R,4R,5S)-3,4,5-tris(benzyloxy)piperidin-2-yl)methanol (0.18 g, 0.42 mmol) (J. Carb. Chem., 2017, 36, 295-306), (3-bromopropyl)benzene (0.40 g, 2.0 mmol) and DIPEA (0.37 g, 2.9 mmol) in anhydrous DMF (5 mL) in a sealed tube was stirred at 85° C. for 16 h. The reaction mixture was cooled at RT and diluted with satd. aqueous $NaHCO_3$ (20 mL). After extraction with EtOAc (3×15 mL) the combined extract was washed with brine (3×20 mL) and dried over anhydrous $Na_2SO_4$. After filtration the solvent was evaporated under reduced pressure, and the residue was purified on silica gel by flash chromatography (EtOAc/hexanes, 1:4 to 1:3), affording ((2R,3R,4R,5S)-3,4,5-tris(benzyloxy)-1-(3-phenylpropyl)piperidin-2-yl)methanol as a pale-yellow oil (0.17 g, 73%); ESI MS m/z 552.348 $[M+H]^+$.

At 0° C., to a solution of the above material (0.17 g, 0.31 mmol) in anhydrous DCM (10 mL) was added $PPh_3$ (0.20 g, 0.76 mmol), and $CBr_4$ (0.20 g, 0.60 mmol), and the mixture was stirred at RT for 1 h. The solvent was evaporated under reduced pressure, and the residue was purified on silica gel by flash chromatography (EtOAc/hexanes, 1:7 to 1:5), affording (2S,3R,4R,5S)-3,4,5-tris(benzyloxy)-2-(bromomethyl)-1-(3-phenylpropyl)piperidine as a white foam (0.15 g, 79%); ESI MS m/z 614.262 and 616.260 $[M+H]^+$.

A mixture of the above material (0.14 g, 0.23 mmol), $Bu_3SnH$ (0.44 g, 1.5 mmol) and ABCN (0.020 g, 0.082 mmol) in anhydrous toluene (15 mL) was stirred at 95° C. for 16 h. After cooling the solvent was evaporated under reduced pressure, and the residue was purified on silica gel by flash chromatography (EtOAc/hexanes, 1:4 to 2:3), affording a mixture containing (2R,3R,4R,5S)-3,4,5-tris(benzyloxy)-2-methyl-1-(3-phenylpropyl)piperidine and its partially protected analogues with two benzyl groups.

At −78° C. and under $N_2$, to a solution of the above mixture in anhydrous DCM (5 mL) was added $BCl_3$ (1.0 M in DCM, 1.5 mL, 1.5 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:6), affording (2R,3R,4R,5S)-2-methyl-1-(3-phenylpropyl)piperidine-3,4,5-triol as a white solid (0.028 g, 46%, two steps). $^{1}H$ NMR (400 MHz, $CD_3OD$) δ 7.34-7.22 (m, 2H), 7.22-7.08 (m, 3H), 3.47 (ddd, J=10.6, 9.0, 4.9 Hz, 1H), 3.09 (t, J=9.0 Hz, 1H), 3.03-2.88 (m, 2H), 2.81-2.73 (m, 1H), 2.70-2.45 (m, 3H), 2.17 (t, J=10.9 Hz, 2H), 1.80 (p, J=7.5 Hz, 2H), 1.13 (d, J=6.1 Hz, 3H); ESI MS m/z 266.192 $[M+H]^+$.

Example 78

(2R,3R,4R,5S)-1-(3-(2-fluorophenyl)propyl)-2-methylpiperidine-3,4,5-triol

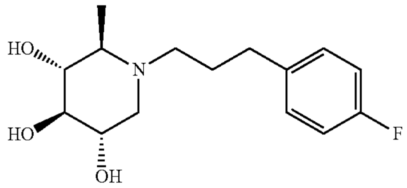 [SMILES: C[C@@H]1[C@@H](O)[C@H](O)[C@@H](O)CN1CCCc1ccc(F)cc1]

To a stirred solution of (2R,3R,4R,5S)-3,4,5-tris(benzyloxy)-2-methylpiperidine (80 mg, 0.19 mmol) and 3-(2-fluorophenyl)propanal (58 mg, 0.38 mmol) in anhydrous DCM (5 mL) was added HOAc (0.10 mL, 1.75 mmol) and stirred for 30 min. $Na(OAc)_3CN$ (81 mg, 0.38 mmol) was added, and the resulting mixture was stirred at RT for 18 h. The reaction was quenched with satd. aqueous $NaHCO_3$ at 0° C. The mixture was extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-1-(3-(2-fluorophenyl)propyl)-2-methylpiperidine as an oil (87 mg, 65%).

To a stirred solution of the above material (87 mg, 0.16 mmol) in anhydrous DCM (5 mL) was added $BCl_3$ solution (1M in DCM, 1.27 mL, 1.27 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-1-(3-(2-fluorophenyl)propyl)-2-methylpiperidine-3,4,5-triol as a white solid (35 mg, 77%). $^{1}H$ NMR (400 MHz, $CD_3OD$) δ 7.27 (td, J=7.6, 1.8 Hz, 1H), 7.24-7.19 (m, 1H), 7.10 (td, J=7.5, 1.3 Hz, 1H), 7.04 (ddd, J=10.4, 8.1, 1.2 Hz, 1H), 3.53-3.45 (m, 1H), 3.10 (t, J=9.0 Hz, 1H), 3.00-2.90 (m, 2H), 2.84-2.74 (m, 1H), 2.73-2.58 (m, 2H), 2.56-2.47 (m, 1H), 2.21-2.09 (m, 2H), 1.86-1.73 (m, 2H), 1.15 (d, J=6.2 Hz, 3H); ESI MS m/z 284.16 $[M+H]^+$.

Example 79

(2R,3R,4R,5S)-1-(3-(4-fluorophenyl)propyl)-2-methylpiperidine-3,4,5-triol

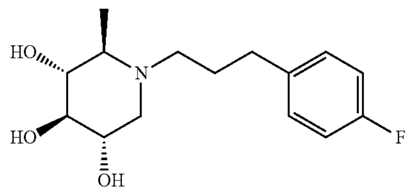 [SMILES: C[C@@H]1[C@@H](O)[C@H](O)[C@@H](O)CN1CCCc1ccc(F)cc1]

A mixture of ((2R,3R,4R,5S)-3,4,5-tris(benzyloxy)piperidin-2-yl)methanol (0.20 g, 0.46 mmol), 1-(3-bromopropyl)-4-fluorobenzene (0.25 g, 1.2 mmol) and DIPEA (0.37 g, 2.9 mmol) in anhydrous DMF (5 mL) in a sealed tube was stirred at 85° C. for 16 h. The reaction mixture was cooled at RT and diluted with satd. aqueous $NaHCO_3$ (20 mL). After extraction with EtOAc (3×15 mL) the combined extract was washed with brine (3×20 mL) and dried over anhydrous $Na_2SO_4$. After filtration the solvent was evaporated under reduced pressure, and the residue was purified on silica gel by flash chromatography (EtOAc/hexanes, 1:4 to 1:3), affording ((2R,3R,4R,5S)-3,4,5-tris(benzyloxy)-1-(3-(4-fluorophenyl)propyl)piperidin-2-yl)methanol as a pale-yellow oil (0.19 g, 73%); ESI MS m/z 570.327 $[M+H]^+$.

At 0° C., to a solution of the above material (0.19 g, 0.33 mmol) in anhydrous DCM (10 mL) was added $PPh_3$ (0.20 g, 0.76 mmol) and $CBr_4$ (0.20 g, 0.60 mmol), and the mixture was stirred at RT for 1 h. The solvent was evaporated under reduced pressure, and the residue was purified on silica gel by flash chromatography (EtOAc/hexanes, 1:9 to 1:5), affording (2S,3R,4R,5S)-3,4,5-tris(benzyloxy)-2-(bromomethyl)-1-(3-(4-fluorophenyl)propyl)piperidine as a white foam (0.11 g, 53%); ESI MS m/z 632.243 and 634.241 $[M+H]^+$.

A mixture of the above material (0.11 g, 0.17 mmol), $Bu_3SnH$ (0.27 g, 0.93 mmol) and ABCN (0.012 g, 0.050 mmol) in anhydrous toluene (10 mL) was stirred at 95° C. for 4 h. After cooling the solvent was evaporated under reduced pressure, and the residue was purified on silica gel by flash chromatography (EtOAc/hexanes, 1:4 to 2:3), affording a mixture containing (2R,3R,4R,5S)-3,4,5-tris(benzyloxy)-2-methyl-1-(3-(4-fluorophenyl)propyl)piperidine and its partially protected analogues with two benzyl groups.

At −78° C. and under $N_2$, to a solution of the above mixture in anhydrous DCM (5 mL) was added $BCl_3$ (1.0 M in DCM, 1.0 mL, 1.0 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:6), affording (2R,3R,4R,5S)-1-(3-(4-fluorophenyl)propyl)-2-methylpiperidine-3,4,5-triol as a white solid (0.022 g, 46%, two steps). $^1H$ NMR (400 MHz, $CD_3OD$) δ 7.28-7.13 (m, 2H), 7.07-6.92 (m, 2H), 3.47 (ddd, J=10.5, 9.0, 4.8 Hz, 1H), 3.09 (t, J=9.0 Hz, 1H), 3.01-2.89 (m, 2H), 2.78-2.71 (m, 1H), 2.67-2.43 (m, 3H), 2.17-2.10 (m, 2H), 1.84-1.71 (m, 2H), 1.13 (d, J=6.2 Hz, 3H); ESI MS m/z 284.179 $[M+H]^+$.

Example 80

(2R,3R,4R,5S)-2-methyl-1-(3-(thiophen-2-yl)propyl)piperidine-3,4,5-triol

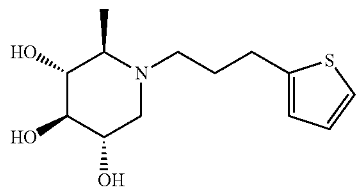 [SMILES: C[C@@H]1[C@@H](O)[C@H](O)[C@@H](O)CN1CCCc1cccs1]

A mixture of ((2R,3R,4R,5S)-3,4,5-tris(benzyloxy)piperidin-2-yl)methanol (0.20 g, 0.46 mmol), 2-(3-bromopropyl)thiophene (0.40 g, 2.0 mmol) (J. Am. Chem. Soc., 2015, 137, 10100-10103) and DIPEA (0.26 g, 2.0 mmol) in anhydrous DMF (5 mL) in a sealed tube was stirred at 80° C. for 64 h. The reaction mixture was cooled at RT and diluted with satd. aqueous $NaHCO_3$ (20 mL). After extraction with EtOAc (3×20 mL) the combined extract was washed with brine (2×20 mL) and dried over anhydrous $Na_2SO_4$. After filtration the solvent was evaporated under reduced pressure, and the residue was purified on silica gel by flash chromatography (EtOAc/hexanes, 1:4 to 1:3), affording ((2R,3R,4R,5S)-3,4,5-tris(benzyloxy)-1-(3-(thiophen-2-yl)propyl)piperidin-2-yl)methanol as a pale-yellow oil (0.20 g, 78%); ESI MS m/z 558.267 $[M+H]^+$.

At 0° C., to a solution of the above material (0.20 g, 0.36 mmol) in anhydrous DCM (10 mL) was added $PPh_3$ (0.20 g, 0.76 mmol) and $CBr_4$ (0.20 g, 0.60 mmol). After the mixture was stirred at RT for 16 h the solvent was evaporated under reduced pressure, and the residue was purified on silica gel by flash chromatography (EtOAc/hexanes, 1:9 to 1:7), affording (2S,3R,4R,5S)-3,4,5-tris(benzyloxy)-2-(bromomethyl)-1-(3-(thiophen-2-yl)propyl)piperidine as a clear oil (0.20 g, 90%); ESI MS m/z 620.179 and 622.178 $[M+H]^+$.

A mixture of the above material (0.20 g, 0.32 mmol), $Bu_3SnH$ (0.40 g, 1.4 mmol) and ABCN (0.020 g, 0.089 mmol) in anhydrous toluene (10 mL) was stirred at 95° C. for 16 h. After cooling the solvent was evaporated under reduced pressure, and the residue was purified on silica gel by flash chromatography (EtOAc/hexanes, 1:4 to 2:3), affording a mixture containing (2R,3R,4R,5S)-3,4,5-tris(benzyloxy)-2-methyl-1-(3-(thiophen-2-yl)propyl)piperidine and its partially protected analogue with two benzyl groups.

At −78° C. and under $N_2$, to a solution of the above mixture in anhydrous DCM (5 mL) was added $BCl_3$ (1.0 M in DCM, 1.5 mL, 1.5 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:8), affording (2R,3R,4R,5S)-2-methyl-1-(3-(thiophen-2-yl)propyl)piperidine-3,4,5-triol as a white solid (0.015 g, 17%, two steps). $^1H$ NMR (500 MHz, $CD_3OD$) δ 7.19-7.15 (m, 1H), 6.92-6.88 (m, 1H), 6.84-6.80 (m, 1H), 3.50-3.45 (m, 1H), 3.11-3.07 (m, 1H), 2.99-2.92 (m, 2H), 2.85-2.75 (m, 3H), 2.55-2.48 (m, 1H), 2.18-2.11 (m, 2H), 1.85-1.80 (m, 2H), 1.15 (dd, J=6.0 Hz, 3H); ESI MS m/z 272.130 $[M+H]^+$.

Example 81

(2R,3R,4R,5S)-2-methyl-1-(3-(thiophen-3-yl)propyl)piperidine-3,4,5-triol

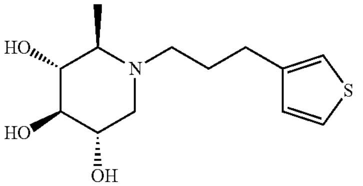 [SMILES: C[C@@H]1[C@@H](O)[C@H](O)[C@@H](O)CN1CCCc1ccsc1]

A mixture of ((2R,3R,4R,5S)-3,4,5-tris(benzyloxy)piperidin-2-yl)methanol (0.20 g, 0.46 mmol), 3-(3-bromopropyl)thiophene (0.45 g, 2.2 mmol) (Tetrahedron, 2006, 62, 6551-6557) and DIPEA (0.30 g, 2.3 mmol) in anhydrous DMF (5 mL) in a sealed tube was stirred at 85° C. for 16 h. The reaction mixture was cooled at RT and diluted with satd. aqueous $NaHCO_3$ (20 mL). After extraction with EtOAc (3×20 mL) the combined extract was washed with brine (2×20 mL) and dried over anhydrous $Na_2SO_4$. After filtration the solvent was evaporated under reduced pressure, and the residue was purified on silica gel by flash chromatography (EtOAc/hexanes, 1:4 to 1:3), affording ((2R,3R,4R,5S)-3,4,5-tris(benzyloxy)-1-(3-(thiophen-3-yl)propyl)piperidin-2-yl)methanol as a pale-yellow oil (0.20 g, 78%); ESI MS m/z 558.263 $[M+H]^+$.

At 0° C., to a solution of the above material (0.20 g, 0.36 mmol) in anhydrous DCM (10 mL) was added $PPh_3$ (0.20 g, 0.76 mmol) and $CBr_4$ (0.20 g, 0.60 mmol), and the mixture was stirred at RT for 16 h. The solvent was evaporated under reduced pressure, and the residue was purified on silica gel by flash chromatography (EtOAc/hexanes, 1:9 to 1:7), affording (2S,3R,4R,5S)-3,4,5-tris(benzyloxy)-2-(bromomethyl)-1-(3-(thiophen-3-yl)propyl)piperidine as a clear oil (0.20 g, 90%).

A mixture of the above material (0.20 g, 0.32 mmol), $Bu_3SnH$ (0.40 g, 1.4 mmol) and ABCN (0.016 g, 0.072 mmol) in anhydrous toluene (20 mL) was stirred at 95° C. for 16 h. After cooling the solvent was evaporated under reduced pressure, and the residue was purified on silica gel by flash chromatography (EtOAc/hexanes, 1:4 to 2:3), affording a mixture containing (2R,3R,4R,5S)-3,4,5-tris(benzyloxy)-2-methyl-1-(3-(thiophen-3-yl)propyl)piperidine and its partially protected analogue with two benzyl groups.

At −78° C. and under $N_2$, to a solution of the above mixture in anhydrous DCM (5 mL) was added $BCl_3$ (1.0 M in DCM, 1.0 mL, 1.0 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:8), affording (2R,3R,4R,5S)-2-methyl-1-(3-(thiophen-3-yl)propyl)piperidine-3,4,5-triol as a white solid (0.014 g, 16%, two steps). $^1H$ NMR (500 MHz, $CD_3OD$) δ 7.31 (d, J=3.5 Hz, 1H), 7.03 (s, 1H), 6.97 (d, J=3.5 Hz, 1H), 3.53-3.46 (m, 1H), 3.12-3.08 (m, 1H), 3.00-2.93 (m, 2H), 2.80-2.73 (m, 1H), 2.67-2.59 (m, 2H), 2.55-2.49 (m, 1H), 2.21-2.16 (m, 2H), 1.83-1.77 (m, 2H), 1.15 (dd, J=6.0 Hz, 3H); ESI MS m/z 272.129 $[M+H]^+$.

Example 82

(2R,3R,4R,5S)-2-methyl-1-((1-phenylpiperidin-4-yl)methyl)piperidine-3,4,5-triol

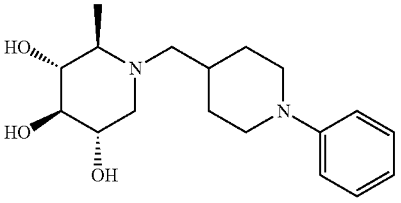 [SMILES: C[C@@H]1[C@@H](O)[C@H](O)[C@@H](O)CN1CC1CCN(c2ccccc2)CC1]

At 0° C. under Ar, to a solution of (1-phenylpiperidin-4-yl)methanol (495 mg, 2.59 mmol) in anhydrous DCM (20 mL) was added DMP (1.60 g, 3.77 mmol). The mixture was stirred at 0° C. for 2 h, satd. aqueous $NaHCO_3$ (10 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 25% EtOAc in hexanes, affording 1-phenylpiperidine-4-carbaldehyde as a white foam (147 mg, 30%).

Under Ar, to a solution of 1-phenylpiperidine-4-carbaldehyde (147 mg, 0.70 mmol), ((2R,3R,4R,5S)-3,4,5-tris(benzyloxy)piperidin-2-yl)methanol (244 mg, 0.46 mmol) and HOAc (three drops) in anhydrous MeOH (10 mL) was added $NaBH_3CN$ (46 mg, 95%, 0.71 mmol). The mixture was stirred at RT for 18 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 30% EtOAc in hexanes, affording ((2R,3R,4R,5S)-3,4,5-tris(benzyloxy)-1-((1-phenylpiperidin-4-yl)methyl)piperidin-2-yl)methanol as a white foam (249 mg, 89%).

At 0° C. under Ar, to a solution of the above material (249 mg, 0.41 mmol) and $Ph_3P$ (215 mg, 0.82 mmol) in anhydrous DCM (12 mL) was added $CBr_4$ (271 mg, 0.82 mmol). The mixture was stirred at 0° C. for 2 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 20% EtOAc in hexanes, affording (2S,3R,4R,5S)-3,4,5-tris(benzyloxy)-2-(bromomethyl)-1-((1-phenylpiperidin-4-yl)methyl)piperidine as a white foam (223 mg, 82%).

The above material (86 mg, 0.13 mmol) in MeOH (10 mL) was treated with hydrogen (50 psi) overnight in presence of Ra/Ni. Removal of Ra/Ni, followed by evaporation of solvent under reduced pressure, afforded (2R,3R,4R,5S)-3,4,5-tris(benzyloxy)-2-methyl-1-((1-phenylpiperidin-4-yl)methyl)piperidine (45 mg, 58%).

At −78° C. under Ar, to a solution of the above material (45 mg, 0.067 mmol) in anhydrous DCM (2 mL) was added $BCl_3$ solution (1.0 mL, 1 M in DCM, 1.00 mmol). The mixture was stirred at −78 for 1 h and 0° C. for 4 h, MeOH (20 mL) was added. The mixture was stirred for an additional 2 h at 0° C., and evaporated to dryness under reduced pressure. The residue was purified on silica gel by flash chromatography (dry load) using 10% MeOH and 2% $NH_3$ solution in DCM, affording (2R,3R,4R,5S)-2-methyl-1-((1-phenylpiperidin-4-yl)methyl)piperidine-3,4,5-triol as a white foam (3.7 mg, 15%). $^1$H NMR (500 MHz, $CD_3OD$) δ 7.31-7.20 (m, 2H), 7.06-6.98 (m, 2H), 6.86 (t, J=7.3 Hz, 1H), 3.69-3.60 (m, 2H), 3.51 (ddd, J=10.6, 9.1, 4.8 Hz, 1H), 3.15 (dd, J=9.0, 9.0 Hz, 1H), 3.08 (dd, J=11.3, 4.8 Hz, 1H), 2.99 (t, J=9.1 Hz, 1H), 2.78-2.56 (m, 3H), 2.19-2.08 (m, 2H), 2.07-1.93 (m, 2H), 1.80 (dt, J=12.8, 3.1 Hz, 1H), 1.69-1.62 (m, 1H), 1.44-1.26 (m, 2H), 1.22 (d, J=6.1 Hz, 3H); ESI MS m/z 321.21 $[M+H]^+$.

Example 83

(2R,3R,4R,5S)-1-((1-(2-fluorophenyl)piperidin-4-yl)methyl)-2-methylpiperidine-3,4,5-triol

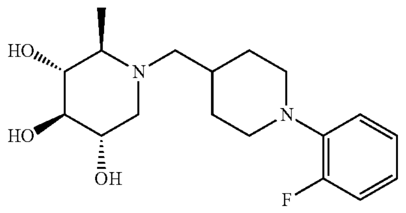 [SMILES: C[C@@H]1[C@@H](O)[C@H](O)[C@@H](O)CN1CC1CCN(c2ccccc2F)CC1]

Under Ar, to a solution of tert-butyl 4-formylpiperidine-1-carboxylate (168 mg, 0.79 mmol), (2R,3R,4R,5S)-3,4,5-tris(benzyloxy)-2-methylpiperidine (220 mg, 0.53 mmol) and HOAc (three drops) in anhydrous MeOH (5 mL) was added $NaBH_3CN$ (53 mg, 95%, 0.81 mmol). The mixture was stirred at RT for 18 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 20% EtOAc in hexanes, affording tert-butyl 4-(((2R,3R,4R,5S)-3,4,5-tris(benzyloxy)-2-methylpiperidin-1-yl)methyl)piperidine-1-carboxylate as a white foam (236 mg, 73%).

At 0° C., the above material (236 mg, 0.35 mmol) in DCM (4 mL) was treated with TFA (1 mL) 2 h, then ice bath was removed, and the reaction was continued for additional 2 h. After evaporation of solvent under reduced pressure, the residue was dissolved in DCM (30 mL), the organic layer was washed with sat. $Na_2CO_3$, brine and dried over $Na_2SO_4$. After filtration the solvent was evaporated and the residue was purified on silica gel by flash chromatography using 10% MeOH and 2% $NH_3$ solution in DCM, affording (2R,3R,4R,5S)-3,4,5-tris(benzyloxy)-2-methyl-1-(piperidin-4-ylmethyl)piperidine as an oil (150 mg, 78%).

Under Ar, to a mixture of (2R,3R,4R,5S)-3,4,5-tris(benzyloxy)-2-methyl-1-(piperidin-4-ylmethyl)piperidine (50 mg, 0.10 mmol), 1-bromo-2-fluorobenzene (50 mg, 0.29 mmol), KO$^t$Bu (17 mg, 0.15 mmol) and BINAP (5.4 mg, 0.009 mmol) in anhydrous and degassed toluene (5 mL) was added $Pd_2(dba)_3$ (3 mg, 0.003 mmol). The mixture was stirred at 85° C. in a sealed tube for 2 h, then cooled to RT. $Et_2O$ (50 mL) was added, and the resulted precipitate was filtered off. The filtrate was concentrated under reduced pressure, and the residue was purified on silica gel by flash chromatography using 15% EtOAc in hexanes, affording (2R,3R,4R,5S)-3,4,5-tris(benzyloxy)-1-((1-(2-fluorophenyl)piperidin-4-yl)methyl)-2-methylpiperidine as a white solid (11 mg, 18%).

At −78° C. under Ar, to a solution of the above material (11 mg, 0.018 mmol) in anhydrous DCM (2 mL) was added $BCl_3$ solution (0.5 mL, 1 M in DCM, 0.50 mmol). The mixture was stirred at −78 for 1 h and 0° C. for 4 h, MeOH (20 mL) was added. The mixture was stirred for an additional 2 h at 0° C., and evaporated to dryness under reduced pressure. The residue was purified on silica gel by flash chromatography (dry load) using 10% MeOH and 2% $NH_3$ solution in DCM, affording (2R,3R,4R,5S)-1-((1-(2-fluorophenyl)piperidin-4-yl)methyl)-2-methylpiperidine-3,4,5-triol as a white foam (5.9 mg, 96%). $^1$H NMR (400 MHz, $CD_3OD$) δ 7.18-6.82 (m, 4H), 3.61-3.37 (m, 3H), 3.14 (dd, J=9.0, 9.0 Hz, 1H), 3.07 (dd, J=11.3, 4.8 Hz, 1H), 2.97 (dd, J=9.0, 9.0 Hz, 1H), 2.78-2.59 (m, 3H), 2.19-1.91 (m, 4H), 1.79 (d, J=12.9 Hz, 1H), 1.70-1.60 (m, 1H), 1.50-1.29 (m, 2H), 1.23 (d, J=6.1 Hz, 3H); ESI MS m/z 339.20 $[M+H]^+$.

Example 84

(2R,3R,4R,5S)-1-((1-(3-fluorophenyl)piperidin-4-yl)methyl)-2-methylpiperidine-3,4,5-triol

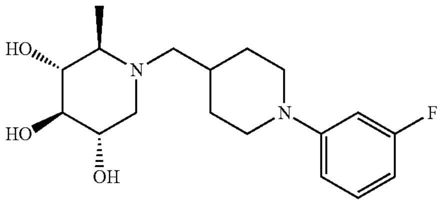 [SMILES: C[C@@H]1[C@@H](O)[C@H](O)[C@@H](O)CN1CC1CCN(c2cccc(F)c2)CC1]

Under Ar, to a mixture of (2R,3R,4R,5S)-3,4,5-tris(benzyloxy)-2-methyl-1-(piperidin-4-ylmethyl)piperidine (72 mg, 0.14 mmol), 1-bromo-3-fluorobenzene (36 mg, 0.21 mmol), KO$^t$Bu (24 mg, 0.21 mmol) and BINAP (8 mg, 0.013 mmol) in anhydrous and degassed toluene (5 mL) was added $Pd_2(dba)_3$ (4 mg, 0.004 mmol). The mixture was stirred at 85° C. in a sealed tube for 2 h, then cooled to RT. $Et_2O$ (50 mL) was added, and the resulted precipitate was filtered off. The filtrate was concentrated under reduced pressure, and the residue was purified on silica gel by flash chromatography using 15% EtOAc in hexanes, affording (2R,3R,4R,5S)-3,4,5-tris(benzyloxy)-1-((1-(4-fluorophenyl)piperidin-4-yl)methyl)-2-methylpiperidine as a white solid (14 mg, 16%).

At −78° C. under Ar, to a solution of the above material (14 mg, 0.023 mmol) in anhydrous DCM (2 mL) was added $BCl_3$ solution (0.3 mL, 1 M in DCM, 0.50 mmol). The mixture was stirred at −78 for 1 h and 0° C. for 4 h, MeOH (20 mL) was added. The mixture was stirred for an additional 2 h at 0° C., and evaporated to dryness under reduced pressure. The residue was purified on silica gel by flash chromatography (dry load) using 10% MeOH and 2% $NH_3$ solution in DCM, affording (2R,3R,4R,5S)-1-((1-(3-fluorophenyl)piperidin-4-yl)methyl)-2-methylpiperidine-3,4,5-triol as a white foam (5.7 mg, 73%). $^1$H NMR (500 MHz, $CD_3OD$) δ 7.19 (dd, J=8.3, 7.0 Hz, 1H), 6.77 (dd, J=8.3, 2.4 Hz, 1H), 6.67 (dt, J=12.8, 2.4 Hz, 1H), 6.55-6.42 (m, 1H), 3.72 (dd, J=12.4, 3.7 Hz, 2H), 3.53-3.44 (m, 1H), 3.14 (dd, J=9.7, 8.6 Hz, 1H), 3.07 (dd, J=11.4, 4.8 Hz, 1H), 2.97 (td, J=9.0, 1.5 Hz, 1H), 2.81-2.60 (m, 3H), 2.19-1.89 (m, 4H), 1.84-1.63 (m, 2H), 1.42-1.24 (m, 2H), 1.21 (d, J=6.1 Hz, 3H); ESI MS m/z 339.20 $[M+H]^+$.

Example 85

(2R,3R,4R,5S)-1-((1-(4-fluorophenyl)piperidin-4-yl)methyl)-2-methylpiperidine-3,4,5-triol

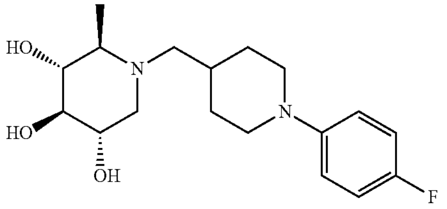 [SMILES: C[C@@H]1[C@@H](O)[C@H](O)[C@@H](O)CN1CC1CCN(c2ccc(F)cc2)CC1]

Under Ar, to a mixture of (2R,3R,4R,5S)-3,4,5-tris(benzyloxy)-2-methyl-1-(piperidin-4-ylmethyl)piperidine (100 mg, 0.19 mmol), 1-bromo-4-fluorobenzene (47 mg, 0.26 mmol), KO$^t$Bu (34 mg, 0.30 mmol) and BINAP (11 mg, 0.018 mmol) in anhydrous and degassed toluene (3 mL) was added $Pd_2(dba)_3$ (6 mg, 0.006 mmol). The mixture was stirred at 85° C. in a sealed tube for 2 h, then cooled to RT. $Et_2O$ (50 mL) was added, and the resulted precipitate was filtered off. The filtrate was concentrated under reduced pressure, and the residue was purified on silica gel by flash chromatography using 15% EtOAc in hexanes, affording (2R,3R,4R,5S)-3,4,5-tris(benzyloxy)-1-((1-(4-fluorophenyl)piperidin-4-yl)methyl)-2-methylpiperidine as a white solid (85 mg, 72%).

At −78° C. under Ar, to a solution of the above material (80 mg, 0.13 mmol) in anhydrous DCM (2 mL) was added $BCl_3$ solution (1.3 mL, 1 M in DCM, 1.30 mmol). The mixture was stirred at −78 for 1 h and 0° C. for 4 h, MeOH (20 mL) was added. The mixture was stirred for an additional 2 h at 0° C., and evaporated to dryness under reduced pressure. The residue was purified on silica gel by flash chromatography (dry load) using 10% MeOH and 2% $NH_3$ solution in DCM, affording (2R,3R,4R,5S)-1-((1-(4-fluorophenyl)piperidin-4-yl)methyl)-2-methylpiperidine-3,4,5-triol (4) as a white foam (20 mg, 45%). $^1$H NMR (500 MHz, $CD_3OD$) δ 7.07-6.89 (m, 4H), 3.59-3.54 (m, 2H), 3.52-3.43 (m, 1H), 3.14 (dd, J=9.0, 9.0 Hz, 1H), 3.07 (dd, J=11.3, 4.8 Hz, 1H), 2.97 (t, J=9.0 Hz, 1H), 2.77-2.58 (m, 3H), 2.18-1.93 (m, 4H), 1.85-1.75 (m, 1H), 1.65 (qt, J=8.3, 4.6 Hz, 1H), 1.40-1.29 m, 2H), 1.22 (d, J=6.1 Hz, 3H); ESI MS m/z 339.20 $[M+H]^+$.

Example 86

(2R,3R,4R,5S)-2-methyl-1-((1-(4-(trifluoromethyl)phenyl)piperidin-4-yl)methyl)piperidine-3,4,5-triol

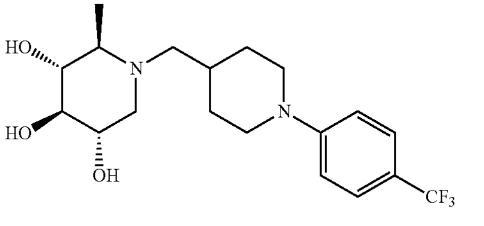 [SMILES: C[C@@H]1[C@@H](O)[C@H](O)[C@@H](O)CN1CC1CCN(c2ccc(C(F)(F)F)cc2)CC1]

Under Ar, to a mixture of ethyl piperidine carboxylate (1 mL, 6.48 mmol), 1-bromo-4-(trifluoromethyl)benzene (0.82 mL, 5.80 mmol), KO$^t$Bu (894 mg, 7.80 mmol) and BINAP (325 mg, 0.52 mmol) in anhydrous and degassed toluene (10 mL) was added $Pd_2(dba)_3$ (191 mg, 0.20 mmol). The mixture was stirred at 85° C. in a sealed tube for 2 h, then cooled to RT. $Et_2O$ (50 mL) was added, and the resulted precipitate was filtered off. The filtrate was concentrated under reduced pressure, and the residue was purified on silica gel by flash chromatography using 15% EtOAc in hexanes, affording ethyl 1-(4-(trifluoromethyl)phenyl)piperidine-4-carboxylate as a white solid (854 mg, 49%).

At 0° C. under Ar, to a solution of the above material (854 mg, 2.83 mmol) in anhydrous THE (15 mL) was added LAH (142 mg, 3.55 mmol). The mixture was stirred at 0° C. for 2 h, satd. aqueous $NH_4Cl$ (10 mL) was added slowly and white solid was formed. The resulted precipitate was filtered off, then washed with excess EtOAc. The combined organic solution was washed with satd. $NaHCO_3$, followed by brine, dried over $Na_2SO_4$, and then concentrated under reduced pressure. The resulting residue was purified on silica gel by flash chromatography using 25% EtOAc in hexanes, affording (1-(4-(trifluoromethyl) phenyl) piperidin-4-yl) methanol as a white solid (736 mg, 99%). $^1$H NMR (400 MHz, $CDCl_3$) δ 7.50 (d, J=8.5 Hz, 2H), 7.01 (d, J=7.0 Hz, 2H), 3.85 (dq, J=12.3, 2.7, 2.2 Hz, 2H), 3.58 (d, J=6.4 Hz, 2H), 3.02-2.69 (m, 2H), 1.99-1.80 (m, 2H), 1.75-1.72 (m, 1H), 1.45-1.43 (m, 2H).

At 0° C. under Ar, to a solution of the above material (385 mg, 1.48 mmol) in anhydrous THE (20 mL) was added DMP (945 mg, 2.23 mmol). The mixture was stirred at 0° C. for 2 h, satd. aqueous $NaHCO_3$ (10 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 25% EtOAc in hexanes, affording 1-(4(trifluoromethyl)phenyl)piperidine-4-carbaldehyde as a white foam (262 mg, 68%). $^1$H NMR (400 MHz, $CDCl_3$) δ 9.73 (d, J=1.0 Hz, 1H), 7.50 (d, J=8.6 Hz, 2H), 6.96 (d, J=8.6 Hz, 2H), 3.75 (dt, J=12.7, 4.0 Hz, 2H), 3.01 (ddd, J=13.2, 10.7, 3.0 Hz, 2H), 2.49-2.46 (m, 1H), 2.20-1.96 (m, 2H), 1.80 (dtd, J=14.3, 10.6, 4.0 Hz, 2H).

Under Ar, to a solution of 1-(4(trifluoromethyl)phenyl)piperidine-4-carbaldehyde (147 mg, 0.57 mmol), ((2R,3R,4R,5S)-3,4,5-tris(benzyloxy)piperidin-2-yl)methanol (200 mg, 0.38 mmol) and HOAc (three drops) in anhydrous MeOH (10 mL) was added $NaBH_3CN$ (37 mg, 95%, 0.57 mmol). The mixture was stirred at RT for 18 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 30% EtOAc in hexanes, affording ((2R,3R,4R,5S)-3,4,5-tris(benzyloxy)-1-((1-(4-(trifluoromethyl)phenyl)piperidin-4-yl)methyl)piperidin-2-yl)methanol as a white foam (250 mg, 90%).

At 0° C. under Ar, to a solution of the above material (250 mg, 0.37 mmol) and $Ph_3P$ (194 mg, 0.74 mmol) in anhydrous DCM (15 mL) was added $CBr_4$ (245 mg, 0.74 mmol). The mixture was stirred at 0° C. for 2 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 15% EtOAc in hexanes, affording (2S,3R,4R,5S)-3,4,5-tris(benzyloxy)-2-(bromomethyl)-1-((1-(4-(trifluoromethyl)phenyl)piperidin-4-yl)methyl)piperidine as a white foam (102 mg, 37%).

Under Ar, to a solution of the above material (102 mg, 0.14 mmol) and $Bu_3SnH$ (0.23 mL, 0.82 mmol) in anhydrous and degassed toluene (5 mL) was added ABCN (10 mg, 0.041 mmol). The mixture was stirred at 85° C. for 12 h, cooled to RT, and satd. aqueous $NaHCO_3$ (30 mL) was added. The mixture was extracted with EtOAc (3×30 mL) and the combined organic extract was dried over anhydrous $Na_2SO_4$. After filtration the solvent was evaporated under reduced pressure, and the residue was purified on silica gel by flash chromatography using 15% EtOAc in hexanes, affording (2R,3R,4R,5S)-3,4,5-tris(benzyloxy)-2-methyl-1-((1-(4-(trifluoromethyl)phenyl)piperidin-4-yl)methyl)piperidine as a white foam (57 mg, 62%).

At −78° C. under Ar, to a solution of the above material (27 mg, 0.047 mmol) in anhydrous DCM (2 mL) was added $BCl_3$ solution (0.5 mL, 1 M in DCM, 0.5 mmol). The mixture was stirred at −78° C. for 1 h and 0° C. for 4 h, MeOH (20 mL) was added. The mixture was stirred for an additional 2 h at 0° C., and evaporated to dryness under reduced pressure. The residue was purified on silica gel by flash chromatography (dry load) using 10% MeOH and 2% $NH_3$ solution in DCM, affording (2R,3R,4R,5S)-2-methyl-1-((1-(4-(trifluoromethyl)phenyl)piperidin-4-yl)methyl)piperidine-3,4,5-triol as a white foam (6.9 mg, 38%). $^1H$ NMR (500 MHz, $CD_3OD$) δ 7.46 (d, J=8.4 Hz, 2H), 7.04 (d, J=8.4 Hz, 2H), 3.88 (d, J=12.6 Hz, 2H), 3.56-3.40 (m, 1H), 3.16-3.11 (m, 1H), 3.08 (dd, J=11.2, 4.5 Hz, 1H), 2.97 (ddd, J=10.5, 8.8, 2.2 Hz, 1H), 2.82 (dt, J=22.9, 12.5 Hz, 2H), 2.65 (dd, J=12.8, 9.1 Hz, 1H), 2.17-1.94 (m, 4H), 1.79 (d, J=14.0 Hz, 2H), 1.40-1.23 (m, 2H), 1.21 (d, J=6.2 Hz, 3H); ESI MS m/z 389.20 $[M+H]^+$.

Example 87

(2R,3R,4R,5S)-2-methyl-1-((4-methyl-1-phenylpiperidin-4-yl)methyl)piperidine-3,4,5-triol

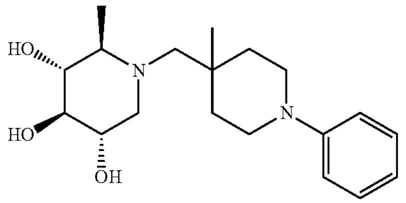

A mixture of ethyl 4-methylpiperidine-4-carboxylate (0.68 g, 4.0 mmol) (*Bioorg. Med. Chem. Lett.,* 2013, 23, 6598-6603), bromobenzene (0.78 g, 0.50 mmol), KO$^t$Bu (0.67 g, 6.0 mmol), BINAP (0.37 g, 0.60 mmol) and $Pd_2(dba)_3$ (0.18 g, 0.20 mmol) in anhydrous toluene (40 mL) was bubbled with Ar for 10 min, and then stirred at 85° C. for 20 h. The reaction mixture was cooled at RT and filtered through a celite cake. The filtrate was collected and concentrated to dryness, and the residue was purified on silica gel by flash chromatography (EtOAc/hexanes, 1:11 to 1:7), affording ethyl 4-methyl-1-phenylpiperidine-4-carboxylate as a pale-yellow oil (0.35 g, 74%); ESI MS m/z 248.159 $[M+H]^+$.

At 0° C. and under $N_2$, to a solution of the above material (0.35 g, 1.4 mmol) in anhydrous THE (20 mL) was added diisobutylaluminium hydride (1.0 M in THF, 4.0 mL, 4.0 mmol), and the mixture was stirred at RT for 1 h. Wet sodium sulfate heptahydrate (50 g) was added to quench the reaction, and the suspension was stirred at RT for 30 min. After filtration the solvent was evaporated, and the residue was purified on silica gel by flash chromatography (EtOAc/hexanes, 1:3 to 1:2), affording (4-methyl-1-phenylpiperidin-4-yl)methanol as a white solid (0.28 g, 98%).

At −78° C. and under $N_2$, to a solution of oxalyl chloride (0.26 g, 2.0 mmol) in anhydrous DCM (15 mL) was added anhydrous DMSO (0.31 g, 4.0 mmol), and the mixture was stirred at −78° C. for 30 min. A solution of (4-methyl-1-phenylpiperidin-4-yl)methanol (0.28 g, 1.4 mmol) in anhydrous DCM (5 mL) was added slowly, and the mixture was stirred at −78° C. for 30 min. $Et_3N$ (0.61 g, 6.0 mmol) was then added, and the mixture was stirred at −78° C. for 30 min. The reaction mixture was brought to RT and stirred for another 30 min. Satd. aqueous $NaHCO_3$ (20 mL) was added, and the mixture was extracted with DCM (3×20 mL). The combined extract was dried over anhydrous $Na_2SO_4$. After filtration the solvent was evaporated under reduced pressure, and the residue was purified on silica gel by flash chromatography (EtOAc/hexanes, 1:20 to 1:10), affording 4-methyl-1-phenylpiperidine-4-carbaldehyde as a pale-yellow solid (0.20 g, 70%); ESI MS m/z 204.134 $[M+H]^+$.

Under $N_2$, a mixture of (2R,3R,4R,5S)-3,4,5-tris(benzyloxy)-2-methylpiperidine (0.18 g, 0.43 mmol), 4-methyl-1-phenylpiperidine-4-carbaldehyde (0.11 g, 0.54 mmol), $NaBH(OAc)_3$ (0.13 g, 0.61 mmol) and one drop of AcOH in DCE (5 mL) was stirred at 65° C. for 16 h. The reaction mixture was cooled at RT and diluted with satd. aqueous $NaHCO_3$ (20 mL). After extraction with DCM (3×20 mL) the combined extract was dried over anhydrous $Na_2SO_4$. After filtration the solvent was evaporated under reduced pressure, and the residue was purified on silica gel by flash chromatography (EtOAc/hexanes, 1:20 to 1:8), affording (2R,3R,4R,5S)-3,4,5-tris(benzyloxy)-2-methyl-1-((4-methyl-1-phenylpiperidin-4-yl)methyl)piperidine as a pale-yellow oil (0.080 g, 31%); ESI MS m/z 605.366 $[M+H]^+$.

At −78° C. and under $N_2$, to a solution of the above material (0.080 g, 0.13 mmol) in anhydrous DCM (6 mL) was added $BCl_3$ (1.0 M in DCM, 1.5 mL, 1.5 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:9), affording (2R,3R,4R,5S)-2-methyl-1-((4-methyl-1-phenylpiperidin-4-yl)methyl)piperidine-3,4,5-triol as a white solid (0.038 g, 87%). $^1H$ NMR (400 MHz, $CD_3OD$) δ 7.24-7.21 (m, 2H), 7.03-6.96 (m, 2H), 6.82 (t, J=7.3 Hz, 1H), 3.51 (ddd, J=10.4, 8.8, 4.6 Hz, 1H), 3.43-3.33 (m, 2H), 3.12 (t, J=8.9 Hz, 1H), 3.04 (dd, J=11.7, 4.6 Hz, 1H), 3.00-2.87 (m, 3H), 2.63 (d, J=14.3 Hz, 1H), 2.26-2.12 (m, 2H), 2.06 (d, J=14.3 Hz, 1H), 1.83-1.66 (m, 2H), 1.48-1.38 (m, 2H), 1.20 (d, J=6.2 Hz, 3H), 0.99 (s, 3H); ESI MS m/z 335.223 $[M+H]^+$.

Example 88

(2R,3R,4R,5S)-1-((4-fluoro-1-phenylpiperidin-4-yl)methyl)-2-methylpiperidine-3,4,5-triol

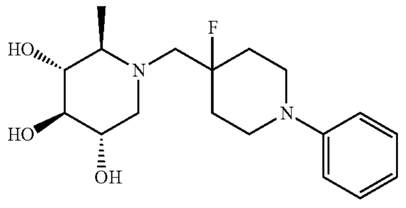 [SMILES: C[C@@H]1[C@@H](O)[C@H](O)[C@@H](O)CN1CC1(C)CCN(c2ccccc2)CC1]

To a solution of trimethylsulfoxonium iodide (3.00 g, 13.6 mmol) in DMSO (40 mL) was added KO$^t$Bu (1.53 g, 13.6 mmol), and the mixture was stirred at RT for 1 h. To the reaction mixture was then added 1-phenylpiperidin-4-one (2.00 g, 11.7 mmol), and the mixture was stirred at RT for another 1 h. The reaction was quenched with cold water and diluted with diluted aqueous $Na_2SO_4$ (200 mL). After extraction with EtOAc (2×100 mL) the combined extract was washed with diluted aqueous $Na_2SO_4$ (2×100 mL) and dried over anhydrous $Na_2SO_4$. After filtration the solvent was evaporated under reduced pressure, and the residue was purified on silica gel by flash chromatography (EtOAc/hexanes, 1:3 to 1:2), affording 6-phenyl-1-oxa-6-azaspiro[2.5]octane as a pale-yellow oil (1.96 g, 88%). $^1$H NMR (400 MHz, $CDCl_3$) δ 7.47-7.25 (m, 2H), 7.12-6.94 (m, 2H), 6.88 (t, J=7.4 Hz, 1H), 3.47-3.33 (m, 4H), 2.73 (s, 2H), 2.02 (s, br., 1H), 1.64 (dt, J=13.4, 4.7 Hz, 1H).

Under $N_2$, to a solution of the above material (1.90 g, 10.0 mmol) in anhydrous DCM (50 mL) was added pyridine hydrofluoride (Py 30%; HF 70%) (2.2 g, 77 mmol), and the mixture was stirred at RT for 16 h. The reaction was then quenched with cold water and diluted with satd. aqueous $NaHCO_3$ (30 mL). After extraction with DCM (2×30 mL) the combined extract was dried over anhydrous $Na_2SO_4$. After filtration the solvent was evaporated, and the residue was purified on silica gel by flash chromatography (EtOAc/hexanes, 1:3 to 1:2), affording (4-fluoro-1-phenylpiperidin-4-yl)methanol as a pale-yellow oil (1.20 g, 57%). $^1$H NMR (400 MHz, $CDCl_3$) δ 7.33-7.27 (m, 2H), 7.06-7.02 (m, 2H), 6.91 (t, J=7.3 Hz, 1H), 3.66 (d, J=20.5 Hz, 2H), 3.58-3.46 (m, 2H), 3.16 (td, J=12.2, 3.0 Hz, 2H), 2.10-1.78 (m, 4H); ESI MS m/z 210.129 [M+H]$^+$.

A mixture of the above material (0.30 g, 1.4 mmol) and DMP (0.84 g, 2.0 mmol) in DCM (15 mL) was stirred at RT for 1 h, forming a white suspension. Hexanes (20 mL) was added, and the suspension was filtered through a celite cake. The filtrate was collected and concentrated under reduced pressure, and the residue was purified on silica gel by flash chromatography (EtOAc/hexanes, 1:3 to 1:2), affording 4-fluoro-1-phenylpiperidine-4-carbaldehyde as a pale-yellow solid (0.17 g, 58%).

Under $N_2$, a mixture of (2R,3R,4R,5S)-3,4,5-tris(benzyloxy)-2-methylpiperidine (0.13 g, 0.31 mmol), 4-fluoro-1-phenylpiperidine-4-carbaldehyde (0.17 g, 0.78 mmol) and $NaBH(OAc)_3$ (0.35 g, 1.7 mmol) in DCE (10 mL) was stirred at 45° C. for 16 h. The reaction mixture was diluted with satd. aqueous $NaHCO_3$ (15 mL), and then extracted with DCM (2×15 mL). The combined extract was dried over anhydrous $Na_2SO_4$. After filtration the solvent was evaporated under reduced pressure, and the residue was purified on silica gel by flash chromatography (EtOAc/hexanes, 1:9 to 1:7), affording (2R,3R,4R,5S)-3,4,5-tris(benzyloxy)-1-((4-fluoro-1-phenylpiperidin-4-yl)methyl)-2-methylpiperidine as a pale-yellow solid (0.16 g, 85%); ESI MS m/z 609.335 [M+H]$^+$.

At −78° C. and under $N_2$, to a solution of the above material (0.15 g, 0.25 mmol) in anhydrous DCM (5 mL) was added $BCl_3$ (1.0 M in DCM, 2.0 mL, 2.0 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:9), affording (2R,3R,4R,5S)-1-((4-fluoro-1-phenylpiperidin-4-yl)methyl)-2-methylpiperidine-3,4,5-triol as a white solid (0.014 g, 17%). $^1$H NMR (400 MHz, $CD_3OD$) δ 7.26 (dd, J=8.6, 7.2 Hz, 2H), 7.03 (d, J=8.6 Hz, 2H), 6.86 (t, J=7.2 Hz, 1H), 3.56-3.40 (m, 3H), 3.29 (dd, J=11.6, 4.9 Hz, 1H), 3.14 (t, J=9.0 Hz, 1H), 3.07-2.86 (m, 4H), 2.43 (t, J=15.7 Hz, 1H), 2.26-2.09 (m, 3H), 1.96-1.70 (m, 3H), 1.21 (d, J=6.1 Hz, 3H); ESI MS m/z 339.198 [M+H]$^+$.

Example 89

(2R,3R,4R,5S)-2-methyl-1-(2-(1-phenylpiperidin-4-yl)ethyl)piperidine-3,4,5-triol

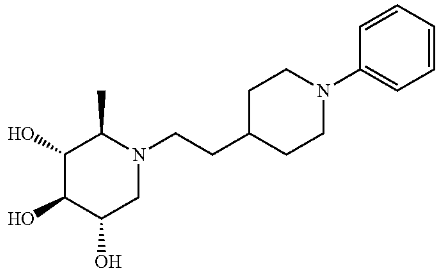 [SMILES: C[C@@H]1[C@@H](O)[C@H](O)[C@@H](O)CN1CCC1CCN(c2ccccc2)CC1]

A mixture of ethyl 2-(piperidin-4-yl)acetate (0.68 g, 4.0 mmol), bromobenzene (0.78 g, 0.50 mmol), KO$^t$Bu (0.67 g, 6.0 mmol), BINAP (0.37 g, 0.60 mmol) and $Pd_2(dba)_3$ (0.18 g, 0.20 mmol) in anhydrous toluene (40 mL) was bubbled with Ar for 10 min, and then stirred at 85° C. for 16 h. The reaction mixture was cooled at RT and diluted with satd. aqueous $NaHCO_3$ (50 mL). After extraction with EtOAc (3×50 mL) the combined extract was dried over anhydrous $Na_2SO_4$. After filtration the solvent was evaporated under reduced pressure, and the residue was purified on silica gel by flash chromatography (EtOAc/hexanes, 1:11 to 1:9), affording ethyl 2-(1-phenylpiperidin-4-yl)acetate as a pale-yellow oil (0.25 g, 25%).

At 0° C. and under $N_2$, to a solution of the above material (0.25 g, 1.0 mmol) in anhydrous THE (6 mL) was added LAH (0.10 g, 2.6 mmol), and the mixture was stirred at 0° C. for 1 h. Wet sodium sulfate heptahydrate (50 g) was added to quench the reaction, and the suspension was stirred at RT for 30 min. After filtration the solvent was evaporated, and the residue was purified on silica gel by flash chromatography (EtOAc/hexanes, 1:3 to 1:1), affording 2-(1-phenylpiperidin-4-yl)ethanol as a pale-yellow oil (0.17 g, 83%); ESI MS m/z 206.152 [M+H]$^+$.

A mixture of the above material (0.17 g, 0.83 mmol) and DMP (0.52 g, 1.2 mmol) in DCM (20 mL) was stirred at RT for 1.5 h, forming a white suspension. Hexanes (20 mL) was added, and the suspension was filtered through a celite cake.

The filtrate was collected and concentrated to dryness under reduced pressure, and the residue was purified on silica gel by flash chromatography (EtOAc/hexanes, 1:4 to 1:3), affording 2-(1-phenylpiperidin-4-yl)acetaldehyde as a pale-yellow oil (0.15 g, 89%); ESI MS m/z 204.135 $[M+H]^+$.

Under $N_2$, a mixture of (2R,3R,4R,5S)-3,4,5-tris(benzyloxy)-2-methylpiperidine (0.18 g, 0.43 mmol), 2-(1-phenylpiperidin-4-yl)acetaldehyde (0.13 g, 0.64 mmol) and $NaBH(OAc)_3$ (0.16 g, 0.75 mmol) in DCE (5 mL) was stirred at RT for 16 h. The reaction mixture was diluted with satd. aqueous $NaHCO_3$ (20 mL), and then extracted with DCM (2×15 mL). The combined extract was dried over anhydrous $Na_2SO_4$. After filtration the solvent was evaporated under reduced pressure, and the residue was purified on silica gel by flash chromatography (EtOAc/hexanes, 1:7 to 1:4), affording (2R,3R,4R,5S)-3,4,5-tris(benzyloxy)-2-methyl-1-(2-(1-phenylpiperidin-4-yl)ethyl)piperidine as a pale-yellow solid (0.16 g, 62%); ESI MS m/z 605.369 $[M+H]^+$.

At −78° C. and under $N_2$, to a solution of the above material (0.15 g, 0.25 mmol) in anhydrous DCM (5 mL) was added $BCl_3$ (1.0 M in DCM, 2.0 mL, 2.0 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:8), affording (2R,3R,4R,5S)-2-methyl-1-(2-(1-phenylpiperidin-4-yl)ethyl)piperidine-3,4,5-triol as a white solid (0.075 g, 90%). $^1H$ NMR (400 MHz, DMSO-$d_6$) δ 7.18 (dd, J=8.7, 7.1 Hz, 2H), 6.90 (d, J=8.2 Hz, 2H), 6.72 (t, J=7.2 Hz, 1H), 4.67-4.64 (m, 3H), 3.68-3.60 (m, 2H), 3.26-3.17 (m, 1H), 2.88 (td, J=8.8, 4.3 Hz, 1H), 2.80 (dd, J=11.1, 4.9 Hz, 1H), 2.73-2.68 (m, 2H), 2.63-2.57 (m, 2H), 2.37-2.27 (m, 1H), 1.96-1.89 (m, 2H), 1.78-1.68 (m, 2H), 1.34-1.20 (m, 5H), 1.07 (d, J=6.0 Hz, 3H); ESI MS m/z 335.229 $[M+H]^+$.

Example 90

(2R,3R,4R,5S)-2-methyl-1-((1-(pyridin-3-yl)piperidin-4-yl)methyl)piperidine-3,4,5-triol

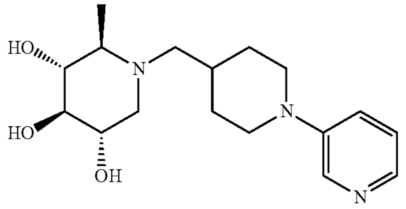 [SMILES: C[C@@H]1[C@@H](O)[C@H](O)[C@@H](O)CN1CC1CCN(c2cccnc2)CC1]

Under Ar, to a mixture of (2R,3R,4R,5S)-3,4,5-tris(benzyloxy)-2-methyl-1-(piperidin-4-ylmethyl)piperidine (116 mg, 0.23 mmol), 3-bromopyridine (56 mg, 0.34 mmol), KO$^t$Bu (40 mg, 0.34 mmol) and BINAP (14 mg, 0.022 mmol) in anhydrous and degassed toluene (5 mL) was added $Pd_2dba_3$ (6.8 mg, 0.007 mmol). The mixture was stirred at 85° C. in a sealed tube for 2 h, then cooled to RT. $Et_2O$ (50 mL) was added, and the resulting precipitate was filtered off. The filtrate was concentrated under reduced pressure, and the residue was purified on silica gel by flash chromatography using 50% EtOAc in DCM, affording 3-(4-(((2R,3R,4R,5S)-3,4,5-tris(benzyloxy)-2-methylpiperidin-1-yl)methyl)piperidin-1-yl)pyridine as a white solid (38 mg, 28%).

At −78° C. under Ar, to a solution of the above material (38 mg, 0.064 mmol) in anhydrous DCM (2 mL) was added $BCl_3$ solution (1 mL, 1 M in DCM, 1.0 mmol). The mixture was stirred at −78 for 1 h and 0° C. for 4 h, then MeOH (20 mL) was added. The mixture was stirred for an additional 2 h at 0° C., and evaporated to dryness under rotavap. The residue was purified on silica gel by flash chromatography (dry load) using 10% MeOH and 2% $NH_3$ solution in DCM, affording (2R,3R,4R,5S)-2-methyl-1-((1-(pyridin-3-yl)piperidin-4-yl)methyl)piperidine-3,4,5-triol as a white foam (7.2 mg, 34%). $^1H$ NMR (400 MHz, $CD_3OD$) δ 8.24 (s, 1H), 7.95 (s, 1H), 7.55-7.37 (m, 1H), 7.28 (s, 1H), 3.78 (d, J=12.3 Hz, 2H), 3.49 (ddd, J=10.4, 9.0, 4.8 Hz, 1H), 3.14 (t, J=9.0 Hz, 1H), 3.08 (dd, J=11.3, 4.8 Hz, 1H), 2.96 (t, J=9.0 Hz, 1H), 2.79 (dtd, J=15.4, 12.2, 2.7 Hz, 2H), 2.67 (dd, J=12.9, 9.0 Hz, 1H), 2.17-2.06 (m, 2H), 2.02 (t, J=11.0 Hz, 2H), 1.81 (d, J=13.0 Hz, 1H), 1.77-1.66 (m, 1H), 1.44-1.25 (m, 2H), 1.21 (d, J=6.1 Hz, 3H); ESI MS m/z 322.2 $[M+H]^+$.

Example 91

(2R,3R,4R,5S)-2-methyl-1-((1-(2,2,2-trifluoroethyl)piperidin-4-yl)methyl)piperidine-3,4,5-triol

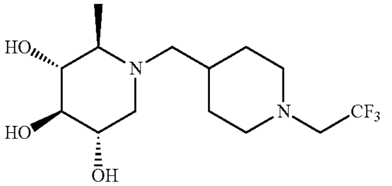 [SMILES: C[C@@H]1[C@@H](O)[C@H](O)[C@@H](O)CN1CC1CCN(CC(F)(F)F)CC1]

Under Ar, to a mixture of (2R,3R,4R,5S)-3,4,5-tris(benzyloxy)-2-methyl-1-(piperidin-4-ylmethyl)piperidine (98 mg, 0.19 mmol), and $Et_3N$ (0.10 mL, 0.69 mmol) in anhydrous THE (4 mL) was added 2,2,2-trifluoroethyl trifluoromethanesulfonate (44 mg, 0.19 mmol) in THE (1 mL). The mixture was stirred at RT for 18 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 40% EtOAc in hexanes, affording (2R,3R,4R,5S)-3,4,5-tris(benzyloxy)-2-methyl-1-((1-(2,2,2-trifluoroethyl)piperidin-4-yl)methyl)piperidine as a white foam (74 mg, 66%).

At −78° C. under Ar, to a solution of the above material (74 mg, 0.12 mmol) in anhydrous DCM (2 mL) was added $BCl_3$ solution (1 mL, 1 M in DCM, 1.00 mmol). The mixture was stirred at −78 for 1 h and 0° C. for 4 h; MeOH (20 mL) was added. The mixture was stirred for an additional 2 h at 0° C., and evaporated to dryness under reduced pressure. The residue was purified on silica gel by flash chromatography (dry load) using 10% MeOH and 2% $NH_3$ solution in DCM, affording (2R,3R,4R,5S)-2-methyl-1-((1-(2,2,2-trifluoroethyl)piperidin-4-yl)methyl)piperidine-3,4,5-triol as a white foam (15 mg, 38%). $^1H$ NMR (400 MHz, DMSO) δ 4.90-4.31 (m, 3H), 3.25-3.18 (m, 1H), 3.10 (q, J=10.3 Hz, 2H), 2.96-2.78 (m, 4H), 2.70 (td, J=8.8, 5.0 Hz, 1H), 2.48-2.42 (m, 1H), 2.33-2.22 (m, 2H), 1.94-1.84 (m, 2H), 1.78 (t, J=10.8 Hz, 1H), 1.72-1.64 (m, 1H), 1.59-1.48 (m, 1H), 1.43-1.35 (m, 1H), 1.05 (d, J=6.0 Hz, 3H), 1.13-1.00 (m, 2H); ESI MS m/z 327.18 $[M+H]^+$.

Example 92

2-methyl-1-(4-(((2R,3R,4R,5S)-3,4,5-trihydroxy-2-methylpiperidin-1-yl)methyl)piperidin-1-yl)propan-1-one

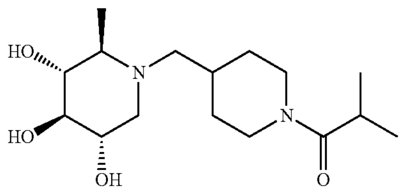 [SMILES: CC(C)C(=O)N1CCC(CN2C[C@H](O)[C@@H](O)[C@H](O)[C@H]2C)CC1]

Under Ar, to a mixture of (2R,3R,4R,5S)-3,4,5-tris(benzyloxy)-2-methyl-1-(piperidin-4-ylmethyl)piperidine (50 mg, 0.10 mmol), DMAP (cat) and DIPEA (0.060 mL, 0.30 mmol) in anhydrous DCM (1 mL) was added isobutyryl chloride (12 mg, 0.10 mmol) in DCM (1 mL). The mixture was stirred at RT for 18 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 30% EtOAc in hexanes, affording 2-methyl-1-(4-(((2R,3R,4R,5S)-3,4,5-tris(benzyloxy)-2-methylpiperidin-1-yl)methyl)piperidin-1-yl)propan-1-one as a white foam (46 mg, 79%).

At −78° C. under Ar, to a solution of the above material (46 mg, 0.09 mmol) in anhydrous DCM (2 mL) was added $BCl_3$ solution (1.0 mL, 1 M in DCM, 1.00 mmol). The mixture was stirred at −78 for 1 h and 0° C. for 4 h, MeOH (20 mL) was added. The mixture was stirred for an additional 2 h at 0° C., and evaporated to dryness under reduced pressure. The residue was purified on silica gel by flash chromatography (dry load) using 10% MeOH and 2% $NH_3$ solution in DCM, affording 2-methyl-1-(4-(((2R,3R,4R,5S)-3,4,5-trihydroxy-2-methylpiperidin-1-yl)methyl)piperidin-1-yl)propan-1-one as a white foam (13 mg, 52%). $^1H$ NMR (400 MHz, $CD_3OD$) δ 4.55 (d, J=13.6 Hz, 1H), 4.08 (d, J=13.7 Hz, 1H), 3.51 (s, 1H), 3.25-2.86 (m, 5H), 2.66-2.59 (m, 2H), 2.41-1.56 (m, 6H), 1.48-0.64 (m, 11H); ESI MS m/z 315.20 $[M+H]^+$.

Example 93

2,2-dimethyl-1-(4-(((2R,3R,4R,5S)-3,4,5-trihydroxy-2-methylpiperidin-1-yl)methyl)piperidin-1-yl)propan-1-one

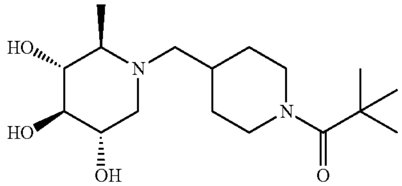 [SMILES: C[C@@H]1[C@@H](O)[C@H](O)[C@@H](O)CN1CC1CCN(C(=O)C(C)(C)C)CC1]

Under Ar, to a mixture of (2R,3R,4R,5S)-3,4,5-tris(benzyloxy)-2-methyl-1-(piperidin-4-ylmethyl)piperidine (36 mg, 0.07 mmol), pivalic acid (10 mg, 0.09 mmol), hydroxybenzotriazole (14 mg, 0.10 mmol) and DIPEA (0.062 mL, 0.34 mmol) in anhydrous DMF (1 mL) was added (1-[bis(dimethylamino)methylene]-1H-1,2,3-triazolo[4,5-b]pyridinium 3-oxid hexafluorophosphate) (40 mg, 0.10 mmol). The mixture was stirred at RT for 18 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 3000 EtOAc in hexanes, affording 2,2-dimethyl-1-(4-(((2R,3R,4R,5S)-3,4,5-tris(benzyloxy)-2-methylpiperidin-1-yl)methyl)piperidin-1-yl)propan-H-one as a white foam (35 mg, 83%).

The above material (35 mg, 0.6 mmol), 2N HCl (three drops) in EtOH (10 mL) was treated with hydrogen in balloon overnight in presence of $Pd(OH)_2$ (cat.). Removal of $Pd(OH)_2$ by filtration and evaporation of solvent followed by purification on silica gel chromatography using 10% MeOH and 2% $NH_3$ solution in DCM and dry load, afforded 2,2-dimethyl-1-(4-(((2R,3R,4R,5S)-3,4,5-trihydroxy-2-methylpiperidin-1-yl)methyl)piperidin-1-yl)propan-1-one (7 mg, 37%). $^1H$ NMR (400 MHz, $CD_3OD$) δ 4.42 (d, J=13.1 Hz, 2H), 3.47 (ddd, J=10.5, 9.0, 4.8 Hz, 1H), 3.13 (dd, J=9.0, 9.0 Hz, 1H), 3.05 (dd, J=11.3, 4.8 Hz, 1H), 2.95 (dd, J=9.0, 9.0 Hz, 1H), 2.89-2.87 (m, 2H), 2.63 (dd, J=13.0, 9.0 Hz, 1H), 2.13-1.89 (m, 6H), 1.29 (s, 9H), 1.19 (d, J=6.1 Hz, 3H), 1.12-0.88 (m, 2H); ESI=MS m/z 329.24 $[M+H]^+$.

The following examples were synthesized according to procedures analogous to the schemes and examples outlined herein.

TABLE 2

| Example | Structure | Name |
|---|---|---|
| 94 | 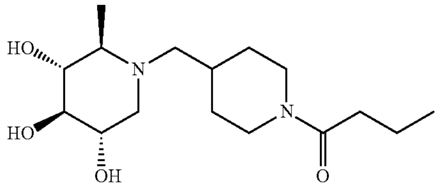 [SMILES: CCCC(=O)N1CCC(CN2C[C@H](O)[C@@H](O)[C@H](O)[C@H]2C)CC1] | 1-(4-(((2R,3R,4R,5S)-3,4,5-trihydroxy-2-methylpiperidin-1-yl)methyl)piperidin-1-yl)butan-1-one |

$^1H$ NMR (400 MHz, $CD_3OD$) δ 4.58-4.47 (m, 1H), 3.98 (d, J = 14.1 Hz, 1H), 3.47 (dddd, J = 10.6, 9.0, 4.8, 1.8 Hz, 1H), 3.16-3.01 (m, 3H), 2.94 (td, J = 9.0, 2.2 Hz, 1H), 2.70-2.56 (m, 2H), 2.42-2.34 (m, 2H), 2.11-2.02 (m, 2H), 1.99 (dd, J = 10.9, 3.2 Hz, 1H), 1.97-1.86 (m, 1H), 1.85-1.69 (m, 2H), 1.64 (h, J = 7.4 Hz, 2H), 1.19 (dd, J = 6.1, 0.9 Hz, 3H), 1.17-1.02 (m, 2H), 0.99 (t, J = 7.4 Hz, 3H); ESI MS m/z 315.22 $[M + H]^+$.

TABLE 2-continued

| Example | Structure | Name |
|---|---|---|
| 95 | 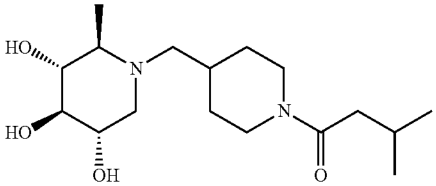 [SMILES: CC(C)CC(=O)N1CCC(CN2C[C@H](O)[C@@H](O)[C@H](O)[C@H]2C)CC1] | 3-methyl-1-(4-(((2R,3R,4R,5S)-3,4,5-trihydroxy-2-methylpiperidin-1-yl)methyl)piperidin-1-yl)butan-1-one |
| $^1$H NMR (400 MHz, $CD_3OD$) δ 4.59-4.50 (m, 1H), 4.00 (d, J = 14.1 Hz, 1H), 3.52-3.42 (m, 1H), 3.17-3.02 (m, 3H), 2.95 (td, J = 9.0, 2.4 Hz, 1H), 2.71-2.57 (m, 2H), 2.28 (d, J = 7.2 Hz, 2H), 2.12-1.87 (m, 5H), 1.87-1.66 (m, 2H), 1.19 (d, J = 6.1 Hz, 3H), 1.16-1.01 (m, 2H), 0.98 (dd, J = 6.7, 1.0 Hz, 6H); ESI MS m/z 329.23 $[M + H]^+$. | | |
| 96 | 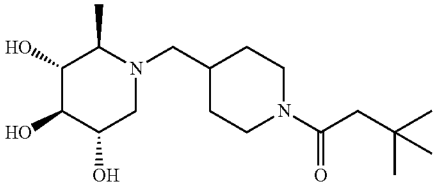 [SMILES: C[C@@H]1[C@@H](O)[C@H](O)[C@@H](O)CN1CC1CCN(C(=O)CC(C)(C)C)CC1] | 3,3-dimethyl-1-(4-(((2R,3R,4R,5S)-3,4,5-trihydroxy-2-methylpiperidin-1-yl)methyl)piperidin-1-yl)butan-1-one |
| $^1$H NMR (400 MHz, $CD_3OD$) δ 4.72-4.43 (m, 1H), 4.07 (d, J = 13.8 Hz, 1H), 3.56-3.40 (m, 1H), 3.22-2.86 (m, 4H), 2.75-2.53 (m, 2H), 2.40 (d, J = 13.6 Hz, 1H), 2.29 (dd, J = 13.6, 1.5 Hz, 1H), 2.18-1.65 (m, 6H), 1.19 (d, J = 6.1 Hz, 3H), 1.06 (s, 9H), 1.08-1.04 (m, 2H); ESI MS m/z 343.25 $[M + H]^+$. | | |
| 97 | 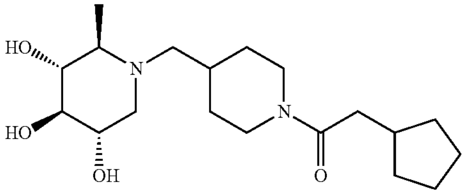 [SMILES: C[C@@H]1[C@@H](O)[C@H](O)[C@@H](O)CN1CC1CCN(C(=O)CC2CCCC2)CC1] | 2-cyclopentyl-1-(4-(((2R,3R,4R,5S)-3,4,5-trihydroxy-2-methylpiperidin-1-yl)methyl)piperidin-1-yl)ethanone |
| $^1$H NMR (400 MHz, $CD_3OD$) δ 4.57-4.49 (m, 1H), 4.00 (d, J = 13.3 Hz, 1H), 3.47 (ddt, J = 10.5, 6.8, 2.0 Hz, 1H), 3.17-3.02 (m, 3H), 2.95 (td, J = 9.0, 2.2 Hz, 1H), 2.70-2.56 (m, 2H), 2.42 (d, J = 7.4 Hz, 2H), 2.20 (hept, J = 7.7 Hz, 1H), 2.12-2.02 (m, 2H), 1.99 (dd, J = 10.9, 3.1 Hz, 1H), 1.96-1.72 (m, 5H), 1.72-1.63 (m, 2H), 1.62-1.55 (m, 2H), 1.26-1.14 (m, 2H), 1.19 (d, J = 6.0 Hz, 3H), 1.15-0.93 (m, 2H); ESI MS m/z 355.25 $[M + H]^+$. | | |
| 98 | 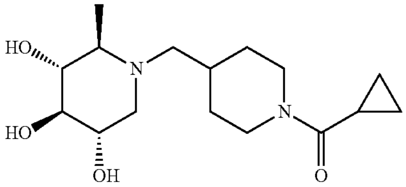 [SMILES: C[C@@H]1[C@@H](O)[C@H](O)[C@@H](O)CN1CC1CCN(C(=O)C2CC2)CC1] | cyclopropyl(4-(((2R,3R,4R,5S)-3,4,5-trihydroxy-2-methylpiperidin-1-yl)methyl)piperidin-1-yl)methanone |
| $^1$H NMR (500 MHz, $CD_3OD$) δ 4.50 (d, J = 13.0 Hz, 1H), 4.35 (d, J = 13.6 Hz, 1H), 3.51 (ddd, J = 10.6, 9.1, 4.8 Hz, 1H), 3.23-3.10 (m, 3H), 3.01 (t, J = 9.0 Hz, 1H), 2.76-2.63 (m, 2H), 2.26-2.09 (m, 3H), 2.04-1.85 (m, 3H), 1.85-1.68 (m, 1H), 1.24 (d, J = 6.2 Hz, 3H), 1.21-0.99 (m, 2H), 0.87 (m, 2H), 0.83-0.77 (m, 2H); ESI MS m/z 313.20 $[M + H]^+$. | | |
| 99 | 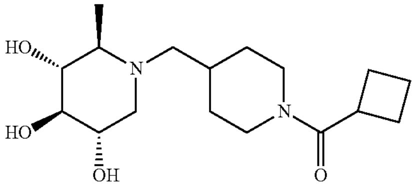 [SMILES: C[C@@H]1[C@@H](O)[C@H](O)[C@@H](O)CN1CC1CCN(C(=O)C2CCC2)CC1] | cyclobutyl(4-(((2R,3R,4R,5S)-3,4,5-trihydroxy-2-methylpiperidin-1-yl)methyl)piperidin-1-yl)methanone |
| $^1$H NMR (400 MHz, $CD_3OD$) δ 4.52-4.45 (m, 1H), 3.82 (d, J = 14.2 Hz, 1H), 3.50-3.37 (m, 2H), 3.12 (td, J = 9.0, 1.0 Hz, 1H), 3.08-2.98 (m, 2H), 2.94 (td, J = 9.0, 3.1 Hz, 1H), 2.71-2.56 (m, 2H), 2.33-2.12 (m, 4H), 2.11-1.94 (m, 4H), 1.90-1.67 (m, 4H), 1.19 (d, J = 6.1 Hz, 3H), 1.11-0.89 (m, 2H); ESI MS m/z 327.22 $[M + H]^+$. | | |

TABLE 2-continued

| Example | Structure | Name |
|---|---|---|
| 100 | 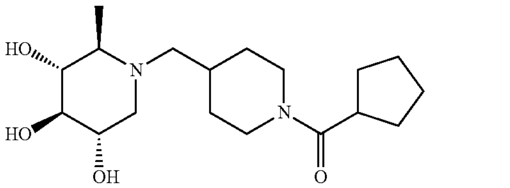 [SMILES: C[C@@H]1[C@@H](O)[C@H](O)[C@@H](O)CN1CC1CCN(C(=O)C2CCCC2)CC1] | cyclopentyl(4-(((2R,3R,4R,5S)-3,4,5-trihydroxy-2-methylpiperidin-1-yl)methyl)piperidin-1-yl)methanone |

$^1$H NMR (400 MHz, $CD_3OD$) δ 4.66-4.38 (m, 1H), 4.10 (dd, J = 15.0, 4.7 Hz, 1H), 3.47 (ddd, J = 10.6, 9.1, 4.8 Hz, 1H), 3.23-3.01 (m, 3H), 2.95 (dd, J = 9.0, 2.0 Hz, 1H), 2.64-2.60 (m, 2H), 2.30-1.47 (m, 15H), 1.29-0.89 (m, 5H); ESI MS rn/z 341.22 $[M + H]^+$.

| Example | Structure | Name |
|---|---|---|
| 101 | 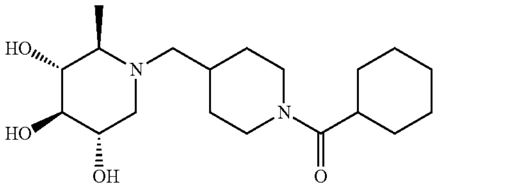 [SMILES: C[C@@H]1[C@@H](O)[C@H](O)[C@@H](O)CN1CC1CCN(C(=O)C2CCCCC2)CC1] | cyclohexyl(4-(((2R,3R,4R,5S)-3,4,5-trihydroxy-2-methylpiperidin-1-yl)methyl)piperidin-1-yl)methanone |

$^1$H NMR (500 MHz, $CD_3OD$) δ 4.53 (d, J = 13.1 Hz, 1H), 4.05 (d, J = 13.7 Hz, 1H), 3.52-3.40 (m, 1H), 3.16-3.02 (m, 3H), 2.94 (td, J = 9.0, 1.8 Hz, 1H), 2.68-2.57 (m, 3H), 2.12-1.88 (m, 4H), 1.86-1.64 (m, 7H), 1.54-1.23 (m, 5H), 1.19 (d, J = 6.1 Hz, 3H), 1.15-0.86 (m, 2H); ESI MS m/z 355.25 $[M + H]^+$.

| Example | Structure | Name |
|---|---|---|
| 102 | 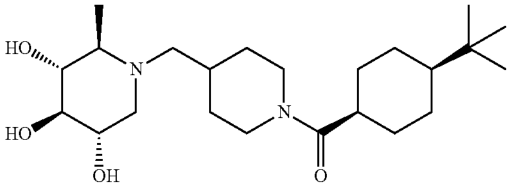 [SMILES: C[C@@H]1[C@@H](O)[C@H](O)[C@@H](O)CN1CC1CCN(C(=O)[C@H]2CC[C@@H](C(C)(C)C)CC2)CC1] | ((1s,4S)-4-(tert-butyl)cyclohexyl)(4-(((2R,3R,4R,5S)-3,4,5-trihydroxy-2-methylpiperidin-1-yl)methyl)piperidin-1-yl)methanone |

$^1$H NMR (400 MHz, $CD_3OD$) δ 4.53 (d, J = 13.3 Hz, 1H), 4.05 (d, J = 13.6 Hz, 1H), 3.47 (td, J = 9.8, 4.7 Hz, 1H), 3.16-3.12 (m, 1H), 3.12-3.02 (m, 2H), 2.98-2.91 (m, 1H), 2.68-2.53 (m, 3H), 2.11-2.06 (m, 1H), 2.06-1.96 (m, 2H), 1.67 (m, 8H), 1.54-1.37 (m, 2H), 1.19 (dd, J = 6.1, 1.4 Hz, 3H), 1.17-0.95 (m, 5H), 0.89 (s, 9H); ESI MS m/z 411.31 $[M + H]^+$.

| Example | Structure | Name |
|---|---|---|
| 103 | 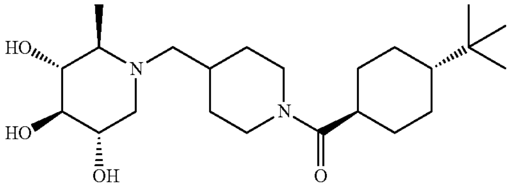 [SMILES: C[C@@H]1[C@@H](O)[C@H](O)[C@@H](O)CN1CC1CCN(C(=O)[C@H]2CC[C@H](C(C)(C)C)CC2)CC1] | ((1r,4R)-4-(tert-butyl)cyclohexyl)(4-(((2R,3R,4R,5S)-3,4,5-trihydroxy-2-methylpiperidin-1-yl)methyl)piperidin-1-yl)methanone |

$^1$H NMR (400 MHz, DMSO-$d_6$) δ 4.68 (d, J = 4.4 Hz, 1H), 4.67 (s, 1H), 4.66 (s, 1H), 4.43-4.31 (m, 1H), 3.85-3.74 (m, 1H), 3.27-3.17 (m, 1H), 3.02-2.83 (m, 3H), 2.83-2.79 (m, 1H), 2.71 (td, J = 8.9, 5.4 Hz, 1H), 2.50-2.40 (m, 3H), 1.93-1.84 (m, 2H), 1.84-1.72 (m, 4H), 1.69-1.53 (m, 2H), 1.52-1.44 (m, 2H), 1.44-1.29 (m, 4H), 1.05 (d, J = 6.0 Hz, 3H), 0.97-0.85 (m, 2H), 0.80 (s, 9H); ESI MS rn/z 411.30 $[M + H]^+$.

| Example | Structure | Name |
|---|---|---|
| 104 | 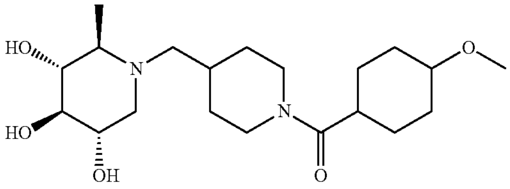 [SMILES: COC1CCC(C(=O)N2CCC(CN3C[C@H](O)[C@@H](O)[C@H](O)[C@H]3C)CC2)CC1] | (4-methoxycyclohexyl)(4-(((2R,3R,4R,5S)-3,4,5-trihydroxy-2-methylpiperidin-1-yl)methyl)piperidin-1-yl)methanone |

$^1$H NMR indicated a ~1:1 mixture of cis/trans isomers. ESI MS m/z 385.26 $[M + H]^+$.

| Example | Structure | Name |
|---|---|---|
| 105 | 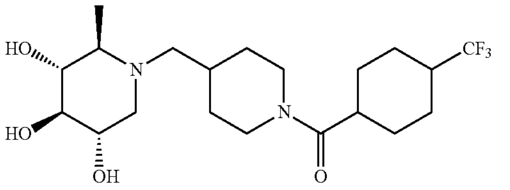 [SMILES: C[C@@H]1[C@@H](O)[C@H](O)[C@@H](O)CN1CC1CCN(C(=O)C2CCC(C(F)(F)F)CC2)CC1] | (4-(trifluoromethyl)cyclohexyl)(4-(((2R,3R,4R,5S)-3,4,5-trihydroxy-2-methylpiperidin-1-yl)methyl)piperidin-1-yl)methanone |

TABLE 2-continued

| Example | Structure | Name |
|---|---|---|
| | $^1$H NMR (400 MHz, $CD_3OD$) δ 4.52 (d, J = 13.2 Hz, 1H), 3.98 (d, J = 13.5 Hz, 1H), 3.51 (td, J = 9.9, 4.7 Hz, 1H), 3.20-3.06 (m, 3H), 3.06-2.97 (m, 1H), 2.91 (q, J = 5.0 Hz, 1H), 2.77-2.68 (m, 1H), 2.62 (q, J = 14.0 Hz, 1H), 2.28-2.08 (m, 4H), 1.99-1.80 (m, 6H), 1.79-1.69 (m, 3H), 1.68-1.57 (m, 2H), 1.24 (d, J = 6.1 Hz, 3H), 1.07 (m, 2H); ESI MS m/z 423.23 [M + H]$^+$. | |
| 106 | 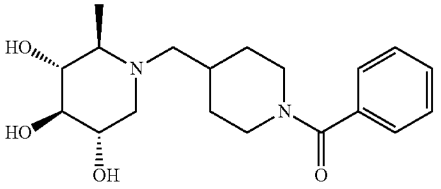 [SMILES: C[C@@H]1[C@@H](O)[C@H](O)[C@@H](O)CN1CC1CCN(C(=O)c2ccccc2)CC1] | phenyl(4-(((2R,3R,4R,5S)-3,4,5-trihydroxy-2-methylpiperidin-1-yl)methyl)piperidin-1-yl)methanone |
| | $^1$H NMR (400 MHz, DMSO) δ 7.45-7.40 (m 3H), 7.38-7.34 (m, 2H), 4.70-4.64 (m, 2H), 4.45 (bs, 1H), 3.56 (s, 1H), 3.22 (s, 1H), 3.00-2.60 (m, 5H), 2.53-2.50 (m, 2H), 2.09-1.43 (m, 6H), 1.07-0.99 (m, 5H); ESI MS m/z 349.20 [M + H]$^+$. | |
| 107 | 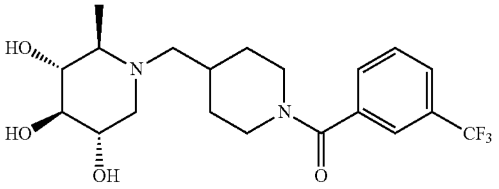 [SMILES: C[C@@H]1[C@@H](O)[C@H](O)[C@@H](O)CN1CC1CCN(C(=O)c2cccc(C(F)(F)F)c2)CC1] | (3-(trifluoromethyl)phenyl)(4-(((2R,3R,4R,5S)-3,4,5-trihydroxy-2-methylpiperidin-1-yl)methyl)piperidin-1-yl)methanone |
| | $^1$H NMR (400 MHz, $CD_3OD$) δ 7.85-7.79 (m, 1H), 7.75 (s, 1H), 7.73-7.67 (m, 2H), 4.65 (dd, J = 18.7, 12.3 Hz, 1H), 3.67 (d, J = 13.6 Hz, 1H), 3.52 (s, 1H), 3.27-2.66 (m, 6H), 2.3-1.7 (m, 6H), 1.40-0.88 (m, 5H); ESI MS m/z 343.25 [M + H]$^+$. | |
| 108 | 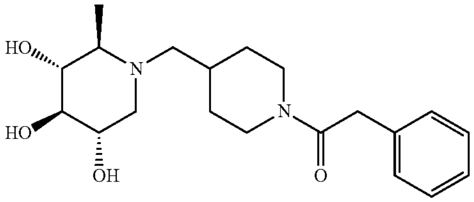 [SMILES: C[C@@H]1[C@@H](O)[C@H](O)[C@@H](O)CN1CC1CCN(C(=O)Cc2ccccc2)CC1] | 2-phenyl-1-(4-(((2R,3R,4R,5S)-3,4,5-trihydroxy-2-methylpiperidin-1-yl)methyl)piperidin-1-yl)ethanone |
| | $^1$H NMR (400 MHz, $CD_3OD$) δ 7.42-7.16 (m, 5H), 4.54 (d, J = 13.4 Hz, 1H), 4.00 (d, J = 13.6 Hz, 1H), 3.87-3.71 (m, 2H), 3.50-3.39 (m, 1H), 3.20-2.83 (m, 4H), 2.74-2.46 (m, 2H), 2.13-1.48 (m, 6H), 1.22-0.57 (m, 5H); ESI MS m/z 363.22 [M + H]$^+$. | |
| 109 | 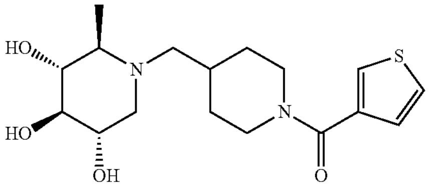 [SMILES: C[C@@H]1[C@@H](O)[C@H](O)[C@@H](O)CN1CC1CCN(C(=O)c2ccsc2)CC1] | thiophen-3-yl(4-(((2R,3R,4R,5S)-3,4,5-trihydroxy-2-methylpiperidin-1-yl)methyl)piperidin-1-yl)methanone |
| | $^1$H NMR (400 MHz, $CD_3OD$) δ 7.67 (dd, J = 2.9, 1.3 Hz, 1H), 7.52 (dd, J = 5.0, 3.0 Hz, 1H), 7.21 (dd, J = 5.1, 1.3 Hz, 1H), 4.60 (bs, 1H), 3.95 (bs, 1H), 3.47 (td, J = 9.8, 4.6 Hz, 1H), 3.21-3.10 (m, 2H), 3.06 (dd, J = 11.3, 4.8 Hz, 1H), 2.95 (t, J = 9.0 Hz, 1H), 2.91-2.80 (m, 1H), 2.66 (dd, J = 13.0, 9.0 Hz, 1H), 2.13-2.05 (m, 2H), 2.01 (t, J = 10.9 Hz, 1H), 1.92-1.66 (m, 3H), 1.20 (d, J = 6.1 Hz, 3H), 1.18-1.06 (m, 2H); ESI MS m/z 355.16 [M + H]$^+$. | |

Example 110

N-cyclohexyl-4-(((2R,3R,4R,5S)-3,4,5-trihydroxy-2-methylpiperidin-1-yl)methyl)piperidine-1-carboxamide

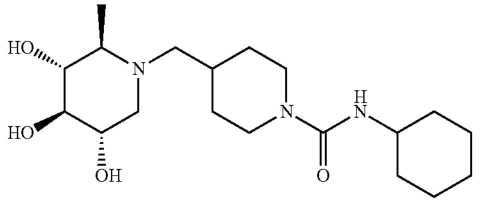 [SMILES: C[C@@H]1[C@@H](O)[C@H](O)[C@@H](O)CN1CC1CCN(C(=O)NC2CCCCC2)CC1]

Under Ar, to a solution of (2R,3R,4R,5S)-3,4,5-tris(benzyloxy)-2-methyl-1-(piperidin-4-ylmethyl)piperidine (56 mg, 0.11 mmol) in anhydrous DCM (3.5 mL) was added cyclohexyl isocyanate (15 mg, 0.12 mmol). The mixture was stirred at RT for 18 h, satd. $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 40% EtOAc in hexanes, affording N-cyclohexyl-4-(((2R,3R,4R,5S)-3,4,5-tris(benzyloxy)-2-methylpiperidin-1-yl)methyl)piperidine-1-carboxamide as a white foam (40 mg, 57%).

At −78° C. under Ar, to a solution of the above material (40 mg, 0.063 mmol) in anhydrous DCM (2 mL) was added $BCl_3$ solution (0.8 mL, 1 M in DCM, 0.8 mmol). The mixture was stirred at −78 for 1 h and 0° C. for 4 h, MeOH (20 mL) was added. The mixture was stirred for an additional 2 h at 0° C., and evaporated to dryness under rotavap. The residue was purified on silica gel by flash chromatography (dry load) using 10% MeOH and 2% $NH_3$ solution in DCM, affording N-cyclohexyl-4-(((2R,3R,4R,5S)-3,4,5-trihydroxy-2-methylpiperidin-1-yl)methyl)piperidine-1-carboxamide (2) as a white foam (10.8 mg, 47%). $^1H$ NMR (400 MHz, $CD_3OD$) δ 6.01 (d, J=7.7 Hz, 1H), 4.69-4.71 (m, 3H), 3.92 (d, J=13.0 Hz, 2H), 3.36-3.39 (m 1H), 3.28-3.15 (m, 1H), 3.00-2.80 (m, 2H), 2.71 (td, J=8.8, 5.4 Hz, 1H), 2.64-2.54 (m, 1H), 2.47-2.40 (m, 1H), 1.95-1.84 (m, 2H), 1.79 (t, J=10.8 Hz, 1H), 1.76-1.60 (m, 4H), 1.53 (dd, J=20.8, 13.0 Hz, 3H), 1.25-1.09 (m, 4H), 1.05 (d, J=6.1 Hz, 3H), 0.87 (dtd, J=36.1, 11.9, 3.7 Hz, 2H); ESI MS m/z 370.25 $[M+H]^+$.

Example 111

N-cyclohexyl-4-(((2R,3R,4R,5S)-3,4,5-trihydroxy-2-methylpiperidin-1-yl)methyl)piperidine-1-carbothioamide

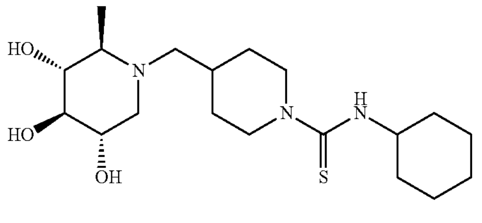 [SMILES: C[C@@H]1[C@@H](O)[C@H](O)[C@@H](O)CN1CC1CCN(C(=S)NC2CCCCC2)CC1]

Under Ar, to a solution of (2R,3R,4R,5S)-3,4,5-tris(benzyloxy)-2-methyl-1-(piperidin-4-ylmethyl)piperidine (56 mg, 0.11 mmol) in anhydrous DCM (3.5 mL) was added cyclohexyl isothiocyanate (17 mg, 0.12 mmol). The mixture was stirred at RT for 18 h, satd. $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 40% EtOAc in hexanes, affording N-cyclohexyl-4-(((2R,3R,4R,5S)-3,4,5-tris(benzyloxy)-2-methylpiperidin-1-yl)methyl)piperidine-1-carbothioamide as a white foam (40 mg, 56%).

At −78° C. under Ar, to a solution of the above material (40 mg, 0.061 mmol) in anhydrous DCM (2 mL) was added $BCl_3$ solution (0.8 mL, 1 M in DCM, 0.8 mmol). The mixture was stirred at −78 for 1 h and 0° C. for 4 h, MeOH (20 mL) was added. The mixture was stirred for an additional 2 h at 0° C., and evaporated to dryness under rotavap. The residue was purified on silica gel by flash chromatography (dry load) using 10% MeOH and 2% $NH_3$ solution in DCM, affording N-cyclohexyl-4-(((2R,3R,4R,5S)-3,4,5-trihydroxy-2-methylpiperidin-1-yl)methyl)piperidine-1-carbothioamide as a white foam (8 mg, 34%). $^1H$ NMR (400 MHz, $CD_3OD$) δ 7.10 (d, J=7.8 Hz, 1H), 4.88-4.45 (m, 4H), 4.17 (d, J=9.7 Hz, 1H), 3.21 (qt, J=9.2, 5.0 Hz, 1H), 2.99-2.79 (m, 4H), 2.71 (td, J=8.9, 5.5 Hz, 1H), 2.48-2.41 (m, 1H), 1.88-1.84 (m, 5H), 1.72-1.68 (m, 3H), 1.58 (t, J=10.8 Hz, 2H), 1.27-1.23 (m, 4H), 1.05 (d, J=6.0 Hz, 3H), 1.00-0.80 (m, 2H); ESI MS m/z 386.22 $[M+H]^+$.

Example 112

(2R,3R,4R,5S)-2-methyl-1-((1-((1S,2R)-2-(trifluoromethyl)cyclohexyl)azetidin-3-yl)methyl)piperidine-3,4,5-triol

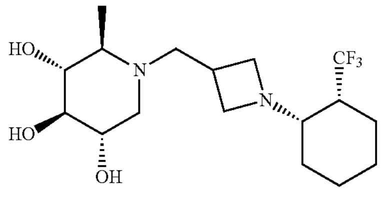 [SMILES: C[C@@H]1[C@@H](O)[C@H](O)[C@@H](O)CN1CC1CN([C@H]2CCCC[C@H]2C(F)(F)F)C1]

To a solution of (2R,3R,4R,5S)-3,4,5-tris(benzyloxy)-2-methylpiperidine (0.75 g, 1.81 mmol) in DCM (20 mL) was added tert-butyl 3-formylazetidine-1-carboxylate (0.37 g, 1.80 mmol), then $NaBH(OAc)_3$ (0.57 g, 2.7 mmol) was added and the mixture was stirred at RT overnight. The reaction mixture was concentrated before diluting with DCM (25 mL). Organics were washed with satd. aqueous of $NaHCO_3$, brine, dried over anhydrous $Na_2SO_4$ and concentrated. The residue was further treated with 20% TFA in DCM (20 mL) and stirred for 3 h at RT. The reaction mixture was concentrated and treated with 1M $NH_3$ solution in MeOH. The mixture was concentrated to provide (2R,3R,4R,5S)-1-(azetidin-3-ylmethyl)-3,4,5-tris(benzyloxy)-2-methylpiperidine (0.8 g, 91%) as an oil. ESI MS m/z 487.562 $[M+H]^+$.

To a stirred solution of the above material (0.13 g, 0.26 mmol) and 2-bromobenzotrifluoride (0.1 mL, 0.7 mmol) in toluene (5 mL) was added $Pd_2(dba)_3$ (25 mg, 0.026 mmol) and RuPhos (25 mg, 0.52 mmol), followed by $Cs_2CO_3$ (0.32 g, 1.0 mmol) under Ar. The mixture was stirred at 100° C. for 18 h, then water was added at 0° C. The mixture was extracted with EtOAc (2×20 mL). The combined organic layer was washed with water (2×10 mL), separated, and dried over $Na_2SO_4$. After filtration the solvent was evaporated under reduced pressure, and the residue was purified on silica gel by flash chromatography affording (2R,3R,4R,5S)-3,4,5-tris(benzyloxy)-2-methyl-1-((1-(2-(trifluoromethyl)phenyl)azetidin-3-yl)methyl)piperidine as an oil (0.1 g, 63%). $^1$H NMR (500 MHz, $CDCl_3$) δ 7.52 (dd, J=8.0, 1.5 Hz, 1H), 7.43-7.27 (m, 15H), 6.78 (t, J=7.5 Hz, 1H), 6.49 (d, J=8.3 Hz, 1H), 4.99 (dd, J=12.8, 10.9 Hz, 2H), 4.87 (d, J=11.0 Hz, 1H), 4.78 (d, J=11.7 Hz, 1H), 4.66 (dd, J=20.8, 11.2 Hz, 2H), 4.11 (m, 2H), 3.69 (t, J=6.8 Hz, 1H), 3.62 (m, 2H), 3.53 (t, J=9.0 Hz, 1H), 3.19-3.08 (m, 1H), 3.07-2.96 (m, 2H), 2.84-2.75 (m, 1H), 2.58 (dd, J=13.0, 6.1 Hz, 1H), 2.33 (s, 1H), 2.12 (t, J=10.8 Hz, 1H), 1.25 (d, J=6.1 Hz, 3H); ESI MS m/z 631.285 $[M+H]^+$.

A mixture of the above material (0.05 g, 0.08 mmol) and $Pd(OH)_2$/C (20% wt, 0.02 g) in MeOH/2N HCl (25/1 mL) was stirred under 50 psi hydrogen pressure overnight. The mixture was filtered through a celite cake, and the filtrate was collected and concentrated to dryness. To the residue was added $NH_4OH$ solution (3 mL) and the mixture was concentrated again. The crude residue was purified and separated on silica gel by flash chromatography (MeOH/DCM, 1:9), affording (2R,3R,4R,5S)-2-methyl-1-((1-((1S,2R)-2-(trifluoromethyl)cyclohexyl)azetidin-3-yl)methyl)piperidine-3,4,5-triol (0.0067 g, 22.7%) as a white solid. $^1$H NMR (400 MHz, $CD_3OD$) δ 4.11-4.01 (m, 2H), 3.66-3.55 (m, 2H), 3.47 (ddd, J=10.5, 9.1, 4.8 Hz, 1H), 3.40-3.35 (m, 1H), 3.14 (t, J=9.0 Hz, 1H), 3.13-3.06 (m, 1H), 3.01-2.90 (m, 3H), 2.88-2.76 (m, 1H), 2.62 (ddd, J=13.3, 5.8, 2.9 Hz, 1H), 2.20 (dd, J=8.8, 6.4 Hz, 1H), 2.11 (t, J=10.9 Hz, 1H), 2.07-2.01 (m, 1H), 1.79-1.58 (m, 5H), 1.57-1.47 (m, 2H), 1.26 (d, J=6.2 Hz, 3H); ESI MS m/z 367.181 $[M+H]^+$.

Example 113

(2R,3R,4R,5S)-2-methyl-1-(((R)-1-phenylpyrrolidin-3-yl)methyl)piperidine-3,4,5-triol

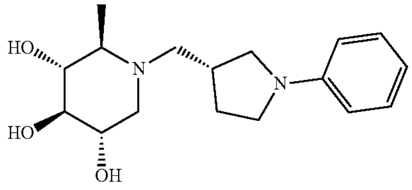 [SMILES: C[C@@H]1[C@@H](O)[C@H](O)[C@@H](O)CN1C[C@H]1CCN(c2ccccc2)C1]

Under Ar, to a mixture of (2R,3R,4R,5S)-3,4,5-tris(benzyloxy)-2-methyl-1-((S)-pyrrolidin-3-ylmethyl)piperidine (142 mg, 0.28 mmol), phenylboronic acid (68 mg, 0.55 mmol), $NEt_3$ (0.082 mL, 0.56 mmol) and 4 Å molecular sieves (200 mg) in anhydrous and degassed DCM (3 mL) was added anhydrous $Cu(OAc)_2$ (57 mg, 0.28 mmol). The mixture was stirred at 85° C. in a sealed tube for 18 h, then cooled to RT. $Et_2O$ (50 mL) was added, and the resulting precipitate was filtered off. The filtrate was concentrated under reduced pressure, and the residue was purified on silica gel by flash chromatography using 15% EtOAc in hexanes, affording (2R,3R,4R,5S)-3,4,5-tris(benzyloxy)-2-methyl-1-(((R)-1-phenylpyrrolidin-3-yl)methyl)piperidine (26 mg, 16%).

At −78° C. under Ar, to a solution of the above material (26 mg, 0.045 mmol) in anhydrous DCM (2 mL) was added $BCl_3$ solution (0.5 mL, 1 M in DCM, 0.50 mmol). The mixture was stirred at −78 for 1 h and 0° C. for 4 h, MeOH (20 mL) was added. The mixture was stirred for an additional 2 h at 0° C., and evaporated to dryness under rotavap. The residue was purified on silica gel by flash chromatography (dry load) using 10% MeOH and 2% $NH_3$ solution in DCM, affording (2R,3R,4R,5S)-2-methyl-1-(((R)-1-phenylpyrrolidin-3-yl)methyl)piperidine-3,4,5-triol as a white foam (6.5 mg, 47%). $^1$H NMR (400 MHz, $CD_3OD$) δ 7.27-7.05 (m, 2H), 6.61 (tt, J=7.4, 1.1 Hz, 1H), 6.58-6.55 (m, 2H), 3.51 (ddd, J=10.4, 9.0, 4.8 Hz, 1H), 3.41 (dd, J=9.3, 7.2 Hz, 1H), 3.38-3.31 (m, 1H), 3.28 (dd, J=8.1, 8.1 Hz, 1H), 3.20-3.11 (m, 2H), 3.10-3.03 (m, 1H), 2.98 (t, J=9.0 Hz, 1H), 2.83 (dd, J=13.0, 9.6 Hz, 1H), 2.74-2.58 (m, 1H), 2.41 (dd, J=13.0, 4.6 Hz, 1H), 2.25-1.99 (m, 3H), 1.71 (dd, J=12.1, 8.2 Hz, 1H), 1.21 (d, J=6.1 Hz, 3H); ESI MS m/z 307.16 $[M+H]^+$.

Example 114

(2R,3R,4R,5S)-2-methyl-1-(((R)-1-(o-tolyl)pyrrolidin-3-yl)methyl)piperidine-3,4,5-triol

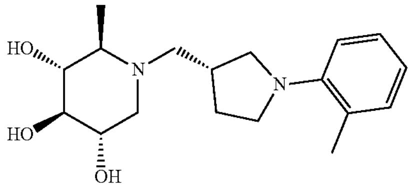 [SMILES: Cc1ccccc1N1CC[C@H](CN2C[C@H](O)[C@@H](O)[C@H](O)[C@H]2C)C1]

To a solution of (2R,3R,4R,5S)-3,4,5-tris(benzyloxy)-2-methyl-1-((S)-pyrrolidin-3-ylmethyl)piperidine (130 mg, 0.26 mmol) and 1-bromo-2-methylbenzene (88 mg, 0.52 mmol) in toluene (5 mL) was added $Pd_2(dba)_3$ (46 mg, 0.050 mmol) and RuPhos (46 mg, 0.10 mmol), followed with $Cs_2CO_3$ (326 mg, 1.0 mmol) under Ar. The mixture was stirred at 100° C. for 18 h, and then $H_2O$ was added at 0° C. The mixture was extracted with EtOAc (2×20 mL). The combined organic layer was washed with $H_2O$ (2×10 mL), separated, and dried over $Na_2SO_4$. After filtration the solvent was evaporated under reduced pressure, and the residue was purified on silica gel by flash chromatography affording (2R,3R,4R,5S)-3,4,5-tris(benzyloxy)-2-methyl-1-(((R)-1-(o-tolyl)pyrrolidin-3-yl)methyl)piperidine as an oil (121 mg, 79%). ESI MS m/z 591.33 $[M+H]^+$.

To a solution of the above material (120 mg, 0.20 mmol) in anhydrous DCM (5 mL) was added $BCl_3$ (1M in DCM, 0.97 mL, 0.97 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((R)-1-(o-tolyl)pyrrolidin-3-yl)methyl)piperidine-3,4,5-triol as a white solid (47 mg, 73%). $^1$H NMR (400 MHz, $CD_3OD$) δ 7.13-7.02 (m, 2H), 6.93 (dd, J=8.0, 1.2 Hz, 1H), 6.83 (td, J=7.4, 1.2 Hz, 1H), 3.52-3.44 (m, 1H), 3.28-3.20 (m, 1H), 3.19-3.04 (m, 5H), 2.96 (t, J=9.1 Hz, 1H), 2.90 (dd, J=12.9, 9.8 Hz, 1H), 2.60-2.47 (m, 1H), 2.34 (dd, J=12.9, 4.6

Hz, 1H), 2.31 (s, 3H), 2.18-2.07 (m, 2H), 2.04 (t, J=11.2 Hz, 1H), 1.64-1.52 (m, 1H), 1.23 (d, J=6.1 Hz, 3H); ESI MS m/z 321.18 $[M+H]^+$.

Example 115

(2R,3R,4R,5S)-2-methyl-1-(((R)-1-(2-(trifluoromethyl)phenyl)pyrrolidin-3-yl)methyl)piperidine-3,4,5-triol

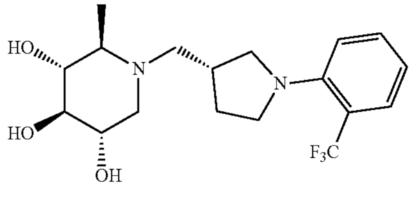 [SMILES: C[C@@H]1[C@@H](O)[C@H](O)[C@@H](O)CN1C[C@H]1CCN(c2ccccc2C(F)(F)F)C1]

Under Ar, to a solution of (S)-tert-butyl 3-formylpyrrolidine-1-carboxylate (420 mg, 2.1 mmol), (2R,3R,4R,5S)-3,4,5-tris(benzyloxy)-2-methylpiperidine (880 mg, 2.1 mmol) in anhydrous DCM (20 mL) was added $NaBH(OAc)_3$ (890 mg, 4.2 mmol). The mixture was stirred at RT for 18 h, satd. $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 30% EtOAc in hexanes, affording (R)-tert-butyl 3-(((2R,3R,4R,5S)-3,4,5-tris(benzyloxy)-2-methylpiperidin-1-yl)methyl)pyrrolidine-1-carboxylate as a white foam (1190 mg, 94%).

At 0° C. the above material (1190 mg, 1.98 mmol) in DCM (16 mL) was treated with TFA (4 mL) 2 h, then ice bath was removed, and the reaction was continued for additional 2 h. After evaporation of solvent under reduced pressure, the residue was dissolved in DCM (30 mL), the organic layer was washed with sat. $Na_2CO_3$, brine and dried over $Na_2SO_4$. After filtration the solvent was evaporated and the residue was purified on silica gel by flash chromatography using 10% MeOH and 2% $NH_3$ solution in DCM, affording (2R,3R,4R,5S)-3,4,5-tris(benzyloxy)-2-methyl-1-((S)-pyrrolidin-3-ylmethyl)piperidine as an oil (780 mg, 79%).

Under Ar, to a mixture of the above material (242 mg, 0.48 mmol), 1-bromo-2-$CF_3$-benzene (164 mg, 0.73 mmol), $Cs_2CO_3$ (184 mg, 0.6 mmol) and XPhos (11.5 mg, 0.024 mmol) in anhydrous and degassed toluene (5 mL) was added $Pd_2dba_3$ (4.4 mg, 0.005 mmol). The mixture was stirred at 85° C. in a sealed tube for 18 h, then cooled to RT. $Et_2O$ (50 mL) was added, and the resulting precipitate was filtered off. The filtrate was concentrated under reduced pressure, and the residue was purified on silica gel by flash chromatography using 15% EtOAc in hexanes, affording (2R,3R,4R,5S)-3,4,5-tris(benzyloxy)-2-methyl-1-(((R)-1-(2-(trifluoromethyl)phenyl)pyrrolidin-3-yl)methyl)piperidine as a white solid (43 mg, 14%).

At −78° C. under Ar, to a solution of the above material (40 mg, 0.062 mmol) in anhydrous DCM (2 mL) was added $BCl_3$ solution (0.5 mL, 1 M in DCM, 0.50 mmol). The mixture was stirred at −78 for 1 h and 0° C. for 4 h, MeOH (20 mL) was added. The mixture was stirred for an additional 2 h at 0° C., and evaporated to dryness under rotavap. The residue was purified on silica gel by flash chromatography (dry load) using 10% MeOH and 2% $NH_3$ solution in DCM, affording (2R,3R,4R,5S)-2-methyl-1-(((R)-1-(2-(trifluoromethyl)phenyl)pyrrolidin-3-yl)methyl)piperidine-3,4,5-triol as a white foam (10 mg, 60%). $^1H$ NMR (400 MHz, $CD_3OD$) δ 7.56 (dd, J=7.9, 1.7 Hz, 1H), 7.50-7.37 (m, 1H), 7.16 (d, J=8.4 Hz, 1H), 7.01-6.86 (m, 1H), 3.47 (ddd, J=10.5, 9.1, 4.8 Hz, 1H), 3.35-3.31 (m, 3H), 3.23-3.05 (m, 3H), 2.94 (t, J=9.0 Hz, 1H), 2.86 (dd, J=12.9, 9.7 Hz, 1H), 2.53 (td, J=11.6, 9.4, 5.8 Hz, 1H), 2.34 (dd, J=12.9, 4.5 Hz, 1H), 2.22-1.95 (m, 3H), 1.65-1.62 (m, 1H), 1.20 (d, J=6.1 Hz, 3H); ESI MS m/z 375.15 $[M+H]^+$.

Example 116

(2R,3R,4R,5S)-1-(((R)-1-(2-fluorophenyl)pyrrolidin-3-yl)methyl)-2-methylpiperidine-3,4,5-triol

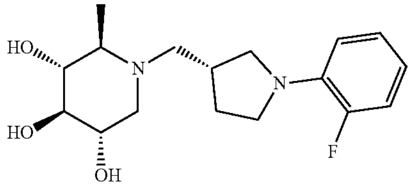 [SMILES: C[C@@H]1[C@@H](O)[C@H](O)[C@@H](O)CN1C[C@H]1CCN(c2ccccc2F)C1]

To a solution of (2R,3R,4R,5S)-3,4,5-tris(benzyloxy)-2-methyl-1-((S)-pyrrolidin-3-ylmethyl)piperidine (160 mg, 0.32 mmol) and 1-bromo-2-fluorobenzene (112 mg, 0.64 mmol) in toluene (5 mL) was added $Pd_2(dba)_3$ (59 mg, 0.064 mmol) and RuPhos (60 mg, 0.13 mmol), followed with $Cs_2CO_3$ (417 mg, 1.28 mmol) under Ar. The mixture was stirred at 100° C. for 18 h, and then $H_2O$ was added at 0° C. The mixture was extracted with EtOAc (2×20 mL). The combined organic layer was washed with $H_2O$ (2×10 mL), separated, and dried over $Na_2SO_4$. After filtration the solvent was evaporated under reduced pressure, and the residue was purified on silica gel by flash chromatography affording (2R,3R,4R,5S)-3,4,5-tris(benzyloxy)-1-(((R)-1-(2-fluorophenyl)pyrrolidin-3-yl)methyl)-2-methylpiperidine as an oil (101 mg, 53%). ESI MS m/z 595.30 $[M+H]^+$.

To a solution of the above material (100 mg, 0.17 mmol) in anhydrous DCM (5 mL) was added $BCl_3$ (1M in DCM, 0.84 mL, 0.84 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-1-(((R)-1-(2-fluorophenyl)pyrrolidin-3-yl)methyl)-2-methylpiperidine-3,4,5-triol as a white solid (38 mg, 69%). $^1H$ NMR (400 MHz, $CD_3OD$) δ 7.02-6.91 (m, 2H), 6.74 (td, J=8.7, 8.2, 1.6 Hz, 1H), 6.71-6.64 (m, 1H), 3.56-3.36 (m, 4H), 3.21 (ddd, J=9.5, 7.0, 2.4 Hz, 1H), 3.17-3.10 (m, 2H), 2.97 (t, J=9.1 Hz, 1H), 2.88-2.77 (m, 1H), 2.61-2.47 (m, 1H), 2.38 (dd, J=13.0, 4.5 Hz, 1H), 2.19-2.00 (m, 3H), 1.70-1.57 (m, 1H), 1.22 (d, J=6.1 Hz, 3H); ESI MS m/z 325.16 $[M+H]^+$.

Example 117

(2R,3R,4R,5S)-1-(((R)-1-(3-fluorophenyl)pyrrolidin-3-yl)methyl)-2-methylpiperidine-3,4,5-triol

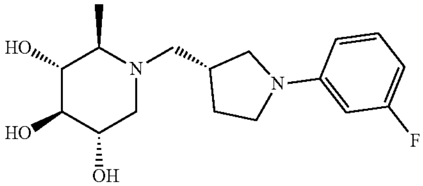 [SMILES: C[C@@H]1[C@@H](O)[C@H](O)[C@@H](O)CN1C[C@H]1CCN(c2cccc(F)c2)C1]

To a solution of (2R,3R,4R,5S)-3,4,5-tris(benzyloxy)-2-methyl-1-((S)-pyrrolidin-3-ylmethyl)piperidine (160 mg, 0.32 mmol) and 1-bromo-3-fluorobenzene (112 mg, 0.64 mmol) in toluene (5 mL) was added $Pd_2(dba)_3$ (59 mg, 0.064 mmol) and RuPhos (60 mg, 0.13 mmol), followed with $Cs_2CO_3$ (417 mg, 1.28 mmol) under Ar. The mixture was stirred at 100° C. for 18 h, and then $H_2O$ was added at 0° C. The mixture was extracted with EtOAc (2×20 mL). The combined organic layer was washed with $H_2O$ (2×10 mL), separated, and dried over $Na_2SO_4$. After filtration the solvent was evaporated under reduced pressure, and the residue was purified on silica gel by flash chromatography affording (2R,3R,4R,5S)-3,4,5-tris(benzyloxy)-1-(((R)-1-(3-fluorophenyl)pyrrolidin-3-yl)methyl)-2-methylpiperidine as an oil (163 mg, 85%). ESI MS m/z 595.30 $[M+H]^+$.

To a solution of the above material (160 mg, 0.27 mmol) in anhydrous DCM (5 mL) was added $BCl_3$ (1M in DCM, 1.35 mL, 1.35 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-1-(((R)-1-(3-fluorophenyl)pyrrolidin-3-yl)methyl)-2-methylpiperidine-3,4,5-triol as a white solid (71 mg, 81%). $^1$H NMR (400 MHz, DMSO-$d_6$) δ 7.14 (td, J=8.2, 7.2 Hz, 1H), 6.40-6.26 (m, 3H), 4.71-4.67 (m, 3H), 3.31-3.16 (m, 4H), 3.01-2.88 (m, 3H), 2.78-2.70 (m, 1H), 2.66 (dd, J=12.8, 9.7 Hz, 1H), 2.50-2.42 (m, 1H), 2.21 (dd, J=12.7, 4.7 Hz, 1H), 2.11-2.00 (m, 1H), 1.99-1.84 (m, 2H), 1.69-1.58 (m, 1H), 1.05 (d, J=6.1 Hz, 3H); ESI MS m/z 325.16 $[M+H]^+$.

Example 118

(2R,3R,4R,5S)-2-methyl-1-(((R)-1-(2-(trifluoromethoxy)phenyl)pyrrolidin-3-yl)methyl)piperidine-3,4,5-triol

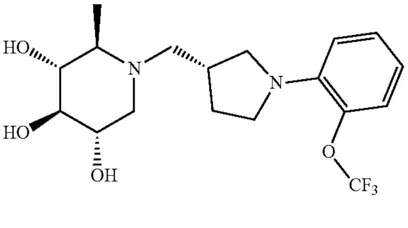 [SMILES: C[C@@H]1[C@@H](O)[C@H](O)[C@@H](O)CN1C[C@H]1CCN(c2ccccc2OC(F)(F)F)C1]

To a solution of (2R,3R,4R,5S)-3,4,5-tris(benzyloxy)-2-methyl-1-((S)-pyrrolidin-3-ylmethyl)piperidine (130 mg, 0.26 mmol) and 1-bromo-2-(trifluoromethoxy)benzene (125 mg, 0.52 mmol) in toluene (5 mL) was added $Pd_2(dba)_3$ (46 mg, 0.050 mmol) and RuPhos (46 mg, 0.10 mmol), followed with $Cs_2CO_3$ (326 mg, 1.0 mmol) under Ar. The mixture was stirred at 100° C. for 18 h, and then $H_2O$ was added at 0° C. The mixture was extracted with EtOAc (2×20 mL). The combined organic layer was washed with $H_2O$ (2×10 mL), separated, and dried over $Na_2SO_4$. After filtration the solvent was evaporated under reduced pressure, and the residue was purified on silica gel by flash chromatography affording (2R,3R,4R,5S)-3,4,5-tris(benzyloxy)-2-methyl-1-(((R)-1-(2-(trifluoromethoxy)phenyl)pyrrolidin-3-yl)methyl)piperidine as an oil (83 mg, 48%). ESI MS m/z 661.30 $[M+H]^+$.

To a solution of the above material (80 mg, 0.12 mmol) in anhydrous DCM (5 mL) was added $BCl_3$ (1M in DCM, 0.97 mL, 0.97 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((R)-1-(2-(trifluoromethoxy)phenyl)pyrrolidin-3-yl)methyl)piperidine-3,4,5-triol as a white solid (15 mg, 32%). $^1$H NMR (400 MHz, $CD_3OD$) δ 7.21-7.11 (m, 2H), 6.84 (dd, J=8.3, 1.5 Hz, 1H), 6.73 (ddd, J=8.0, 7.3, 1.5 Hz, 1H), 3.54-3.38 (m, 4H), 3.25 (dd, J=9.5, 6.7 Hz, 1H), 3.17-3.10 (m, 2H), 2.96 (t, J=9.1 Hz, 1H), 2.83 (dd, J=12.9, 9.7 Hz, 1H), 2.60-2.47 (m, 1H), 2.37 (dd, J=12.9, 4.5 Hz, 1H), 2.18-2.01 (m, 3H), 1.71-1.60 (m, 1H), 1.20 (d, J=6.1 Hz, 3H); ESI MS m/z 391.15 $[M+H]^+$.

Example 119

(2R,3R,4R,5S)-2-methyl-1-(((R)-1-(6-(trifluoromethyl)pyridin-2-yl)pyrrolidin-3-yl)methyl)piperidine-3,4,5-triol

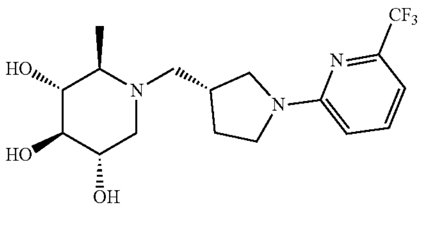 [SMILES: C[C@@H]1[C@@H](O)[C@H](O)[C@@H](O)CN1C[C@H]1CCN(c2cccc(C(F)(F)F)n2)C1]

To a solution of (2R,3R,4R,5S)-3,4,5-tris(benzyloxy)-2-methyl-1-((S)-pyrrolidin-3-ylmethyl)piperidine (125 mg, 0.25 mmol) and 2-chloro-6-(trifluoromethyl)pyridine (91 mg, 0.50 mmol) in toluene (5 mL) was added $Pd_2(dba)_3$ (26 mg, 0.028 mmol) and RuPhos (26 mg, 0.056 mmol), followed with $Cs_2CO_3$ (182 mg, 0.56 mmol) under Ar. The mixture was stirred at 100° C. for 18 h, and then $H_2O$ was added at 0° C. The mixture was extracted with EtOAc (2×20 mL). The combined organic layer was washed with $H_2O$ (2×10 mL), separated, and dried over $Na_2SO_4$. After filtration the solvent was evaporated under reduced pressure, and the residue was purified on silica gel by flash chromatography affording 2-(trifluoromethyl)-6-((R)-3-(((2R,3R,4R, 5S)-3,4,5-tris(benzyloxy)-2-methylpiperidin-1-yl)methyl)pyrrolidin-1-yl)pyridine as an oil (158 mg, 98%). ESI MS m/z 646.30 [M+H]+.

To a solution of the above material (158 mg, 0.24 mmol) in anhydrous DCM (5 mL) was added $BCl_3$ (1M in DCM, 0.97 mL, 0.97 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((R)-1-(6-(trifluoromethyl)pyridin-2-yl)pyrrolidin-3-yl)methyl)piperidine-3,4,5-triol as a white solid (49 mg, 54%). $^1$H NMR (400 MHz, $CD_3OD$) δ 7.60 (ddd, J=8.5, 7.3, 0.9 Hz, 1H), 6.87 (d, J=7.2 Hz, 1H), 6.62 (d, J=8.6 Hz, 1H), 3.68 (dd, J=10.6, 7.1 Hz, 1H), 3.63-3.48 (m, 2H), 3.47-3.38 (m, 1H), 3.22 (dd, J=10.6, 7.5 Hz, 1H), 3.19-3.12 (m, 2H), 2.99 (t, J=9.1 Hz, 1H), 2.82 (dd, J=13.0, 9.7 Hz, 1H), 2.65-2.51 (m, 1H), 2.46-2.33 (m, 1H), 2.22-2.04 (m, 3H), 1.78-1.66 (m, 1H), 1.20 (d, J=6.1 Hz, 3H); ESI MS m/z 376.15 [M+H]+.

Example 120

(2R,3R,4R,5S)-2-methyl-1-(((R)-1-(3-(trifluoromethyl)pyridin-2-yl)pyrrolidin-3-yl)methyl)piperidine-3,4,5-triol

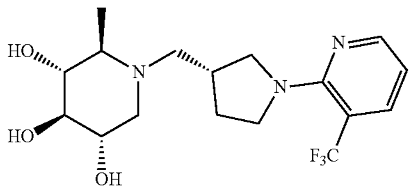 [SMILES: C[C@@H]1[C@@H](O)[C@H](O)[C@@H](O)CN1C[C@H]1CCN(c2ncccc2C(F)(F)F)C1]

To a solution of (2R,3R,4R,5S)-3,4,5-tris(benzyloxy)-2-methyl-1-((S)-pyrrolidin-3-ylmethyl)piperidine (125 mg, 0.25 mmol) and 2-chloro-3-(trifluoromethyl)pyridine (91 mg, 0.50 mmol) in toluene (5 mL) was added $Pd_2(dba)_3$ (26 mg, 0.028 mmol) and RuPhos (26 mg, 0.056 mmol), followed with $Cs_2CO_3$ (182 mg, 0.56 mmol) under Ar. The mixture was stirred at 100° C. for 18 h, and then $H_2O$ was added at 0° C. The mixture was extracted with EtOAc (2×20 mL). The combined organic layer was washed with $H_2O$ (2×10 mL), separated, and dried over $Na_2SO_4$. After filtration the solvent was evaporated under reduced pressure, and the residue was purified on silica gel by flash chromatography affording 3-(trifluoromethyl)-2-((R)-3-(((2R,3R,4R,5S)-3,4,5-tris(benzyloxy)-2-methylpiperidin-1-yl)methyl)pyrrolidin-1-yl)pyridine as an oil (157 mg, 98%). ESI MS m/z 646.30 [M+H]+.

To a solution of the above material (154 mg, 0.24 mmol) in anhydrous DCM (5 mL) was added $BCl_3$ (1M in DCM, 0.97 mL, 0.97 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((R)-1-(3-(trifluoromethyl)pyridin-2-yl)pyrrolidin-3-yl)methyl)piperidine-3,4,5-triol as a white solid (35 mg, 39%). $^1$H NMR (400 MHz, $CD_3OD$) δ 8.30-8.23 (m, 1H), 7.87 (dd, J=7.8, 1.9 Hz, 1H), 6.74 (dd, J=7.8, 4.7 Hz, 1H), 3.72-3.58 (m, 3H), 3.52-3.40 (m, 2H), 3.18-3.06 (m, 2H), 2.94 (t, J=9.0 Hz, 1H), 2.77 (dd, J=13.0, 9.6 Hz, 1H), 2.57-2.46 (m, 1H), 2.45-2.33 (m, 1H), 2.19-1.98 (m, 3H), 1.72-1.59 (m, 1H), 1.16 (d, J=6.1 Hz, 3H); ESI MS m/z 376.15 [M+H]+.

Example 121

(2R,3R,4R,5S)-2-methyl-1-(((R)-1-(4-(trifluoromethyl)pyridin-2-yl)pyrrolidin-3-yl)methyl)piperidine-3,4,5-triol

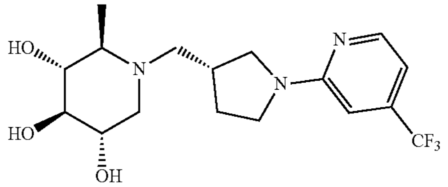 [SMILES: C[C@@H]1[C@@H](O)[C@H](O)[C@@H](O)CN1C[C@H]1CCN(c2cc(C(F)(F)F)ccn2)C1]

To a solution of (2R,3R,4R,5S)-3,4,5-tris(benzyloxy)-2-methyl-1-((S)-pyrrolidin-3-ylmethyl)piperidine (125 mg, 0.25 mmol) and 2-bromo-4-(trifluoromethyl)pyridine (113 mg, 0.50 mmol) in toluene (5 mL) was added $Pd_2(dba)_3$ (46 mg, 0.050 mmol) and RuPhos (46 mg, 0.10 mmol), followed with $Cs_2CO_3$ (326 mg, 1.0 mmol) under Ar. The mixture was stirred at 100° C. for 18 h, and then $H_2O$ was added at 0° C. The mixture was extracted with EtOAc (2×20 mL). The combined organic layer was washed with $H_2O$ (2×10 mL), separated, and dried over $Na_2SO_4$. After filtration the solvent was evaporated under reduced pressure, and the residue was purified on silica gel by flash chromatography affording 4-(trifluoromethyl)-2-((R)-3-(((2R,3R,4R,5S)-3,4,5-tris(benzyloxy)-2-methylpiperidin-1-yl)methyl)pyrrolidin-1-yl)pyridine as an oil (127 mg, 78%). ESI MS m/z 646.30 [M+H]+.

To a solution of the above material (128 mg, 0.20 mmol) in anhydrous DCM (5 mL) was added $BCl_3$ (1M in DCM, 0.97 mL, 0.97 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((R)-1-(4-(trifluoromethyl)pyridin-2-yl)pyrrolidin-3-yl)methyl)piperidine-3,4,5-triol as a white solid (36 mg, 48%). $^1$H NMR (400 MHz, $CD_3OD$) δ 8.21 (d, J=5.3 Hz, 1H), 6.75 (dd, J=5.3, 1.5 Hz, 1H), 6.66 (s, 1H), 3.67 (dd, J=10.5, 7.1 Hz, 1H), 3.64-3.56 (m, 1H), 3.56-3.41 (m, 2H), 3.26 (dd, J=10.5, 7.4 Hz, 1H), 3.18-3.11 (m, 2H), 2.97 (t, J=9.0 Hz, 1H), 2.82 (dd, J=13.0, 9.8 Hz, 1H), 2.70-2.56 (m, 1H), 2.41 (dd, J=12.9, 4.5 Hz, 1H), 2.27-2.04 (m, 3H), 1.81-1.71 (m, 1H), 1.20 (d, J=6.1 Hz, 3H); ESI MS m/z 376.15 [M+H]+.

Example 122

(2R,3R,4R,5S)-2-methyl-1-(((R)-1-(pyridin-3-yl)pyrrolidin-3-yl)methyl)piperidine-3,4,5-triol

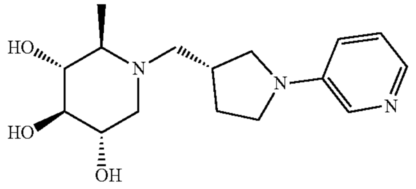 [SMILES: C[C@@H]1[C@@H](O)[C@H](O)[C@@H](O)CN1C[C@H]1CCN(c2cccnc2)C1]

To a solution of (2R,3R,4R,5S)-3,4,5-tris(benzyloxy)-2-methyl-1-((S)-pyrrolidin-3-ylmethyl)piperidine (125 mg, 0.25 mmol) and 3-bromopyridine (78 mg, 0.50 mmol) in toluene (5 mL) was added $Pd_2(dba)_3$ (46 mg, 0.050 mmol) and RuPhos (46 mg, 0.10 mmol), followed with $Cs_2CO_3$ (326 mg, 1.0 mmol) under Ar. The mixture was stirred at 100° C. for 18 h, and then $H_2O$ was added at 0° C. The mixture was extracted with EtOAc (2×20 mL). The combined organic layer was washed with $H_2O$ (2×10 mL), separated, and dried over $Na_2SO_4$. After filtration the solvent was evaporated under reduced pressure, and the residue was purified on silica gel by flash chromatography affording 3-((R)-3-(((2R,3R,4R,5S)-3,4,5-tris(benzyloxy)-2-methylpiperidin-1-yl)methyl)pyrrolidin-1-yl)pyridine as an oil (66 mg, 46%). ESI MS m/z 578.31 $[M+H]^+$.

To a solution of the above material (66 mg, 0.11 mmol) in anhydrous DCM (5 mL) was added $BCl_3$ (1M in DCM, 0.97 mL, 0.97 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((R)-1-(pyridin-3-yl)pyrrolidin-3-yl)methyl)piperidine-3,4,5-triol as a white solid (13 mg, 38%). $^1H$ NMR (400 MHz, $CD_3OD$) δ 7.87 (s, 1H), 7.79 (d, J=4.6 Hz, 1H), 7.22 (dd, J=8.5, 4.7 Hz, 1H), 7.00 (ddd, J=8.5, 3.0, 1.3 Hz, 1H), 3.57-3.37 (m, 3H), 3.36-3.23 (m, 1H), 3.18-3.09 (m, 3H), 2.97 (t, J=9.0 Hz, 1H), 2.83 (dd, J=13.0, 9.7 Hz, 1H), 2.70-2.56 (m, 1H), 2.40 (dd, J=12.9, 4.5 Hz, 1H), 2.27-2.04 (m, 3H), 1.81-1.68 (m, 1H), 1.20 (d, J=6.1 Hz, 3H); ESI MS m/z 308.16 $[M+H]^+$.

Example 123

(2R,3R,4R,5S)-2-methyl-1-(((R)-1-(4-methylpyridin-3-yl)pyrrolidin-3-yl)methyl)piperidine-3,4,5-triol

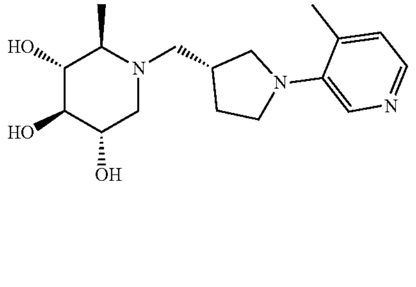 [SMILES: Cc1ccncc1N1CC[C@H](CN2C[C@H](O)[C@@H](O)[C@H](O)[C@H]2C)C1]

To a solution of (2R,3R,4R,5S)-3,4,5-tris(benzyloxy)-2-methyl-1-((S)-pyrrolidin-3-ylmethyl)piperidine (70 mg, 0.14 mmol) and 3-bromo-4-methylpyridine (48 mg, 0.28 mmol) in toluene (5 mL) was added $Pd_2(dba)_3$ (26 mg, 0.028 mmol) and RuPhos (26 mg, 0.056 mmol), followed with $Cs_2CO_3$ (182 mg, 0.56 mmol) under Ar. The mixture was stirred at 100° C. for 18 h, and then $H_2O$ was added at 0° C. The mixture was extracted with EtOAc (2×20 mL). The combined organic layer was washed with $H_2O$ (2×10 mL), separated, and dried over $Na_2SO_4$. After filtration the solvent was evaporated under reduced pressure, and the residue was purified on silica gel by flash chromatography affording 4-methyl-3-((R)-3-(((2R,3R,4R,5S)-3,4,5-tris(benzyloxy)-2-methylpiperidin-1-yl)methyl)pyrrolidin-1-yl)pyridine as an oil (38 mg, 46%). ESI MS m/z 592.36 $[M+H]^+$.

To a solution of the above material (38 mg, 0.064 mmol) in anhydrous DCM (5 mL) was added $BCl_3$ (1M in DCM, 0.97 mL, 0.97 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((R)-1-(4-methylpyridin-3-yl)pyrrolidin-3-yl)methyl)piperidine-3,4,5-triol as a white solid (5 mg, 24%). $^1H$ NMR (400 MHz, $CD_3OD$) δ 8.02 (s, 1H), 7.93 (s, 1H), 7.15 (d, J=4.7 Hz, 1H), 3.53-3.45 (m, 2H), 3.43-3.27 (m, 3H), 3.21 (dd, J=9.1, 6.6 Hz, 1H), 3.18-3.10 (m, 2H), 2.96 (t, J=9.1 Hz, 1H), 2.90 (dd, J=12.9, 9.7 Hz, 1H), 2.63-2.50 (m, 1H), 2.43-2.32 (m, 4H), 2.21-2.11 (m, 2H), 2.06 (t, J=10.9 Hz, 1H), 1.72-1.59 (m, 1H), 1.23 (d, J=6.1 Hz, 3H); ESI MS m/z 322.21 $[M+H]^+$.

Example 124

(2R,3R,4R,5S)-2-methyl-1-(((R)-1-(4-(trifluoromethyl)pyridin-3-yl)pyrrolidin-3-yl)methyl)piperidine-3,4,5-triol

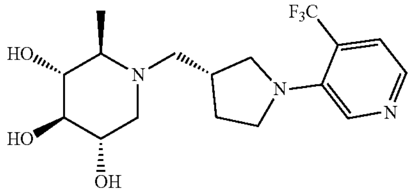 [SMILES: C[C@@H]1[C@@H](O)[C@H](O)[C@@H](O)CN1C[C@H]1CCN(c2cnccc2C(F)(F)F)C1]

To a solution of (2R,3R,4R,5S)-3,4,5-tris(benzyloxy)-2-methyl-1-((S)-pyrrolidin-3-ylmethyl)piperidine (120 mg, 0.24 mmol) and 3-bromo-4-(trifluoromethyl)pyridine (108 mg, 0.48 mmol) in toluene (5 mL) was added $Pd_2(dba)_3$ (46 mg, 0.050 mmol) and RuPhos (46 mg, 0.10 mmol), followed with $Cs_2CO_3$ (326 mg, 1.0 mmol) under Ar. The mixture was stirred at 100° C. for 18 h, and then $H_2O$ was added at 0° C. The mixture was extracted with EtOAc (2×20 mL). The combined organic layer was washed with $H_2O$ (2×10 mL), separated, and dried over $Na_2SO_4$. After filtration the solvent was evaporated under reduced pressure, and the residue was purified on silica gel by flash chromatography affording 4-(trifluoromethyl)-3-((R)-3-(((2R,3R,4R,5S)-3,4,5-tris (benzyloxy)-2-methylpiperidin-1-yl)methyl)pyrrolidin-1-yl)pyridine as an oil (75 mg, 48%). ESI MS m/z 646.31 $[M+H]^+$.

To a solution of the above material (75 mg, 0.12 mmol) in anhydrous DCM (5 mL) was added $BCl_3$ (1M in DCM, 0.97 mL, 0.97 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((R)-1-(4-(trifluoromethyl)pyridin-3-yl)pyrrolidin-3-yl)methyl)piperidine-3,4,5-triol as a white solid (18 mg, 41%). $^1H$ NMR (400 MHz, $CD_3OD$) δ 8.32 (s, 1H), 8.01 (d, J=5.2 Hz, 1H), 7.50 (d, J=5.2 Hz, 1H), 3.58-3.43 (m, 4H), 3.39-3.34 (m, 1H), 3.17-3.08 (m, 2H), 2.94 (t, J=9.0 Hz, 1H), 2.83 (dd, J=13.0, 9.8 Hz, 1H), 2.64-2.52 (m, 1H), 2.37 (dd, J=13.0, 4.6 Hz, 1H), 2.25-1.97 (m, 3H), 1.78-1.66 (m, 1H), 1.18 (d, J=6.1 Hz, 3H); ESI MS m/z 376.15 $[M+H]^+$.

Example 125

(2R,3R,4R,5S)-2-methyl-1-(((R)-1-(5-(trifluoromethyl)pyridin-3-yl)pyrrolidin-3-yl)methyl)piperidine-3,4,5-triol

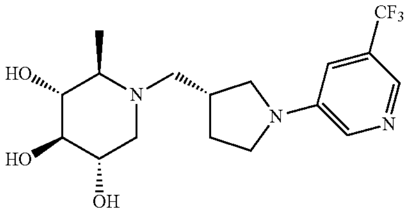 [SMILES: C[C@@H]1[C@@H](O)[C@H](O)[C@@H](O)CN1C[C@H]1CCN(c2cncc(C(F)(F)F)c2)C1]

To a solution of (2R,3R,4R,5S)-3,4,5-tris(benzyloxy)-2-methyl-1-((S)-pyrrolidin-3-ylmethyl)piperidine (125 mg, 0.25 mmol) and 3-bromo-5-(trifluoromethyl)pyridine (113 mg, 0.50 mmol) in toluene (5 mL) was added $Pd_2(dba)_3$ (46 mg, 0.050 mmol) and RuPhos (46 mg, 0.10 mmol), followed with $Cs_2CO_3$ (326 mg, 1.0 mmol) under Ar. The mixture was stirred at 100° C. for 18 h, and then $H_2O$ was added at 0° C. The mixture was extracted with EtOAc (2×20 mL). The combined organic layer was washed with $H_2O$ (2×10 mL), separated, and dried over $Na_2SO_4$. After filtration the solvent was evaporated under reduced pressure, and the residue was purified on silica gel by flash chromatography affording 3-(trifluoromethyl)-5-((R)-3-(((2R,3R,4R,5S)-3,4,5-tris(benzyloxy)-2-methylpiperidin-1-yl)methyl)pyrrolidin-1-yl)pyridine as an oil (128 mg, 78%). ESI MS m/z 646.31 $[M+H]^+$.

To a solution of the above material (127 mg, 0.20 mmol) in anhydrous DCM (5 mL) was added $BCl_3$ (1M in DCM, 0.97 mL, 0.97 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((R)-1-(5-(trifluoromethyl)pyridin-3-yl)pyrrolidin-3-yl)methyl)piperidine-3,4,5-triol as a white solid (35 mg, 48%). $^1H$ NMR (400 MHz, $CD_3OD$) δ 8.10 (d, J=2.8 Hz, 1H), 8.05 (t, J=1.2 Hz, 1H), 7.12 (t, J=2.3 Hz, 1H), 3.56-3.44 (m, 3H), 3.42-3.34 (m, 1H), 3.21-3.11 (m, 3H), 2.98 (t, J=9.0 Hz, 1H), 2.84 (dd, J=13.0, 9.8 Hz, 1H), 2.73-2.59 (m, 1H), 2.41 (dd, J=12.9, 4.6 Hz, 1H), 2.29-2.18 (m, 1H), 2.18-2.02 (m, 2H), 1.86-1.73 (m, 1H), 1.20 (d, J=6.1 Hz, 3H); ESI MS m/z 376.15 $[M+H]^+$.

Example 126

(2R,3R,4R,5S)-2-methyl-1-(((R)-1-(2-(trifluoromethyl)pyridin-3-yl)pyrrolidin-3-yl)methyl)piperidine-3,4,5-triol

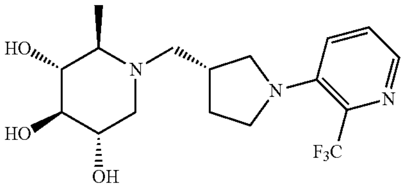 [SMILES: C[C@@H]1[C@@H](O)[C@H](O)[C@@H](O)CN1C[C@H]1CCN(c2cccnc2C(F)(F)F)C1]

To a solution of (2R,3R,4R,5S)-3,4,5-tris(benzyloxy)-2-methyl-1-((S)-pyrrolidin-3-ylmethyl)piperidine (120 mg, 0.24 mmol) and 3-bromo-2-(trifluoromethyl)pyridine (108 mg, 0.48 mmol) in toluene (5 mL) was added $Pd_2(dba)_3$ (46 mg, 0.050 mmol) and RuPhos (46 mg, 0.10 mmol), followed with $Cs_2CO_3$ (326 mg, 1.0 mmol) under Ar. The mixture was stirred at 100° C. for 18 h, and then $H_2O$ was added at 0° C. The mixture was extracted with EtOAc (2×20 mL). The combined organic layer was washed with $H_2O$ (2×10 mL), separated, and dried over $Na_2SO_4$. After filtration the solvent was evaporated under reduced pressure, and the residue was purified on silica gel by flash chromatography affording 2-(trifluoromethyl)-3-((R)-3-(((2R,3R,4R,5S)-3,4,5-tris(benzyloxy)-2-methylpiperidin-1-yl)methyl)pyrrolidin-1-yl)pyridine as an oil (80 mg, 51%). ESI MS m/z 646.31 $[M+H]^+$.

To a solution of the above material (80 mg, 0.12 mmol) in anhydrous DCM (5 mL) was added $BCl_3$ (1M in DCM, 0.97 mL, 0.97 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((R)-1-(2-(trifluoromethyl)pyridin-3-yl)pyrrolidin-3-yl)methyl)piperidine-3,4,5-triol as a white solid (23 mg, 51%). $^1H$ NMR (400 MHz, $CD_3OD$) δ 8.01 (dd, J=4.3, 1.3 Hz, 1H), 7.51 (dd, J=8.6, 1.3 Hz, 1H), 7.43 (dd, J=8.6, 4.2 Hz, 1H), 3.51-3.39 (m, 4H), 3.31-3.24 (m, 1H), 3.16-3.04 (m, 2H), 2.94 (t, J=9.0 Hz, 1H), 2.82 (dd, J=13.0, 9.8 Hz, 1H), 2.62-2.50 (m, 1H), 2.36 (dd, J=13.0, 4.6 Hz, 1H), 2.20-2.01 (m, 3H), 1.75-1.64 (m, 1H), 1.17 (d, J=6.1 Hz, 3H); ESI MS m/z 376.15 $[M+H]^+$.

Example 127

(2R,3R,4R,5S)-2-methyl-1-(((R)-1-(4-(trifluoromethyl)pyrimidin-5-yl)pyrrolidin-3-yl)methyl)piperidine-3,4,5-triol

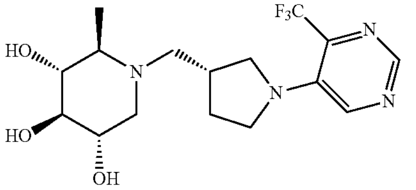 [SMILES: C[C@@H]1[C@@H](O)[C@H](O)[C@@H](O)CN1C[C@H]1CCN(c2cncnc2C(F)(F)F)C1]

To a solution of (2R,3R,4R,5S)-3,4,5-tris(benzyloxy)-2-methyl-1-((S)-pyrrolidin-3-ylmethyl)piperidine (125 mg, 0.25 mmol) and 5-bromo-4-(trifluoromethyl)pyrimidine (113 mg, 0.50 mmol) in toluene (5 mL) was added $Pd_2(dba)_3$ (46 mg, 0.050 mmol) and RuPhos (46 mg, 0.10 mmol), followed with $Cs_2CO_3$ (326 mg, 1.0 mmol) under Ar. The mixture was stirred at 100° C. for 18 h, and then $H_2O$ was added at 0° C. The mixture was extracted with EtOAc (2×20 mL). The combined organic layer was washed with $H_2O$ (2×10 mL), separated, and dried over $Na_2SO_4$. After filtration the solvent was evaporated under reduced pressure, and the residue was purified on silica gel by flash chromatography affording 4-(trifluoromethyl)-5-((R)-3-(((2R,3R,4R,5S)-3,4,5-tris(benzyloxy)-2-methylpiperidin-1-yl)methyl)pyrrolidin-1-yl)pyrimidine as an oil (82 mg, 51%). ESI MS m/z 647.30 $[M+H]^+$.

To a solution of the above material (82 mg, 0.13 mmol) in anhydrous DCM (5 mL) was added $BCl_3$ (1M in DCM, 0.97 mL, 0.97 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((R)-1-(4-(trifluoromethyl)pyrimidin-5-yl)pyrrolidin-3-yl)methyl)piperidine-3,4,5-triol as a white solid (16 mg, 33%). $^1H$ NMR (400 MHz, $CD_3OD$) δ 8.55 (s, 1H), 8.53 (s, 1H), 3.60-3.52 (m, 3H), 3.52-3.43 (m, 1H), 3.40-3.34 (m, 1H), 3.19-3.07 (m, 2H), 2.94 (t, J=9.0 Hz, 1H), 2.80 (dd, J=13.0, 9.8 Hz, 1H), 2.65-2.54 (m, 1H), 2.38 (dd, J=13.0, 4.6 Hz, 1H), 2.23-2.10 (m, 2H), 2.10-2.00 (m, 1H), 1.81-1.68 (m, 1H), 1.17 (d, J=6.1 Hz, 3H); ESI MS m/z 377.14 $[M+H]^+$.

Example 128

(2R,3R,4R,5S)-2-methyl-1-(((R)-1-(thiophen-3-yl)pyrrolidin-3-yl)methyl)piperidine-3,4,5-triol

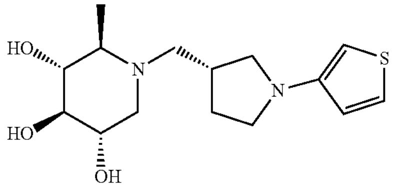 [SMILES: C[C@@H]1[C@@H](O)[C@H](O)[C@@H](O)CN1C[C@H]1CCN(c2ccsc2)C1]

To a solution of (2R,3R,4R,5S)-3,4,5-tris(benzyloxy)-2-methyl-1-((S)-pyrrolidin-3-ylmethyl)piperidine (220 mg, 0.44 mmol) and 3-bromothiophene (143 mg, 0.88 mmol) in deanol (5 mL) was added copper powder (11 mg, 0.18 mmol) and CuI (35 mg, 0.18 mmol), followed with $K_3PO_4$ (187 mg, 0.88 mmol) under Ar. The mixture was stirred at 80° C. for 48 h, and then $H_2O$ was added at 0° C. The mixture was extracted with EtOAc (2×20 mL).

The combined organic layer was washed with $H_2O$ (2×10 mL), separated, and dried over $Na_2SO_4$. After filtration the solvent was evaporated under reduced pressure, and the residue was purified on silica gel by flash chromatography affording (2R,3R,4R,5S)-3,4,5-tris(benzyloxy)-2-methyl-1-(((R)-1-(thiophen-3-yl)pyrrolidin-3-yl)methyl)piperidine as an oil (44 mg, 17%). ESI MS m/z 583.26 $[M+H]^+$.

To a solution of (2R,3R,4R,5S)-3,4,5-tris(benzyloxy)-2-methyl-1-(((R)-1-(thiophen-3-yl)pyrrolidin-3-yl)methyl)piperidine (40 mg, 0.069 mmol) in anhydrous DCM (5 mL) was added $BCl_3$ (1M in DCM, 0.50 mL, 0.50 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((R)-1-(thiophen-3-yl)pyrrolidin-3-yl)methyl)piperidine-3,4,5-triol as a white solid (6.0 mg, 28%). $^1H$ NMR (400 MHz, $CD_3OD$) δ 7.25 (dd, J=5.2, 3.2 Hz, 1H), 6.73 (dd, J=5.2, 1.2 Hz, 1H), 5.92 (dd, J=3.1, 1.5 Hz, 1H), 3.54-3.46 (m, 1H), 3.41-3.34 (m, 1H), 3.32-3.20 (m, 2H), 3.17-3.10 (m, 2H), 3.04 (dd, J=9.2, 6.7 Hz, 1H), 2.97 (t, J=9.1 Hz, 1H), 2.83 (dd, J=12.9, 9.8 Hz, 1H), 2.64-2.52 (m, 1H), 2.36 (dd, J=12.9, 4.6 Hz, 1H), 2.19-2.01 (m, 3H), 1.72-1.60 (m, 1H), 1.21 (d, J=6.1 Hz, 3H); ESI MS m/z 313.12 $[M+H]^+$.

Example 129

(2R,3R,4R,5S)-1-(((R)-1-(benzo[d]thiazol-4-yl)pyrrolidin-3-yl)methyl)-2-methylpiperidine-3,4,5-triol

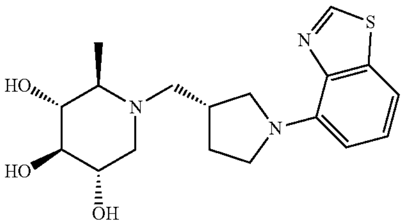 [SMILES: C[C@@H]1[C@@H](O)[C@H](O)[C@@H](O)CN1C[C@H]1CCN(c2cccc3scnc23)C1]

To a solution of (2R,3R,4R,5S)-3,4,5-tris(benzyloxy)-2-methyl-1-((S)-pyrrolidin-3-ylmethyl)piperidine (70 mg, 0.14 mmol) and 4-bromo-1,3-benzothiazole (60 mg, 0.28 mmol) in toluene (5 mL) was added $Pd_2(dba)_3$ (26 mg, 0.028 mmol) and RuPhos (26 mg, 0.056 mmol), followed with $Cs_2CO_3$ (182 mg, 0.56 mmol) under Ar. The mixture was stirred at 100° C. for 18 h, and then $H_2O$ was added at 0° C. The mixture was extracted with EtOAc (2×20 mL). The combined organic layer was washed with $H_2O$ (2×10 mL), separated, and dried over $Na_2SO_4$. After filtration the solvent was evaporated under reduced pressure, and the residue was purified on silica gel by flash chromatography affording 7-((R)-3-(((2R,3R,4R,5S)-3,4,5-tris(benzyloxy)-2-methylpiperidin-1-yl)methyl)pyrrolidin-1-yl)benzo[d]thiazole as an oil (31 mg, 35%). ESI MS m/z 634.31 $[M+H]^+$.

To a solution of the above material (31 mg, 0.049 mmol) in anhydrous DCM (5 mL) was added $BCl_3$ (1M in DCM, 0.97 mL, 0.97 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-1-(((R)-1-(benzo[d]thiazol-4-yl)pyrrolidin-3-yl)methyl)-2-methylpiperidine-3,4,5-triol as a white solid (12 mg, 67%). $^1H$ NMR (400 MHz, $CD_3OD$) δ 8.86 (s, 1H), 7.31-7.20 (m, 2H), 6.61 (dd, J=6.9, 2.1 Hz, 1H), 3.88 (dd, J=10.2, 7.1 Hz, 1H), 3.84-3.71 (m, 2H), 3.59-3.47 (m, 2H), 3.21-3.11 (m, 2H), 2.99 (t, J=9.0 Hz, 1H), 2.89 (dd, J=13.0, 9.4 Hz, 1H), 2.66-2.53 (m, 1H), 2.45 (dd, J=13.0, 4.7 Hz, 1H), 2.24-2.07 (m, 3H), 1.77-1.66 (m, 1H), 1.22 (d, J=6.1 Hz, 3H); ESI MS m/z 364.17 $[M+H]^+$.

Example 130

(4-(trifluoromethyl)phenyl)((R)-3-(((2R,3R,4R,5S)-3,4,5-trihydroxy-2-methylpiperidin-1-yl)methyl)pyrrolidin-1-yl)methanone

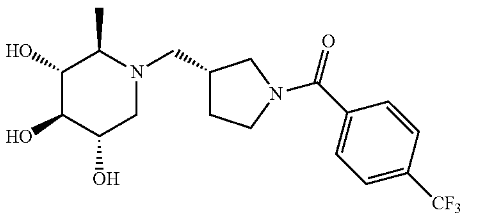 [SMILES: C[C@@H]1[C@@H](O)[C@H](O)[C@@H](O)CN1C[C@H]1CCN(C(=O)c2ccc(C(F)(F)F)cc2)C1]

Under Ar, to a mixture of (2R,3R,4R,5S)-3,4,5-tris(benzyloxy)-2-methyl-1-((S)-pyrrolidin-3-ylmethyl)piperidine (85 mg, 0.17 mmol), 4-(trifluoromethyl)benzoic acid (32.3 mg, 0.17 mmol), and DIPEA (0.11 mL, 0.54 mmol) in anhydrous DMF (1 mL) was added HATU (65 mg, 0.17 mmol). The mixture was stirred at RT for 18 h, satd. $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 30% EtOAc in hexanes, affording (4-(trifluoromethyl)phenyl)((R)-3-(((2R,3R,4R,5S)-3,4,5-tris(benzyloxy)-2-methylpiperidin-1-yl)methyl)pyrrolidin-1-yl)methanone as a white foam (102 mg, 89%).

At −78° C. under Ar, to a solution of the above material (102 mg, 0.15 mmol) in anhydrous DCM (2 mL) was added $BCl_3$ solution (1.50 mL, 1 M in DCM, 1.50 mmol). The mixture was stirred at −78 for 1 h and 0° C. for 4 h, MeOH (20 mL) was added. The mixture was stirred for an additional 2 h at 0° C., and evaporated to dryness under rotavap. The residue was purified on silica gel by flash chromatography (dry load) using 10% MeOH and 2% $NH_3$ solution in DCM, affording (4-(trifluoromethyl)phenyl)((R)-3-(((2R,3R,4R,5S)-3,4,5-trihydroxy-2-methylpiperidin-1-yl)methyl)pyrrolidin-1-yl)methanone (5) (42 mg, 70%). $^1H$ NMR (400 MHz, $CD_3OD$) δ 7.79 (dd, J=8.4, 3.2 Hz, 2H), 7.72 (t, J=8.1 Hz, 2H), 3.87-3.69 (m, 1H), 3.67-3.46 (m, 2H), 3.39 (dd, J=12.4, 8.0 Hz, 1H), 3.41-3.37 (m, 1H), 3.07 (td, J=8.9, 8.1, 2.0 Hz, 1H), 3.0-2.97 (m, 1H), 2.82 (ddd, J=11.6, 9.5, 3.2 Hz, 1H), 2.72 (dd, J=12.9, 10.2 Hz, 1H), 2.65-2.47 (two peaks, 1H), 2.45-2.32 (m, 1H), 2.21-2.00 (m, 2H), 1.93 (td, J=10.8, 2.6 Hz, 1H), 1.72-1.67 (m, 1H), 1.19 (two peaks, 3H); ESI MS m/z 403.15 $[M+H]^+$.

Example 131

(2R,3R,4R,5S)-2-methyl-1-(((S)-1-(2-(trifluoromethyl)phenyl)pyrrolidin-3-yl)methyl)piperidine-3,4,5-triol

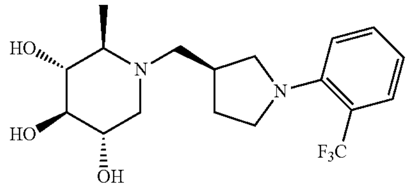 [SMILES: C[C@@H]1[C@@H](O)[C@H](O)[C@@H](O)CN1C[C@@H]1CCN(c2ccccc2C(F)(F)F)C1]

Under Ar, to a solution of (R)-tert-butyl 3-formylpyrrolidine-1-carboxylate (126 mg, 0.63 mmol), (2R,3R,4R,5S)-3,4,5-tris(benzyloxy)-2-methylpiperidine (530 mg, 1.27 mmol) in anhydrous DCM (20 mL) was added $NaBH(OAc)_3$ (539 mg, 2.5 mmol). The mixture was stirred at RT for 18 h, satd. $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 30% EtOAc in hexanes, affording (S)-tert-butyl 3-(((2R,3R,4R,5S)-3,4,5-tris(benzyloxy)-2-methylpiperidin-1-yl)methyl)pyrrolidine-1-carboxylate as a white foam (330 mg, 87%).

At 0° C. the above material (330 mg, 0.55 mmol) in DCM (8 mL) was treated with TFA (2 mL) 2 h, then ice bath was removed, and the reaction was continued for additional 2 h. After evaporation of solvent under reduced pressure, the residue was dissolved in DCM (30 mL), the organic layer was washed with sat. $Na_2CO_3$, brine and dried over $Na_2SO_4$. After filtration the solvent was evaporated and the residue was purified on silica gel by flash chromatography using 10% MeOH and 2% $NH_3$ solution in DCM, affording (2R,3R,4R,5S)-3,4,5-tris(benzyloxy)-2-methyl-1-((R)-pyrrolidin-3-ylmethyl)piperidine as an oil (276 mg, 100%).

Under Ar, to a mixture of the above material (276 mg, 0.55 mmol), 1-bromo-2-$CF_3$-benzene (186 mg, 0.83 mmol), $Cs_2CO_3$ (210 mg, 0.7 mmol) and XPhos (13 mg, 0.027 mmol) in anhydrous and degassed toluene (5 mL) was added $Pd_2dba_3$ (5 mg, 0.005 mmol). The mixture was stirred at 85° C. in a sealed tube for 18 h, then cooled to RT. $Et_2O$ (50 mL) was added, and the resulting precipitate was filtered off. The filtrate was concentrated under reduced pressure, and the residue was purified on silica gel by flash chromatography using 15% EtOAc in hexanes, affording (2R,3R,4R,5S)-3,4,5-tris(benzyloxy)-2-methyl-1-(((S)-1-(2-(trifluoromethyl)phenyl)pyrrolidin-3-yl)methyl)piperidine as a white solid (36 mg, 10%).

At −78° C. under Ar, to a solution of the above material (36 mg, 0.056 mmol) in anhydrous DCM (2 mL) was added $BCl_3$ solution (0.5 mL, 1 M in DCM, 0.50 mmol). The mixture was stirred at −78 for 1 h and 0° C. for 4 h, MeOH (20 mL) was added. The mixture was stirred for an additional 2 h at 0° C., and evaporated to dryness under rotavap. The residue was purified on silica gel by flash chromatography (dry load) using 10% MeOH and 2% $NH_3$ solution in DCM, affording (2R,3R,4R,5S)-2-methyl-1-(((S)-1-(2-(trifluoromethyl)phenyl)pyrrolidin-3-yl)methyl)piperidine-3,4,5-triol as a white foam (9.1 mg, 45%). $^1$H NMR (400 MHz, $CD_3OD$) δ 7.57 (dd, J=7.9, 1.7 Hz, 1H), 7.49-7.41 (m, 1H), 7.17 (d, J=8.4 Hz, 1H), 6.96 (t, J=7.6 Hz, 1H), 3.50 (ddd, J=10.5, 9.0, 4.8 Hz, 1H), 3.35-3.31 (m, 3H), 3.14 (t, J=8.9 Hz, 1H), 3.11-3.07 (m, 1H), 3.04 (dd, J=9.1, 6.0 Hz, 1H), 2.98 (t, J=9.1 Hz, 1H), 2.86 (dd, J=13.0, 8.7 Hz, 1H), 2.53 (dt, J=14.1, 6.6 Hz, 1H), 2.35 (dd, J=13.0, 5.7 Hz, 1H), 2.22-2.01 (m, 3H), 1.92-1.69 (m, 1H), 1.24 (d, J=6.1 Hz, 3H); ESI MS m/z 375.15 $[M+H]^+$.

Example 132

(2R,3R,4R,5S)-2-methyl-1-(((S)-1-(3-(trifluoromethyl)pyridin-2-yl)pyrrolidin-3-yl)methyl)piperidine-3,4,5-triol

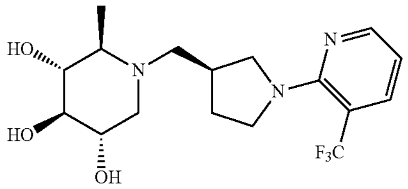 [SMILES: C[C@@H]1[C@@H](O)[C@H](O)[C@@H](O)CN1C[C@@H]1CCN(c2ncccc2C(F)(F)F)C1]

To a stirred solution of (2R,3R,4R,5S)-3,4,5-tris(benzyloxy)-2-methyl-1-((R)-pyrrolidin-3-ylmethyl)piperidine (280 mg, 0.51 mmol) and 2-chloro-3-(trifluoromethyl)pyridine (465 mg, 2.57 mmol) in DMF (5 mL) was added DIPEA (0.71 mL, 4.08 mmol). The mixture was stirred at 100° C. for 18 h, and then water was added at 0° C. The mixture was extracted with EtOAc (2×30 mL). The combined organic layer was washed with water (2×10 mL), separated, and dried over $Na_2SO_4$. After filtration the solvent was evaporated under reduced pressure, and the residue was purified on silica gel by flash chromatography affording 3-(trifluoromethyl)-2-((S)-3-(((2R,3R,4R,5S)-3,4,5-tris(benzyloxy)-2-methylpiperidin-1-yl)methyl)pyrrolidin-1-yl)pyridine as an oil (257 mg, 78%). ESI MS m/z 646.32 $[M+H]^+$.

To a stirred solution of the above material (250 mg, 0.39 mmol) in anhydrous DCM (10 mL) was added $BCl_3$ solution (1M in DCM, 1.94 mL, 1.94 mmol) at −78° C. under $N_2$. The mixture was stirred at 0° C. for 4 h before being quenched with anhydrous MeOH (1 mL). The mixture was stirred at RT for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((S)-1-(3-(trifluoromethyl)pyridin-2-yl)pyrrolidin-3-yl)methyl)piperidine-3,4,5-triol as a white solid (140 mg, 96%). $^1$H NMR (400 MHz, DMSO-$d_6$) δ 8.33 (dd, J=4.7, 1.7 Hz, 1H), 7.90 (dd, J=7.8, 1.8 Hz, 1H), 6.78 (dd, J=7.8, 4.6 Hz, 1H), 4.72-4.66 (m, 3H), 3.64-3.47 (m, 3H), 3.30-3.16 (m, 2H), 2.98-2.84 (m, 2H), 2.73 (td, J=8.9, 5.4 Hz, 1H), 2.65 (dd, J=13.1, 8.7 Hz, 1H), 2.44-2.37 (m, 1H), 2.25-2.13 (m, 1H), 2.05-1.86 (m, 3H), 1.74-1.61 (m, 1H), 1.07 (d, J=6.1 Hz, 3H); ESI MS m/z 376.18 $[M+H]^+$.

Example 133

(2R,3R,4R,5S)-2-methyl-1-(((S)-1-(4-(trifluoromethyl)pyridin-3-yl)pyrrolidin-3-yl)methyl)piperidine-3,4,5-triol

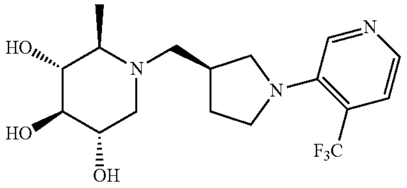 [SMILES: C[C@@H]1[C@@H](O)[C@H](O)[C@@H](O)CN1C[C@@H]1CCN(c2cnccc2C(F)(F)F)C1]

To a solution of (R)-3-hydroxymethyl-pyrrolidine-1-carboxylic acid tert-butyl ester (2.0 g, 10.0 mmol) in anhydrous DCM (40 mL) at 0° C., was added DMP (5.5 g, 13 mmol), and the mixture was stirred at 0° C. for 2 h. The mixture was quenched slowly with $Na_2S_3O_5$ solution. The mixture was extracted with DCM (3×20 mL). The combined organic layer was washed with water (2×10 mL), separated, and dried over $Na_2SO_4$. After filtration, the solvent was evaporated under reduced pressure, and the residue was purified on silica gel by flash chromatography affording (R)-tert-butyl 3-formylpyrrolidine-1-carboxylate as an oil (1.43 g, 72%).

To a stirred solution of (2R,3R,4R,5S)-3,4,5-tris(benzyloxy)-2-methylpiperidine (2.30 g, 5.52 mmol) and (R)-tert-butyl 3-formylpyrrolidine-1-carboxylate (1.43 g, 7.18 mmol) in anhydrous DCM (40 mL) was added HOAc (0.5 mL) and the mixture was stirred for 30 min. $NaBH(OAc)_3$ (1.64 g, 7.73 mmol) was added, and the resulting mixture was stirred at RT for 18 h. The reaction was quenched with $NaHCO_3$ solution at 0° C. The mixture was extracted with EtOAc (3×30 mL). The combined organic layer was washed with water (2×10 mL), separated, and dried over $Na_2SO_4$. After filtration, the solvent was evaporated under reduced pressure, and the residue was purified on silica gel by flash chromatography affording (S)-tert-butyl 3-(((2R,3R,4R,5S)-3,4,5-tris(benzyloxy)-2-methylpiperidin-1-yl)methyl)pyrrolidine-1-carboxylate as an oil (2.63 g, 79%). ESI MS m/z 601.36 $[M+H]^+$.

TFA (7 mL) was cooled to 0° C. and added to the above material (2.63 g, 4.38 mmol) in DCM (20 mL). The mixture was stirred at 0° C. for 10 min, then at RT for 2 h. TFA and DCM were removed under vacuum. The residue was dissolved in EtOAc (80 mL) and washed with $NaHCO_3$ solution (2×20 mL) then washed with water, separated, and dried over $Na_2SO_4$. After filtration, the solvent was evaporated under reduced pressure, and the crude (2R,3R,4R,5S)-3,4,5-tris(benzyloxy)-2-methyl-1-((R)-pyrrolidin-3-ylmethyl)piperidine was used directly in the next step without further purification (2.14 g, 98%). ESI MS m/z 501.31 $[M+H]^+$.

To a stirred solution of the above material (300 mg, 0.60 mmol) and 3-bromo-4-(trifluoromethyl)pyridine (271 mg, 1.20 mmol) in toluene (10 mL) was added $Pd_2(dba)_3$ (55 mg, 0.060 mmol) and RuPhos (56 mg, 0.12 mmol), followed by $Cs_2CO_3$ (586 mg, 1.80 mmol) under Ar. The mixture was stirred at 90° C. for 18 h, and then water was added at 0° C. The mixture was extracted with EtOAc (2×30 mL). The combined organic layer was washed with water (2×10 mL), separated, and dried over $Na_2SO_4$. After filtration the solvent was evaporated under reduced pressure, and the residue was purified on silica gel by flash chromatography affording 4-(trifluoromethyl)-3-((S)-3-(((2R,3R,4R,5S)-3,4,5-tris(benzyloxy)-2-methylpiperidin-1-yl)methyl)pyrrolidin-1-yl)pyridine as an oil (153 mg, 40%). ESI MS m/z 646.32 $[M+H]^+$.

To a stirred solution of the above material (85 mg, 0.13 mmol) in anhydrous DCM (5 mL) was added $BCl_3$ solution (1M in DCM, 0.66 mL, 0.66 mmol) at −78° C. under $N_2$. The mixture was stirred at 0° C. for 2 h before being quenched with anhydrous MeOH (1 mL). The mixture was stirred at RT for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((S)-1-(4-(trifluoromethyl)pyridin-3-yl)pyrrolidin-3-yl)methyl)piperidine-3,4,5-triol as a white solid (35 mg, 72%). $^1H$ NMR (400 MHz, $CD_3OD$) δ 8.33 (s, 1H), 8.01 (d, J=5.2 Hz, 1H), 7.51 (d, J=5.2 Hz, 1H), 3.62-3.45 (m, 4H), 3.24-3.19 (m, 1H), 3.18-3.05 (m, 2H), 2.97 (t, J=9.0 Hz, 1H), 2.84 (dd, J=13.1, 8.6 Hz, 1H), 2.63-2.55 (m, 1H), 2.37 (dd, J=13.1, 5.6 Hz, 1H), 2.22-2.08 (m, 3H), 1.91-1.78 (m, 1H), 1.24 (d, J=6.1 Hz, 3H); ESI MS m/z 376.18 $[M+H]^+$.

Example 134

(2R,3R,4R,5S)-2-methyl-1-(((S)-1-(4-(trifluoromethyl)pyrimidin-5-yl)pyrrolidin-3-yl)methyl)piperidine-3,4,5-triol

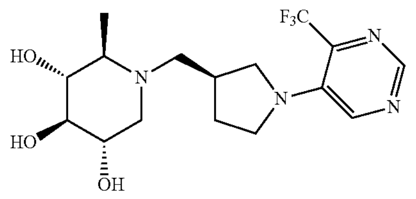 [SMILES: C[C@@H]1[C@@H](O)[C@H](O)[C@@H](O)CN1C[C@@H]1CCN(c2cncnc2C(F)(F)F)C1]

To a stirred solution of (2R,3R,4R,5S)-3,4,5-tris(benzyloxy)-2-methyl-1-((R)-pyrrolidin-3-ylmethyl)piperidine (290 mg, 0.58 mmol) and 5-bromo-4-(trifluoromethyl)pyrimidine (197 mg, 0.87 mmol) in toluene (10 mL) was added $Pd_2(dba)_3$ (53 mg, 0.058 mmol) and RuPhos (56 mg, 0.12 mmol), followed by $Cs_2CO_3$ (567 mg, 1.74 mmol) under Ar. The mixture was stirred at 90° C. for 18 h, and then water was added at 0° C. The mixture was extracted with EtOAc (2×30 mL). The combined organic layer was washed with water (2×10 mL), separated, and dried over $Na_2SO_4$. After filtration the solvent was evaporated under reduced pressure, and the residue was purified on silica gel by flash chromatography affording 4-(trifluoromethyl)-5-((S)-3-(((2R,3R,4R,5S)-3,4,5-tris(benzyloxy)-2-methylpiperidin-1-yl)methyl)pyrrolidin-1-yl)pyrimidine as an oil (130 mg, 35%). ESI MS m/z 647.31 $[M+H]^+$.

To a stirred solution of the above material (130 mg, 0.20 mmol) in anhydrous DCM (5 mL) was added $BCl_3$ solution (1M in DCM, 1.0 mL, 1.0 mmol) at −78° C. under $N_2$. The mixture was stirred at 0° C. for 4 h before being quenched with anhydrous MeOH (1 mL).

The mixture was stirred at RT for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((S)-1-(4-(trifluoromethyl)pyrimidin-5-yl)pyrrolidin-3-yl)methyl)piperidine-3,4,5-triol as a white solid (25 mg, 33%). $^1H$ NMR (400 MHz, $CD_3OD$) δ 8.56 (s, 1H), 8.53 (s, 1H), 3.64-3.42 (m, 4H), 3.27-3.20 (m, 1H), 3.14 (t, J=9.0 Hz, 1H), 3.11-3.05 (m, 1H), 2.97 (t, J=9.0 Hz, 1H), 2.83 (dd, J=13.1, 8.6 Hz, 1H), 2.65-2.53 (m, 1H), 2.38 (dd, J=13.1, 5.6 Hz, 1H), 2.24-2.03 (m, 3H), 1.90-1.79 (m, 1H), 1.23 (d, J=6.1 Hz, 3H); ESI MS m/z $[M+H]^+$ 377.18.

Example 135

(2R,3R,4R,5S)-2-methyl-1-(((S)-1-(4-(trifluoromethyl)thiazol-2-yl)pyrrolidin-3-yl)methyl)piperidine-3,4,5-triol

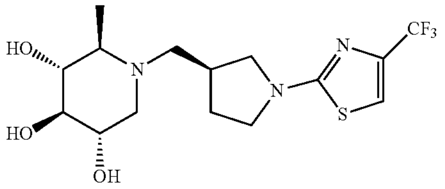 [SMILES: C[C@@H]1[C@@H](O)[C@H](O)[C@@H](O)CN1C[C@@H]1CCN(c2nc(C(F)(F)F)cs2)C1]

To a stirred solution of (2R,3R,4R,5S)-3,4,5-tris(benzyloxy)-2-methyl-1-((R)-pyrrolidin-3-ylmethyl)piperidine (290 mg, 0.60 mmol) and 2-bromo-4-(trifluoromethyl)thiazole (208 mg, 0.90 mmol) in DMA (5 mL) was added $Cs_2CO_3$ (789 mg, 2.40 mmol). The mixture was stirred at 70° C. for 18 h, and then water was added at 0° C. The mixture was extracted with EtOAc (2×30 mL). The combined organic layer was washed with water (2×10 mL), separated, and dried over $Na_2SO_4$. After filtration the solvent was evaporated under reduced pressure, and the residue was purified on silica gel by flash chromatography affording 4-(trifluoromethyl)-2-((S)-3-(((2R,3R,4R,5S)-3,4,5-tris(benzyloxy)-2-methylpiperidin-1-yl)methyl)pyrrolidin-1-yl)thiazole as an oil (227 mg, 58%). ESI MS m/z 652.27 $[M+H]^+$.

To a stirred solution of the above material (225 mg, 0.35 mmol) in anhydrous DCM (10 mL) was added $BCl_3$ solution (1M in DCM, 1.73 mL, 1.73 mmol) at −78° C. under $N_2$. The mixture was stirred at 0° C. for 4 h before being quenched with anhydrous MeOH (1 mL). The mixture was stirred at RT for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2R,3R,4R,5S)-2-methyl-1-(((S)-1-(4-(trifluoromethyl)thiazol-2-yl)pyrrolidin-3-yl)methyl)piperidine-3,4,5-triol as a white solid (110 mg, 82%). $^1H$ NMR (400 MHz, DMSO-$d_6$) δ 7.43-7.40 (m, 1H), 4.72-4.67 (m, 3H), 3.53 (dd, J=9.9, 7.1 Hz, 1H), 3.47-3.35 (m, 2H), 3.31-3.21 (m, 1H), 3.05 (dd, J=9.9, 6.7 Hz, 1H), 2.97-2.86 (m, 2H), 2.78-2.61 (m, 2H), 2.60-2.53 (m, 1H), 2.20 (dd, J=12.7, 5.5 Hz, 1H), 2.12-2.02 (m, 1H), 2.00-1.88 (m, 2H), 1.84-1.72 (m, 1H), 1.08 (d, J=6.0 Hz, 3H); ESI MS m/z 382.13 $[M+H]^+$.

Example 136

(2R,3R,4R,5S)-2-methyl-1-(((R)-1-(o-tolyl)piperidin-3-yl)methyl)piperidine-3,4,5-triol

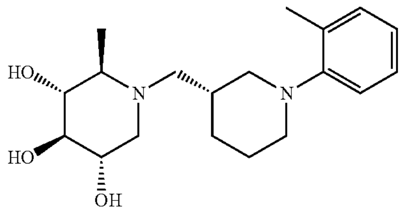 [SMILES: Cc1ccccc1N1CCC[C@H](CN2C[C@H](O)[C@@H](O)[C@H](O)[C@H]2C)C1]

Under Ar, to a mixture of (2R,3R,4R,5S)-3,4,5-tris(benzyloxy)-2-methyl-1-((S)-piperidin-3-ylmethyl)piperidine (130 mg, 0.25 mmol), 1-bromo-2-Me-benzene (86 mg, 0.51 mmol), $Cs_2CO_3$ (330 mg, 1.0 mmol) and RuPhos (23 mg, 0.05 mmol) in anhydrous and degassed toluene (5 mL) was added $Pd_2dba_3$ (23 mg, 0.025 mmol). The mixture was stirred at 85° C. in a sealed tube for 18 h, then cooled to RT. $Et_2O$ (50 mL) was added, and the resulting precipitate was filtered off. The filtrate was concentrated under reduced pressure, and the residue was purified on silica gel by flash chromatography using 15% EtOAc in hexanes, affording (2R,3R,4R,5S)-3,4,5-tris(benzyloxy)-2-methyl-1-(((R)-1-(o-tolyl)piperidin-3-yl)methyl)piperidine as a oil (130 mg, 86%).

At −78° C. under Ar, to a solution of the above material (130 mg, 0.021 mmol) in anhydrous DCM (2 mL) was added $BCl_3$ solution (0.5 mL, 1 M in DCM, 0.50 mmol). The mixture was stirred at −78 for 1 h and 0° C. for 4 h, MeOH (20 mL) was added. The mixture was stirred for an additional 2 h at 0° C., and evaporated to dryness under rotavap. The residue was purified on silica gel by flash chromatography (dry load) using 10% MeOH and 2% $NH_3$ solution in DCM, affording (2R,3R,4R,5S)-2-methyl-1-(((R)-1-(o-tolyl)piperidin-3-yl)methyl)piperidine-3,4,5-triol as a white foam (16 mg, 22%). $^1$H NMR (400 MHz, $CD_3OD$) δ 7.15 (d, J=7.0 Hz, 1H), 7.11 (dd, J=7.5, 1.7 Hz, 1H), 7.04-6.98 (m, 1H), 6.93 (td, J=7.4, 1.3 Hz, 1H), 3.44 (ddd, J=10.5, 9.1, 4.8 Hz, 1H), 3.29 (d, J=12.1 Hz, 1H), 3.23-3.06 (m, 2H), 3.02 (d, J=11.5 Hz, 1H), 2.91 (t, J=9.0 Hz, 1H), 2.83-2.72 (m, 1H), 2.64 (td, J=10.9, 3.3 Hz, 1H), 2.30 (s, 3H), 2.27-2.15 (m, 1H), 2.09-1.90 (m, 4H), 1.85-1.78 (m, 3H), 1.17 (d, J=6.1 Hz, 3H); 1.15-1.12 (m, 1H); ESI MS m/z 335.23 $[M+H]^+$.

Example 137

(2R,3R,4R,5S)-1-(((R)-1-(2-fluorophenyl)piperidin-3-yl)methyl)-2-methylpiperidine-3,4,5-triol

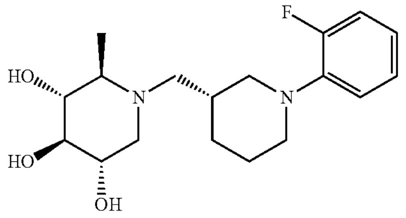 [SMILES: C[C@@H]1[C@@H](O)[C@H](O)[C@@H](O)CN1C[C@H]1CCCN(c2ccccc2F)C1]

Under Ar, to a solution of (S)-tert-butyl 3-formylpiperidine-1-carboxylate (229 mg, 1.07 mmol), (2R,3R,4R,5S)-3,4,5-tris(benzyloxy)-2-methylpiperidine (300 mg, 0.71 mmol) in anhydrous DCM (20 mL) was added $NaBH(OAc)_3$ (229 mg, 1.07 mmol). The mixture was stirred at RT for 18 h, satd. $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 30% EtOAc in hexanes, affording (R)-tert-butyl 3-(((2R,3R,4R,5S)-3,4,5-tris(benzyloxy)-2-methylpiperidin-1-yl)methyl)piperidine-1-carboxylate as a crude oil.

At 0° C. the above crude material in DCM (12 mL) was treated with TFA (3 mL) 2 h, then the ice bath was removed and the reaction was continued for an additional 2 h. After evaporation of solvent under reduced pressure, the residue was dissolved in DCM (30 mL), the organic layer was washed with satd. $Na_2CO_3$, brine and dried over $Na_2SO_4$. After filtration the solvent was evaporated and the residue was purified on silica gel by flash chromatography using 10% MeOH and 2% $NH_3$ solution in DCM, affording (2R,3R,4R,5S)-3,4,5-tris(benzyloxy)-2-methyl-1-((S)-piperidin-3-ylmethyl)piperidine as an oil (370 mg, 100% over two steps).

Under Ar, to a mixture of the above material (177 mg, 0.34 mmol), 1-bromo-2-F-benzene (91 mg, 0.52 mmol), $Cs_2CO_3$ (277 mg, 0.85 mmol) and XPhos (8 mg, 0.017 mmol) in anhydrous and degassed toluene (5 mL) was added $Pd_2dba_3$ (3 mg, 0.003 mmol). The mixture was stirred at 85° C. in a sealed tube for 18 h, then cooled to RT. $Et_2O$ (50 mL) was added, and the resulting precipitate was filtered off. The filtrate was concentrated under reduced pressure, and the residue was purified on silica gel by flash chromatography using 15% EtOAc in hexanes, affording (2R,3R,4R,5S)-3,4,5-tris(benzyloxy)-1-(((R)-1-(2-fluorophenyl)piperidin-3-yl)methyl)-2-methylpiperidine as a crude oil.

At −78° C. under Ar, to a solution of the above crude material in anhydrous DCM (2 mL) was added $BCl_3$ solution (0.5 mL, 1 M in DCM, 0.50 mmol). The mixture was stirred at −78 for 1 h and 0° C. for 4 h, MeOH (20 mL) was added. The mixture was stirred for an additional 2 h at 0° C., and evaporated to dryness under rotavap. The residue was purified on silica gel by flash chromatography (dry load) using 10% MeOH and 2% $NH_3$ solution in DCM, affording (2R,3R,4R,5S)-1-(((R)-1-(2-fluorophenyl)piperidin-3-yl)methyl)-2-methylpiperidine-3,4,5-triol as a white foam (16 mg, 12% over two steps). $^1$H NMR (400 MHz, $CD_3OD$) δ 7.14-6.99 (m, 3H), 7.00-6.93 (m, 1H), 3.59-3.42 (m, 2H), 3.33 (t, J=1.7 Hz, 1H), 3.19-3.06 (m, 2H), 2.94 (t, J=9.0 Hz, 1H), 2.82-2.61 (m, 2H), 2.33 (dd, J=11.6, 9.7 Hz, 1H), 2.13-1.91 (m, 4H), 1.86-1.78 (m, 3H), 1.19 (d, J=6.1 Hz, 3H), 1.15-1.07 (m, 1H); ESI MS m/z 339.17 $[M+H]^+$.

Example 138

(2R,3R,4R,5S)-2-methyl-1-(((R)-1-(3-(trifluoromethyl)pyridin-2-yl)piperidin-3-yl)methyl)piperidine-3,4,5-triol

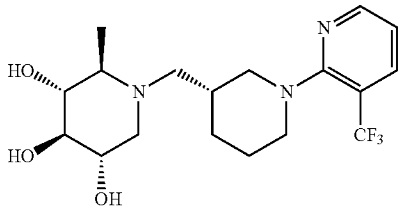 [SMILES: C[C@@H]1[C@@H](O)[C@H](O)[C@@H](O)CN1C[C@H]1CCCN(c2ncccc2C(F)(F)F)C1]

Under Ar, to a mixture of (2R,3R,4R,5S)-3,4,5-tris(benzyloxy)-2-methyl-1-((S)-piperidin-3-ylmethyl)piperidine (120 mg, 0.23 mmol), 2-chloro-3-(trifluoromethyl)pyridine (85 mg, 0.47 mmol), $Cs_2CO_3$ (303 mg, 0.93 mmol) and RuPhos (22 mg, 0.05 mmol) in anhydrous and degassed toluene (5 mL) was added $Pd_2dba_3$ (21 mg, 0.023 mmol). The mixture was stirred at 85° C. in a sealed tube for 18 h, then cooled to RT. $Et_2O$ (50 mL) was added, and the resulting precipitate was filtered off. The filtrate was concentrated under reduced pressure, and the residue was purified on silica gel by flash chromatography using 15% EtOAc in hexanes, affording 3-(trifluoromethyl)-2-((R)-3-(((2R,3R,4R,5S)-3,4,5-tris(benzyloxy)-2-methylpiperidin-1-yl)methyl)piperidin-1-yl)pyridine as a oil (30 mg, 20%).

At −78° C. under Ar, to a solution of the above material (30 mg, 0.045 mmol) in anhydrous DCM (2 mL) was added $BCl_3$ solution (0.5 mL, 1 M in DCM, 0.5 mmol). The mixture was stirred at −78 for 1 h and 0° C. for 4 h, MeOH (20 mL) was added. The mixture was stirred for an additional 2 h at 0° C., and evaporated to dryness under rotavap. The residue was purified on silica gel by flash chromatography (dry load) using 10% MeOH and 2% $NH_3$ solution in DCM, affording (2R,3R,4R,5S)-2-methyl-1-(((R)-1-(3-(trifluoromethyl)pyridin-2-yl)piperidin-3-yl)methyl)piperidine-3,4,5-triol as a white foam (7.2 mg, 40%). $^1H$ NMR (400 MHz, $CD_3OD$) δ 8.43 (dd, J=5.0, 1.8 Hz, 1H), 7.98 (dd, J=7.8, 1.9 Hz, 1H), 7.10 (dd, J=7.8, 4.9 Hz, 1H), 3.82-3.65 (m, 1H), 3.50-3.46 (m, 2H), 3.21-3.05 (m, 2H), 2.95-2.90 (m 2H), 2.79-2.65 (m, 1H), 2.55 (dd, J=12.4, 9.7 Hz, 1H), 2.09-1.89 (m, 4H), 1.84-1.66 (m, 3H), 1.14 (d, J=6.1 Hz, 3H), 1.16-1.13 (m, 1H); ESI MS m/z 390.20 $[M+H]^+$.

Example 139

(2R,3R,4R,5S)-2-methyl-1-(((R)-1-(6-(trifluoromethyl)pyridin-2-yl)piperidin-3-yl)methyl)piperidine-3,4,5-triol

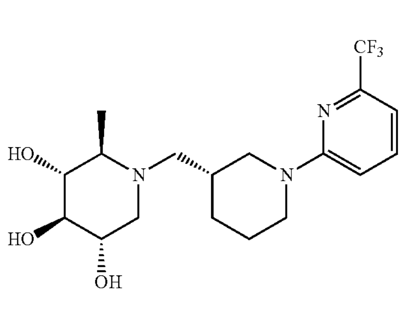 [SMILES: C[C@@H]1[C@@H](O)[C@H](O)[C@@H](O)CN1C[C@H]1CCCN(c2cccc(C(F)(F)F)n2)C1]

Under Ar, to a mixture of (2R,3R,4R,5S)-3,4,5-tris(benzyloxy)-2-methyl-1-((S)-piperidin-3-ylmethyl)piperidine (120 mg, 0.23 mmol), 2-chloro-6-(trifluoromethyl)pyridine (85 mg, 0.47 mmol), $Cs_2CO_3$ (303 mg, 0.93 mmol) and RuPhos (22 mg, 0.05 mmol) in anhydrous and degassed toluene (5 mL) was added $Pd_2dba_3$ (21 mg, 0.023 mmol). The mixture was stirred at 85° C. in a sealed tube for 18 h, then cooled to RT. $Et_2O$ (50 mL) was added, and the resulting precipitate was filtered off. The filtrate was concentrated under reduced pressure, and the residue was purified on silica gel by flash chromatography using 15% EtOAc in hexanes, affording 2-(trifluoromethyl)-6-((R)-3-(((2R,3R,4R,5S)-3,4,5-tris(benzyloxy)-2-methylpiperidin-1-yl)methyl)piperidin-1-yl)pyridine as a oil (117 mg, 76%).

At −78° C. under Ar, to a solution of the above material (117 mg, 0.18 mmol) in anhydrous DCM (2 mL) was added $BCl_3$ solution (1.0 mL, 1 M in DCM, 1.0 mmol). The mixture was stirred at −78 for 1 h and 0° C. for 4 h, MeOH (20 mL) was added. The mixture was stirred for an additional 2 h at 0° C., and evaporated to dryness under rotavap. The residue was purified on silica gel by flash chromatography (dry load) using 10% MeOH and 2% $NH_3$ solution in DCM, affording (2R,3R,4R,5S)-2-methyl-1-(((R)-1-(6-(trifluoromethyl)pyridin-2-yl)piperidin-3-yl)methyl)piperidine-3,4,5-triol as a white foam (38 mg, 55%). $^1H$ NMR (400 MHz, $CD_3OD$) δ 7.64 (dd, J=8.7, 7.3 Hz, 1H), 6.94 (d, J=8.7 Hz, 1H), 6.90 (d, J=7.2 Hz, 1H), 4.34 (dd, J=13.1, 3.5 Hz, 1H), 4.27-4.14 (m, 1H), 3.55 (ddd, J=10.4, 9.0, 4.8 Hz, 1H), 3.23-3.10 (m, 2H), 3.06 (ddd, J=13.6, 11.0, 3.1 Hz, 1H), 2.99 (t, J=9.1 Hz, 1H), 2.75 (ddd, J=20.4, 13.1, 9.8 Hz, 2H), 2.17-1.91 (m, 3H), 1.81-1.77 (m, 3H), 1.60-1.56 (m, 1H), 1.37-1.24 (m, 1H), 1.18 (d, J=6.1 Hz, 3H); ESI MS m/z 390.20 $[M+H]^+$.

Example 140

(2R,3R,4R,5S)-2-methyl-1-(((R)-1-(4-(trifluoromethyl)pyridin-3-yl)piperidin-3-yl)methyl)piperidine-3,4,5-triol

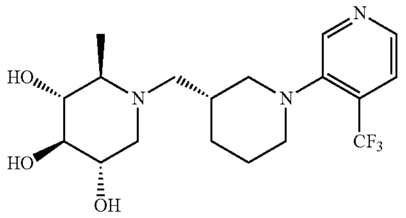 [SMILES: C[C@@H]1[C@@H](O)[C@H](O)[C@@H](O)CN1C[C@H]1CCCN(c2cnccc2C(F)(F)F)C1]

Under Ar, to a mixture of (2R,3R,4R,5S)-3,4,5-tris(benzyloxy)-2-methyl-1-((S)-piperidin-3-ylmethyl)piperidine (120 mg, 0.23 mmol), 3-bromo-4-(trifluoromethyl)pyridine (108.7 mg, 0.48 mmol), $Cs_2CO_3$ (303 mg, 0.93 mmol) and RuPhos (22 mg, 0.05 mmol) in anhydrous and degassed toluene (5 mL) was added $Pd_2dba_3$ (21 mg, 0.023 mmol). The mixture was stirred at 85° C. in a sealed tube for 18 h, then cooled to RT. $Et_2O$ (50 mL) was added, and the resulting precipitate was filtered off. The filtrate was concentrated under reduced pressure, and the residue was purified on silica gel by flash chromatography using 15% EtOAc in hexanes, affording 4-(trifluoromethyl)-3-((R)-3-(((2R,3R,4R,5S)-3,4,5-tris(benzyloxy)-2-methylpiperidin-1-yl)methyl)piperidin-1-yl)pyridine as a oil (80 mg, 52%).

At −78° C. under Ar, to a solution of the above material (80 mg, 0.12 mmol) in anhydrous DCM (2 mL) was added $BCl_3$ solution (0.5 mL, 1 M in DCM, 0.50 mmol). The mixture was stirred at −78 for 1 h and 0° C. for 4 h, MeOH (20 mL) was added. The mixture was stirred for an additional 2 h at 0° C., and evaporated to dryness under rotavap. The residue was purified on silica gel by flash chromatography (dry load) using 10% MeOH and 2% $NH_3$ solution in DCM, affording (2R,3R,4R,5S)-2-methyl-1-(((R)-1-(4-(trifluoromethyl)pyridin-3-yl)piperidin-3-yl)methyl)piperidine-3,4,5-triol as a white foam (27 mg, 66%). $^1$H NMR (400 MHz, $CD_3OD$) δ 8.65 (s, 1H), 8.48 (d, J=5.1 Hz, 1H), 7.64 (d, J=5.1 Hz, 1H), 3.46-3.42 (m, 2H), 3.24-3.07 (m, 3H), 3.01-2.84 (m, 2H), 2.81-2.67 (m, 1H), 2.59-2.45 (m, 1H), 2.18-1.89 (m, 4H), 1.88-1.69 (m, 3H), 1.17 (d, J=6.1 Hz, 3H), 1.20-1.01 (m, 1H); ESI MS m/z 390.19 [M+H]$^+$.

Example 141

(2R,3R,4R,5S)-2-methyl-1-(((S)-1-(3-(trifluoromethyl)pyridin-2-yl)piperidin-3-yl)methyl)piperidine-3,4,5-triol

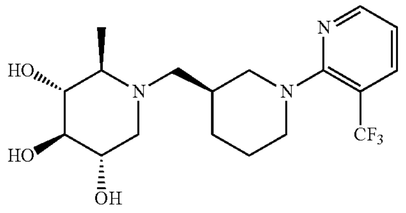 [SMILES: C[C@@H]1[C@@H](O)[C@H](O)[C@@H](O)CN1C[C@@H]1CCCN(c2ncccc2C(F)(F)F)C1]

To a solution of ((2R,3R,4R,5S)-3,4,5-tris(benzyloxy)-2-methyl-1-((R)-piperidin-3-ylmethyl)piperidine (0.3 g, 0.6 mmol) and 2-chloro-3-(trifluoromethyl)pyridine (0.2 g, 1.2 mmol) in dry DMF (6 mL) was added $K_2CO_3$ (0.12 g, 0.9 mmol) and the reaction mixture was heated at 120° C. overnight. The reaction mixture was partitioned between EtOAc (50 mL) and water, organics were separated, then dried over anhydrous $Na_2SO_4$. After filtration the solvent was evaporated under reduced pressure, and the residue was purified on silica gel by flash chromatography (EtOAc/hexanes, 2:8) affording 3-(trifluoromethyl)-2-((S)-3-(((2R,3R,4R,5S)-3,4,5-tris(benzyloxy)-2-methylpiperidin-1-yl)methyl)piperidin-1-yl)pyridine as an oil (0.2 g, 97%). $^1$H NMR (500 MHz, $CDCl_3$) δ 8.43 (dd, J=4.9, 1.8 Hz, 1H), 7.86 (dd, J=7.7, 1.9 Hz, 1H), 7.38-7.27 (m, 15H), 6.96 (dd, J=7.8, 4.8 Hz, 1H), 4.98 (d, J=11.0 Hz, 1H), 4.95 (d, J=10.8 Hz, 1H), 4.84 (d, J=11.0 Hz, 1H), 4.72 (d, J=11.6 Hz, 1H), 4.66-4.60 (m, 2H), 3.58 (td, J=9.8, 4.6 Hz, 1H), 3.54-3.44 (m, 3H), 3.10 (t, J=9.0 Hz, 1H), 3.02 (dd, J=11.5, 4.7 Hz, 1H), 2.93 (ddd, J=12.8, 10.5, 2.6 Hz, 1H), 2.69-2.61 (m, 2H), 2.27 (dt, J=12.1, 6.1 Hz, 1H), 2.10-2.01 (m, 2H), 1.88-1.73 (m, 3H), 1.72-1.59 (m, 1H), 1.20 (d, J=6.1 Hz, 3H), 1.16-1.06 (m, 1H); ESI MS m/z 660.335 [M+H]$^+$.

At −78° C., under Ar, to a solution of the above material (0.25 g, 0.37 mmol) in DCM (10 ml) was added $BCl_3$ (1.0 M in DCM, 1.9 mL, 1.9 mmol), and the mixture was stirred for 3 h while the bath temperature reached 0° C. The mixture was then cooled at −78° C., and MeOH (2 mL) was added carefully. After stirring at RT for 30 min the mixture was concentrated under reduced pressure. The resulting residue was neutralized with 1M $NH_3$ in MeOH solution (2×5 mL) and concentrated again under reduced pressure. The residue was purified on silica gel by flash chromatography (MeOH/DCM, 1:9) yielding (2R,3R,4R,5S)-2-methyl-1-(((S)-1-(3-(trifluoromethyl)pyridin-2-yl)piperidin-3-yl)methyl)piperidine-3,4,5-triol (0.087 g, 60%) as a white solid. $^1$H NMR (400 MHz, $CD_3OD$) δ 8.45 (dd, J=5.0, 1.8 Hz, 1H), 7.99 (dd, J=7.8, 1.9 Hz, 1H), 7.12 (ddd, J=7.9, 4.8, 0.9 Hz, 1H), 3.55-3.44 (m, 2H), 3.39 (dt, J=12.3, 4.4 Hz, 1H), 3.13 (t, J=9.0 Hz, 1H), 3.02 (dd, J=11.5, 5.0 Hz, 1H), 2.99-2.92 (m, 2H), 2.78 (dd, J=13.0, 8.0 Hz, 1H), 2.68 (dd, J=12.2, 8.9 Hz, 1H), 2.14-2.01 (m, 3H), 1.99-1.87 (m, 2H), 1.80 (dq, J=12.3, 4.2 Hz, 1H), 1.65 (dtt, J=14.2, 10.4, 3.8 Hz, 1H), 1.27-1.22 (m, 1H), 1.22 (d, J=6.1 Hz, 3H); ESI MS m/z 390.193 [M+H]$^+$.

Example 142

(2R,3R,4R,5S)-2-methyl-1-(((S)-1-(4-(trifluoromethyl)pyridin-3-yl)piperidin-3-yl)methyl)piperidine-3,4,5-triol

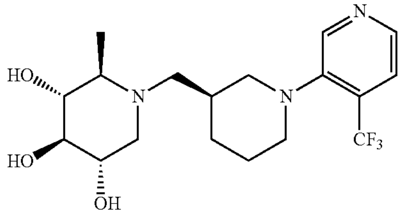 [SMILES: C[C@@H]1[C@@H](O)[C@H](O)[C@@H](O)CN1C[C@@H]1CCCN(c2cnccc2C(F)(F)F)C1]

To a stirred solution of (2R,3R,4R,5S)-3,4,5-tris(benzyloxy)-2-methyl-1-((R)-piperidin-3-ylmethyl)piperidine (0.15 g, 0.29 mmol) and 3-bromo-4-(trifluoromethyl)pyridine (0.13 g, 0.6 mmol) in toluene (5 mL) was added $Pd_2(dba)_3$ (28 mg, 0.03 mmol) and RuPhos (28 mg, 0.06 mmol), followed by $Cs_2CO_3$ (0.3 g, 0.9 mmol) under Ar. The mixture was stirred at 100° C. for 18 h, and then water was added at 0° C. The mixture was extracted with EtOAc (2×20 mL). The combined organic layer was washed with water (2×20 mL), separated, then dried over $Na_2SO_4$. After filtration the solvent was evaporated under reduced pressure, and the residue was purified on silica gel by flash chromatography (EtOAc/hexanes, 1:1) affording 4-(trifluoromethyl)-3-((S)-3-(((2R,3R,4R,5S)-3,4,5-tris(benzyloxy)-2-methylpiperidin-1-yl)methyl)piperidin-1-yl)pyridine as an oil (0.08 g, 41%). $^1$H NMR (500 MHz, $CDCl_3$) δ 8.62 (s, 1H), 8.48 (d, J=5.0 Hz, 1H), 7.47 (d, J=5.1 Hz, 1H), 7.37-7.26 (m, 15H), 4.98 (d, J=11.0 Hz, 1H), 4.95 (d, J=10.8 Hz, 1H), 4.84 (d, J=11.0 Hz, 1H), 4.73 (d, J=11.6 Hz, 1H), 4.66-4.60 (m, 2H), 3.57 (td, J=9.8, 4.6 Hz, 1H), 3.50 (t, J=9.0 Hz, 1H), 3.17 (dd, J=11.1, 3.4 Hz, 1H), 3.12-3.04 (m, 2H), 2.98 (dd, J=11.5, 4.7 Hz, 1H), 2.87 (t, J=9.8 Hz, 1H), 2.70 (dd, J=13.0, 8.3 Hz, 1H), 2.57-2.47 (m, 1H), 2.27 (dq, J=11.9, 6.2 Hz, 1H), 2.10-1.98 (m, 2H), 1.84 (dt, J=8.8, 4.6 Hz, 1H), 1.80-1.73 (m, 2H), 1.66 (qd, J=11.7, 10.4, 4.8 Hz, 1H), 1.20 (d, J=6.1 Hz, 3H), 1.16-1.07 (m, 1H); ESI MS m/z 660.338 [M+H]$^+$.

At −78° C., under Ar, to a solution of the above material (0.08 g, 0.12 mmol) in DCM (8 ml) was added $BCl_3$ (1.0 M in DCM, 0.6 mL, 0.6 mmol), and the mixture was stirred for 3 h while the bath temperature reached 0° C. The mixture was then cooled at −78° C., and MeOH (2 mL) was added carefully. After stirring at RT for 30 min the mixture was concentrated under reduced pressure. The resulting residue was neutralized with 1M $NH_3$ in MeOH solution (2×5 mL)

and concentrated again under reduced pressure. The residue was purified on silica gel by flash chromatography (MeOH/DCM, 1:9), affording (2R,3R,4R,5S)-2-methyl-1-(((S)-1-(4-(trifluoromethyl)pyridin-3-yl)piperidin-3-yl)methyl)piperidine-3,4,5-triol (0.03 g, 68%) as a white solid. $^1$H NMR (400 MHz, $CD_3OD$) δ 8.68 (s, 1H), 8.49 (d, J=5.1 Hz, 1H), 7.64 (d, J=5.1 Hz, 1H), 3.48 (ddd, J=10.5, 9.0, 4.8 Hz, 1H), 3.23 (dd, J=11.1, 3.3 Hz, 1H), 3.13 (t, J=9.0 Hz, 1H), 3.10-3.05 (m, 1H), 3.01 (dd, J=11.4, 4.9 Hz, 1H), 2.96 (t, J=9.1 Hz, 2H), 2.92-2.81 (m, 1H), 2.64 (dd, J=11.1, 8.3 Hz, 1H), 2.13-1.95 (m, 4H), 1.94-1.78 (m, 2H), 1.74-1.62 (m, 1H), 1.30-1.23 (m, 1H), 1.22 (d, J=6.1 Hz, 3H); ESI MS m/z 390.195 $[M+H]^+$.

Example 143

(2R,3R,4R,5S)-2-methyl-1-(((S)-1-(6-(trifluoromethyl)pyridin-2-yl)piperidin-3-yl)methyl)piperidine-3,4,5-triol

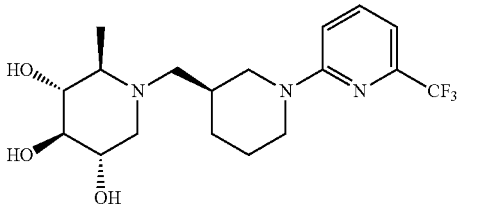 [SMILES: C[C@@H]1[C@@H](O)[C@H](O)[C@@H](O)CN1C[C@@H]1CCCN(c2cccc(C(F)(F)F)n2)C1]

To a solution of (R)-tert-butyl 3-(hydroxymethyl)piperidine-1-carboxylate (2.15 g, 10 mmol) at 0° C. in dry DCM (30 mL) was added DMP (5.5 g, 13 mmol). After stirring at 0° C. for 30 min, the reaction mixture was warmed to RT for 1.5 h. The reaction mixture was diluted with a 1:1 mixture of 1 M $Na_2S_2O_3$ and satd. $NaHCO_3$ (50 mL) and stirred for 30 min.

DCM (30 mL) was added and organics were separated, and dried over anhydrous $Na_2SO_4$ and concentrated. The residue was purified on silica gel by flash chromatography (EtOAc/hexanes, 1:1), affording (R)-tert-butyl 3-formylpiperidine-1-carboxylate (1.7 g, 79%) as a gummy solid. $^1$H NMR (500 MHz, $CDCl_3$) δ 9.63 (s, 1H), 3.93-3.79 (m, 1H), 3.57 (dt, J=13.1, 4.6 Hz, 1H), 3.27 (dd, J=13.5, 8.3 Hz, 1H), 3.08-2.99 (m, 1H), 2.36 (tq, J=12.5, 8.6, 6.2 Hz, 1H), 1.95-1.84 (m, 1H), 1.68-1.56 (m, 2H), 1.49-1.42 (m, 1H), 1.41 (s, 9H).

To a solution of (2R,3R,4R,5S)-3,4,5-tris(benzyloxy)-2-methylpiperidine (1.98 g, 4.7 mmol) in DCM (30 mL) was added (R)-tert-butyl 3-formylpiperidine-1-carboxylate (1.5 g, 7.0 mmol) and HOAc (0.5 mL). After stirring at RT for 10 min, $NaBH(OAc)_3$ (1.7 g, 8.0 mmol) was added and the mixture was stirred at RT overnight. The reaction mixture was concentrated before diluting with DCM (25 mL). Organics were washed with satd. aqueous $NaHCO_3$, brine, dried over anhydrous $Na_2SO_4$ and concentrated. The residue was purified on silica gel by flash chromatography (EtOAc/hexanes, 3:7) affording (S)-tert-butyl 3-(((2R,3R,4R,5S)-3,4,5-tris(benzyloxy)-2-methylpiperidin-1-yl)methyl)piperidine-1-carboxylate (2.7 g, 94%) as an oil. $^1$H NMR (400 MHz, $CDCl_3$) δ 7.38-7.27 (m, 15H), 4.99-4.92 (m, 2H), 4.83 (d, J=11.0 Hz, 1H), 4.76-4.57 (m, 3H), 3.90-3.78 (m, 2H), 3.56 (td, J=9.7, 4.5 Hz, 1H), 3.49 (t, J=8.9 Hz, 1H), 3.08 (t, J=9.0 Hz, 1H), 3.01 (d, J=11.8 Hz, 1H), 2.86 (td, J=12.6, 11.7, 3.2 Hz, 1H), 2.50 (m, 2H), 2.25 (dq, J=12.5, 6.4 Hz, 1H), 2.04-1.98 (m, 3H), 1.83-1.74 (m, 1H), 1.68-1.53 (m, 2H), 1.47 (s, 9H), 1.39 (m, 1H), 1.17 (d, J=6.1 Hz, 3H); ESI MS m/z 615.379 $[M+H]^+$.

The above material (2.7 g, 4.4 mmol) was taken up in 3:7 TFA:DCM (30 mL) solution at 0° C. and stirred for 30 min. The reaction mixture was warmed to RT over 2 h before being concentrated to dryness. Diluted with EtOAc (30 mL) and washed organics with satd. $NaHCO_3$ (2×50 mL), dried over anhydrous $Na_2SO_4$ concentrated to yield (2R,3R,4R,5S)-3,4,5-tris(benzyloxy)-2-methyl-1-((R)-piperidin-3-ylmethyl)piperidine as an oil (2.3 g, 99%). $^1$H NMR (400 MHz, $CDCl_3$) δ 7.42-7.26 (m, 15H), 4.98 (d, J=11.0 Hz, 1H), 4.94 (d, J=10.8 Hz, 1H), 4.84 (d, J=11.0 Hz, 1H), 4.72 (d, J=11.6 Hz, 1H), 4.66 (d, J=11.7 Hz, 1H), 4.60 (d, J=10.8 Hz, 1H), 4.46 (s, 1H), 3.58 (td, J=9.7, 4.6 Hz, 1H), 3.50 (t, J=8.9 Hz, 1H), 3.14-3.00 (m, 3H), 2.60 (td, J=12.0, 3.0 Hz, 1H), 2.51 (dd, J=13.0, 8.4 Hz, 1H), 2.33-2.21 (m, 2H), 2.10-2.02 (m, 2H), 1.99 (dd, J=13.0, 5.6 Hz, 1H), 1.86 (dt, J=13.6, 3.7 Hz, 1H), 1.73-1.65 (m, 2H), 1.59-1.46 (m, 1H), 1.17 (d, J=6.2 Hz, 3H), 1.03-0.90 (m, 1H); ESI MS m/z 514.323 $[M+H]^+$.

To a stirred solution of the above material (0.15 g, 0.29 mmol) and 2-chloro-6-(trifluoromethyl)pyridine (0.1 g, 0.6 mmol) in toluene (5 mL) was added $Pd_2(dba)_3$ (28 mg, 0.03 mmol) and RuPhos (28 mg, 0.06 mmol), followed by $Cs_2CO_3$ (0.3 g, 0.9 mmol) under Ar. The mixture was stirred at 100° C. for 18 h, and then water was added at 0° C. The mixture was extracted with EtOAc (2×20 mL). The combined organic layer was washed with water (2×20 mL), separated, and dried over $Na_2SO_4$. After filtration the solvent was evaporated under reduced pressure, and the residue was purified on silica gel by flash chromatography (EtOAc/hexanes, 2:8), affording 2-(trifluoromethyl)-6-((S)-3-(((2R,3R,4R,5S)-3,4,5-tris(benzyloxy)-2-methylpiperidin-1-yl)methyl)piperidin-1-yl)pyridine as an oil (0.16 g, 83%). $^1$H NMR (400 MHz, $CDCl_3$) δ 7.55 (t, J=8.0 Hz, 1H), 7.41-7.23 (m, 15H), 6.90 (d, J=7.2 Hz, 1H), 6.77 (d, J=8.7 Hz, 1H), 4.98 (m, 2H), 4.86 (d, J=11.0 Hz, 1H), 4.73 (d, J=11.6 Hz, 1H), 4.65 (d, J=7.7 Hz, 1H), 4.62 (d, J=6.9 Hz, 1H), 4.21-4.13 (m, 2H), 3.61 (td, J=9.7, 4.5 Hz, 1H), 3.53 (t, J=8.9 Hz, 1H), 3.13 (t, J=9.0 Hz, 1H), 3.07-2.97 (m, 2H), 2.68 (dd, J=12.9, 9.8 Hz, 1H), 2.58 (dd, J=13.1, 8.1 Hz, 1H), 2.32 (dq, J=12.2, 6.1 Hz, 1H), 2.17-2.09 (m, 2H), 1.92-1.83 (m, 1H), 1.78-1.65 (m, 2H), 1.60-1.47 (m, 1H), 1.20 (d, J=6.1 Hz, 3H), 1.19-1.09 (m, 1H); ESI MS m/z 660.335 $[M+H]^+$.

At −78° C., under Ar, to a solution of the above material (0.14 g, 0.21 mmol) in DCM (5 mL) was added $BCl_3$ (1.0 M in DCM, 1.0 mL, 1.0 mmol), and the mixture was stirred for 3 h while the bath temperature reached 0° C. The mixture was then cooled at −78° C., and MeOH (2 mL) was added carefully. After stirring at RT for 30 min the mixture was concentrated under reduced pressure. The resulting residue was neutralized with 1M $NH_3$ in MeOH solution (2×5 mL) and concentrated again under reduced pressure. The residue was purified on silica gel by flash chromatography (MeOH/DCM, 1:9), affording (2R,3R,4R,5S)-2-methyl-1-(((S)-1-(6-(trifluoromethyl)pyridin-2-yl)piperidin-3-yl)methyl)piperidine-3,4,5-triol (0.07 g, 85%) as a white solid. $^1$H NMR (400 MHz, $CD_3OD$) δ 7.65 (ddd, J=8.8, 7.2, 0.8 Hz, 1H), 6.98 (d, J=8.7 Hz, 1H), 6.91 (d, J=7.2 Hz, 1H), 4.27-4.21 (m, 1H), 4.19-4.11 (m, 1H), 3.51 (ddd, J=10.6, 9.0, 4.8 Hz, 1H), 3.16 (t, J=9.0 Hz, 1H), 3.12-3.04 (m, 2H), 3.01 (t, J=9.0 Hz, 1H), 2.82 (dd, J=13.0, 9.7 Hz, 1H), 2.72 (dd, J=13.1, 8.3 Hz, 1H), 2.27-2.18 (m, 2H), 2.15 (t, J=11.1 Hz, 1H), 2.02-1.94 (m, 1H), 1.83 (dq, J=9.0, 4.4 Hz, 1H), 1.77 (dt, J=13.1, 3.9 Hz, 1H), 1.61-1.48 (m, 1H), 1.31 (td, J=12.2, 11.6, 3.6 Hz, 1H), 1.23 (d, J=6.1 Hz, 3H); ESI MS m/z 390.194 $[M+H]^+$.

Example 144

(2R,3R,4R,5S)-2-methyl-1-(((S)-1-(4-(trifluoromethyl)thiazol-2-yl)piperidin-3-yl)methyl)piperidine-3,4,5-triol

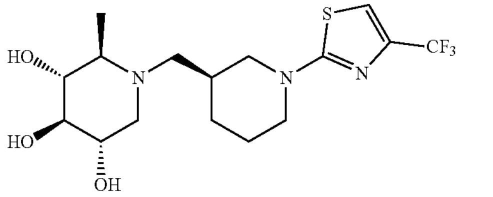 [SMILES: C[C@@H]1[C@@H](O)[C@H](O)[C@@H](O)CN1C[C@@H]1CCCN(c2nc(C(F)(F)F)cs2)C1]

To a stirred solution of (2R,3R,4R,5S)-3,4,5-tris(benzyloxy)-2-methyl-1-((R)-piperidin-3-ylmethyl)piperidine (0.15 g, 0.29 mmol) and 2-bromo-4-(trifluoromethyl)thiazole (0.13 g, 0.58 mmol) in DMA (5 mL) was added $Cs_2CO_3$ (0.28 g, 0.87 mmol) under Ar. The mixture was stirred at 100° C. for 18 h, and then water was added at 0° C. The mixture was extracted with EtOAc (2×20 mL). The combined organic layer was washed with water (2×20 mL), separated, and dried over $Na_2SO_4$. After filtration the solvent was evaporated under reduced pressure, and the residue was purified on silica gel by flash chromatography affording 4-(trifluoromethyl)-2-((S)-3-(((2R,3R,4R,5S)-3,4,5-tris(benzyloxy)-2-methylpiperidin-1-yl)methyl)piperidin-1-yl)thiazole as an oil (0.16 g, 85%). $^1H$ NMR (500 MHz, $CDCl_3$) δ 7.39-7.27 (m, 15H), 6.95 (s, 1H), 5.00 (d, J=10.9 Hz, 1H), 4.97 (d, J=10.8 Hz, 1H), 4.86 (d, J=11.0 Hz, 1H), 4.75 (d, J=11.6 Hz, 1H), 4.65 (d, J=11.8 Hz, 1H), 4.63 (d, J=10.9 Hz, 1H), 3.89-3.83 (m, 1H), 3.81 (dd, J=13.0, 3.9 Hz, 1H), 3.61 (td, J=9.8, 4.6 Hz, 1H), 3.53 (t, J=9.0 Hz, 1H), 3.17-3.08 (m, 2H), 2.98 (dd, J=11.6, 4.7 Hz, 1H), 2.79 (dd, J=12.6, 9.8 Hz, 1H), 2.58 (dd, J=13.1, 8.2 Hz, 1H), 2.31 (dq, J=12.2, 6.3 Hz, 1H), 2.16-2.07 (m, 2H), 1.87 (dt, J=13.3, 4.3 Hz, 1H), 1.80-1.70 (m, 2H), 1.65-1.54 (m, 1H), 1.19 (d, J=6.1 Hz, 3H), 1.18-1.07 (m, 1H); ESI MS m/z 666.294 $[M+H]^+$.

At −78° C., under Ar, to a solution of the above material (0.16 g, 0.24 mmol) in DCM (5 ml) was added $BCl_3$ (1.0 M in DCM, 1.2 mL, 1.2 mmol), and the mixture was stirred for 3 h while the bath temperature reached 0° C. The mixture was then cooled at −78° C., and MeOH (2 mL) was added carefully. After stirring at RT for 30 min the mixture was concentrated under reduced pressure. The resulting residue was neutralized with 1M $NH_3$ in MeOH solution (2×5 mL) and concentrated again under reduced pressure. The residue was purified on silica gel by flash chromatography (MeOH/DCM, 1:9), affording (2R,3R,4R,5S)-2-methyl-1-(((S)-1-(4-(trifluoromethyl)thiazol-2-yl)piperidin-3-yl)methyl)piperidine-3,4,5-triol (0.075 g, 79%) as a white solid. $^1H$ NMR (400 MHz, $CD_3OD$) δ 7.20 (s, 1H), 3.90 (dd, J=13.0, 4.3 Hz, 1H), 3.87-3.81 (m, 1H), 3.50 (ddd, J=10.4, 9.0, 4.8 Hz, 1H), 3.05-2.94 (m, 2H), 3.04-2.94 (m, 2H), 2.90 (dd, J=12.7, 9.8 Hz, 1H), 2.69 (dd, J=13.1, 8.1 Hz, 1H), 2.18-2.05 (m, 3H), 2.02-1.93 (m, 1H), 1.92-1.76 (m, 2H), 1.63 (dddd, J=17.9, 13.7, 9.4, 5.5 Hz, 1H), 1.33-1.23 (m, 1H), 1.21 (d, J=6.1 Hz, 3H); ESI MS m/z 396.149 $[M+H]^+$.

Example 145

(2S,3R,4R,5S)-2-(fluoromethyl)-1-((4-isopropylcyclohexyl)methyl)piperidine-3,4,5-triol

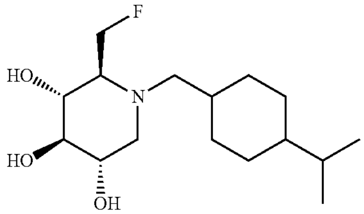

Under Ar, to a solution of 4-isopropylcyclohexanecarbaldehyde (80 mg, 0.43 mmol), ((2R,3R,4R,5S)-3,4,5-tris(benzyloxy)piperidin-2-yl)methanol (150 mg, 0.36 mmol) and HOAc (three drops) in anhydrous MeOH (10 mL) was added $NaBH_3CN$ (40 mg, 95%, 0.57 mmol). The mixture was stirred at RT for 18 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 30% EtOAc in hexanes, affording ((2R,3R,4R,5S)-3,4,5-tris(benzyloxy)-1-((4-isopropylcyclohexyl)methyl)piperidin-2-yl)methanol as a white foam (234 mg, 100%).

To a stirred solution of the above material (234 mg, 0.41 mmol) and $Et_3N$ (0.35 mL, 2.46 mmol) in DCM (5 mL) was added MsCl (188 mg, 1.64 mmol) in DCM (1 mL) slowly at 0° C. The reaction mixture was stirred at 0° C. for 2 h, and quenched with satd. aqueous $NaHCO_3$ solution (20 mL). The mixture was extracted with EtOAc (3×20 mL). The combined organic layer was washed with water (2×20 mL), separated, and dried over $Na_2SO_4$. After filtration, the solvent was evaporated under reduced pressure. The obtained residue was dissolved in tert-butanol (5 mL) in a sealed tube, and CsF (623 mg, 4.1 mmol) was added. The mixture was stirred at 90° C. for 8 h, and cooled to ambient temperature. The reaction mixture was poured into ice water (30 mL) and extracted with EtOAc (3×20 mL). The combined organic layer was washed with water (2×20 mL), separated, and dried over $Na_2SO_4$. After filtration, the solvent was evaporated under reduced pressure, and the residue was purified on silica gel by flash chromatography affording (2S,3R,4R,5S)-3,4,5-tris(benzyloxy)-2-(fluoromethyl)-1-((4-isopropylcyclohexyl)methyl)piperidine (149 mg, 63%) as a clear oil.

The above material (149 mg, 0.26 mmol) and 2N HCl (0.3 mL) in EtOH (10 mL) was treated with hydrogen in balloon overnight in the presence of $Pd(OH)_2$ (cat.). Removal of $Pd(OH)_2$ by filtration and evaporation of solvent followed by purification on silica gel chromatography using 10% MeOH and 2% $NH_3$ solution in DCM, afforded (2S,3R,4R,5S)-2-(fluoromethyl)-1-((4-isopropylcyclohexyl)methyl)piperidine-3,4,5-triol (40 mg, 51%) as a white solid; this material was isolated as a mixture of cis and trans isomers. $^1H$ NMR (500 MHz, $CD_3OD$) δ 4.83-4.58 (m, 2H), 3.52-3.43 (m, 1H), 3.31-3.26 (m, 1H), 3.20 (t, J=8.9 Hz, 1H), 3.17-3.10 (m, 1H), 3.09-3.05 (m, 0.47H), 2.74 (s, 0.39H), 2.56-1.93 (m, 3H), 1.94-1.61 (m, 2H), 1.57-1.28 (m, 7H), 1.23-0.93 (m, 2H), 0.90 (dd, J=6.8, 1.1 Hz, 6H); ESI MS m/z 304.2 $[M+H]^+$.

Example 146

(2S,3R,4R,5S)-1-((4-(tert-butyl)cyclohexyl)methyl)-2-(fluoromethyl)piperidine-3,4,5-triol

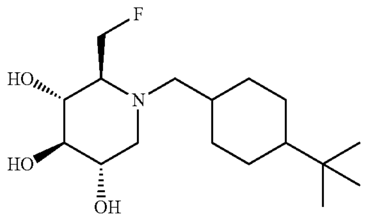 [SMILES: CC(C)(C)C1CCC(CN2C[C@H](O)[C@@H](O)[C@H](O)[C@H]2CF)CC1]

Under Ar, to a solution of 4-(tert-butyl)cyclohexanecarbaldehyde (96 mg, 0.57 mmol), ((2R,3R,4R,5S)-3,4,5-tris(benzyloxy)piperidin-2-yl)methanol (165 mg, 0.38 mmol) and HOAc (three drops) in anhydrous MeOH (10 mL) was added $NaBH_3CN$ (38 mg, 95%, 0.57 mmol). The mixture was stirred at RT for 18 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 30% EtOAc in hexanes, affording ((2R,3R,4R,5S)-3,4,5-tris(benzyloxy)-1-((4-(tert-butyl)cyclohexyl)methyl)piperidin-2-yl)methanol (mixture of cis and trans isomers) as a white foam (158 mg, 71%).

To a stirred solution of the above material (158 mg, 0.27 mmol) and $Et_3N$ (0.2 mL, 1.38 mmol) in DCM (5 mL) was added MsCl (106 mg, 0.93 mmol) in DCM (1 mL) slowly at 0° C. The reaction mixture was stirred at 0° C. for 2 h, and quenched with satd. aqueous $NaHCO_3$ (20 mL). The mixture was extracted with EtOAc (3×20 mL). The combined organic layer was washed with water (2×20 mL), separated, and dried over $Na_2SO_4$. After filtration, the solvent was evaporated under reduced pressure. The residue was dissolved in tert-butanol (5 mL) in a sealed tube, and CsF (350 mg, 2.3 mmol) was added. The mixture was stirred at 90° C. for 8 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2S,3R,4R,5S)-3,4,5-tris(benzyloxy)-1-((4-(tert-butyl)cyclohexyl)methyl)-2-(fluoromethyl)piperidine (mixture of cis and trans isomers) as a clear oil (158 mg, 100%).

The above material (158 mg, 0.27 mmol), 2N HCl (0.5 mL) in EtOH (10 mL) was treated with hydrogen in balloon overnight in presence of $Pd(OH)_2$ (cat.). Removal of $Pd(OH)_2$ by filtration and evaporation of solvent followed by purification on silica gel chromatography using 10% MeOH and 2% $NH_3$ solution in DCM, afforded (2S,3R,4R,5S)-1-((4-(tert-butyl)cyclohexyl)methyl)-2-(fluoromethyl)piperidine-3,4,5-triol (38 mg, 44%) as a white solid; this material was isolated as a mixture of cis and trans isomers. $^1H$ NMR (400 MHz, $CD_3OD$) S 4.90-4.57 (m, 2H), 3.53-3.39 (m, 1H), 3.28-3.02 (m, 3.75H), 2.78-2.59 (m, 0.25H), 2.44-0.94 (m, 13H), 0.91-0.75 (M, 9H); ESI MS m/z 319.2 $[M+H]^+$.

Example 147

(2S,3R,4R,5S)-2-(fluoromethyl)-1-(((1r,4S)-4-(trifluoromethyl)cyclohexyl)methyl)piperidine-3,4,5-triol

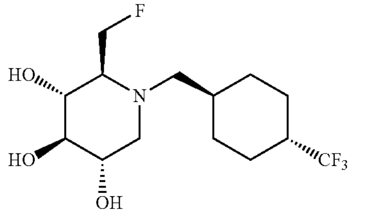 [SMILES: O[C@H]1[C@H](O)[C@@H](O)CN(C[C@H]2CC[C@H](C(F)(F)F)CC2)[C@@H]1CF]

Under Ar, to a solution of trans-4-(trifluoromethyl)cyclohexanecarbaldehyde (72 mg, 0.40 mmol), ((2R,3R,4R,5S)-3,4,5-tris(benzyloxy)piperidin-2-yl)methanol (110 mg, 0.25 mmol) and HOAc (three drops) in anhydrous MeOH (10 mL) was added $NaBH_3CN$ (27 mg, 95%, 0.40 mmol). The mixture was stirred at RT for 18 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 30% EtOAc in hexanes, affording ((2R,3R,4R,5S)-3,4,5-tris(benzyloxy)-1-(((1r,4R)-4-(trifluoromethyl) cyclohexyl) methyl) piperidin-2-yl)methanol as a white foam (123 mg, 83%).

To a stirred solution of the above material (123 mg, 0.21 mmol) and $Et_3N$ (0.2 mL, 1.38 mmol) in DCM (5 mL) was added MsCl (97 mg, 0.83 mmol) in DCM (1 mL) slowly at 0° C. The reaction mixture was stirred at 0° C. for 2 h, and quenched with satd. aqueous $NaHCO_3$ (20 mL). The mixture was extracted with EtOAc (3×20 mL). The combined organic layer was washed with water (2×20 mL), separated, and dried over $Na_2SO_4$. After filtration, the solvent was evaporated under reduced pressure. The obtained residue was dissolved in tert-butanol (5 mL) in a sealed tube, and CsF (319 mg, 2.1 mmol) was added. The mixture was stirred at 90° C. for 8 h, and cooled to ambient temperature. The reaction mixture was poured into ice water (30 mL) and extracted with EtOAc (3×20 mL). The combined organic layer was washed with water (2×20 mL), separated, and dried over $Na_2SO_4$. After filtration, the solvent was evaporated under reduced pressure, and the residue was purified on silica gel by flash chromatography affording (2S,3R,4R,5S)-3,4,5-tris(benzyloxy)-2-(fluoromethyl)-1-(((1r,4S)-4-trifluoromethyl)cyclohexyl)methyl)piperidine as a clear oil (85 mg, 69%).

The above material (85 mg, 0.14 mmol) and 2N HCl (0.3 mL) in EtOH (10 mL) was treated with hydrogen in balloon overnight in presence of $Pd(OH)_2$ (cat.). Removal of $Pd(OH)_2$ by filtration and evaporation of solvent followed by purification on silica gel chromatography using 10% MeOH and 2% NH solution in DCM, afforded (2S,3R,4R,5S)-2-(fluoromethyl)-1-(((1r,4S)-4-trifluoromethyl)cyclohexyl) methyl)piperidine-3,4,5-triol (19 mg, 40%) as a white solid. $^1H$ NMR (400 MHz, $CD_3OD$) δ 4.83 (d, J=1.5 Hz, 0.5H), 4.77-4.63 (m, 1H), 4.56 (dd, J=10.4, 4.0 Hz, 0.5H), 3.45 (ddd, J=10.4, 8.6, 4.8 Hz, 1H), 3.26-3.13 (m, 2H), 3.05 (dd, J=11.3, 4.8 Hz, 1H), 2.68 (dd, J=13.0, 9.1 Hz, 1H), 2.31-1.90

(m, 7H), 1.85 (d, J=13.3 Hz, 1H), 1.55-1.52 (m, 1H), 1.35-1.32 (m, 2H), 1.11-0.78 (m, 2H); ESI MS m/z 330.1 $[M+H]^+$.

Example 148

(2S,3R,4R,5S)-2-(fluoromethyl)-1-phenethylpiperidine-3,4,5-triol

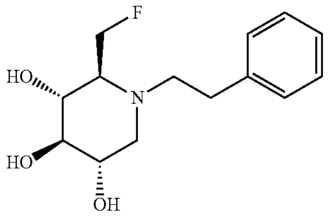 [SMILES: O[C@H]1[C@H](O)[C@@H](O)CN(CCc2ccccc2)[C@@H]1CF]

$K_2CO_3$ (1.64 g, 11.8 mmol) was added to a solution of ((2R,3R,4R,5S)-3,4,5-tris(benzyloxy)piperidin-2-yl)methanol (641 mg, 1.48 mmol) and (2-bromoethyl)benzene (1.09 g, 5.92 mmol) in DMF (20 mL) in a sealed tube. The mixture was stirred at 80° C. for 18 h, and cooled to ambient temperature. The reaction mixture was poured into ice water (50 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording ((2R,3R,4R,5S)-3,4,5-tris(benzyloxy)-1-phenethylpiperidin-2-yl)methanol as a clear oil (615 mg, 77%). ESI MS m/z 538.29 $[M+H]^+$.

To a stirred solution of the above material (92 mg, 0.17 mmol) and $Et_3N$ (0.14 mL, 1.02 mmol) in DCM (5 mL) was added MsCl (0.053 mL, 0.68 mmol) slowly at 0° C. The reaction mixture was stirred at 0° C. for 2 h, and quenched with satd. aqueous $NaHCO_3$ solution (20 mL). The mixture was extracted with EtOAc (3×20 mL). The combined organic layer was washed with water (2×20 mL), separated, dried over $Na_2SO_4$. After filtration, the solvent was evaporated under reduced pressure. The residue was dissolved in tert-butanol (5 mL) in a sealed tube, and CsF (303 mg, 2.0 mmol) was added. The mixture was stirred at 90° C. for 8 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording ((2S,3R,4R,5S)-3,4,5-tris(benzyloxy)-2-(fluoromethyl)-1-phenethylpiperidine as a clear oil (30 mg, 43%). ESI MS m/z 540.29 $[M+H]^+$.

To a solution of the above material (30 mg, 0.056 mmol) in EtOH (10 mL) was added $Pd(OH)_2/C$ (20 wt. %, 8.6 mg, 0.012 mmol) and 6N HCl (0.1 mL). The mixture was treated with hydrogen (1 atm) for 18 h. Catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2S,3R,4R,5S)-2-(fluoromethyl)-1-phenethylpiperidine-3,4,5-triol as a white solid (8 mg, 53%). $^1H$ NMR (400 MHz, $CD_3OD$) δ 7.32-7.24 (m, 2H), 7.23-7.14 (m, 3H), 4.96-4.59 (m, 2H), 3.55-3.45 (m, 1H), 3.29-3.14 (m, 2H), 3.12-3.05 (m, 1H), 3.05-2.96 (m, 1H), 2.96-2.72 (m, 3H), 2.54-2.34 (m, 2H); ESI MS m/z 270.15 $[M+H]^+$.

Example 149

(2S,3R,4R,5S)-2-(fluoromethyl)-1-(2-fluorophenethyl)piperidine-3,4,5-triol

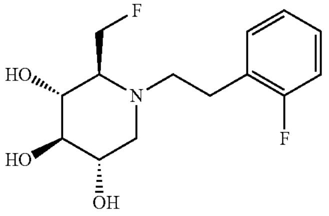 [SMILES: O[C@H]1[C@H](O)[C@@H](O)CN(CCc2ccccc2F)[C@@H]1CF]

$K_2CO_3$ (630 mg, 4.56 mmol) was added to a solution of ((2R,3R,4R,5S)-3,4,5-tris(benzyloxy)piperidin-2-yl)methanol (300 mg, 0.69 mmol) and 1-(2-bromoethyl)-2-fluorobenzene (582 mg, 2.86 mmol) in DMF (5 mL) in a sealed tube. The mixture was stirred at 80° C. for 18 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording ((2R,3R,4R,5S)-3,4,5-tris(benzyloxy)-1-(2-fluorophenethyl)piperidin-2-yl)methanol as a clear oil (225 mg, 59%). ESI MS m/z 556.29 $[M+H]^+$.

To a stirred solution of the above material (110 mg, 0.20 mmol) and $Et_3N$ (0.14 mL, 0.80 mmol) in DCM (5 mL) was added MsCl (0.031 mL, 0.40 mmol) slowly at 0° C. The reaction mixture was stirred at 0° C. for 2 h, and quenched with satd. aqueous $NaHCO_3$ solution (20 mL). The mixture was extracted with EtOAc (3×20 mL). The combined organic layer was washed with water (2×20 mL), separated, dried over $Na_2SO_4$. After filtration, the solvent was evaporated under reduced pressure. The residue was dissolved in tert-butanol (5 mL) in a sealed tube, and CsF (303 mg, 2.0 mmol) was added. The mixture was stirred at 90° C. for 8 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2S,3R,4R,5S)-3,4,5-tris(benzyloxy)-2-(fluoromethyl)-1-(2-fluorophenethyl)piperidine as a clear oil (77 mg, 69%). ESI MS m/z 558.27 $[M+H]^+$.

To a stirred solution of the above material (43 mg, 0.077 mmol) in anhydrous DCM (3 mL) was added $BCl_3$ solution (1M in DCM, 0.77 mL, 0.77 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (10 mL) and stirred for another 10 min, after which solvent was removed under vacuum. The residue was purified by silica gel chromatography to give (2S,3R,4R,5S)-2-(fluoromethyl)-1-(2-fluorophenethyl)piperidine-3,4,5-triol as a white solid (11 mg, 50%). $^1H$ NMR (400 MHz, $CD_3OD$) δ

7.31-7.20 (m, 2H), 7.14-7.02 (m, 2H), 4.87-4.09 (m, 2H), 3.55-3.45 (m, 1H), 3.28-3.15 (m, 2H), 3.13-3.06 (m, 1H), 3.06-2.96 (m, 1H), 2.96-2.81 (m, 3H), 2.51-2.37 (m, 2H); ESI MS m/z 288.14 $[M+H]^+$.

Example 150

(2S,3R,4R,5S)-1-(2,6-difluoro-4-isopropylphenethyl)-2-(fluoromethyl)piperidine-3,4,5-triol

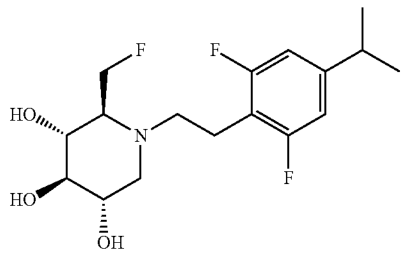 [SMILES: CC(C)c1cc(F)c(CCN2C[C@H](O)[C@@H](O)[C@H](O)[C@H]2CF)c(F)c1]

To a stirred solution of ((2R,3R,4R,5S)-3,4,5-tris(benzyloxy)piperidin-2-yl)methanol (400 mg, 0.92 mmol) and 2-(4-bromo-2,6-difluorophenyl)acetaldehyde (432 mg, 1.85 mmol) in anhydrous MeOH (10 mL) was added HOAc (0.20 mL, 3.5 mmol) and the mixture was stirred for 30 min. $NaBH_3CN$ (116 mg, 1.85 mmol) was added, and the resulting mixture was stirred at RT for 18 h. The reaction was quenched with satd. aqueous $NaHCO_3$ at 0° C. The mixture was extracted with EtOAc (3×30 mL). The combined organic layer was washed with water (2×20 mL), separated, dried over $Na_2SO_4$. After filtration, the solvent was evaporated under reduced pressure, and the residue was purified on silica gel by flash chromatography affording ((2R,3R,4R,5S)-3,4,5-tris(benzyloxy)-1-(4-bromo-2,6-difluorophenethyl)piperidin-2-yl)methanol as a brown solid (580 mg, 97%). ESI MS m/z 652.18, 654.18 $[M+H]^+$.

To a stirred solution of the above material (400 mg, 0.61 mmol) and $Et_3N$ (0.34 mL, 2.46 mmol) in DCM (10 mL) was added MsCl (0.095 mL, 1.23 mmol) slowly at 0° C. The reaction mixture was stirred at 0° C. for 2 h, and quenched with satd. aqueous $NaHCO_3$ (20 mL). The mixture was extracted with EtOAc (3×20 mL). The combined organic layer was washed with water (2×20 mL), separated, dried over $Na_2SO_4$. After filtration, the solvent was evaporated under reduced pressure. The residue was dissolved in tert-butanol (10 mL) in a sealed tube, and CsF (983 mg, 6.1 mmol) was added. The mixture was stirred at 90° C. for 8 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2S,3R,4R,5S)-3,4,5-tris(benzyloxy)-1-(4-bromo-2,6-difluorophenethyl)-2-(fluoromethyl)piperidine as a clear oil (200 mg, 50%). ESI MS m/z 654.17, 656.17 $[M+H]^+$.

To a stirred solution of the above material (84 mg, 0.13 mmol) and 2-isopropenylboronic acid pinacol ester (43 mg, 0.26 mmol) in toluene (5 mL) was added $Pd(PPh_3)_4$ (30 mg, 0.026 mmol), followed with $K_2CO_3$ (90 mg, 0.65 mmol) and water (1 mL) under Ar. The mixture was stirred at 100° C. for 18 h, and then water was added. The mixture was extracted with EtOAc (2×20 mL). The combined organic layer was washed with water (2×10 mL), separated, dried over $Na_2SO_4$. After filtration the solvent was evaporated under reduced pressure, and the residue was purified on silica gel by flash chromatography affording (2S,3R,4R,5S)-3,4,5-tris(benzyloxy)-1-(2,6-difluoro-4-(prop-1-en-2-yl)phenethyl)-2-(fluoromethyl)piperidine as a white solid (50 mg, 63%). ESI MS m/z 616.30 $[M+H]^+$.

To a solution of the above material (50 mg, 0.081 mmol) in EtOH (10 mL) was added $Pd(OH)_2/C$ (20 wt. %, 8.6 mg, 0.012 mmol) and 6N HCl (0.1 mL). The mixture was treated with $H_2$ (1 atm) for 18 h. Catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2S,3R,4R,5S)-1-(2,6-difluoro-4-isopropylphenethyl)-2-(fluoromethyl)piperidine-3,4,5-triol as a white solid (18 mg, 64%). $^1H$ NMR (400 MHz, $CD_3OD$) δ 6.94-6.73 (m, 2H), 4.79-4.55 (m, 2H), 3.49 (ddd, J=10.4, 8.8, 4.9 Hz, 1H), 3.29-3.14 (m, 2H), 3.10 (dd, J=11.1, 4.9 Hz, 1H), 3.02-2.76 (m, 5H), 2.50-2.31 (m, 2H), 1.24 (d, J=6.9 Hz, 6H); ESI MS m/z 348.18 $[M+H]^+$.

Example 151

(2S,3R,4R,5S)-1-(2-(3,5-difluoro-[1,1'-biphenyl]-4-yl)ethyl)-2-(fluoromethyl)piperidine-3,4,5-triol

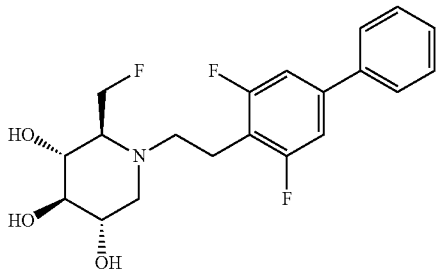 [SMILES: O[C@H]1[C@H](O)[C@@H](O)CN(CCc2c(F)cc(-c3ccccc3)cc2F)[C@@H]1CF]

To a stirred solution of (2S,3R,4R,5S)-3,4,5-tris(benzyloxy)-1-(4-bromo-2,6-difluorophenethyl)-2-(fluoromethyl)piperidine (100 mg, 0.15 mmol) and phenylboronic acid (37 mg, 0.31 mmol) in toluene (5 mL) was added $Pd(PPh_3)_4$ (35 mg, 0.031 mmol), followed with $K_2CO_3$ (104 mg, 0.75 mmol) and water (1 mL) under Ar. The mixture was stirred at 100° C. for 18 h, and then water was added. The mixture was extracted with EtOAc (2×20 mL). The combined organic layer was washed with water (2×10 mL), separated, dried over $Na_2SO_4$. After filtration the solvent was evaporated under reduced pressure, and the residue was purified on silica gel by flash chromatography affording (2S,3R,4R,5S)-3,4,5-tris(benzyloxy)-1-(2-(3,5-difluoro-[1,1'-biphenyl]-4-yl)ethyl)-2-(fluoromethyl)piperidine as a white solid (96 mg, 98%). ESI MS m/z 652.31 $[M+H]^+$.

To a solution of the above material (96 mg, 0.15 mmol) in EtOH (10 mL) was added $Pd(OH)_2/C$ (20 wt. %, 8.6 mg, 0.012 mmol) and 6N HCl (0.1 mL). The mixture was treated with $H_2$ (1 atm) for 18 h. Catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2S,3R,4R,5S)-1-(2-(3,5-difluoro-[1,1'-biphenyl]-4-yl)ethyl)-2-(fluoromethyl)piperidine-3,4,5-triol as a white solid (37 mg, 65%). $^1$H NMR (400 MHz, DMSO-$d_6$) δ 7.76-7.71 (m, 2H), 7.52-7.38 (m, 5H), 5.05 (d, J=5.0 Hz, 1H), 4.86 (d, J=3.9 Hz, 1H), 4.81 (d, J=4.8 Hz, 1H), 4.72 (dd, J=46.8, 10.2 Hz, 1H), 4.54 (ddd, J=46.8, 10.2, 3.9 Hz, 1H), 3.31-3.20 (m, 1H), 3.03-2.72 (m, 7H), 2.40-2.27 (m, 1H), 2.25 (t, J=10.7 Hz, 1H); ESI MS m/z 382.16 $[M+H]^+$.

Example 152

(2S,3R,4R,5S)-1-(2-(6-fluorobenzo[d][1,3]dioxol-5-yl)ethyl)-2-(fluoromethyl)piperidine-3,4,5-triol

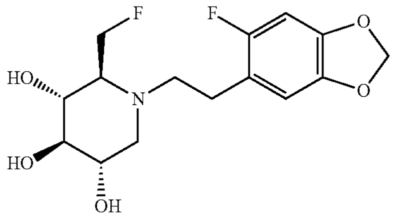 [SMILES: O[C@H]1[C@H](O)[C@@H](O)CN(CCc2cc3c(cc2F)OCO3)[C@@H]1CF]

To a stirred solution of ((2R,3R,4R,5S)-3,4,5-tris(benzyloxy)piperidin-2-yl)methanol (99 mg, 0.23 mmol) and 2-(6-fluorobenzo[d][1,3]dioxol-5-yl)acetaldehyde (50 mg, 0.27 mmol) in anhydrous DCM (5 mL) was added HOAc (0.20 mL, 3.5 mmol) and the mixture was stirred for 30 min. $Na(OAc)_3BH$ (57 mg, 0.27 mmol) was added, and the resulting mixture was stirred at RT for 18 h. The reaction was quenched with satd. aqueous $NaHCO_3$ at 0° C. The mixture was extracted with EtOAc (3×30 mL). The combined organic layer was washed with water (2×20 mL), separated, dried over $Na_2SO_4$. After filtration, the solvent was evaporated under reduced pressure, and the residue was purified on silica gel by flash chromatography affording ((2R,3R,4R,5S)-3,4,5-tris(benzyloxy)-1-(2-(6-fluorobenzo [d][1,3]dioxol-5-yl)ethyl)piperidin-2-yl)methanol as an oil (72 mg, 52%). ESI MS m/z 600.30 $[M+H]^+$.

To a stirred solution of the above material (72 mg, 0.12 mmol) and $Et_3N$ (0.067 mL, 0.48 mmol) in DCM (5 mL) was added MsCl (0.019 mL, 0.24 mmol) slowly at 0° C. The reaction mixture was stirred at 0° C. for 2 h, and quenched with satd. aqueous $NaHCO_3$ (20 mL). The mixture was extracted with EtOAc (3×20 mL). The combined organic layer was washed with water (2×20 mL), separated, dried over $Na_2SO_4$. After filtration, the solvent was evaporated under reduced pressure. The residue was dissolved in tert-butanol (5 mL) in a sealed tube, and CsF (182 mg, 1.2 mmol) was added. The mixture was stirred at 90° C. for 8 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2S,3R,4R,5S)-3,4,5-tris(benzyloxy)-1-(2-(6-fluorobenzo[d][1,3]dioxol-5-yl)ethyl)-2-(fluoromethyl)piperidine as a clear oil (35 mg, 49%). ESI MS m/z 602.27 $[M+H]^+$.

To a solution of the above material (35 mg, 0.058 mmol) in EtOH (10 mL) was added $Pd(OH)_2/C$ (20 wt. %, 8.6 mg, 0.012 mmol) and 6N HCl (0.1 mL). The mixture was treated with $H_2$ (1 atm) for 18 h. Catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2S,3R,4R,5S)-1-(2-(6-fluorobenzo[d][1,3]dioxol-5-yl)ethyl)-2-(fluoromethyl)piperidine-3,4,5-triol as a white solid (12 mg, 62%). $^1$H NMR (400 MHz, $CD_3OD$) δ 6.73 (s, 1H), 6.66 (s, 1H), 5.95 (s, 2H), 4.80-4.60 (m, 2H), 3.53-3.43 (m, 1H), 3.25 (t, J=9.2 Hz, 1H), 3.17 (s, 1H), 3.06 (dd, J=11.1, 4.9 Hz, 1H), 3.01-2.91 (m, 1H), 2.90-2.81 (m, 1H), 2.80-2.67 (m, 2H), 2.50-2.33 (m, 2H); ESI MS m/z 332.13 $[M+H]^+$.

Example 153

(2S,3R,4R,5S)-1-(2-(2,3-dihydrobenzo[b][1,4]dioxin-6-yl)ethyl)-2-(fluoromethyl)piperidine-3,4,5-triol

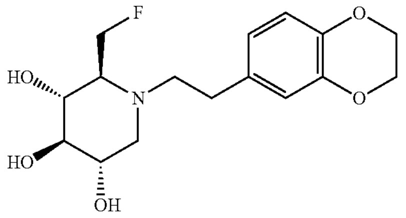 [SMILES: O[C@H]1[C@H](O)[C@@H](O)CN(CCc2ccc3c(c2)OCCO3)[C@@H]1CF]

DIPEA (0.38 mL, 2.2 mmol) was added to a solution of ((2R,3R,4R,5S)-3,4,5-tris(benzyloxy)piperidin-2-yl)methanol (150 mg, 0.35 mmol) and 6-(2-bromoethyl)-2,3-dihydrobenzo[b][1,4]dioxine (128 mg, 0.53 mmol) in DMF (5 mL) in a sealed tube. The mixture was stirred at 80° C. for 18 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording ((2R,3R,4R,5S)-3,4,5-tris(benzyloxy)-1-(2-(2,3-dihydrobenzo[b][1,4]dioxin-6-yl) ethyl)piperidin-2-yl)methanol as a white solid (126 mg, 60%). ESI MS m/z 596.29 $[M+H]^+$.

To a stirred solution of the above material (120 mg, 0.20 mmol) and $Et_3N$ (0.11 mL, 0.80 mmol) in DCM (5 mL) was added MsCl (0.031 mL, 0.40 mmol) slowly at 0° C. The reaction mixture was stirred at 0° C. for 2 h, and quenched with satd. aqueous $NaHCO_3$ (20 mL). The mixture was extracted with EtOAc (3×20 mL). The combined organic layer was washed with water (2×20 mL), separated, dried over $Na_2SO_4$. After filtration, the solvent was evaporated under reduced pressure. The residue was dissolved in tert-butanol (5 mL) in a sealed tube, and CsF (303 mg, 2.0 mmol) was added. The mixture was stirred at 90° C. for 8 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording ((2S(2S,3R,4R,5S)-3,4,5-tris (benzyloxy)-1-(2-(2,3-dihydrobenzo[b][1,4]dioxin-6-yl) ethyl)-2-(fluoromethyl)piperidine as a clear oil (60 mg, 50%). ESI MS m/z 598.28 $[M+H]^+$.

To a solution of the above material (60 mg, 0.10 mmol) in EtOH (10 mL) was added $Pd(OH)_2/C$ (20 wt. %, 8.6 mg, 0.012 mmol) and 6N HCl (0.1 mL). The mixture was treated with $H_2$ (1 atm) for 18 h. Catalyst was filtered off through celite and the solvent was evaporated under reduced pressure. The residue was dissolved in 1M $NH_3$ in MeOH (10 mL) and stirred for another 10 min, after which solvent was removed under vacuum. The residue was purified by silica gel chromatography to give (2S,3R,4R,5S)-1-(2-(2,3-dihydrobenzo[b][1,4]dioxin-6-yl)ethyl)-2-(fluoromethyl)piperidine-3,4,5-triol as a white solid (10 mg, 31%). $^1H$ NMR (400 MHz, DMSO-$d_6$) δ 6.74 (d, J=8.2 Hz, 1H), 6.69 (d, J=2.0 Hz, 1H), 6.64 (dd, J=8.2, 2.1 Hz, 1H), 5.02 (d, J=4.9 Hz, 1H), 4.84 (d, J=3.7 Hz, 1H), 4.76 (d, J=4.7 Hz, 1H), 4.74 (dd, J=46.9, 10.2 Hz, 1H), 4.58 (ddd, J=46.9, 10.2, 4.1 Hz, 1H), 4.26-4.13 (m, 4H), 3.27-3.16 (m, 1H), 3.01-2.93 (m, 2H), 2.89 (dd, J=11.2, 4.9 Hz, 1H), 2.86-2.78 (m, 1H), 2.74-2.65 (m, 1H), 2.64-2.53 (m, 2H), 2.36-2.22 (m, 1H), 2.17 (t, J=10.7 Hz, 1H); ESI MS m/z 328.15 $[M+H]^+$.

Example 154

(2S,3R,4R,5S)-2-(fluoromethyl)-1-((1-phenylpiperidin-4-yl)methyl)piperidine-3,4,5-triol

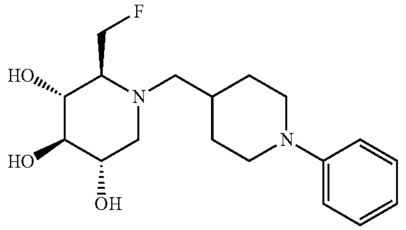 [SMILES: O[C@H]1[C@H](O)[C@@H](O)CN(CC2CCN(c3ccccc3)CC2)[C@@H]1CF]

Under $N_2$, a mixture of ((2R,3R,4R,5S)-3,4,5-tris(benzyloxy)piperidin-2-yl)methanol (0.217 g, 0.500 mmol), 1-phenylpiperidine-4-carbaldehyde (0.126 g, 0.667 mmol), $NaBH_3CN$ (0.070 g, 1.1 mmol) and two drops of AcOH in MeOH (10 mL) was stirred at 60° C. for 16 h. The reaction mixture was cooled at RT and diluted with satd. aqueous $NaHCO_3$ (30 mL). After extraction with DCM (3×20 mL) the combined extract was dried over anhydrous $Na_2SO_4$. After filtration the solvent was evaporated under reduced pressure, and the residue was purified on silica gel by flash chromatography (EtOAc/hexanes, 1:3 to 1:2), affording ((2R,3R,4R,5S)-3,4,5-tris(benzyloxy)-1-((1-phenylpiperidin-4-yl)methyl)piperidin-2-yl)methanol as a pale-yellow oil (0.22 g, 72%); ESI MS m/z 607.342 $[M+H]^+$.

At 0° C., to a solution of the above material (0.17 g, 0.28 mmol) and DIPEA (0.19 g, 1.5 mmol) in anhydrous DCM (6 mL) was added MsCl (0.087 g, 0.76 mmol) dropwise, and the mixture was stirred at 0° C. for 2 h. The reaction mixture was diluted with satd. aqueous $NaHCO_3$ (15 mL) and extracted with DCM (3×20 mL). The combined extract was washed with water (30 mL) and dried over anhydrous $Na_2SO_4$. After filtration the solvent was evaporated under reduced pressure at RT to give a residue containing unstable ((2R,3R,4R,5S)-3,4,5-tris(benzyloxy)-1-((1-phenylpiperidin-4-yl)methyl)piperidin-2-yl)methyl methanesulfonate, and immediately the crude residue was treated with excess CsF (0.50 g, 3.3 mmol) in t-BuOH (5 mL) in a sealed tube at 85° C. for 16 h. After cooling the mixture was diluted with satd. aqueous $NaHCO_3$ (20 mL) and extracted with EtOAc (3×10 mL). The combined extract was dried over anhydrous $Na_2SO_4$. After filtration the solvent was evaporated under reduced pressure, and the residue was purified on silica gel by flash chromatography (EtOAc/hexanes, 1:9 to 1:4), affording (2S,3R,4R,5S)-3,4,5-tris(benzyloxy)-2-(fluoromethyl)-1-((1-phenylpiperidin-4-yl)methyl)piperidine as a clear oil (0.12 g, 70%); ESI MS m/z 609.349 $[M+H]^+$.

At −78° C. and under $N_2$, to a solution of the above material (0.12 g, 0.20 mmol) in anhydrous DCM (6 mL) was added $BCl_3$ (1.0 M in DCM, 1.5 mL, 1.5 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:9), affording (2S,3R,4R,5S)-2-(fluoromethyl)-1-((1-phenylpiperidin-4-yl)methyl)piperidine-3,4,5-triol as a white solid (0.040 g, 59%, two steps). $^1H$ NMR (400 MHz, DMSO-$d_6$) δ 7.23-7.14 (m, 2H), 6.96-6.86 (m, 2H), 6.75-6.69 (m, 1H), 5.00 (d, J=4.7 Hz, 1H), 4.83 (d, J=3.6 Hz, 1H), 4.74 (d, J=4.7 Hz, 1H), 4.72 (dd, J=49.0, 10.2 Hz, 1H), 4.53 (ddd, J=46.8, 10.2, 3.9 Hz, 1H), 3.70-3.62 (m, 2H), 3.22-3.17 (m, 1H), 3.04-2.95 (m, 2H), 2.91 (dd, J=11.2, 4.6 Hz, 1H), 2.70-2.56 (m, 3H), 2.15-2.04 (m, 2H), 1.90-1.81 (m, 2H), 1.70-1.63 (m, 2H), 1.24-1.05 (m, 2H); ESI MS m/z 339.204 $[M+H]^+$.

Example 155

(2S,3R,4R,5S)-2-(fluoromethyl)-1-((1-(4-(trifluoromethyl)phenyl)piperidin-4-yl)methyl)piperidine-3,4,5-triol

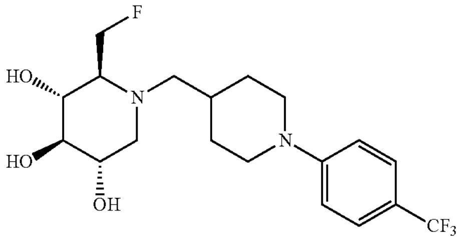 [SMILES: O[C@H]1[C@H](O)[C@@H](O)CN(CC2CCN(c3ccc(C(F)(F)F)cc3)CC2)[C@@H]1CF]

Under Ar, to a solution of 1-(4(trifluoromethyl)phenyl)piperidine-4-carbaldehyde (75 mg, 0.29 mmol), ((2R,3R,4R,5S)-3,4,5-tris(benzyloxy)piperidin-2-yl)methanol (126 mg, 0.39 mmol) and HOAc (three drops) in anhydrous MeOH (10 mL) was added $NaBH_3CN$ (30 mg, 95%, 0.45 mmol). The mixture was stirred at RT for 18 h, satd. aqueous $NaHCO_3$ (30 mL) was added, and the mixture was extracted with EtOAc (3×30 mL). The combined organic extract was dried over anhydrous $Na_2SO_4$. After filtration the solvent was evaporated under reduced pressure, and the residue was purified on silica gel by flash chromatography using 30% EtOAc in hexanes, affording ((2R,3R,4R,5S)-3,4,5-tris(benzyloxy)-1-((1-(4-(trifluoromethyl)phenyl)piperidin-4-yl)methyl)piperidin-2-yl)methanol as a white foam (157 mg, 81%).

To a stirred solution of the above material (157 mg, 0.23 mmol) and $Et_3N$ (0.2 mL, 1.38 mmol) in DCM (5 mL) was added MsCl (106 mg, 0.93 mmol) in DCM (1 mL) slowly at 0° C. The reaction mixture was stirred at 0° C. for 2 h, and quenched with satd. aqueous $NaHCO_3$ (20 mL). The mixture was extracted with EtOAc (3×20 mL). The combined organic layer was washed with water (2×20 mL), separated, dried over $Na_2SO_4$. After filtration, the solvent was evaporated under reduced pressure. The residue was dissolved in tert-butanol (5 mL) in a sealed tube, and CsF (350 mg, 2.3 mmol) was added. The mixture was stirred at 90° C. for 8 h, and cooled to ambient temperature. The reaction mixture was poured into ice water (30 mL) and extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2S,3R,4R,5S)-3,4,5-tris(benzyloxy)-2-(fluoromethyl)-1-((1-(4(trifluoromethyl)phenyl)piperidin-4-yl)methyl)piperidine as a clear oil (86 mg, 55%).

The above material (86 mg, 0.50 mmol), 2N HCl (0.5 mL) in EtOH (10 mL) was treated with hydrogen in balloon overnight in presence of $Pd(OH)_2$ (cat.). Removal of $Pd(OH)_2$ by filtration and evaporation of solvent followed by purification on silica gel chromatography using 10% MeOH and 2% $NH_3$ solution in DCM, afforded (2S,3R,4R,5S)-2-(fluoromethyl)-1-((1-(4-(trifluoromethyl)phenyl)piperidin-4-yl)methyl)piperidine-3,4,5-triol (8 mg, 10%) as a white solid. $^1H$ NMR (400 MHz, $CD_3OD$) δ 7.46 (d, J=8.7 Hz, 2H), 7.04 (d, J=8.7 Hz, 2H), 4.81-4.38 (m, 1H), 3.87 (d, J=12.4 Hz, 1H), 3.47 (td, J=9.7, 4.8 Hz, 1H), 3.28-3.03 (m, 3H), 2.91-2.59 (m, 3H), 2.41-2.14 (m, 2H), 2.13-1.93 (m, 2H), 1.83-1.80 (m, 2H), 1.34-1.30 (m, 4H); ESI MS m/z 407.2 $[M+H]^+$.

Example 156

(2S,3R,4R,5S)-2-(difluoromethyl)-1-phenethylpiperidine-3,4,5-triol

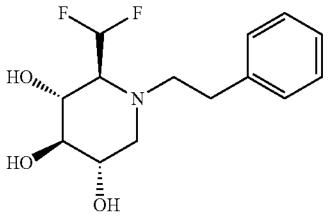 [SMILES: O[C@H]1[C@H](O)[C@@H](O)CN(CCc2ccccc2)[C@@H]1C(F)F]

$K_2CO_3$ (4.0 g, 29.0 mmol) was added to a solution of (2R,3R,4R,5S)-3,4,5-tris(benzyloxy)-2-((benzyloxy)methyl)piperidine (1.9 g, 3.63 mmol) and (2-bromoethyl)benzene (3.36 g, 18.1 mmol) in DMF (30 mL). The mixture was stirred at 90° C. for 18 h, and cooled to ambient temperature. The reaction mixture was poured into ice water (100 mL) and extracted with EtOAc (3×30 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-3,4,5-tris(benzyloxy)-2-((benzyloxy)methyl)-1-phenethylpiperidine as a white solid (1.67 g, 73%). ESI MS m/z 628.35 $[M+H]^+$.

To a stirred solution of the above material (1.67 g, 2.66 mmol) in anhydrous DCM (30 mL) was added $BCl_3$ solution (1M in DCM, 21.2 mL, 13.3 mmol) at −78° C. under $N_2$. The mixture was stirred at 0° C. for 2 h before being quenched with anhydrous MeOH (1 mL). The mixture was stirred at ambient temperature for 10 min. Solvent was removed under vacuum, the residue was dissolved in 1M $NH_3$ in MeOH (20 mL) and stirred for another 10 min, after which solvent was removed under vacuum. The residue was purified by silica gel chromatography to give (2R,3R,4R,5S)-2-(hydroxymethyl)-1-phenethylpiperidine-3,4,5-triol as a white solid (463 mg, 65%). ESI MS m/z 268.16 $[M+H]^+$.

To a stirred solution of the above material (450 mg, 1.68 mmol) in DMF (6 mL) was added TBDMSCl (310 mg, 2.02 mmol) at 0° C., followed by the addition of imidazole (206 mg, 3.02 mmol). The mixture was stirred at ambient temperature for 18 h. The reaction was quenched with satd. aqueous $NaHCO_3$ solution, then extracted with EtOAc (3×20 mL). The combined organic layer was washed with water (2×20 mL), separated, dried over $Na_2SO_4$.

After filtration, the solvent was evaporated under reduced pressure, and the residue was purified on silica gel by flash chromatography affording (2R,3R,4R,5S)-2-(((tert-butyldimethylsilyl)oxy)methyl)-1-phenethylpiperidine-3,4,5-triol as a white solid (115 mg, 18%). ESI MS m/z 382.24 $[M+H]^+$.

To a stirred solution of the above material (115 mg, 0.30 mmol) in pyridine (2 mL) was added BzCl (0.14 mL, 1.21 mmol) at 0° C., followed with the addition of DMAP (10 mg, cat. amount). The mixture was stirred at ambient temperature for 18 h. The reaction was quenched with satd. aqueous $NaHCO_3$. The mixture was extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2R,3R,4R,5S)-2-(hydroxymethyl)-1-phenethylpiperidine-3,4,5-triyl tribenzoate as a white solid (190 mg, 91%). ESI MS m/z 694.31 $[M+H]^+$.

To a stirred solution of the above material (190 mg, 0.27 mmol) in MeOH (10 mL) was added 4N HCl (0.50 mL, 2 mmol) at 0° C. The mixture was stirred at ambient temperature for 18 h. Solvent was removed under vacuum. The residue was dissolved in EtOAc (30 mL) and washed with $NaHCO_3$ solution, dried over $Na_2SO_4$. After filtration, the solvent was evaporated under reduced pressure, and the residue was purified on silica gel by flash chromatography affording (2R,3R,4R,5S)-2-(hydroxymethyl)-1-phenethylpiperidine-3,4,5-triyl tribenzoate as a white solid (126 mg, 81%). ESI MS m/z 580.22 $[M+H]^+$.

To a stirred solution of oxalyl chloride (0.05 mL, 0.58 mmol) in DCM (3 mL) was added DMSO (0.08 mL, 1.13 mmol) at −78° C. The mixture was stirred at −78° C. for 15 min, (2R,3R,4R,5S)-2-(hydroxymethyl)-1-phenethylpiperidine-3,4,5-triyl tribenzoate (25 mg, 0.043 mmol) in DCM (1 mL) was added. The mixture was stirred at −78° C. for 15 min and triethylamine (0.3 mL, 2.1 mmol) was added. The mixture was stirred at −78° C. for 15 min, then 0° C. for another 15 min, quenched with water. The mixture was extracted with EtOAc (3×20 mL). The combined organic layer was washed with sat. $NaHCO_3$ (30 mL), separated, dried over $Na_2SO_4$. After filtration the solvent was evaporated under reduced pressure, and the crude (2S,3R,4R,5S)-2-formyl-1-phenethylpiperidine-3,4,5-triyl tribenzoate was used on next step reaction without further purification. ESI MS m/z 578.21 $[M+H]^+$.

To a stirred solution of the above material (crude, 0.043 mmol) in DCM (2 mL) was added DAST (0.10 mL, 0.76 mmol) at −78° C. The mixture was stirred at ambient temperature for 18 h. The reaction was quenched with satd. aqueous $NaHCO_3$ solution at 0° C. The mixture was extracted with EtOAc (3×20 mL). The combined organic layer was washed with water (2×20 mL), separated, dried over $Na_2SO_4$. After filtration, the solvent was evaporated under reduced pressure, and the residue was purified on silica gel by flash chromatography affording (2S,3R,4R,5S)-

2-(difluoromethyl)-1-phenethylpiperidine-3,4,5-triyl tribenzoate as an oil (7 mg, 27% over two steps). ESI MS m/z 600.22 $[M+H]^+$.

To a stirred solution of the above material (23 mg, 0.038 mmol) in MeOH (3 mL) was added $K_2CO_3$ (23 mg, 0.17 mmol) at ambient temperature. The mixture was stirred at ambient temperature for 18 h. After filtration, the solvent was evaporated under reduced pressure, and the residue was purified on silica gel by flash chromatography affording (2S,3R,4R,5S)-2-(difluoromethyl)-1-phenethylpiperidine-3,4,5-triol as a white solid (4.0 mg, 37%). $^1H$ NMR (400 MHz, $CD_3OD$) δ 7.31-7.24 (m, 2H), 7.23-7.14 (m, 3H), 6.46-6.14 (m, 1H), 3.55-3.45 (m, 1H), 3.38-3.34 (m, 1H), 3.25-3.17 (m, 1H), 3.10-3.06 (m, 1H), 3.04-2.96 (m, 2H), 2.91-2.70 (m, 3H), 2.47 (t, J=10.9 Hz, 1H); ESI MS m/z 288.14 $[M+H]^+$.

Example 157

(2S,3R,4R,5S)-1-(2-fluorophenethyl)-2-methylpiperidine-3,4,5-triol

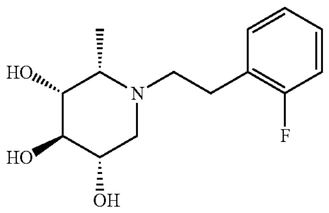 [SMILES: C[C@H]1[C@@H](O)[C@H](O)[C@@H](O)CN1CCc1ccccc1F]

At 0° C., to a solution of (2S,3R,4R,5S)-1-(2-fluorophenethyl)-2-(hydroxymethyl)piperidine-3,4,5-triyl tribenzoate (0.200 g, 0.335 mmol) in anhydrous DCM (10 mL) was added $PPh_3$ (0.16 g, 0.61 mmol) and $CBr_4$ (0.166 g, 0.500 mmol). After the mixture was stirred at RT for 1 h the solvent was evaporated under reduced pressure, and the residue was purified on silica gel by flash chromatography (EtOAc/hexanes, 1:6 to 1:4), affording (2R,3R,4R,5S)-2-(bromomethyl)-1-(2-fluorophenethyl)piperidine-3,4,5-triyl tribenzoate as a white foam (0.170 g, 77%); ESI MS m/z 660.131 and 662.130 $[M+H]^+$.

A mixture of the above material (0.160 g, 0.242 mmol), $Bu_3SnH$ (0.44 g, 1.5 mmol) and ABCN (0.020 g, 0.082 mmol) in anhydrous toluene (15 mL) was stirred at 100° C. for 4 h. After cooling the solvent was evaporated under reduced pressure, and the residue was purified on silica gel by flash chromatography (EtOAc/hexanes, 1:6 to 1:4), affording (2S,3R,4R,5S)-1-(2-fluorophenethyl)-2-methylpiperidine-3,4,5-triyl tribenzoate as a white solid (0.130 g, 93%); ESI MS m/z 582.229 $[M+H]^+$.

A mixture of the above material (0.12 g, 0.21 mmol) and $K_2CO_3$ (0.50 g, 0.36 mmol) in anhydrous MeOH (10 mL) was stirred at RT for 5 h. The solvent was removed under reduced pressure, and the residue was purified on silica gel by flash chromatography (1 M $NH_3$ in MeOH/DCM, 1:7), affording (2S,3R,4R,5S)-1-(2-fluorophenethyl)-2-methylpiperidine-3,4,5-triol as a white solid (0.037, 65%). $^1H$ NMR (400 MHz, $CD_3OD$) δ 7.26 (td, J=7.5, 2.0 Hz, 1H), 7.22-7.18 (m, 1H), 7.08 (td, J=7.5, 1.3 Hz, 1H), 7.05-7.00 (m, 1H), 3.63-3.45 (m, 2H), 3.45-3.35 (m, 1H), 3.24-3.09 (m, 1H), 2.93-2.71 (m, 4H), 2.71-2.60 (m, 1H), 2.48 (dd, J=11.7, 9.8 Hz, 1H), 1.00 (d, J=6.8 Hz, 3H); ESI MS m/z 270.144 $[M+H]^+$.

Example 158

(2S,3R,4R,5S)-1-(4-butoxy-2,6-difluorophenethyl)-2-methylpiperidine-3,4,5-triol

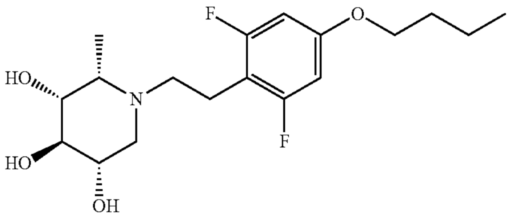 [SMILES: CCCCOc1cc(F)c(CCN2C[C@H](O)[C@@H](O)[C@H](O)[C@@H]2C)c(F)c1]

At 0° C., to a solution of (2S,3R,4R,5S)-1-(4-butoxy-2,6-difluorophenethyl)-2-(hydroxymethyl)piperidine-3,4,5-triyl tribenzoate (0.250 g, 0.364 mmol) in anhydrous DCM (15 mL) was added $PPh_3$ (0.25 g, 0.95 mmol) and $CBr_4$ (0.25 g, 0.75 mmol). After the mixture was stirred at RT for 3 h the solvent was evaporated under reduced pressure, and the residue was purified on silica gel by flash chromatography (EtOAc/hexanes, 1:9 to 1:6), affording (2R,3R,4R,5S)-2-(bromomethyl)-1-(4-butoxy-2,6-difluorophenethyl)piperidine-3,4,5-triyl tribenzoate as a white solid (0.25 g, 92%). ESI MS m/z 750.1696 and 752.16830 $[M+H]^+$.

A mixture of the above material (0.25 g, 0.33 mmol), $Bu_3SnH$ (0.55 g, 1.8 mmol) and ABCN (0.025 g, 0.10 mmol) in anhydrous toluene (20 mL) was stirred at 95° C. for 16 h. After cooling the solvent was evaporated under reduced pressure, and the residue was purified on silica gel by flash chromatography (EtOAc/hexanes, 1:9 to 1:6), affording (2S,3R,4R,5S)-1-(4-butoxy-2,6-difluorophenethyl)-2-methylpiperidine-3,4,5-triyl tribenzoate as a clear oil (0.18 g, 80%). ESI MS m/z 672.2459 $[M+H]^+$.

A mixture of the above material (0.18 g, 0.27 mmol) and $K_2CO_3$ (0.15 g, 0.11 mmol) in mixed anhydrous MeOH/THF (20/2 mL) was stirred at RT for 16 h. The solvent was removed under reduced pressure, and the residue was purified on silica gel by flash column chromatography (0.5 M $NH_3$ in MeOH/DCM, 1:9), affording (2S,3R,4R,5S)-1-(4-butoxy-2,6-difluorophenethyl)-2-methylpiperidine-3,4,5-triol as a white solid (0.085, 89%). $^1H$ NMR (400 MHz, $CD_3OD$) δ 6.56-6.46 (m, 2H), 3.94 (t, J=6.4 Hz, 2H), 3.52-3.45 (m, 2H), 3.43-3.35 (m, 1H), 3.19-3.08 (m, 1H), 2.82-2.66 (m, 4H), 2.64-2.56 (m, 1H), 1.80-1.68 (m, 2H), 1.54-1.44 (m, 2H), 1.02-0.94 (m, 6H); ESI MS m/z 360.1582 $[M+H]^+$.

Example 159

(2R,3R,4R,5S)-2-(fluoromethyl)-1-(2-fluorophenethyl)piperidine-3,4,5-triol

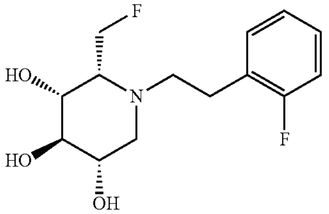 [SMILES: O[C@H]1[C@H](O)[C@H](CF)N(CCc2ccccc2F)C[C@@H]1O]

A mixture of (2S,3R,4R,5S)-3,4,5-tris(benzyloxy)-2-((benzyloxy)methyl)piperidine (7.50 g, 14.3 mmol) (J. Am. Chem. Soc. 2017, 139, 14192-14197), 1-(2-bromoethyl)-2-fluorobenzene (4.14 g, 20.4 mmol) (Tetrahedron Asymmetry, 2001, 12, 4, 585-596), tetra-butylammonium iodide ($Bu_4NI$) (0.450 g, 1.22 mmol) and $K_2CO_3$ (4.14 g, 30.0 mmol) in anhydrous DMF (40 mL) was stirred at 100° C. for 16 h. The reaction mixture was cooled at RT and diluted with water (300 mL). After extraction with $Et_2O$ (2×100 mL) the combined extract was washed with brine (3×100 mL) and dried over anhydrous $Na_2SO_4$. After filtration the solvent was evaporated under reduced pressure, and the residue was purified on silica gel by flash chromatography (EtOAc/hexanes, 1:10 to 1:5), affording (2S,3R,4R,5S)-3,4,5-tris(benzyloxy)-2-((benzyloxy)methyl)-1-(2-fluorophenethyl)piperidine as a pale-yellow oil (3.60 g, 39%); ESI MS m/z 646.327 $[M+H]^+$.

At −78° C. and under $N_2$, to a solution of the above material (3.60 g, 5.57 mmol) in anhydrous DCM (40 mL) was added $BCl_3$ (1.0 M in DCM, 33 mL, 33 mmol), and the mixture was stirred at 0° C. for 3 h. The reaction mixture was cooled at −78° C., quenched with MeOH, and then concentrated to dryness. The residue was neutralized with 1 M $NH_3$ in MeOH and purified on silica gel by flash chromatography (1 M $NH_3$ in MeOH/DCM, 1:5), affording (2S,3R,4R,5S)-1-(2-fluorophenethyl)-2-(hydroxymethyl)piperidine-3,4,5-triol as a white solid (1.48 g, 93%). $^1H$ NMR (400 MHz, $CD_3OD$) δ 7.26 (td, J=7.5, 1.8 Hz, 1H), 7.22-7.16 (m, 1H), 7.07 (td, J=7.5, 1.2 Hz, 1H), 7.04-6.99 (m, 1H), 3.94-3.75 (m, 2H), 3.67 (dd, J=8.8, 5.2 Hz, 1H), 3.53 (ddd, J=9.5, 8.0, 4.9 Hz, 1H), 3.38 (t, J=8.5 Hz, 1H), 3.12-2.97 (m, 2H), 2.95-2.77 (m, 4H), 2.63 (dd, J=12.4, 9.5 Hz, 1H); ESI MS m/z 286.139 $[M+H]^+$.

At 0° C. and under $N_2$, to a solution of the above material (1.48 g, 5.19 mmol) and imidazole (0.72 g, 11 mmol) in anhydrous DMF (30 mL) was added TBDMSCl (0.791 g, 5.25 mmol). The mixture was stirred at RT for 16 h, and then diluted with brine (150 mL). The mixture was extracted with EtOAc (3×80 mL), and the combined extract was washed with brine (2×100 mL) and dried over anhydrous $Na_2SO_4$. After filtration the solvent was evaporated under reduced pressure, and the residue was purified on silica gel by flash chromatography (MeOH/DCM, 1:14), affording (2S,3R,4R,5S)-2-(((tert-butyldimethylsilyl)oxy)methyl)-1-(2-fluorophenethyl)piperidine-3,4,5-triol as a white solid (1.40 g, 68%); ESI MS m/z 400.226 $[M+H]^+$.

At 0° C. and under $N_2$, to a solution of the above material (1.00 g, 2.50 mmol) in anhydrous pyridine (20 mL) was added BzCl (1.75 g, 12.4 mmol). The mixture was stirred at RT for 16 h, and then diluted with water (50 mL). The mixture was extracted with EtOAc (2×60 mL), and the combined extract was washed with diluted aqueous HCl (2×50 mL) and dried over anhydrous $Na_2SO_4$. After filtration the solvent was evaporated under reduced pressure, and the residue was co-evaporated with hexane (4×50 mL), affording a white solid containing (2S,3R,4R,5S)-2-(((tert-butyldimethylsilyl)oxy)methyl)-1-(2-fluorophenethyl)piperidine-3,4,5-triyl tribenzoate.

The white solid containing the above material was treated with 1.5 M HCl in MeOH (50 mL) at RT for 5 h. After removal of the solvent satd. aqueous $NaHCO_3$ (50 mL) was added. The mixture was extracted with EtOAc (2×50 mL), and the combined extract was dried over anhydrous $Na_2SO_4$. After filtration the solvent was evaporated under reduced pressure, and the residue was purified on silica gel by flash chromatography (EtOAc/hexanes, 1:4 to 1:3), affording (2S,3R,4R,5S)-1-(2-fluorophenethyl)-2-(hydroxymethyl)piperidine-3,4,5-triyl tribenzoate as a white solid (1.45 g, 97%, two steps); ESI MS m/z 598.215 $[M+H]^+$.

To a solution of the above material (0.168 g, 0.281 mmol) in anhydrous DCM (10 mL), at −78° C. and under $N_2$, was added DAST (0.43 g, 2.7 mmol). After addition the mixture was stirred at RT for 16 h. The reaction mixture was cooled at −78° C., and then quenched with satd. aqueous $NaHCO_3$ (10 mL). The organic layer was collected, and the aqueous was extracted with DCM (2×10 mL). The combined extract was dried over anhydrous $Na_2SO_4$. After filtration the solvent was evaporated under reduced pressure, and the residue was purified on silica gel by flash chromatography (EtOAc/hexanes, 1:6 to 1:4), affording a white foam (0.149 g) containing (2R,3R,4R,5S)-2-(fluoromethyl)-1-(2-fluorophenethyl)piperidine-3,4,5-triyl tribenzoate and its unknown stereoisomer; ESI MS m/z 600.220 $[M+H]^+$.

To a solution of the white foam (0.149 g) containing the above material and its unknown stereoisomer in anhydrous MeOH (10 mL) was added $K_2CO_3$ (0.10 g, 0.72 mmol), and the mixture was stirred at RT for 5 h. The solvent was removed under reduced pressure, and the residue was purified on silica gel by flash chromatography (1 M $NH_3$ in MeOH/DCM, 1:7), affording (2R,3R,4R,5S)-2-(fluoromethyl)-1-(2-fluorophenethyl)piperidine-3,4,5-triol as a white solid (0.031 g, 37% two steps). $^1H$ NMR (400 MHz, $CD_3OD$) δ 7.25 (td, J=7.5, 1.9 Hz, 1H), 7.24-7.17 (m, 1H), 7.07 (td, J=7.5, 1.3 Hz, 1H), 7.04-6.99 (m, 1H), 4.86 (ddd, J=47.8, 10.3, 6.1 Hz, 1H), 4.71 (ddd, J=47.7, 10.3, 2.2 Hz, 1H), 3.46-3.58 (m, 1H), 3.49 (tdd, J=8.9, 5.5, 2.8 Hz, 1H), 3.35-3.28 (m, 1H), 3.25-3.09 (m, 1H), 3.01-2.77 (m, 5H), 2.65 (ddd, J=11.4, 9.6, 1.4 Hz, 1H); ESI MS m/z 288.139 $[M+H]^+$.

Example 160

(2R,3R,4R,5S)-1-(4-butoxy-2,6-difluorophenethyl)-2-(fluoromethyl)piperidine-3,4,5-triol

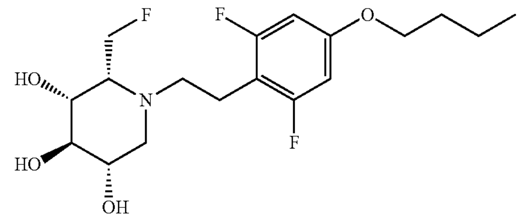 [SMILES: CCCCOc1cc(F)c(CCN2C[C@H](O)[C@@H](O)[C@H](O)[C@@H]2CF)c(F)c1]

Under $N_2$, a mixture of (2S,3R,4R,5S)-3,4,5-tris(benzyloxy)-2-((benzyloxy)methyl)piperidine (1.20 g, 2.29 mmol), 2-(4-butoxy-2,6-difluorophenyl)acetaldehyde (0.68 g, 3.0 mmol) and $NaBH(OAc)_3$ (0.85 g, 4.0 mmol) in DCM (30 mL) was stirred at RT for 3 days. The reaction mixture was diluted with satd. aqueous $NaHCO_3$ (30 mL), and extracted with DCM (3×20 mL). The combined extract was dried over anhydrous $Na_2SO_4$. After filtration the solvent was evaporated under reduced pressure, and the residue was purified on silica gel by flash chromatography (EtOAc/hexanes, 1:12 to 1:7), affording (2S,3R,4R,5S)-3,4,5-tris(benzyloxy)-2-((benzyloxy)methyl)-1-(4-butoxy-2,6-difluorophenethyl)piperidine as a pale-yellow oil (1.3 g, 77%). ESI MS m/z 736.3689 $[M+H]^+$.

A mixture of the above material (1.30 g, 1.76 mmol), $Pd(OH)_2/C$ (20% Pd in weight, 0.25 g, 0.47 mmol) and concentrated HCl (0.5 mL) in MeOH (80 mL) was stirred under hydrogen at one atmosphere of pressure overnight. The mixture was filtered through a celite cake, and the filtrate was collected and concentrated to dryness. The residue was neutralized with 1 M $NH_3$ in MeOH and subsequently purified on silica gel by flash column chromatography (0.5 M $NH_3$ MeOH/DCM, 1:4), affording (2S,3R,4R,5S)-1-(4-butoxy-2,6-difluorophenethyl)-2-(hydroxymethyl)piperidine-3,4,5-triol (0.58 g, 88%) as a white solid. $^1$H NMR (400 MHz, $CD_3OD$) δ 6.53-6.47 (m, 2H), 3.94 (t, J=6.4 Hz, 2H), 3.88-3.75 (m, 2H), 3.63 (dd, J=8.9, 5.3 Hz, 1H), 3.50 (ddd, J=9.5, 8.1, 5.0 Hz, 1H), 3.36 (t, J=8.5 Hz, 1H), 3.06-2.90 (m, 2H), 2.88 (dd, J=12.4, 5.0 Hz, 1H), 2.83-2.74 (m, 3H), 2.61 (dd, J=12.4, 9.5 Hz, 1H), 1.80-1.68 (m, 2H), 1.54-1.44 (m, 2H), 0.98 (t, J=7.4 Hz, 3H); ESI MS m/z 376.1604 $[M+H]^+$.

At 0° C. and under $N_2$, to a solution of the above material (0.56 g, 1.5 mmol) and imidazole (0.30 g, 4.4 mmol) in anhydrous DMF (15 mL) was added TBDMSCl (0.25 g, 1.7 mmol). The mixture was stirred at RT for 16 h, and then diluted with brine (50 mL). The mixture was extracted with EtOAc (3×30 mL), and the combined extract was washed with brine (50 mL) and dried over anhydrous $Na_2SO_4$. After filtration the solvent was evaporated under reduced pressure, and the residue was purified on silica gel by flash column chromatography (EtOAc/hexanes, 2:3 to 10:1), affording (2S,3R,4R,5S)-1-(4-butoxy-2,6-difluorophenethyl)-2-(((tert-butyldimethylsilyl)oxy)methyl)piperidine-3,4,5-triol as a white solid (0.37 g, 51%). ESI MS m/z 490.2500 $[M+H]^+$.

At 0° C. and under $N_2$, to a solution of the above material (0.37 g, 0.76 mmol) in anhydrous pyridine (8 mL) was added BzCl (0.64 g, 4.6 mmol). The mixture was stirred at RT for 16 h, and then diluted with water (30 mL). The mixture was extracted with EtOAc (2×30 mL), and the combined extract was dried over anhydrous $Na_2SO_4$. After filtration the solvent was evaporated under reduced pressure, and the residue was co-evaporated with hexane (3×30 mL). The residue was treated with 1.5 M HCl in MeOH (30 mL) at RT for 3 h. After removal of the solvent satd. aqueous $NaHCO_3$ (40 mL) was added. The mixture was extracted with EtOAc (2×20 mL), and the combined extract was dried over anhydrous $Na_2SO_4$. After filtration the solvent was evaporated under reduced pressure, and the residue was purified on silica gel by flash chromatography (EtOAc/hexanes, 1:4 to 1:3), affording (2S,3R,4R,5S)-1-(4-butoxy-2,6-difluorophenethyl)-2-(hydroxymethyl)piperidine-3,4,5-triyl tribenzoate as a white solid (0.48 g, 92%, two steps). ESI MS m/z 688.2536 $[M+H]^+$.

To a solution of the above material (0.230 g, 0.334 mmol) in anhydrous DCM (8 mL), at −78° C. and under $N_2$, was added DAST (0.48 g, 3.0 mmol). After addition the mixture was stirred at RT for 16 h. The reaction mixture was cooled at −78° C., and then quenched with satd. aqueous $NaHCO_3$ (20 mL). The organic layer was collected, and the aqueous was extracted with DCM (2×20 mL). The combined extract was dried over anhydrous $Na_2SO_4$. After filtration the solvent was evaporated under reduced pressure, and the residue was purified on silica gel by flash chromatography (EtOAc/hexanes, 1:9 to 1:6), affording colorless oil (0.20 g) containing the desired product and its unknown stereoisomer. ESI MS m/z 690.2472 $[M+H]^+$. The colorless oil was dissolved in mixed anhydrous MeOH/THF (15/2 mL), and $K_2CO_3$ (0.20 g, 1.4 mmol) was added. After stirring at RT for 5 h the reaction mixture was concentrated under reduced pressure, and the residue was purified on silica gel by flash column chromatography (0.5 M $NH_3$ in MeOH/DCM, 1:9), affording (2R,3R,4R,5S)-1-(4-butoxy-2,6-difluorophenethyl)-2-(fluoromethyl)piperidine-3,4,5-triol as a white solid (0.065 g, 51% two steps). $^1$H NMR (400 MHz, $CD_3OD$) S 6.55-6.44 (m, 2H), 4.85 (ddd, J=48.3, 10.2, 6.0 Hz, 1H), 4.70 (ddd, J=47.7, 10.2, 2.3 Hz, 1H), 3.94 (t, J=6.4 Hz, 2H), 3.58 (ddd, J=9.3, 5.8, 1.1 Hz, 1H), 3.50-3.43 (m, 1H), 3.30-3.26 (m, 1H), 3.18-3.08 (m, 1H), 2.93-2.84 (m, 2H), 2.81-2.70 (m, 3H), 2.62 (ddd, J=11.5, 9.8, 1.1 Hz, 1H), 1.80-1.68 (m, 2H), 1.56-1.42 (m, 2H), 0.98 (t, J=7.4 Hz, 3H); ESI MS m/z 378.1480 $[M+H]^+$.

Examples 161 to 175, as indicated in Table 1, are synthesized according to procedures analogous to the schemes and examples outlined herein.

Biological Activity

Assay for Determination of $IC_{50}$ Values for Inhibition of GBA2 in Cell Lysate Stable GBA2-expressing HEK293T cells were generated as follows. The PCR-amplified human GBA2 (GBA2 nucleotide accession number BC011363) using the following primers: Sense 5'---CGC AAA TGG GCG GTA GGC GTG (SEQ ID NO:2)---3' and antisense 5'---TAG TCA GCC ATG GGG CGG AGA (SEQ ID NO:3)---3') was cloned into pLenti-GIII-CMV by ABM Inc. The correctness of the construct was verified by sequencing. Lentivirus particles containing GBA2 in the pLenti-GIII-CMV plasmid were prepared using a third Generation Virus Packaging Mix (ABM cat #LV053-G074) in HEK293T cells and supplied as a virus particle suspension. The virus suspension was used for infection of HEK293T cells. Cell populations stably expressing human GBA2 were selected using puromycin for several weeks as determined by activity assays and western blot.

Various concentrations of test compounds were prepared in DMSO and then diluted into buffer consisting of 100 mM citric acid, 200 mM disodium phosphate with 1% v/v C10E6, pH 5.5. Cellular homogenates (0.25 mg/mL) of the stable HEK293T-overexpressing GBA2 cell line were pre-incubated for 10 min on ice with an inhibitor of GCase (20 μM (6R,7R,8S)-8-ethyl-4-azaspiro[2.5]octane-6,7-diol). The reaction solution consisted of 20 μL of 750 μM 4-methylumbelliferone-β-D glucopyranoside in 5% DMSO in the same buffer, 20 μL of GBA2-cellular homogenate pre-treated with (6R,7R,8S)-8-ethyl-4-azaspiro[2.5]octane-6,7-diol and 20 μL of various concentrations of test compound in 10% DMSO in the same buffer. The final concentrations in the reaction were 0.083 mg/mL GBA2-cellular homogenate, 250 μM 4-methylumbelliferone-β-D glucopyranoside, and various concentrations of inhibitor. The inhibitor and GBA2-cellular homogenate were preincubated together for 5 min at 37° C. The reaction was initiated by addition of substrate and allowed to proceed for 20 min at 37° C. to assess GBA2 activity. Reactions were stopped by the addition of an equal volume (60 μL) of 0.5 M NaOH, 0.3 M glycine, pH 10.5. Fluorescence was measured on a Biotek Synergy H4 plate reader at wavelengths of 365 nm for excitation and 450 nm for emission. Incubations without added enzyme or added inhibitors were used to define no enzyme activity and maximal enzyme activity, respectively. $IC_{50}$ values were determined by fitting the data to a log [inhibitor concentration] versus response curve using GraphPad Prism. $IC_{50}$ values were calculated as the concentration of inhibitor required to inhibit GBA2 activity by 50%.

The compounds of the invention tested exhibit $IC_{50}$ values for inhibition of GBA2 in the range 0.1 nM-50 μM.

Representative data from the GBA2 inhibition assay described above are shown in Table 3, where the symbol "*" indicates $IC_{50}$<100 nM; the symbol "" indicates 100 nM<$IC_{50}$<1 μM; and the symbol "*" indicates 1 μM<$IC_{50}$<25 μM.

TABLE 3

| Example | Name | GBA2 $IC_{50}$ |
|---|---|---|
| 1 | (2R,3R,4R,5S)-1-(cyclohexylmethyl)-2-methylpiperidine-3,4,5-triol | ** |
| 2 | (2R,3R,4R,5S)-1-((4,4-dimethylcyclohexyl)methyl)-2-methylpiperidine-3,4,5-triol | ** |
| 3 | (2R,3R,4R,5S)-1-((4,4-difluorocyclohexyl)methyl)-2-methylpiperidine-3,4,5-triol | * |
| 4 | (2R,3R,4R,5S)-1-((4,4-dichlorocyclohexyl)methyl)-2-methylpiperidine-3,4,5-triol | *** |
| 5 | (2R,3R,4R,5S)-1-((4-ethylcyclohexyl)methyl)-2-methylpiperidine-3,4,5-triol | *** |
| 6 | (2R,3R,4R,5S)-2-methyl-1-(((1s,4S)-4-vinylcyclohexyl)methyl)piperidine-3,4,5-triol | *** |
| 7 | (2R,3R,4R,5S)-1-(((1s,4S)-4-isopropylcyclohexyl)methyl)-2-methylpiperidine-3,4,5-triol | *** |
| 8 | (2R,3R,4R,5S)-1-(((1r,4R)-4-isopropylcyclohexyl)methyl)-2-methylpiperidine-3,4,5-triol | *** |
| 9 | (2R,3R,4R,5S)-1-(((1s,4S)-4-(tert-butyl)cyclohexyl)methyl)-2-methylpiperidine-3,4,5-triol | *** |
| 10 | (2R,3R,4R,5S)-1-(((1r,4R)-4-(tert-butyl)cyclohexyl)methyl)-2-methylpiperidine-3,4,5-triol | *** |
| 11 | (2R,3R,4R,5S)-2-methyl-1-(((1s,4S)-4-(trifluoromethyl)cyclohexyl)methyl)piperidine-3,4,5-triol | *** |
| 12 | (2R,3R,4R,5S)-2-methyl-1-(((1r,4R)-4-(trifluoromethyl)cyclohexyl)methyl)piperidine-3,4,5-triol | *** |
| 13 | (2R,3R,4R,5S)-1-(((1s,4S)-4-(2-fluoropropan-2-yl)cyclohexyl)methyl)-2-methylpiperidine-3,4,5-triol | *** |
| 14 | (2R,3R,4R,5S)-1-(((1r,4R)-4-(2-fluoropropan-2-yl)cyclohexyl)methyl)-2-methylpiperidine-3,4,5-triol | *** |
| 15 | (2R,3R,4R,5S)-2-methyl-1-(((trans)-3-(trifluoromethyl)cyclohexyl)methyl)piperidine-3,4,5-triol | *** |
| 16 | (2R,3R,4R,5S)-2-methyl-1-(((cis)-3-(trifluoromethyl)cyclohexyl)methyl)piperidine-3,4,5-triol | ** |
| 17 | (2R,3R,4R,5S)-1-(((1s,4S)-4-methoxycyclohexyl)methyl)-2-methylpiperidine-3,4,5-triol | * |
| 18 | (2R,3R,4R,5S)-1-(((1r,4R)-4-methoxycyclohexyl)methyl)-2-methylpiperidine-3,4,5-triol | * |
| 19 | (2R,3R,4R,5S)-1-((4-(methoxymethyl)cyclohexyl)methyl)-2-methylpiperidine-3,4,5-triol | ** |
| 20 | (2R,3R,4R,5S)-1-(((1s,4S)-4-cyclopropylcyclohexyl)methyl)-2-methylpiperidine-3,4,5-triol | *** |
| 21 | (2R,3R,4R,5S)-1-(((1r,4R)-4-cyclopropylcyclohexyl)methyl)-2-methylpiperidine-3,4,5-triol | *** |
| 22 | (2R,3R,4R,5S)-2-methyl-1-((4-phenylcyclohexyl)methyl)piperidine-3,4,5-triol | *** |
| 23 | (2R,3R,4R,5S)-2-methyl-1-(spiro[2.5]octan-6-ylmethyl)piperidine-3,4,5-triol | ** |
| 24 | (2R,3R,4R,5S)-2-methyl-1-(spiro[3.5]nonan-7-ylmethyl)piperidine-3,4,5-triol | *** |
| 25 | (2R,3R,4R,5S)-2-methyl-1-(spiro[4.5]decan-8-ylmethyl)piperidine-3,4,5-triol | *** |
| 26 | (2R,3R,4R,5S)-1-(((5S,8s)-3,3-dimethyl-2-oxaspiro[4.5]decan-8-yl)methyl)-2-methylpiperidine-3,4,5-triol | ** |
| 27 | (2R,3R,4R,5S)-2-methyl-1-((1,2,3,4-tetrahydronaphthalen-2-yl)methyl)piperidine-3,4,5-triol | *** |
| 28 | (2R,3R,4R,5S)-1-((2,3-dihydro-1H-inden-2-yl)methyl)-2-methylpiperidine-3,4,5-triol | *** |
| 29 | (2R,3R,4R,5S)-1-(2-cyclohexylethyl)-2-methylpiperidine-3,4,5-triol | ** |
| 30 | (2R,3R,4R,5S)-1-(2-(4,4-difluorocyclohexyl)ethyl)-2-methylpiperidine-3,4,5-triol | ** |

TABLE 3-continued

| Example | Name | GBA2 $IC_{50}$ |
|---|---|---|
| 31 | (2R,3R,4R,5S)-2-methyl-1-(2-((1s,4S)-4-(trifluoromethyl)cyclohexyl)ethyl)piperidine-3,4,5-triol | *** |
| 32 | (2R,3R,4R,5S)-2-methyl-1-(2-((1r,4R)-4-(trifluoromethyl)cyclohexyl)ethyl)piperidine-3,4,5-triol | *** |
| 33 | (2R,3R,4R,5S)-1-((2-adamantan-1-yl)ethyl)-2-methylpiperidine-3,4,5-triol | *** |
| 34 | (2R,3R,4R,5S)-1-(3-cyclohexylpropyl)-2-methylpiperidine-3,4,5-triol | *** |
| 35 | (2R,3R,4R,5S)-2-methyl-1-phenethylpiperidine-3,4,5-triol | ** |
| 36 | (2R,3R,4R,5S)-2-methyl-1-(2-methylphenethyl)piperidine-3,4,5-triol | ** |
| 37 | (2R,3R,4R,5S)-1-(2-methoxyphenethyl)-2-methylpiperidine-3,4,5-triol | ** |
| 38 | (2R,3R,4R,5S)-1-(2-fluorophenethyl)-2-methylpiperidine-3,4,5-triol | ** |
| 39 | (2R,3R,4R,5S)-1-(2-chlorophenethyl)-2-methylpiperidine-3,4,5-triol | ** |
| 40 | (2R,3R,4R,5S)-1-(2,3-difluorophenethyl)-2-methylpiperidine-3,4,5-triol | ** |
| 41 | (2R,3R,4R,5S)-1-(2,4-difluorophenethyl)-2-methylpiperidine-3,4,5-triol | ** |
| 42 | (2R,3R,4R,5S)-1-(2,5-difluorophenethyl)-2-methylpiperidine-3,4,5-triol | *** |
| 43 | (2R,3R,4R,5S)-1-(3,4-difluorophenethyl)-2-methylpiperidine-3,4,5-triol | ** |
| 44 | (2R,3R,4R,5S)-1-(2-fluoro-4-methoxyphenethyl)-2-methylpiperidine-3,4,5-triol | ** |
| 45 | (2R,3R,4R,5S)-1-(3-chloro-2-fluorophenethyl)-2-methylpiperidine-3,4,5-triol | *** |
| 46 | (2R,3R,4R,5S)-1-(4-chloro-2-fluorophenethyl)-2-methylpiperidine-3,4,5-triol | ** |
| 47 | (2R,3R,4R,5S)-1-(5-chloro-2-fluorophenethyl)-2-methylpiperidine-3,4,5-triol | *** |
| 48 | (2R,3R,4R,5S)-1-(2,6-difluorophenethyl)-2-methylpiperidine-3,4,5-triol | *** |
| 49 | (2R,3R,4R,5S)-1-(3-chloro-2,6-difluorophenethyl)-2-methylpiperidine-3,4,5-triol | *** |
| 50 | (2R,3R,4R,5S)-1-(2,6-difluoro-4-(prop-1-en-2-yl)phenethyl)-2-methylpiperidine-3,4,5-triol | *** |
| 51 | (2R,3R,4R,5S)-1-(2,6-difluoro-4-isopropylphenethyl)-2-methylpiperidine-3,4,5-triol | *** |
| 52 | (2R,3R,4R,5S)-1-(2,6-difluoro-3-isopropylphenethyl)-2-methylpiperidine-3,4,5-triol | *** |
| 53 | (2R,3R,4R,5S)-1-(4-cyclopropyl-2,6-difluorophenethyl)-2-methylpiperidine-3,4,5-triol | *** |
| 54 | (2R,3R,4R,5S)-1-(2,6-difluoro-4-(tetrahydro-2H-pyran-4-yl)phenethyl)-2-methylpiperidine-3,4,5-triol | *** |
| 55 | (2R,3R,4R,5S)-1-(2,6-difluoro-4-(trifluoromethyl)phenethyl)-2-methylpiperidine-3,4,5-triol | ** |
| 56 | (2R,3R,4R,5S)-1-(2,6-difluoro-4-(pyrrolidin-1-yl)phenethyl)-2-methylpiperidine-3,4,5-triol | *** |
| 57 | (2R,3R,4R,5S)-1-(2,6-difluoro-4-(piperidin-1-yl)phenethyl)-2-methylpiperidine-3,4,5-triol | *** |
| 58 | (2R,3R,4R,5S)-1-(2,6-difluoro-4-morpholinophenethyl)-2-methylpiperidine-3,4,5-triol | *** |
| 59 | (2R,3R,4R,5S)-1-(4-butoxy-2,6-difluorophenethyl)-2-methylpiperidine-3,4,5-triol | *** |
| 60 | (2R,3R,4R,5S)-1-(4-(cyclopropylmethoxy)-2,6-difluorophenethyl)-2-methylpiperidine-3,4,5-triol | *** |
| 61 | (2R,3R,4R,5S)-2-methyl-1-(4-((tetrahydrofuran-3-yl)oxy)phenethyl)piperidine-3,4,5-triol | *** |
| 62 | (2R,3R,4R,5S)-2-methyl-1-(4-((tetrahydro-2H-pyran-3-yl)oxy)phenethyl)piperidine-3,4,5-triol | *** |
| 63 | (2R,3R,4R,5S)-2-methyl-1-(4-((tetrahydro-2H-pyran-4-yl)oxy)phenethyl)piperidine-3,4,5-triol | *** |
| 64 | (2R,3R,4R,5S)-2-methyl-1-(4-phenoxyphenethyl)piperidine-3,4,5-triol | *** |
| 65 | (2R,3R,4R,5S)-2-methyl-1-(4-((tetrahydrofuran-3-yl)methoxy)phenethyl)piperidine-3,4,5-triol | *** |
| 66 | (2R,3R,4R,5S)-2-methyl-1-((R)-2-phenylpropyl)piperidine-3,4,5-triol | ** |

TABLE 3-continued

| Example | Name | GBA2 $IC_{50}$ |
|---|---|---|
| 67 | (2R,3R,4R,5S)-2-methyl-1-((S)-2-phenylpropyl) piperidine-3,4,5-triol | ** |
| 68 | (2R,3R,4R,5S)-1-(2-([1,1'-biphenyl]-4-yl)ethyl)-2-methylpiperidine-3,4,5-triol | *** |
| 69 | (2R,3R,4R,5S)-1-(2-(3,5-difluoro-[1,1'-biphenyl]-4-yl)ethyl)-2-methylpiperidine-3,4,5-triol | *** |
| 70 | (2R,3R,4R,5S)-1-(2-(benzo[d][1,3]dioxol-5-yl) ethyl)-2-methylpiperidine-3,4,5-triol | *** |
| 71 | (2R,3R,4R,5S)-1-(2-(6-fluorobenzo[d][1,3]dioxol-5-yl)ethyl)-2-methylpiperidine-3,4,5-triol | *** |
| 72 | (2R,3R,4R,5S)-1-(2-(2,2-difluorobenzo[d][1,3] dioxol-5-yl)ethyl)-2-methylpiperidine-3,4,5-triol | *** |
| 73 | (2R,3R,4R,5S)-1-(2-(2,3-dihydrobenzo[b][1,4] dioxin-6-yl)ethyl)-2-methylpiperidine-3,4,5-triol | *** |
| 74 | (2R,3R,4R,5S)-2-methyl-1-(2-(thiophen-2-yl) ethyl)piperidine-3,4,5-triol | ** |
| 75 | (2R,3R,4R,5S)-2-methyl-1-(2-(thiophen-3-yl) ethyl)piperidine-3,4,5-triol | ** |
| 76 | (2R,3R,4R,5S)-2-methyl-1-(2-(pyridin-2-yl)ethyl) piperidine-3,4,5-triol | * |
| 77 | (2R,3R,4R,5S)-2-methyl-1-(3-phenylpropyl) piperidine-3,4,5-triol | *** |
| 78 | (2R,3R,4R,5S)-1-(3-(2-fluorophenyl)propyl)-2-methylpiperidine-3,4,5-triol | *** |
| 79 | (2R,3R,4R,5S)-1-(3-(4-fluorophenyl)propyl)-2-methylpiperidine-3,4,5-triol | *** |
| 80 | (2R,3R,4R,5S)-2-methyl-1-(3-(thiophen-2-yl) propyl)piperidine-3,4,5-triol | *** |
| 81 | (2R,3R,4R,5S)-2-methyl-1-(3-(thiophen-3-yl) propyl)piperidine-3,4,5-triol | *** |
| 82 | (2R,3R,4R,5S)-2-methyl-1-((1-phenylpiperidin-4-yl)methyl)piperidine-3,4,5-triol | ** |
| 83 | (2R,3R,4R,5S)-1-((1-(2-fluorophenyl)piperidin-4-yl)methyl)-2-methylpiperidine-3,4,5-triol | *** |
| 84 | (2R,3R,4R,5S)-1-((1-(3-fluorophenyl)piperidin-4-yl)methyl)-2-methylpiperidine-3,4,5-triol | *** |
| 85 | (2R,3R,4R,5S)-1-((1-(4-fluorophenyl)piperidin-4-yl)methyl)-2-methylpiperidine-3,4,5-triol | *** |
| 86 | (2R,3R,4R,5S)-2-methyl-1-((1-(4-(trifluoromethyl)phenyl)piperidin-4-yl) methyl)piperidine-3,4,5-triol | *** |
| 87 | (2R,3R,4R,5S)-2-methyl-1-((4-methyl-1-phenylpiperidin-4-yl)methyl)piperidine-3,4,5-triol | * |
| 88 | (2R,3R,4R,5S)-1-((4-fluoro-1-phenylpiperidin-4-yl)methyl)-2-methylpiperidine-3,4,5-triol | ** |
| 89 | (2R,3R,4R,5S)-2-methyl-1-(2-(1-phenylpiperidin-4-yl)ethyl)piperidine-3,4,5-triol | *** |
| 90 | (2R,3R,4R,5S)-2-methyl-1-((1-(pyridin-3-yl) piperidin-4-yl)methyl)piperidine-3,4,5-triol | * |
| 91 | (2R,3R,4R,5S)-2-methyl-1-((1-(2,2,2-trifluoroethyl)piperidin-4-yl)methyl)piperidine-3,4,5-triol | ** |
| 92 | 2-methyl-1-(4-(((2R,3R,4R,5S)-3,4,5-trihydroxy-2-methylpiperidin-1-yl)methyl)piperidin-1-yl) propan-1-one | * |
| 93 | 2,2-dimethyl-1-(4-(((2R,3R,4R,5S)-3,4,5-trihydroxy-2-methylpiperidin-1-yl)methyl) piperidin-1-yl)propan-1-one | ** |
| 94 | 1-(4-(((2R,3R,4R,5S)-3,4,5-trihydroxy-2-methylpiperidin-1-yl)methyl)piperidin-1-yl)butan-1-one | * |
| 95 | 3-methyl-1-(4-(((2R,3R,4R,5S)-3,4,5-trihydroxy-2-methylpiperidin-1-yl)methyl)piperidin-1-yl) butan-1-one | ** |
| 96 | 3,3-dimethyl-1-(4-(((2R,3R,4R,5S)-3,4,5-trihydroxy-2-methylpiperidin-1-yl)methyl) piperidin-1-yl)butan-1-one | ** |
| 97 | 2-cyclopentyl-1-(4-(((2R,3R,4R,5S)-3,4,5-trihydroxy-2-methylpiperidin-1-yl)methyl) piperidin-1-yl)ethanone | ** |
| 98 | cyclopropyl(4-(((2R,3R,4R,5S)-3,4,5-trihydroxy-2-methylpiperidin-1-yl)methyl)piperidin-1-yl) methanone | * |
| 99 | cyclobutyl(4-(((2R,3R,4R,5S)-3,4,5-trihydroxy-2-methylpiperidin-1-yl)methyl)piperidin-1-yl) methanone | ** |

TABLE 3-continued

| Example | Name | GBA2 $IC_{50}$ |
|---|---|---|
| 100 | cyclopentyl(4-(((2R,3R,4R,5S)-3,4,5-trihydroxy-2-methylpiperidin-1-yl)methyl)piperidin-1-yl) methanone | ** |
| 101 | cyclohexyl(4-(((2R,3R,4R,5S)-3,4,5-trihydroxy-2-methylpiperidin-1-yl)methyl)piperidin-1-yl) methanone | ** |
| 102 | ((1s,4S)-4-(tert-butyl)cyclohexyl)(4-(((2R,3R,4R,5S)-3,4,5-trihydroxy-2-methylpiperidin-1-yl) methyl)piperidin-1-yl)methanone | *** |
| 103 | ((1r,4R)-4-(tert-butyl)cyclohexyl)(4-(((2R,3R,4R,5S)-3,4,5-trihydroxy-2-methylpiperidin-1-yl) methyl)piperidin-1-yl)methanone | *** |
| 104 | (4-methoxycyclohexyl)(4-(((2R,3R,4R,5S)-3,4,5-trihydroxy-2-methylpiperidin-1-yl)methyl) piperidin-1-yl)methanone | * |
| 105 | (4-(trifluoromethyl)cyclohexyl)(4-(((2R,3R,4R,5S)-3,4,5-trihydroxy-2-methylpiperidin-1-yl) methyl)piperidin-1-yl)methanone | *** |
| 106 | phenyl(4-(((2R,3R,4R,5S)-3,4,5-trihydroxy-2-methylpiperidin-1-yl)methyl)piperidin-1-yl) methanone | ** |
| 107 | (3-(trifluoromethyl)phenyl)(4-(((2R,3R,4R,5S)-3,4,5-trihydroxy-2-methylpiperidin-1-yl)methyl) piperidin-1-yl)methanone | *** |
| 108 | 2-phenyl-1-(4-(((2R,3R,4R,5S)-3,4,5-trihydroxy-2-methylpiperidin-1-yl)methyl)piperidin-1-yl) ethanone | ** |
| 109 | thiophen-3-yl(4-(((2R,3R,4R,5S)-3,4,5-trihydroxy-2-methylpiperidin-1-yl)methyl) piperidin-1-yl)methanone | ** |
| 110 | N-cyclohexyl-4-(((2R,3R,4R,5S)-3,4,5-trihydroxy-2-methylpiperidin-1-yl)methyl) piperidine-1-carboxamide | ** |
| 111 | N-cyclohexyl-4-(((2R,3R,4R,5S)-3,4,5-trihydroxy-2-methylpiperidin-1-yl)methyl) piperidine-1-carbothioamide | ** |
| 112 | (2R,3R,4R,5S)-2-methyl-1-((1-((1S,2R)-2-(trifluoromethyl)cyclohexyl)azetidin-3-yl)methyl) piperidine-3,4,5-triol | * |
| 113 | (2R,3R,4R,5S)-2-methyl-1-(((R)-1-phenylpyrrolidin-3-yl)methyl)piperidine-3,4,5-triol | *** |
| 114 | (2R,3R,4R,5S)-2-methyl-1-(((R)-1-(o-tolyl) pyrrolidin-3-yl)methyl)piperidine-3,4,5-triol | *** |
| 115 | (2R,3R,4R,5S)-2-methyl-1-(((R)-1-(2-(trifluoromethyl)phenyl)pyrrolidin-3-yl)methyl) piperidine-3,4,5-triol | *** |
| 116 | (2R,3R,4R,5S)-1-(((R)-1-(2-fluorophenyl) pyrrolidin-3-yl)methyl)-2-methylpiperidine-3,4,5-triol | *** |
| 117 | (2R,3R,4R,5S)-1-(((R)-1-(3-fluorophenyl) pyrrolidin-3-yl)methyl)-2-methylpiperidine-3,4,5-triol | *** |
| 118 | (2R,3R,4R,5S)-2-methyl-1-(((R)-1-(2-(trifluoromethoxy)phenyl)pyrrolidin-3-yl)methyl) piperidine-3,4,5-triol | *** |
| 119 | (2R,3R,4R,5S)-2-methyl-1-(((R)-1-(6-(trifluoromethyl)pyridin-2-yl)pyrrolidin-3-yl) methyl)piperidine-3,4,5-triol | *** |
| 120 | (2R,3R,4R,5S)-2-methyl-1-(((R)-1-(3-(trifluoromethyl)pyridin-2-yl)pyrrolidin-3-yl) methyl)piperidine-3,4,5-triol | *** |
| 121 | (2R,3R,4R,5S)-2-methyl-1-(((R)-1-(4-(trifluoromethyl)pyridin-2-yl)pyrrolidin-3-yl) methyl)piperidine-3,4,5-triol | *** |
| 122 | (2R,3R,4R,5S)-2-methyl-1-(((R)-1-(pyridin-3-yl) pyrrolidin-3-yl)methyl)piperidine-3,4,5-triol | * |
| 123 | (2R,3R,4R,5S)-2-methyl-1-(((R)-1-(4-methylpyridin-3-yl)pyrrolidin-3-yl)methyl) piperidine-3,4,5-triol | ** |
| 124 | (2R,3R,4R,5S)-2-methyl-1-(((R)-1-(4-(trifluoromethyl)pyridin-3-yl)pyrrolidin-3-yl) methyl)piperidine-3,4,5-triol | *** |
| 125 | (2R,3R,4R,5S)-2-methyl-1-(((R)-1-(5-(trifluoromethyl)pyridin-3-yl)pyrrolidin-3-yl) methyl)piperidine-3,4,5-triol | *** |

TABLE 3-continued

| Example | Name | GBA2 $IC_{50}$ |
|---|---|---|
| 126 | (2R,3R,4R,5S)-2-methyl-1-(((R)-1-(2-(trifluoromethyl)pyridin-3-yl)pyrrolidin-3-yl) methyl)piperidine-3,4,5-triol | *** |
| 127 | (2R,3R,4R,5S)-2-methyl-1-(((R)-1-(4-(trifluoromethyl)pyrimidin-5-yl)pyrrolidin-3-yl) methyl)piperidine-3,4,5-triol | *** |
| 128 | (2R,3R,4R,5S)-2-methyl-1-(((R)-1-(thiophen-3-yl) pyrrolidin-3-yl)methyl)piperidine-3,4,5-triol | *** |
| 129 | (2R,3R,4R,5S)-1-(((R)-1-(benzo[d]thiazol-4-yl) pyrrolidin-3-yl)methyl)-2-methylpiperidine-3,4,5-triol | *** |
| 130 | (4-(trifluoromethyl)phenyl)((R)-3-(((2R,3R,4R,5S)-3,4,5-trihydroxy-2-methylpiperidin-1-yl) methyl)pyrrolidin-1-yl)methanone | *** |
| 131 | (2R,3R,4R,5S)-2-methyl-1-(((S)-1-(2-(trifluoromethyl)phenyl)pyrrolidin-3-yl)methyl) piperidine-3,4,5-triol | *** |
| 132 | (2R,3R,4R,5S)-2-methyl-1-(((S)-1-(3-(trifluoromethyl)pyridin-2-yl)pyrrolidin-3-yl) methyl)piperidine-3,4,5-triol | *** |
| 133 | (2R,3R,4R,5S)-2-methyl-1-(((S)-1-(4-(trifluoromethyl)pyridin-3-yl)pyrrolidin-3-yl) methyl)piperidine-3,4,5-triol | *** |
| 134 | (2R,3R,4R,5S)-2-methyl-1-(((S)-1-(4-(trifluoromethyl)pyrimidin-5-yl)pyrrolidin-3-yl) methyl)piperidine-3,4,5-triol | *** |
| 135 | (2R,3R,4R,5S)-2-methyl-1-(((S)-1-(4-(trifluoromethyl)thiazol-2-yl)pyrrolidin-3-yl) methyl)piperidine-3,4,5-triol | *** |
| 136 | (2R,3R,4R,5S)-2-methyl-1-(((R)-1-(o-tolyl) piperidin-3-yl)methyl)piperidine-3,4,5-triol | *** |
| 137 | (2R,3R,4R,5S)-1-(((R)-1-(2-fluorophenyl) piperidin-3-yl)methyl)-2-methylpiperidine-3,4,5-triol | *** |
| 138 | (2R,3R,4R,5S)-2-methyl-1-(((R)-1-(3-(trifluoromethyl)pyridin-2-yl)piperidin-3-yl) methyl)piperidine-3,4,5-triol | *** |
| 139 | (2R,3R,4R,5S)-2-methyl-1-(((R)-1-(6-(trifluoromethyl)pyridin-2-yl)piperidin-3-yl) methyl)piperidine-3,4,5-triol | *** |
| 140 | (2R,3R,4R,5S)-2-methyl-1-(((R)-1-(4-(trifluoromethyl)pyridin-3-yl)piperidin-3-yl) methyl)piperidine-3,4,5-triol | *** |
| 141 | (2R,3R,4R,5S)-2-methyl-1-(((S)-1-(3-(trifluoromethyl)pyridin-2-yl)piperidin-3-yl) methyl)piperidine-3,4,5-triol | *** |
| 142 | (2R,3R,4R,5S)-2-methyl-1-(((S)-1-(4-(trifluoromethyl)pyridin-3-yl)piperidin-3-yl) methyl)piperidine-3,4,5-triol | *** |
| 143 | (2R,3R,4R,5S)-2-methyl-1-(((S)-1-(6-(trifluoromethyl)pyridin-2-yl)piperidin-3-yl) methyl)piperidine-3,4,5-triol | *** |
| 144 | (2R,3R,4R,5S)-2-methyl-1-(((S)-1-(4-(trifluoromethyl)thiazol-2-yl)piperidin-3-yl) methyl)piperidine-3,4,5-triol | ** |
| 145 | (2S,3R,4R,5S)-2-(fluoromethyl)-1-((4-isopropylcyclohexyl)methyl)piperidine-3,4,5-triol | *** |
| 146 | (2S,3R,4R,5S)-1-((4-(tert-butyl)cyclohexyl) methyl)-2-(fluoromethyl)piperidine-3,4,5-triol | *** |
| 147 | (2S,3R,4R,5S)-2-(fluoromethyl)-1-(((1r,4S)-4-(trifluoromethyl)cyclohexyl)methyl)piperidine-3,4,5-triol | *** |
| 148 | (2S,3R,4R,5S)-2-(fluoromethyl)-1-phenethylpiperidine-3,4,5-triol | ** |
| 149 | (2S,3R,4R,5S)-2-(fluoromethyl)-1-(2-fluorophenethyl)piperidine-3,4,5-triol | ** |
| 150 | (2S,3R,4R,5S)-1-(2,6-difluoro-4-isopropylphenethyl)-2-(fluoromethyl)piperidine-3,4,5-triol | *** |
| 151 | (2S,3R,4R,5S)-1-(2-(3,5-difluoro-[1,1'-biphenyl]-4-yl)ethyl)-2-(fluoromethyl)piperidine-3,4,5-triol | *** |
| 152 | (2S,3R,4R,5S)-1-(2-(6-fluorobenzo[d][1,3]dioxol-5-yl)ethyl)-2-(fluoromethyl)piperidine-3,4,5-triol | *** |
| 153 | (2S,3R,4R,5S)-1-(2-(2,3-dihydrobenzo[b][1,4] dioxin-6-yl)ethyl)-2-(fluoromethyl)piperidine-3,4,5-triol | *** |
| 154 | (2S,3R,4R,5S)-2-(fluoromethyl)-1-((1-phenylpiperidin-4-yl)methyl)piperidine-3,4,5-triol | *** |
| 155 | (2S,3R,4R,5S)-2-(fluoromethyl)-1-((1-(4-(trifluoromethyl)phenyl)piperidin-4-yl)methyl) piperidine-3,4,5-triol | *** |
| 156 | (2S,3R,4R,5S)-2-(difluoromethyl)-1-phenethylpiperidine-3,4,5-triol | * |
| 157 | (2S,3R,4R,5S)-1-(2-fluorophenethyl)-2-methylpiperidine-3,4,5-triol | * |
| 158 | (2S,3R,4R,5S)-1-(4-butoxy-2,6-difluorophenethyl)-2-methylpiperidine-3,4,5-triol | ** |
| 159 | (2R,3R,4R,5S)-2-(fluoromethyl)-1-(2-fluorophenethyl)piperidine-3,4,5-triol | * |
| 160 | (2R,3R,4R,5S)-1-(4-butoxy-2,6-difluorophenethyl)-2-(fluoromethyl)piperidine-3,4,5-triol | ** |

The present invention has been described with regard to one or more embodiments. However, it will be apparent to persons skilled in the art that a number of variations and modifications can be made without departing from the scope of the invention as defined in the claims.

REFERENCES

1. G. A. Grabowski, *Lancet* 2008, 372, 1263-1271.
2. A. Massimo, et al., *Neurochem Res* 2016, 41, 210-20.
3. M. A. Woeste, D. Wachten, *Front Mol Neurosci* 2017, 10, 386.
4. Y. Hayashi, et al., *J Biol Chem* 2007, 282, 30889-30900.
5. S. Lahiri, A. H. Futerman, *Cell Mol Life Sci* 2007, 64, 2270-2284.
6. T. Mutoh, et al., *CNS Neurol Disord Drug Targets* 2006, 5, 375-380.
7. S. Kim, et al., *Proc Natl Acad Sci USA* 2018, 115, 798-803.
8. R. Halmer, S. Walter, and K. Fassbender, *Cell Physiol Biochem* 2014, 34, 111-118.
9. A. Di Pardo, et al., *Front Neurosci* 2017, 11, 698.
10. J. C. Dodge, et al., *Proc Natl Acad Sci USA* 2015, 112, 8100-5.
11. M. Zervas, et al., *Curr Biol* 2001, 11, 1283-7.
12. L. C. Boudewyn, et al., *Neurobiol Dis* 2017, 105, 257-270.
13. K. M. Ashe, et al., *PLoS One* 2011, 6, e21758.
14. Y. Ilan, *Am J Physiol-Gast Liver Physiol* 2016, 310, G1102-G1117.
15. A. R. Marques, et al., *PLoS One* 2015, 10, e0135889.
16. J. B. Nietupski, et al., *Mol Genet Metab* 2012, 105, 621-8.
17. P. K. Mistry, et al., *Proc Natl Acad Sci USA* 2014, 111, 4934-9.
18. N. Loberto, et al., *PLoS One* 2014, 9, e104763.
19. M. Margalit, et al., *J Pharm Exp Ther* 2006, 319, 105-110.
20. M. Margalit, et al., *Am J Physiol-Gast Liver Physiol* 2005, 289, G917-G925.
21. E. Zigmond, et al., *Gut* 2007, 56, 82-89.
22. W. Zhang, et al., *Clin & Exp Immunol* 2009, 157, 359-364.
23. M. Mizrahi, et al., *J Clin Trans Hepatol* 2018, 6, 127-134.
24. A. T. Ghisaidoobe, et al., *J Med Chem* 2014, 57, 9096-104.
25. T. Farfel-Becker, E. B. Vitner, and A. H. Futerman, *Dis Model Mech* 2011, 4, 746-752.

What is claimed is:

1. A compound of Formula (I) or a pharmaceutically acceptable salt thereof:

(I)

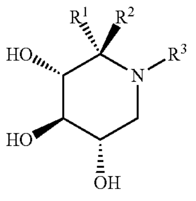

wherein $R^1$ is H and $R^2$ is $CH_3$, $CH_2F$, or $CHF_2$; or $R^1$ is $CH_3$ or $CH_2F$ and $R^2$ is H; and $R^3$ is $(CH_2)_nR^4$, wherein n is 1 or 2, and $R^4$ is cyclohexyl, cyclohexylmethyl, phenylethyl, 4-phenylcyclohexyl, spiro[2.5]octan-6-yl, spiro[3.5]nonan-7-yl, spiro[4.5]decan-8-yl, (5S,8s)-3,3-dimethyl-2-oxaspiro[4.5]decan-8-yl, 1,2,3,4-tetrahydronaphthalen-2-yl, 2,3-dihydro-1H-inden-2-yl, (adamantyl)methyl, (pyridine-2-yl)methyl, (benzo[d][1,3]dioxol-5-yl)methyl, (2,3-dihydrobenzo[b][1,4]dioxin-6-yl)methyl, ([1,1'-biphenyl]-4-yl)methyl, 1-(2,2,2-trifluoroethyl)piperidin-4-yl, 1-(pyridin-3-yl)piperidin-4-yl, 1-(cyclohexylcarbamoyl)piperidin-4-yl, 1-(cyclohexylcarbamothioyl)piperidin-4-yl, 1-phenylpiperidin-4-yl, 1-cyclohexylazetidin-3-yl, 2-(thiophen-2-yl)methyl, or 2-(thiophen-3-yl)methyl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$; or $R^3$ is 2-phenylethyl, optionally substituted from one up to the maximum number of substituents with one or more of pyrrolidin-1-yl, piperidin-1-yl, 4-morpholino, cyclopropylmethoxy, (tetrahydrofuran-3-yl)oxy, (tetrahydro-2H-pyran-3-yl)oxy, (tetrahydro-2H-pyran-4-yl)oxy, phenoxy, (tetrahydrofuran-3-yl)methoxy, tetrahydro-2H-pyran-4-yl, 3,5-dimethylisoxazol-4-yl, 3,5-dimethyl-1H-pyrazol-4-yl, F, Cl, $C_{1-6}$ alkyl, cyclopropyl, propen-2-yl, $OCH_3$, and/or $CF_3$; or $R^3$ is (1-formylpiperidin-4-yl)methyl, substituted on the formyl group with one of: $C_{1-6}$ alkyl, $C_{3-7}$ cycloalkyl, phenyl, thiophen-3-yl, phenylmethyl, or cyclopentylmethyl, each optionally substituted from one up to the maximum number of substituents with one or more of F, $C_{1-6}$ alkyl, $OCH_3$, and/or $CF_3$; or $R^3$ is

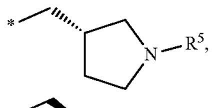

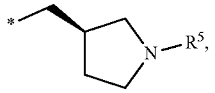

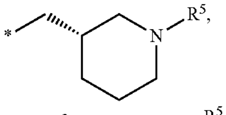

or

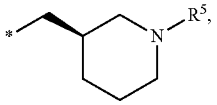

wherein $R^5$ is selected from the group consisting of: phenyl, pyridin-2-yl, pyridin-3-yl, pyrimidin-5-yl, thiophen-3-yl, benzo[d]thiazol-4-yl, benzo[d]thiazol-2-yl, phenylcarbonyl, thiazol-2-yl, benzo[d]oxazol-2-yl, and benzo[d]thiazol-2-yl, each optionally substituted from one up to the maximum number of substituents with one or more of F, Cl, $C_{1-6}$ alkyl, $C_{1-6}$ alkoxyl, $OCF_3$, and/or $CF_3$.

2. The compound of claim 1 wherein:

$R^1$ is H;

$R^2$ is $CH_3$ or $CH_2F$; and $R^3$ is cyclohexylmethyl, (4,4-dimethylcyclohexyl)methyl, (4,4-difluorocyclohexyl)methyl, (4,4-dichlorocyclohexyl)methyl, (4-ethylcyclohexyl)methyl, ((1s,4S)-4-vinylcyclohexyl)methyl, ((1s,4S)-4-isopropylcyclohexyl)methyl, ((1r,4R)-4-isopropylcyclohexyl)methyl, 4-(tert-butyl)cyclohexyl)methyl, ((1s,4S)-4-(tert-butyl)cyclohexyl)methyl, ((1r,4R)-4-(tert-butyl)cyclohexyl)methyl, ((1s,4S)-4-(trifluoromethyl)cyclohexyl)methyl, ((1r,4R)-4-(trifluoromethyl)cyclohexyl)methyl, ((1s,4S)-4-(2-fluoropropan-2-yl)cyclohexyl)methyl, ((1r,4R)-4-(2-fluoropropan-2-yl)cyclohexyl)methyl, ((trans)-3-(trifluoromethyl)cyclohexyl)methyl, ((cis)-3-(trifluoromethyl)cyclohexyl)methyl, ((1s,4S)-4-methoxycyclohexyl)methyl, ((1r,4R)-4-methoxycyclohexyl)methyl, (4-(methoxymethyl)cyclohexyl)methyl, ((1s,4S)-4-cyclopropylcyclohexyl)methyl, ((1r,4R)-4-cyclopropylcyclohexyl)methyl, (4-phenylcyclohexyl)methyl, (spiro[2.5]octan-6-yl)methyl, (spiro[3.5]nonan-7-yl)methyl, (spiro[4.5]decan-8-yl)methyl, 2-cyclohexylethyl, 2-(4,4-difluorocyclohexyl)ethyl, 2-((1s,4S)-4-(trifluoromethyl)cyclohexyl)ethyl, 2-((1r,4R)-4-(trifluoromethyl)cyclohexyl)ethyl, 2-(adamantan-1-yl)ethyl, 3-cyclohexylpropyl, phenethyl, 2-methylphenethyl, 2-methoxyphenethyl, 2-fluorophenethyl, 2-chlorophenethyl, 2,3-difluorophenethyl, 2,4-difluorophenethyl, 2,5-difluorophenethyl, 3,4-difluorophenethyl, 2-fluoro-4-methoxyphenethyl, 3-chloro-2-fluorophenethyl, 4-chloro-2-fluorophenethyl, 5-chloro-2-fluorophenethyl, 2,6-difluorophenethyl, 3-chloro-2,6-difluorophenethyl, 2,6-difluoro-4-(prop-1-en-2-yl)phenethyl, 2,6-difluoro-4-isopropylphenethyl, 2,6-difluoro-3-isopropylphenethyl, 4-cyclopropyl-2,6-difluorophenethyl, 2,6-difluoro-4-(trifluoromethyl)phenethyl, 2,6-difluoro-4-(pyrrolidin-1-yl)phenethyl, 2,6-difluoro-4-(piperidin-1-yl)phenethyl, 2,6-difluoro-4-morpholinophenethyl, 4-butoxy-2,6-difluorophenethyl, 4-(cyclopropylmethoxy)-2,6-difluorophenethyl, 4-((tetrahydrofuran-3-yl)oxy)phenethyl, 4-((tetrahydro-2H-pyran-3-yl)oxy)phenethyl, 4-((tetrahydro-2H-pyran-4-yl)oxy)phenethyl, 4-phenoxyphenethyl, 4-((tetrahydrofuran-3-yl)methoxy)phenethyl, (R)-2-phenylpropyl, (S)-2-phenylpropyl, 2-([1,1'-biphenyl]-4-yl)ethyl, 2-(3,5-difluoro-[1,1'-biphenyl]-4-yl)ethyl, 2-(benzo[d][1,3]dioxol-5-yl)ethyl, 2-(6-fluorobenzo[d][1,3]dioxol-5-yl)ethyl, 2-(2,2-difluorobenzo[d][1,3]dioxol-5-yl)ethyl, 2-(2,3-dihydrobenzo[b][1,4]dioxin-6-yl)ethyl, 2-(thiophen-2-yl)ethyl, 2-(thiophen-3-yl)ethyl, 2-(pyridine-2-yl)ethyl, 3-phenylpropyl, 3-(2-fluorophenyl)propyl, 3-(4-fluorophenyl)propyl, 3-(thiophen-2-yl)propyl, 3-(thiophen-3-yl)propyl, (1-phenylpiperidin-4-yl)methyl, (1-(2-fluorophenyl)piperidin-4-yl)methyl, (1-(3-fluorophenyl)piperidin-4-yl)methyl, (1-(4-fluorophenyl)piperidin-4-yl)methyl, (1-(4-(trifluoromethyl)phenyl)piperidin-4-yl)methyl, (4-methyl-1-phenylpiperidin-4-yl)methyl, (4-fluoro-1-phenylpiperidin-4-yl)methyl, 2-(1-phenylpiperidin-4-yl)ethyl, (1-(2,2,2-trifluoroethyl)piperidin-4-yl)methyl, (1-isobutyrylpiperidin-4-yl)methyl, (1-pivaloylpiperidin-4-yl)methyl, (1-butyrylpiperidin-4-yl)methyl, (1-(3-methylbutanoyl)piperidin-4-yl)methyl, (1-(3,3-dimethylbutanoyl)piperidin-4-yl)methyl, (1-(2-cyclopentylacetyl)piperidin-4-yl)methyl, (1-(cyclopropanecarbonyl)piperidin-4-yl)methyl, (1-(cyclobutanecarbonyl)piperidin-4-yl)methyl, (1-(cyclopentanecarbonyl)piperidin-4-yl)methyl, (1-(cyclohexanecarbonyl)piperidin-4-yl)methyl, (1-((1s,4s)-4-(tert-butyl)cyclohexanecarbonyl)piperidin-4-yl)methyl, (1-((1r,4r)-4-(tert-butyl)cyclohexanecarbonyl)piperidin-4-yl)methyl, (1-(4-methoxycyclohexanecarbonyl)piperidin-4-yl)methyl, (1-(4-(trifluoromethyl)cyclohexanecarbonyl)piperidin-4-yl)methyl, (1-benzoylpiperidin-4-yl)methyl, (1-(3-(trifluoromethyl)benzoyl)piperidin-4-yl)methyl, (1-(2-phenylacetyl)piperidin-4-yl)methyl, (1-(thiophene-3-carbonyl)piperidin-4-yl)methyl, ((5S,8s)-3,3-dimethyl-2-oxaspiro[4.5]decan-8-yl)methyl, (1,2,3,4-tetrahydronaphthalen-2-yl)methyl, (2,3-dihydro-1H-inden-2-yl)methyl, 2,6-difluoro-4-(tetrahydro-2H-pyran-4-yl)phenethyl, (1-(pyridin-3-yl)piperidin-4-yl)methyl, (1-(cyclohexylcarbamoyl)piperidin-4-yl)methyl, (1-(cyclohexylcarbamothioyl)piperidin-4-yl)methyl, (1-((1S,2R)-2-(trifluoromethyl)cyclohexyl)azetidin-3-yl)methyl, ((R)-1-phenylpyrrolidin-3-yl)methyl, ((R)-1-(o-tolyl)pyrrolidin-3-yl)methyl, ((R)-1-(2-(trifluoromethyl)phenyl)pyrrolidin-3-yl)methyl, ((S)-1-(2-(trifluoromethyl)phenyl)pyrrolidin-3-yl)methyl, (R)-1-(2-fluorophenyl)pyrrolidin-3-yl)methyl, (R)-1-(3-fluorophenyl)pyrrolidin-3-yl)methyl, ((R)-1-(2-(trifluoromethoxy)phenyl)pyrrolidin-3-yl)methyl, ((R)-1-(6-(trifluoromethyl)pyridin-2-yl)pyrrolidin-3-yl)methyl, ((R)-1-(3-(trifluoromethyl)pyridin-2-yl)pyrrolidin-3-yl)methyl, ((R)-1-(4-(trifluoromethyl)pyridin-2-yl)pyrrolidin-3-yl)methyl, ((R)-1-(pyridin-3-yl)pyrrolidin-3-yl)methyl, ((R)-1-(4-methylpyridin-3-yl)pyrrolidin-3-yl)methyl, ((R)-1-(4-(trifluoromethyl)pyridin-3-yl)pyrrolidin-3-yl)methyl, ((R)-1-(5-(trifluoromethyl)pyridin-3-yl)pyrrolidin-3-yl)methyl, ((R)-1-(2-(trifluoromethyl)pyridin-3-yl)pyrrolidin-3-yl)methyl, ((R)-1-(4-(trifluoromethyl)pyrimidin-5-yl)

pyrrolidin-3-yl)methyl, ((R)-1-(thiophen-3-yl)pyrrolidin-3-yl)methyl, ((R)-1-(benzo[d]thiazol-4-yl)pyrrolidin-3-yl)methyl, (S)-(1-(4-(trifluoromethyl)benzoyl)pyrrolidin-3-yl)methyl, ((R)-1-(o-tolyl)piperidin-3-yl)methyl, ((R)-1-(2-fluorophenyl)piperidin-3-yl)methyl, ((R)-1-(3-(trifluoromethyl)pyridin-2-yl)piperidin-3-yl)methyl, ((R)-1-(6-(trifluoromethyl)pyridin-2-yl)piperidin-3-yl)methyl, ((R)-1-(4-(trifluoromethyl)pyridin-3-yl)piperidin-3-yl)methyl, 3-fluorophenethyl, 4-fluorophenethyl, 3,4-dichlorophenethyl, 3-(trifluoromethyl)phenethyl, 4-(trifluoromethyl)phenethyl, ((R)-1-(benzo[d]thiazol-2-yl)pyrrolidin-3-yl)methyl, ((R)-1-(2-(trifluoromethyl)pyridin-3-yl)piperidin-3-yl)methyl, 4-(3,5-dimethylisoxazol-4-yl)-2,6-difluorophenethyl, 4-(3,5-dimethyl-1H-pyrazol-4-yl)-2,6-difluorophenethyl, ((R)-1-(4-(trifluoromethyl)thiazol-2-yl)pyrrolidin-3-yl)methyl, ((R)-1-(benzo[d]oxazol-2-yl)pyrrolidin-3-yl)methyl, ((R)-1-(5-isopropylthiazol-2-yl)piperidin-3-yl)methyl, ((R)-1-(4-(trifluoromethyl)thiazol-2-yl)piperidin-3-yl)methyl, ((R)-1-(benzo[d]thiazol-2-yl)piperidin-3-yl)methyl, ((R)-1-(benzo[d]thiazol-4-yl)piperidin-3-yl)methyl, ((S)-1-(3-(trifluoromethyl)pyridin-2-yl)pyrrolidin-3-yl)methyl, ((S)-1-(4-(trifluoromethyl)pyridin-3-yl)pyrrolidin-3-yl)methyl, ((S)-1-(4-(trifluoromethyl)pyrimidin-5-yl)pyrrolidin-3-yl)methyl, ((S)-1-(4-(trifluoromethyl)thiazol-2-yl)pyrrolidin-3-yl)methyl, ((S)-1-(3-(trifluoromethyl)pyridin-2-yl)piperidin-3-yl)methyl, ((S)-1-(4-(trifluoromethyl)pyridin-3-yl)piperidin-3-yl)methyl, ((S)-1-(6-(trifluoromethyl)pyridin-2-yl)piperidin-3-yl)methyl, or ((S)-1-(4-(trifluoromethyl)thiazol-2-yl)piperidin-3-yl)methyl.

3. The compound of claim 1 wherein the compound is any one of:

(2R,3R,4R,5S)-1-(cyclohexylmethyl)-2-methylpiperidine-3,4,5-triol;
(2R,3R,4R,5S)-1-((4,4-dimethylcyclohexyl)methyl)-2-methylpiperidine-3,4,5-triol;
(2R,3R,4R,5S)-1-((4,4-difluorocyclohexyl)methyl)-2-methylpiperidine-3,4,5-triol;
(2R,3R,4R,5S)-1-((4,4-dichlorocyclohexyl)methyl)-2-methylpiperidine-3,4,5-triol;
(2R,3R,4R,5S)-1-((4-ethylcyclohexyl)methyl)-2-methylpiperidine-3,4,5-triol;
(2R,3R,4R,5S)-2-methyl-1-(((1s,4S)-4-vinylcyclohexyl)methyl)piperidine-3,4,5-triol;
(2R,3R,4R,5S)-1-(((1s,4S)-4-isopropylcyclohexyl)methyl)-2-methylpiperidine-3,4,5-triol;
(2R,3R,4R,5S)-1-(((1r,4R)-4-isopropylcyclohexyl)methyl)-2-methylpiperidine-3,4,5-triol;
(2R,3R,4R,5S)-1-(((1s,4S)-4-(tert-butyl)cyclohexyl)methyl)-2-methylpiperidine-3,4,5-triol;
(2R,3R,4R,5S)-1-(((1r,4R)-4-(tert-butyl)cyclohexyl)methyl)-2-methylpiperidine-3,4,5-triol;
(2R,3R,4R,5S)-2-methyl-1-(((1s,4S)-4-(trifluoromethyl)cyclohexyl)methyl)piperidine-3,4,5-triol;
(2R,3R,4R,5S)-2-methyl-1-(((1r,4R)-4-(trifluoromethyl)cyclohexyl)methyl)piperidine-3,4,5-triol;
(2R,3R,4R,5S)-1-(((1s,4S)-4-(2-fluoropropan-2-yl)cyclohexyl)methyl)-2-methylpiperidine-3,4,5-triol;
(2R,3R,4R,5S)-1-(((1r,4R)-4-(2-fluoropropan-2-yl)cyclohexyl)methyl)-2-methylpiperidine-3,4,5-triol;
(2R,3R,4R,5S)-2-methyl-1-(((trans)-3-(trifluoromethyl)cyclohexyl)methyl)piperidine-3,4,5-triol;
(2R,3R,4R,5S)-2-methyl-1-(((cis)-3-(trifluoromethyl)cyclohexyl)methyl)piperidine-3,4,5-triol;
(2R,3R,4R,5S)-1-(((1s,4S)-4-methoxy cyclohexyl)methyl)-2-methylpiperidine-3,4,5-triol;
(2R,3R,4R,5S)-1-(((1r,4R)-4-methoxycyclohexyl)methyl)-2-methylpiperidine-3,4,5-triol;
(2R,3R,4R,5S)-1-((4-(methoxymethyl)cyclohexyl)methyl)-2-methylpiperidine-3,4,5-triol;
(2R,3R,4R,5S)-1-(((1s,4S)-4-cyclopropylcyclohexyl)methyl)-2-methylpiperidine-3,4,5-triol;
(2R,3R,4R,5S)-1-(((1r,4R)-4-cyclopropylcyclohexyl)methyl)-2-methylpiperidine-3,4,5-triol;
(2R,3R,4R,5S)-2-methyl-1-((4-phenylcyclohexyl)methyl)piperidine-3,4,5-triol;
(2R,3R,4R,5S)-2-methyl-1-(spiro[2.5]octan-6-ylmethyl)piperidine-3,4,5-triol;
(2R,3R,4R,5S)-2-methyl-1-(spiro[3.5]nonan-7-ylmethyl)piperidine-3,4,5-triol;
(2R,3R,4R,5S)-2-methyl-1-(spiro[4.5]decan-8-ylmethyl)piperidine-3,4,5-triol;
(2R,3R,4R,5S)-1-(((5S,8s)-3,3-dimethyl-2-oxaspiro[4.5]decan-8-yl)methyl)-2-methylpiperidine-3,4,5-triol;
(2R,3R,4R,5S)-2-methyl-1-((1,2,3,4-tetrahydronaphthalen-2-yl)methyl)piperidine-3,4,5-triol;
(2R,3R,4R,5S)-1-((2,3-dihydro-1H-inden-2-yl)methyl)-2-methylpiperidine-3,4,5-triol;
(2R,3R,4R,5S)-1-(2-cyclohexylethyl)-2-methylpiperidine-3,4,5-triol;
(2R,3R,4R,5S)-1-(2-(4,4-difluorocyclohexyl)ethyl)-2-methylpiperidine-3,4,5-triol;
(2R,3R,4R,5S)-2-methyl-1-(2-((1s,4S)-4-(trifluoromethyl)cyclohexyl)ethyl)piperidine-3,4,5-triol;
(2R,3R,4R,5S)-2-methyl-1-(2-((1r,4R)-4-(trifluoromethyl)cyclohexyl)ethyl)piperidine-3,4,5-triol;
(2R,3R,4R,5S)-1-((2-adamantan-1-yl)ethyl)-2-methylpiperidine-3,4,5-triol;
(2R,3R,4R,5S)-1-(3-cyclohexylpropyl)-2-methylpiperidine-3,4,5-triol;
(2R,3R,4R,5S)-2-methyl-1-phenethylpiperidine-3,4,5-triol;
(2R,3R,4R,5S)-2-methyl-1-(2-methylphenethyl)piperidine-3,4,5-triol;
(2R,3R,4R,5S)-1-(2-methoxyphenethyl)-2-methylpiperidine-3,4,5-triol;
(2R,3R,4R,5S)-1-(2-fluorophenethyl)-2-methylpiperidine-3,4,5-triol;
(2R,3R,4R,5S)-1-(2-chlorophenethyl)-2-methylpiperidine-3,4,5-triol;
(2R,3R,4R,5S)-1-(2,3-difluorophenethyl)-2-methylpiperidine-3,4,5-triol;
(2R,3R,4R,5S)-1-(2,4-difluorophenethyl)-2-methylpiperidine-3,4,5-triol;
(2R,3R,4R,5S)-1-(2,5-difluorophenethyl)-2-methylpiperidine-3,4,5-triol;
(2R,3R,4R,5S)-1-(3,4-difluorophenethyl)-2-methylpiperidine-3,4,5-triol;
(2R,3R,4R,5S)-1-(2-fluoro-4-methoxyphenethyl)-2-methylpiperidine-3,4,5-triol;
(2R,3R,4R,5S)-1-(3-chloro-2-fluorophenethyl)-2-methylpiperidine-3,4,5-triol;
(2R,3R,4R,5S)-1-(4-chloro-2-fluorophenethyl)-2-methylpiperidine-3,4,5-triol;
(2R,3R,4R,5S)-1-(5-chloro-2-fluorophenethyl)-2-methylpiperidine-3,4,5-triol;
(2R,3R,4R,5S)-1-(2,6-difluorophenethyl)-2-methylpiperidine-3,4,5-triol;
(2R,3R,4R,5S)-1-(3-chloro-2,6-difluorophenethyl)-2-methylpiperidine-3,4,5-triol;

(2R,3R,4R,5S)-1-(2,6-difluoro-4-(prop-1-en-2-yl)phenethyl)-2-methylpiperidine-3,4,5-triol;

(2R,3R,4R,5S)-1-(2,6-difluoro-4-isopropylphenethyl)-2-methylpiperidine-3,4,5-triol;

(2R,3R,4R,5S)-1-(2,6-difluoro-3-isopropylphenethyl)-2-methylpiperidine-3,4,5-triol;

(2R,3R,4R,5S)-1-(4-cyclopropyl-2,6-difluorophenethyl)-2-methylpiperidine-3,4,5-triol;

(2R,3R,4R,5S)-1-(2,6-difluoro-4-(tetrahydro-2H-pyran-4-yl)phenethyl)-2-methylpiperidine-3,4,5-triol;

(2R,3R,4R,5S)-1-(2,6-difluoro-4-(trifluoromethyl)phenethyl)-2-methylpiperidine-3,4,5-triol;

(2R,3R,4R,5S)-1-(2,6-difluoro-4-(pyrrolidin-1-yl)phenethyl)-2-methylpiperidine-3,4,5-triol;

(2R,3R,4R,5S)-1-(2,6-difluoro-4-(piperidin-1-yl)phenethyl)-2-methylpiperidine-3,4,5-triol;

(2R,3R,4R,5S)-1-(2,6-difluoro-4-morpholinophenethyl)-2-methylpiperidine-3,4,5-triol;

(2R,3R,4R,5S)-1-(4-butoxy-2,6-difluorophenethyl)-2-methylpiperidine-3,4,5-triol;

(2R,3R,4R,5S)-1-(4-(cyclopropylmethoxy)-2,6-difluorophenethyl)-2-methylpiperidine-3,4,5-triol;

(2R,3R,4R,5S)-2-methyl-1-(4-((tetrahydrofuran-3-yl)oxy)phenethyl)piperidine-3,4,5-triol;

(2R,3R,4R,5S)-2-methyl-1-(4-((tetrahydro-2H-pyran-3-yl)oxy)phenethyl)piperidine-3,4,5-triol;

(2R,3R,4R,5S)-2-methyl-1-(4-((tetrahydro-2H-pyran-4-yl)oxy)phenethyl)piperidine-3,4,5-triol;

(2R,3R,4R,5S)-2-methyl-1-(4-phenoxyphenethyl)piperidine-3,4,5-triol;

(2R,3R,4R,5S)-2-methyl-1-(4-((tetrahydrofuran-3-yl)methoxy)phenethyl)piperidine-3,4,5-triol;

(2R,3R,4R,5S)-2-methyl-1-((R)-2-phenylpropyl)piperidine-3,4,5-triol;

(2R,3R,4R,5S)-2-methyl-1-((S)-2-phenylpropyl)piperidine-3,4,5-triol;

(2R,3R,4R,5S)-1-(2-([1,1'-biphenyl]-4-yl)ethyl)-2-methylpiperidine-3,4,5-triol;

(2R,3R,4R,5S)-1-(2-(3,5-difluoro-[1,1'-biphenyl]-4-yl)ethyl)-2-methylpiperidine-3,4,5-triol;

(2R,3R,4R,5S)-1-(2-(benzo[d][1,3]dioxol-5-yl)ethyl)-2-methylpiperidine-3,4,5-triol;

(2R,3R,4R,5S)-1-(2-(6-fluorobenzo[d][1,3]dioxol-5-yl)ethyl)-2-methylpiperidine-3,4,5-triol;

(2R,3R,4R,5S)-1-(2-(2,2-difluorobenzo[d][1,3]dioxol-5-yl)ethyl)-2-methylpiperidine-3,4,5-triol;

(2R,3R,4R,5S)-1-(2-(2,3-dihydrobenzo[b][1,4]dioxin-6-yl)ethyl)-2-methylpiperidine-3,4,5-triol;

(2R,3R,4R,5S)-2-methyl-1-(2-(thiophen-2-yl)ethyl)piperidine-3,4,5-triol;

(2R,3R,4R,5S)-2-methyl-1-(2-(thiophen-3-yl)ethyl)piperidine-3,4,5-triol;

(2R,3R,4R,5S)-2-methyl-1-(2-(pyridin-2-yl)ethyl)piperidine-3,4,5-triol;

(2R,3R,4R,5S)-2-methyl-1-(3-phenylpropyl)piperidine-3,4,5-triol;

(2R,3R,4R,5S)-1-(3-(2-fluorophenyl)propyl)-2-methylpiperidine-3,4,5-triol;

(2R,3R,4R,5S)-1-(3-(4-fluorophenyl)propyl)-2-methylpiperidine-3,4,5-triol;

(2R,3R,4R,5S)-2-methyl-1-(3-(thiophen-2-yl)propyl)piperidine-3,4,5-triol;

(2R,3R,4R,5S)-2-methyl-1-(3-(thiophen-3-yl)propyl)piperidine-3,4,5-triol;

(2R,3R,4R,5S)-2-methyl-1-((1-phenylpiperidin-4-yl)methyl)piperidine-3,4,5-triol;

(2R,3R,4R,5S)-1-((1-(2-fluorophenyl)piperidin-4-yl)methyl)-2-methylpiperidine-3,4,5-triol;

(2R,3R,4R,5S)-1-((1-(3-fluorophenyl)piperidin-4-yl)methyl)-2-methylpiperidine-3,4,5-triol;

(2R,3R,4R,5S)-1-((1-(4-fluorophenyl)piperidin-4-yl)methyl)-2-methylpiperidine-3,4,5-triol;

(2R,3R,4R,5S)-2-methyl-1-((1-(4-(trifluoromethyl)phenyl)piperidin-4-yl)methyl)piperidine-3,4,5-triol;

(2R,3R,4R,5S)-2-methyl-1-((4-methyl-1-phenylpiperidin-4-yl)methyl)piperidine-3,4,5-triol;

(2R,3R,4R,5S)-1-((4-fluoro-1-phenylpiperidin-4-yl)methyl)-2-methylpiperidine-3,4,5-triol;

(2R,3R,4R,5S)-2-methyl-1-(2-(1-phenylpiperidin-4-yl)ethyl)piperidine-3,4,5-triol;

(2R,3R,4R,5S)-2-methyl-1-((1-(pyridin-3-yl)piperidin-4-yl)methyl)piperidine-3,4,5-triol;

(2R,3R,4R,5S)-2-methyl-1-((1-(2,2,2-trifluoroethyl)piperidin-4-yl)methyl)piperidine-3,4,5-triol;

2-methyl-1-(4-(((2R,3R,4R,5S)-3,4,5-trihydroxy-2-methylpiperidin-1-yl)methyl)piperidin-1-yl)propan-1-one;

2,2-dimethyl-1-(4-(((2R,3R,4R,5S)-3,4,5-trihydroxy-2-methylpiperidin-1-yl)methyl)piperidin-1-yl)propan-1-one;

1-(4-(((2R,3R,4R,5S)-3,4,5-trihydroxy-2-methylpiperidin-1-yl)methyl)piperidin-1-yl)butan-1-one;

3-methyl-1-(4-(((2R,3R,4R,5S)-3,4,5-trihydroxy-2-methylpiperidin-1-yl)methyl)piperidin-1-yl)butan-1-one;

3,3-dimethyl-1-(4-(((2R,3R,4R,5S)-3,4,5-trihydroxy-2-methylpiperidin-1-yl)methyl)piperidin-1-yl)butan-1-one;

2-cyclopentyl-1-(4-(((2R,3R,4R,5S)-3,4,5-trihydroxy-2-methylpiperidin-1-yl)methyl)piperidin-1-yl)ethanone;

cyclopropyl(4-(((2R,3R,4R,5S)-3,4,5-trihydroxy-2-methylpiperidin-1-yl)methyl)piperidin-1-yl)methanone;

cyclobutyl(4-(((2R,3R,4R,5S)-3,4,5-trihydroxy-2-methylpiperidin-1-yl)methyl)piperidin-1-yl)methanone;

cyclopentyl(4-(((2R,3R,4R,5S)-3,4,5-trihydroxy-2-methylpiperidin-1-yl)methyl)piperidin-1-yl)methanone;

cyclohexyl(4-(((2R,3R,4R,5S)-3,4,5-trihydroxy-2-methylpiperidin-1-yl)methyl)piperidin-1-yl)methanone;

((1s,4S)-4-(tert-butyl)cyclohexyl)(4-(((2R,3R,4R,5S)-3,4,5-trihydroxy-2-methylpiperidin-1-yl)methyl)piperidin-1-yl)methanone;

((1r,4R)-4-(tert-butyl)cyclohexyl)(4-(((2R,3R,4R,5S)-3,4,5-trihydroxy-2-methylpiperidin-1-yl)methyl)piperidin-1-yl)methanone;

(4-methoxycyclohexyl)(4-(((2R,3R,4R,5S)-3,4,5-trihydroxy-2-methylpiperidin-1-yl)methyl)piperidin-1-yl)methanone;

(4-(trifluoromethyl)cyclohexyl)(4-(((2R,3R,4R,5S)-3,4,5-trihydroxy-2-methylpiperidin-1-yl)methyl)piperidin-1-yl)methanone;

phenyl(4-(((2R,3R,4R,5S)-3,4,5-trihydroxy-2-methylpiperidin-1-yl)methyl)piperidin-1-yl)methanone;

(3-(trifluoromethyl)phenyl)(4-(((2R,3R,4R,5S)-3,4,5-trihydroxy-2-methylpiperidin-1-yl)methyl)piperidin-1-yl)methanone;

2-phenyl-1-(4-(((2R,3R,4R,5S)-3,4,5-trihydroxy-2-methylpiperidin-1-yl)methyl)piperidin-1-yl)ethanone;

thiophen-3-yl(4-(((2R,3R,4R,5S)-3,4,5-trihydroxy-2-methylpiperidin-1-yl)methyl)piperidin-1-yl)methanone;

N-cyclohexyl-4-(((2R,3R,4R,5S)-3,4,5-trihydroxy-2-methylpiperidin-1-yl)methyl)piperidine-1-carboxamide;

N-cyclohexyl-4-(((2R,3R,4R,5S)-3,4,5-trihydroxy-2-methylpiperidin-1-yl)methyl)piperidine-1-carbothioamide;
(2R,3R,4R,5S)-2-methyl-1-((1-((1S,2R)-2-(trifluoromethyl)cyclohexyl)azetidin-3-yl)methyl)piperidine-3,4,5-triol;
(2R,3R,4R,5S)-2-methyl-1-(((R)-1-phenylpyrrolidin-3-yl)methyl)piperidine-3,4,5-triol;
(2R,3R,4R,5S)-2-methyl-1-(((R)-1-(o-tolyl)pyrrolidin-3-yl)methyl)piperidine-3,4,5-triol;
(2R,3R,4R,5S)-2-methyl-1-(((R)-1-(2-(trifluoromethyl)phenyl)pyrrolidin-3-yl)methyl)piperidine-3,4,5-triol;
(2R,3R,4R,5S)-1-(((R)-1-(2-fluorophenyl)pyrrolidin-3-yl)methyl)-2-methylpiperidine-3,4,5-triol;
(2R,3R,4R,5S)-1-(((R)-1-(3-fluorophenyl)pyrrolidin-3-yl)methyl)-2-methylpiperidine-3,4,5-triol;
(2R,3R,4R,5S)-2-methyl-1-(((R)-1-(2-(trifluoromethoxy)phenyl)pyrrolidin-3-yl)methyl)piperidine-3,4,5-triol;
(2R,3R,4R,5S)-2-methyl-1-(((R)-1-(6-(trifluoromethyl)pyridin-2-yl)pyrrolidin-3-yl)methyl)piperidine-3,4,5-triol;
(2R,3R,4R,5S)-2-methyl-1-(((R)-1-(3-(trifluoromethyl)pyridin-2-yl)pyrrolidin-3-yl)methyl)piperidine-3,4,5-triol;
(2R,3R,4R,5S)-2-methyl-1-(((R)-1-(4-(trifluoromethyl)pyridin-2-yl)pyrrolidin-3-yl)methyl)piperidine-3,4,5-triol;
(2R,3R,4R,5S)-2-methyl-1-(((R)-1-(pyridin-3-yl)pyrrolidin-3-yl)methyl)piperidine-3,4,5-triol;
(2R,3R,4R,5S)-2-methyl-1-(((R)-1-(4-methylpyridin-3-yl)pyrrolidin-3-yl)methyl)piperidine-3,4,5-triol;
(2R,3R,4R,5S)-2-methyl-1-(((R)-1-(4-(trifluoromethyl)pyridin-3-yl)pyrrolidin-3-yl)methyl)piperidine-3,4,5-triol;
(2R,3R,4R,5S)-2-methyl-1-(((R)-1-(5-(trifluoromethyl)pyridin-3-yl)pyrrolidin-3-yl)methyl)piperidine-3,4,5-triol;
(2R,3R,4R,5S)-2-methyl-1-(((R)-1-(2-(trifluoromethyl)pyridin-3-yl)pyrrolidin-3-yl)methyl)piperidine-3,4,5-triol;
(2R,3R,4R,5S)-2-methyl-1-(((R)-1-(4-(trifluoromethyl)pyrimidin-5-yl)pyrrolidin-3-yl)methyl)piperidine-3,4,5-triol;
(2R,3R,4R,5S)-2-methyl-1-(((R)-1-(thiophen-3-yl)pyrrolidin-3-yl)methyl)piperidine-3,4,5-triol;
(2R,3R,4R,5S)-1-(((R)-1-(benzo[d]thiazol-4-yl)pyrrolidin-3-yl)methyl)-2-methylpiperidine-3,4,5-triol;
(4-(trifluoromethyl)phenyl)((R)-3-(((2R,3R,4R,5S)-3,4,5-trihydroxy-2-methylpiperidin-1-yl)methyl)pyrrolidin-1-yl)methanone;
(2R,3R,4R,5S)-2-methyl-1-(((S)-1-(2-(trifluoromethyl)phenyl)pyrrolidin-3-yl)methyl)piperidine-3,4,5-triol;
(2R,3R,4R,5S)-2-methyl-1-(((S)-1-(3-(trifluoromethyl)pyridin-2-yl)pyrrolidin-3-yl)methyl)piperidine-3,4,5-triol;
(2R,3R,4R,5S)-2-methyl-1-(((S)-1-(4-(trifluoromethyl)pyridin-3-yl)pyrrolidin-3-yl)methyl)piperidine-3,4,5-triol;
(2R,3R,4R,5S)-2-methyl-1-(((S)-1-(4-(trifluoromethyl)pyrimidin-5-yl)pyrrolidin-3-yl)methyl)piperidine-3,4,5-triol;
(2R,3R,4R,5S)-2-methyl-1-(((S)-1-(4-(trifluoromethyl)thiazol-2-yl)pyrrolidin-3-yl)methyl)piperidine-3,4,5-triol;
(2R,3R,4R,5S)-2-methyl-1-(((R)-1-(o-tolyl)piperidin-3-yl)methyl)piperidine-3,4,5-triol;

(2R,3R,4R,5S)-1-(((R)-1-(2-fluorophenyl)piperidin-3-yl)methyl)-2-methylpiperidine-3,4,5-triol;
(2R,3R,4R,5S)-2-methyl-1-(((R)-1-(3-(trifluoromethyl)pyridin-2-yl)piperidin-3-yl)methyl)piperidine-3,4,5-triol;
(2R,3R,4R,5S)-2-methyl-1-(((R)-1-(6-(trifluoromethyl)pyridin-2-yl)piperidin-3-yl)methyl)piperidine-3,4,5-triol;
(2R,3R,4R,5S)-2-methyl-1-(((R)-1-(4-(trifluoromethyl)pyridin-3-yl)piperidin-3-yl)methyl)piperidine-3,4,5-triol;
(2R,3R,4R,5S)-2-methyl-1-(((S)-1-(3-(trifluoromethyl)pyridin-2-yl)piperidin-3-yl)methyl)piperidine-3,4,5-triol;
(2R,3R,4R,5S)-2-methyl-1-(((S)-1-(4-(trifluoromethyl)pyridin-3-yl)piperidin-3-yl)methyl)piperidine-3,4,5-triol;
(2R,3R,4R,5S)-2-methyl-1-(((S)-1-(6-(trifluoromethyl)pyridin-2-yl)piperidin-3-yl)methyl)piperidine-3,4,5-triol;
(2R,3R,4R,5S)-2-methyl-1-(((S)-1-(4-(trifluoromethyl)thiazol-2-yl)piperidin-3-yl)methyl)piperidine-3,4,5-triol;
(2S,3R,4R,5S)-2-(fluoromethyl)-1-((4-isopropylcyclohexyl)methyl)piperidine-3,4,5-triol;
(2S,3R,4R,5S)-1-((4-(tert-butyl)cyclohexyl)methyl)-2-(fluoromethyl)piperidine-3,4,5-triol;
(2S,3R,4R,5S)-2-(fluoromethyl)-1-(((1r,4S)-4-(trifluoromethyl)cyclohexyl)methyl)piperidine-3,4,5-triol;
(2S,3R,4R,5S)-2-(fluoromethyl)-1-phenethylpiperidine-3,4,5-triol;
(2S,3R,4R,5S)-2-(fluoromethyl)-1-(2-fluorophenethyl)piperidine-3,4,5-triol;
(2S,3R,4R,5S)-1-(2,6-difluoro-4-isopropylphenethyl)-2-(fluoromethyl)piperidine-3,4,5-triol;
(2S,3R,4R,5S)-1-(2-(3,5-difluoro-[1,1'-biphenyl]-4-yl)ethyl)-2-(fluoromethyl)piperidine-3,4,5-triol;
(2S,3R,4R,5S)-1-(2-(6-fluorobenzo[d][1,3]dioxol-5-yl)ethyl)-2-(fluoromethyl)piperidine-3,4,5-triol;
(2S,3R,4R,5S)-1-(2-(2,3-dihydrobenzo[b][1,4]dioxin-6-yl)ethyl)-2-(fluoromethyl)piperidine-3,4,5-triol;
(2S,3R,4R,5S)-2-(fluoromethyl)-1-((1-phenylpiperidin-4-yl)methyl)piperidine-3,4,5-triol;
(2S,3R,4R,5S)-2-(fluoromethyl)-1-((1-(4-(trifluoromethyl)phenyl)piperidin-4-yl)methyl)piperidine-3,4,5-triol;
(2S,3R,4R,5S)-2-(difluoromethyl)-1-phenethylpiperidine-3,4,5-triol;
(2S,3R,4R,5S)-1-(2-fluorophenethyl)-2-methylpiperidine-3,4,5-triol;
(2S,3R,4R,5S)-1-(4-butoxy-2,6-difluorophenethyl)-2-methylpiperidine-3,4,5-triol;
(2R,3R,4R,5S)-2-(fluoromethyl)-1-(2-fluorophenethyl)piperidine-3,4,5-triol;
(2R,3R,4R,5S)-1-(4-butoxy-2,6-difluorophenethyl)-2-(fluoromethyl)piperidine-3,4,5-triol;
(2R,3R,4R,5S)-1-(3-fluorophenethyl)-2-methylpiperidine-3,4,5-triol;
(2R,3R,4R,5S)-1-(4-fluorophenethyl)-2-methylpiperidine-3,4,5-triol;
(2R,3R,4R,5S)-1-(3,4-dichlorophenethyl)-2-methylpiperidine-3,4,5-triol;
(2R,3R,4R,5S)-2-methyl-1-(3-(trifluoromethyl)phenethyl)piperidine-3,4,5-triol;
(2R,3R,4R,5S)-2-methyl-1-(4-(trifluoromethyl)phenethyl)piperidine-3,4,5-triol;

(2R,3R,4R,5S)-1-(4-(3,5-dimethylisoxazol-4-yl)-2,6-difluorophenethyl)-2-methylpiperidine-3,4,5-triol;

(2R,3R,4R,5S)-1-(4-(3,5-dimethyl-1H-pyrazol-4-yl)-2,6-difluorophenethyl)-2-methylpiperidine-3,4,5-triol;

(2R,3R,4R,5S)-2-methyl-1-(((R)-1-(4-(trifluoromethyl)thiazol-2-yl)pyrrolidin-3-yl)methyl)piperidine-3,4,5-triol;

(2R,3R,4R,5S)-1-(((R)-1-(benzo[d]oxazol-2-yl)pyrrolidin-3-yl)methyl)-2-methylpiperidine-3,4,5-triol;

(2R,3R,4R,5S)-1-(((R)-1-(benzo[d]thiazol-2-yl)pyrrolidin-3-yl)methyl)-2-methylpiperidine-3,4,5-triol;

(2R,3R,4R,5S)-1-(((R)-1-(5-isopropylthiazol-2-yl)piperidin-3-yl)methyl)-2-methylpiperidine-3,4,5-triol;

(2R,3R,4R,5S)-2-methyl-1-(((R)-1-(4-(trifluoromethyl)thiazol-2-yl)piperidin-3-yl)methyl)piperidine-3,4,5-triol;

(2R,3R,4R,5S)-2-methyl-1-(((R)-1-(2-(trifluoromethyl)pyridin-3-yl)piperidin-3-yl)methyl)piperidine-3,4,5-triol;

(2R,3R,4R,5S)-1-(((R)-1-(benzo[d]thiazol-2-yl)piperidin-3-yl)methyl)-2-methylpiperidine-3,4,5-triol;

(2R,3R,4R,5S)-1-(((R)-1-(benzo[d]thiazol-4-yl)piperidin-3-yl)methyl)-2-methylpiperidine-3,4,5-triol;

or a pharmaceutically acceptable salt of any of the foregoing compounds.

4. The compound of claim 1 wherein the compound is a prodrug.

5. The compound of claim 1 wherein the compound inhibits a non-lysosomal glucosylceramidase (GBA2), specifically binds a GBA2, or decreases the enzyme activity levels of a GBA2.

6. The compound of claim 5 wherein the GBA2 is a mammalian GBA2.

7. A pharmaceutical composition comprising the compound of claim 1 or a pharmaceutically acceptable salt thereof in combination with a pharmaceutically acceptable carrier.

8. A method of inhibiting a GBA2 in a subject in need thereof, the method comprising administering to the subject an effective amount of a compound of Formula (I) or a pharmaceutically acceptable salt thereof:

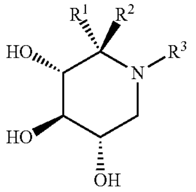

(I)

wherein $R^1$ is H and $R^2$ is $CH_3$, $CH_2F$, or $CHF_2$; or $R^1$ is $CH_3$ or $CH_2F$ and $R^2$ is H; and $R^3$ is $(CH_2)_nR^4$, wherein n is 1 or 2, and $R^4$ is cyclohexyl, cyclohexylmethyl, phenylethyl, 4-phenylcyclohexyl, spiro[2.5]octan-6-yl, spiro[3.5]nonan-7-yl, spiro[4.5]decan-8-yl, (5S,8s)-3,3-dimethyl-2-oxaspiro[4.5]decan-8-yl, 1,2,3,4-tetrahydronaphthalen-2-yl, 2,3-dihydro-1H-inden-2-yl, (adamantyl)methyl, (pyridine-2-yl)methyl, (benzo[d][1,3]dioxol-5-yl)methyl, (2,3-dihydrobenzo[b][1,4]dioxin-6-yl)methyl, ([1,1'-biphenyl]-4-yl)methyl, 1-(2,2,2-trifluoroethyl)piperidin-4-yl, 1-(pyridin-3-yl)piperidin-4-yl, 1-(cyclohexylcarbamoyl)piperidin-4-yl, 1-(cyclohexylcarbamothioyl)piperidin-4-yl, 1-phenylpiperidin-4-yl, 1-cyclohexylazetidin-3-yl, 2-(thiophen-2-yl)methyl, or 2-(thiophen-3-yl)methyl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$; or $R^3$ is 2-phenylethyl, optionally substituted from one up to the maximum number of substituents with one or more of pyrrolidin-1-yl, piperidin-1-yl, 4-morpholino, cyclopropylmethoxy, (tetrahydrofuran-3-yl)oxy, (tetrahydro-2H-pyran-3-yl)oxy, (tetrahydro-2H-pyran-4-yl)oxy, phenoxy, (tetrahydrofuran-3-yl)methoxy, tetrahydro-2H-pyran-4-yl, 3,5-dimethylisoxazol-4-yl, 3,5-dimethyl-1H-pyrazol-4-yl, F, Cl, $C_{1-6}$ alkyl, cyclopropyl, propen-2-yl, $OCH_3$, and/or $CF_3$; or $R^3$ is (1-formylpiperidin-4-yl)methyl, substituted on the formyl group with one of: $C_{1-6}$ alkyl, $C_{3-7}$ cycloalkyl, phenyl, thiophen-3-yl, phenylmethyl, or cyclopentylmethyl, each optionally substituted from one up to the maximum number of substituents with one or more of F, $C_{1-6}$ alkyl, $OCH_3$, and/or $CF_3$; or $R^3$ is

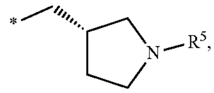

,

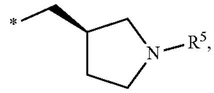

,

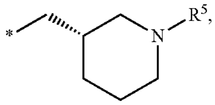

, or

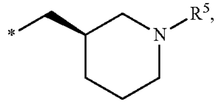

, wherein $R^5$ is selected from the group consisting of: phenyl, pyridin-2-yl, pyridin-3-yl, pyrimidin-5-yl, thiophen-3-yl, benzo[d]thiazol-4-yl, benzo[d]thiazol-2-yl, phenylcarbonyl, thiazol-2-yl, benzo[d]oxazol-2-yl, and benzo[d]thiazol-2-yl, each optionally substituted from one up to the maximum number of substituents with one or more of F, Cl, $C_{1-6}$ alkyl, $C_{1-6}$ alkoxyl, $OCF_3$, and/or $CF_3$.

9. A method of reducing GBA2 enzyme activity in a subject in need thereof, the method comprising administering to the subject an effective amount of a compound of Formula (I) or a pharmaceutically acceptable salt thereof:

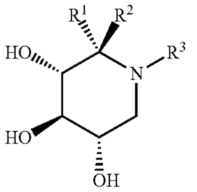

(I)

wherein $R^1$ is H and $R^2$ is $CH_3$, $CH_2F$, or $CHF_2$; or $R^1$ is $CH_3$ or $CH_2F$ and $R^2$ is H; and $R^3$ is $(CH_2)_nR^4$, wherein n is 1 or 2, and $R^4$ is cyclohexyl, cyclohexylmethyl, phenylethyl, 4-phenylcyclohexyl, spiro[2.5]octan-6-yl, spiro[3.5]nonan-7-yl, spiro[4.5]decan-8-yl, (5S,8s)-3,3-dimethyl-2-oxaspiro[4.5]decan-8-yl, 1,2,3,4-tetrahydronaphthalen-2-yl, 2,3-dihydro-1H-inden-2-yl, (adamantyl)methyl, (pyridine-2-yl)methyl, (benzo[d][1,3]dioxol-5-yl)methyl, (2,3-dihydrobenzo[b][1,4]dioxin-6-yl)methyl, ([1,1'-biphenyl]-4-yl)methyl, 1-(2,2,2-trifluoroethyl)piperidin-4-yl, 1-(pyridin-3-yl)piperidin-4-yl, 1-(cyclohexylcarbamoyl)piperidin-4-yl, 1-(cyclohexylcarbamothioyl)piperidin-4-yl, 1-phenylpiperidin-4-yl, 1-cyclohexylazetidin-3-yl, 2-(thiophen-2-yl)methyl, or 2-(thiophen-3-yl)methyl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$; or $R^3$ is 2-phenylethyl, optionally substituted from one up to the maximum number of substituents with one or more of pyrrolidin-1-yl, piperidin-1-yl, 4-morpholino, cyclopropylmethoxy, (tetrahydrofuran-3-yl)oxy, (tetrahydro-2H-pyran-3-yl)oxy, (tetrahydro-2H-pyran-4-yl)oxy, phenoxy, (tetrahydrofuran-3-yl)methoxy, tetrahydro-2H-pyran-4-yl, 3,5-dimethylisoxazol-4-yl, 3,5-dimethyl-1H-pyrazol-4-yl, F, Cl, $C_{1-6}$ alkyl, cyclopropyl, propen-2-yl, $OCH_3$, and/or $CF_3$; or $R^3$ is (1-formylpiperidin-4-yl)methyl, substituted on the formyl group with one of $C_{1-6}$ alkyl, $C_{3-7}$ cycloalkyl, phenyl, thiophen-3-yl, phenylmethyl, or cyclopentylmethyl, each optionally substituted from one up to the maximum number of substituents with one or more of F, $C_{1-6}$ alkyl, $OCH_3$, and/or $CF_3$; or $R^3$ is

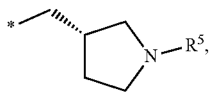

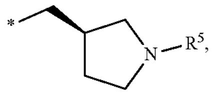

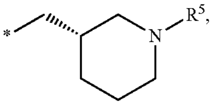 or

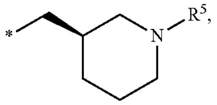

wherein $R^5$ is selected from the group consisting of: phenyl, pyridin-2-yl, pyridin-3-yl, pyrimidin-5-yl, thiophen-3-yl, benzo[d]thiazol-4-yl, benzo[d]thiazol-2-yl, phenylcarbonyl, thiazol-2-yl, benzo[d]oxazol-2-yl, and benzo[d]thiazol-2-yl, each optionally substituted from one up to the maximum number of substituents with one or more of F, Cl, $C_{1-6}$ alkyl, $C_{1-6}$ alkoxyl, $OCF_3$, and/or $CF_3$.

10. A method of treating a condition that is modulated by a GBA2, in a subject in need thereof, the method comprising administering to the subject an effective amount of a compound of Formula (I) or a pharmaceutically acceptable salt thereof:

(I)

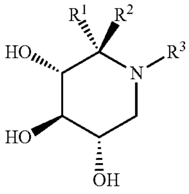

wherein $R^1$ is H and $R^2$ is $CH_3$, $CH_2F$, or $CHF_2$; or $R^1$ is $CH_3$ or $CH_2F$ and $R^2$ is H; and $R^3$ is $(CH_2)_nR^4$, wherein n is 1 or 2, and $R^4$ is cyclohexyl, cyclohexylmethyl, phenylethyl, 4-phenylcyclohexyl, spiro[2.5]octan-6-yl, spiro[3.5]nonan-7-yl, spiro[4.5]decan-8-yl, (5S,8s)-3,3-dimethyl-2-oxaspiro[4.5]decan-8-yl, 1,2,3,4-tetrahydronaphthalen-2-yl, 2,3-dihydro-1H-inden-2-yl, (adamantyl)methyl, (pyridine-2-yl)methyl, (benzo[d][1,3]dioxol-5-yl)methyl, (2,3-dihydrobenzo[b][1,4]dioxin-6-yl)methyl, ([1,1'-biphenyl]-4-yl)methyl, 1-(2,2,2-trifluoroethyl)piperidin-4-yl, 1-(pyridin-3-yl)piperidin-4-yl, 1-(cyclohexylcarbamoyl)piperidin-4-yl, 1-(cyclohexylcarbamothioyl)piperidin-4-yl, 1-phenylpiperidin-4-yl, 1-cyclohexylazetidin-3-yl, 2-(thiophen-2-yl)methyl, or 2-(thiophen-3-yl)methyl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$; or $R^3$ is 2-phenylethyl, optionally substituted from one up to the maximum number of substituents with one or more of pyrrolidin-1-yl, piperidin-1-yl, 4-morpholino, cyclopropylmethoxy, (tetrahydrofuran-3-yl)oxy, (tetrahydro-2H-pyran-3-yl)oxy, (tetrahydro-2H-pyran-4-yl)oxy, phenoxy, (tetrahydrofuran-3-yl)methoxy, tetrahydro-2H-pyran-4-yl, 3,5-dimethylisoxazol-4-yl, 3,5-dimethyl-1H-pyrazol-4-yl, F, Cl, $C_{1-6}$ alkyl, cyclopropyl, propen-2-yl, $OCH_3$, and/or $CF_3$; or $R^3$ is (1-formylpiperidin-4-yl)methyl, substituted on the formyl group with one of: $C_{1-6}$ alkyl, $C_{3-7}$ cycloalkyl, phenyl, thiophen-3-yl, phenylmethyl, or cyclopentylmethyl, each optionally substituted from one up to the maximum number of substituents with one or more of F, $C_{1-6}$ alkyl, $OCH_3$, and/or $CF_3$; or $R^3$ is

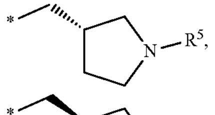

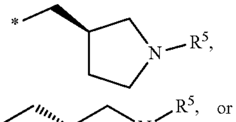

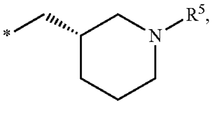 or

-continued

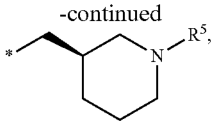

wherein $R^5$ is selected from the group consisting of: phenyl, pyridin-2-yl, pyridin-3-yl, pyrimidin-5-yl, thiophen-3-yl, benzo[d]thiazol-4-yl, benzo[d]thiazol-2-yl, phenylcarbonyl, thiazol-2-yl, benzo[d]oxazol-2-yl, and benzo[d]thiazol-2-yl, each optionally substituted from one up to the maximum number of substituents with one or more of F, Cl, $C_{1-6}$ alkyl, $C_{1-6}$ alkoxyl, $OCF_3$, and/or $CF_3$.

11. A method of treating a condition selected from a neurological disease, a lysosomal storage disease, and a liver disease, in a subject in need thereof, the method comprising administering to the subject an effective amount of a compound of Formula (I) or a pharmaceutically acceptable salt thereof:

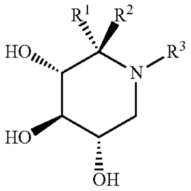

(I)

wherein $R^1$ is H and $R^2$ is $CH_3$, $CH_2F$, or $CHF_2$; or $R^1$ is $CH_3$ or $CH_2F$ and $R^2$ is H; and $R^3$ is $(CH_2)_nR^4$, wherein n is 1 or 2, and $R^4$ is cyclohexyl, cyclohexylmethyl, phenylethyl, 4-phenylcyclohexyl, spiro[2.5]octan-6-yl, spiro[3.5]nonan-7-yl, spiro[4.5]decan-8-yl, (5S,8s)-3,3-dimethyl-2-oxaspiro[4.5]decan-8-yl, 1,2,3,4-tetrahydronaphthalen-2-yl, 2,3-dihydro-1H-inden-2-yl, (adamantyl)methyl, (pyridine-2-yl)methyl, (benzo[d][1,3]dioxol-5-yl)methyl, (2,3-dihydrobenzo[b][1,4]dioxin-6-yl)methyl, ([1,1'-biphenyl]-4-yl)methyl, 1-(2,2,2-trifluoroethyl)piperidin-4-yl, 1-(pyridin-3-yl)piperidin-4-yl, 1-(cyclohexylcarbamoyl)piperidin-4-yl, 1-(cyclohexylcarbamothioyl)piperidin-4-yl, 1-phenylpiperidin-4-yl, 1-cyclohexylazetidin-3-yl, 2-(thiophen-2-yl)methyl, or 2-(thiophen-3-yl)methyl, each optionally substituted from one up to the maximum number of substituents with one or more of F, Cl, $C_{1-6}$ alkyl, cyclopropyl, vinyl, 2-fluoropropan-2-yl, methoxymethyl, $C_{1-6}$ alkoxy, and/or $CF_3$; or $R^3$ is 2-phenylethyl, optionally substituted from one up to the maximum number of substituents with one or more of pyrrolidin-1-yl, piperidin-1-yl, 4-morpholino, cyclopropylmethoxy, (tetrahydrofuran-3-yl)oxy, (tetrahydro-2H-pyran-3-yl)oxy, (tetrahydro-2H-pyran-4-yl)oxy, phenoxy, (tetrahydrofuran-3-yl)methoxy, tetrahydro-2H-pyran-4-yl, 3,5-dimethylisoxazol-4-yl, 3,5-dimethyl-1H-pyrazol-4-yl, F, Cl, $C_{1-6}$ alkyl, cyclopropyl, propen-2-yl, $OCH_3$, and/or $CF_3$; or $R^3$ is (1-formylpiperidin-4-yl)methyl, substituted on the formyl group with one of $C_{1-6}$ alkyl, $C_{3-7}$ cycloalkyl, phenyl, thiophen-3-yl, phenylmethyl, or cyclopentylmethyl, each optionally substituted from one up to the maximum number of substituents with one or more of F, $C_{1-6}$ alkyl, $OCH_3$, and/or $CF_3$; or $R^3$ is

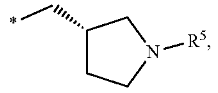

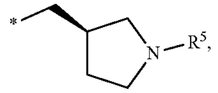

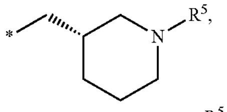

or

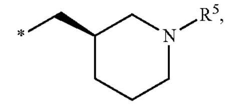

wherein $R^5$ is selected from the group consisting of: phenyl, pyridin-2-yl, pyridin-3-yl, pyrimidin-5-yl, thiophen-3-yl, benzo[d]thiazol-4-yl, benzo[d]thiazol-2-yl, phenylcarbonyl, thiazol-2-yl, benzo[d]oxazol-2-yl, and benzo[d]thiazol-2-yl, each optionally substituted from one up to the maximum number of substituents with one or more of F, Cl, $C_{1-6}$ alkyl, $C_{1-6}$ alkoxyl, $OCF_3$, and/or $CF_3$.

12. The method of claim 11 wherein the condition is Alzheimer's disease, Parkinson's disease, multiple sclerosis, Huntington's disease, amyotrophic lateral sclerosis (ALS), amyotrophic lateral sclerosis with cognitive impairment (ALSci), addiction, anxiety, argyrophilic grain dementia, ataxia-telangiectasia (A-T), attention deficit/hyperactivity disorder (ADHD), autism spectrum disorder (ASD), Becker muscular dystrophy (BMD), bipolar disorder (BD), Bluit disease, cerebellar ataxia, Charcot-Marie-Tooth disease (CMT), chronic fatigue syndrome, corticobasal degeneration (CBD), dementia pugilistica, dementia with Lewy bodies (DLB), Dejerine-Sottas disease, diffuse neurofibrillary tangles with calcification, Down's syndrome, Duchenne muscular dystrophy (DMD), epilepsy, essential tremor (ET), familial British dementia, familial Danish dementia, fibromyalgia, frontotemporal dementia with parkinsonism linked to chromosome 17 (FTDP-17), Friedreich's ataxia, Gerstmann-Straussler-Scheinker disease, glaucoma, Guadeloupean parkinsonism, Guillain-Barré syndrome, Hallevorden-Spatz disease (neurodegeneration with brain iron accumulation type 1), insomnia, Lambert-Eaton myasthenic syndrome (LEMS), major depressive disorder (MDD), migraine, mild cognitive impairment (MCI), multi-infarct dementia, multiple system atrophy (MSA), myasthenia gravis, myotonic dystrophy (including types DM1 and DM2), neuronal ceroid lipofuscinosis, neuropathy, oculopharyngeal muscular dystrophy, pain, pallido-ponto-nigral degeneration, parkinsonism-dementia complex of Guam, Pick's disease (PiD), post-encephalitic parkinsonism (PEP), primary lateral sclerosis (PLS), prion diseases, progressive supercortical gliosis, progressive supranuclear palsy (PSP), Richardson's syndrome, schizophrenia, seizures, spinal cord injury, spinal muscular atrophy (SMA), spinocerebellar ataxia, stroke, subacute sclerosing panencephalitis, tangle-only dementia, tardive dyskinesia, Tourette syndrome (TS), vascular dementia, Wilson's disease, Gaucher disease, Niemann-Pick disease, mucolipidosis, cerebrotendineous xanthomatosis, Fabry disease, Farber disease, GM1 gangliosidosis, Krabbe disease, metachromatic leukodystrophy (MILD), multiple sulfatase deficiency, Pompe disease, Sandhoff disease, Tay-Sach's disease, non-alcoholic fatty liver disease (NAFLD), non-alcoholic steatohepatitis (NASH), Alagille syndrome, alcohol-related liver disease, alpha-1 antitrypsin deficiency, autoimmune hepatitis, autoimmune cholangitis, benign liver tumors, biliary atresia, cirrhosis, Crigler-Najjar syndrome, drug-induced liver injury (DILI), galactosemia, Gilbert syndrome, hemochromatosis, hepatic encephalopathy, hepatocellular carcinoma (HCC), intrahepatic cholestasis of pregnancy (ICP), lysosomal acid lipase deficiency (LAL-D), liver cysts, liver cancer, newborn jaundice, primary biliary cholangitis (PBC), primary sclerosing cholangitis (PSC), Reye syndrome, type I glycogen storage disease, or viral hepatitis.

13. The method of claim 10 wherein the condition is Parkinson's disease.

14. The method of claim 10 wherein the condition is Alzheimer's disease, Huntington's disease, amyotrophic lateral sclerosis (ALS), or multiple sclerosis.

15. The method of claim 10 wherein the condition is Niemann-Pick type C disease.

16. The method of claim 10 wherein the condition is Gaucher disease, mucolipidosis type IV, or Sandhoff disease.

17. The method of claim 10 wherein the condition is non-alcoholic steatohepatitis (NASH).

18. The method of claim 11 wherein the compound is any one of:

(2R,3R,4R,5S)-1-(cyclohexylmethyl)-2-methylpiperidine-3,4,5-triol;

(2R,3R,4R,5S)-1-((4,4-dimethylcyclohexyl)methyl)-2-methylpiperidine-3,4,5-triol; (2R,3R,4R,5S)-1-((4,4-difluorocyclohexyl)methyl)-2-methylpiperidine-3,4,5-triol; (2R,3R,4R,5S)-1-((4,4-dichlorocyclohexyl)methy)-2-methylpiperidine-3,4,5-triol; (2R,3R,4R,5S)-1-((4-ethylcyclohexyl)methyl)-2-methylpiperidine-3,4,5-triol;

(2R,3R,4R,5S)-2-methyl-1-(((1s,4S)-4-vinylcyclohexyl)methyl)piperidine-3,4,5-triol;

(2R,3R,4R,5S)-1-(((1s,4S)-4-isopropylcyclohexyl)methyl)-2-methylpiperidine-3,4,5-triol;

(2R,3R,4R,5S)-1-(((1r,4R)-4-isopropylcyclohexyl)methyl)-2-methylpiperidine-3,4,5-triol;

(2R,3R,4R,5S)-1-(((1s,4S)-4-(tert-butyl)cyclohexyl)methyl)-2-methylpiperidine-3,4,5-triol;

(2R,3R,4R,5S)-1-(((1r,4R)-4-(tert-butyl)cyclohexyl)methyl)-2-methylpiperidine-3,4,5-triol;

(2R,3R,4R,5S)-2-methyl-1-(((1s,4S)-4-(trifluoromethyl)cyclohexyl)methyl)piperidine-3,4,5-triol;

(2R,3R,4R,5S)-2-methyl-1-(((1r,4R)-4-(trifluoromethyl)cyclohexyl)methyl)piperidine-3,4,5-triol;

(2R,3R,4R,5S)-1-(((1s,4S)-4-(2-fluoropropan-2-yl)cyclohexyl)methyl)-2-methylpiperidine-3,4,5-triol;

(2R,3R,4R,5S)-1-(((1r,4R)-4-(2-fluoropropan-2-yl)cyclohexyl)methyl)-2-methylpiperidine-3,4,5-triol;

(2R,3R,4R,5S)-2-methyl-1-(((trans)-3-(trifluoromethyl)cyclohexyl)methyl)piperidine-3,4,5-triol;

(2R,3R,4R,5S)-2-methyl-1-(((cis)-3-(trifluoromethyl)cyclohexyl)methyl)piperidine-3,4,5-triol;

(2R,3R,4R,5S)-1-(((1s,4S)-4-methoxycyclohexyl)methyl)-2-methylpiperidine-3,4,5-triol;

(2R,3R,4R,5S)-1-(((1r,4R)-4-methoxycyclohexyl)methyl)-2-methylpiperidine-3,4,5-triol;

(2R,3R,4R,5S)-1-((4-(methoxymethyl)cyclohexyl)methyl)-2-methylpiperidine-3,4,5-triol;

(2R,3R,4R,5S)-1-(((1s,4S)-4-cyclopropylcyclohexyl)methyl)-2-methylpiperidine-3,4,5-triol;

(2R,3R,4R,5S)-1-(((1r,4R)-4-cyclopropylcyclohexyl)methyl)-2-methylpiperidine-3,4,5-triol;

(2R,3R,4R,5S)-2-methyl-1-((4-phenylcyclohexyl)methyl)piperidine-3,4,5-triol;

(2R,3R,4R,5S)-2-methyl-1-(spiro[2.5]octan-6-ylmethyl)piperidine-3,4,5-triol;

(2R,3R,4R,5S)-2-methyl-1-(spiro[3.5]nonan-7-ylmethyl)piperidine-3,4,5-triol;

(2R,3R,4R,5S)-2-methyl-1-(spiro[4.5]decan-8-ylmethyl)piperidine-3,4,5-triol;

(2R,3R,4R,5S)-1-(((5S,8s)-3,3-dimethyl-2-oxaspiro[4.5]decan-8-yl)methyl)-2-methylpiperidine-3,4,5-triol;

(2R,3R,4R,5S)-2-methyl-1-((1,2,3,4-tetrahydronaphthalen-2-yl)methyl)piperidine-3,4,5-triol;

(2R,3R,4R,5S)-1-((2,3-dihydro-1H-inden-2-yl)methyl)-2-methylpiperidine-3,4,5-triol;

(2R,3R,4R,5S)-1-(2-cyclohexylethyl)-2-methylpiperidine-3,4,5-triol;

(2R,3R,4R,5S)-1-(2-(4,4-difluorocyclohexyl)ethyl)-2-methylpiperidine-3,4,5-triol;

(2R,3R,4R,5S)-2-methyl-1-(2-((1s,4S)-4-(trifluoromethyl)cyclohexyl)ethyl)piperidine-3,4,5-triol;

(2R,3R,4R,5S)-2-methyl-1-(2-((1r,4R)-4-(trifluoromethyl)cyclohexyl)ethyl)piperidine-3,4,5-triol;

(2R,3R,4R,5S)-1-((2-adamantan-1-yl)ethyl)-2-methylpiperidine-3,4,5-triol;

(2R,3R,4R,5S)-1-(3-cyclohexylpropyl)-2-methylpiperidine-3,4,5-triol;

(2R,3R,4R,5S)-2-methyl-1-phenethylpiperidine-3,4,5-triol;

(2R,3R,4R,5S)-2-methyl-1-(2-methylphenethyl)piperidine-3,4,5-triol;

(2R,3R,4R,5S)-1-(2-methoxyphenethyl)-2-methylpiperidine-3,4,5-triol;

(2R,3R,4R,5S)-1-(2-fluorophenethyl)-2-methylpiperidine-3,4,5-triol;

(2R,3R,4R,5S)-1-(2-chlorophenethyl)-2-methylpiperidine-3,4,5-triol;

(2R,3R,4R,5S)-1-(2,3-difluorophenethyl)-2-methylpiperidine-3,4,5-triol;

(2R,3R,4R,5S)-1-(2,4-difluorophenethyl)-2-methylpiperidine-3,4,5-triol;

(2R,3R,4R,5S)-1-(2,5-difluorophenethyl)-2-methylpiperidine-3,4,5-triol;

(2R,3R,4R,5S)-1-(3,4-difluorophenethyl)-2-methylpiperidine-3,4,5-triol;

(2R,3R,4R,5S)-1-(2-fluoro-4-methoxyphenethyl)-2-methylpiperidine-3,4,5-triol;

(2R,3R,4R,5S)-1-(3-chloro-2-fluorophenethyl)-2-methylpiperidine-3,4,5-triol;

(2R,3R,4R,5S)-1-(4-chloro-2-fluorophenethyl)-2-methylpiperidine-3,4,5-triol;

(2R,3R,4R,5S)-1-(5-chloro-2-fluorophenethyl)-2-methylpiperidine-3,4,5-triol;

(2R,3R,4R,5S)-1-(2,6-difluorophenethyl)-2-methylpiperidine-3,4,5-triol;

(2R,3R,4R,5S)-1-(3-chloro-2,6-difluorophenethyl)-2-methylpiperidine-3,4,5-triol;

(2R,3R,4R,5S)-1-(2,6-difluoro-4-(prop-1-en-2-yl)phenethyl)-2-methylpiperidine-3,4,5-triol;

(2R,3R,4R,5S)-1-(2,6-difluoro-4-isopropylphenethyl)-2-methylpiperidine-3,4,5-triol;

(2R,3R,4R,5S)-1-(2,6-difluoro-3-isopropylphenethyl)-2-methylpiperidine-3,4,5-triol;

(2R,3R,4R,5S)-1-(4-cyclopropyl-2,6-difluorophenethyl)-2-methylpiperidine-3,4,5-triol;

(2R,3R,4R,5S)-1-(2,6-difluoro-4-(tetrahydro-2H-pyran-4-yl)phenethyl)-2-methylpiperidine-3,4,5-triol;

(2R,3R,4R,5S)-1-(2,6-difluoro-4-(trifluoromethyl)phenethyl)-2-methylpiperidine-3,4,5-triol;

(2R,3R,4R,5S)-1-(2,6-difluoro-4-(pyrrolidin-1-yl)phenethyl)-2-methylpiperidine-3,4,5-triol;

(2R,3R,4R,5S)-1-(2,6-difluoro-4-(piperidin-1-yl)phenethyl)-2-methylpiperidine-3,4,5-triol;

(2R,3R,4R,5S)-1-(2,6-difluoro-4-morpholinophenethyl)-2-methylpiperidine-3,4,5-triol;

(2R,3R,4R,5S)-1-(4-butoxy-2,6-difluorophenethyl)-2-methylpiperidine-3,4,5-triol;

(2R,3R,4R,5S)-1-(4-(cyclopropylmethoxy)-2,6-difluorophenethyl)-2-methylpiperidine-3,4,5-triol;

(2R,3R,4R,5S)-2-methyl-1-(4-((tetrahydrofuran-3-yl)oxy)phenethyl)piperidine-3,4,5-triol;

(2R,3R,4R,5S)-2-methyl-1-(4-((tetrahydro-2H-pyran-3-yl)oxy)phenethyl)piperidine-3,4,5-triol;

(2R,3R,4R,5S)-2-methyl-1-(4-((tetrahydro-2H-pyran-4-yl)oxy)phenethyl)piperidine-3,4,5-triol;

(2R,3R,4R,5S)-2-methyl-1-(4-phenoxyphenethyl)piperidine-3,4,5-triol;

(2R,3R,4R,5S)-2-methyl-1-(4-((tetrahydrofuran-3-yl)methoxy)phenethyl)piperidine-3,4,5-triol;

(2R,3R,4R,5S)-2-methyl-1-((R)-2-phenylpropyl)piperidine-3,4,5-triol;

(2R,3R,4R,5S)-2-methyl-1-((S)-2-phenylpropyl)piperidine-3,4,5-triol;

(2R,3R,4R,5S)-1-(2-([1,1'-biphenyl]-4-yl)ethyl)-2-methylpiperidine-3,4,5-triol;

(2R,3R,4R,5S)-1-(2-(3,5-difluoro-[1,1'-biphenyl]-4-yl)ethyl)-2-methylpiperidine-3,4,5-triol;

(2R,3R,4R,5S)-1-(2-(benzo[d][1,3]dioxol-5-yl)ethyl)-2-methylpiperidine-3,4,5-triol;

(2R,3R,4R,5S)-1-(2-(6-fluorobenzo[d][1,3]dioxol-5-yl)ethyl)-2-methylpiperidine-3,4,5-triol;

(2R,3R,4R,5S)-1-(2-(2,2-difluorobenzo[d][1,3]dioxol-5-yl)ethyl)-2-methylpiperidine-3,4,5-triol;

(2R,3R,4R,5S)-1-(2-(2,3-dihydrobenzo[b][1,4]dioxin-6-yl)ethyl)-2-methylpiperidine-3,4,5-triol;

(2R,3R,4R,5S)-2-methyl-1-(2-(thiophen-2-yl)ethyl)piperidine-3,4,5-triol;

(2R,3R,4R,5S)-2-methyl-1-(2-(thiophen-3-yl)ethyl)piperidine-3,4,5-triol;

(2R,3R,4R,5S)-2-methyl-1-(2-(pyridin-2-yl)ethyl)piperidine-3,4,5-triol;

(2R,3R,4R,5S)-2-methyl-1-(3-phenylpropyl)piperidine-3,4,5-triol;

(2R,3R,4R,5S)-1-(3-(2-fluorophenyl)propyl)-2-methylpiperidine-3,4,5-triol;

(2R,3R,4R,5S)-1-(3-(4-fluorophenyl)propyl)-2-methylpiperidine-3,4,5-triol;

(2R,3R,4R,5S)-2-methyl-1-(3-(thiophen-2-yl)propyl)piperidine-3,4,5-triol;

(2R,3R,4R,5S)-2-methyl-1-(3-(thiophen-3-yl)propyl)piperidine-3,4,5-triol;

(2R,3R,4R,5S)-2-methyl-1-((1-phenylpiperidin-4-yl)methyl)piperidine-3,4,5-triol;

(2R,3R,4R,5S)-1-((1-(2-fluorophenyl)piperidin-4-yl)methyl)-2-methylpiperidine-3,4,5-triol;

(2R,3R,4R,5S)-1-((1-(3-fluorophenyl)piperidin-4-yl)methyl)-2-methylpiperidine-3,4,5-triol;

(2R,3R,4R,5S)-1-((1-(4-fluorophenyl)piperidin-4-yl)methyl)-2-methylpiperidine-3,4,5-triol;

(2R,3R,4R,5S)-2-methyl-1-((1-(4-(trifluoromethyl)phenyl)piperidin-4-yl)methyl)piperidine-3,4,5-triol;

(2R,3R,4R,5S)-2-methyl-1-((4-methyl-1-phenylpiperidin-4-yl)methyl)piperidine-3,4,5-triol;

(2R,3R,4R,5S)-1-((4-fluoro-1-phenylpiperidin-4-yl)methyl)-2-methylpiperidine-3,4,5-triol;

(2R,3R,4R,5S)-2-methyl-1-(2-(1-phenylpiperidin-4-yl)ethyl)piperidine-3,4,5-triol;

(2R,3R,4R,5S)-2-methyl-1-((1-(pyridin-3-yl)piperidin-4-yl)methyl)piperidine-3,4,5-triol;

(2R,3R,4R,5S)-2-methyl-1-((1-(2,2,2-trifluoroethyl)piperidin-4-yl)methyl)piperidine-3,4,5-triol;

2-methyl-1-(4-(((2R,3R,4R,5S)-3,4,5-trihydroxy-2-methylpiperidin-1-yl)methyl)piperidin-1-yl)propan-1-one;

2,2-dimethyl-1-(4-(((2R,3R,4R,5S)-3,4,5-trihydroxy-2-methylpiperidin-1-yl)methyl)piperidin-1-yl)propan-1-one;

1-(4-(((2R,3R,4R,5S)-3,4,5-trihydroxy-2-methylpiperidin-1-yl)methyl)piperidin-1-yl)butan-1-one;

3-methyl-1-(4-(((2R,3R,4R,5S)-3,4,5-trihydroxy-2-methylpiperidin-1-yl)methyl)piperidin-1-yl)butan-1-one;

3,3-dimethyl-1-(4-(((2R,3R,4R,5S)-3,4,5-trihydroxy-2-methylpiperidin-1-yl)methyl)piperidin-1-yl)butan-1-one;

2-cyclopentyl-1-(4-(((2R,3R,4R,5S)-3,4,5-trihydroxy-2-methylpiperidin-1-yl)methyl)piperidin-1-yl)ethanone;

cyclopropyl(4-(((2R,3R,4R,5S)-3,4,5-trihydroxy-2-methylpiperidin-1-yl)methyl)piperidin-1-yl)methanone;

cyclobutyl(4-(((2R,3R,4R,5S)-3,4,5-trihydroxy-2-methylpiperidin-1-yl)methyl)piperidin-1-yl)methanone;

cyclopentyl(4-(((2R,3R,4R,5S)-3,4,5-trihydroxy-2-methylpiperidin-1-yl)methyl)piperidin-1-yl)methanone;

cyclohexyl(4-(((2R,3R,4R,5S)-3,4,5-trihydroxy-2-methylpiperidin-1-yl)methyl)piperidin-1-yl)methanone;

((1s,4S)-4-(tert-butyl)cyclohexyl)(4-(((2R,3R,4R,5S)-3,4,5-trihydroxy-2-methylpiperidin-1-yl)methyl)piperidin-1-yl)methanone;

((1r,4R)-4-(tert-butyl)cyclohexyl)(4-(((2R,3R,4R,5S)-3,4,5-trihydroxy-2-methylpiperidin-1-yl)methyl)piperidin-1-yl)methanone;

(4-methoxycyclohexyl)(4-(((2R,3R,4R,5S)-3,4,5-trihydroxy-2-methylpiperidin-1-yl)methyl)piperidin-1-yl)methanone;

(4-(trifluoromethyl)cyclohexyl)(4-(((2R,3R,4R,5S)-3,4,5-trihydroxy-2-methylpiperidin-1-yl)methyl)piperidin-1-yl)methanone;

phenyl(4-(((2R,3R,4R,5S)-3,4,5-trihydroxy-2-methylpiperidin-1-yl)methyl)piperidin-1-yl)methanone;

(3-(trifluoromethyl)phenyl)(4-(((2R,3R,4R,5S)-3,4,5-trihydroxy-2-methylpiperidin-1-yl)methyl)piperidin-1-yl)methanone;

2-phenyl-1-(4-(((2R,3R,4R,5S)-3,4,5-trihydroxy-2-methylpiperidin-1-yl)methyl)piperidin-1-yl)ethanone;

thiophen-3-yl(4-(((2R,3R,4R,5S)-3,4,5-trihydroxy-2-methylpiperidin-1-yl)methyl)piperidin-1-yl)methanone;

N-cyclohexyl-4-(((2R,3R,4R,5S)-3,4,5-trihydroxy-2-methylpiperidin-1-yl)methyl)piperidine-1-carboxamide;

N-cyclohexyl-4-(((2R,3R,4R,5S)-3,4,5-trihydroxy-2-methylpiperidin-1-yl)methyl)piperidine-1-carbothioamide;

(2R,3R,4R,5S)-2-methyl-1-((1-((1S,2R)-2-(trifluoromethyl)cyclohexyl)azetidin-3-yl)methyl)piperidine-3,4,5-triol;

(2R,3R,4R,5S)-2-methyl-1-(((R)-1-phenylpyrrolidin-3-yl)methyl)piperidine-3,4,5-triol;

(2R,3R,4R,5S)-2-methyl-1-(((R)-1-(o-tolyl)pyrrolidin-3-yl)methyl)piperidine-3,4,5-triol;

(2R,3R,4R,5S)-2-methyl-1-(((R)-1-(2-(trifluoromethyl)phenyl)pyrrolidin-3-yl)methyl)piperidine-3,4,5-triol;
(2R,3R,4R,5S)-1-(((R)-1-(2-fluorophenyl)pyrrolidin-3-yl)methyl)-2-methylpiperidine-3,4,5-triol;
(2R,3R,4R,5S)-1-(((R)-1-(3-fluorophenyl)pyrrolidin-3-yl)methyl)-2-methylpiperidine-3,4,5-triol;
(2R,3R,4R,5S)-2-methyl-1-(((R)-1-(2-(trifluoromethoxy)phenyl)pyrrolidin-3-yl)methyl)piperidine-3,4,5-triol;
(2R,3R,4R,5S)-2-methyl-1-(((R)-1-(6-(trifluoromethyl)pyridin-2-yl)pyrrolidin-3-yl)methyl)piperidine-3,4,5-triol;
(2R,3R,4R,5S)-2-methyl-1-(((R)-1-(3-(trifluoromethyl)pyridin-2-yl)pyrrolidin-3-yl)methyl)piperidine-3,4,5-triol;
(2R,3R,4R,5S)-2-methyl-1-(((R)-1-(4-(trifluoromethyl)pyridin-2-yl)pyrrolidin-3-yl)methyl)piperidine-3,4,5-triol;
(2R,3R,4R,5S)-2-methyl-1-(((R)-1-(pyridin-3-yl)pyrrolidin-3-yl)methyl)piperidine-3,4,5-triol;
(2R,3R,4R,5S)-2-methyl-1-(((R)-1-(4-methylpyridin-3-yl)pyrrolidin-3-yl)methyl)piperidine-3,4,5-triol;
(2R,3R,4R,5S)-2-methyl-1-(((R)-1-(4-(trifluoromethyl)pyridin-3-yl)pyrrolidin-3-yl)methyl)piperidine-3,4,5-triol;
(2R,3R,4R,5S)-2-methyl-1-(((R)-1-(5-(trifluoromethyl)pyridin-3-yl)pyrrolidin-3-yl)methyl)piperidine-3,4,5-triol;
(2R,3R,4R,5S)-2-methyl-1-(((R)-1-(2-(trifluoromethyl)pyridin-3-yl)pyrrolidin-3-yl)methyl)piperidine-3,4,5-triol;
(2R,3R,4R,5S)-2-methyl-1-(((R)-1-(4-(trifluoromethyl)pyrimidin-5-yl)pyrrolidin-3-yl)methyl)piperidine-3,4,5-triol;
(2R,3R,4R,5S)-2-methyl-1-(((R)-1-(thiophen-3-yl)pyrrolidin-3-yl)methyl)piperidine-3,4,5-triol;
(2R,3R,4R,5S)-1-(((R)-1-(benzo[d]thiazol-4-yl)pyrrolidin-3-yl)methyl)-2-methylpiperidine-3,4,5-triol;
(4-(trifluoromethyl)phenyl)((R)-3-(((2R,3R,4R,5S)-3,4,5-trihydroxy-2-methylpiperidin-1-yl)methyl)pyrrolidin-1-yl)methanone;
(2R,3R,4R,5S)-2-methyl-1-(((S)-1-(2-(trifluoromethyl)phenyl)pyrrolidin-3-yl)methyl)piperidine-3,4,5-triol;
(2R,3R,4R,5S)-2-methyl-1-(((S)-1-(3-(trifluoromethyl)pyridin-2-yl)pyrrolidin-3-yl)methyl)piperidine-3,4,5-triol;
(2R,3R,4R,5S)-2-methyl-1-(((S)-1-(4-(trifluoromethyl)pyridin-3-yl)pyrrolidin-3-yl)methyl)piperidine-3,4,5-triol;
(2R,3R,4R,5S)-2-methyl-1-(((S)-1-(4-(trifluoromethyl)pyrimidin-5-yl)pyrrolidin-3-yl)methyl)piperidine-3,4,5-triol;
(2R,3R,4R,5S)-2-methyl-1-(((S)-1-(4-(trifluoromethyl)thiazol-2-yl)pyrrolidin-3-yl)methyl)piperidine-3,4,5-triol;
(2R,3R,4R,5S)-2-methyl-1-(((R)-1-(o-tolyl)piperidin-3-yl)methyl)piperidine-3,4,5-triol;
(2R,3R,4R,5S)-1-(((R)-1-(2-fluorophenyl)piperidin-3-yl)methyl)-2-methylpiperidine-3,4,5-triol;
(2R,3R,4R,5S)-2-methyl-1-(((R)-1-(3-(trifluoromethyl)pyridin-2-yl)piperidin-3-yl)methyl)piperidine-3,4,5-triol;
(2R,3R,4R,5S)-2-methyl-1-(((R)-1-(6-(trifluoromethyl)pyridin-2-yl)piperidin-3-yl)methyl)piperidine-3,4,5-triol;
(2R,3R,4R,5S)-2-methyl-1-(((R)-1-(4-(trifluoromethyl)pyridin-3-yl)piperidin-3-yl)methyl)piperidine-3,4,5-triol;
(2R,3R,4R,5S)-2-methyl-1-(((S)-1-(3-(trifluoromethyl)pyridin-2-yl)piperidin-3-yl)methyl)piperidine-3,4,5-triol;
(2R,3R,4R,5S)-2-methyl-1-(((S)-1-(4-(trifluoromethyl)pyridin-3-yl)piperidin-3-yl)methyl)piperidine-3,4,5-triol;
(2R,3R,4R,5S)-2-methyl-1-(((S)-1-(6-(trifluoromethyl)pyridin-2-yl)piperidin-3-yl)methyl)piperidine-3,4,5-triol;
(2R,3R,4R,5S)-2-methyl-1-(((S)-1-(4-(trifluoromethyl)thiazol-2-yl)piperidin-3-yl)methyl)piperidine-3,4,5-triol;
(2S,3R,4R,5S)-2-(fluoromethyl)-1-((4-isopropylcyclohexyl)methyl)piperidine-3,4,5-triol;
(2S,3R,4R,5S)-1-((4-(tert-butyl)cyclohexyl)methyl)-2-(fluoromethyl)piperidine-3,4,5-triol;
(2S,3R,4R,5S)-2-(fluoromethyl)-1-(((1r,4S)-4-(trifluoromethyl)cyclohexyl)methyl)piperidine-3,4,5-triol;
(2S,3R,4R,5S)-2-(fluoromethyl)-1-phenethylpiperidine-3,4,5-triol;
(2S,3R,4R,5S)-2-(fluoromethyl)-1-(2-fluorophenethyl)piperidine-3,4,5-triol;
(2S,3R,4R,5S)-1-(2,6-difluoro-4-isopropylphenethyl)-2-(fluoromethyl)piperidine-3,4,5-triol;
(2S,3R,4R,5S)-1-(2-(3,5-difluoro-[1,1'-biphenyl]-4-yl)ethyl)-2-(fluoromethyl)piperidine-3,4,5-triol;
(2S,3R,4R,5S)-1-(2-(6-fluorobenzo[d][1,3]dioxol-5-yl)ethyl)-2-(fluoromethyl)piperidine-3,4,5-triol;
(2S,3R,4R,5S)-1-(2-(2,3-dihydrobenzo[b][1,4]dioxin-6-yl)ethyl)-2-(fluoromethyl)piperidine-3,4,5-triol;
(2S,3R,4R,5S)-2-(fluoromethyl)-1-((1-phenylpiperidin-4-yl)methyl)piperidine-3,4,5-triol;
(2S,3R,4R,5S)-2-(fluoromethyl)-1-((1-(4-(trifluoromethyl)phenyl)piperidin-4-yl)methyl)piperidine-3,4,5-triol;
(2S,3R,4R,5S)-2-(difluoromethyl)-1-phenethylpiperidine-3,4,5-triol;
(2S,3R,4R,5S)-1-(2-fluorophenethyl)-2-methylpiperidine-3,4,5-triol;
(2S,3R,4R,5S)-1-(4-butoxy-2,6-difluorophenethyl)-2-methylpiperidine-3,4,5-triol;
(2R,3R,4R,5S)-2-(fluoromethyl)-1-(2-fluorophenethyl)piperidine-3,4,5-triol;
(2R,3R,4R,5S)-1-(4-butoxy-2,6-difluorophenethyl)-2-(fluoromethyl)piperidine-3,4,5-triol;
(2R,3R,4R,5S)-1-(3-fluorophenethyl)-2-methylpiperidine-3,4,5-triol;
(2R,3R,4R,5S)-1-(4-fluorophenethyl)-2-methylpiperidine-3,4,5-triol;
(2R,3R,4R,5S)-1-(3,4-dichlorophenethyl)-2-methylpiperidine-3,4,5-triol;
(2R,3R,4R,5S)-2-methyl-1-(3-(trifluoromethyl)phenethyl)piperidine-3,4,5-triol;
(2R,3R,4R,5S)-2-methyl-1-(4-(trifluoromethyl)phenethyl)piperidine-3,4,5-triol;
(2R,3R,4R,5S)-1-(4-(3,5-dimethylisoxazol-4-yl)-2,6-difluorophenethyl)-2-methylpiperidine-3,4,5-triol;
(2R,3R,4R,5S)-1-(4-(3,5-dimethyl-1H-pyrazol-4-yl)-2,6-difluorophenethyl)-2-methylpiperidine-3,4,5-triol;
(2R,3R,4R,5S)-2-methyl-1-(((R)-1-(4-(trifluoromethyl)thiazol-2-yl)pyrrolidin-3-yl)methyl)piperidine-3,4,5-triol;
(2R,3R,4R,5S)-1-(((R)-1-(benzo[d]oxazol-2-yl)pyrrolidin-3-yl)methyl)-2-methylpiperidine-3,4,5-triol;
(2R,3R,4R,5S)-1-(((R)-1-(benzo[d]thiazol-2-yl)pyrrolidin-3-yl)methyl)-2-methylpiperidine-3,4,5-triol;

(2R,3R,4R,5S)-1-(((R)-1-(5-isopropylthiazol-2-yl)piperidin-3-yl)methyl)-2-methylpiperidine-3,4,5-triol;

(2R,3R,4R,5S)-2-methyl-1-(((R)-1-(4-(trifluoromethyl)thiazol-2-yl)piperidin-3-yl)methyl)piperidine-3,4,5-triol;

(2R,3R,4R,5S)-2-methyl-1-(((R)-1-(2-(trifluoromethyl)pyridin-3-yl)piperidin-3-yl)methyl)piperidine-3,4,5-triol;

(2R,3R,4R,5S)-1-(((R)-1-(benzo[d]thiazol-2-yl)piperidin-3-yl)methyl)-2-methylpiperidine-3,4,5-triol;

(2R,3R,4R,5S)-1-(((R)-1-(benzo[d]thiazol-4-yl)piperidin-3-yl)methyl)-2-methylpiperidine-3,4,5-triol;

or a pharmaceutically acceptable salt of any of the foregoing compounds.

19. The method of claim 11 wherein said administering decreases the level of GBA2 enzyme activity in the subject.

20. The method of claim 11 wherein the subject is a human.

21. The method of claim 12 wherein the myotonic dystrophy is myotonic dystrophy type DM1 or myotonic dystrophy type DM2; the neuronal ceroid lipofuscinosis is neuronal ceroid lipofuscinosis type 1, neuronal ceroid lipofuscinosis type 2, neuronal ceroid lipofuscinosis type 3, neuronal ceroid lipofuscinosis type 4, neuronal ceroid lipofuscinosis type 5, neuronal ceroid lipofuscinosis type 6, neuronal ceroid lipofuscinosis type 7, neuronal ceroid lipofuscinosis type 8, neuronal ceroid lipofuscinosis type 9, or neuronal ceroid lipofuscinosis type 10; the neuropathy is peripheral neuropathy, autonomic neuropathy, neuritis, or diabetic neuropathy; the prion disease is Creutzfeldt-Jakob Disease (CJD), variant Creutzfeldt-Jakob Disease (vCJD), fatal familial insomnia, or kuru; the spinocerebellar ataxia is spinocerebellar ataxia type 1, spinocerebellar ataxia type 2, spinocerebellar ataxia type 3, spinocerebellar ataxia type 4, spinocerebellar ataxia type 5, spinocerebellar ataxia type 6, spinocerebellar ataxia type 7, spinocerebellar ataxia type 8, spinocerebellar ataxia type 10, spinocerebellar ataxia type 11, spinocerebellar ataxia type 12, spinocerebellar ataxia type 13, spinocerebellar ataxia type 14, spinocerebellar ataxia type 16, spinocerebellar ataxia type 17, spinocerebellar ataxia type 18, spinocerebellar ataxia type 19, spinocerebellar ataxia type 20, spinocerebellar ataxia type 21, spinocerebellar ataxia type 22, spinocerebellar ataxia type 23, spinocerebellar ataxia type 25, spinocerebellar ataxia type 26, spinocerebellar ataxia type 27, spinocerebellar ataxia type 28, or spinocerebellar ataxia type 29; the Gaucher disease is Gaucher disease type I, Gaucher disease type II, or Gaucher disease type III; the Niemann-Pick disease is Niemann-Pick disease type A, Niemann-Pick disease type B, or Niemann-Pick disease type C; the mucolipidosis is mucolipidosis type I, mucolipidosis type II, mucolipidosis type III, mucolipidosis type IV, mucolipidosis type VI, or mucolipidosis type VII; or the viral hepatitis is viral hepatitis type A, viral hepatitis type B, viral hepatitis type C, viral hepatitis type D, or viral hepatitis type E.

22. The method of claim 12 wherein the spinocerebellar ataxia is spinocerebellar ataxia type 1.

23. The method of claim 12 wherein the Niemann-Pick disease is Niemann-Pick type C disease.

24. The method of claim 12 wherein the neuronal ceroid lipofuscinosis is neuronal ceroid lipofuscinosis type 3.

25. The compound of claim 1 wherein the compound is any one of:

(2R,3R,4R,5S)-2-methyl-1-(((1r,4R)-4-(trifluoromethyl)cyclohexyl)methyl)piperidine-3,4,5-triol;

(2R,3R,4R,5S)-1-(((1s,4S)-4-(2-fluoropropan-2-yl)cyclohexyl)methyl)-2-methylpiperidine-3,4,5-triol;

(2R,3R,4R,5S)-1-(3-chloro-2-fluorophenethyl)-2-methylpiperidine-3,4,5-triol;

(2R,3R,4R,5S)-1-(3-chloro-2,6-difluorophenethyl)-2-methylpiperidine-3,4,5-triol;

(2R,3R,4R,5S)-1-((1-(4-fluorophenyl)piperidin-4-yl)methyl)-2-methylpiperidine-3,4,5-triol;

(2R,3R,4R,5S)-2-methyl-1-(((R)-1-(4-(trifluoromethyl)pyridin-3-yl)pyrrolidin-3-yl)methyl)piperidine-3,4,5-triol;

(2R,3R,4R,5S)-1-(((R)-1-(2-fluorophenyl)piperidin-3-yl)methyl)-2-methylpiperidine-3,4,5-triol;

(2R,3R,4R,5S)-2-methyl-1-(((R)-1-(3-(trifluoromethyl)pyridin-2-yl)piperidin-3-yl)methyl)piperidine-3,4,5-triol;

or a pharmaceutically acceptable salt of any of the foregoing compounds.

26. A pharmaceutical composition comprising the compound of claim 3 or a pharmaceutically acceptable salt thereof in combination with a pharmaceutically acceptable carrier.

27. A pharmaceutical composition comprising the compound of claim 25 or a pharmaceutically acceptable salt thereof in combination with a pharmaceutically acceptable carrier.

* * * * *

SEQUENCE LISTING

<160> NUMBER OF SEQ ID NOS: 3

<210> SEQ ID NO 1
<211> LENGTH: 927
<212> TYPE: PRT
<213> ORGANISM: Homo Sapiens

<400> SEQUENCE: 1

```
Met Gly Thr Gln Asp Pro Gly Asn Met Gly Thr Gly Val Pro Ala Ser
1               5                   10                  15

Glu Gln Ile Ser Cys Ala Lys Glu Asp Pro Gln Val Tyr Cys Pro Glu
            20                  25                  30

Glu Thr Gly Gly Thr Lys Asp Val Gln Val Thr Asp Cys Lys Ser Pro
        35                  40                  45

Glu Asp Ser Arg Pro Pro Lys Glu Thr Asp Cys Cys Asn Pro Glu Asp
    50                  55                  60

Ser Gly Gln Leu Met Val Ser Tyr Glu Gly Lys Ala Met Gly Tyr Gln
65                  70                  75                  80

Val Pro Pro Phe Gly Trp Arg Ile Cys Leu Ala His Glu Phe Thr Glu
                85                  90                  95

Lys Arg Lys Pro Phe Gln Ala Asn Asn Val Ser Leu Ser Asn Met Ile
            100                 105                 110

Lys His Ile Gly Met Gly Leu Arg Tyr Leu Gln Trp Trp Tyr Arg Lys
        115                 120                 125

Thr His Val Glu Lys Lys Thr Pro Phe Ile Asp Met Ile Asn Ser Val
    130                 135                 140

Pro Leu Arg Gln Ile Tyr Gly Cys Pro Leu Gly Gly Ile Gly Gly Gly
145                 150                 155                 160

Thr Ile Thr Arg Gly Trp Arg Gly Gln Phe Cys Arg Trp Gln Leu Asn
                165                 170                 175

Pro Gly Met Tyr Gln His Arg Thr Val Ile Ala Asp Gln Phe Thr Val
            180                 185                 190

Cys Leu Arg Arg Glu Gly Gln Thr Val Tyr Gln Gln Val Leu Ser Leu
        195                 200                 205

Glu Arg Pro Ser Val Leu Arg Ser Trp Asn Trp Gly Leu Cys Gly Tyr
    210                 215                 220

Phe Ala Phe Tyr His Ala Leu Tyr Pro Arg Ala Trp Thr Val Tyr Gln
225                 230                 235                 240

Leu Pro Gly Gln Asn Val Thr Leu Thr Cys Arg Gln Ile Thr Pro Ile
                245                 250                 255

Leu Pro His Asp Tyr Gln Asp Ser Ser Leu Pro Val Gly Val Phe Val
            260                 265                 270

Trp Asp Val Glu Asn Glu Gly Asp Glu Ala Leu Asp Val Ser Ile Met
        275                 280                 285

Phe Ser Met Arg Asn Gly Leu Gly Gly Gly Asp Asp Ala Pro Gly Gly
    290                 295                 300

Leu Trp Asn Glu Pro Phe Cys Leu Glu Arg Ser Gly Glu Thr Val Arg
305                 310                 315                 320

Gly Leu Leu Leu His His Pro Thr Leu Pro Asn Pro Tyr Thr Met Ala
                325                 330                 335

Val Ala Ala Arg Val Thr Ala Ala Thr Thr Val Thr His Ile Thr Ala
            340                 345                 350

Phe Asp Pro Asp Ser Thr Gly Gln Gln Val Trp Gln Asp Leu Leu Gln
        355                 360                 365
```

-continued

```
Asp Gly Gln Leu Asp Ser Pro Thr Gly Gln Ser Thr Pro Thr Gln Lys
    370                 375                 380

Gly Val Gly Ile Ala Gly Ala Val Cys Val Ser Ser Lys Leu Arg Pro
385                 390                 395                 400

Arg Gly Gln Cys Arg Leu Glu Phe Ser Leu Ala Trp Asp Met Pro Arg
                405                 410                 415

Ile Met Phe Gly Ala Lys Gly Gln Val His Tyr Arg Arg Tyr Thr Arg
            420                 425                 430

Phe Phe Gly Gln Asp Gly Asp Ala Ala Pro Ala Leu Ser His Tyr Ala
        435                 440                 445

Leu Cys Arg Tyr Ala Glu Trp Glu Glu Arg Ile Ser Ala Trp Gln Ser
    450                 455                 460

Pro Val Leu Asp Asp Arg Ser Leu Pro Ala Trp Tyr Lys Ser Ala Leu
465                 470                 475                 480

Phe Asn Glu Leu Tyr Phe Leu Ala Asp Gly Gly Thr Val Trp Leu Glu
                485                 490                 495

Val Leu Glu Asp Ser Leu Pro Glu Glu Leu Gly Arg Asn Met Cys His
            500                 505                 510

Leu Arg Pro Thr Leu Arg Asp Tyr Gly Arg Phe Gly Tyr Leu Glu Gly
        515                 520                 525

Gln Glu Tyr Arg Met Tyr Asn Thr Tyr Asp Val His Phe Tyr Ala Ser
    530                 535                 540

Phe Ala Leu Ile Met Leu Trp Pro Lys Leu Glu Leu Ser Leu Gln Tyr
545                 550                 555                 560

Asp Met Ala Leu Ala Thr Leu Arg Glu Asp Leu Thr Arg Arg Arg Tyr
                565                 570                 575

Leu Met Ser Gly Val Met Ala Pro Val Lys Arg Arg Asn Val Ile Pro
            580                 585                 590

His Asp Ile Gly Asp Pro Asp Asp Glu Pro Trp Leu Arg Val Asn Ala
        595                 600                 605

Tyr Leu Ile His Asp Thr Ala Asp Trp Lys Asp Leu Asn Leu Lys Phe
    610                 615                 620

Val Leu Gln Val Tyr Arg Asp Tyr Tyr Leu Thr Gly Asp Gln Asn Phe
625                 630                 635                 640

Leu Lys Asp Met Trp Pro Val Cys Leu Ala Val Met Glu Ser Glu Met
                645                 650                 655

Lys Phe Asp Lys Asp His Asp Gly Leu Ile Glu Asn Gly Gly Tyr Ala
            660                 665                 670

Asp Gln Thr Tyr Asp Gly Trp Val Thr Thr Gly Pro Ser Ala Tyr Cys
        675                 680                 685

Gly Gly Leu Trp Leu Ala Ala Val Ala Val Met Val Gln Met Ala Ala
    690                 695                 700

Leu Cys Gly Ala Gln Asp Ile Gln Asp Lys Phe Ser Ser Ile Leu Ser
705                 710                 715                 720

Arg Gly Gln Glu Ala Tyr Glu Arg Leu Leu Trp Asn Gly Arg Tyr Tyr
                725                 730                 735

Asn Tyr Asp Ser Ser Ser Arg Pro Gln Ser Arg Ser Val Met Ser Asp
            740                 745                 750

Gln Cys Ala Gly Gln Trp Phe Leu Lys Ala Cys Gly Leu Gly Glu Gly
        755                 760                 765

Asp Thr Glu Val Phe Pro Thr Gln His Val Val Arg Ala Leu Gln Thr
    770                 775                 780

Ile Phe Glu Leu Asn Val Gln Ala Phe Ala Gly Gly Ala Met Gly Ala
```

-continued

```
785                 790                 795                 800

Val Asn Gly Met Gln Pro His Gly Val Pro Asp Lys Ser Ser Val Gln
                805                 810                 815

Ser Asp Glu Val Trp Val Gly Val Val Tyr Gly Leu Ala Ala Thr Met
            820                 825                 830

Ile Gln Glu Gly Leu Thr Trp Glu Gly Phe Gln Thr Ala Glu Gly Cys
        835                 840                 845

Tyr Arg Thr Val Trp Glu Arg Leu Gly Leu Ala Phe Gln Thr Pro Glu
    850                 855                 860

Ala Tyr Cys Gln Gln Arg Val Phe Arg Ser Leu Ala Tyr Met Arg Pro
865                 870                 875                 880

Leu Ser Ile Trp Ala Met Gln Leu Ala Leu Gln Gln Gln Gln His Lys
                885                 890                 895

Lys Ala Ser Trp Pro Lys Val Lys Gln Gly Thr Gly Leu Arg Thr Gly
            900                 905                 910

Pro Met Phe Gly Pro Lys Glu Ala Met Ala Asn Leu Ser Pro Glu
        915                 920                 925


<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2

cgcaaatggg cggtaggcgt g                                              21


<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3

tagtcagcca tggggcggag a                                              21
```